United States Patent
Bignan et al.

(10) Patent No.: US 10,981,926 B2
(45) Date of Patent: *Apr. 20, 2021

(54) SUBSTITUTED THIOHYDANTOIN DERIVATIVES AS ANDROGEN RECEPTOR ANTAGONISTS

(71) Applicant: Janssen Pharmaceutica NV, Beerse (BE)

(72) Inventors: Gilles Bignan, Bridgewater, NJ (US); Peter J. Connolly, New Providence, NJ (US); Ian Hickson, Tyne & Wear (GB); Lieven Meerpoel, Beerse (BE); Vineet Pande, Vosselaar (BE); Zhuming Zhang, Hillsborough, NJ (US); Jonathan Branch, Hatfield, PA (US); Christian Rocaboy, Murcia (ES); Luis B. Trabalón Escolar, Murcia (ES)

(73) Assignee: Janssen Pharmaceutica NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 16/677,906

(22) Filed: Nov. 8, 2019

(65) Prior Publication Data
US 2020/0109150 A1  Apr. 9, 2020

Related U.S. Application Data

(63) Continuation of application No. 16/012,160, filed on Jun. 19, 2018, now Pat. No. 10,501,469, which is a continuation of application No. 15/403,741, filed on Jan. 11, 2017, now Pat. No. 10,000,502.

(60) Provisional application No. 62/363,534, filed on Jul. 18, 2016, provisional application No. 62/277,009, filed on Jan. 11, 2016.

(51) Int. Cl.
| | | |
|---|---|---|
| C07D 491/10 | (2006.01) |
| C07D 491/107 | (2006.01) |
| C07D 401/14 | (2006.01) |
| C07D 405/14 | (2006.01) |
| C07D 413/14 | (2006.01) |
| C07D 401/04 | (2006.01) |
| C07D 409/14 | (2006.01) |
| C07D 451/02 | (2006.01) |
| C07D 451/06 | (2006.01) |
| C07D 487/04 | (2006.01) |
| C07D 491/044 | (2006.01) |
| C07D 491/048 | (2006.01) |
| A61K 9/00 | (2006.01) |
| A61K 31/4439 | (2006.01) |
| A61K 31/4545 | (2006.01) |
| A61K 31/46 | (2006.01) |
| A61K 31/506 | (2006.01) |
| A61K 31/5377 | (2006.01) |
| A61K 31/55 | (2006.01) |
| A61K 31/573 | (2006.01) |
| A61K 31/58 | (2006.01) |

(52) U.S. Cl.
CPC ........ *C07D 491/107* (2013.01); *A61K 9/0053* (2013.01); *A61K 31/4439* (2013.01); *A61K 31/4545* (2013.01); *A61K 31/46* (2013.01); *A61K 31/506* (2013.01); *A61K 31/5377* (2013.01); *A61K 31/55* (2013.01); *A61K 31/573* (2013.01); *A61K 31/58* (2013.01); *C07D 401/04* (2013.01); *C07D 401/14* (2013.01); *C07D 405/14* (2013.01); *C07D 409/14* (2013.01); *C07D 413/14* (2013.01); *C07D 451/02* (2013.01); *C07D 451/06* (2013.01); *C07D 487/04* (2013.01); *C07D 491/044* (2013.01); *C07D 491/048* (2013.01)

(58) Field of Classification Search
CPC .................................................. C07D 491/107
See application file for complete search history.

(56) References Cited

U.S. PATENT DOCUMENTS

| | | |
|---|---|---|
| 3,798,233 A | 3/1974 | Akiba et al. |
| 3,823,240 A | 7/1974 | Sauli |

(Continued)

FOREIGN PATENT DOCUMENTS

| | | |
|---|---|---|
| AU | 217893 | 6/1958 |
| CN | 101032483 A | 9/2007 |

(Continued)

OTHER PUBLICATIONS

Wainstein et al., "CWR22: Androgen-Dependent Xenograft Model Derived from a Primary Human Prostatic Carcinoma", Cancer Res, 1994, 54, 6049-6052.

(Continued)

*Primary Examiner* — Shawquia Jackson
(74) *Attorney, Agent, or Firm* — BakerHostetler

(57) ABSTRACT

Disclosed are compounds, compositions and methods for treating of disorders that are affected by the antagonism of one or more androgen receptor types. Such compounds are represented by Formula (I) as follows:

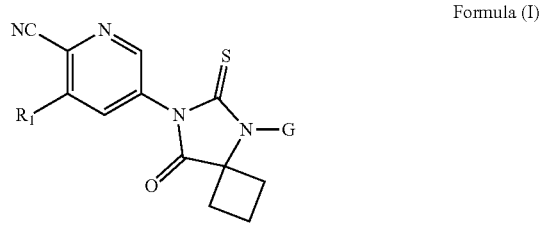

Formula (I)

wherein R₁ and G are defined herein.

51 Claims, No Drawings

(56) References Cited

U.S. PATENT DOCUMENTS

| | | |
|---|---|---|
| 3,984,430 A | 10/1976 | Curran |
| 4,097,578 A | 6/1978 | Perronnet et al. |
| 4,229,447 A | 10/1980 | Porter |
| 4,234,736 A | 11/1980 | Bernauer et al. |
| 4,304,782 A | 12/1981 | Dumont et al. |
| 4,312,881 A | 1/1982 | Wootton |
| 4,399,216 A | 8/1983 | Axel et al. |
| 4,407,814 A | 10/1983 | Bernauer et al. |
| 4,427,438 A | 1/1984 | Nagano et al. |
| 4,473,393 A | 9/1984 | Nagpal |
| 4,482,739 A | 11/1984 | Bernauer et al. |
| 4,559,157 A | 12/1985 | Smith et al. |
| 4,596,795 A | 6/1986 | Pitha |
| 4,608,392 A | 8/1986 | Jacquet et al. |
| 4,749,403 A | 6/1988 | Liebl et al. |
| 4,755,386 A | 7/1988 | Hsiao et al. |
| 4,820,508 A | 4/1989 | Wortzman |
| 4,859,228 A | 8/1989 | Prisbylla |
| 4,873,256 A | 10/1989 | Coussediere et al. |
| 4,938,949 A | 7/1990 | Borch et al. |
| 4,944,791 A | 7/1990 | Schroeder et al. |
| 4,992,478 A | 2/1991 | Geria |
| 5,010,182 A | 4/1991 | Brake et al. |
| 5,011,692 A | 4/1991 | Fujioka et al. |
| 5,017,381 A | 5/1991 | Maruyama et al. |
| 5,033,252 A | 7/1991 | Carter |
| 5,052,558 A | 10/1991 | Carter |
| 5,069,711 A | 12/1991 | Fischer et al. |
| 5,071,773 A | 12/1991 | Evans et al. |
| 5,166,358 A | 11/1992 | Seuron et al. |
| 5,229,135 A | 7/1993 | Philippon et al. |
| 5,323,907 A | 6/1994 | Kalvelage |
| 5,411,981 A | 5/1995 | Gaillard-Kelly et al. |
| 5,434,176 A | 7/1995 | Claussner et al. |
| 5,554,607 A | 9/1996 | Elokdah et al. |
| 5,556,983 A | 9/1996 | Claussner et al. |
| 5,589,497 A | 12/1996 | Claussner et al. |
| 5,614,620 A | 3/1997 | Liao et al. |
| 5,627,201 A | 5/1997 | Gaillard-Kelly et al. |
| 5,646,172 A | 7/1997 | Claussner et al. |
| 5,656,651 A | 8/1997 | Sovak et al. |
| 5,705,654 A | 1/1998 | Claussner et al. |
| 5,726,061 A | 3/1998 | Robbins et al. |
| 5,739,136 A | 4/1998 | Ellinwood et al. |
| 5,750,553 A | 5/1998 | Claussner et al. |
| 5,783,707 A | 7/1998 | Elokdah et al. |
| RE35,956 E | 11/1998 | Gaillard-Kelly et al. |
| 5,837,284 A | 11/1998 | Mehta et al. |
| 5,840,329 A | 11/1998 | Bai |
| 5,958,936 A | 9/1999 | Claussner et al. |
| 5,968,875 A | 10/1999 | Bis et al. |
| 5,985,868 A | 11/1999 | Gray |
| 6,107,488 A | 8/2000 | Bouchet et al. |
| 6,172,076 B1 | 1/2001 | Embrey et al. |
| 6,235,910 B1 | 5/2001 | Beller et al. |
| 6,242,611 B1 | 6/2001 | Claussner et al. |
| 6,307,030 B1 | 10/2001 | French et al. |
| 6,350,763 B1 | 2/2002 | Kelly et al. |
| 6,472,415 B1 | 10/2002 | Sovak et al. |
| 6,479,063 B2 | 11/2002 | Weisman et al. |
| 6,489,163 B1 | 12/2002 | Roy et al. |
| 6,506,607 B1 | 1/2003 | Shyjan |
| 6,710,037 B2 | 3/2004 | Wang et al. |
| 6,828,471 B2 | 12/2004 | Sawyers et al. |
| 7,271,188 B2 | 9/2007 | Tachibana et al. |
| 7,390,923 B2 | 6/2008 | Ratilainen et al. |
| 7,855,225 B2 | 12/2010 | Niimi et al. |
| 8,445,507 B2 | 5/2013 | Jung et al. |
| 8,461,343 B2 | 6/2013 | Ouerfelli et al. |
| 8,470,829 B2 | 6/2013 | Tachibana et al. |
| 8,501,814 B2 | 8/2013 | Ratilainen et al. |
| 8,802,689 B2 | 8/2014 | Jung et al. |
| 8,987,452 B2 | 3/2015 | Ouerfelli et al. |
| 9,108,944 B2 | 8/2015 | Smith et al. |
| 2002/0133833 A1 | 9/2002 | Sawyers et al. |
| 2003/0225138 A1 | 12/2003 | Sircar et al. |
| 2004/0009969 A1 | 1/2004 | Cleve et al. |
| 2004/0077605 A1 | 4/2004 | Salvati et al. |
| 2004/0116417 A1 | 6/2004 | Boubia et al. |
| 2005/0153968 A1 | 7/2005 | Bi et al. |
| 2006/0025589 A1 | 2/2006 | Binet et al. |
| 2006/0127902 A1 | 6/2006 | Madden et al. |
| 2006/0160845 A1 | 7/2006 | Schlienger et al. |
| 2007/0249697 A1 | 10/2007 | Tachibana et al. |
| 2007/0254933 A1 | 11/2007 | Jung et al. |
| 2010/0063120 A1 | 3/2010 | Nique et al. |
| 2010/0178324 A1 | 7/2010 | Ahn |
| 2011/0003839 A1 | 1/2011 | Jung et al. |
| 2012/0095068 A1 | 4/2012 | Bigg et al. |
| 2013/0045204 A1 | 2/2013 | Andersen et al. |
| 2013/0072511 A1 | 3/2013 | Jung et al. |
| 2013/0079241 A1 | 3/2013 | Luo et al. |
| 2013/0116258 A1 | 5/2013 | Smith et al. |
| 2013/0116269 A1 | 5/2013 | Ivachtchenko et al. |
| 2013/0225821 A1 | 8/2013 | Ouerfelli et al. |
| 2013/0252992 A1 | 9/2013 | Ivachtchenko et al. |
| 2013/0253035 A1 | 9/2013 | McDonnell et al. |
| 2014/0088129 A1 | 3/2014 | Chen |
| 2014/0094474 A1 | 4/2014 | Toermakaengas et al. |
| 2014/0155390 A1 | 6/2014 | Anderson et al. |
| 2014/0199236 A1 | 7/2014 | Chen et al. |
| 2014/0309262 A1 | 10/2014 | Jung et al. |
| 2016/0244444 A1 | 8/2016 | Minamiguchi et al. |

FOREIGN PATENT DOCUMENTS

| | | |
|---|---|---|
| CN | 101032486 A | 9/2007 |
| CN | 104844521 A | 8/2015 |
| DE | 2102605 | 7/1971 |
| DE | 2614831 | 10/1977 |
| EP | 0002259 A2 | 6/1979 |
| EP | 0017976 A2 | 10/1980 |
| EP | 0144098 A1 | 6/1985 |
| EP | 0331232 A2 | 9/1989 |
| EP | 0362179 A2 | 4/1990 |
| EP | 0494819 A1 | 7/1992 |
| EP | 0572191 A1 | 12/1993 |
| EP | 0578516 A1 | 1/1994 |
| EP | 0580459 A1 | 1/1994 |
| EP | 0721944 A1 | 7/1996 |
| EP | 0770613 A1 | 5/1997 |
| EP | 1632477 A1 | 3/2006 |
| EP | 1790640 A1 | 5/2007 |
| FR | 2693461 A1 | 1/1994 |
| FR | 2715402 A1 | 7/1995 |
| FR | 2845384 A1 | 4/2004 |
| JP | 59-210083 A | 11/1984 |
| JP | 64-009978 A | 1/1989 |
| JP | 02-019363 A | 1/1990 |
| JP | 2002-088073 A | 3/2002 |
| JP | 2004-252175 A | 9/2004 |
| JP | 2006-510600 | 3/2006 |
| JP | 2009-531439 | 9/2009 |
| JP | 2014-133744 A | 7/2014 |
| WO | 90/13646 A1 | 11/1990 |
| WO | 97/00071 A1 | 1/1997 |
| WO | 97/19064 A1 | 5/1997 |
| WO | 97/19931 A1 | 6/1997 |
| WO | 00/17163 A1 | 3/2000 |
| WO | 00/26195 A1 | 5/2000 |
| WO | 00/44731 A1 | 8/2000 |
| WO | 01/07048 A1 | 2/2001 |
| WO | 01/92253 A2 | 12/2001 |
| WO | 01/94346 A1 | 12/2001 |
| WO | 02/53155 | 7/2002 |
| WO | 02/81453 | 10/2002 |
| WO | 03/29245 | 4/2003 |
| WO | 03/32994 | 4/2003 |
| WO | 03/57220 | 7/2003 |
| WO | 03/93243 | 11/2003 |
| WO | 03/96980 | 11/2003 |
| WO | 2004/022572 A1 | 3/2004 |
| WO | 2004/031160 A2 | 4/2004 |
| WO | 2004/070050 A2 | 8/2004 |

(56) References Cited

FOREIGN PATENT DOCUMENTS

| | | |
|---|---|---|
| WO | 2004/111031 A1 | 12/2004 |
| WO | 2005/042488 A1 | 5/2005 |
| WO | 2005/059109 A2 | 6/2005 |
| WO | 2005/060661 A2 | 7/2005 |
| WO | 2005/089752 A2 | 9/2005 |
| WO | 2005/099693 A2 | 10/2005 |
| WO | 2006/010642 A1 | 2/2006 |
| WO | 2006/028226 A1 | 3/2006 |
| WO | 2006/124118 A1 | 11/2006 |
| WO | 2007/012661 A1 | 2/2007 |
| WO | 2007/045877 A1 | 4/2007 |
| WO | 2007/126765 A2 | 11/2007 |
| WO | 2007/127010 A2 | 11/2007 |
| WO | 2008/112939 A2 | 9/2008 |
| WO | 2008/119015 A2 | 10/2008 |
| WO | 2009/055053 A2 | 4/2009 |
| WO | 2010/020055 A1 | 2/2010 |
| WO | 2010/083215 A2 | 7/2010 |
| WO | 2010/099238 A1 | 9/2010 |
| WO | 2011/029537 A1 | 3/2011 |
| WO | 2011/103202 A2 | 8/2011 |
| WO | 2011/106570 A1 | 9/2011 |
| WO | 2012/011840 A1 | 1/2012 |
| WO | 2012/050868 A1 | 4/2012 |
| WO | 2012/119559 A1 | 9/2012 |
| WO | 2012/139039 A2 | 10/2012 |
| WO | 2012/143599 A1 | 10/2012 |
| WO | 2012/158884 A1 | 11/2012 |
| WO | 2013/028572 A1 | 2/2013 |
| WO | 2013/028791 A1 | 2/2013 |
| WO | 2013/047144 A1 | 4/2013 |
| WO | 2013/056547 A1 | 4/2013 |
| WO | 2013/067142 A1 | 5/2013 |
| WO | 2013/067151 A1 | 5/2013 |
| WO | 2013/079964 A1 | 6/2013 |
| WO | 2013/123511 A1 | 8/2013 |
| WO | 2014/001247 A1 | 1/2014 |
| WO | 2014/036897 A1 | 3/2014 |
| WO | 2014/052237 A1 | 4/2014 |
| WO | 2014/066799 A2 | 5/2014 |
| WO | 2014/066864 A2 | 5/2014 |
| WO | 2014/075387 A1 | 5/2014 |
| WO | 2014/125121 A1 | 8/2014 |
| WO | 2014/130932 A2 | 8/2014 |
| WO | 2014/158528 A1 | 10/2014 |
| WO | 2014/202827 A1 | 12/2014 |
| WO | 2015/018356 A1 | 2/2015 |
| WO | 2015/042297 A1 | 3/2015 |
| WO | 2015/089634 A1 | 6/2015 |
| WO | 2015/100617 A1 | 7/2015 |
| WO | 2015/181747 A1 | 12/2015 |
| WO | 2015/182712 A1 | 12/2015 |
| WO | 2015/184393 A1 | 12/2015 |

OTHER PUBLICATIONS

Wallen et al., "Androgen Receptor Gene Mutations in Hormone-Refractory Prostate Cancer", J. Pathology 1999, vol. 189, pp. 559-563.

Waltering et al., "Androgen receptor (AR) aberrations in castration-resistant prostate cancer", Molecular and Cellular Endocrinology, 2012, 360, 38-43.

Wang et al., "Discovery of (2E)-3-(2-Butyl-1-[2-(diethylamino)ethyl]-1H-benzimidazol-5-yl)-N-hydroxy-acrylamide (SB939), an Orally Active Histone Deacetylase Inhibitor with a Superior Preclinical Profile", J. Med. Chem., 2011, 54, 4694-4720.

Wang et al., "Overexpressed Androgen Receptor Linked to p21 WAF1 Silencing May Be Responsible for Androgen Independence and Resistance to Apoptosis of a Prostate Cancer Cell Line", Cancer Research, 2001, 61(20), 7544-7551.

Wang et al., "Prostate-Specific Deletion of the Murine Pten Tumor Suppressor Gene Leads to Metastatic Prostate Cancer", Cancer Cell, 2003, 4, 209-221.

Wang et al., "Small Molecule Inhibition of the Steroid Receptor Coactivators, SRC-3 and SRC-1", Mol. Endocrinol., Dec. 2011, 25(12), 2041-2053.

Watson et al., "Constitutively active androgen receptor splice variants expressed in castration-resistant prostate cancer require full-length androgen receptor", PNAS, 2010, 107, 16759-16765.

Weidner-Wells et al., "Novel Piperidinyloxy Oxazolidinone Antimicrobial Agents", Bioorganic & Medicinal Chemistry, 2001, 11, 1829-1832.

Wermuth et al., "Designing Prodrugs and Bioprecursors, I: Carrier Prodrugs", The Pharmacological Basis of Therapeutics, The Practice of Medicinal Chemistry, Goodman and Gilman, eds., Macmillan Publishing Co., New York, Chapter 31, 1996, 28 pages.

Wermuth, "Molecular Variations Based on Isosteric Replacements", The Practice of Medicinal Chemistry, 1996, 13, 203-237.

Whitby et al., "Design, Synthesis, and Validation of a .beta.-Turn Mimetic Library Targeting Protein—Protein and Peptide—Receptor Interactions", Journal of the American Chemical Society, 2011, 133, 10184-10194.

Whitby et al., "Discovery of HIV fusion inhibitors targeting gp41 using a comprehensive .alpha.-helix mimetic library", Bioorganic & Medicinal Chemistry Letters, Apr. 2012, 2(8)2861-5.

Wooster et al., "A Germline Mutation in the Androgen Receptor Gene in Two Brothers with Breast Cancer and Reifenstein Syndrome", Nat. Genet., 1992, 2, 132-134.

Wu et al., "Slug, a Unique Androgen-Regulated Transcription Factor, Coordinates Androgen Receptor to Facilitate Castration Resistance in Prostate Cancer", Molecular Endocrinology, Sep. 2012, 26(9), 1496-1507.

Xia et al., "Novel Triazole Ribonucleoside Down-Regulates Heat Shock Protein 27 and Induces Potent Anticancer Activity on Drug-Resistant Pancreatic Cancer", J. Med. Chem., 2009, 52, 6083-6096.

Xu et al., "The Three Dimensional Quantitative Structure Activity Relationships (3D-QSAR) and Docking Studies of Curcumin Derivatives as Androgen Receptor Antagonists", Int. J. Biol. Sci., 2012, 3, 6138-6155.

Yamada et al., "Design and Synthesis of 4-(4-Benzoylaminophenoxy)phenol Derivatives As Androgen Receptor Antagonists", ACS Medicinal Chemistry Letters, Oct. 2013, 4(1), 937-41.

Yang et al., "1456: Central Role for PELP1-Androgen Receptor Complex in Prostate Cancer", Prostate Cancer: Basic Research Moderated Poster, May 17, 2011, 1 page.

Yang et al., "Central Role for PELP1 in Nonandrogenic Activation of the Androgen Receptor in Prostate Cancer", Mol. Endocrinol., Apr. 2012, 26(4), 550-561.

Yang et al., "Discovery of 1,4-Substituted Piperidines as Potent and Selective Inhibitors of T-Type Calcium Channels", J. Med. Chem., 2008, 51, 6471-6477.

Yang et al., "Inhibition of androgen receptor activity by histone deacetylase 4 through receptor SUMOylation", Oncogene, 2011, 30, 2207-2218.

Yeh et al., "Functional Analysis of Androgen Receptor N-terminal and Ligand Binding Domain Interacting Coregulators in Prostate Cancer", J Formos Med Assoc., 2000, vol. 99, No. 12, 885-894.

Yi et al., "Structure of a Biologically Active Estrogen Receptor-Coactivator Complex on DNA", Molecular Cell, Mar. 2015, 57, 1047-1058.

Yin et al., "Recent Progress in Pharmaceutical Therapies for Castration-Resistant Prostate Cancer", Int. J. Biol. Sci., 2013, 14, 13958-13978.

Ying et al., "Ganetespib et al., a Unique Triazolone-Containing Hsp90 Inhibitor, Exhibits Potent Antitumor Activity and a Superior Safety Profile for Cancer Therapy", Molecular Cancer Therapeutics, 2012, 11, 475-484.

Yoshino et al., "Design and synthesis of an androgen receptor pure antagonist (CH5137291) for the treatment of castration-resistant prostate cancer", Bioorganic & Medicinal Chemistry, 2010, 18, 8150-8157.

Zakikhani et al., "Metformin is an AMP Kinase-Dependent Growth Inhibitor for Breast Cancer Cells", Cancer Res, 2006, 66(21), 10269-10273.

(56) References Cited

OTHER PUBLICATIONS

Zarghami et al., "Steroid Hormone Regulation of Prostate-Specific Antigen Gene Expression in Breast Cancer", British Journal of Cancer, 1997, 75(4), 579-588.
Zhang et al., "Deciphering the selective androgen receptor modulators paradigm", Expert Opinion Drug Discov., 2013, 8(2), 191-218.
Zhang et al., "Development of .beta.-amino-carbonyl compounds as androgen receptor antagonists", Acta Pharmacologica Sinica, 2014, 35, 664-673.
Zhang et al., "Recent advances in the development of selective androgen receptor modulators", Expert Opinion Ther. Patents. 2009, 19(9), 1239-1258.
Zhau, H.Y. et al. "Androgen-repressed phenotype in human prostate cancer," Proc. Natl. Acad. Sci. USA, 1996, 33, 15152-7.
Zhou et al., "A Ligand-Dependent Bipartite Nuclear Targeting Signal in the Human Androgen Receptor, Requirement for the DNA-Binding Domain and Modulation by NH2-Terminal and Carboxyl-Terminal Sequences", J Bio Chem, 1994, 269(18), 13115-13123.
Zhou et al., "Expression, purification and primary crystallographic study of human androgen receptor in complex with DNA and coactivator motifs", Protein Expr. Purif., May 2010, 71(1), 21-27.
Zhu et al., "Dose-dependent effects of small-molecule antagonists on the genomic landscape of androgen receptor binding", BMC Genomics, 2012, 13:355.
Zoppi et al., "Amino Acid Substitutions in the DNA-Binding Domain of the Human Androgen Receptor are a Frequent Cause of Receptor-Binding Positive Androgen Resistance", Mol. Endo., 1992, 6, 409-415.
Zoubeidi et al., "Small heat shock proteins in cancer therapy and prognosis", The International Journal of Biochemistry & Cell Biology, May 2012, 44(10), 1646-56.
Zoubeidi et al., "Targeting HSP 27 for the Treatment of Castration-Resistant Prostate Cancer", Drugs of the Future, 2011, 36(3), 241-247.
Singh et al., "Androgen Receptor Antagonists (Antiandrogens): Structure-Activity Relationships", Current Medicinal Chemistry, 2000, 7, 211-247.
Singh et al., "Rational Design of Novel Antiandrogens for Neutralizing Androgen Receptor Function in Hormone Refractory Prostate Cancer", The Prostate, 2008, 68, 1570-1581.
Smith et al., "ARN-509 in Men with High Risk Non-Metastatic Castration-Resistant Prostate Cancer", Annals of Oncology; Abstract Book of the 37th ESMO Congress, 2012, 23(9), No. Suppl. 9, 1 page.
Smith et al., "ARN-509 in Men with High Risk Non-Metastatic Castration-Resistant Prostate Cancer", European Journal of Cancer; European Cancer Congress, 2013, 49(2), 1 page.
Soderholm et al., "Three-Dimensional Structure—Activity Relationships of Nonsteroidal Ligands in Complex with Androgen Receptor Ligand-Binding Domain", J. Med. Chem., 2005, 48, 917-925.
Sonnichsen et al., "Effect of Trifluoroethanol on Protein Secondary Structure: An NMR and CD Study Using a Synthetic Actin Peptide", Biochemistry, 1992, 31, 8790-8798.
Soto et al., "Control of Cell Proliferation: Evidence for Negative Control on C141 Estrogen-Sensitive T47D Human Breast Cancer Cells", Cancer Research, 1986, 46, 2271-2275.
Souers et al., "ABT-199, a potent and selective BCL-2 inhibitor, achieves antitumor activity while sparing platelets", Nature Medicine, Jan. 2013, 19(2), 202-8.
Sperry et al., Androgen Binding Profiles of Two Distinct Nuclear Androgen Receptors in Atlantic Croaker (*Micropogonias undulates*), Journal of Steroid Biochemistry & Molecular Biology, 2000, 73, 93-103.
Stinchcomb et al., "Isolation and Characterisation of a Yeast Chromosomal Replicator", 1979, 282, 39-43.
Stope et al., "Androgen receptor and heat shock proteins in progression of prostate cancer cells", International Journal of Clinical and Therapeutics, Jan. 2012, 50, 65-67.
Stope et al., "Effect of the heat shock HSP27 on androgen receptor expression and function in prostate cancer cells", World J. Urol., Feb. 2012, 03(3), 327-31.
Streicher et al., "Stilbene Induced Inhibition of Androgen Receptor Dimerization: Implications for AR and AR.DELTA.LBD-Signalling in Human Prostate Cancer Cells", PLoS One, 2014, 9(6), e98566.
Su et al., "Polymorphisms of Androgen Receptor Gene in Childhood and Adolescent Males with First-Onset Major Depressive Disorder and Association with Related Symptomatology", Int. J. Neurosci., 2007, 117, 903-917.
Sugawara et al., "BAY 1024767 blocks androgen receptor mutants found in castration-resistant prostate cancer patients", Oncotarget, Feb. 2016, 7(5):6015-28.
Sweet et al., "A Unique Point Mutation in the Androgen Receptor Gene in a Family with Complete Androgen Insensitivity Syndrome", Fertil. Steril., 1992, 58(4), 703-707.
Szelei et al. Androgen-Induced Inhibition of Proliferation in Human Breast Cancer MCF7 Cells Transfected with Androgen Receptor. Endocrinology. 1997. v. 138 (4). pp. 1406-1412.
Takemoto et al., "Novel Potassium Chanel Openers: Synthesis and Pharmacological Evaluation of New N-substituted-3-pyridyl)-N'-alkylthioureas and Related Compounds", J. Med. Chem., 1994, 37(1), 18-25.
Tammela et al., "Endocrine prevention and treatment of prostate cancer", Molecular and Cellular Endocrinology, 2012, 360, 59-67.
Tammela et al., "Safety and efficacy of ODM-201 in chemotherapy and CYP17-inhibitor naive patients: Analysis of data from the ARADES and the ARAFOR trials", Orion Corp., 29.sup.th EAU Annual Congress, Apr. 11-15, 2014, 1 page.
Tanner et al., "A .sup.629RKLKK.sup.633 motif in the hinge region controls the androgen receptor at multiple levels", Cellular and Molecular Life Sciences, 2010, 67, 1919-1927.
Taplin et al., "Androgen Receptor Mutations in Androgen-Independent Prostate Cancer: Cancer and Leukemia Group B Study 9663", J Clin Oncol, 2003, 21, 2673-2678.
Taplin et al., "Mutation of the Androgen-Receptor Gene in Metastatic Androgen Independent Prostate Cancer", N Engl J Med, 1995, 332(21), 1393-1398.
Taplin et al., "Selection for Androgen Receptor Mutations in Prostate Cancers Treated with Androgen Antagonist", Cancer Research, 1999, 59, 2511-2515.
Taplin, Drug Insight: role of the androgen receptor in the development and progression of prostate cancer, Nature Clinical Practice, Apr. 2007, 4, 236-244.
Teutsch et al., "Non-steroidal Antiandrogens: Synthesis and Biological Profile of High-affinity Ligands for the Androgen Receptor", J. Steroid Biochem. Mol. Biol., 1994, 48, 111-119.
Thompson, "Grappling with the Androgen Receptor: A New Approach for Treating Advanced Prostate Cancer", Cancer Cell, Jun. 15, 2010, 525-526.
Tombal, "Non-metastatic CRPC and asymptomatic metastatic CRPC: which treatment for which patient?", Annals of Oncology, 2012, 23(Suppl. 10), x251-x258.
Tran et al., "Development of a Second-Generation Antiandrogen for Treatment of Advanced Prostate Cancer", Science, May 2009, 324, 787-790.
Tremblay et al., "Ligand-Independent Recruitment of SRC-1 to Estrogen Receptor Beta through Phosphorylation of Activation Function AF-1", Mol Cell, 1999, 3, 513-519.
Tschumper et al., "Sequence of a Yeast DNA Fragment Containing a Chromosomal Replicator and the TRP1 Gene", Gene, 1980, 10, 157-166.
Tucker et al., "Nonsteroidal Antiandrogens. Synthesis and Structure-Activity Relationships of 3-Substituted Derivatives of 2-Hydroxypropionanilides", J. Med. Chem., 1988, 31, 954-959.
Ulmed et al., "Imaging Androgen Receptor Signaling with a Radiotracer Targeting Free Prostate-Specific Antigen", Cancer Discovery, 2012, 2, 320-327.
Urlaub et al., "Isolation of Chinese Hamster Cell Mutants Deficient in Dihydrofolate Reductase Activity", Proc. Natl. Acad. Sci. USA, 1980, 77(7), 4216-4220.
U.S. Appl. Jan. 9, 2014, Chen et al., U.S. Appl. No. 14/151,106.

(56) References Cited

OTHER PUBLICATIONS

Vadlamudi et al., "Functional and biological properties of the nuclear receptor coregulatory PELP1/MNAR", Nuclear Receptor Signaling, May 2007, 5, e004.
Vallee et al., "Tricyclic Series of Heat Shock Protein 90 (Hsp90) Inhibitors Part 1: Discovery of Tricyclic Imidazo[4,5-c]pyridines as Potent Inhibitors of the Hsp90 Molecular Chaperone", J. Med. Chem., 2011, 54, 7206-7219.
van de Horst et al., "Metastatic properties and genomic amplification of the tyrosine kinase gene ACK1", PNAS, 2005, 102, 15901-15906.
van de Wjngaart et al., "Androgen receptor coregulators: Recruitment via the coactivator binding groove", Molecular and Cellular Endocrinology, 2012, 352, 57-69.
van de Wjngaart et al., "Functional Screening of FxxLF-Like Peptide Motifs Identifies SMARCD1?BAF60a as an Androgen Receptor Cofactor that Modulates TMPRSS2 Expression", Molecular Endocrinology, Nov. 2009, 23(11), 1776-1786.
van der Lee et al., "Classification of Intrinsically Disordered Regions and Proteins", Chemical Reviews, 2014, 114, 6589-6631.
Van Dort et al., "Design, Synthesis, and Pharmacological Characterization of 4-[4,4-Dimethyl-3-(4-hydroxybutyl_-5-oxo-2-thioxo-1-imidazolidinyl]-2-iodobenzonitrile as a High-Affinity Nonsteroidal Androgen Receptor Ligand", J. Med. Chem., 2000, 43, 3344-3347.
van Royen et al., "Compartmentalization of androgen receptor protein-protein interactions in living cells", The Journal of Cell Biology, 2007, 177, 63-72.
van Royen et al., "Stepwise androgen receptor dimerization", Journal of Cell Science, 125, 1970-1979.
Vasaitis et al., "Androgen receptor inactivation contributes to antitumor efficacy of 17.alpha.-hydroxylase/17,20-lyase inhibitor 3.beta.-hydroxy-17-(1H-benzimidazole-1-yl)androsta-5, 16-diene in prostate cancer", Molecular Cancer Therapeutics, 2008, 7, 2348-2357.
Vasaitis et al., "Novel, potent anti-androgens of therapeutic potential: recent advances and promising developments", Future Med. Chem., 2010, 2(4), 667-680.
Veldscholte et al., "A Mutation in the Ligand Binding Domain of the Androgen Receptor of Human LNCaP Cells Affects Steroid Binding Characteristics and Response to Antiandrogens", Biochem Biophys Res Commun, 1990, 173, 534-540.
Visakorpi et al., "In Vivo Amplification of the Androgen Receptor Gene and Progression of Human Prostate Cancer", Nat Genetics, 1995, 9, 401-406.
Voet et al., "The Discovery of Novel Human Androgen Receptor Antagonist Chemotypes Using a Combined Pharmacophore Screening Procedure", Chem Med Chem, 2013, 8, 644-651.
Voisin-Chiret et al., "Aromatic garlands, as new foldamers, to mimic protein secondary structure", Tetrahedron, 2012, 68, 4381-4389.
Poutiainen et al., "Preclinical pharmacology of FL442, a novel nonsteroidal androgen receptor modulator", Molecular and Cellular Endocrinology, 2014, 387, 8-18.
Poutianen et al., "Design, Synthesis, and Biological Evaluation of Nonsteroidal Cycloalkane[d]isoxazole-Containing Androgen Receptor Modulators", J. Med. Chem., 2012, 55, 6316-6327.
Prensner et al., "Beyond PSA: The Next Generation of Prostate Cancer Biomarkers", Science Translation Medicine, Mar. 2012, 4, 127, 127rv3.
Prostate-Specific Antigen (PSA) Test, National Cancer Institute, 2012, 6 pages.
Provins et al., "Lead Optimization of Thiazolo[5,4-c]piperidines: 3-Cyclobutoxy Linker as a Key Spacer for H.sub.3R Inverse Agonists", Chem Med Chem, 2012, 7, 2087-2092.
Quayle et al., "Androgen receptor decoy molecules block the growth of prostate cancer", PNAS, 2007, 104, 1331-1336.
Raffo et al., "Overexpression of bcl-2 Protects Prostate Cancer Cells from Apoptosis in Vitro and Confers Resistance to Androgen Depletion in Vivo", Cancer Research, 1995, 55, 4438-4445.

Rathkopf et al., "A first-in-human, open-label, phase 1/11 safety, pharmacokinetic, and proof-of-concept study of ARN 509 in patients with progressive advanced castration-resistant prostate cancer (CRPC)", Journal of Clinical Oncology; ASCO Annual Meeting 2011, American Society of Clinical Oncology, US; Chicago IL, US, May 20, 2011, vol. 29, No. 15, Suppl. 1, p. TPS190.
Rathkopf et al., "A Phase I Study of the Androgen Signaling Inhibitor ARN-509 in Patients with Metastatic Castration-Resistant Prostate Cancer (mCRPC)", J. Clin. Oncol., 2012, 2 pages.
Rathkopf et al., "Androgen receptor mutations in patients with castration-resistant prostate cancer treated with apalutamide", Annals of Oncology, Sep. 2017, 28(9), 2264-2271.
Rathkopfet al., "Phase I study of ARN-509, a novel antiandrogen, in the treatment of castration-resistant prostate jancer", J. Clin. One., Oct. 1, 2013, 31 (28), pp. 3525-3530.
Reagan-Shaw et al., "Dose translation from animal to human studies revisited", FASEB Journal Fed. of American Soc or Experimental Biology, US, Jan. 1, 2007, 22, pp. 659-661.
Reid et al., "Conformational Analysis of the Androgen Receptor Amino-terminal Domain Involved in Transactivation", The Journal of Biological Chemistry, May 2002, 277, 22, 20079-20086.
Reid et al., "The androgen receptor transactivation domain: the interplay between protein conformation and protein-protein interactions", Biochemical Society Transactions, 2003, 1042-1046.
Remington: Practice of the Science and Pharmacy, 19th Edition, Table of Contents, Gennaro (ed.), 1995, Mack Publishing Company, Easton, PA, 5 pages.
Richards et al., "Interactions of abiraterone, eplerenone and prednisolone with wild-type and mutant androgen receptor: a rationale for increasing abiraterone exposure or combining with MDV3100", Cancer Research, Mar. 2012, 72(9), 2176-82.
Robins et al., "Androgen receptor gene polymorphisms and alterations in prostate cancer: of humanized mice and men", Molecular and Cellular Endocrinology, 2012, 352, 26-33.
Rooseboom et al., "Enzyme-Catalyzed Activation of Anticancer Prodrugs", Pharmacological Reviews, 2004, 56, 53-102.
Russell et al., "Establishing Prostate Cancer Patient Derived Xenografts: Lessons Learned From Older Studies", The Prostate, 2015, 75, 628-636.
Ryu et al., "Discovery of non-LBD inhibitor for androgen receptor by structure-guide design", Bioorganic & Medicinal Chemistry, 2013, 23, 3887-3990.
Sack et al., "Crystallographic Structures of the Ligand-Binding Domains of the Androgen Receptor and its T877A Mutant Complexed with the Natural Agonist Dihydrotestosterone", Proc Natl Acad Sci, 2001, 98(9), 4904-4909.
Sadar et al., "Advances in small molecule inhibitors of androgen receptor for the treatment of advanced prostate cancer", World J. Urol., Aug. 2011, 30(3), 311-8.
Sadar et al., "Sintokamides A to E, Chlorinated Peptides from the *Dysidea* sp. That Inhibit Transactivation of the N-Terminus of the Androgen Receptor in Prostate Cancer Cells", Organic Letters, 2008, 10, 21, 4947-4950.
Sadar, "Small Molecule Inhibitors Targeting the "Achilles' Heel" of Androegn Receptor Activity", Cancer Research, 2011, 71, 1208-1213.
Saito et al., "Antarlides: A New Type of Androgen Receptor (AR) Antagonist that Overcomes Resistance to AR-Targeted Therapy", Angewandte Chemie International Edition, 2016, 55, 1-6.
Saito et al., "Studies on Tertiary Amine Oxides. LXIII. Nitration of 1-Cyanoisoquinoline 2-Oxide and Isoquinoline 2-Oxide", Journal of Pharmaceutical Society of Japan, 1979, 99, 23-29.
Sambrook et al., "Molecular Cloning: A Laboratory Manual", 2nd Edition, Table of Contents, Cold Spring Harbor Laboratory Press, Cold Spring Harbor, 1989, 30 pages.
Saunders et al., "Point Mutations Detected in the Androgen Receptor Gene of Three Men with Partial Androgen Insensitivity Syndrome", Clin. Endocrinol., 1992, 37, 214-220.
Schafmeister et al., "An All-Hydrocarbon Cross-Linking System for Enhancing the Helicity and Metabolic Stability of Peptides", J. Am. Chem. Soc., 2000, 122, 5891-5892.

(56) References Cited

OTHER PUBLICATIONS

Schellhammer et al., "Prostate Specific Antigen Decreases after Withdrawal of Antiandrogen Therapy with Bicalutamide or Flutamide in Patients Receiving Combined Androgen Blockade", J Urol, 1997, 157, 1731-1735.
Scher et al., "The Flutamide Withdrawal Syndrome: Its Impact on Clinical Trials in Hormone-Refractory Prostatic Cancer", J Clin Oncol 1993, 11, 1566-1572.
Schiewer et al., "The AR dependent cell cycle: Mechanisms and cancer relevance", Molecular and Cellular Endocrinology, 2012, 352, 34-45.
Schleutker et al., "Polymorphisms in androgen signaling pathway predisposing to prostate cancer", Molecular and Cellular Endocrinology, 2012, 360, 25-37.
Schlienger et al., "Synthesis, Structure—Activity Relationships, and Characterization of Novel Nonsteroidal and Selective Androgen Receptor Modulators", J. Med. Chem., 2009, 52, 7186-7191.
Schoch et al., "Molecular Switch in the Glucocorticoid Receptor: Active and Passive Antagonist Conformations", Journal of Molecular Biology, 2010, 395, 568-577.
Sderholm et al., "Three-Dimensional Structure-Activity Relationships of Nonsteroidal Ligands in Complex with Androgen Receptor Ligand-Binding Domain," J. Med. Chem., 2005, 48(4), 917-925.
Seebach et al., ".beta.-Peptidic Peptidomimetics", Accounts of Chemical Research, Oct. 2008, vol. 41, No. 10, 1366-1375.
Shafi et al., "Androgen receptor splice variants are resistant to inhibitors of Hsp90 nad FKBP52, which alter androgen receptor activity and expression", Steroids, 2013, 78, 548-554.
Shafi et al., "Differential Responsiveness of Androgen Receptor Splice Variants to Regulators of Androgen Receptor Action", ENDO, Baylor College of Medicine, Poster No. SUN-530, 2012, 1 page.
Shaginan et al., "Design, Synthesis, and Evaluation of an .alpha.-Helix Mimetic Library Targeting Protein-Protein Interactions", J. Am. Chem. Soc., 2009, 131, 5564-5572.
Shang et al., "Molecular Determinants for the Tissue Specificity of SERMs", Science, 2002, 295, 2465-2468.
Shang, Y., Myers, M. & Brown, M. "Formation of the androgen receptor transcription complex", Mol. Cell., 2002, 9, 601-610.
Shapiro et al., "Small Molecule Inhibitors as Probes for Estrogen and Androgen Receptor Action", Journal of Biological Chemistry, Feb. 2011, 286, 4043-4048.
Sharma et al., "Mouse models of prostate cancer", Oncogene, 1999, 18, 5349-5355.
Shen et al., "In Silico Discovery of Androgen Receptor Antagonists with Activity in Castration Resistant Prostate Cancer", Molecular Endocrinology, Jun. 2012, 26(11), 1836-1846.
Shi et al., "Functional Analysis of 44 Mutant Androgen Receptors from Human Prostate Cancer", Can Res, 2002, 62(5), 1496-1502.
Shiau et al., "The Structural Basis of Estrogen Receptor/Coactivator Recognition and the Antagonism of this Interaction by Tamoxifen", Cell, 1998, 95, 927-937.
Shiota et al., "Androgen Receptor Cofactors in Prostate Cancer: Potential Therapeutic Targets of Castration-Resistant Prostate Cancer", Current Cancer Drug Targets, 2011, 11, 870-881.
Shore et al., "ODM-201 and the central nervous system—A clinical perspective", Orion Pharma, 2014 Genitourinary Cancers Symposium, Jan. 30-Feb. 1, 2014, 1 page.
Simone, "Oncology: Introduction", Cecil Textbook of Medicine, 20th Edition, vol. 1, 1996, 1004-1010.
Hormonal Treatments for Uterine Fibroids, Hormone Therapy for Fibroids, http://www.uterine-fibroids.org/HormonalTreatments.html, 2010, 2 pages.
Horoszewicz et al., "LNCaP Model of Human Prostatic Carcinoma", Cancer Res., 1983, 43, 1809-1818.
Hsing et al., "Polymorphic CAG and GGN Repeat Lengths in the Androgen Receptor Gene and Prostate Cancer Risk: A Population-based Case-Control Study in China", Cancer Research, 2000, 60, 5111-5116.
Huang et al., "AR Possess an Intrinsic Hormone-Independent Transcriptional Activity", Mol Endocrinol., 2002, 16(5), 924-937.
Huang et al., The enhancement of nuclear receptor transcriptional activation by a mouse actin-binding protein, alpha actinin 2, Journal of Molecular Endocrinology, 2004, 32, 481-496.
Hur et al., "Recognition and Accommodation at the Androgen Receptor Coactivator Binding Interface", PLoS Biology, 2004, 2, 1303-1312.
Hynes et al., "Prostate cancer stem cells: The case for model systems", Journal of Carcionogenesis, 2012, 24-30.
Itkonen et al., "Chromatin binding by the androgen receptor in prostate cancer", Molecular and Cellular Endocrinology, 2012, 360, 44-51.
Ivachtchenko et al., "Design, synthesis and biological evaluation of novel 5-oxo-2-thioxoimidazolidine derivatives as potent androgen receptor antagonists", European Journal of Medicinal Chemistry, 2015, 99, 51-66.
Ivachtenko et al., "Preclinical Development of ONCI-13B, Novel Antiandrogen for Prostate Cancer Treatment", Journal of Cancer, 2014, vol. 5, 133-142.
Jaaskelainen et al., "Molecular biology of androgen insensitivity", Mol. Cell Endocrinol., Aug. 2011, 352, 4-12.
Jackson et al., "General Approach to the Synthesis of Short .alpha.-Helical Peptides", J. Am. Chem. Soc., 1991, 113, 9391-9392.
Jagla et al., "A Splicing Variant of the Androgen Receptor Detected in a Metastatic Prostate Cancer Exhibits Exclusively Cytoplasmic Actions", Endocrinology, Sep. 2007, 148(9), 4334-4343.
James et al., "A Two-step Synthesis of the Anti-cancer Drug (R,S)-Bicalutamide", Synthesis, 2002, 7, 850-852.
Jamieson et al., "Medicinal Chemistry of hERG Optimizations: Highlights and Hang-Ups", J. Med. Chem., Aug. 2006, 49, 5030-5046.
Jehle et al., "Gene Regulation: Coregulator Control of Androgen Receptor Action by a Novel Nuclear Receptor-binding Motif", The Journal of Biological Chemistry, 2014, 289, 8839-8851.
Jin et al., "Total Synthesis of Sintokamide C", Organic Letters, 2010, 12, 5, 1100-1103.
Johnson et al., "Broad Distribution of Energetically Important Contacts across an Extended Protein Interface", Journal of the American Chemical Society, 2011, 133, 10038-10041.
Johnson et al., "Enhancement of .alpha.-Helix Mimicry by an .alpha./.beta.-Peptide Foldamer via Incorporation of a Dense Ionic Side-Chain Array", J. Am. Chem. Soc., Apr. 2012, 134(17), 7317-20.
Johnson et al., "Relationships between drug activity in NCI preclinical in vitro and in vivo models and early clinical trials", British Journal of Cancer, 2001, 84(10), 1424-1431.
Jones, "Proteinase Mutants of *Saccharomyces cerevisae*", Genetics, 1977, 85, 23-33.
Joseph et al., "A Clinically Relevant Androgen Receptor Mutation Confers Resistance to Second-Generation Antiandrogens Enzalutamide and ARN-509", Cancer Discovery, Jun. 2013, 3(9):1020-9.
Joseph et al., "Inhibition of prostate cancer cell growth by second-site androgen receptor antagonists", PNAS, 2009, 106, 12178-12183.
Jung et al., "Structure-Activity Relationship for Thiohydantoin Androgen Receptor Antagonists for Castration-Resistant Prostate Cancer (CRPC)", J. Med. Chem., 2010, 53, 2779-2796.
Kagabu, "Methyl, Trifluoromethyl, and Methoxycarbonyl-Introduction to the Fifth Position on the Pyridine Ring of Chloronicotinyl Insecticide Imidacloprid", Synth. Comm., 2006, 36(9), 1235-1245.
Kaku et al., "17,20-Lyase inhibitors. Part 3: Design, synthesis, and structure-activity relationships of biphenylymethylimidazole derivatives as novel 17,20-lyase inhibitors", Bioorganic & Medicinal Chemistry, 2011, 19, 2428-2442.
Kaku et al., "Discovery of orteronel (TAK-700), a naphthylmethtlimidazole derivative, as a highly selective 17,20-lyase inhibitor with potential utility in the treatment of prostate cancer", Bioorganic & Medicinal Chemistry, 2011, 19, 6383-6399.
Karageorgis et al., "Efficient discovery of bioactive scaffolds by activity-directed synthesis", Nature Chemistry, Aug. 2014, 6(1), 872-6.
Karp et al., "Prostate Cancer Prevention: Investigational Approaches and Opportunities", Cancer Res., v. 56 (Dec. 15, 1996) pp. 5547-5556.

(56) References Cited

OTHER PUBLICATIONS

Karvonen et al., "Interaction of Androgen Receptors with Androgen Response Element in Intact Cells", The Journal of Biological Chemistry, 1997, 272(25), 15973-15979.
Kato et al., "Activation of the Estrogen Receptor through Phosphorylation by Mitogenactivated Protein Kinase", Science, 1995, 270, 1491-1494.
Kauppi et al., "Protein Structure and Folding: The Three-dimensional Structures of Antagonistic and Agonistic Forms of the Glucocorticoid Receptor Ligand-binding Domain: RU-486 Induces a Transconformation That Leads to Active Antagonism", The Journal of Biological Chemistry, 2003, 278, 22748-22754.
Kawai et al., "Site-Specific Fluorescent Labeling of Rna Molecules by Specific Transcription Using Unnatural Base Pairs", J. Am Chem. Soc., 2005, 127(49), 17286-17295.
Kemppainen et al., "Distinguishing Androgen Receptor Agonists and Antagonistis: Distinct Mechanisms of Activation by Medroxyprogesterone Acetate and Dihydrotestosterone", Molecular Endocrinology, 1999, 440-454.
Keown et al., "Methods for Introducing DNA Into Mammalian Cells", Methods in Enzymology, 1990, 185, 527-537.
Khayum et al., "In vivo imaging of brain androgen receptors in rats: a [.sup.18F]FDHT PET study", Nuclear medicine and Biology, Feb. 2015, 42(6), 561-9.
Kim et al., "Determination of the Androgenicity of Ligands Using a Single-chain Probe Carrying Androgen Receptor N-Terminal Peptides", Analytical Sciences, Dec. 2009, 25, 1415-1420.
Kim et al., "Methoxychalcone Inhibitors of Androgen Receptor Translocation and Function", Bioorganic & Medicinal Chemistry Letters, Mar. 2012, 22(5):2105-9.
Kingsman et al., "Replication in *Saccharomyces cerevisiae* of Plasmid pBR313 Carrying DNA from the Yeast trpl Region", Gene, 1979, 7, 141-152.
Kinoshita et al., "Methylation of the Androgen Receptor Minimal Promoter Silences Transcription in Human Prostate Cancer", Cancer Res, 2000, 60, 3623-3630.
Kinoyama et al., "(+)-(2R,5S)-4-[4-Cyano-3-(trifluoromethyl)phenyl]-2,2-dimethyl-N-[6-(tri-fluoromethyl)pyridine-3-yl]piperazine-1-carboxamide (YM580) as an Orally Potent Peripherally Selective Nonsteroidal Androgen Receptor Antagonist", J. Med. Chem., 2006, 49, 716-726.
Klein et al., "Progression of Metastatic Human Prostate Cancer to Androgen Independence in Immunodeficient SCID Mice", Nat Med, 1997, 3(4), 402-408.
Kliment Jan: "Re: Salvage Therapy With Bicalutamide 150 mg in Nonmetastatic Castration-resistant Prostate Cancer", European Urology, vol. 59, No. 6, Jun. 2011 (Jun. 2011), pp. 1066-1067.
Korpal et al., "An F876L Mutation in Androgen Receptor Confers Genetic and Phenotypic Resistance to MDV3100 (Enzalutamide)", Cancer Discovery, 2013, 3, 1030-1043.
Kousteni et al., "Nongenotropic, Sex-Nonspecific Signaling through the Estrogen or Androgen Receptors: Dissociation from Transcriptional Activity", Cell, 2001, 104, 719-730.
Kraus et al., "Receptor for Activated C Kinase 1 (RACK1) and Src Regulate the Tyrosine Phosphorylation and Function of the Androgen Receptor", Cancer Research, 2006, 66, 11047-11054.
Kritzer et al., ".beta.-Peptides as inhibitors of protein-protein interactions", Bioorganic & Medicinal Chemistry, 2005, 13, 11-16.
Kuethe et al., "Synthesis of Disubstituted Imidazo[4,5-b]pyridin-2-ones", J. Org. Chem., 2004, 29, 69(22), 7752-7754.
Kumar et al., "Allosteric Modulators of Steroid Hormone Receptors: Structural Dynamics and Gene Regulation", Endocrine Reviews, Apr. 2012, 33(2), 271-299.
Kumar et al., "Exome sequencing identifies a spectrum of mutation frequencies in advanced and lethal prostate cancers", PNAS, Sep. 2011, 108(41), 17087-92.
McConnell et al., "Heat shock proteins 27, 40, and 70 as combinational and dual therapeutic cancer targets", Bioorganic & Medicinal Chemistry Letters, 2013, 23, 1923-1928.

McDonnell et al., "Expression of the Protooncogene bcl-2 in the Prostate and its Association with Emergence of Androgen-Independent Prostate Cancer", Cancer Res, 1992, 52, 6940-6944.
McEwan et al., "Intrinsic disorder in the androgen receptor: identification, characterization and drugability", Molecular BioSystems, 2012, 8, 82-90.
McEwan, "Androgen receptor modulators: a marriage of chemistry and biology", Future med. Chem., 2013, 5(10), 1109-1120.
Meimetis et al., "Niphatenones, Glycerol Ethers from the Sponge Niphates digitalis Block Androgen receptor Transcriptional Activity in Prostate Cancer Cells: Structure Elucidation, Synthesis, and Biological Activity", Journal of Medicinal Chemistry, 2012, 55, 503-514.
Metallo et al., "Intrinsically disordered proteins are potential drug targets", Current Opinion in Chemical Biology, 2010, 14, 481-488.
Metzger et al., "A novel inducible transactivation domain in the androgen receptor: implications for PRK in prostate cancer", The EMBO Journal, 2003, 22, 270-280.
Migliaccio et al., "Steroid-Induced Androgen Receptor-Oestradiol Receptor beta-SRC Complex Triggers Prostate Cancer Cell Proliferation", Embo J, 2000, 19(20), 5406-5417.
Mijambili et al., "Synthesis and biological evaluation of 2-aminothiazole derivatives as antimycobacterial and antiplasmodial agents", Bioorganic & Medicinal Chemistry, 20114 24, 560-564.
Miller et al., "Crystal structure of a human GABA.sub.A receptor", Nature, Jun. 2014, 512(7514), 270-5.
Mitchell et al., "Rational Design of a Topical Androgen Receptor Antagonist for the Suppression of Sebum Production with Properties Suitable for Follicular Delivery", J. Med. Chem., 2010, 53, 4422-4427.
Mitsiades, "A Road Map to Comprehensive Androgen Receptor Axis Targeting for Castration-Resistant Prostate Cancer", Cancer Research, Jul. 2013, 8 73(15), 4599-4605.
Mochly-Rosen et al., "Peptide inhibitors of protein-protein interactions From rational design to the clinic", Chemistry Today, Jan./Feb. 2010, 28, 1, 14-16.
Mocklinghoff, "Modulating the Nuclear Receptor-Cofactor Interaction", Thesis, Eindhoven University, 2010, 208 pages.
Mohler et al., "2008 Medicinal Chemistry Division Award Address", Jun. 2009, 52, 3957-3617.
Moilanen et al., "Discovery of ODM-201, a new generation androgen receptor inhibitor targeting resistance mechanisms to androgen signaling-directed prostate cancer therapies", with Supplementary Information, Scientific Reports, Jul. 3, 2015 5:12007.
Moilanen et al., "ODM-201—New generation antiandrogen with excellent antiandrogenic and antitumor activity in nonclinical models of CRPC", European Cancer Congress, Sep. 27-Oct. 1, 2013, 1 page.
Mooslehner et al., "A Cell Model for Conditional Profiling of Androgen-Receptor-Interacting Proteins", International Journal of Endocrinology, Feb. 2012, 15 pages.
Mulero et al., "Androgen Receptor Splice Variants Determine Taxane Sensitivity in Prostate Cancer", Cancer Research, Feb. 2014, 74(8)2270-2282.
Mulholland et al., "Cell Autonomous Role of PTEN in Regulating Castration-Resistant Prostate Cancer Growth", Cancer Cell., 2011, 19, 792-804.
Muller et al., "BCR First Exon Sequences Specifically Activate the BCRIABL Tyrosine Kinase Oncogene of Philadelphia Chromosome Positive Human Leukemias", Mol. & Cell, Biol., 1991,11(4), 1785-1792.
Murphy et al., "Solid-Phase Methodology for Synthesis of O-Alkylated Aromatic Oligoamide Inhibitors of .alpha.-Helix-Mediated Protein-Protein Interactions", Chemistry A European Journal, 2013, 19, 5546-5550.
Myung et al., "An androgen receptor N-terminal domain antagonist for treating prostate cancer", The Journal of Clinical Investigation, Jun. 2013, 123(7), 2948-60.
Nagase et al., "Synthesis and Evaluation of Structurally Constrained Quinazolinone Derivatives as Potent and Selective Histamine H.sub.3 Receptor Inverse Agonists", J. med. Chem., 2008, 51, 6889-6901.

(56) References Cited

OTHER PUBLICATIONS

Naik et al., "Synthesis, Spectroscopic and Thermal Studies of Bivalent Transition Metal Complexes with the Hydrazone Derived from 2 Benzimidazolyl Mercaptoaceto Hydrazile and o-Hydroxy Aromatic Aldehyde", Indian Journal of Chemistry, 2008, 1793-1797.

Nair et al., "PELP1 is a reader of histone H3 methylation that facilitates oestrogen receptor-.alpha. target gene activation by regulating lysine demethylase 1 specificity", EMBO Reports, 2010, 11, 438-444.

Nair et al., "Proline-, Glutamic Acid-, and Leucine-Rich Protein-1/Modulator of Nongenomic Activity of Estrogen Receptor Enhances Androgen Receptor Functions through LIM-Only Coactivator, Four-and-a-Half LIM-Only Protein 2", Molecular Endocrinology, Mar. 2007, 21(3), 613-624.

Nam et al., "Action of the Src Family Kinase Inhibitor, Dasatinib (BMS-354825), on Human Prostate Cancer Cells", Cancer Res., 2005, 65(20), 9185-9189.

Navone et al., "Model Systems of Prostate Cancer: Uses and Limitations", Cancer Metastasis, 1999, 17, 361-371.

NCBI, "Definition: Homo sapiens Androgen", Nucleotide, 2007, 7 pages NM.sub.-000044<http://www.ncbi.nlm.nih.gov:80/entrez/viewer.fcgi?cmd=- Retrieve&db=nucleotide&list.sub.- uids= 21322251 &dopt=Gen Ban k&term=sapiens+AR+androgen+receptor+ prostate+cancer&qty= 1>gi:21322251.

Nelson, "Targeting the Androgen Receptor in prostate Cancer—A Resilient Foe", The New England Journal of Medicine, Sep. 2014, 371(11, 1067-9.

Nique et al., "Discovery of Diarylhydantoins as New Selective Androgen Receptor Modulators", J. Med. Chem., 2012, 55, 8225-8235.

Niraula et al., "Beyond Castration—Defining Future Directions in the Hormonal Treatment of Prostate Cancer", Horm. Canc., Apr. 2011, 3(1-2), 3-13.

Nirschl et al., "N-Aryl-oxazolidin-2-imine Muscle Selective Androgen Receptor Modulators Enhance Potency through Pharmacophore Reorientation", J. Med. Chem., 2009, 52, 2794-2798.

Nishiyama, "Prostate cancer and androgens: New strategies of androgen deprivation therapy", Current Topics in Steroid Research, 2010, 7, 35-45.

Norris et al. "Peptide Antagonists of the Human Estrogen Receptor", Science, 1999, 285, 744-746.

Norris et al., "Differential Presentation of Protein Interaction Surfaces on the Androgen Receptor Defines the Pharmacological Actions of Bound Ligands", Chemistry & Biology, 2009, 452-460.

Oldridge et al., Prostate cancer stem cells: Are the androgen-responsive, Molecular and Cellular Endocrinology, 2012, 360, 14-24.

Osguthorpe et al., "Mechanism of Androgen Receptor Antagonism by Bicalutamide in the Treatment of Prostate Cancer", Biochemistry, 2011, 50, 4105-4113.

Ouaissi et al., "Rationale for Possible Targeting of Histone Deacetylase Signaling in Cancer Diseases with a Special Reference to Pancreatic Cancer", Journal of Biomedicine and Biotechnology, 2011, 8 pages.

Ouk et al., "Development of Androgen Receptor Inhibitors for Hormone-Refractory Prostate Cancer", Prostate Cancer Foundation Meeting, Scottsdale, AZ, Sep. 29-Oct. 1, 2005, 1 page.

Palvimo, "The androgen receptor", Molecular and Cellular Endocrinology, 2012, 352, 1-3.

Papadopoulou et al., "Membrane Androgen Receptor Activation in Prostate and Breast Tumor Cells: Molecular Signaling and Clinical Impact", Life, Jan. 2009, 61(1), 56-61.

Parent et al., "Synthesis and Biological Evaluation of [.sup.18F]Bicalutamide, 4-[.sup.Br]Bromobicalutamide, and 4--[.sup.76Br]Bromo-thiobicalutamide as Non-Steroidal Androgens for Prostate Cancer Imaging", J. Med. Chem., 2007, 50, 1028-1040.

Park et al., "A new type of amide formation from thiocarboxylic acid and alkyl azide", Tetrahedron letters, 2002, 43, 6309-6311.

Park et al., "Diastereoselective Synthesis of Hydantoin- and Isoxazoline-Substituted Dispirocyclobutanoids", J. Org. Chem., 2000, 65, 3520-3524.

Pepe et al., "Synthesis and structure-activity relationship studies of novel dihydropyridones as androgen receptor modulators", Journal of Medicinal Chemistry, Oct. 2013, 56(21), 8280-97.

Perou et al., "Molecular Portraits of Human Breast Tumors", Nature, 2000, 406, 747-752.

Petre-Draviam et al., "A central domain of cyclin D1 mediates nuclear receptor corepressor activity", Oncogene, 2005, 24, 431-444.

Phelan et al., "A General Method for Constraining Short Peptides to an .alpha.-Helical Conformation", J. Am. Chem. Soc., 1997, 119, 455-460.

Chang et al., "Molecular Cloning of Human and Rat Complementary DNA Encoding Androgen Receptors", Science, 1988, 240, 324-326.

Changxue et al., "Distinct Transcriptional Programs Mediated by the Ligand-Dependent Full-Length Androgen Receptor and Its Splice Variants in Castration-Resistant Prostate Cancer", Cancer Research, 2012, 3457-3462.

Chen et al., "Agonist and antagonist switch DNA motifs recognized by human androgen receptor in prostate cancer", The EMBO Journal, Dec. 22, 2014, 34(4), 502-15.

Chen et al., "Crystal structures of AKR1C3 containing an N-(aryl)aminobenzoate inhibitor and a bifunctional AKR1C3 inhibitor and androgen receptor antagonist. Therapeutic leads for castrate resistant prostate cancer", Bioorganic & Medicinal Chemistry Letters, Mar. 2012, 22(1), 3492-7.

Chen et al., "Hitting old targets better and identifying new targets", Nature, Feb. 2012, 9, 70-72.

Chen et al., "Molecular determinants of resistance to antiandrogen therapy", Nat. Med., Jan. 2004;10(1):33-9. Epub Jec. 21, 2003.

Chen et al., "Trip Report for" 235.sup.th ACS National Meeting, AMRI, Technical Reports, Apr. 6-10, 2008, 29 pages.

Chen et al., Molecular determinants of resistance to antiandrogen therapy. Nat Med. Jan. 2004;10(1):33-9. Epub Dec. 21, 2003.

Cheng et al., "A Solution-Phase Strategy for the Synthesis of Chemical Libraries Containing Small Organic Molecules: A Universal and Dipeptide Mimetic Template", Bioorganic & Medicinal Chemistry, 1996, 4, 727-737.

Chenoweth et al., "Cyclic-Pyrrole-Imidazole Polyamides Targeted to the Androgen Response Element", J. am. Chem. Soc., 2009, 131, 7182-7188.

Chobanian et al., A facile microwave-assisted palladium-catalyzed cyanation of aryl chlorides. Tetrahed Lett. May 8, 2006;47(19):3303-5.

Cinar et al. Androgen Receptor Mediates the Reduced Tumor Growth, Enhanced Androgen Responsiveness, and Selected Target Gene Transactivation in Human Prostate Cancer Cell Line. Cancer Research. 2001 v. 61. pp. 7310-7317.

Claessens et al., "Diverse roles of androgen receptor (AR) domains in AR-mediated signaling", Nuclear Receptor Signaling, Jun. 2008, 6, e008.

Clark, Glucocorticoid Receptor Antagonists, Current Topics in Medicinal Chemistry, 2008, 8, 813-838.

Clegg et al., "ARN-509: a novel anti-androgen for prostate cancer treatment", Cancer Research, Jan. 2012, 72(6), 1494-503.

Clinckemalie et al., "The hinge region in androgen receptor control", Molecular and Cellular Endocrinology, Mar. 2012, 358(1), 1-8.

Cook et al., "Development of GnRH Antagonists for Prostate Cancer: New Approaches to Treatment", The Oncologist, 2000, 5, 162-168.

Cousty-Berlin, et al., "Preliminary Pharmacokinetics and Metabolism of Novel Non-steroidal Antiandrogens in the Rat: Relation of their Systemic Activity to the Formation of a Common Metabolite", J. Steroid Biochem. Molecular Bio., 1994, 51(1/2), 47-55.

Craft et al., "A Mechanism for Hormone-Independent Prostate Cancer Through Modulation of Androgen Receptor Signaling by the HER-2/Neu Tyrosine Kinase", Nature Medicine, 1999, 5(3), 280-285.

(56) References Cited

OTHER PUBLICATIONS

Craft et al., "Evidence for Clonal Outgrowth of Androgen-Independent Prostate Cancer Cells from Androgen-Dependent Tumors Through a Two-Step Process", Cancer Res, 1999, 59,5030-5036.
Creaven et al., "Pharmacokinetics and Metabolism of Nilutamide", Supp. Urology, 1991, 37(2), 13-19.
Culig et al., "Interleukin-6: A multifunctional targetable cytokine in human prostate cancer", Molecular and Cellular Endocrinology, 2012, 360, 52-58.
Dar et al., "The N-terminal domain of the androgen receptor drives its nuclear localization in castration-resistant prostate cancer cells", Journal of Steroid Biochemistry & Molecular Biology, Mar. 2014, 143, 473-80.
Dasgupta et al., "Oncogenic activation in prostate cancer progression and metastasis: Molecular insights and future challenges", Journal of Carcinogenesis, 2012, 39-49.
Day et al., "Development of hormone-dependent prostate cancer models for the evaluation of inhibitors of 17.beta.-hydroxysteroid dehydrogenase Type 3", Molecular and Cellular Endocrinology, 2009, 301, 251-258.
Dehm et al., "Selective Role of an NH.sub.2-Terminal WxxLF Motif for Aberrant Androgen Receptor Activation in Androgen Depletion—Independent Prostate Cancer Cells", Cancer Research, 2007, 67, 10067-10077.
Dellis et al., "Phase I and II therapies targeting the androgen receptor for the treatment of castration resistant prostate cancer", Expert Opinion on Investigational Drugs, 2016, 25, 6, 697-707.
Depalo et al., "GnRH agonist versus GnRH antagonist in in vitro fertilization and embryo transfer (IVF/ET)", Reproductive Biology and Endocrinology, 2012, 10, 26-33.
DePrimo et al. "Transcriptional Programs Activated by Exposure of Human Prostate Cancer Cells to Androgen", Genome Biology, 2002, 3(7), 1-12.
DeVore et al., "Structures of cytochrome P450 17A1 with prostate cancer drugs abiraterone and TOK-001", Nature, Feb. 2012, 482, 116-119.
Dhal et al., "Synthesis of Thiohydantoins, Thiazolidones and their Derivatives from N1-(4'-aryl thiazole 2'-YL) Thioureas", J. Indian Chem. Soc., 1973, 50(1), 680-684.
Didelot et al., "Anti-Cancer Therapeutic Approaches Based on Intracellular and Extracellular Heat Shock Proteins", Current Medicinal Chemistry, 2007, vol. 14, No. 27, 2839-2847.
Dubbink et al., "Distinct Recognition Modes of FXXLF and LXXLL Motifs by the Androgen Receptor", Mol. Endocrinology, 2004, 18(9), 2132-2150.
Edwards et al., "Androgen Receptor Gene Amplification and Protein Expression in Hormone Refractory Prostate Cancer", British Journal of Cancer, 2003, 89, 552-556.
Eichholz et al., "Putting the brakes on continued androgen receptor signaling in castration-resistant prostate cancer", Molecular and Cellular Endocrinology, 2012, 360, 68-75.
Ellis et al., "Characterization of a Novel Androgen-Sensitive, Prostate-Specific Antigen-Producing Prostatic Carcinoma Xenograft: LuCaP 23", Clin Cancer Res, 1996, 2, 1039-1048.
Ellwood-Yen et al., "Myc-Driven Murine Prostate Cancer Shares Molecular Features with Human Prostate Tumors", Cancer Cell, 2003, 4(3), 223-238.
Elmore et al., "Nonsteroidal Selective Glucocorticoid Modulators: the Effect of C-5 Alkyl Substitution on the Transcriptional Activation/Repression Profile of 2,5-Dihydro-10-methoxy-2,2,4-trimethyl-1H-[1] benzopyrano [3,4-f] quinolones", J. Med. Chem., 2001, 44, 4481-4491.
Elokdah et al., "Design, Synthesis, and Biological Evaluation of Thia-Containing Compounds with Serum HDL-Cholesterol-Elevating Properties", J. Med. Chem., 2004, 47(3), 681-695.
Estebanez-Perpina et al., "A surface on the androgen receptor that allosterically regulates coactivator binding", PNAS, 2007, 104, 16074-16079.
Estebanez-Perpina et al., "Structural Insight into the Mode of Action of a Direct Inhibitor of Coregulator Binding to the Thyroid Hormone Receptor", Molecular Endocrinology, Dec. 2007, 21(12), 2919-2928.
Estebanez-Perpina et al., "The Androgen Receptor Coactivator-Binding Interface", Androgen Action in Prostate Cancer, 2009, 297-311.
Feau et al., "Novel Flufenamic Acid Analogs as Inhibitors of Androgen Receptor Mediated Transcription", ACS Chemical Biology, Oct. 2009, 4(10), 834-843.
Feher et al., "BHB: A Simple Knowledge-Based Scoring Function to Improve the C95 Efficiency of Database Screening", J. Chem. Inf. Comput. Sci., 2003, 43(4), 1316-1327.
Feldman et al., "The Development of Androgen-Independent Prostate Cancer", Nature Reviews Cancer, 2001, 1, 34-45.
Fizazi et al., "Activity and safety of ODM-201 in patients with progressive metastatic castration-resistant prostate cancer (ARADES): and open-label phase 1 dose-escalation and randomized phase 2 dose expansion trial", The Lancet, Oncology, 2014, 15, 975-985.
Fizazi et al., "An open-label, phase I/II safety, pharmacokinetic, and proof-of concept study of ODM-201 in patients with progressive metastatic castration-resistant cancer (CRPC)", www.ecco-org.eu, 2013, 15 pages.
Fizazi et al., "ODM-201, a new generation androgen receptor inhibitor for castration resistant prostate cancer: preclinical and phase I data", Orion Pharma, 2013 Genitourinary Cancers Symposium, Feb. 14-16, 2013, 1 page.
Foks et al., "Synthesis, Fungicidal and Antibacterial Activity of New Pyridazine Derivatives", Heterocycles, 2009, 78(4), 961-975.
Font de Mora et al., "AIB1 is a Conduit for Kinase-Mediated Growth Factor Signaling to the Estrogen Receptor", Mol. Cell. Biol., 2000, 20(14), 5041-5047.
Foster et al., "Drug Safety Is a Barrier to the Discovery and Development of New Androgen Receptor Antagonists", The Prostate, 2011, 71, 480-488.
Foury et al., "Control of the Proliferation of Prostate Cancer Cells by an Androgen and Two Antiandrogens. Cell Specific Sets of Responses", J. Steroid Biochem. Molec. Bioi., 1998, 66(4), 235-240.
Gao et al., "Chemistry and Structural Biology of Androgen Receptor", Chemical Reviews, 2005, vol. 105, No. 9, 3352-3370.
Gao et al., "Peptide Antagonist of the Androgen Receptor", Current Pharmaceutical Design, 2010, 16, 1106-1113.
Garcia et al, "Bone and soft tissue response from a phase I/II study with ODM-201 in metastatic castration-resistant prostate cancer (mCRPC)", Orion Pharma, 2014 Genitourinary Cancers Symposium, Jan. 30-Feb. 1, 2014, 1 page.
Gelmann et al., "Molecular Biology of the Androgen Receptor", Journal of Clinical Oncology, Jul. 2002, 20, 13, 3001-3015.
Gendt et al., "Tissue- and cell-specific functions of the androgen receptor revealed through conditional knockout models in mice", Molecular and Cellular Endocrinology, 2012, 352, 13-25.
Gioeli et al., "Androgen Receptor Phosphorylation Regulation and Identification of the Phosphorylation Sites", J Biol Chem, 2002, 277(32), 29304-29314.
Gioeli et al., "Post-transitional modification of the androgen receptor", Molecular and Cellular Endocrinology, 2012, 352, 70-78.
Glass et al., "The Coregulator Exchange on Transcriptional Functions of Nuclear Receptors", Genes Dev., 2000, 14, 121-141.
Godbole et al., "New Insights into the Androgen-Targeted Therapies and Epigenetic Therapies in prostate Cancer", Prostate Cancer, 2011, Article ID 918707, 13 pages.
Golub et al., "Molecular Classification of Cancer: Class Discovery and Class Prediction by Gene Expression Monitoring", Science, Oct. 1999, vol. 286, 531-537.
Goubet et al., "Conversion of a Thiohydantoin to the Corresponding Hydantoin via a Ring-Opening/Ring Closure Mechanism", Tetrahedron Letters, 1996, 37(43), 7727-7730.
Grad et al., "Multiple Androgen Response Elements and a Myc Consensus Site in the Androgen Receptor (AR) Coding Region are Involved in Androgen-Mediated Up-Regulation of AR Messenger RNA", Mol Endocrinol, 1999, 13, 1896-1911.

(56) References Cited

OTHER PUBLICATIONS

Graham et al., "A New Technique for the Assay of Infectivity of Human Adenovirus 5 DNA", Virology, 1973, 52, 456-467.

Green et al., "Androgen action and metabolism in prostate cancer", Molecular and Cellular Endocrinology, 2012, 360, 3-13.

Gregory et al., "A Mechanism for Androgen Receptor-Mediated Prostate Cancer Recurrence After Androgen Deprivation Therapy", Cancer Res., 2001, 61, 4315-4319.

Gregory et al., "Androgen Receptor Stabilization in Recurrent Prostate Cancer is Associated with Hypersensitivity to Low Androgen", Cancer Res, 2001, 61, 2892-2898.

Gronemeyer et al., "Principles for Modulation of the Nuclear Receptor Superfamily", Nature, Nov. 2004, 3, 950-964.

Grosdidier et al., "Allosteric Conversation in the Androgen Receptor Ligand-Binding Domain Surfaces", Mol. Endocrinol., May 2012, 26(7), 1078-90.

Grosse et al., "Androgen receptor-mediated gene repression", Molecular and Cellular Endocrinology, 2012, 352, 46-56.

Gryder et al., "Selectively Targeting Prostate Cancer with Antiandrogen Equipped Histone Deacetylase Inhibitors", ACS Chemical Biology, Sep. 2013, 8(11), 2550-60.

Gu et al., "Concise Total Synthesis of Sintokamides A, B, and E by a Unified, Protecting-Group-Free Strategy", Angewandte Chemie International Edition, 2010, 49, 9702-9705.

Guerrero et al., "Enzalutamide, an Androgen Receptor Signaling Inhibitor, Induces Tumor Regression in a Mouse Model of Castration-Resistant Prostate Cancer", The Prostate, 2013, 73, 1291-1305.

Guerrini et al., "A New Avenue toward Androgen Receptor Panantagonists: C2 Sterically Hindered Substitution of Hydroxypropanamides", J. Med. Chem., Aug. 2014, 57(17), 7263-79.

Guo et al., "A New Trick of an Old Molecule: Androgen Receptor Splice Variants Taking the Stage?", Int. J. Biol. Sci., 2011, 7, 815-822.

Guo et al., "Discovery of 3-aryloxy-lactam-analogs as potent androgen receptor full antagonists for treating castration resistant prostate cancer", Bioorganic & Medicinal Chemistry, 2012, 22, 1230-1236.

Guo et al., "Discovery, of Aryloxy Tetramethylcyclobutanes as Novel Androgen Receptor Antagonists", Journal of Medicinal Chemistry, 2011, 54, 7693-7704.

Gura, "Cancer Models: Systems for Identifying New Drugs Are Often Faulty", Science, Nov. 1997, vol. 278, No. 5340, 1041-1042.

Habchi et al., "Introducing Protein Intrinsic Disorder", Chemical Reviews, 2014, 114, 6561-6588.

Haelens et al., "The Hinge Region Regulates DNA binding, Nuclear Translocation, and Transactivation of the Androgen Receptor", Cancer Research, 2007, 67, 4514-4523.

Haendler et al., "Recent developments in antiandrogens and selective androgen receptor modulators", Molecular and Cellular Endocrinology, 2012, 352, 79-91.

Haile et al., "Androgen receptor and its splice variants in prostate cancer", Cellular and Molecular Life Sciences, 2011, 68, 3971-3981.

Hamilton-Reeves et al, "Isoflavone-Rich Soy Protein Isolate Suppresses Androgen Receptor Expression Without Altering Estrogen Receptor-Beta Expression or Serum Hormonal Profiles in Men at High Risk of Prostate Cancer", J. Nutr., 2007, 137, 1769-1775.

Hari et al., "Sequence Determinants of a Specific Inactive Protein Kinase Conformation", Chemistry & Biology, 2013, 20, 806-815.

Hassan et al., "Heat shock protein 27 mediates repression of androgen receptor function by protein kinase D1 in prostate cancer cells", Oncogene, 2009, 28, 4386-4396.

He et al., "Activation Function 2 in the Human Androgen Receptor Ligand Binding Domain Mediates Interdomain Communication with the $NH_2$-terminal Domain", The Journal of Biological Chemistry, Dec. 1999, 274, 52, 37219-37225.

He et al., "Mechanisms of Signal Transduction: FXXLF and WXXLF Sequences Mediate the $NH_2$-terminal Interaction with the Ligand Binding Domain of the Androgen Receptor", The Journal of Biological Chemistry, 2000, 275, 22986-22994.

He et al., "New Approaches to target the Androgen Receptor and STAT3 for Prostate Cancer Treatments", Mini-Reviews in Medicinal Chemistry, 2009, 9, 395-400.

Heath Elisabeth I et al: "A phase I dose-escalation study of oral BR-DIM (BioResponse 3,3 '-Diindolylmethane) in castrate-resistant, non-metastatic prostate cancer", American Journal of Translational Research, vol. 2, No. 4, 2010, pp. 402-411.

Heemers et al., "Androgen Receptor (AR) Coregulators: A Diversity of Functions Converging on and Regulating the AR Transcriptional Complex", Endocrine Reviews, Dec. 2007, 28(7), 778-808.

Heinlein et al., "Androgen Receptor in Prostate Cancer", Endocrine Reviews, Apr. 2004, 25(2), 276-308.

Hessenkemper et al., "Chaperones for proper androgen action—a plethora of assistance to androgen receptor function", Horm Mol Biol Clin Invest, 2012, 11(1), 321-328.

Hessenkemper et al., "Targeting Heat Shock Proteins in Prostate Cancer", Current Medicinal Chemistry, 2013, 20, 2731-2740.

Heuvel, "The Androgen Receptor", Nuclear Receptor Resource, 2011, 1-3.

Hicken et al., "Discovery of a Novel Class of Imidazo[1,2-a]Pyridines with Potent PDGFR Activity and Oral Bioavailability", ACS Medicinal Chemistry Letters, 2014, 5, 78-83.

Higuchi et al., "Pro-Drugs as Novel Delivery Systems", 1975, vol. 14 of the A.C.S. Symposium Series, 6 pages.

Holzbeierlein et al., "Gene Expression Analysis of Human Prostate Carcinoma During Hormonal Therapy Identifies Androgen-Responsive Genes and Mechanisms of Therapy Resistance", Am. J. Pathology, 2004, 164(1), 217-227.

Homma et al., "Differential Levels of Human Leukocyte Antigen—Class I, Multidrugresistance 1 and Androgen Receptoi Expressions in Untreated Prostate Cancer Cells: The Robustness of Prostate Cancer", Oncol. Rep., 2007,18, 343-346.

Hong et al., "Aromatase, estrone sulfatase, and 17.beta.-hydroxysteroid dehydrogenase" Structure-function studies and inhibitor development, Molecular and Cellular Endocrinology, 2011, 340, 120-126.

Aeluri et al., "Small Molecule Modulators of Protein-Protein Interactions: Selected Case Studies", Chemical Reviews, Mar. 2014, 114(9), 4640-94.

Agarwal et al., "Novel Molecular Targets for the Therapy of Castration-Resistant Prostate Cancer", European Urology, Dec. 2011, 61(5), 950-60.

Ahn et al., "Facile synthesis of benzamides to mimic an .alpha.-helix", Tetrahedron Letters, 2007, 48, 3543-3547.

Altimari et al., "Preliminary investigations into triazole derived androgen receptor antagonists", Bioorganic & Medicinal Chemistry, 2014, 22, 2692-2706.

Altintas et al., "Direct Cooperation Between Androgen Receptor and E2F1 Reveals a Common Regulation Mechanism for Androgen-Responsive Genes in Prostate Cells", Molecular Endocrinology, Sep. 2012, 26(9), 1531-1541.

Amaral et al., "Castration-Resistant Prostate Cancer: mechanisms, Targets, and Treatment", Prostate Cancer, Mar. 2012, Article ID 327259, 11 pages.

Andersen et al., "Regression of Castrate-Recurrent Prostate Cancer by a Small-Molecule Inhibitor of the Amino-Terminus Domain of the Androgen Receptor", Cancer Cell, Jun. 15, 2010, 17, 535-546.

Andrieu et al., "Heat shock protein 27 confers resistance to androgen ablation and chemotherapy in prostate cancer cells through eIF4E", Oncogene, 2010, 29, 1883-1896.

Antonarakis et al., "AR-V7 and Resistance to Enzalutamide and Abiraterone in Prostate Cancer", The New England Journal of Medicine, Sep. 2014, 371(11), 1028-38.

Antonarakis et al., "Emerging therapeutic approaches in the management of metastatic castration-resistant prostate cancer", Prostate Cancer and Prostatic Diseases, 2011, 14, 206-218.

ARN-509 Update: Phase I Study—Prostrate Cancer, HealingWell.com, 2014, 3 pages.

Arnold et al., "Discovery of Small Molecule Inhibitors of the Interaction of Thyroid Hormone Receptor with Transcriptional Coregulators", The Journal of Biological Chemistry, Dec. 2005, 280, 43048-43055.

(56) References Cited

OTHER PUBLICATIONS

Arora et al., "Glucocorticoid Receptor Confers Resistance to Antiandrogens by Bypassing Androgen Receptor Blockade", Cell, Dec. 2013, 155, 1309-1322.
Asangani et al., "Therapeutic targeting of BET bromodomain proteins in castration-resistant prostate cancer", Nature, Apr. 2014, 510(7504), 278-82.
Attard et al., "Characterization of ERG, AR and PTEN Gene Status in Circulating Tumor Cells from Patients with Castration-Resistant Prostate Cancer", Cancer Research, Apr. 2009, 69, 2912-2918.
Attard et al., "New Strategies in Metastatic Prostate Cancer: Targeting the Androgen Receptor Signaling Pathway", Clinical Cancer Research, 2011, 17, 1649-1657.
Auricchio et al., VAL201—An Inhibitor of Androgen Receptor-associated Srcand a Potential Treatment of Castration-resistant Prostate Cancer, European Oncology & Haematology, 2012, vol. 8, Issue 1, 32-35.
Ausubel et al., "Current Protocols in Molecular Biology", Wiley Interscience Publishers, 1995, 2, 18 pages.
Axerio-Cilies et al., "Inhibitors of Androgen Receptor Activation Function-2 (AF2) Site Identified through Virtual Screening", J. Med. Chem., 2011, 6197-6205.
Baek et al., "Exchange of N-CoR Corepressor and Tip60 Coactivator Complexes Links Gene Expression by NF-kappaB and Beta-Amyloid Precursor Protein", Cell, 2002, 110, 55-67.
Balbas et al., "Overcoming mutation-based resistance to antiandrogens with rational drug design", eLife, Apr. 2013, e00499.
Balk, "Androgen Receptor as a Target in Androgen-Independent Prostate Cancer", Urology, 2002, 60(3A), 132-138.
Barf et al., "Irreversible Protein Kinase Inhibitors: Balancing the Benefits and Risks", Journal of Medicinal Chemistry, 2012, 55, 6243-6262.
Batch et al., "Androgen Receptor Gene Mutations Identified by SSCP in Fourteen Subjects with Androgen Insensitivity Syndrome", Hum. Mol. Genet., 1992, 1(7), 497-503.
Bhuiyan et al., "Down-regulation of Androgen Receptor by 3,3'-Diindolylmethane Contributes to Inhibition of Cell Proliferation and Induction of Apoptosis in Both Hormone-Sensitive LNCaP and Insensitive C4-2B Prostate Cancer Cells", Cancer Research, 2006, 66, 10064-10072.
Bilodeau et al., "Potent N-(1,3-Thiazol-2-yl)pyridine-2-amine Vascular Endothelial Growth Factor Receptor Tyrosine Kinase Inhibitors with Excellent Pharmacokinetics and Low Affinity for the hERG Ion Channel", J. Med. Chem., 2004, 47, 6363-6372.
Biron et al., "Recent progress in the development of protein-protein interaction inhibitors targeting androgen receptor-coactivator binding in prostate cancer", Journal of Steroid Biochemistry & Molecular Biology, Jul. 2015, 161, 36-44.
Bisson et al., "Molecular basis of agonicity and antagonicity in the androgen receptor studied by molecular dynamics simulations", Journal of Molecular Graphics and Modelling, 2008, 27, 452-458.
Bohl et al., "Protein Structure and Folding: Crystal Structure of the T877A Human Androgen Receptor Ligand-binding Domain Complexed to Cyproterone Acetate Provides Insight for Ligand-induced Conformational Changes and Structure-based Drug Design", The Journal of Biological Chemistry, 2007, 282, 13648-13655.
Bohl et al., "Protein Structure and Folding: Structural Basis for Accommodation of Nonsteroidal Ligands in the Androgen Receptor", The Journal of Biological Chemistry, 2005, 280, 37747-37754.
Bohl et al., "Structural basis for antagonism and resistance of bicalutamide in prostate cancer", PNAS, Apr. 2005, vol. 102, No. 17, 6201-6206.
Brann et al., "PELP1—A novel estrogen receptor-interacting protein", Molecular and Cellular Endocrinology, 2008, 290, 2-7.
Brockschmidt et al., "The Two Most Common Alleles of the Coding GGN Repeat in the Androgen Receptor Gene Cause Differences in Protein Function", J. Mol. Endocrinol., 2007, 39, 1-8.
Brozowski et al., "Molecular basis of agonism and antagonism in the oestrogen receptor", Nature, Oct. 1997, 389, 753-758.
Bruncko et al., "Studies Leading to Potent, Dual Inhibitors of Bcl-2 and Bcl-xL", J. Med. Chem., 2007, 50, 641-662.
Bullock et al., "Assessing Helical Protein Interfaces for Inhibitor Design", Journal of the American Chemical Society, 2011, 133, 14220-14223.
Bundgaard, "Design of Application of Prodrugs", Harwood Academic Publishers, 1991, Chapter 5, 113-191.
Burnstein et al. Androgen Glucocorticoid Regulation of Androgen Receptor cDNA Expression. Molecular and Cellular Endocrinology. 1995. v. 115, pp. 177-186.
Butler, "Mammalian Cell Biotechnology: A Practical Approach", 1991, 6 pages.
Bydal et al., "Steroidal lactones as inhibitors of 17.beta.-hydroxysteroid dehydrogenase type 5: Chemical synthesis, enzyme inhibitory activity, and assessment of estrogenic and androgenic activities", Eur. J. Med. Chem., Apr. 8, 2008, 44(2), 632-44.
Caboni et al., "True" Antiandrogens—Selective Non-Ligand-Binding Pocket Disruptors of Androgen Receptor—Coactivator Interaction: Novel Tools for Prostate Cancer, J. Med. Chem., 2012, 55, 1635-1644.
Cai et al., "c-Jun Has Multiple Enhancing Activities in the Novel Cross Talk Between the Androgen Receptor and ETS Variant Gene 1 in Prostate Cancer", Mol. Cancer Res., 2007, 5(7), 725-735.
Callewaert et al., "Interplay between Two Hormone-Independent Activation Domains in the Androgen Receptor", Cancer Research, 2006, 66, 543-553.
Cancer [online], [retrieved on Jul. 6, 2007]. Retrieved from the internet, URL http://www.nlm.nih.gov/medlineplus/cancer.html>.
Cao et al., "20(S)-Protopanaxadiol Inhibition of Progression and Growth of Castration-Resistant Prostate Cancer", PLoS One, Nov. 2014, 9(11), e111201.
Carver et al., "Reciprocal Feedback Regulation of PI3K and Androgen Receptor Signaling in PTEN-Deficient Prostate Cancer", Cancer Cell., 2011, 19, 575-586.
Chakravarty et al., "PELP1: A Novel Therapeutic Target for Hormonal Cancers", Life, Mar. 2010, 62(3), 163-169.
Chan et al., "Androgen receptor splice variants activate AR target genes and support aberrant prostate cancer cell growth independent of canonical AR nuclear localization signal", The Journal of Biological Chemistry, Apr. 2012, 287(23), 19736-49.
Chang et al., "Androgen receptor-cofactor interactions as targets for new drug discovery", Trends in Pharmacological Sciences, May 2005, 26, 5, 225-228.
Chang et al., "Development of Peptide Antagonists for the Androgen Receptor Using Combinatorial Peptide Phage Display", Molecular Endocrinology, Oct. 2005, 19(10), 2478-2490.
Kuo et al., "Design of a Coumarin-Based Triketone as a Fluorescent Protecting Group for Primary Amines", J. Org. Chem., 2008, 73, 6455-6458.
Kuruma et al., "A Novel Antiandrogen, Compound 30, Suppresses Castration-Resistant and MDV3100-Reisistant Prostate Cancer Growth in Vitro and in Vivo", Molecular Cancer Therapeutics, 2013, 12, 567-576.
Lack et al., "Targeting the Binding Function 3 (BF3) Site of the Human Androgen Receptor through Virtual Screening", Journal of Medicinal Chemistry, 2011, 54(24), 8563-8573.
Laitinen et al., "Chromosomal Aberrations in Prostate Cancer Xenografts Detected by Comparative Genomic Hybridization", Genes Chromosomes Cancer, 2002, 35, 66-73.
Lala et al., "Role of nitric oxide in tumor progression: lessons from experimental tumors", Cancer and Metastasis Reviews, 1998, 17(1), 91-106.
Lallous et al., "Targeting Alternative Sites on the Androgen Receptor to Treat Castration-Resistant Prostate Cancer", International Journal of Molecular Sciences, 2013, 14, 12496-12519.
Lamont et al., "Minireview: Alternative Activation Pathways for the Androgen Receptor in Prostate Cancer", Molecular Endocrinology, Jun. 2011, 25(6), 897-907.
Lao et al., "In vivo modulation of hypoxia-inducible signaling by topographical helix mimetics", PNAS, May 2014, 111(21), 7531-6.
Lavery et al., "Androgen Receptor Signalling in Prostate Cancer: The Functional Consequences of Acetylation", Journal of Biomedicine and Biotechnology, Dec. 2010, 7 pages.

(56) References Cited

OTHER PUBLICATIONS

Lee et al., "Novel Pyrrolopyrimidine-Based .alpha.-Helix Mimetics: Cell-Permeable Inhibitors of Protein-Protein Interactions", Journal of the American Chemical Society, 2011, 133, 676-679.
Lee et al., "Solid-Phase Synthesis of Tris-Benzamides as .alpha.-Helix Mimetics", ACS Combinatorial Science, 2011, 13, 107-111.
LeRoith et al., "The insulin-like growth factor system and cancer", Cancer Letters, 2003, 195, 127-137.
Levine et al., "Multivalent Peptidomimetic Conjugates: A Versatile Platform for Modulating Androgen Receptor Activity", Journal of the American Chemical Society, 2012, 134, 6912-6915.
Levine et al., "Targeting the Androgen Receptor with Steroid Conjugates", J. Med. Chem., Jul. 2014, 57(2), 8224-37.
Li et al., "Heterogeneous Expression and Functions of Androgen Receptor Co-Factors in Primary Prostate Cancer", Am J Pathol, 2002, 161(4), 1467-1474.
Li et al., "ZMIZ1 preferably Enhances the Transcriptional Activity of Androgen Receptor with Short Polyglutamine Tract", PLoS One, Sep. 2011, 6(9), e25040.
Lill et al., "Toward understanding ubiquitin-modifying enzymes: from pharmacological targeting to proteomics", Trends in Pharmacological Sciences, Apr. 2014, 35, 4, 187-207.
Lim et al., "Ligand-Independent and Tissue-Selective Androgen Receptor Inhibition by Pyrvinium", ACS Chemical Biology, 2014, 9, 692-702.
Lim et al., "Total Synthesis of the Potent Androgen Receptor Antagonist (−)-Arabilin: A Strategic, Biomimetic [1,7]-Hydrogen Shift", Journal of the American Chemical Society, 2011, 133, 20149-20151.
Linja et al., "Amplification and Overexpression of Androgen Receptor Gene in Hormone-Refractory Prostate Cancer", Cancer Research, 2001, 61, 3550-3555.
Liu et al., "Dasatinib inhibits site-specific tyrosine phosphorylation of androgen receptor by Ack1 and Src kinases", Oncogene, 2010, 29, 3208-3216.
Liu et al., "Developments in Nonsteroidal Antiandrogens Targeting the Androgen Receptor", Chem Med Chem, 2010, 5, 1651-1661.
Liu et al., "Lineage relationship between LNCaP and LNCaPderived prostate cancer cell lines", Prostate, Jul. 1, 2004, 60(2), 98-108.
Lobaccaro et al., "Molecular Modeling and in Vitro Investigations of the Human Androgen Receptor DNA-Binding Domain: Application for the Study of Two Mutations", Mol. Cell. Endocrinol., 1996, 116, 137-147.
Loddick et al., "Pre-clinical profile of AZD3514: a small molecule targeting androgen receptor function with a novel mechanism of action and the potential to treat castration resistant prostate cancer", AACR Annual Meeting, AstraZeneca, 2012, 1 page.
Lodish et al., "Endocrine side effects of broad-acting kinase inhibitors", Endocrine-Related Cancer, 2010, 17, R233-R244.
Lonergan et al., "Androgen receptor signaling on prostate cancer development and progression", Journal of Carcionogenesis, 2011, 10-20.
Loriot et al. "Recent developments in treatments targeting castration-resistant prostate cancer bone metastases", Annals of Oncology, Jan. 20, 2012, 23(50), 1085-94.
Lu et al. "Molecular Mechanisms of Androgen-Independent Growth of Human Prostate Cancer LNCaP-Al Cells", Endocrinology 1999, vol. 140, No. 11, pp. 5054-5059.
Lu et al., "Recent Androgen Receptor Antagonists in Prostate Cancer", Mini-Reviews in Medicinal Chemistry, 2014, 14, 655-663.
Luo et al., "Decoding the androgen receptor splice variants", Transl. Androl. Urol., 2013, 2(3), 178-186.
Mahajan et al., "Activated Cdc42-associated kinase Ack1 promotes prostate cancer progression via androgen receptor tyrosine phosphorylation", PNAS, 2007, 104, 8438-8443.
Mahajan et al., "Effect of Ack1 Tyrosine Kinase Inhibitor on Ligand-Independent Androgen Receptor Activity", The Prostate, 2010, 70, 1274-1285.
Mahajan et al., "Sheperding AKT and Androgen Receptor by Ack1 Tyrosine Kinase", Journal of Cellular Physiology, 2010, 224, 327-333.
Malik et al., "Targeting the MLL complex in castration-resistant prostate cancer", Nature Medicine, Apr. 2015, 21, 344-352.
Manolagas et al., "Sex Steroids and Bone", Recent Prog Harm Res, 2002, 57, 385-409.
Mansour et al., "Disruption of the Proto-Oncogene int-2 in Mouse Embryo-Derived Stem Cells: A General Strategy for Targeting Mutations to Non-Selectable Genes", Nature, 1988, 336, 348-352.
Marhefka et al., "Homology Modeling Using Multiple Molecular Dynamics Simulations and Docking Studies of the Human Androgen Receptor Ligand Binding Domain Bound to Testosterone and Nonsteroidal Ligands", J. Med. Chem., 2001, 44, 1729-1740.
Marimganti et al., "Novel Amphiphilic .alpha.-Helix Mimetics Based on a Bis-benzamide Scaffold", Organic Letters, 2009, 11, 19, 4418-4421.
Marqusee et al., "Helix stabilization by Glu.sup._Lys.sup.+ salt bridges in short peptides of de novo design", Proc. Natl. Acad. Sci., Dec. 1987, 84, 8898-8902.
Martin et al., "N-terminal targeting of androgen receptor variant enhances response of castration resistant prostate cancer to taxane chemotherapy", Molecular Oncology, Oct. 2014, 9(3), 628-639.
Mashima et al., "Molecular Pharmacological Approach Reveals Potential New Strategies to Suppress Androgen Receptor Signaling in Prostate Cancer", Molecular and Cellular Pharmacology, 2011, 3(1), 7-12.
Masiello et al., "Bicalutamide Functions as an Androgen Receptor Antagonist by Assembly of a Transcriptionally Inactive Receptor", J Biol Chem, 2002, 277(29), 26321-26326.
Massard et al., "A study of ODM-201 formulations with a safety and tolerability extension phase in patients with metastatic chemotherapy-naive castration-resistant prostate cancer (CRPC)", Orion Pharma, 2014 Genitourinary Cancers Symposium, Jan. 30-Feb. 1, 2014, 1 page.
Massard et al., "ARADES trial: A first-in-man, open-label, phase I/II safety, pharmacokinetic, and proof-of-concept study of ODM-201 in patients with progressive metastatic castration-resistant prostate cancer", ESMO Congress, Sep. 28-Oct. 2, 2012, 1 page.
Massard et al., "Long-term efficacy and safety of androgen receptor inhibitor ODM-201 in ARADES phase I/II trial", Orion Pharma, ASCO, May 30-Jun. 3, 2014, 1 page.
Massie et al., "The androgen receptor fuels prostate cancer by regulating central metabolism and biosynthesis", The EMBO Journal, 2011, 30, 2719-2733.
Matias et al., "Local Inhibition of Sebaceous Gland Growth by Topically Applied RU 58841", NY Acad. Sci., 1995, 761, 56-65.
Matias et al., "Structural Basis for the Glucocorticoid Response in a Mutant Human Androgen Receptor (AR.sup.ccr) Derived from an Androgen-Independent Prostate Cancer", J. Med. Chem., 2002, 45, 1439-1446.
Matias et al., "Structural Evidence for Ligand Specificity in the Binding Domain of the Human Androgen Receptor: Implications for Pathogenic Gene Mutations", J Biol Chem, 2000, 275(34), 26164-26171.

SUBSTITUTED THIOHYDANTOIN DERIVATIVES AS ANDROGEN RECEPTOR ANTAGONISTS

CROSS-REFERENCE TO RELATED APPLICATIONS

This application is a continuation of U.S. patent application Ser. No. 16/012,160, filed Jun. 19, 2018, which is a continuation of U.S. patent application Ser. No. 15/403,741, filed Jan. 11, 2017, now U.S. Pat. No. 10,000,502, which claims the benefit of U.S. Provisional Patent Application Nos. 62/277,009, filed Jan. 11, 2016, and 62/363,534, filed Jul. 18, 2016, the entireties of each of which are incorporated by reference herein.

FIELD OF THE INVENTION

The present invention relates to thiohydantoin compounds that are androgen receptor antagonists and are useful for the treatment of disorders that are affected by the modulation of the androgen receptor (AR). The invention also relates to pharmaceutical compositions that include one or more of such compounds, to processes to prepare such compounds and compositions, and to the use of such compounds or pharmaceutical compositions for the treatment of prostate cancer and other diseases, syndromes, disorders, or conditions associated with androgen-resistant ARs or an AR mutant associated with "castration-resistant" prostate cancer.

BACKGROUND OF THE INVENTION

Prostate cancer is the most common non-cutaneous malignancy in men and the second leading cause of death in men from cancer in the western world (Jemal A, Siegel R, Xu J, Ward E. Cancer Statistics. *Cancer J Clin* 2010; 60:277-300). As a male sexual organ, development of the prostate is highly regulated by androgens, the AR and by the products of androgen dependent genes. During all stages of prostate cancer progression, the disease remains dependent upon androgens. Anti-androgens, including AR antagonists, are used therapeutically to reverse the dependence of the tumor upon the actions of androgen (Scher H, Sawyers C. Biology of progressive, castration-resistant prostate cancer: directed therapies targeting the androgen-receptor signaling axis. *J Clin Oncol* 2005; 23:8253-8261; Tran C, Ouk S, Clegg N, Chen Y, Watson P, Arora V, et al. Development of a second-generation antiandrogen for treatment of advanced prostate cancer. *Science* 2009; 324:787-790; Scher H, Fizazi K, Saad F, Taplin M, Sternberg C, Miller K, et al. Increased survival with enzalutamide in prostate cancer after chemotherapy. *N Engl J Med* 2012; 367:1187-1197). Unfortunately, the efficacy of even second-generation, highly potent AR antagonists, such as MDV-3100 (enzalutamide, Xtandi®), is short-lived in many patients.

AR antagonists have transformed patient care by targeting a key nodal point in tumor cell signaling. However, as with other molecularly targeted cancer therapies across different oncology indications, the emergence of acquired resistance via mutation of the therapeutic target is not uncommon. This is best exemplified by imatinib-treated patients with chronic myeloid leukemia in whom ABL kinase mutations render leukemia cells resistant to imatinib. Multiple next-generation ABL inhibitors have since been developed to circumvent the mutation and with activity in this setting (Gorre M, Mohammed M, Ellwood K, Hsu N, Paquette R, Rao P, Sawyers C. Clinical resistance to STI-571 cancer therapy caused by BCRABL gene mutation or amplification. *Science* 2001; 293:876-80; O'Hare T, Deininger M W, Eide C A, Clackson T, Druker B J. Targeting the BCR-ABL signaling pathway in therapy-resistant Philadelphia chromosome-positive leukemia. *Clin Cancer Res* 2011. 17: 212-21).

Importantly, the activity of second- and third-generation AR inhibitors indicates that the disease remains "addicted" to a deregulated driver. This has led to the paradigm of sequential therapy targeting the same driver oncogene in distinct resistant states and is applicable herein to targeting of AR and the lineage dependence of AR signaling.

AR mutations that result in receptor promiscuity and the ability of these anti-androgens to exhibit agonist activity might at least partially account for this phenomenon. For example, hydroxyflutamide and bicalutamide act as AR agonists in T877A and W741L/W741C AR mutants, respectively.

In the setting of prostate cancer cells that were rendered castration resistant via overexpression of AR, it has been demonstrated that certain anti-androgen compounds, such as bicalutamide, have a mixed antagonist/agonist profile (Tran C, Ouk S, Clegg N, Chen Y, Watson P, Arora V, et al. Development of a second-generation antiandrogen for treatment of advanced prostate cancer. *Science* 2009; 324:787-790). This agonist activity helps to explain a clinical observation, called the anti-androgen withdrawal syndrome, whereby about 30% of men who progress on AR antagonists experience a decrease in serum PSA when therapy is discontinued (Scher, H. I. and Kelly, W. K., *J Urol* 1993 March; 149(3): 607-9). Prostate specific antigen decline after anti-androgen withdrawal: the flutamide withdrawal syndrome.

Accumulating evidence indicates that castration-resistant prostate cancer (CRPC) remains dependent upon AR signaling through reactivation of AR signaling (Yuan X, Balk S. Mechanisms mediating androgen receptor reactivation after castration. *Urol Oncol* 2009; 27: 36-41; Linja M, Savinainen K, Saramaki O, Tammela T, Vessella R, Visakorpi T. Amplification and overexpression of androgen receptor gene in hormone-refractory prostate cancer. *Cancer Res* 2001; 61:3550-; Chen C, Welsbie D, Tran C, Baek S, Chen R, Vessella R, Rosenfeld M, Sawyers C. Molecular determinants of resistance to antiandrogen therapy. *Nat Med* 2004; 10(1): 33-9.555). Point mutation in the ligand-binding domain (LBD) of AR accounts for 10-20% of resistance and is characterized by receptor activation, rather than inhibition, by anti-androgen drugs (Beltran H, Yelensky R, Frampton G, Park K, Downing S, MacDonald T, et al. Targeted next-generation sequencing of advanced prostate cancer identifies potential therapeutic targets and disease heterogeneity. *Eur Urol* 2013; 63(5): 920-6; Bergerat J, Céraline J. Pleiotropic functional properties of androgen receptor mutants in prostate cancer. *Hum Mutat* 2009; 30(2):145-57). Many of these mutations broaden ligand specificity, and some confer resistance by converting the AR antagonist into an agonist of the mutant receptor (Veldscholte J, Ris-Stalpers C, Kuiper G G, Jenster G, Berrevoets C, Claassen E, van Rooij H C, Trapman J, Brinkmann A O, Mulder E. A mutation in the ligand binding domain of the androgen receptor of human LNCaP cells affects steroid binding characteristics and response to anti-androgens. *Biochem Biophys Res Commun.* 1990; 173: 534-40; Haapala K, Hyytinen E, Roiha M, Laurila M, Rantala I, Helin H, Koivisto P. Androgen receptor alterations in prostate cancer relapsed during a combined androgen blockade by orchiectomy and bicalutamide. *Lab Invest* 2001; 81(12):1647-1651; Hara T, Miyazaki J, Araki H, Yamaoka M, Kanzaki N, Kusaka M, Miyamoto M. Novel mutations of androgen receptor: a possible mechanism of bicalutamide withdrawal syndrome. *Cancer Res* 2003; 63(1):149-153).

One mutation, phenylalanine to leucine at position 876 (F876L) of AR, was recently shown to arise in response to MDV-3100 and ARN-509 in preclinical models and in patients undergoing therapy with ARN-509 (Clegg N, Wongvipat J, Joseph J, Tran C, Ouk S, Dilhas A, et al. ARN-509: a novel antiandrogen for prostate cancer treatment. *Cancer Res* 2012; 72(6):1494-503; Balbas M, Evans M, Hosfield D, Wongvipat J, Arora V, Watson P, et al. Overcoming mutation-based resistance to antiandrogens with rational drug design. *Elife* 2013. 2: e00499; Korpal M, Korn J, Gao X, Rakiec D, Ruddy D, Doshi S, et al. An F876L mutation in androgen receptor confers genetic and phenotypic resistance to MDV3100 (enzalutamide). *Cancer Discov* 2013; 39:1030-1043; Joseph J D, Lu N, Qian J, Sensintaffar J, Shao G, Brigham D, Moon M, Maneval E C, Chen I, Darimont B, Hager J H. A clinically relevant androgen receptor mutation confers resistance to second-generation antiandrogens enzalutamide and ARN-509. *Cancer Discov* 2013; 3:1020-1029).

AR F876L confers resistance to MDV-3100 and ARN-509. Comprehensive biological studies have demonstrated that prostate cancer cells harboring this mutation continued to grow when treated with either compound. In vitro reporter assays confirmed resistance and demonstrate agonist conversion of both compounds and in tumors engineered to express AR F876L, neither compound controlled tumor growth. Furthermore, the AR F876L mutant is detected in ARN-509—treated patients with progressive CRPC. The mutation was detected in the plasma DNA of patients undergoing longitudinal analysis in 3 of 29 patients eligible for assessment. All 3 of the patients were amongst the 18 patients with an increase in prostate specific antigen (PSA) whilst on drug, indicative of disease progression (Joseph 2013).

Structural modeling of wild-type (WT) and F876L mutated AR bound with MDV-3100, indicated that helices 11 and 12 were differentially displaced. Within the LBD of AR in the F876L mutant, helix 12 is not displaced by MDV-3100 as it is in WT AR, and this allows MDV 3100 to function as an agonist. The compounds described herein are designed to act as antagonists (third-generation), where second-generation compounds are not active.

Thus, androgen receptor antagonists of the present invention may provide therapeutic benefit for the treatment of prostate cancer and other diseases, syndromes, disorders, or conditions associated with androgen-resistant ARs or an AR mutant associated with castration-resistant prostate cancer.

SUMMARY OF THE INVENTION

The present invention is directed to compounds of Formula (I)

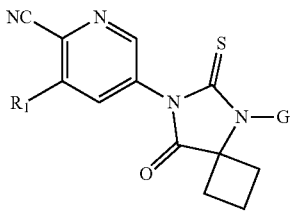

Formula (I)

wherein
$R_1$ is chloro, methyl, methoxy, difluoromethyl, or trifluoromethyl;
G is
i)

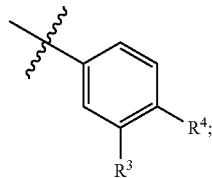

wherein $R^4$ is selected from the group consisting of bromo, morpholin-2-yl, morpholin-4-yl, morpholin-4-ylmethyl, morpholin-2-ylmethoxy, 5-methylmorpholin-2-ylmethoxy, 4,4-difluoropyrrolidin-2-ylmethoxy, (1-methylcarbonyl)-4,4-difluoropyrrolidin-2-ylmethoxy, (1-t-butoxycarbonyl)-4,4-difluoropyrrolidin-2-ylmethoxy, (2-oxa-6-azaspiro[3.3]heptan-6-yl)ethoxy, (6,6-difluoro-2-methyl-2-azaspiro[3.3]heptan-6-yl)ethoxy, 2-oxa-8-azaspiro[4.5]decan-8-yl)ethoxy, 1H-pyrazol-4-yl, 1H-pyrazol-3-yl, (1-aminocarbonyl)pyrazol-4-yl, (1-ethylaminocarbonyl)pyrazol-4-yl, methylaminocarbonylmethyl, 2-oxo-imidazolidin-1-yl, (5-methoxymethyl)furan-2-yl, 5-methylfuran-2-yl, tetrahydrofuran-2-yloxy, 4-methylmorpholin-2-yl, 1-methylpyrrolidin-3-yloxy, 8-azabicyclo[3.2.1]oct-3-en-3-yl, 8-methyl-8-azabicyclo[3.2.1]oct-3-en-3-yl, 8-azabicyclo[3.2.1]octan-3-yl, 8-methyl-8-azabicyclo[3.2.1]octan-3-yl, 5,8-diazaspiro[2.5]octan-5-ylmethyl, 1-azaspiro[3.3]heptan-6-yloxy, 2-azaspiro[3.3]heptan-6-yloxy, 2-azabicyclo[2.2.1]heptan-5-yloxy, (4-aminopiperidin-1-yl)methyl, (2S,3R,4S)-3,4-dihydroxy-2-methyl-3,4-dihydro-2H-pyran-6-yl, 3,4-dihydroxy-3,4-dihydro-2H-pyran-6-yl, 2-(hydroxymethyl)-3,4-dihydro-2H-pyran-6-yl, 2-methyl-2-azaspiro[3.3]heptan-6-yl)oxy, 1-methylpiperidin-4-ylcarbonyl, (1-methyl-1-azaspiro[3.3]heptan-6-yl)oxy, (2-methyl-2-azabicyclo[2.2.1]heptan-5-yl)oxy, (3-methyl-3-azaspiro[3.3]heptan-6-yl)oxy, 3-azabicyclo[3.2.1]octan-8-yloxy, (3-t-butoxycarbonyl-3-azaspiro[3.3]heptan-6-yl)oxy, (1R,5S)-8-azabicyclo[3.2.1]octan-3-yl]oxy, (1-methylazetidin-3-yl)methylaminocarbonyl, 1-methylpyrrolidin-3-ylaminocarbonyl, (1-methyl-1-oxido-piperidin-1-ium-4-yl)oxy, (3-methyl-3-azabicyclo[3.2.1]octan-8-yl)oxy, [(1R,5S)-8-methyl-8-azabicyclo[3.2.1]octan-3-yl]oxy, (1,2,3,5,6,7,8,8a-octahydroindolizin-7-yl)oxy, 9-azaspiro[3.5]nonan-6-yloxy, (9-methyl-9-azaspiro[3.5]nonan-6-yl)oxy, (1-methylpyrrolidin-3-yl)methylaminocarbonyl, (piperidin-3-yl)methylaminocarbonyl, (4-fluoro-8-azabicyclo[3.2.1]octan-3-yl)oxy, (4-fluoro-8-methyl-8-azabicyclo[3.2.1]octan-3-yl)oxy, (4-fluoro-8-(t-butoxycarbonyl)-8-azabicyclo[3.2.1]octan-3-yl)oxy, (1-methyl-piperidin-4-yl)methylaminocarbonyl, piperidin-4-ylmethylaminocarbonyl, (1-methyl-piperidin-3-yl)methylaminocarbonyl, 1-(methyl)piperidin-4-ylmethyl-N(methyl)aminocarbonyl, 1-(methylaminocarbonyl)piperidin-4-ylmethylaminocarbonyl, 1-(ethoxycarbonyl)piperidin-4-ylmethylaminocarbonyl, 1-(t-butoxycarbonyl)piperidin-4-ylmethylaminocarbonyl, 8-(t-butoxycarbonyl)-8-azabicyclo[3.2.1]octan-3-yl, methylaminothiocarbonyl, 3-(t-butoxycarbonylamino)-2,2,4,4-tetramethylcyclobut-1-yloxy, or a substituent selected from a) to e);
a)

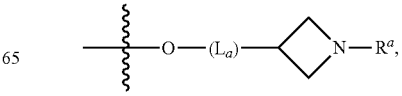

wherein $L_a$ is absent or —(CH$_2$)$_r$—, wherein r is an integer of 1 or 2; $R^a$ is a substituent selected from methyl, prop-2-yn-1-yl, 2-hydroxyethyl, 2-methoxyethyl, or cyanomethyl;

b)

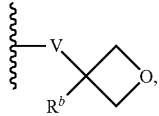

wherein V is absent or —OCH$_2$—; and wherein $R^b$ is amino, dimethylamino, or t-butoxycarbonyl(N-methyl)amino;

c)

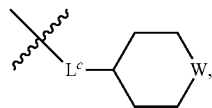

wherein $L^c$ is absent or selected from O, S, or —CH$_2$—; and wherein W is selected from NH, N(methyl), N(cyclopropyl), N(2-hydroxyethyl), N(2-methoxyethyl), N(2-fluoroethyl), N(2,2,2-trifluoroethyl), N(cyanomethyl), N(allyl), N(1-prop-2-ynyl), N(3-fluoropropyl), N(methoxycarbonylmethyl), N(3-amino-2-hydroxy-prop-1-yl), N(3,3-dimethyl-butyl), CH(amino), CH(methylamino), CH(dimethylamino), S, or SO$_2$;

d) a substituent selected from the group consisting of 2-oxo-piperidin-4-yloxy, 4-methyl-piperidin-4-yloxy, 1-methyl-2-trifluoromethyl-piperidin-4-yloxy, 1-methyl-piperidin-3-yloxy, 2-trifluoromethyl-piperidin-4-yloxy, azepan-4-yloxy, azepan-3-yloxy, 1-methyl-azepan-4-yloxy, 1-methyl-2-oxo-piperidin-4-yloxy, 1,4-dimethyl-piperidin-4-yloxy, 2-hydroxymethyl-piperidin-4-yloxy, 2-hydroxymethyl-1-methyl-piperidin-4-yloxy, 3-fluoro-piperidin-4-yloxy, 3-fluoro-1-methyl-piperidin-4-yloxy, 3,3-difluoro-piperidin-4-yloxy, 3,3-difluoro-1-methyl-piperidin-4-yloxy, piperazin-1-ylmethyl, 4-methyl-piperazin-1-ylmethyl, 3-oxopiperazin-1-ylmethyl, 4-cyclopropyl-piperazin-1-ylmethyl, 3-hydroxymethyl-piperazin-1-ylmethyl, 4-(2-hydroxyethyl)piperazin-1-ylmethyl, 4-(methylaminocarbonyl)piperazin-1-ylmethyl, 4-(ethoxycarbonyl)piperazin-1-yl, 4-(ethoxycarbonyl) piperazin-1-ylmethyl, 4-(ethoxycarbonyl)piperazin-1-ylcarbonyl, 4-(pyrrolidin-1-ylcarbonyl)piperazin-1-yl, 4-(t-butoxycarbonyl)piperazin-1-ylmethyl, and 4-(t-butoxycarbonyl)piperazin-1-ylcarbonyl;

and $R^3$ is hydrogen, fluoro, or methoxy;
provided that when $R^4$ is bromo, $R^3$ is hydrogen or methoxy;
provided that when $R^4$ is

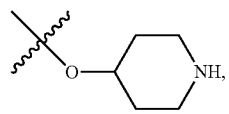 [SMILES: *OC1CCNCC1]

$R^1$ is chloro, methoxy, or difluoromethyl;
provided that when $R^4$ is

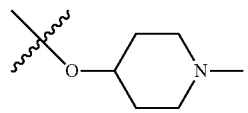 [SMILES: *OC1CCN(C)CC1]

and $R^3$ is hydrogen or fluoro, $R^1$ is chloro, methoxy, or difluoromethyl;

provided that when $R^4$ is

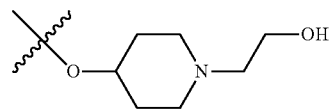 [SMILES: *OC1CCN(CCO)CC1]

and $R^3$ is hydrogen, $R^1$ is chloro, methoxy, or difluoromethyl;
provided that when $R^4$ is

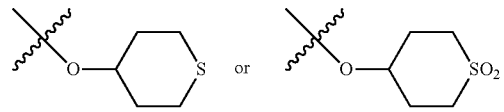 [SMILES: *OC1CCSCC1 ; "or" ; *OC1CCS(=O)(=O)CC1]

and $R^3$ is hydrogen, $R^1$ is chloro, methoxy, difluoromethyl, or trifluoromethyl;
provided that when $R^4$ is

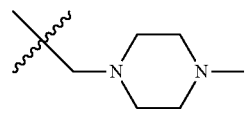 [SMILES: *CN1CCN(C)CC1]

and $R^3$ is hydrogen, $R^1$ is chloro, methyl, methoxy, or difluoromethyl;

ii)

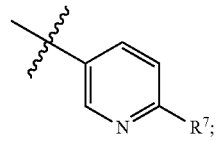

wherein $R^7$ is selected from the group consisting of hydroxy, methoxy, cyanomethyl, 1,4-(dimethyl)piperidin-4-yl)oxy, tetrahydro-2H-thiopyran-4-yloxy, aminosulfonyl, 2-azabicyclo[2.2.1]heptan-5-yloxy, 2-methyl-2-azabicyclo[2.2.1]heptan-5-yloxy, (3-methyl-3-azaspiro[3.3]heptan-6-yl)oxy, 3-azabicyclo[3.2.1]octan-8-yloxy, (3-methyl-3-azabicyclo[3.2.1]octan-8-yl)oxy, 9-azaspiro[3.5]nonan-6-yloxy, (9-methyl-9-azaspiro[3.5]nonan-6-yl)oxy, 4-(ethoxycarbonyl)piperazin-1-yl, 3-(dimethylamino)propyloxy, 3-(t-butoxycarbonyl)-3-azaspiro[3.3]heptan-6-yloxy, and substituent f)

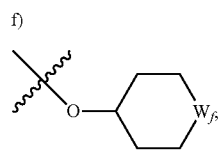

wherein $W_f$ is selected from NH, N(methyl), N(2-hydroxyethyl), N(2-methoxyethyl), N(2-fluoroethyl), N(2,2,2-trifluoroethyl), N(cyanomethyl), N(allyl), N(isopentyl), N(prop-2-yn-1-yl), N(3,3-dimethyl-butyl), N(3-fluoropropyl), N(3,3,3-trifluoropropyl), N(methoxycarbonylmethyl), N(3-amino-2-hydroxy-propyl), N(3,3-dimethyl-butyl), CH(amino), CH(methylamino), CH(dimethylamino), S, or SO$_2$;

iii) a heteroaryl selected from the group consisting of indazol-5-yl, indazol-6-yl, benzimidazol-5-yl, indol-5-yl, and indol-6-yl; wherein said heteroaryl is optionally independently substituted on the nitrogen-containing portion of the heteroaryl with a substituent selected from methyl, 2-hydroxyethyl, 2-methoxyethyl, piperidin-4-yl, 1-(methyl)piperidin-4-yl, 1-(methylcarbonyl)piperidin-4-yl, 1-(t-butoxycarbonyl)piperidin-4-yl, piperidin-4-ylmethyl, 1-(methylcarbonyl)piperidin-4-ylmethyl, 1-methyl-piperidin-4-ylmethyl, or 1-(t-butoxycarbonyl)piperidin-4-ylmethyl;

and wherein said heteroaryl of iii) is optionally further substituted with an additional methyl substituent;

provided that when G is selected from 1-methyl-2-(1-methyl-piperidin-4-yl)benzimidazol-5-yl, 1-methyl-2-(piperidin-4-yl)benzimidazol-5-yl, unsubstituted indazol-5-yl, or unsubstituted indazol-6-yl, then $R^1$ is chloro, methyl, methoxy, or difluoromethyl;

iv)

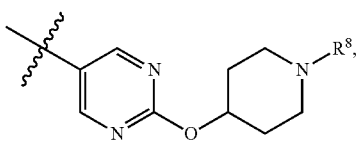

wherein $R^8$ is selected from the group consisting of hydrogen, methyl, cyclopropyl, 2-hydroxyethyl, 2-methoxyethyl, 2-fluoroethyl, 2,2,2-trifluoroethyl, cyanomethyl, allyl, 1-prop-2-ynyl, 3-fluoropropyl, methoxycarbonylmethyl, 3-amino-2-hydroxy-propyl, and 3,3-dimethyl-butyl;

v) 2-($R^9$)-1,2,3,4-tetrahydroisoquinolin-6-yl, wherein $R^9$ is selected from the group consisting of hydrogen, methyl, methylcarbonyl, and t-butoxycarbonyl;

vi)

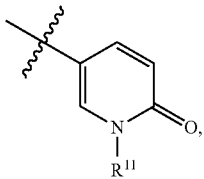

wherein $R^{11}$ is methyl or 1-(t-butoxycarbonyl)-azetidin-3-ylmethyl; or vii)

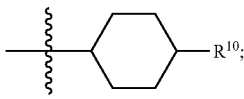

wherein $R^{11}$ is selected from the group consisting of
methoxycarbonyl, phenyloxy, and phenylcarbonylamino;
wherein any nitrogen-containing heterocyclic substituent of G is optionally substituted with an oxido substituent to form an N-oxide;
or an enantiomer, diastereomer, or pharmaceutically acceptable salt form thereof.

The present invention also provides a pharmaceutical composition comprising, consisting of and/or consisting essentially of a pharmaceutically acceptable carrier, a pharmaceutically acceptable excipient, a pharmaceutically acceptable diluent and a compound of Formula (I) or a pharmaceutically acceptable salt form thereof.

Also provided are processes for making a pharmaceutical composition comprising, consisting of, and/or consisting essentially of admixing a compound of Formula (I), and a pharmaceutically acceptable carrier, a pharmaceutically acceptable excipient, and a pharmaceutically acceptable diluent.

The present invention further provides methods for treating or ameliorating a disease, syndrome, condition, or disorder in a subject, including a mammal and/or human, in which the disease, syndrome, condition, or disorder is affected by the antagonism of one or more androgen receptor types, such as prostate cancer, castration-resistant prostate cancer, and metastatic castration-resistant prostate cancer, using a compound of Formula (I).

The present invention also is directed to the use of any of the compounds described herein in the preparation of a medicament wherein the medicament is prepared for treating a disease, syndrome, condition, or disorder that is affected by the antagonism of one or more androgen receptor types, such as prostate cancer, castration-resistant prostate cancer, and metastatic castration-resistant prostate cancer.

The present invention is also directed to the preparation of substituted thiohydantoin derivatives that act as antagonists of one or more androgen receptors.

Exemplifying the invention are methods of treating a disease, syndrome, condition, or disorder mediated by one or more androgen receptors, selected from the group consisting of prostate cancer, castration-resistant prostate cancer, and metastatic castration-resistant prostate cancer, comprising, consisting of, and/or consisting essentially of, administering to a subject in need thereof a therapeutically effective amount of any of the compounds or pharmaceutical compositions described in the present invention.

In another embodiment, the present invention is directed to a compound of Formula (I) for use in the treatment of a disease, syndrome, condition, or disorder affected by the antagonism of one or more androgen receptor types, selected from the group consisting of prostate cancer, castration-resistant prostate cancer, and metastatic castration-resistant prostate cancer.

In another embodiment, the present invention is directed to a composition comprising a compound of Formula (I) for the treatment of a disease, syndrome, condition, or disorder affected by the antagonism of one or more androgen receptors, selected from the group consisting of prostate cancer, castration-resistant prostate cancer, and metastatic castration-resistant prostate cancer.

Another embodiment of the present invention is directed to a pharmaceutical composition comprising a compound of Formula (I)

DETAILED DESCRIPTION OF THE INVENTION

With reference to substituents, the term "independently" refers to the situation where when more than one substituent is possible, the substituents may be the same or different from each other.

The term "alkyl" whether used alone or as part of a substituent group, refers to straight and branched carbon chains having 1 to 8 carbon atoms. Therefore, designated numbers of carbon atoms (e.g., C1-8) refer independently to the number of carbon atoms in an alkyl moiety or to the alkyl portion of a larger alkyl-containing substituent. In substituent groups with multiple alkyl groups such as, $(C_{1-6}alkyl)_2$ amino-, the $C_{1-6}$alkyl groups of the dialkylamino may be the same or different.

The term "alkoxy" refers to an —O-alkyl group, wherein the term "alkyl" is as defined above.

The terms "alkenyl" and "alkynyl" refer to straight and branched carbon chains having 2 to 8 carbon atoms, wherein an alkenyl chain contains at least one double bond and an alkynyl chain contains at least one triple bond.

The term "cycloalkyl" refers to saturated or partially saturated, monocyclic or polycyclic hydrocarbon rings of 3 to 14 carbon atoms. Examples of such rings include cyclopropyl, cyclobutyl, cyclopentyl, cyclohexyl, cycloheptyl, and adamantyl.

The term "heterocyclyl" refers to a nonaromatic monocyclic or bicyclic ring system having 3 to 10 ring members that include at least 1 carbon atom and from 1 to 4 heteroatoms independently selected from N, O, and S. Included within the term heterocyclyl is a nonaromatic cyclic ring of 5 to 7 members in which 1 to 2 members are N, or a nonaromatic cyclic ring of 5 to 7 members in which 0, 1 or 2 members are N and up to 2 members are 0 or S and at least one member must be either N, O, or S; wherein, optionally, the ring contains 0 to 1 unsaturated bonds, and, optionally, when the ring is of 6 or 7 members, it contains up to 2 unsaturated bonds. The carbon atom ring members that form a heterocycle ring may be fully saturated or partially saturated. The term "heterocyclyl" also includes two 5 membered monocyclic heterocycloalkyl groups bridged to form a bicyclic ring. Such groups are not considered to be fully aromatic and are not referred to as heteroaryl groups. When a heterocycle is bicyclic, both rings of the heterocycle are non-aromatic and at least one of the rings contains a heteroatom ring member. Examples of heterocycle groups include, and are not limited to, pyrrolinyl (including 2H-pyrrole, 2-pyrrolinyl or 3-pyrrolinyl), pyrrolidinyl, imidazolinyl, imidazolidinyl, pyrazolyl, pyrazolidinyl, piperidinyl, morpholinyl, thiomorpholinyl, and piperazinyl. Unless otherwise noted, the heterocycle is attached to its pendant group at any heteroatom or carbon atom that results in a stable structure.

The term "aryl" refers to an unsaturated, aromatic monocyclic or bicyclic ring of 6 to 10 carbon members. Examples of aryl rings include phenyl and naphthalenyl. The term "heteroaryl" refers to an aromatic monocyclic or bicyclic aromatic ring system having 5 to 10 ring members and which contains carbon atoms and from 1 to 4 heteroatoms independently selected from the group consisting of N, O, and S. Included within the term heteroaryl are aromatic rings of 5 or 6 members wherein the ring consists of carbon atoms and has at least one heteroatom member. Suitable heteroatoms include nitrogen, oxygen, and sulfur. In the case of 5 membered rings, the heteroaryl ring preferably contains one member of nitrogen, oxygen or sulfur and, in addition, up to 3 additional nitrogens. In the case of 6 membered rings, the heteroaryl ring preferably contains from 1 to 3 nitrogen atoms. For the case wherein the 6 membered ring has 3 nitrogens, at most 2 nitrogen atoms are adjacent. Examples of heteroaryl groups include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolyl, isoindolyl, benzofuryl, benzothienyl, indazolyl, benzimidazolyl, benzothiazolyl, benzoxazolyl, benzisoxazolyl, benzothiadiazolyl, benzotriazolyl, quinolinyl, isoquinolinyl and quinazolinyl. Unless otherwise noted, the heteroaryl is attached to its pendant group at any heteroatom or carbon atom that results in a stable structure.

The term "halogen" or "halo" refers to fluorine, chlorine, bromine and iodine atoms.

The term "carboxy" refers to the group —C(=O)OH.

The term "formyl" refers to the group —C(=O)H.

The term "oxo" or "oxido" refers to the group (=O).

Whenever the term "alkyl" or "aryl" or either of their prefix roots appear in a name of a substituent (e.g., arylalkyl, alkylamino) the name is to be interpreted as including those limitations given above for "alkyl" and "aryl." Designated numbers of carbon atoms (e.g., $C_1$-$C_6$) refer independently to the number of carbon atoms in an alkyl moiety, an aryl moiety, or in the alkyl portion of a larger substituent in which alkyl appears as its prefix root. For alkyl and alkoxy substituents, the designated number of carbon atoms includes all of the independent members included within a given range specified. For example $C_{1-6}$ alkyl would include methyl, ethyl, propyl, butyl, pentyl and hexyl individually as well as sub-combinations thereof (e.g., $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

In general, under standard nomenclature rules used throughout this disclosure, the terminal portion of the designated side chain is described first followed by the adjacent functionality toward the point of attachment. Thus, for example, a "$C_1$-$C_6$ alkylcarbonyl" substituent refers to a group of the formula:

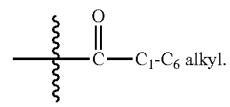

In the present invention, as a non-limiting example, when $R^4$ is

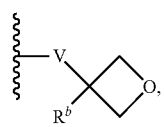

and V is "—$OCH_2$—", the substituent is oriented such that the oxygen atom of —$OCH_2$— is covalently bound to the $(R^3)(R^4)$-substituted phenyl ring as shown:

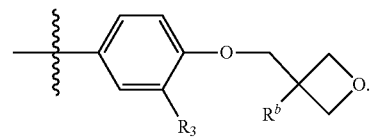

The label "R" at a stereocenter designates that the stereocenter is purely of the R-configuration as defined in the art; likewise, the label "S" means that the stereocenter is purely of the S-configuration. As used herein, the labels "*R" or "*S" at a stereocenter are used to designate that the stereocenter is of pure but unknown absolute configuration. As used herein, the label "RS" refers to a stereocenter that exists as a mixture of the R- and S-configurations.

A compound containing one stereocenter drawn without a stereo bond designation is a mixture of two enantiomers. A compound containing two stereocenters both drawn without stereo bond designations is a mixture of four diastereomers. A compound with two stereocenters both labeled "RS" and drawn with stereo bond designations is a mixture of two enantiomers with relative stereochemistry as drawn. A compound with two stereocenters both labeled "*RS" and drawn with stereo bond designations is a mixture of two enantiomers with a single, but unknown, relative stereochemistry.

Unlabeled stereocenters drawn without stereo bond designations are mixtures of the R- and S-configurations. For unlabeled stereocenters drawn with stereo bond designations, the relative and absolute stereochemistry is as depicted.

Unless otherwise noted, it is intended that the definition of any substituent or variable at a particular location in a molecule be independent of its definitions elsewhere in that molecule. It is understood that substituents and substitution patterns on the compounds of the present invention can be selected by one of ordinary skill in the art to provide compounds that are chemically stable and that can be readily synthesized by techniques known in the art as well as those methods set forth herein.

The term "subject" refers to an animal, preferably a mammal, most preferably a human, who has been the object of treatment, observation or experiment.

The term "therapeutically effective amount" refers to an amount of an active compound or pharmaceutical agent, including a compound of the present invention, which elicits the biological or medicinal response in a tissue system, animal or human that is being sought by a researcher, veterinarian, medical doctor or other clinician, which includes alleviation or partial alleviation of the symptoms of the disease, syndrome, condition, or disorder being treated.

The term "composition" refers to a pharmaceutical product that includes the specified ingredients sometimes in therapeutically effective amounts, as well as any product that results, directly, or indirectly, from combinations of the specified ingredients in the specified amounts.

The term "androgen receptor" as used herein is intended to include the wild-type androgen receptor as well as androgen-resistant ARs and/or AR mutants associated with castration-resistant prostate cancer.

The term "AR-mediated" refers to any disease, syndrome, condition, or disorder that might occur in the absence of androgen receptors but can occur in the presence of androgen receptors. Suitable examples of include, but are not limited to, prostate cancer, castration-resistant prostate cancer, and metastatic castration-resistant prostate cancer.

The term "Androgen-dependent disorder" refers to any disorder that can benefit from a decrease in androgen stimulation and includes pathological conditions that depend on androgen stimulation. An "androgen-dependent disorder" can result from an excessive accumulation of testosterone or other androgenic hormone, increased sensitivity of androgen receptors to androgen, or an increase in androgen-stimulated transcription.

Examples of "androgen-dependent disorders" include prostate cancer and disorders such as, for example, acne, seborrhea, hirsutism, alopecia, and hidradenitis suppurativa.

As used herein, the term "anti-androgen" refers to a group of hormone receptor antagonist compounds that are capable of preventing or inhibiting the biologic effects of androgens on normally responsive tissues in the body. In some embodiments, an anti-androgen is a small molecule. In some embodiments, an anti-androgen is an AR antagonist. In some embodiments, an anti-androgen is an AR full antagonist. In some embodiments, an anti-androgen is a first-generation anti-androgen. In some embodiments, an anti-androgen is a second-generation anti-androgen. In some embodiments, an anti-androgen is a third-generation anti-androgen.

As used herein, the term "AR antagonist" or "AR inhibitor" are used interchangeably and refer to an agent that inhibits or reduces at least one activity of an AR polypeptide. Exemplary AR activities include, but are not limited to, co-activator binding, DNA binding, ligand binding, or nuclear translocation.

As used herein, a "full antagonist" refers to an antagonist which, at an effective concentration, essentially completely inhibits an activity of an AR polypeptide. As used herein, a "partial antagonist" refers an antagonist that is capable of partially inhibiting an activity of an AR polypeptide, but that, even at a highest concentration is not a full antagonist. By 'essentially completely' is meant at least about 80%, at least about 90%, at least about 95%, at least about 96%, at least about 97%, at least about 98% at least about 99%, or greater inhibition of the activity of an AR polypeptide.

As used herein, the term "first-generation anti-androgen" refers to an agent that exhibits antagonist activity against a wild-type AR polypeptide. However, first-generation anti-androgens differ from second-generation anti-androgens in that first-generation anti-androgens can potentially act as agonists in castration resistant prostate cancers (CRPC). Exemplary first-generation anti-androgens include, but are not limited to, flutamide, nilutamide and bicalutamide.

As used herein, the term "second-generation anti-androgen" refers to an agent that exhibits full antagonist activity against a wild-type AR polypeptide. Second-generation anti-androgens differ from first-generation anti-androgens in that second-generation anti-androgens act as full antagonists in cells expressing elevated levels of AR, such as for example, in castration resistant prostate cancers (CRPC). Exemplary second-generation anti-androgens include 4-[7-(6-cyano-5-trifluoromethylpyridin-3-yl)-8-oxo-6-thioxo-5,7-diazaspiro [3.4]oct-5-yl]-2-fluoro-N-methylbenzamide (also known as ARN-509; CAS No. 956104-40-8); 4-(3-(4-cyano-3-(trifluoromethyl)phenyl)-5,5-dimethyl-4-oxo-2-thioxoimidazolidin-1-yl)-2-fluoro-N-methylbenzamide (also known as MDV3100 or enzalutamide; CAS No: 915087-33-1) and RD162 (CAS No. 915087-27-3). In some embodiments, a second-generation anti-androgen binds to an AR polypeptide at or near the ligand binding site of the AR polypeptide.

As used herein, the term "third-generation anti-androgen" refers to an agent that exhibits full antagonist activity against a wild-type AR polypeptide and against mutant forms of the AR polypeptide, with mutations arising in the ligand binding domain (LBD) of the AR polypeptide as set forth below. Third-generation anti-androgens retain the differentiation from first-generation anti-androgens in that third-generation anti-androgens act as full antagonists in cells expressing elevated levels of AR, such as for example, in castration resistant prostate cancers (CRPC).

As used herein, the term "mutant" refers to an altered (as compared with a reference) nucleic acid or polypeptide, or to a cell or organism containing or expressing such altered nucleic acid or polypeptide.

As used herein, unless otherwise noted, the term "affect" or "affected" (when referring to a disease, syndrome, condition or disorder that is affected by antagonism of AR) includes a reduction in the frequency and/or severity of one or more symptoms or manifestations of said disease, syndrome, condition or disorder; and/or include the prevention of the development of one or more symptoms or manifestations of said disease, syndrome, condition or disorder or the development of the disease, condition, syndrome or disorder.

The compounds of the instant invention are useful in methods for treating or ameliorating a disease, a syndrome, a condition or a disorder that is affected by the antagonism of one or more AR receptors. Such methods comprise, consist of and/or consist essentially of administering to a subject, including an animal, a mammal, and a human in need of such treatment, amelioration and/or prevention, a therapeutically effective amount of a compound of Formula (I), or an enantiomer, diastereomer, solvate or pharmaceutically acceptable salt thereof.

One embodiment of the present invention is directed to a method of treating an androgen receptor dependent or androgen receptor mediated disease or condition in a subject in need thereof, including an animal, a mammal, and a human in need of such treatment, comprising administering to the subject a therapeutically effective amount of a compound of Formula (I).

In another embodiment, the androgen receptor dependent or androgen receptor mediated disease or condition is selected from benign prostate hyperplasia, hirsutism, acne, adenomas and neoplasies of the prostate, benign or malignant tumor cells containing the androgen receptor, hyperpilosity, seborrhea, endometriosis, polycystic ovary syndrome, androgenic alopecia, hypogonadism, osteoporosis, suppression of spermatogenesis, libido, cachexia, anorexia, androgen supplementation for age related decreased testosterone levels, prostate cancer, breast cancer, endometrial cancer, uterine cancer, hot flashes, and Kennedy's disease muscle atrophy and weakness, skin atrophy, bone loss, anemia, arteriosclerosis, cardiovascular disease, loss of energy, loss of well-being, type 2 diabetes, or abdominal fat accumulation.

In particular, the compounds of Formula (I), or an enantiomer, diastereomer, solvate or pharmaceutically acceptable salt form thereof are useful for treating or ameliorating diseases, syndromes, conditions, or disorders such as prostate cancer, castration-resistant prostate cancer, and metastatic castration-resistant prostate cancer.

More particularly, the compounds of Formula (I), or an enantiomer, diastereomer, solvate or pharmaceutically acceptable salt form thereof, are useful for treating or ameliorating prostate cancer, castration-resistant prostate cancer, and metastatic castration-resistant prostate cancer, comprising administering to a subject in need thereof a therapeutically effective amount of a compound of Formula (I), or an enantiomer, diastereomer, solvate or pharmaceutically acceptable salt form thereof as herein defined.

Embodiments of the present invention include a compound of Formula (I)

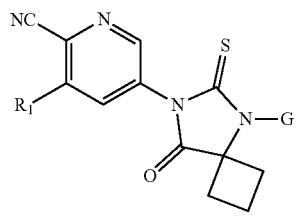

Formula (I)

wherein
AA) $R_1$ is chloro, methyl, methoxy, or trifluoromethyl;
BB) $R_1$ is chloro, methyl, or trifluoromethyl;
CC) G is
  i)

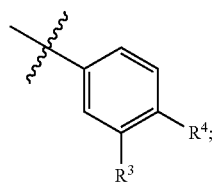

wherein $R^4$ is selected from the group consisting of bromo, morpholin-2-yl, morpholin-4-yl, morpholin-4-ylmethyl, morpholin-2-ylmethoxy, 5-methylmorpholin-2-ylmethoxy, 4,4-difluoropyrrolidin-2-ylmethoxy, (1-methylcarbonyl)-4,4-difluoropyrrolidin-2-ylmethoxy, (1-t-butoxycarbonyl)-4,4-difluoropyrrolidin-2-ylmethoxy, (2-oxa-6-azaspiro[3.3]heptan-6-yl)ethoxy, (6,6-difluoro-2-methyl-2-azaspiro[3.3]heptan-6-yl)ethoxy, 2-oxa-8-azaspiro[4.5]decan-8-yl)ethoxy, 1H-pyrazol-4-yl, 1H-pyrazol-3-yl, (1-aminocarbonyl)pyrazol-4-yl, (1-ethylaminocarbonyl)pyrazol-4-yl, methylaminocarbonylmethyl, 2-oxo-imidazolidin-1-yl, (5-methoxymethyl)furan-2-yl, 5-methylfuran-2-yl, tetrahydrofuran-2-yloxy, 4-methylmorpholin-2-yl, 1-methylpyrrolidin-3-yloxy, 8-azabicyclo[3.2.1]oct-3-en-3-yl, 8-methyl-8-azabicyclo[3.2.1]oct-3-en-3-yl, 8-azabicyclo[3.2.1]octan-3-yl, 8-methyl-8-azabicyclo[3.2.1]octan-3-yl, 5,8-diazaspiro[2.5]octan-5-ylmethyl, 1-azaspiro[3.3]heptan-6-yloxy, (4-aminopiperidin-1-yl)methyl, (2S,3R,4S)-3,4-dihydroxy-2-methyl-3,4-dihydro-2H-pyran-6-yl, 3,4-dihydroxy-3,4-dihydro-2H-pyran-6-yl, 2-(hydroxymethyl)-3,4-dihydro-2H-pyran-6-yl, 2-methyl-2-azaspiro[3.3]heptan-6-yl)oxy, 1-methylpiperidin-4-ylcarbonyl, (1-methyl-1-azaspiro[3.3]heptan-6-yl)oxy, (2-methyl-2-azabicyclo[2.2.1]heptan-5-yl)oxy, (3-methyl-3-azaspiro[3.3]heptan-6-yl)oxy, 3-azabicyclo[3.2.1]octan-8-yloxy, (1R,5S)-8-azabicyclo[3.2.1]octan-3-yl]oxy, (1-methylazetidin-3-yl)methylaminocarbonyl, 1-methylpyrrolidin-3-ylaminocarbonyl, (1-methyl-1-oxido-piperidin-1-ium-4-yl)oxy, (3-methyl-3-azabicyclo[3.2.1]octan-8-yl)oxy, (1,2,3,5,6,7,8,8a-octahydroindolizin-7-yl)oxy, 9-azaspiro[3.5]nonan-6-yloxy, (9-methyl-9-azaspiro[3.5]nonan-6-yl)oxy, (1-methylpyrrolidin-3-yl)methylaminocarbonyl, (piperidin-3-yl)methylaminocarbonyl, (4-fluoro-8-azabicyclo[3.2.1]octan-3-yl)oxy, (4-fluoro-8-methyl-8-azabicyclo[3.2.1]octan-3-yl)oxy, (4-fluoro-8-(t-butoxycarbonyl)-8-azabicyclo[3.2.1]octan-3-yl)oxy, (1-methyl-piperidin-4-yl)methylaminocarbonyl, piperidin-4-ylmethylaminocarbonyl, (1-methyl-piperidin-3-yl)methylaminocarbonyl, 1-(methylaminocarbonyl)piperidin-4-ylmethylaminocarbonyl, 1-(ethoxycarbonyl)piperidin-4-ylmethylaminocarbonyl, 1-(t-butoxycarbonyl)piperidin-4-ylmethylaminocarbonyl, 8-(t-butoxycarbonyl)-8-azabicyclo[3.2.1]octan-3-yl, methylaminothiocarbonyl, 3-(t-butoxycarbonylamino)-2,2,4,4-tetramethylcyclobut-1-yloxy, and a substituent selected from a) to e);
  a)

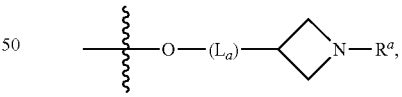

wherein $L_a$ is absent or —(CH$_2$)$_r$—, wherein r is an integer of 1 or 2; $R^a$ is a substituent selected from methyl or prop-2-yn-1-yl;
  b)

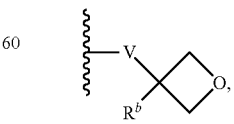

wherein V is absent or —OCH$_2$—; and wherein $R^b$ is amino, dimethylamino, or t-butoxycarbonyl(N-methyl)amino;

c)

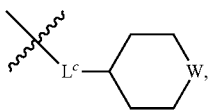

wherein $L^c$ absent or selected from O, S, or —CH$_2$—; and wherein W is selected from NH, N(methyl), N(cyclopropyl), N(2-hydroxyethyl), N(2-fluoroethyl), N(2,2,2-trifluoroethyl), N(cyanomethyl), N(1-prop-2-ynyl), N(3-fluoropropyl), N(methoxycarbonylmethyl), N(3-amino-2-hydroxy-prop-1-yl), N(3,3-dimethyl-butyl), CH(amino), CH(methylamino), CH(dimethylamino), S, or SO$_2$;

d) a substituent selected from the group consisting of 2-oxo-piperidin-4-yloxy, 4-methyl-piperidin-4-yloxy, 1-methyl-2-trifluoromethyl-piperidin-4-yloxy, 1-methyl-piperidin-3-yloxy, 2-trifluoromethyl-piperidin-4-yloxy, azepan-4-yloxy, 1-methyl-azepan-4-yloxy, 1-methyl-2-oxo-piperidin-4-yloxy, 1,4-dimethyl-piperidin-4-yloxy, 2-hydroxymethyl-piperidin-4-yloxy, 2-hydroxymethyl-1-methyl-piperidin-4-yloxy, 3-fluoro-piperidin-4-yloxy, 3-fluoro-1-methyl-piperidin-4-yloxy, 3,3-difluoro-piperidin-4-yloxy, 3,3-difluoro-1-methyl-piperidin-4-yloxy, piperazin-1-ylmethyl, 4-methyl-piperazin-1-ylmethyl, 3-oxopiperazin-1-ylmethyl, 4-cyclopropyl-piperazin-1-ylmethyl, 3-hydroxymethyl-piperazin-1-ylmethyl, 4-(2-hydroxyethyl)piperazin-1-ylmethyl, 4-(methylaminocarbonyl)piperazin-1-ylmethyl, 4-(ethoxycarbonyl)piperazin-1-yl, 4-(ethoxycarbonyl)piperazin-1-ylmethyl, 4-(ethoxycarbonyl)piperazin-1-ylcarbonyl, 4-(pyrrolidin-1-ylcarbonyl)piperazin-1-yl, 4-(t-butoxycarbonyl)piperazin-1-ylmethyl, and 4-(t-butoxycarbonyl)piperazin-1-ylcarbonyl;

and $R^3$ is hydrogen, fluoro, or methoxy;

provided that when $R^4$ is bromo, $R^3$ is hydrogen or methoxy;

provided that when $R^4$ is

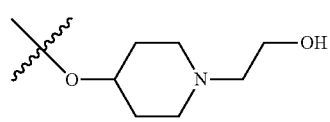

and $R^3$ is hydrogen or fluoro, $R^1$ is chloro, methoxy, or difluoromethyl;

provided that when $R^4$ is

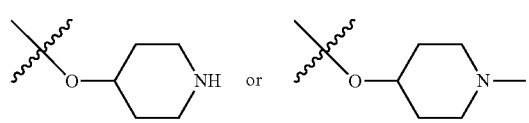

and $R^3$ is hydrogen, $R^1$ is chloro, methoxy, or difluoromethyl;

provided that when $R^4$ is

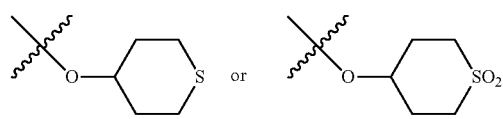 [SMILES: *OC1CCSCC1 ; "or" ; *OC1CCS(=O)(=O)CC1]

and $R^3$ is hydrogen, $R^1$ is chloro, methoxy, difluoromethyl, or trifluoromethyl;

provided that when $R^4$ is

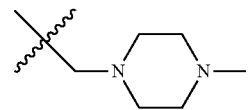 [SMILES: *CN1CCN(C)CC1]

and $R^3$ is hydrogen, $R^1$ is chloro, methyl, methoxy, or difluoromethyl;

ii)

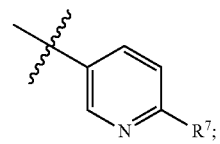

wherein $R^7$ is selected from the group consisting of hydroxy, methoxy, aminosulfonyl, 2-azabicyclo[2.2.1]heptan-5-yloxy, 3-azabicyclo[3.2.1]octan-8-yloxy, (3-methyl-3-azabicyclo[3.2.1]octan-8-yl)oxy, 9-azaspiro[3.5]nonan-6-yloxy, (9-methyl-9-azaspiro[3.5]nonan-6-yl)oxy, 3-(dimethylamino)propyloxy, 3-(t-butoxycarbonyl)-3-azaspiro[3.3]heptan-6-yloxy, and substituent f)

f)

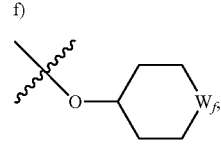

wherein $W_f$ is selected from NH, N(methyl), N(2-hydroxyethyl), N(2-methoxyethyl), N(2-fluoroethyl), N(2,2,2-trifluoroethyl), N(cyanomethyl), N(allyl), N(isopentyl), N(prop-2-yn-1-yl), or S;

iii) a heteroaryl selected from the group consisting of indazol-5-yl, indazol-6-yl, benzimidazol-5-yl, indol-5-yl, and indol-6-yl; wherein said heteroaryl is optionally independently substituted on the nitrogen-containing portion of the heteroaryl with a substituent selected from methyl, 2-hydroxyethyl, 2-methoxyethyl, piperidin-4-yl, 1-(methyl)piperidin-4-yl, 1-(methylcarbonyl)piperidin-4-yl, 1-(t-butoxycarbonyl)piperidin-4-yl, piperidin-4-ylmethyl, 1-(methylcarbonyl)piperidin-4-ylmethyl, 1-methyl-piperidin-4-ylmethyl, or 1-(t-butoxycarbonyl)piperidin-4-ylmethyl;

and wherein said heteroaryl of iii) is optionally further substituted with an additional methyl substituent;

provided that when G is selected from 1-methyl-2-(1-methyl-piperidin-4-yl)benzimidazol-5-yl, 1-methyl-2-(piperidin-4-yl)benzimidazol-5-yl, unsubstituted indazol-5-yl, or unsubstituted indazol-6-yl, then R' is chloro, methyl, methoxy, or difluoromethyl;

iv)

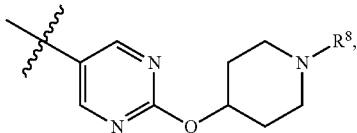

wherein R⁸ is selected from the group consisting of hydrogen, methyl, and 2-hydroxyethyl;

v) 2-(R⁹)-1,2,3,4-tetrahydroisoquinolin-6-yl, wherein R⁹ is selected from the group consisting of hydrogen, methyl, methylcarbonyl, and t-butoxycarbonyl;

vi)

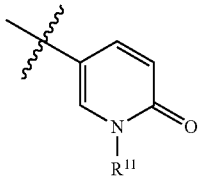

wherein R¹¹ is methyl or 1-(t-butoxycarbonyl)-azetidin-3-ylmethyl; or vii)

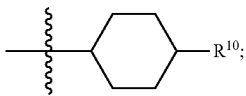

wherein R¹⁰ is selected from the group consisting of methoxycarbonyl, phenyloxy, and phenylcarbonylamino;

DD) G is i)

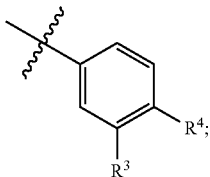

wherein R⁴ is selected from the group consisting of bromo, morpholin-4-yl, morpholin-4-ylmethyl, 5-methylmorpholin-2-ylmethoxy, 4,4-difluoropyrrolidin-2-ylmethoxy, (1-methylcarbonyl)-4,4-difluoropyrrolidin-2-ylmethoxy, (1-t-butoxycarbonyl)-4,4-difluoropyrrolidin-2-ylmethoxy, (2-oxa-6-azaspiro[3.3]heptan-6-yl)ethoxy, (6,6-difluoro-2-methyl-2-azaspiro[3.3]heptan-6-yl)ethoxy, 2-oxa-8-azaspiro[4.5]decan-8-yl)ethoxy, 1H-pyrazol-3-yl, methylaminocarbonylmethyl, 2-oxo-imidazolidin-1-yl, tetrahydrofuran-2-yloxy, 8-methyl-8-azabicyclo[3.2.1]oct-3-en-3-yl, 8-azabicyclo[3.2.1]octan-3-yl, 8-methyl-8-azabicyclo[3.2.1]octan-3-yl, 5,8-diazaspiro[2.5]octan-5-ylmethyl, 1-azaspiro[3.3]heptan-6-yloxy, (4-aminopiperidin-1-yl)methyl, (2S,3R,4S)-3,4-dihydroxy-2-methyl-3,4-dihydro-2H-pyran-6-yl, 3,4-dihydroxy-3,4-dihydro-2H-pyran-6-yl, 2-methyl-2-azaspiro[3.3]heptan-6-yl)oxy, 1-methylpiperidin-4-ylcarbonyl, (1-methyl-1-azaspiro[3.3] heptan-6-yl)oxy, (2-methyl-2-azabicyclo[2.2.1]heptan-5-yl)oxy, (3-methyl-3-azaspiro[3.3]heptan-6-yl)oxy, 3-azabicyclo[3.2.1]octan-8-yloxy, (1-methylazetidin-3-yl)methylaminocarbonyl, 1-methylpyrrolidin-3-ylaminocarbonyl, (1-methyl-1-oxido-piperidin-1-ium-4-yl)oxy, (3-methyl-3-azabicyclo[3.2.1]octan-8-yl)oxy, (1,2,3,5,6,7,8,8a-octahydroindolizin-7-yl)oxy, 9-azaspiro[3.5]nonan-6-yloxy, (9-methyl-9-azaspiro[3.5]nonan-6-yl)oxy, (1-methylpyrrolidin-3-yl)methylaminocarbonyl, (piperidin-3-yl)methylaminocarbonyl, (4-fluoro-8-azabicyclo[3.2.1]octan-3-yl)oxy, (4-fluoro-8-methyl-8-azabicyclo[3.2.1]octan-3-yl)oxy, (4-fluoro-8-(t-butoxycarbonyl)-8-azabicyclo[3.2.1]octan-3-yl)oxy, (1-methyl-piperidin-4-yl)methylaminocarbonyl, piperidin-4-ylmethylaminocarbonyl, (1-methyl-piperidin-3-yl)methylaminocarbonyl, 1-(methylaminocarbonyl)piperidin-4-ylmethylaminocarbonyl, 1-(ethoxycarbonyl)piperidin-4-ylmethylaminocarbonyl, 1-(t-butoxycarbonyl)piperidin-4-ylmethylaminocarbonyl, 3-(t-butoxycarbonylamino)-2,2,4,4-tetramethylcyclobut-1-yloxy, and a substituent selected from a) to e);

a)

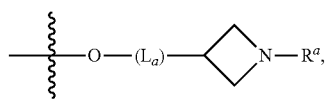

wherein $L_a$ is absent or —(CH₂)ᵣ—, wherein r is an integer of 1 or 2; $R^a$ is methyl;

b)

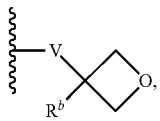

wherein V is absent or —OCH₂—; and wherein $R^b$ is dimethylamino or t-butoxycarbonyl(N-methyl)amino;

c)

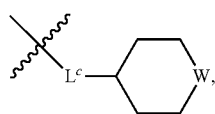

wherein $L^c$ absent or selected from O, S, or —CH₂—; and wherein W is selected from NH, N(methyl), N(cyclopropyl), N(2-fluoroethyl), N(cyanomethyl), N(3-fluoropropyl), N(3-amino-2-hydroxy-prop-1-yl), N(3,3-dimethyl-butyl), CH(amino), CH(methylamino), CH(dimethylamino), or S;

d) a substituent selected from the group consisting of 2-oxo-piperidin-4-yloxy, 4-methyl-piperidin-4-yloxy, 1-methyl-piperidin-3-yloxy, 2-trifluoromethyl-piperidin-4-yloxy, azepan-4-yloxy, 1,4-dimethyl-piperidin-4-yloxy, 2-hydroxymethyl-piperidin-4-yloxy, 2-hydroxymethyl-1-methyl-piperidin-4-yloxy, 3-fluoropiperidin-4-yloxy, 3,3-difluoro-piperidin-4-yloxy, piperazin-1-ylmethyl, 4-methyl-piperazin-1-ylmethyl, 3-oxopiperazin-1-ylmethyl, 4-cyclopropyl-piperazin-1-ylmethyl, 3-hydroxymethyl-piperazin-1-ylmethyl, 4-(2-hydroxyethyl)piperazin-1-ylmethyl, 4-(methylaminocarbonyl)piperazin-1-ylmethyl, 4-(ethoxycarbonyl)piperazin-1-ylmethyl, 4-(ethoxycarbonyl)piper-azin-1-ylcarbonyl, 4-(t-butoxycarbonyl)piperazin-1-ylmethyl, and 4-(t-butoxycarbonyl)piperazin-1-ylcarbonyl;

and $R^3$ is hydrogen, fluoro, or methoxy;

provided that when $R^4$ is bromo, $R^3$ is hydrogen or methoxy;

provided that when $R^4$ is

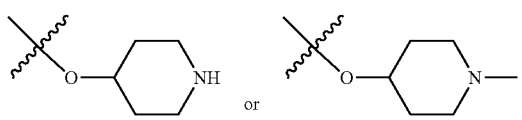

or and $R^3$ is hydrogen or fluoro, $R^1$ is chloro, methoxy, or difluoromethyl;

provided that when $R^4$ is

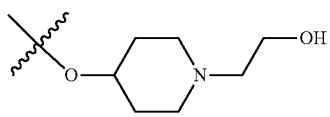 [SMILES: *OC1CCN(CCO)CC1]

and $R^3$ is hydrogen, $R^1$ is chloro, methoxy, or difluoromethyl;

provided that when $R^4$ is

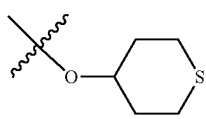 [SMILES: *OC1CCSCC1]

and $R^3$ is hydrogen, $R^1$ is chloro, methoxy, difluoromethyl, or trifluoromethyl;

provided that when $R^4$ is

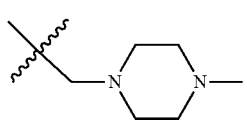 [SMILES: *CN1CCN(C)CC1]

and $R^3$ is hydrogen, $R^1$ is chloro, methyl, methoxy, or difluoromethyl;

ii)

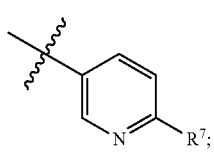

wherein $R^7$ is selected from the group consisting of hydroxy, aminosulfonyl, 2-azabicyclo[2.2.1]heptan-5-yloxy, 3-azabicyclo[3.2.1]octan-8-yloxy, (3-methyl-3-azabicyclo[3.2.1]octan-8-yl)oxy, 9-azaspiro[3.5]nonan-6-yloxy, (9-methyl-9-azaspiro[3.5]nonan-6-yl)oxy, 3-(dimethylamino)propyloxy, 3-(t-butoxycarbonyl)-3-azaspiro[3.3]heptan-6-yloxy, and substituent f)

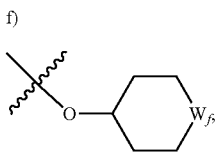

wherein $W_f$ is selected from NH, N(methyl), N(2-hydroxyethyl), N(2-methoxyethyl), N(2-fluoroethyl), N(2,2,2-trifluoroethyl), N(cyanomethyl), N(allyl), N(prop-2-yn-1-yl), or S;

iii) a heteroaryl selected from the group consisting of indazol-5-yl, indazol-6-yl, benzimidazol-5-yl, indol-5-yl, and indol-6-yl; wherein said heteroaryl is independently substituted on the nitrogen-containing portion of the heteroaryl with a substituent selected from methyl, 2-hydroxyethyl, 2-methoxyethyl, piperidin-4-yl, 1-(methyl)piperidin-4-yl, 1-(methylcarbonyl)piperidin-4-yl, 1-(t-butoxycarbonyl)piperidin-4-yl, piperidin-4-ylmethyl, 1-(methylcarbonyl)piperidin-4-ylmethyl, 1-methyl-piperidin-4-ylmethyl, or 1-(t-butoxycarbonyl)piperidin-4-ylmethyl;

and wherein said heteroaryl of iii) is optionally further substituted with an additional methyl substituent;

provided that when G is selected from 1-methyl-2-(1-methyl-piperidin-4-yl)benzimidazol-5-yl, or 1-methyl-2-(piperidin-4-yl)benzimidazol-5-yl, then $R^1$ is chloro, methyl, methoxy, or difluoromethyl;

iv)

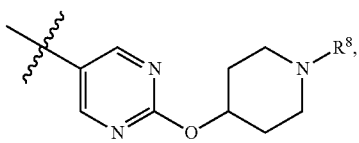

wherein $R^8$ is selected from the group consisting of hydrogen, methyl, and 2-hydroxyethyl;

v) 2-($R^9$)-1,2,3,4-tetrahydroisoquinolin-6-yl, wherein $R^9$ is selected from the group consisting of hydrogen and methyl;

vi)

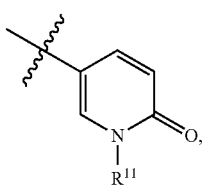

wherein $R^{11}$ is 1-(t-butoxycarbonyl)-azetidin-3-ylmethyl; or vii)

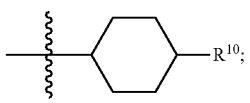

wherein $R^{11}$ is selected from the group consisting of methoxycarbonyl, phenyloxy, and phenylcarbonylamino;

EE) G is i)

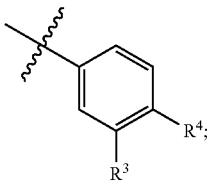

wherein R⁴ is selected from the group consisting of morpholin-4-yl, morpholin-4-ylmethyl, 5-methylmorpholin-2-ylmethoxy, (1-t-butoxycarbonyl)-4,4-difluoropyrrolidin-2-ylmethoxy, (6,6-difluoro-2-methyl-2-azaspiro[3.3]heptan-6-yl)ethoxy, 1H-pyrazol-3-yl, methylaminocarbonylmethyl, 8-methyl-8-azabicyclo[3.2.1]octan-3-yl, 5,8-diazaspiro[2.5]octan-5-ylmethyl, 1-azaspiro[3.3]heptan-6-yloxy, (4-aminopiperidin-1-yl)methyl, (2S,3R,4S)-3,4-dihydroxy-2-methyl-3,4-dihydro-2H-pyran-6-yl, 3,4-dihydroxy-3,4-dihydro-2H-pyran-6-yl, 2-methyl-2-azaspiro[3.3]heptan-6-yl)oxy, (1-methyl-1-azaspiro[3.3]heptan-6-yl)oxy, (2-methyl-2-azabicyclo[2.2.1]heptan-5-yl)oxy, (3-methyl-3-azaspiro[3.3]heptan-6-yl)oxy, 3-azabicyclo[3.2.1]octan-8-yloxy, (1-methylazetidin-3-yl)methylaminocarbonyl, 1-methylpyrrolidin-3-ylaminocarbonyl, (1-methyl-1-oxido-piperidin-1-ium-4-yl)oxy, (3-methyl-3-azabicyclo[3.2.1]octan-8-yl)oxy, 9-azaspiro[3.5]nonan-6-yloxy, (9-methyl-9-azaspiro[3.5]nonan-6-yl)oxy, (1-methylpyrrolidin-3-yl)methylaminocarbonyl, (piperidin-3-yl)methylaminocarbonyl, (4-fluoro-8-azabicyclo[3.2.1]octan-3-yl)oxy, (4-fluoro-8-methyl-8-azabicyclo[3.2.1]octan-3-yl)oxy, (1-methyl-piperidin-4-yl)methylaminocarbonyl, piperidin-4-ylmethylaminocarbonyl, (1-methyl-piperidin-3-yl)methylaminocarbonyl, 1-(ethoxycarbonyl)piperidin-4-ylmethylaminocarbonyl, 1-(t-butoxycarbonyl)piperidin-4-ylmethylaminocarbonyl, 3-(t-butoxy, carbonylamino)-2,2,4,4-tetramethylcyclobut-1-yloxy, and a substituent selected from a) to e);

a)

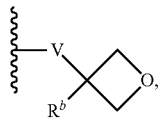

wherein V is absent or —OCH₂—; and wherein $R^b$ is dimethylamino or t-butoxycarbonyl(N-methyl)amino;

b)

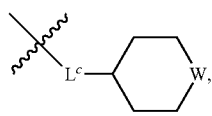

wherein $L^c$ absent or selected from O, S, or —CH₂—; and wherein W is selected from NH, N(methyl), N(cyclopropyl), N(2-fluoroethyl), N(cyanomethyl), N(3-fluoropropyl), N(3-amino-2-hydroxy-prop-1-yl), N(3,3-dimethyl-butyl), CH(amino), CH(methylamino), or CH(dimethylamino);

c) a substituent selected from the group consisting of 4-methyl-piperidin-4-yloxy, 1-methyl-piperidin-3-yloxy, azepan-4-yloxy, 1,4-dimethyl-piperidin-4-yloxy, 2-hydroxymethyl-piperidin-4-yloxy, 2-hydroxymethyl-1-methyl-piperidin-4-yloxy, 3-fluoro-piperidin-4-yloxy, piperazin-1-ylmethyl, 4-methyl-piperazin-1-ylmethyl, 3-oxopiperazin-1-ylmethyl, 4-cyclopropyl-piperazin-1-ylmethyl, 3-hydroxymethyl-piperazin-1-ylmethyl, 4-(2-hydroxyethyl)piperazin-1-ylmethyl, 4-(methylaminocarbonyl)piperazin-1-ylmethyl, and 4-(ethoxycarbonyl)piperazin-1-ylcarbonyl;

and R³ is hydrogen, fluoro, or methoxy;
provided that when R⁴ is bromo. R³ is hydrogen or methoxy;
provided that when R⁴ is

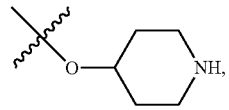

R¹ is chloro, methoxy, or difluoromethyl;
provided that when R⁴ is

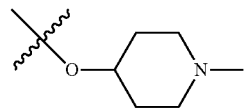 [SMILES: *OC1CCN(C)CC1]

and R³ is hydrogen or fluoro, R¹ is chloro, methoxy, or difluoromethyl;
provided that when R⁴ is

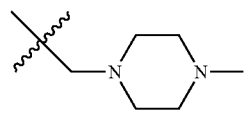 [SMILES: *CN1CCN(C)CC1]

and R³ is hydrogen, R¹ is chloro, methyl, methoxy, or difluoromethyl;

ii)

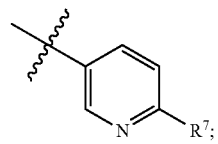

wherein R⁷ is selected from the group consisting of hydroxy, aminosulfonyl, 2-azabicyclo[2.2.1]heptan-5-yloxy, 3-azabicyclo[3.2.1]octan-8-yloxy, (3-methyl-3-azabicyclo[3.2.1]octan-8-yl)oxy, 9-azaspiro[3.5]nonan-6-yloxy, 3-(dimethylamino)propyloxy, 3-(t-butoxycarbonyl)-3-azaspiro[3.3]heptan-6-yloxy, and substituent f)

f)

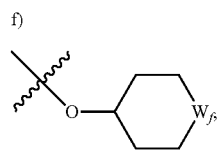

wherein $W_f$ is selected from NH, N(methyl), N(2-methoxyethyl), N(2-fluoroethyl), N(2,2,2-trifluoroethyl), N(allyl), or S;

iii) a heteroaryl selected from the group consisting of indazol-5-yl, indazol-6-yl, and benzimidazol-5-yl; wherein said heteroaryl is independently substituted on the nitrogen-containing portion of the heteroaryl with a substituent selected from methyl, 2-hydroxyethyl, 2-methoxyethyl, piperidin-4-yl, 1-(methyl)piperidin-4-yl, or piperidin-4-ylmethyl;
  and wherein said heteroaryl of iii) is optionally further substituted with an additional methyl substituent;
  provided that when G is selected from 1-methyl-2-(1-methyl-piperidin-4-yl)benzimidazol-5-yl or 1-methyl-2-(piperidin-4-yl)benzimidazol-5-yl, then $R^1$ is chloro, methyl, methoxy, or difluoromethyl;
iv)

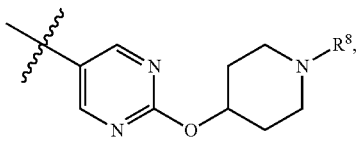

wherein $R^8$ is selected from the group consisting of hydrogen, methyl, and 2-hydroxyethyl;
  v) 2-($R^9$)-1,2,3,4-tetrahydroisoquinolin-6-yl, wherein $R^9$ is selected from the group consisting of hydrogen and methyl;
vi)

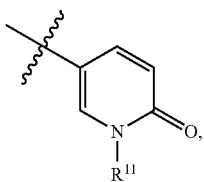

wherein $R^{11}$ is 1-(t-butoxycarbonyl)-azetidin-3-ylmethyl; or
vii)

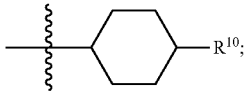

wherein $R^{10}$ is phenylcarbonylamino;
FF) G is
i)

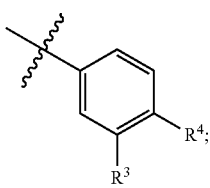

wherein $R^4$ is selected from the group consisting of methylaminocarbonylmethyl, (2S,3R,4S)-3,4-dihydroxy-2-methyl-3,4-dihydro-2H-pyran-6-yl, 9-azaspiro[3.5]nonan-6-yloxy, (piperidin-3-yl)methylaminocarbonyl, 4-methyl-piperidin-4-yloxy, 1-methyl-piperidin-3-yloxy, and substituent a)

a)

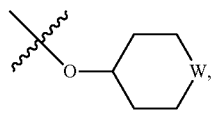

wherein W is selected from N(cyanomethyl), or CH(dimethylamino);
  and $R^3$ is hydrogen, fluoro, or methoxy;
ii)

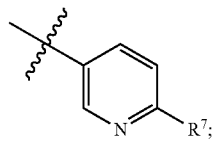

wherein $R^7$ is selected from the group consisting of (3-methyl-3-azabicyclo[3.2.1]octan-8-yl)oxy, 3-(t-butoxycarbonyl)-3-azaspiro[3.3]heptan-6-yloxy, and substituent f)

f)

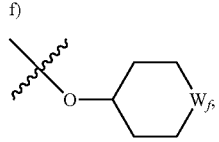

wherein $W_f$ is NH or N(2-fluoroethyl);
  iii) a substituted heteroaryl selected from the group consisting of 1-methylbenzimidazol-5-yl, 2-(2-methoxyethyl)indazol-6-yl, 1-(1-methyl-piperidin-4-yl)indazol-5-yl, 1-(2-methoxyethyl)indazol-6-yl, 2-(2-hydroxyethyl)indazol-5-yl, and 1-(1-methyl-piperidin-4-yl)indazol-5-yl;
GG) G is selected from the group consisting of 4-(((3S)-1-methyl-3-piperidyl)oxy)phenyl, 1-methylbenzimidazol-5-yl, 2-(2-methoxyethyl)indazol-6-yl, 4-(2-azabicyclo[2.2.1]heptan-5-yloxy)phenyl, 4-(methylaminocarbonylmethyl)phenyl, 4-(9-azaspiro[3.5]nonan-6-yloxy)phenyl, 1-(1-methyl-piperidin-4-yl)indazol-5-yl, 4-((1-(cyanomethyl)-piperidin-4-yl)oxy)phenyl, 1-(2-methoxyethyl)indazol-6-yl, 6-((1-(2-fluoroethyl)-piperidin-4-yl)oxy)pyridin-3-yl, 6((3-methyl-3-azabicyclo[3.2.1]octan-8-yl)oxy-pyridin-3-yl, 2-(2-hydroxyethyl)indazol-5-yl, 6-(3-(t-butoxycarbonyl)-3-azaspiro[3.3]heptan-6-yloxy)pyridin-3-yl, 1-(1-methylpiperidin-4-yl)indazol-5-yl, 4-((2S,3R,4S)-3,4-dihydroxy-2-methyl-3,4-dihydro-2H-pyran-6-yl)phenyl, 3-fluoro-4-((3R)-piperidin-3-ylmethylaminocarbonyl)phenyl, 4-((4-methyl-piperidin-4-yl)oxy)phenyl, 6-(piperidin-4-yloxy)-pyridin-3-yl, and 4-(4-(dimethylamino)cyclohexyloxy)phenyl;
  and any combination of embodiments AA) through GG) above, provided that it is understood that combinations in which different embodiments of the same substituent would be combined are excluded; wherein any nitrogen-containing heterocyclic substituent of G is optionally substituted with an oxido substituent to form an N-oxide; or an enantiomer, diastereomer, or pharmaceutically acceptable salt form thereof.

Embodiments of the present invention include a compound of Formula (I)

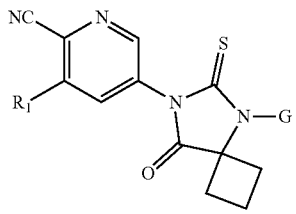

Formula (I)

wherein

R₁ is chloro, methyl, methoxy, difluoromethyl, or trifluoromethyl;

G is i)

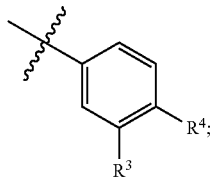

wherein R⁴ is selected from the group consisting of bromo, morpholin-2-yl, morpholin-4-yl, morpholin-4-ylmethyl, morpholin-2-ylmethoxy, 5-methylmorpholin-2-ylmethoxy, 4,4-difluoropyrrolidin-2-ylmethoxy, (1-methylcarbonyl)-4,4-difluoropyrrolidin-2-ylmethoxy, (1-t-butoxycarbonyl)-4,4-difluoropyrrolidin-2-ylmethoxy, (2-oxa-6-azaspiro[3.3]heptan-6-yl)ethoxy, (6,6-difluoro-2-methyl-2-azaspiro[3.3]heptan-6-yl)ethoxy, 2-oxa-8-azaspiro[4.5]decan-8-yl)ethoxy, 1H-pyrazol-4-yl, 1H-pyrazol-3-yl, (1-aminocarbonyl)pyrazol-4-yl, (1-ethylaminocarbonyl)pyrazol-4-yl, methylaminocarbonylmethyl, 2-oxo-imidazolidin-1-yl, (5-methoxymethyl)furan-2-yl, 5-methylfuran-2-yl, tetrahydrofuran-2-yloxy, 4-methylmorpholin-2-yl, 1-methylpyrrolidin-3-yloxy, 8-azabicyclo[3.2.1]oct-3-en-3-yl, 8-methyl-8-azabicyclo[3.2.1]oct-3-en-3-yl, 8-azabicyclo[3.2.1]octan-3-yl, 8-methyl-8-azabicyclo[3.2.1]octan-3-yl, 5,8-diazaspiro[2.5]octan-5-ylmethyl, 1-azaspiro[3.3]heptan-6-yloxy, (4-aminopiperidin-1-yl)methyl, (2S,3R,4S)-3,4-dihydroxy-2-methyl-3,4-dihydro-2H-pyran-6-yl, 3,4-dihydroxy-3,4-dihydro-2H-pyran-6-yl, 2-(hydroxymethyl)-3,4-dihydro-2H-pyran-6-yl, 2-methyl-2-azaspiro[3.3]heptan-6-yl)oxy, 1-methylpiperidin-4-ylcarbonyl, (1-methyl-1-azaspiro[3.3]heptan-6-yl)oxy, (2-methyl-2-azabicyclo[2.2.1]heptan-5-yl)oxy, (3-methyl-3-azaspiro[3.3]heptan-6-yl)oxy, 3-azabicyclo[3.2.1]octan-8-yloxy, (1R,5S)-8-azabicyclo[3.2.1]octan-3-yl]oxy, (1-methylazetidin-3-yl)methylaminocarbonyl, 1-methylpyrrolidin-3-ylaminocarbonyl, (1-methyl-1-oxido-piperidin-1-ium-4-yl)oxy, (3-methyl-3-azabicyclo[3.2.1]octan-8-yl)oxy, (1,2,3,5,6,7,8,8a-octahydroindolizin-7-yl)oxy, 9-azaspiro[3.5]nonan-6-yloxy, (9-methyl-9-azaspiro[3.5]nonan-6-yl)oxy, (1-methylpyrrolidin-3-yl)methylaminocarbonyl, (piperidin-3-yl)methylaminocarbonyl, (4-fluoro-8-azabicyclo[3.2.1]octan-3-yl)oxy, (4-fluoro-8-methyl-8-azabicyclo[3.2.1]octan-3-yl)oxy, (4-fluoro-8-(t-butoxycarbonyl)-8-azabicyclo[3.2.1]octan-3-yl)oxy, (1-methyl-piperidin-4-yl)methylaminocarbonyl, piperidin-4-ylmethylaminocarbonyl, (1-methyl-piperidin-3-yl)methylaminocarbonyl, 1-(methylaminocarbonyl)piperidin-4-ylmethylaminocarbonyl, 1-(ethoxycarbonyl)piperidin-4-ylmethylaminocarbonyl, 1-(t-butoxycarbonyl)piperidin-4-ylmethylaminocarbonyl, 8-(t-butoxycarbonyl)-8-azabicyclo[3.2.1]octan-3-yl, methylaminothiocarbonyl, 3-(t-butoxycarbonylamino)-2,2,4,4-tetramethylcyclobut-1-yloxy, and a substituent selected from a) to e);

a)

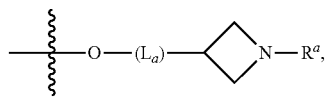

wherein $L_a$ is absent or —(CH₂)$_r$—, wherein r is an integer of 1 or 2; R$^a$ is a substituent selected from methyl or prop-2-yn-1-yl;

b)

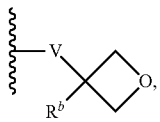

wherein V is absent or —OCH₂—; and wherein R$^b$ is amino, dimethylamino, or t-butoxycarbonyl(N-methyl)amino;

c)

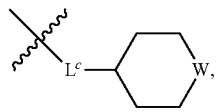

wherein L$^c$ is absent or selected from O, S, or —CH₂—; and wherein W is selected from NH, N(methyl), N(cyclopropyl), N(2-hydroxyethyl), N(2-fluoroethyl), N(2,2,2-trifluoroethyl), N(cyanomethyl), N(1-prop-2-ynyl), N(3-fluoropropyl), N(methoxycarbonylmethyl), N(3-amino-2-hydroxyprop-1-yl), N(3,3-dimethyl-butyl), CH(amino), CH(methylamino), CH(dimethylamino), S, or SO₂;

d) a substituent selected from the group consisting of 2-oxo-piperidin-4-yloxy, 4-methyl-piperidin-4-yloxy, 1-methyl-2-trifluoromethyl-piperidin-4-yloxy, 1-methyl-piperidin-3-yloxy, 2-trifluoromethyl-piperidin-4-yloxy, azepan-4-yloxy, 1-methyl-azepan-4-yloxy, 1-methyl-2-oxo-piperidin-4-yloxy, 1,4-dimethyl-piperidin-4-yloxy, 2-hydroxymethyl-piperidin-4-yloxy, 2-hydroxymethyl-1-methyl-piperidin-4-yloxy, 3-fluoro-piperidin-4-yloxy, 3-fluoro-1-methyl-piperidin-4-yloxy, 3,3-difluoro-piperidin-4-yloxy, 3,3-difluoro-1-methyl-piperidin-4-yloxy, piperazin-1-ylmethyl, 4-methyl-piperazin-1-ylmethyl, 3-oxopiperazin-1-ylmethyl, 4-cyclopropyl-piperazin-1-ylmethyl, 3-hydroxymethyl-piperazin-1-ylmethyl, 4-(2-hydroxyethyl)piperazin-1-ylmethyl, 4-(methylaminocarbonyl)piperazin-1-ylmethyl, 4-(ethoxycarbonyl)piperazin-1-yl, 4-(ethoxycarbonyl)piperazin-1-ylmethyl, 4-(ethoxycarbonyl)piperazin-1-ylcarbonyl, 4-(pyrrolidin-1-ylcarbonyl)piperazin-1-yl, 4-(t-butoxycarbonyl)piperazin-1-ylmethyl, and 4-(t-butoxycarbonyl)piperazin-1-ylcarbonyl;

and R³ is hydrogen, fluoro, or methoxy;
provided that when R⁴ is bromo, R³ is hydrogen or methoxy;
provided that when R⁴ is

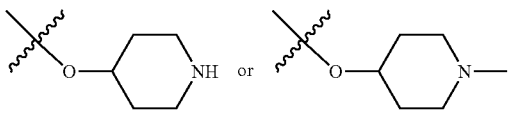

and R³ is hydrogen or fluoro, is chloro, methoxy, or difluoromethyl;
provided that when R⁴ is

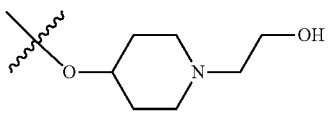 [SMILES: *OC1CCN(CCO)CC1]

and R³ is hydrogen, R¹ is chloro, methoxy, or difluoromethyl;
provided that when R⁴ is

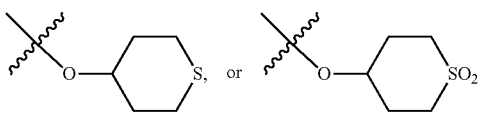 [SMILES: *OC1CCSCC1 ; "or" ; *OC1CCS(=O)(=O)CC1]

and R³ is hydrogen, R¹ is chloro, methoxy, difluoromethyl, or trifluoromethyl;
provided that when R⁴ is

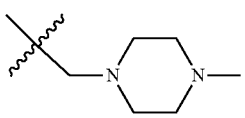

and R³ is hydrogen, R¹ is chloro, methyl, methoxy, or difluoromethyl;
ii)

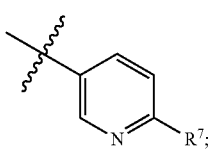

wherein R⁷ is selected from the group consisting of hydroxy, methoxy, aminosulfonyl, 2-azabicyclo[2.2.1]heptan-5-yloxy, 3-azabicyclo[3.2.1]octan-8-yloxy, (3-methyl-3-azabicyclo[3.2.1]octan-8-yl)oxy, 9-azaspiro[3.5]nonan-6-yloxy, (9-methyl-9-azaspiro[3.5]nonan-6-yl)oxy, 3-(dimethylamino)propyloxy, 3-(t-butoxycarbonyl)-3-azaspiro[3.3]heptan-6-yloxy, and substituent f)

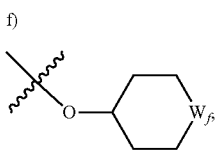

wherein W_f is selected from NH, N(methyl), N(2-hydroxyethyl), N(2-methoxyethyl), N(2-fluoroethyl), N(2,2,2-trifluoroethyl), N(cyanomethyl), N(allyl), N(isopentyl), N(prop-2-yn-1-yl), or S;
iii) a heteroaryl selected from the group consisting of indazol-5-yl, indazol-6-yl, benzimidazol-5-yl, indol-5-yl, and indol-6-yl; wherein said heteroaryl is optionally independently substituted on the nitrogen-containing portion of the heteroaryl with a substituent selected from methyl, 2-hydroxyethyl, 2-methoxyethyl, piperidin-4-yl, 1-(methyl)piperidin-4-yl, 1-(methylcarbonyl)piperidin-4-yl, 1-(t-butoxycarbonyl)piperidin-4-yl, piperidin-4-ylmethyl, 1-(methylcarbonyl)piperidin-4-ylmethyl, 1-methyl-piperidin-4-ylmethyl, or 1-(t-butoxycarbonyl)piperidin-4-ylmethyl;

and wherein said heteroaryl of iii) is optionally further substituted with an additional methyl substituent;

provided that when G is selected from 1-methyl-2-(1-methyl-piperidin-4-yl)benzimidazol-5-yl, 1-methyl-2-(piperidin-4-yl)benzimidazol-5-yl, unsubstituted indazol-5-yl, or unsubstituted indazol-6-yl, then R¹ is chloro, methyl, methoxy, or difluoromethyl;
iv)

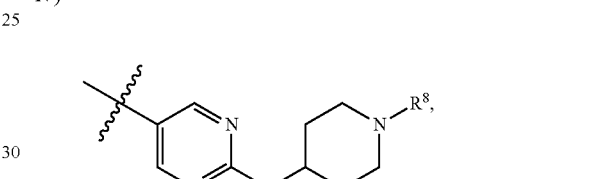

wherein R⁸ is selected from the group consisting of hydrogen, methyl, and 2-hydroxyethyl;
v) 2-(R⁹)-1,2,3,4-tetrahydroisoquinolin-6-yl, wherein R⁹ is selected from the group consisting of hydrogen, methyl, methylcarbonyl, and t-butoxycarbonyl;
vi)

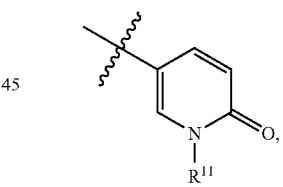

wherein is methyl or 1-(t-butoxycarbonyl)-azetidin-3-ylmethyl; or
vii)

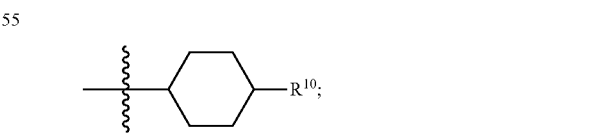

wherein R¹¹ is selected from the group consisting of methoxycarbonyl, phenyloxy, and phenylcarbonylamino;
wherein any nitrogen-containing heterocyclic substituent of G is optionally substituted with an oxido substituent to form an N-oxide; or an enantiomer, diastereomer, or pharmaceutically acceptable salt form thereof.

Embodiments of the present invention include a compound of Formula (I)

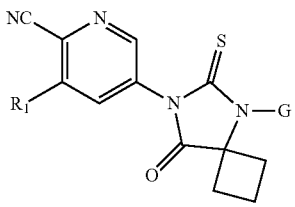

Formula (I)

wherein

R$_1$ is chloro, methyl, methoxy, difluoromethyl, or trifluoromethyl;

G is i)

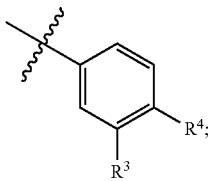

wherein R$^4$ is selected from the group consisting of bromo, morpholin-4-yl, morpholin-4-ylmethyl, 5-methylmorpholin-2-ylmethoxy, 4,4-difluoropyrrolidin-2-ylmethoxy, (1-methylcarbonyl)-4,4-difluoropyrrolidin-2-ylmethoxy, (1-t-butoxycarbonyl)-4,4-difluoropyrrolidin-2-ylmethoxy, (2-oxa-6-azaspiro[3.3]heptan-6-yl)ethoxy, (6,6-difluoro-2-methyl-2-azaspiro[3.3]heptan-6-yl)ethoxy, 2-oxa-8-azaspiro[4.5]decan-8-yl)ethoxy, 1H-pyrazol-3-yl, methylaminocarbonylmethyl, 2-oxo-imidazolidin-1-yl, tetrahydrofuran-2-yloxy, 8-methyl-8-azabicyclo[3.2.1]oct-3-en-3-yl, 8-azabicyclo[3.2.1]octan-3-yl, 8-methyl-8-azabicyclo[3.2.1]octan-3-yl, 5,8-diazaspiro[2.5]octan-5-ylmethyl, 1-azaspiro[3.3]heptan-6-yloxy, (4-aminopiperidin-1-yl)methyl, (2S,3R,4S)-3,4-dihydroxy-2-methyl-3,4-dihydro-2H-pyran-6-yl, 3,4-dihydroxy-3,4-dihydro-2H-pyran-6-yl, 2-methyl-2-azaspiro[3.3]heptan-6-yl)oxy, 1-methylpiperidin-4-ylcarbonyl, (1-methyl-1-azaspiro[3.3]heptan-6-yl)oxy, (2-methyl-2-azabicyclo[2.2.1]heptan-5-yl)oxy, (3-methyl-3-azaspiro[3.3]heptan-6-yl)oxy, 3-azabicyclo[3.2.1]octan-8-yloxy, (1-methylazetidin-3-yl)methylaminocarbonyl, 1-methylpyrrolidin-3-ylaminocarbonyl, (1-methyl-1-oxido-piperidin-1-ium-4-yl)oxy, (3-methyl-3-azabicyclo[3.2.1]octan-8-yl)oxy, (1,2,3,5,6,7,8,8a-octahydroindolizin-7-yl)oxy, 9-azaspiro[3.5]nonan-6-yloxy, (9-methyl-9-azaspiro[3.5]nonan-6-yl)oxy, (1-methylpyrrolidin-3-yl)methylaminocarbonyl, (piperidin-3-yl)methylaminocarbonyl, (4-fluoro-8-azabicyclo[3.2.1]octan-3-yl)oxy, (4-fluoro-8-methyl-8-azabicyclo[3.2.1]octan-3-yl)oxy, (4-fluoro-8-(t-butoxycarbonyl)-8-azabicyclo[3.2.1]octan-3-yl)oxy, (1-methyl-piperidin-4-yl)methylaminocarbonyl, piperidin-4-ylmethylaminocarbonyl, (1-methyl-piperidin-3-yl)methylaminocarbonyl, 1-(methylaminocarbonyl)piperidin-4-ylmethylaminocarbonyl, 1-(ethoxycarbonyl)piperidin-4-ylmethylaminocarbonyl, 1-(t-butoxycarbonyl)piperidin-4-ylmethylaminocarbonyl, 3-(t-butoxycarbonylamino)-2,2,4,4-tetramethylcyclobut-1-yloxy, and a substituent selected from a) to e);

a)

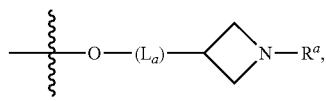

wherein L$_a$ is absent or —(CH$_2$)$_r$—, wherein r is an integer of 1 or 2; R$^a$ is methyl;

b)

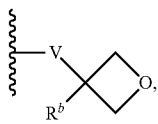

wherein V is absent or —OCH$_2$—; and wherein R$^b$ is dimethylamino or t-butoxycarbonyl(N-methyl)amino;

c)

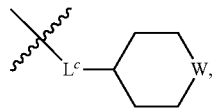

wherein L$^c$ absent or selected from O, S, or —CH$_2$—; and wherein W is selected from NH, N(methyl), N(cyclopropyl), N(2-fluoroethyl), N(cyanomethyl), N(3-fluoropropyl), N(3-amino-2-hydroxy-prop-1-yl), N(3,3-dimethyl-butyl), CH(amino), CH(methylamino), CH(dimethylamino), or S;

d) a substituent selected from the group consisting of 2-oxo-piperidin-4-yloxy, 4-methyl-piperidin-4-yloxy, 1-methyl-piperidin-3-yloxy, 2-trifluoromethyl-piperidin-4-yloxy, azepan-4-yloxy, 1,4-dimethyl-piperidin-4-yloxy, 2-hydroxymethyl-piperidin-4-yloxy, 2-hydroxymethyl-1-methyl-piperidin-4-yloxy, 3-fluoro-piperidin-4-yloxy, 3,3-difluoro-piperidin-4-yloxy, piperazin-1-ylmethyl, 4-methyl-piperazin-1-ylmethyl, 3-oxopiperazin-1-ylmethyl, 4-cyclopropyl-piperazin-1-ylmethyl, 3-hydroxymethyl-piperazin-1-ylmethyl, 4-(2-hydroxyethyl)piperazin-1-ylmethyl, 4-(methylaminocarbonyl)piperazin-1-ylmethyl, 4-(ethoxycarbonyl)piperazin-1-ylmethyl, 4-(ethoxycarbonyl)piperazin-1-ylcarbonyl, 4-(t-butoxycarbonyl)piperazin-1-ylmethyl, and 4-(t-butoxycarbonyl)piperazin-1-ylcarbonyl;

and R$^3$ is hydrogen, fluoro, or methoxy;

provided that when R$^4$ is bromo, R$^3$ is hydrogen or methoxy;

provided that when R$^4$ is

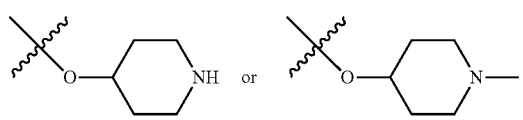

and R$^3$ is hydrogen or fluoro, is chloro, methoxy, or difluoromethyl;

provided that when R⁴ is

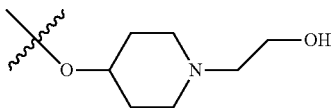 [SMILES: *OC1CCN(CCO)CC1]

and R³ is hydrogen, R¹ is chloro, methoxy, or difluoromethyl;
provided that when R⁴ is

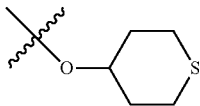 [SMILES: *OC1CCSCC1]

and R³ is hydrogen, R¹ is chloro, methoxy, difluoromethyl, or trifluoromethyl;
provided that when R⁴ is

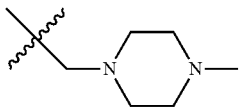 [SMILES: *CN1CCN(C)CC1]

and R³ is hydrogen, R¹ is chloro, methyl, methoxy, or difluoromethyl;
ii)

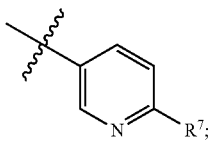

wherein R⁷ is selected from the group consisting of hydroxy, aminosulfonyl, 2-azabicyclo[2.2.1]heptan-5-yloxy, 3-azabicyclo[3.2.1]octan-8-yloxy, (3-methyl-3-azabicyclo[3.2.1]octan-8-yl)oxy, 9-azaspiro[3.5]nonan-6-yloxy, (9-methyl-9-azaspiro[3.5]nonan-6-yl)oxy, 3-(dimethylamino)propyloxy, 3-(t-butoxycarbonyl)-3-azaspiro[3.3]heptan-6-yloxy, and substituent f)

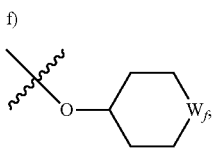

wherein W_f is selected from NH, N(methyl), N(2-hydroxyethyl), N(2-methoxyethyl), N(2-fluoroethyl), N(2,2,2-trifluoroethyl), N(cyanomethyl), N(allyl), N(prop-2-yn-1-yl), or S;
iii) a heteroaryl selected from the group consisting of indazol-5-yl, indazol-6-yl, benzimidazol-5-yl, indol-5-yl, and indol-6-yl; wherein said heteroaryl is independently substituted on the nitrogen-containing portion of the heteroaryl with a substituent selected from methyl, 2-hydroxyethyl, 2-methoxyethyl, piperidin-4-yl, 1-(methyl)piperidin-4-yl, 1-(methylcarbonyl)piperidin-4-yl, 1-(t-butoxycarbonyl)piperidin-4-yl, piperidin-4-ylmethyl, 1-(methylcarbonyl)piperidin-4-ylmethyl, 1-methyl-piperidin-4-ylmethyl, or 1-(t-butoxycarbonyl)piperidin-4-ylmethyl;
and wherein said heteroaryl of iii) is optionally further substituted with an additional methyl substituent;
provided that when G is selected from 1-methyl-2-(1-methyl-piperidin-4-yl)benzimidazol-5-yl, or 1-methyl-2-(piperidin-4-yl)benzimidazol-5-yl, then R¹ is chloro, methyl, methoxy, or difluoromethyl;
iv)

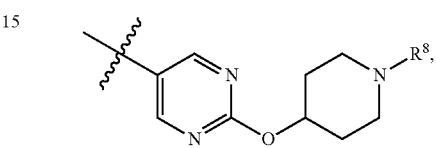

wherein R⁸ is selected from the group consisting of hydrogen, methyl, and 2-hydroxyethyl;
v) 2-(R⁹)-1,2,3,4-tetrahydroisoquinolin-6-yl, wherein R⁹ is selected from the group consisting of hydrogen and methyl;
vi)

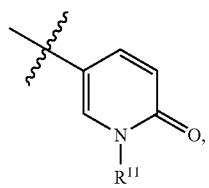

wherein R¹¹ is 1-(t-butoxycarbonyl)-azetidin-3-ylmethyl; or
vii)

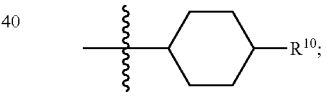

wherein R¹⁰ is selected from the group consisting of methoxycarbonyl, phenyloxy, and phenylcarbonylamino;
wherein any nitrogen-containing heterocyclic substituent of G is optionally substituted with an oxido substituent to form an N-oxide;
or an enantiomer, diastereomer, or pharmaceutically acceptable salt form thereof.

Embodiments of the present invention include a compound of Formula (I)

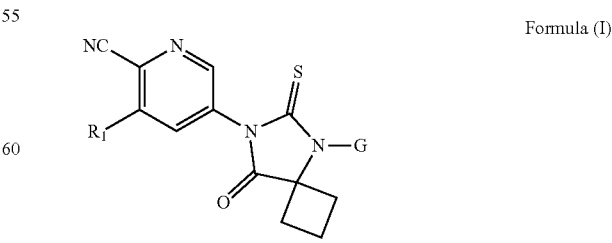

Formula (I)

wherein
R₁ is chloro, methyl, methoxy, difluoromethyl, or trifluoromethyl;

G is i)

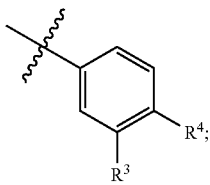

wherein R⁴ is selected from the group consisting of morpholin-4-yl, morpholin-4-ylmethyl, 5-methylmorpholin-2-ylmethoxy, (1-t-butoxycarbonyl)-4,4-difluoropyrrolidin-2-ylmethoxy, (6,6-difluoro-2-methyl-2-azaspiro[3.3]heptan-6-yl)ethoxy, 1H-pyrazol-3-yl, methylaminocarbonylmethyl, 8-methyl-8-azabicyclo[3.2.1]octan-3-yl, 5,8-diazaspiro[2.5]octan-5-ylmethyl, 1-azaspiro[3.3]heptan-6-yloxy, (4-aminopiperidin-1-yl)methyl, (2S,3R,4S)-3,4-dihydroxy-2-methyl-3,4-dihydro-2H-pyran-6-yl, 3,4-dihydroxy-3,4-dihydro-2H-pyran-6-yl, 2-methyl-2-azaspiro[3.3]heptan-6-yl)oxy, (1-methyl-1-azaspiro[3.3]heptan-6-yl)oxy, (2-methyl-2-azabicyclo[2.2.1]heptan-5-yl)oxy, (3-methyl-3-azaspiro[3.3]heptan-6-yl)oxy, 3-azabicyclo[3.2.1]octan-8-yloxy, (1-methylazetidin-3-yl)methylaminocarbonyl, 1-methylpyrrolidin-3-ylaminocarbonyl, (1-methyl-1-oxidopiperidin-1-ium-4-yl)oxy, (3-methyl-3-azabicyclo[3.2.1]octan-8-yl)oxy, 9-azaspiro[3.5]nonan-6-yloxy, (9-methyl-9-azaspiro[3.5]nonan-6-yl)oxy, (1-methylpyrrolidin-3-yl)methylaminocarbonyl, (piperidin-3-yl)methylaminocarbonyl, (4-fluoro-8-azabicyclo[3.2.1]octan-3-yl)oxy, (4-fluoro-8-methyl-8-azabicyclo[3.2.1]octan-3-yl)oxy, (1-methyl-piperidin-4-yl)methylaminocarbonyl, piperidin-4-ylmethylaminocarbonyl, (1-methyl-piperidin-3-yl)methylaminocarbonyl, 1-(ethoxycarbonyl)piperidin-4-ylmethylaminocarbonyl, 1-(t-butoxycarbonyl)piperidin-4-ylmethylaminocarbonyl, 3-(t-butoxycarbonylamino)-2,2,4,4-tetramethylcyclobut-1-yloxy, and a substituent selected from a) to e);

a)

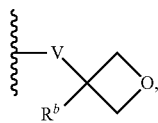

wherein V is absent or —OCH₂—; and wherein $R^b$ is dimethylamino or t-butoxycarbonyl(N-methyl)amino;

b)

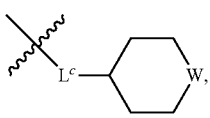

wherein $L^c$ absent or selected from O, S, or —CH₂—; and wherein W is selected from NH, N(methyl), N(cyclopropyl), N(2-fluoroethyl), N(cyanomethyl), N(3-fluoropropyl), N(3-amino-2-hydroxy-prop-1-yl), N(3,3-dimethyl-butyl), CH(amino), CH(methylamino), or CH(dimethylamino);

c) a substituent selected from the group consisting of 4-methyl-piperidin-4-yloxy, 1-methyl-piperidin-3-yloxy, azepan-4-yloxy, 1,4-dimethyl-piperidin-4-yloxy, 2-hydroxymethyl-piperidin-4-yloxy, 2-hydroxymethyl-1-methyl-piperidin-4-yloxy, 3-fluoro-piperidin-4-yloxy, piperazin-1-ylmethyl, 4-methyl-piperazin-1-ylmethyl, 3-oxopiperazin-1-ylmethyl, 4-cyclopropyl-piperazin-1-ylmethyl, 3-hydroxymethyl-piperazin-1-ylmethyl, 4-(2-hydroxyethyl)piperazin-1-ylmethyl, 4-(methylaminocarbonyl)piperazin-1-ylmethyl, and 4-(ethoxycarbonyl)piperazin-1-ylcarbonyl;

and R³ is hydrogen, fluoro, or methoxy;
provided that when R⁴ is bromo, R³ is hydrogen or methoxy;
provided that when R⁴ is

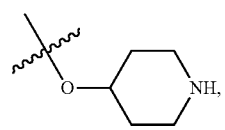 [SMILES: *OC1CCNCC1]

R¹ is chloro, methoxy, or difluoromethyl;
provided that when R⁴ is

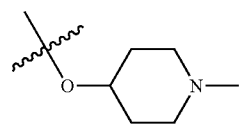 [SMILES: *OC1CCN(C)CC1]

and R³ is hydrogen or fluoro, R¹ is chloro, methoxy, or difluoromethyl;
provided that when R⁴ is

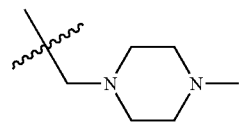 [SMILES: *CN1CCN(C)CC1]

and R³ is hydrogen, R¹ is chloro, methyl, methoxy, or difluoromethyl;

ii)

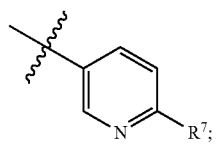

wherein R⁷ is selected from the group consisting of hydroxy, aminosulfonyl, 2-azabicyclo[2.2.1]heptan-5-yloxy, 3-azabicyclo[3.2.1]octan-8-yloxy, (3-methyl-3-azabicyclo[3.2.1]octan-8-yl)oxy, 9-azaspiro[3.5]nonan-6-yloxy, 3-(dimethylamino)propyloxy, 3-(t-butoxycarbonyl)-3-azaspiro[3.3]heptan-6-yloxy, and substituent f)

f)

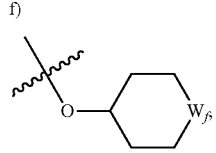

wherein $W_f$ is selected from NH, N(methyl), N(2-methoxyethyl), N(2-fluoroethyl), N(2,2,2-trifluoroethyl), N(allyl), or S;

iii) a heteroaryl selected from the group consisting of indazol-5-yl, indazol-6-yl, and benzimidazol-5-yl; wherein said heteroaryl is independently substituted on the nitrogen-containing portion of the heteroaryl with a substituent selected from methyl, 2-hydroxyethyl, 2-methoxyethyl, piperidin-4-yl, 1-(methyl)piperidin-4-yl, or piperidin-4-ylmethyl;

and wherein said heteroaryl of iii) is optionally further substituted with an additional methyl substituent;

provided that when G is selected from 1-methyl-2-(1-methyl-piperidin-4-yl)benzimidazol-5-yl, or 1-methyl-2-(piperidin-4-yl)benzimidazol-5-yl, then $R^1$ is chloro, methyl, methoxy, or difluoromethyl;

iv)

[structure]

wherein $R^8$ is selected from the group consisting of hydrogen, methyl, and 2-hydroxyethyl;

v) 2-($R^9$)-1,2,3,4-tetrahydroisoquinolin-6-yl, wherein $R^9$ is selected from the group consisting of hydrogen and methyl;

vi)

[structure]

wherein $R^{11}$ is 1-(t-butoxycarbonyl)-azetidin-3-ylmethyl; or vii)

[structure]

wherein $R^{10}$ is phenylcarbonylamino;

wherein any nitrogen-containing heterocyclic substituent of G is optionally substituted with an oxido substituent to form an N-oxide;

or an enantiomer, diastereomer, or pharmaceutically acceptable salt form thereof.

Embodiments of the present invention include a compound of Formula (I)

Formula (I)

[structure]

wherein $R_1$ is chloro, methyl, methoxy, difluoromethyl, or trifluoromethyl;

G is i)

[structure]

wherein $R^4$ is selected from the group consisting of methylaminocarbonylmethyl, (2S,3R,4S)-3,4-dihydroxy-2-methyl-3,4-dihydro-2H-pyran-6-yl, 9-azaspiro[3.5]nonan-6-yloxy, (piperidin-3-yl)methylaminocarbonyl, 4-methyl-piperidin-4-yloxy, 1-methyl-piperidin-3-yloxy, and a substituent a)

a)

[structure]

wherein W is selected from N(cyanomethyl), or CH(dimethylamino);

and $R^3$ is hydrogen, fluoro, or methoxy;

ii)

[structure]

wherein $R^7$ is selected from the group consisting of (3-methyl-3-azabicyclo[3.2.1]octan-8-yl)oxy, 3-(t-butoxycarbonyl)-3-azaspiro[3.3]heptan-6-yloxy, and substituent f)

f)

[structure]

wherein $W_f$ is NH or N(2-fluoroethyl); or iii) a substituted heteroaryl selected from the group consisting of 1-methylbenzimidazol-5-yl, 2-(2-methoxyethyl)indazol-6-yl, 1-(1-methyl-piperidin-4-yl)indazol-5-yl, 1-(2-methoxyethyl)indazol-6-yl, 2-(2-hydroxyethyl)indazol-5-yl, and 1-(1-methyl-piperidin-4-yl)indazol-5-yl;

wherein any nitrogen-containing heterocyclic substituent of G is optionally substituted with an oxido substituent to form an N-oxide;

or an enantiomer, diastereomer, or pharmaceutically acceptable salt form thereof.

Embodiments of the present invention include a compound of Formula (I)

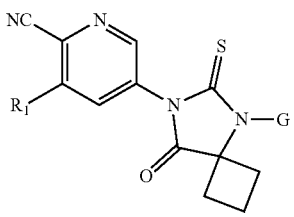

Formula (I)

wherein

R$_1$ is chloro, methyl, methoxy, difluoromethyl, or trifluoromethyl;

G is selected from the group consisting of 4-(((3S)-1-methyl-3-piperidyl)oxy)phenyl, 1-methylbenzimidazol-5-yl, 2-(2-methoxyethyl)indazol-6-yl, 4-(2-azabicyclo[2.2.1]heptan-5-yloxy)phenyl, 4-(methylaminocarbonyl-methyl)phenyl, 4-(9-azaspiro[3.5]nonan-6-yloxy)phenyl, 1-(1-methyl-piperidin-4-yl)indazol-5-yl, 4-((1-(cyanomethyl)-piperidin-4-yl)oxy)phenyl, 1-(2-methoxyethyl)indazol-6-yl, 6-((1-(2-fluoroethyl)-piperidin-4-yl)oxy)pyridin-3-yl, 6-((3-methyl-3-azabicyclo[3.2.1]octan-8-yl)oxy-pyridin-3-yl, 2-(2-hydroxyethyl)indazol-5-yl, 6-(3-(t-butoxycarbonyl)-3-azaspiro[3.3]heptan-6-yloxy)pyridin-3-yl, 1-(1-methylpiperidin-4-yl)indazol-5-yl, 4-((2S,3R,4S)-3,4-dihydroxy-2-methyl-3,4-dihydro-2H-pyran-6-yl)phenyl, 3-fluoro-4-((3R)-piperidin-3-ylmethylaminocarbonyl)phenyl, 4-((4-methyl-piperidin-4-yl)oxy)phenyl, 6-(piperidin-4-yloxy)-pyridin-3-yl, and 4-(4-(dimethylamino)cyclohexyloxy)phenyl;

wherein any nitrogen-containing heterocyclic substituent of G is optionally substituted with an oxido substituent to form an N-oxide;

or an enantiomer, diastereomer, or pharmaceutically acceptable salt form thereof.

Embodiments of the present invention include a compound of Formula (I)

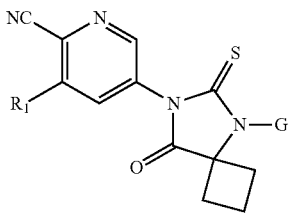

Formula (I)

wherein

R$_1$ is chloro, methyl, methoxy, or trifluoromethyl;

G is selected from the group consisting of 4-(((3S)-1-methyl-3-piperidyl)oxy)phenyl, 1-methylbenzimidazol-5-yl, 2-(2-methoxyethyl)indazol-6-yl, 4-(2-azabicyclo[2.2.1]heptan-5-yloxy)phenyl, 4-(methylaminocarbonyl-methyl)phenyl, 4-(9-azaspiro[3.5]nonan-6-yloxy)phenyl, 1-(1-methyl-piperidin-4-yl)indazol-5-yl, 4-((1-(cyanomethyl)-piperidin-4-yl)oxy)phenyl, 1-(2-methoxyethyl)indazol-6-yl, 6-((1-(2-fluoroethyl)-piperidin-4-yl)oxy)pyridin-3-yl, 6-((3-methyl-3-azabicyclo[3.2.1]octan-8-yl)oxy-pyridin-3-yl, 2-(2-hydroxyethyl)indazol-5-yl, 6-(3-(t-butoxycarbonyl)-3-azaspiro[3.3]heptan-6-yloxy)pyridin-3-yl, 1-(1-methylpiperidin-4-yl)indazol-5-yl, 4-((2S,3R,4S)-3,4-dihydroxy-2-methyl-3,4-dihydro-2H-pyran-6-yl)phenyl, 3-fluoro-4-((3R)-piperidin-3-ylmethylaminocarbonyl)phenyl, 4-((4-methyl-piperidin-4-yl)oxy)phenyl, 6-(piperidin-4-yloxy)-pyridin-3-yl, and 4-(4-(dimethylamino)cyclohexyloxy)phenyl;

wherein any nitrogen-containing heterocyclic substituent of G is optionally substituted with an oxido substituent to form an N-oxide;

or an enantiomer, diastereomer, or pharmaceutically acceptable salt form thereof.

Additional embodiments of the present invention include a compound of Formula (I)

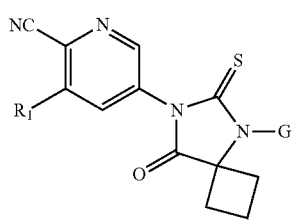

Formula (I)

wherein

R$_1$ is chloro, methyl, methoxy, or trifluoromethyl;

G is

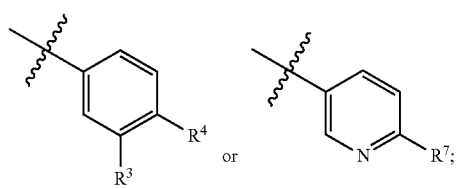

R$^4$ and R$^7$ are independently

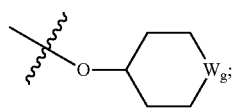

wherein W$_g$ is selected from NH, N(methyl), N(2-methoxyethyl), N(2-fluoroethyl), or N(allyl);

R$^3$ is hydrogen, fluoro, or methoxy;

provided that when R$^4$ is

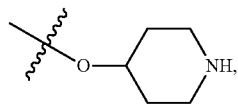 [SMILES: *OC1CCNCC1]

R$^1$ is chloro or methoxy;

provided that when R$^4$ is

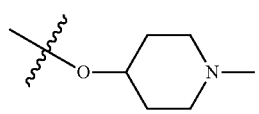 [SMILES: *OC1CCN(C)CC1]

and R$^3$ is hydrogen or fluoro, R$^1$ is chloro or methoxy;

wherein any nitrogen-containing heterocyclic substituent of G is optionally substituted with an oxido substituent to form an N-oxide;

or a pharmaceutically acceptable salt form thereof.

A further embodiment of the present invention is directed to a compound of Formula (I) selected from the group consisting of Cpd 1, 5-[8-[6-[(1-methyl-4-piperidyl)oxy]-3-pyridyl]-5-oxo-7-thioxo-6,8-diazaspiro[3.4]octan-6-yl]-3-(trifluoromethyl)pyridine-2-carbonitrile;

Cpd 2, 3-methyl-5-[8-[6-[(1-methyl-4-piperidyl)oxy]-3-pyridyl]-5-oxo-7-thioxo-6,8-diazaspiro[3.4]octan-6-yl]pyridine-2-carbonitrile;

Cpd 23, 3-methoxy-5-[8-[4-[(1-methyl-4-piperidyl)oxy]phenyl]-5-oxo-7-thioxo-6,8-diazaspiro[3.4]octan-6-yl]pyridine-2-carbonitrile;

Cpd 24, 3-chloro-5-[8-[4-[(1-methyl-4-piperidyl)oxy]phenyl]-5-oxo-7-thioxo-6,8-diazaspiro[3.4]octan-6-yl]pyridine-2-carbonitrile;

Cpd 25, 3-methoxy-5-[8-[4-[(1-methyl-4-piperidyl)oxy]-3-pyridyl]-5-oxo-7-thioxo-6,8-diazaspiro[3.4]octan-6-yl]pyridine-2-carbonitrile;

Cpd 26, 3-chloro-5-[8-[4-[(1-methyl-4-piperidyl)oxy]-3-pyridyl]-5-oxo-7-thioxo-6,8-diazaspiro[3.4]octan-6-yl]pyridine-2-carbonitrile;

Cpd 43, 5-[5-oxo-8-[6-(4-piperidyloxy)-3-pyridyl]-7-thioxo-6,8-diazaspiro[3.4]octan-6-yl]-3-(trifluoromethyl)pyridine-2-carbonitrile;

Cpd 44, 3-chloro-5-[5-oxo-8-[4-(4-piperidyloxy)phenyl]-7-thioxo-6,8-diazaspiro[3.4]octan-6-yl]pyridine-2-carbonitrile;

Cpd 64, 3-chloro-5-[5-oxo-8-[6-(4-piperidyloxy)-3-pyridyl]-7-thioxo-6,8-diazaspiro[3.4]octan-6-yl]pyridine-2-carbonitrile;

Cpd 75, 3-methoxy-5-[5-oxo-8-[6-(4-piperidyloxy)-3-pyridyl]-7-thioxo-6,8-diazaspiro[3.4]octan-6-yl]pyridine-2-carbonitrile;

Cpd 87, 3-methyl-5-[5-oxo-8-[6-(4-piperidyloxy)-3-pyridyl]-7-thioxo-6,8-diazaspiro[3.4]octan-6-yl]pyridine-2-carbonitrile;

and

Cpd 154, 3-methoxy-5-[5-oxo-8-[4-(4-piperidyloxy)phenyl]-7-thioxo-6,8-diazaspiro[3.4]octan-6-yl]pyridine-2-carbonitrile;

or pharmaceutically acceptable salt form thereof.

Additional embodiments of the present invention include compounds of Formula (I) as herein defined, or an enantiomer, diastereomer, solvate, or a pharmaceutically acceptable salt form thereof, as exemplified in the listing in Table 1, below.

TABLE 1

| Structure | Cpd No. | Cpd Name |
| --- | --- | --- |
| 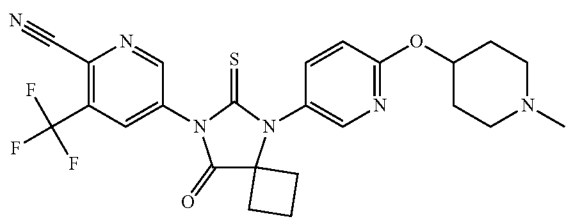 [SMILES: CN1CCC(Oc2ccc(N3C(=S)N(c4cnc(C#N)c(C(F)(F)F)c4)C(=O)C34CCC4)cn2)CC1] | 1 | 5-[8-[6-[(1-methyl-4-piperidyl)oxy]-3-pyridyl]-5-oxo-7-thioxo-6,8-diazaspiro[3.4]octan-6-yl]-3-(trifluoromethyl)pyridine-2-carbonitrile |
| 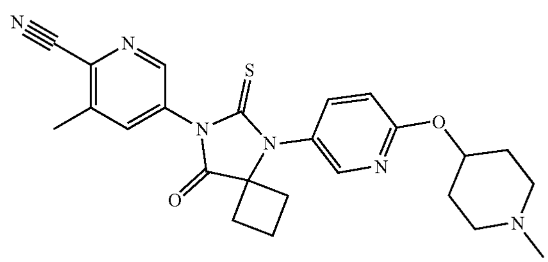 [SMILES: Cc1cc(N2C(=O)C3(CCC3)N(c3ccc(OC4CCN(C)CC4)nc3)C2=S)cnc1CN] | 2 | 3-methyl-5-[8-[6-[(1-methyl-4-piperidyl)oxy]-3-pyridyl]-5-oxo-7-thioxo-6,8-diazaspiro[3.4]octan-6-yl]pyridine-2-carbonitrile |
| 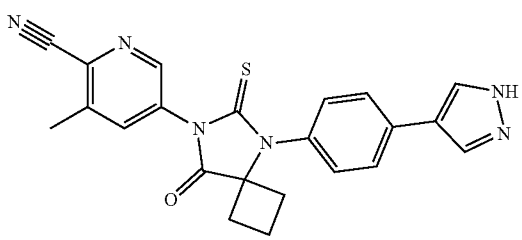 [SMILES: Cc1cc(N2C(=O)C3(CCC3)N(c3ccc(-c4cn[nH]c4)cc3)C2=S)cnc1CN] | 3 | 3-methyl-5-[5-oxo-8-[4-(1H-pyrazol-4-yl)phenyl]-7-thioxo-6,8-diazaspiro[3.4]octan-6-yl]pyridine-2-carbonitrile |
| 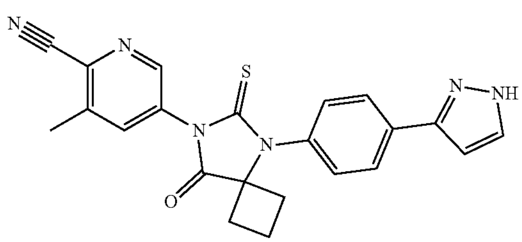 [SMILES: Cc1cc(N2C(=O)C3(CCC3)N(c3ccc(-c4cc[nH]n4)cc3)C2=S)cnc1CN] | 4 | 3-methyl-5-[5-oxo-8-[4-(1H-pyrazol-3-yl)phenyl]-7-thioxo-6,8-diazaspiro[3.4]octan-6-yl]pyridine-2-carbonitrile |

TABLE 1-continued

| Structure | Cpd No. | Cpd Name |
|---|---|---|
| 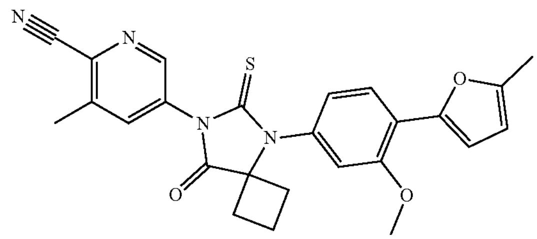 [SMILES: COc1cc(N2C(=S)N(c3cnc(CN)c(C)c3)C(=O)C23CCC3)ccc1-c1ccc(C)o1] | 5 | 5-[8-[3-methoxy-4-(5-methyl-2-furyl)phenyl]-5-oxo-7-thioxo-6,8-diazaspiro[3.4]octan-6-yl]-3-methyl-pyridine-2-carbonitrile |
| 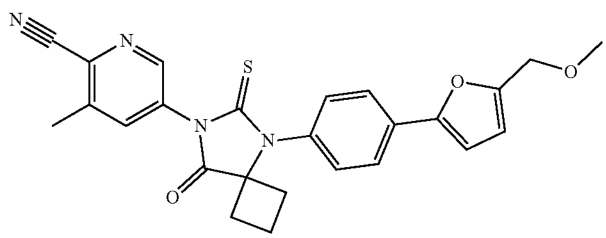 [SMILES: COCc1ccc(-c2ccc(N3C(=S)N(c4cnc(CN)c(C)c4)C(=O)C34CCC4)cc2)o1] | 6 | 5-[8-[4-[5-(methoxymethyl)-2-furyl]phenyl]-5-oxo-7-thioxo-6,8-diazaspiro[3.4]octan-6-yl]-3-methyl-pyridine-2-carbonitrile |
| 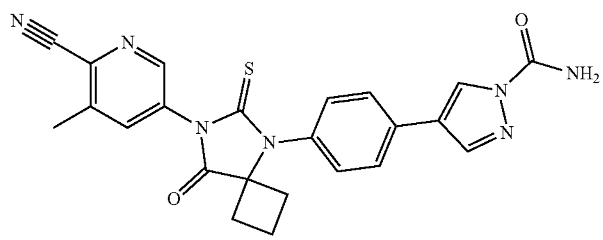 [SMILES: Cc1cc(N2C(=O)C3(CCC3)N(c3ccc(-c4cnn(C(N)=O)c4)cc3)C2=S)cnc1CN] | 7 | 4-[4-[6-(6-cyano-5-methyl-3-pyridyl)-5-oxo-7-thioxo-6,8-diazaspiro[3.4]octan-8-yl]phenyl]pyrazole-1-carboxamide |
| 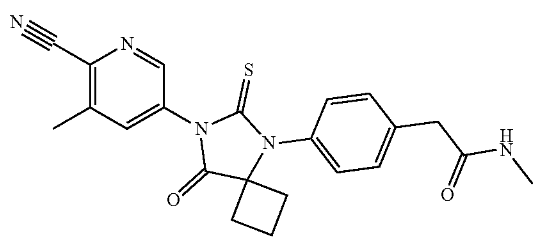 [SMILES: CNC(=O)Cc1ccc(N2C(=S)N(c3cnc(CN)c(C)c3)C(=O)C23CCC3)cc1] | 8 | 2-[4-[6-(6-cyano-5-methyl-3-pyridyl)-5-oxo-7-thioxo-6,8-diazaspiro[3.4]octan-8-yl]phenyl]-N-methyl-acetamide |
| 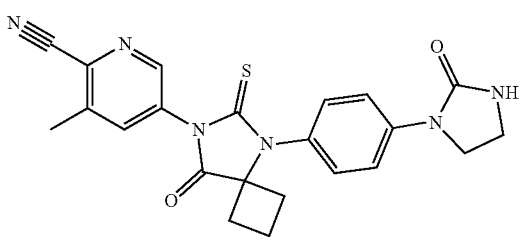 [SMILES: Cc1cc(N2C(=O)C3(CCC3)N(c3ccc(N4CCNC4=O)cc3)C2=S)cnc1CN] | 9 | 3-methyl-5-[5-oxo-8-[4-(2-oxoimidazolidin-1-yl)phenyl]-7-thioxo-6,8-diazaspiro[3.4] octan-6-yl]pyridine-2-carbonitrile |
| 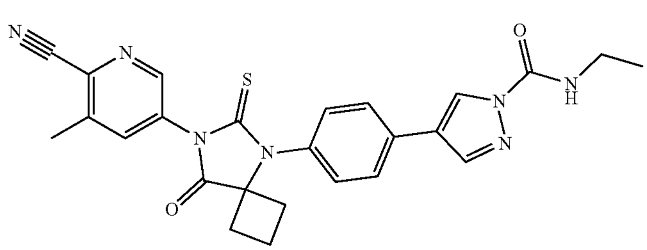 [SMILES: CCNC(=O)n1cc(-c2ccc(N3C(=S)N(c4cnc(CN)c(C)c4)C(=O)C34CCC4)cc2)cn1] | 10 | 4-[4-[6-(6-cyano-5-methyl-3-pyridyl)-5-oxo-7-thioxo-6,8-diazaspiro[3.4]octan-8-yl]phenyl]-N-ethyl-pyrazole-1-carboxamide |

TABLE 1-continued

| Structure | Cpd No. | Cpd Name |
|---|---|---|
| 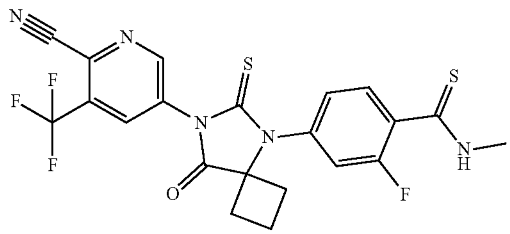 [SMILES: CNC(=S)c1ccc(N2C(=S)N(c3cnc(CN)c(C(F)(F)F)c3)C(=O)C23CCC3)cc1F] | 11 | 4-[6-[6-cyano-5-(trifluoromethyl)-3-pyridyl]-5-oxo-7-thioxo-6,8-diazaspiro[3.4]octan-8-yl]-2-fluoro-N-methyl-benzenecarbothioamide |
| 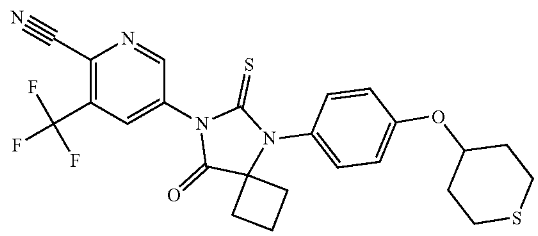 [SMILES: NCc1ncc(N2C(=O)C3(CCC3)N(c3ccc(OC4CCSCC4)cc3)C2=S)cc1C(F)(F)F] | 12 | 5-[5-oxo-8-(4-tetrahydrothiopyran-4-yloxyphenyl)-7-thioxo-6,8-diazaspiro[3.4]octan-6-yl]-3-(trifluoromethyl)pyridine-2-carbonitrile |
| 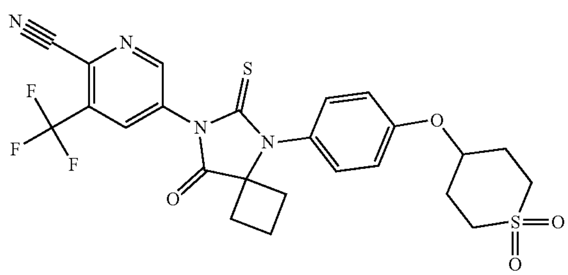 [SMILES: NCc1ncc(N2C(=O)C3(CCC3)N(c3ccc(OC4CCS(=O)(=O)CC4)cc3)C2=S)cc1C(F)(F)F] | 13 | 5-[8-[4-(1,1-dioxothian-4-yl)oxyphenyl]-5-oxo-7-thioxo-6,8-diazaspiro[3.4]octan-6-yl]-3-(trifluoromethyl)pyridine-2-carbonitrile |
| 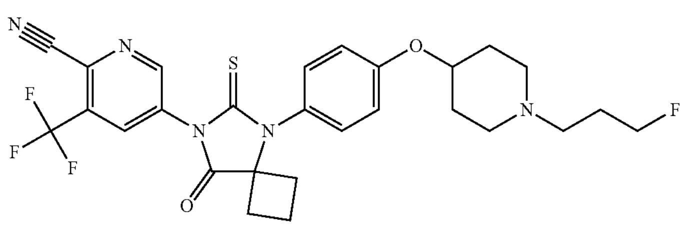 [SMILES: NCc1ncc(N2C(=O)C3(CCC3)N(c3ccc(OC4CCN(CCCF)CC4)cc3)C2=S)cc1C(F)(F)F] | 14 | 5-[8-[4-[[1-(3-fluoropropyl)-4-piperidyl]oxy]phenyl]-5-oxo-7-thioxo-6,8-diazaspiro[3.4]octan-6-yl]-3-(trifluoromethyl)pyridine-2-carbonitrile |
| 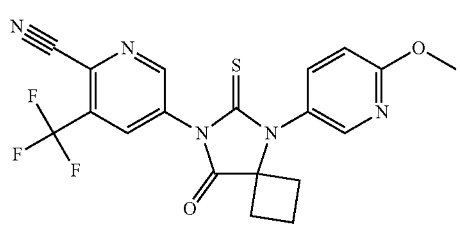 [SMILES: COc1ccc(N2C(=S)N(c3cnc(CN)c(C(F)(F)F)c3)C(=O)C23CCC3)cn1] | 15 | 5-[8-(6-methoxy-3-pyridyl)-5-oxo-7-thioxo-6,8-diazaspiro[3.4]octan-6-yl]-3-(trifluoromethyl)pyridine-2-carbonitrile |
| 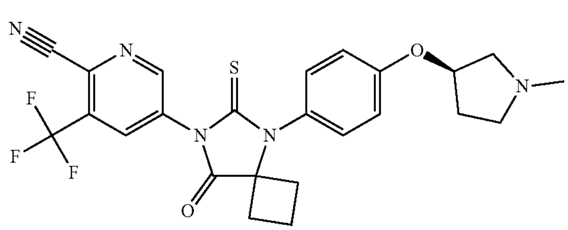 [SMILES: CN1CC[C@@H](Oc2ccc(N3C(=S)N(c4cnc(CN)c(C(F)(F)F)c4)C(=O)C34CCC4)cc2)C1] | 16 | 5-[8-[4-[(3R)-1-methylpyrrolidin-3-yl]oxyphenyl]-5-oxo-7-thioxo-6,8-diazaspiro[3.4]octan-6-yl]-3-(trifluoromethyl)pyridine-2-carbonitrile |

TABLE 1-continued

| Structure | Cpd No. | Cpd Name |
|---|---|---|
| 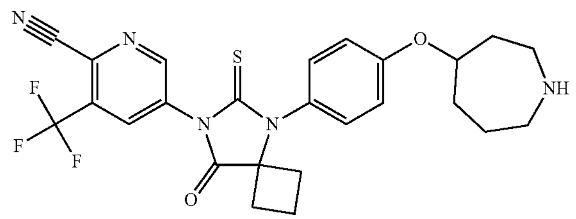 [SMILES: NCc1ncc(N2C(=O)C3(CCC3)N(c3ccc(OC4CCCNCC4)cc3)C2=S)cc1C(F)(F)F] | 17 | 5-[8-[4-(azepan-4-yloxy)phenyl]-5-oxo-7-thioxo-6,8-diazaspiro[3.4]octan-6-yl]-3-(trifluoromethyl)pyridine-2-carbonitrile |
| 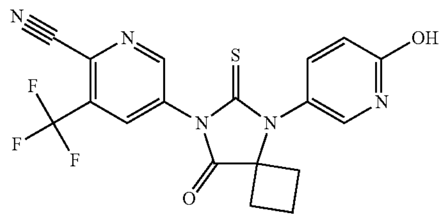 [SMILES: NCc1ncc(N2C(=O)C3(CCC3)N(c3ccc(O)nc3)C2=S)cc1C(F)(F)F] | 18 | 5-[8-(6-hydroxy-3-pyridyl)-5-oxo-7-thioxo-6,8-diazaspiro[3.4]octan-6-yl]-3-(trifluoromethyl)pyridine-2-carbonitrile |
| 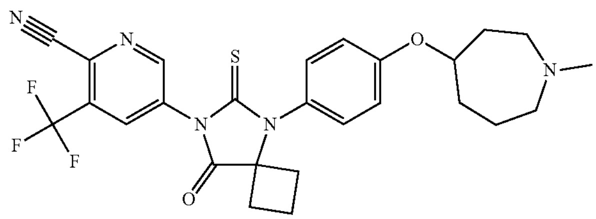 [SMILES: CN1CCCC(Oc2ccc(N3C(=S)N(c4cnc(CN)c(C(F)(F)F)c4)C(=O)C34CCC4)cc2)CC1] | 19 | 5-[8-[4-(1-methylazepan-4-yl)oxyphenyl]-5-oxo-7-thioxo-6,8-diazaspiro[3.4]octan-6-yl]-3-(trifluoromethyl)pyridine-2-carbonitrile |
| 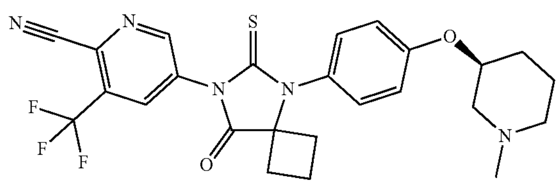 [SMILES: CN1CCC[C@H](Oc2ccc(N3C(=S)N(c4cnc(C#N)c(C(F)(F)F)c4)C(=O)C34CCC4)cc2)C1] | 20 | 5-[8-[4-[[(3S)-1-methyl-3-piperidyl]oxy]phenyl]-5-oxo-7-thioxo-6,8-diazaspiro[3.4]octan-6-yl]-3-(trifluoromethyl)pyridine-2-carbonitrile |
| 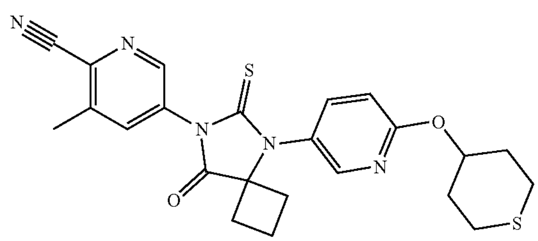 [SMILES: Cc1cc(N2C(=O)C3(CCC3)N(c3ccc(OC4CCSCC4)nc3)C2=S)cnc1CN] | 21 | 3-methyl-5-[5-oxo-8-(6-tetrahydrothiopyran-4-yloxy-3-pyridyl)-7-thioxo-6,8-diazaspiro[3.4]octan-6-yl]pyridine-2-carbonitrile |
| 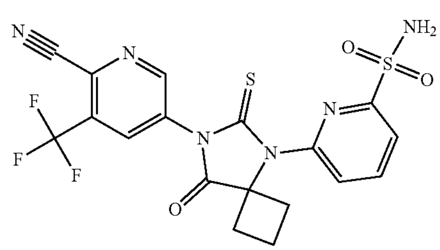 [SMILES: NCc1ncc(N2C(=O)C3(CCC3)N(c3cccc(S(N)(=O)=O)n3)C2=S)cc1C(F)(F)F] | 22 | 6-[6-[6-cyano-5-(trifluoromethyl)-3-pyridyl]-5-oxo-7-thioxo-6,8-diazaspiro[3.4]octan-8-yl]pyridine-2-sulfonamide |
| 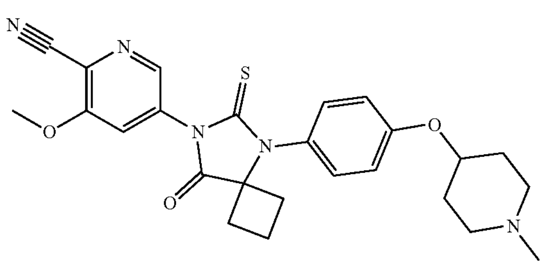 [SMILES: COc1cc(N2C(=O)C3(CCC3)N(c3ccc(OC4CCN(C)CC4)cc3)C2=S)cnc1CN] | 23 | 3-methoxy-5-[8-[4-[(1-methyl-4-piperidyl)oxy]phenyl]-5-oxo-7-thioxo-6,8-diazaspiro[3.4]octan-6-yl]pyridine-2-carbonitrile |

TABLE 1-continued

| Structure | Cpd No. | Cpd Name |
|---|---|---|
| 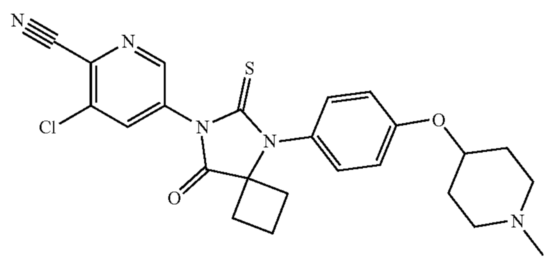 [SMILES: CN1CCC(Oc2ccc(N3C(=S)N(c4cnc(CN)c(Cl)c4)C(=O)C34CCC4)cc2)CC1] | 24 | 3-chloro-5-[8-[4-[(1-methyl-4-piperidyl)oxy]phenyl]-5-oxo-7-thioxo-6,8-diazaspiro[3.4]octan-6-yl]pyridine-2-carbonitrile |
| 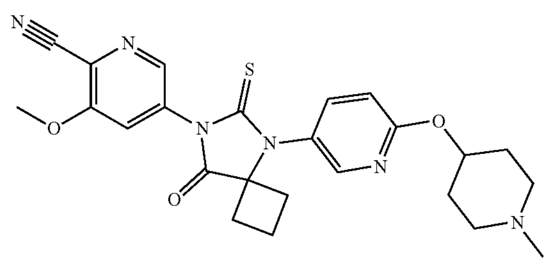 [SMILES: COc1cc(N2C(=O)C3(CCC3)N(c3ccc(OC4CCN(C)CC4)nc3)C2=S)cnc1CN] | 25 | 3-methoxy-5-[8-[6-[(1-methyl-4-piperidyl)oxy]-3-pyridyl]-5-oxo-7-thioxo-6,8-diazaspiro[3.4]octan-6-yl]pyridine-2-carbonitrile |
| 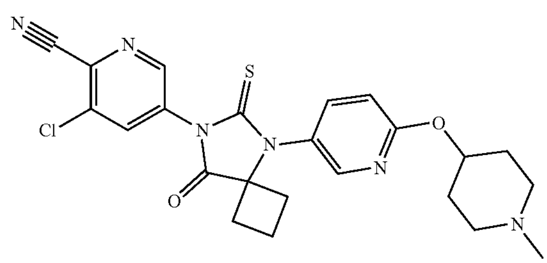 [SMILES: CN1CCC(Oc2ccc(N3C(=S)N(c4cnc(CN)c(Cl)c4)C(=O)C34CCC4)cn2)CC1] | 26 | 3-chloro-5-[8-[6-[(1-methyl-4-piperidyl)oxy]-3-pyridyl]-5-oxo-7-thioxo-6,8-diazaspiro[3.4]octan-6-yl]pyridine-2-carbonitrile |
| 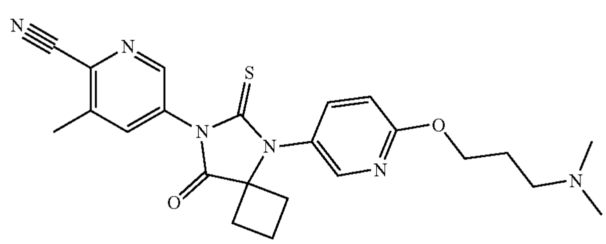 [SMILES: Cc1cc(N2C(=O)C3(CCC3)N(c3ccc(OCCCN(C)C)nc3)C2=S)cnc1CN] | 27 | 5-[8-[6-[3-(dimethylamino)propoxy]-3-pyridyl]-5-oxo-7-thioxo-6,8-diazaspiro[3.4]octan-6-yl]-3-methyl-pyridine-2-carbonitrile |
| 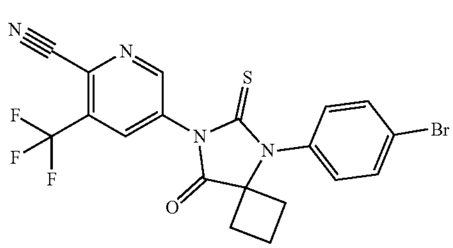 [SMILES: NCc1ncc(N2C(=O)C3(CCC3)N(c3ccc(Br)cc3)C2=S)cc1C(F)(F)F] | 28 | 5-[8-(4-bromophenyl)-5-oxo-7-thioxo-6,8-diazaspiro[3.4]octan-6-yl]-3-(trifluoromethyl)pyridine-2-carbonitrile |
| 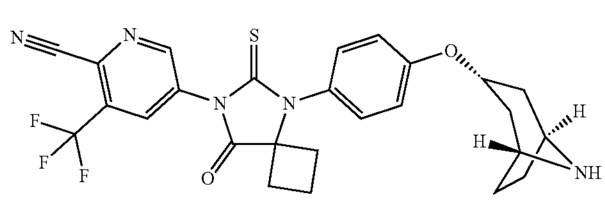 [SMILES: N#Cc1ncc(N2C(=O)C3(CCC3)N(c3ccc(O[C@H]4C[C@H]5CC[C@@H](C4)N5)cc3)C2=S)cc1C(F)(F)F] | 29 | 5-[8-[4-[[(1R,3r,5S)-8-azabicyclo[3.2.1]octan-3-yl]oxy]phenyl]-5-oxo-7-thioxo-6,8-diazaspiro[3.4]octan-6-yl]-3-(trifluoromethyl)pyridine-2-carbonitrile |

TABLE 1-continued

| Structure | Cpd No. | Cpd Name |
|---|---|---|
| 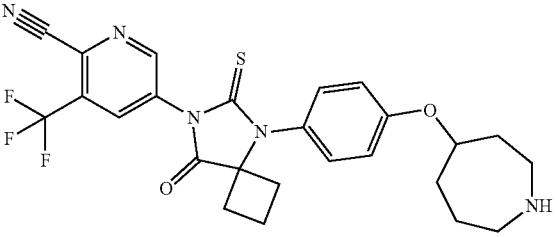 [SMILES: NCc1ncc(N2C(=O)C3(CCC3)N(c3ccc(OC4CCCNCC4)cc3)C2=S)cc1C(F)(F)F] | 30 | 5-[8-[4-(azepan-4-yloxy)phenyl]-5-oxo-7-thioxo-6,8-diazaspiro[3.4]octan-6-yl]-3-(trifluoromethyl)pyridine-2-carbonitrile |
| 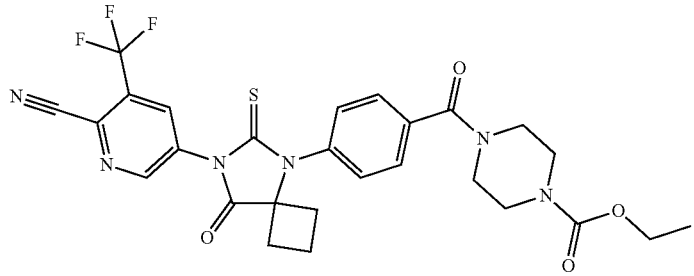 [SMILES: CCOC(=O)N1CCN(C(=O)c2ccc(N3C(=S)N(c4cnc(C#N)c(C(F)(F)F)c4)C(=O)C34CCC4)cc2)CC1] | 31 | ethyl 4-[4-[6-[6-cyano-5-(trifluoromethyl)-3-pyridyl]-5-oxo-7-thioxo-6,8-diazaspiro[3.4]octan-8-yl]benzoyl]piperazine-1-carboxylate |
| 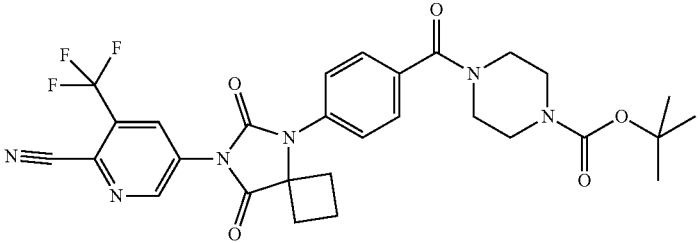 [SMILES: CC(C)(C)OC(=O)N1CCN(C(=O)c2ccc(N3C(=O)N(c4cnc(C#N)c(C(F)(F)F)c4)C(=O)C34CCC4)cc2)CC1] | 32 | tert-butyl 4-[4-[6-[6-cyano-5-(trifluoromethyl)-3-pyridyl]-5-oxo-7-thioxo-6,8-diazaspiro[3.4]octan-8-yl]benzoyl]piperazine-1-carboxylate |
| 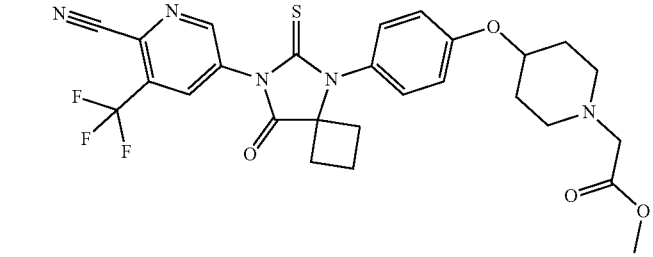 [SMILES: COC(=O)CN1CCC(Oc2ccc(N3C(=S)N(c4cnc(C#N)c(C(F)(F)F)c4)C(=O)C34CCC4)cc2)CC1] | 33 | methyl 2-[4-[4-[6-[6-cyano-5-(trifluoromethyl)-3-pyridyl]-5-oxo-7-thioxo-6,8-diazaspiro[3.4]octan-8-yl]phenoxy]-1-piperidyl]acetate |
| 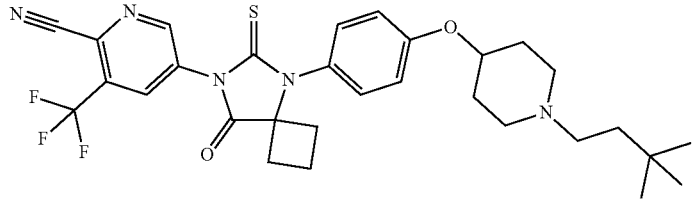 [SMILES: CC(C)(C)CCN1CCC(Oc2ccc(N3C(=S)N(c4cnc(C#N)c(C(F)(F)F)c4)C(=O)C34CCC4)cc2)CC1] | 34 | 5-[8-[4-[[1-(3,3-dimethylbutyl)-4-piperidyl]oxy]phenyl]-5-oxo-7-thioxo-6,8-diazaspiro[3.4]octan-6-yl]-3-(trifluoromethyl)pyridine-2-carbonitrile |
| 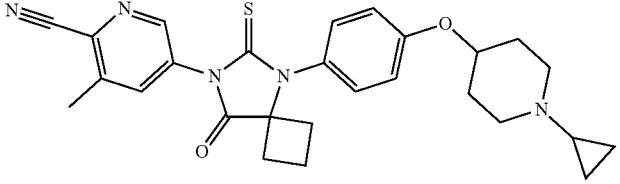 [SMILES: Cc1cc(N2C(=O)C3(CCC3)N(c3ccc(OC4CCN(C5CC5)CC4)cc3)C2=S)cnc1C#N] | 35 | 5-[8-[4-[(1-cyclopropyl-4-piperidyl)oxy]phenyl]-5-oxo-7-thioxo-6,8-diazaspiro[3.4]octan-6-yl]-3-methyl-pyridine-2-carbonitrile |

TABLE 1-continued

| Structure | Cpd No. | Cpd Name |
|---|---|---|
| 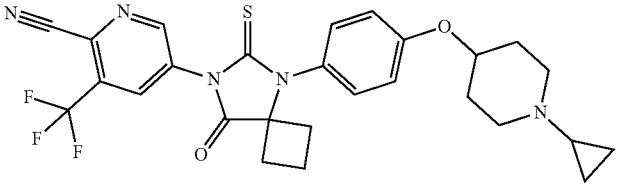 [SMILES: N#Cc1ncc(N2C(=O)C3(CCC3)N(c3ccc(OC4CCN(C5CC5)CC4)cc3)C2=S)cc1C(F)(F)F] | 36 | 5-[8-[4-[(1-cyclopropyl-4-piperidyl)oxy]phenyl]-5-oxo-7-thioxo-6,8-diazaspiro[3.4]octan-6-yl]-3-(trifluoromethyl)pyridine-2-carbonitrile |
| 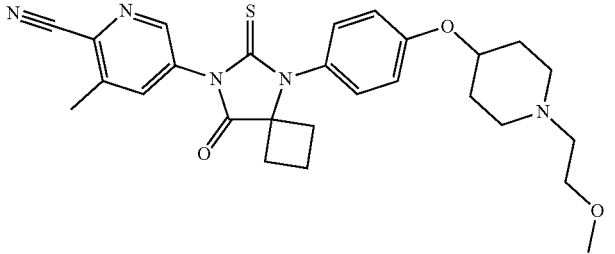 [SMILES: COCCN1CCC(Oc2ccc(N3C(=S)N(c4cnc(C#N)c(C)c4)C(=O)C34CCC4)cc2)CC1] | 37 | 5-[8-[4-[[1-(2-methoxyethyl)-4-piperidyl]oxy]phenyl]-5-oxo-7-thioxo-6,8-diazaspiro[3.4]octan-6-yl]-3-methyl-pyridine-2-carbonitrile |
| 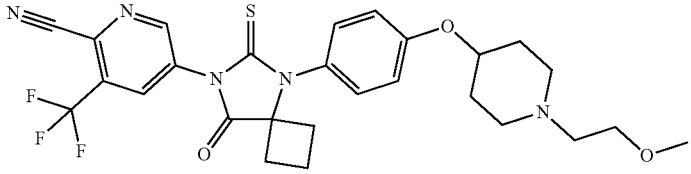 [SMILES: COCCN1CCC(Oc2ccc(N3C(=S)N(c4cnc(C#N)c(C(F)(F)F)c4)C(=O)C34CCC4)cc2)CC1] | 38 | 5-[8-[4-[[1-(2-methoxyethyl)-4-piperidyl]oxy]phenyl]-5-oxo-7-thioxo-6,8-diazaspiro[3.4]octan-6-yl]-3-(trifluoromethyl)pyridine-2-carbonitrile |
| 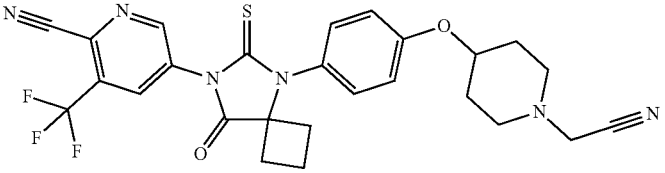 [SMILES: N#CCN1CCC(Oc2ccc(N3C(=S)N(c4cnc(C#N)c(C(F)(F)F)c4)C(=O)C34CCC4)cc2)CC1] | 39 | 5-[8-[4-[[1-(cyanomethyl)-4-piperidyl]oxy]phenyl]-5-oxo-7-thioxo-6,8-diazaspiro[3.4]octan-6-yl]-3-(trifluoromethyl)pyridine-2-carbonitrile |
| 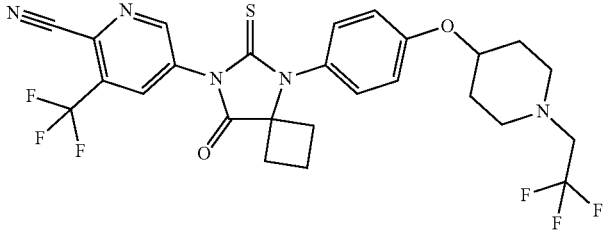 [SMILES: N#Cc1ncc(N2C(=O)C3(CCC3)N(c3ccc(OC4CCN(CC(F)(F)F)CC4)cc3)C2=S)cc1C(F)(F)F] | 40 | 5-[5-oxo-7-thioxo-8-[4-[[1-(2,2,2-trifluoroethyl)-4-piperidyl]oxy]phenyl]-6,8-diazaspiro[3.4]octan-6-yl]-3-(trifluoromethyl)pyridine-2-carbonitrile |
| 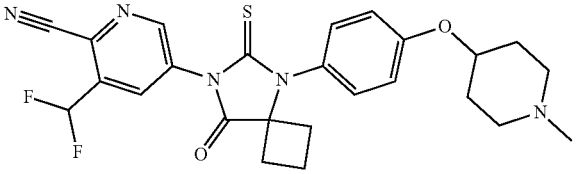 [SMILES: CN1CCC(Oc2ccc(N3C(=S)N(c4cnc(C#N)c(C(F)F)c4)C(=O)C34CCC4)cc2)CC1] | 41 | 3-(difluoromethyl)-5-[8-[4-[(1-methyl-4-piperidyl)oxy]phenyl]-5-oxo-7-thioxo-6,8-diazaspiro[3.4]octan-6-yl]pyridine-2-carbonitrile |
| 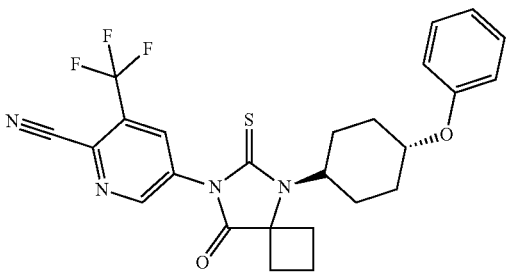 | 42 | 5-[5-oxo-8-(4-phenoxycyclohexyl)-7-thioxo-6,8-diazaspiro[3.4]octan-6-yl]-3-(trifluoromethyl)pyridine-2-carbonitrile |

TABLE 1-continued

| Structure | Cpd No. | Cpd Name |
|---|---|---|
| 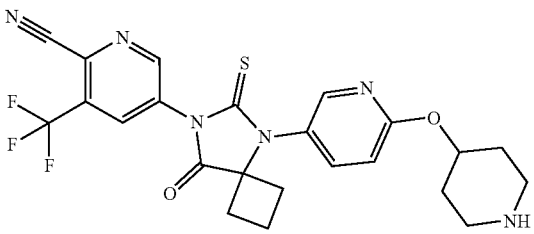 [SMILES: N#Cc1ncc(N2C(=O)C3(CCC3)N(c3ccc(OC4CCNCC4)nc3)C2=S)cc1C(F)(F)F] | 43 | 5-[5-oxo-8-[6-(4-piperidyloxy)-3-pyridyl]-7-thioxo-6,8-diazaspiro[3.4]octan-6-yl]-3-(trifluoromethyl)pyridine-2-carbonitrile |
| 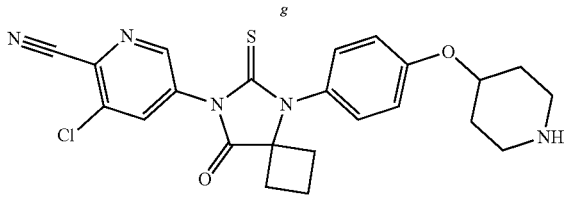 [SMILES: N#Cc1ncc(N2C(=O)C3(CCC3)N(c3ccc(OC4CCNCC4)cc3)C2=S)cc1Cl] | 44 | 3-chloro-5-[5-oxo-8-[4-(4-piperidyloxy)phenyl]-7-thioxo-6,8-diazaspiro[3.4]octan-6-yl]pyridine-2-carbonitrile |
| 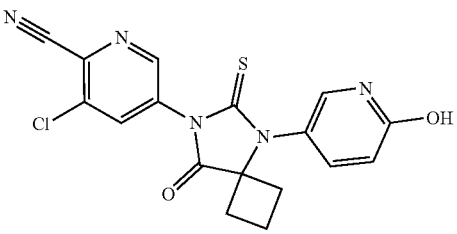 [SMILES: N#Cc1ncc(N2C(=O)C3(CCC3)N(c3ccc(O)nc3)C2=S)cc1Cl] | 45 | 3-chloro-5-[8-(6-hydroxy-3-pyridyl)-5-oxo-7-thioxo-6,8-diazaspiro[3.4]octan-6-yl]pyridine-2-carbonitrile |
| 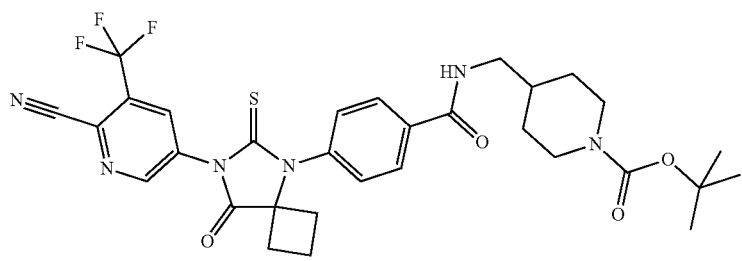 [SMILES: CC(C)(C)OC(=O)N1CCC(CNC(=O)c2ccc(N3C(=S)N(c4cnc(C#N)c(C(F)(F)F)c4)C(=O)C34CCC4)cc2)CC1] | 46 | tert-butyl 4-[[[4-[6-[6-cyano-5-(trifluoromethyl)-3-pyridyl]-5-oxo-7-thioxo-6,8-diazaspiro[3.4]octan-8-yl]benzoyl]amino]methyl]piperidine-1-carboxylate |
| 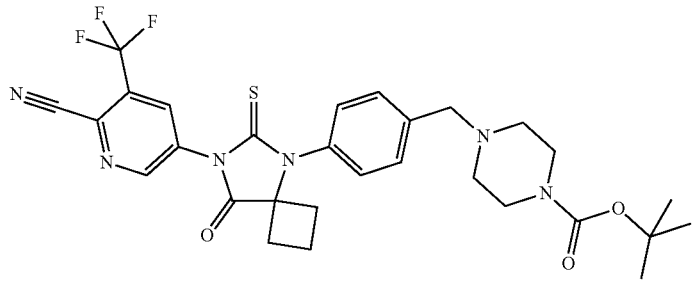 [SMILES: CC(C)(C)OC(=O)N1CCN(Cc2ccc(N3C(=S)N(c4cnc(C#N)c(C(F)(F)F)c4)C(=O)C34CCC4)cc2)CC1] | 47 | tert-butyl 4-[[4-[6-[6-cyano-5-(trifluoromethyl)-3-pyridyl]-5-oxo-7-thioxo-6,8-diazaspiro[3.4]octan-8-yl]phenyl]methyl]piperazine-1-carboxylate |
| 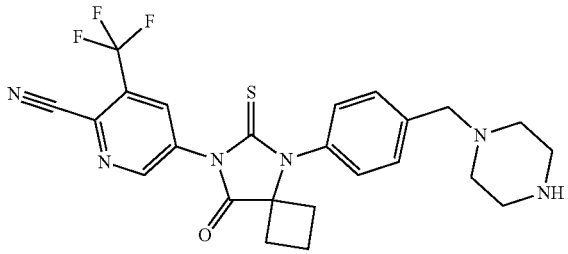 [SMILES: N#Cc1ncc(N2C(=O)C3(CCC3)N(c3ccc(CN4CCNCC4)cc3)C2=S)cc1C(F)(F)F] | 48 | 5-[5-oxo-8-[4-(piperazin-1-ylmethyl)phenyl]-7-thioxo-6,8-diazaspiro[3.4]octan-6-yl]-3-(trifluoromethyl)pyridine-2-carbonitrile |

TABLE 1-continued

| Structure | Cpd No. | Cpd Name |
|---|---|---|
| 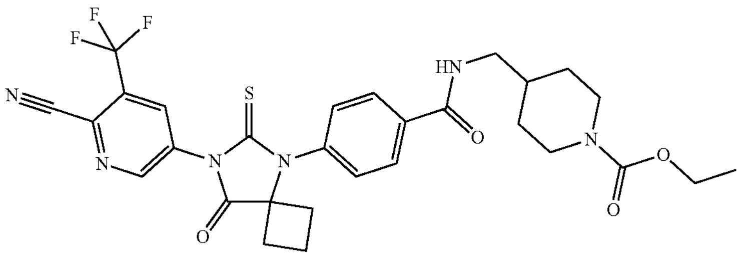 [SMILES: CCOC(=O)N1CCC(CNC(=O)c2ccc(N3C(=S)N(c4cnc(C#N)c(C(F)(F)F)c4)C(=O)C34CCC4)cc2)CC1] | 49 | ethyl 4-[[[4-[6-[6-cyano-5-(trifluoromethyl)-3-pyridyl]-5-oxo-7-thioxo-6,8-diazaspiro[3.4]octan-8-yl]benzoyl]amino]methyl]piperidine-1-carboxylate |
| 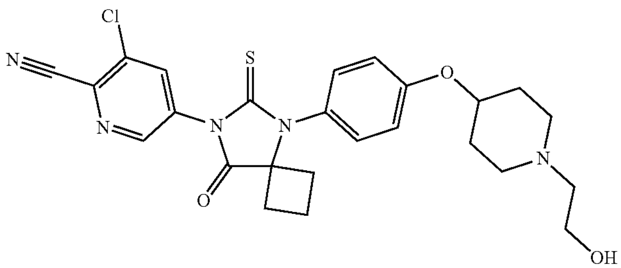 [SMILES: N#Cc1ncc(N2C(=O)C3(CCC3)N(c3ccc(OC4CCN(CCO)CC4)cc3)C2=S)cc1Cl] | 50 | 3-chloro-5-[8-[4-[[1-(2-hydroxyethyl)-4-piperidyl]oxy]phenyl]-5-oxo-7-thioxo-6,8-diazaspiro[3.4]octan-6-yl]pyridine-2-carbonitrile |
| 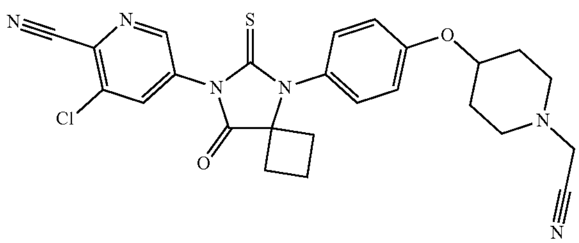 [SMILES: N#CCN1CCC(Oc2ccc(N3C(=S)N(c4cnc(C#N)c(Cl)c4)C(=O)C34CCC4)cc2)CC1] | 51 | 3-chloro-5-[8-[4-[[1-(cyanomethyl)-4-piperidyl]oxy]phenyl]-5-oxo-7-thioxo-6,8-diazaspiro[3.4]octan-6-yl]pyridine-2-carbonitrile |
| 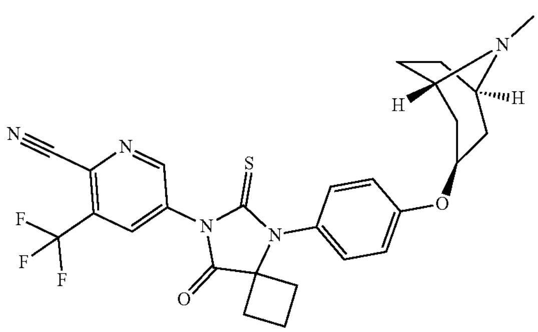 [SMILES: CN1[C@@H]2CC[C@H]1C[C@H](Oc1ccc(N3C(=S)N(c4cnc(C#N)c(C(F)(F)F)c4)C(=O)C34CCC4)cc1)C2] | 52 | 5-[8-[4-[[(1R,3s,5S)-8-methyl-8-azabicyclo[3.2.1]octan-3-yl]oxy]phenyl]-5-oxo-7-thioxo-6,8-diazaspiro[3.4]octan-6-yl]-3-(trifluoromethyl)pyridine-2-carbonitrile |
| 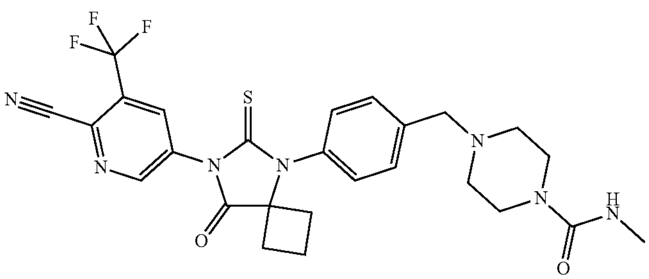 [SMILES: CNC(=O)N1CCN(Cc2ccc(N3C(=S)N(c4cnc(C#N)c(C(F)(F)F)c4)C(=O)C34CCC4)cc2)CC1] | 53 | 4-[[4-[6-[6-cyano-5-(trifluoromethyl)-3-pyridyl]-5-oxo-7-thioxo-6,8-diazaspiro[3.4]octan-8-yl]phenyl]methyl]-N-methyl-piperazine-1-carboxamide |

TABLE 1-continued

| Structure | Cpd No. | Cpd Name |
|---|---|---|
| 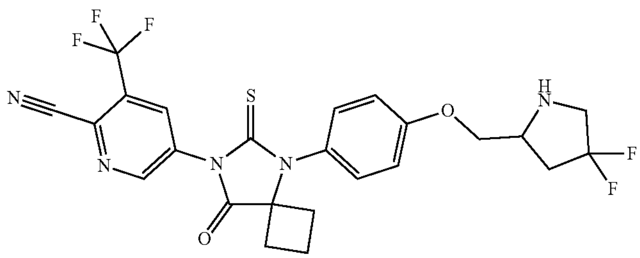 [SMILES: N#Cc1ncc(N2C(=O)C3(CCC3)N(c3ccc(OCC4CC(F)(F)CN4)cc3)C2=S)cc1C(F)(F)F] | 54 | 5-[8-[4-[(4,4-difluoropyrrolidin-2-yl)methoxy]phenyl]-5-oxo-7-thioxo-6,8-diazaspiro[3.4]octan-6-yl]-3-(trifluoromethyl)pyridine-2-carbonitrile |
| 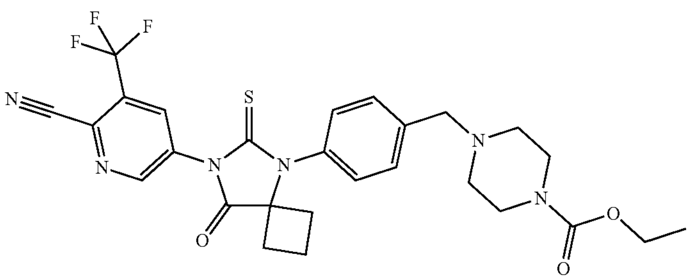 [SMILES: CCOC(=O)N1CCN(Cc2ccc(N3C(=S)N(c4cnc(C#N)c(C(F)(F)F)c4)C(=O)C34CCC4)cc2)CC1] | 55 | ethyl 4-[[4-[6-[6-cyano-5-(trifluoromethyl)-3-pyridyl]-5-oxo-7-thioxo-6,8-diazaspiro[3.4]octan-8-yl]phenyl]methyl]piperazine-1-carboxylate |
| 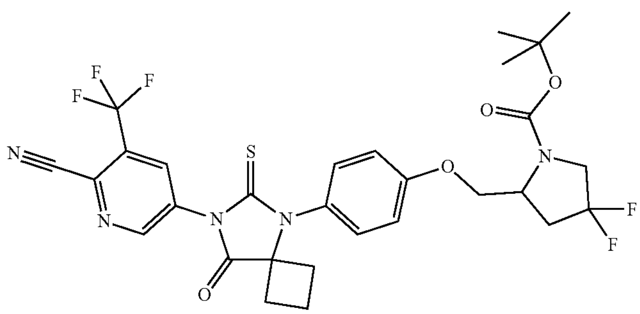 [SMILES: CC(C)(C)OC(=O)N1CC(F)(F)CC1COc1ccc(N2C(=S)N(c3cnc(C#N)c(C(F)(F)F)c3)C(=O)C23CCC3)cc1] | 56 | tert-butyl 2-[[4-[6-[6-cyano-5-(trifluoromethyl)-3-pyridyl]-5-oxo-7-thioxo-6,8-diazaspiro[3.4]octan-8-yl]phenoxy]methyl]-4,4-difluoro-pyrrolidine-1-carboxylate |
| 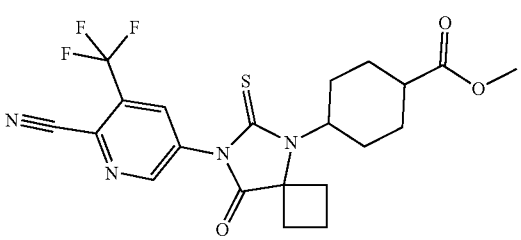 [SMILES: COC(=O)C1CCC(N2C(=S)N(c3cnc(C#N)c(C(F)(F)F)c3)C(=O)C23CCC3)CC1] | 57 | methyl 4-[6-[6-cyano-5-(trifluoromethyl)-3-pyridyl]-5-oxo-7-thioxo-6,8-diazaspiro[3.4]octan-8-yl]cyclohexanecarboxylate |
| 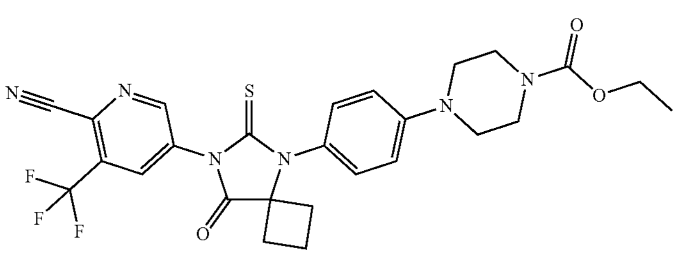 [SMILES: CCOC(=O)N1CCN(c2ccc(N3C(=S)N(c4cnc(C#N)c(C(F)(F)F)c4)C(=O)C34CCC4)cc2)CC1] | 58 | ethyl 4-[4-[6-[6-cyano-5-(trifluoromethyl)-3-pyridyl]-5-oxo-7-thioxo-6,8-diazaspiro[3.4]octan-8-yl]phenyl]piperazine-1-carboxylate |

TABLE 1-continued

| Structure | Cpd No. | Cpd Name |
|---|---|---|
| 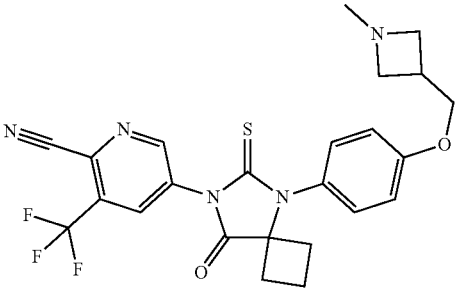 [SMILES: CN1CC(COc2ccc(N3C(=S)N(c4cnc(C#N)c(C(F)(F)F)c4)C(=O)C34CCC4)cc2)C1] | 59 | 5-[8-[4-[(1-methylazetidin-3-yl)methoxy]phenyl]-5-oxo-7-thioxo-6,8-diazaspiro[3.4]octan-6-yl]-3-(trifluoromethyl)pyridine-2-carbonitrile |
| 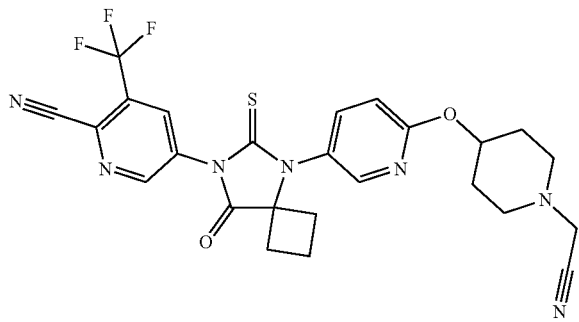 [SMILES: N#CCN1CCC(Oc2ccc(N3C(=S)N(c4cnc(C#N)c(C(F)(F)F)c4)C(=O)C34CCC4)cn2)CC1] | 60 | 5-[8-[6-[[1-(cyanomethyl)-4-piperidyl]oxy]-3-pyridyl]-5-oxo-7-thioxo-6,8-diazaspiro[3.4]octan-6-yl]-3-(trifluoromethyl)pyridine-2-carbonitrile |
| 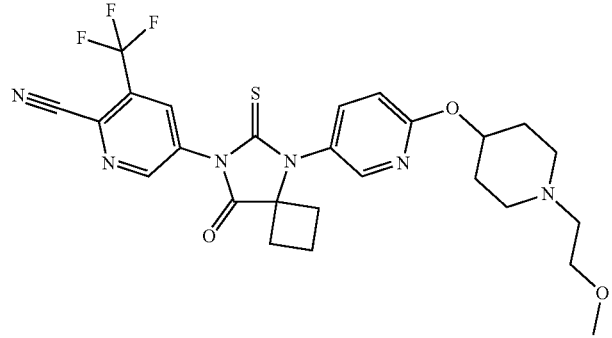 [SMILES: COCCN1CCC(Oc2ccc(N3C(=S)N(c4cnc(C#N)c(C(F)(F)F)c4)C(=O)C34CCC4)cn2)CC1] | 61 | 5-[8-[6-[[1-(2-methoxyethyl)-4-piperidyl]oxy]-3-pyridyl]-5-oxo-7-thioxo-6,8-diazaspiro[3.4]octan-6-yl]-3-(trifluoromethyl)pyridine-2-carbonitrile |
| 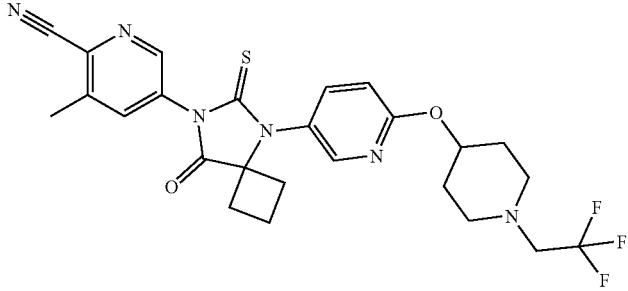 [SMILES: Cc1cc(N2C(=O)C3(CCC3)N(c3ccc(OC4CCN(CC(F)(F)F)CC4)nc3)C2=S)cnc1C#N] | 62 | 3-methyl-5-[5-oxo-7-thioxo-8-[6-[[1-(2,2,2-trifluoroethyl)-4-piperidyl]oxy]-3-pyridyl]-6,8-diazaspiro[3.4]octan-6-yl]pyridine-2-carbonitrile |
| 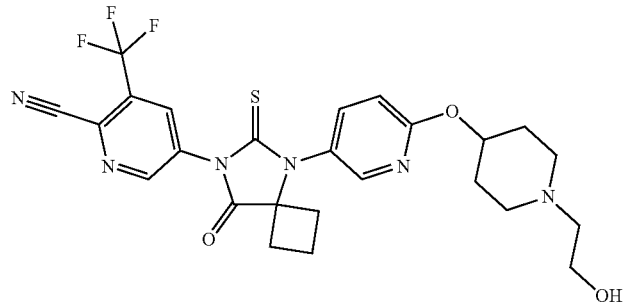 [SMILES: N#Cc1ncc(N2C(=O)C3(CCC3)N(c3ccc(OC4CCN(CCO)CC4)nc3)C2=S)cc1C(F)(F)F] | 63 | 5-[8-[6-[[1-(2-hydroxyethyl)-4-piperidyl]oxy]-3-pyridyl]-5-oxo-7-thioxo-6,8-diazaspiro[3.4]octan-6-yl]-3-(trifluoromethyl)pyridine-2-carbonitrile |

TABLE 1-continued

| Structure | Cpd No. | Cpd Name |
|---|---|---|
| 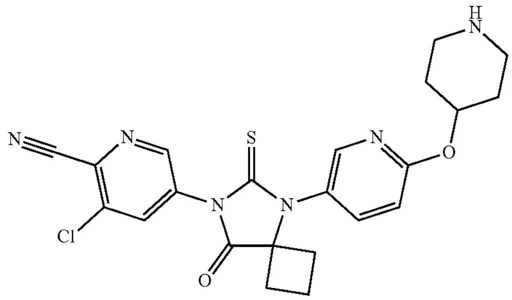 [SMILES: N#Cc1ncc(N2C(=O)C3(CCC3)N(c3ccc(OC4CCNCC4)nc3)C2=S)cc1Cl] | 64 | 3-chloro-5-[5-oxo-8-[6-(4-piperidyloxy)-3-pyridyl]-7-thioxo-6,8-diazaspiro[3.4]octan-6-yl]pyridine-2-carbonitrile |
| 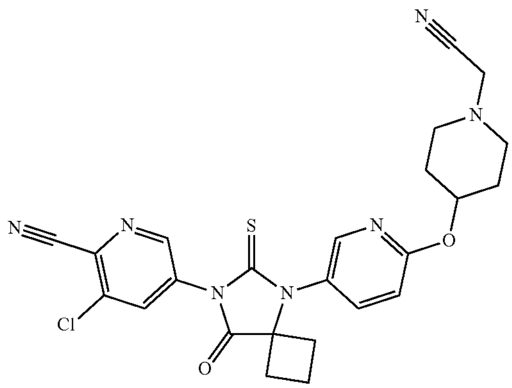 [SMILES: N#CCN1CCC(Oc2ccc(N3C(=S)N(c4cnc(C#N)c(Cl)c4)C(=O)C34CCC4)cn2)CC1] | 65 | 3-chloro-5-[8-[6-[[1-(cyanomethyl)-4-piperidyl]oxy]-3-pyridyl]-5-oxo-7-thioxo-6,8-diazaspiro[3.4]octan-6-yl]pyridine-2-carbonitrile |
| 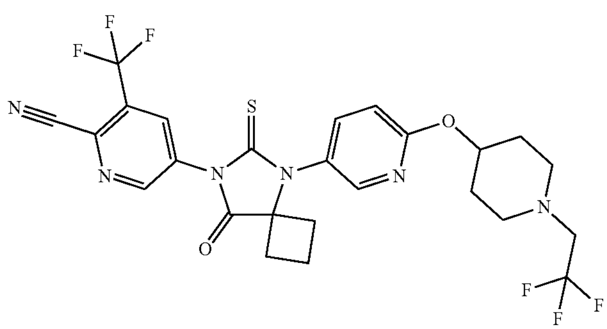 [SMILES: N#Cc1ncc(N2C(=O)C3(CCC3)N(c3ccc(OC4CCN(CC(F)(F)F)CC4)nc3)C2=S)cc1C(F)(F)F] | 66 | 5-[5-oxo-7-thioxo-8-[6-[[1-(2,2,2-trifluoroethyl)-4-piperidyl]oxy]-3-pyridyl]-6,8-diazaspiro[3.4]octan-6-yl]-3-(trifluoromethyl)pyridine-2-carbonitrile |
| 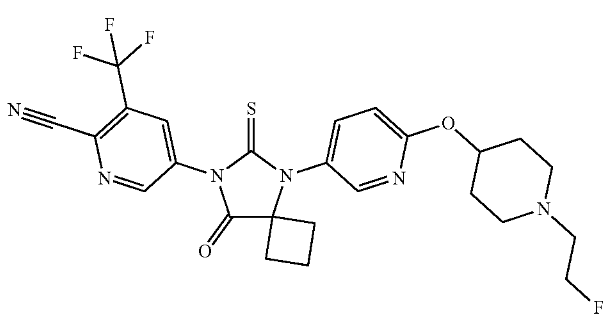 [SMILES: N#Cc1ncc(N2C(=O)C3(CCC3)N(c3ccc(OC4CCN(CCF)CC4)nc3)C2=S)cc1C(F)(F)F] | 67 | 5-[8-[6-[[1-(2-fluoroethyl)-4-piperidyl]oxy]-3-pyridyl]-5-oxo-7-thioxo-6,8-diazaspiro[3.4]octan-6-yl]-3-(trifluoromethyl)pyridine-2-carbonitrile |
| 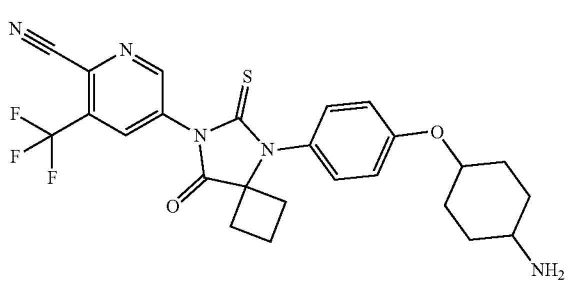 [SMILES: N#Cc1ncc(N2C(=O)C3(CCC3)N(c3ccc(OC4CCC(N)CC4)cc3)C2=S)cc1C(F)(F)F] | 68 | 5-[8-[4-(4-aminocyclohexoxy)phenyl]-5-oxo-7-thioxo-6,8-diazaspiro[3.4]octan-6-yl]-3-(trifluoromethyl)pyridine-2-carbonitrile |

TABLE 1-continued

| Structure | Cpd No. | Cpd Name |
|---|---|---|
| 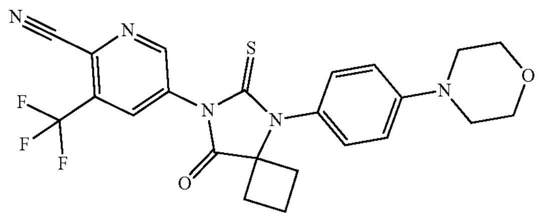 [SMILES: N#Cc1ncc(N2C(=O)C3(CCC3)N(c3ccc(N4CCOCC4)cc3)C2=S)cc1C(F)(F)F] | 69 | 5-[8-(4-morpholinophenyl)-5-oxo-7-thioxo-6,8-diazaspiro[3.4]octan-6-yl]-3-(trifluoromethyl)pyridine-2-carbonitrile |
| 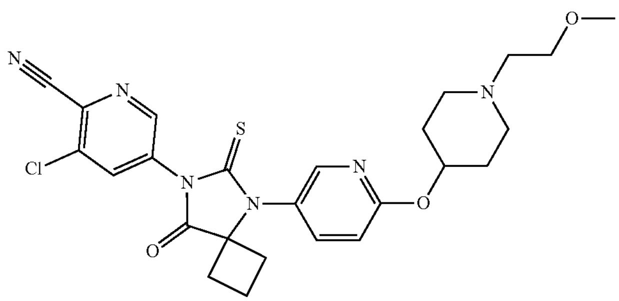 [SMILES: COCCN1CCC(Oc2ccc(N3C(=S)N(c4cnc(C#N)c(Cl)c4)C(=O)C34CCC4)cn2)CC1] | 70 | 3-chloro-5-[8-[6-[[1-(2-methoxyethyl)-4-piperidyl]oxy]-3-pyridyl]-5-oxo-7-thioxo-6,8-diazaspiro[3.4]octan-6-yl]pyridine-2-carbonitrile |
| 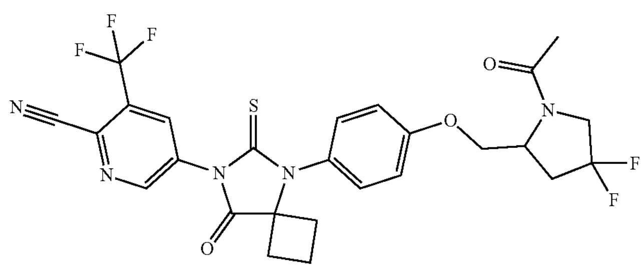 [SMILES: CC(=O)N1CC(F)(F)CC1COc1ccc(N2C(=S)N(c3cnc(C#N)c(C(F)(F)F)c3)C(=O)C23CCC3)cc1] | 71 | 5-[8-[4-[(1-acetyl-4,4-difluoro-pyrrolidin-2-yl)methoxy]phenyl]-5-oxo-7-thioxo-6,8-diazaspiro[3.4]octan-6-yl]-3-(trifluoromethyl)pyridine-2-carbonitrile |
| 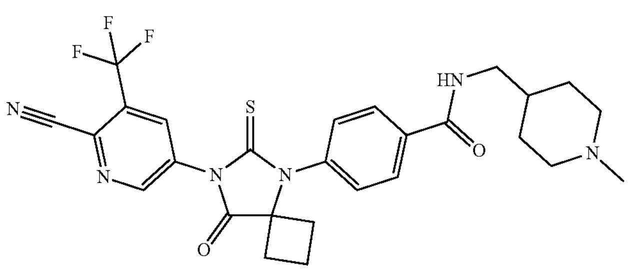 [SMILES: CN1CCC(CNC(=O)c2ccc(N3C(=S)N(c4cnc(C#N)c(C(F)(F)F)c4)C(=O)C34CCC4)cc2)CC1] | 72 | 4-[6-[6-cyano-5-(trifluoromethyl)-3-pyridyl]-5-oxo-7-thioxo-6,8-diazaspiro[3.4]octan-8-yl]-N-[(1-methyl-4-piperidyl)methyl]benzamide |
| 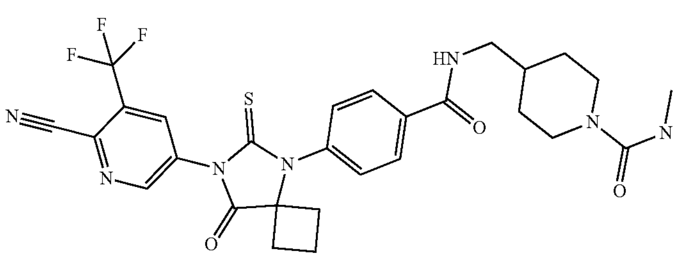 [SMILES: CNC(=O)N1CCC(CNC(=O)c2ccc(N3C(=S)N(c4cnc(C#N)c(C(F)(F)F)c4)C(=O)C34CCC4)cc2)CC1] | 73 | 4-[[[4-[6-[6-cyano-5-(trifluoromethyl)-3-pyridyl]-5-oxo-7-thioxo-6,8-diazaspiro[3.4]octan-8-yl]benzoyl]amino]methyl]-N-methyl-piperidine-1-carboxamide |
| 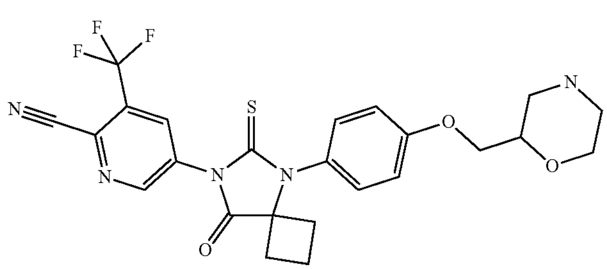 [SMILES: N#Cc1ncc(N2C(=O)C3(CCC3)N(c3ccc(OCC4CNCCO4)cc3)C2=S)cc1C(F)(F)F] | 74 | 5-[8-[4-(morpholin-2-ylmethoxy)phenyl]-5-oxo-7-thioxo-6,8-diazaspiro[3.4]octan-6-yl]-3-(trifluoromethyl)pyridine-2-carbonitrile |

TABLE 1-continued

| Structure | Cpd No. | Cpd Name |
|---|---|---|
| 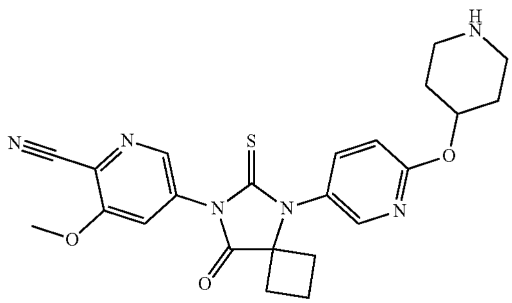 [SMILES: COc1cc(N2C(=O)C3(CCC3)N(c3ccc(OC4CCNCC4)nc3)C2=S)cnc1C#N] | 75 | 3-methoxy-5-[5-oxo-8-[6-(4-piperidyloxy)-3-pyridyl]-7-thioxo-6,8-diazaspiro[3.4]octan-6-yl]pyridine-2-carbonitrile |
| 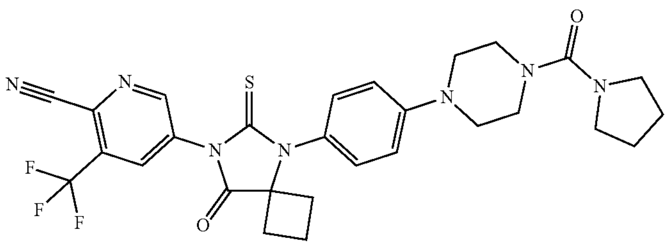 [SMILES: N#Cc1ncc(N2C(=O)C3(CCC3)N(c3ccc(N4CCN(C(=O)N5CCCC5)CC4)cc3)C2=S)cc1C(F)(F)F] | 76 | 5-[5-oxo-8-[4-[4-(pyrrolidine-1-carbonyl)piperazin-1-yl]phenyl]-7-thioxo-6,8-diazaspiro[3.4]octan-6-yl]-3-(trifluoromethyl)pyridine-2-carbonitrile |
| 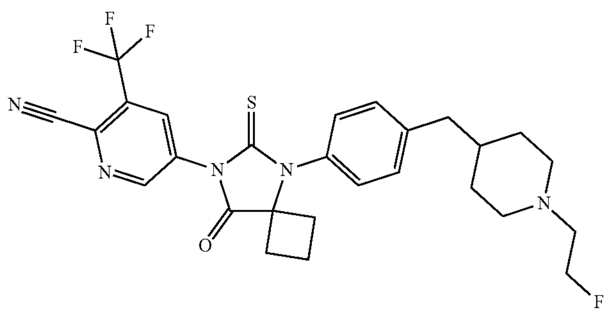 [SMILES: N#Cc1ncc(N2C(=O)C3(CCC3)N(c3ccc(CC4CCN(CCF)CC4)cc3)C2=S)cc1C(F)(F)F] | 77 | 5-[8-[4-[[1-(2-fluoroethyl)-4-piperidyl]oxy]phenyl]-5-oxo-7-thioxo-6,8-diazaspiro[3.4]octan-6-yl]-3-(trifluoromethyl)pyridine-2-carbonitrile |
| 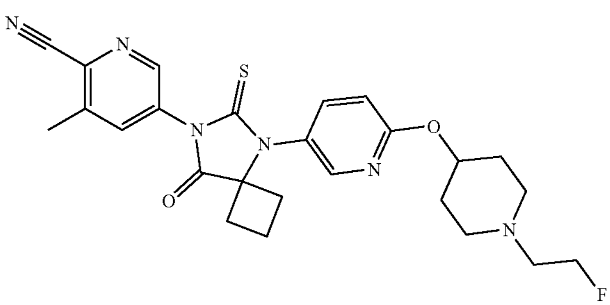 [SMILES: Cc1cc(N2C(=O)C3(CCC3)N(c3ccc(OC4CCN(CCF)CC4)nc3)C2=S)cnc1C#N] | 78 | 5-[8-[6-[[1-(2-fluoroethyl)-4-piperidyl]oxy]-3-pyridyl]-5-oxo-7-thioxo-6,8-diazaspiro[3.4]octan-6-yl]-3-methyl-pyridine-2-carbonitrile |
| 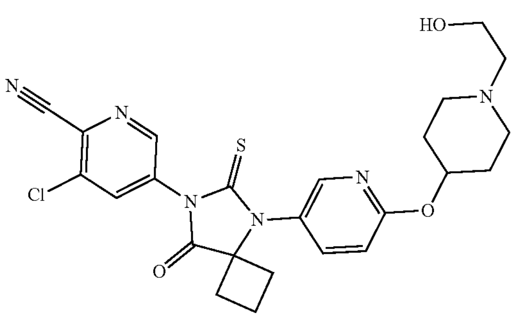 [SMILES: N#Cc1ncc(N2C(=O)C3(CCC3)N(c3ccc(OC4CCN(CCO)CC4)nc3)C2=S)cc1Cl] | 79 | 3-chloro-5-[8-[6-[[1-(2-hydroxyethyl)-4-piperidyl]oxy]-3-pyridyl]-5-oxo-7-thioxo-6,8-diazaspiro[3.4]octan-6-yl]pyridine-2-carbonitrile |

TABLE 1-continued

| Structure | Cpd No. | Cpd Name |
|---|---|---|
| 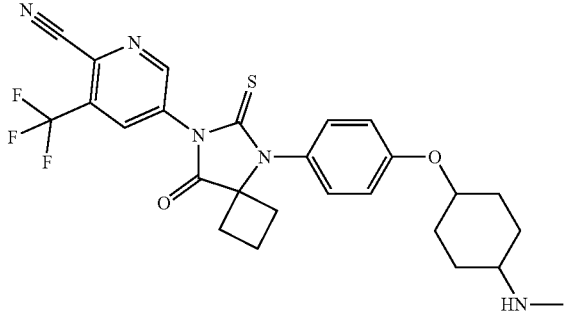 [SMILES: CNC1CCC(Oc2ccc(N3C(=S)N(c4cnc(C#N)c(C(F)(F)F)c4)C(=O)C34CCC4)cc2)CC1] | 80 | 5-[8-[4-[4-(methylamino)cyclohexoxy]phenyl]-5-oxo-7-thioxo-6,8-diazaspiro[3.4]octan-6-yl]-3-(trifluoromethyl)pyridine-2-carbonitrile |
| 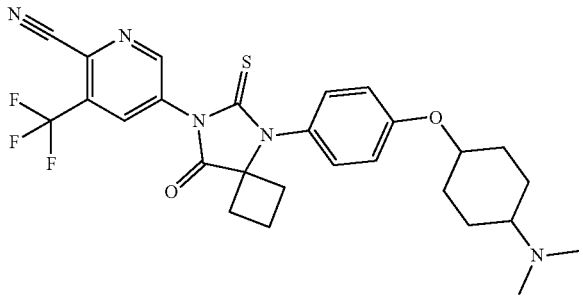 [SMILES: CN(C)C1CCC(Oc2ccc(N3C(=S)N(c4cnc(C#N)c(C(F)(F)F)c4)C(=O)C34CCC4)cc2)CC1] | 81 | 5-[8-[4-[4-(dimethylamino)cyclohexoxy]phenyl]-5-oxo-7-thioxo-6,8-diazaspiro[3.4]octan-6-yl]-3-(trifluoromethyl)pyridine-2-carbonitrile |
| 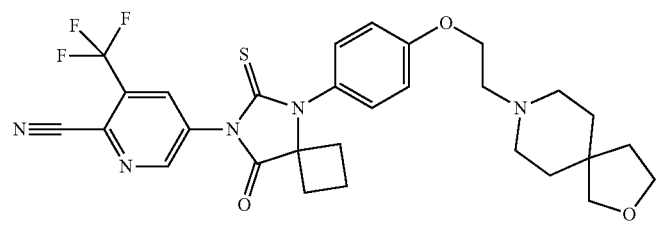 [SMILES: N#Cc1ncc(N2C(=O)C3(CCC3)N(c3ccc(OCCN4CCC5(CCOC5)CC4)cc3)C2=S)cc1C(F)(F)F] | 82 | 5-[8-[4-[2-(3-oxa-8-azaspiro[4.5]decan-8-yl)ethoxy]phenyl]-5-oxo-7-thioxo-6,8-diazaspiro[3.4]octan-6-yl]-3-(trifluoromethyl)pyridine-2-carbonitrile |
| 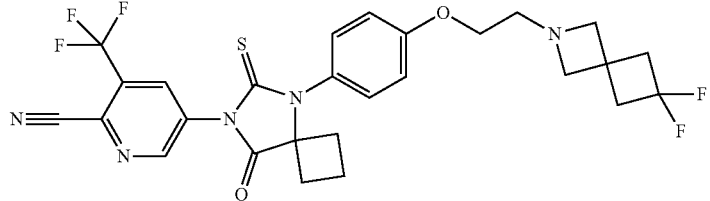 [SMILES: N#Cc1ncc(N2C(=O)C3(CCC3)N(c3ccc(OCCN4CC5(C4)CC(F)(F)C5)cc3)C2=S)cc1C(F)(F)F] | 83 | 5-[8-[4-[2-(2,2-difluoro-6-azaspiro[3.3]heptan-6-yl)ethoxy]phenyl]-5-oxo-7-thioxo-6,8-diazaspiro[3.4]octan-6-yl]-3-(trifluoromethyl)pyridine-2-carbonitrile |
| 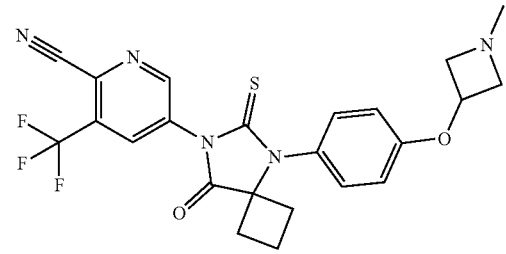 [SMILES: CN1CC(Oc2ccc(N3C(=S)N(c4cnc(C#N)c(C(F)(F)F)c4)C(=O)C34CCC4)cc2)C1] | 84 | 5-[8-[4-(1-methylazetidin-3-yl)oxyphenyl]-5-oxo-7-thioxo-6,8-diazaspiro[3.4]octan-6-yl]-3-(trifluoromethyl)pyridine-2-carbonitrile |

TABLE 1-continued

| Structure | Cpd No. | Cpd Name |
|---|---|---|
| 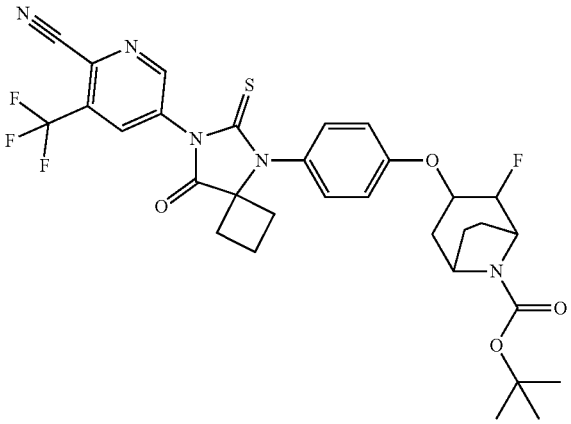 [SMILES: CC(C)(C)OC(=O)N1C2CCC1C(F)C(Oc1ccc(N3C(=S)N(c4cnc(C#N)c(C(F)(F)F)c4)C(=O)C34CCC4)cc1)C2] | 85 | tert-butyl 3-[4-[6-[6-cyano-5-(trifluoromethyl)-3-pyridyl]-5-oxo-7-thioxo-6,8-diazaspiro[3.4]octan-8-yl]phenoxy]-4-fluoro-8-azabicyclo[3.2.1]octane-8-carboxylate |
| 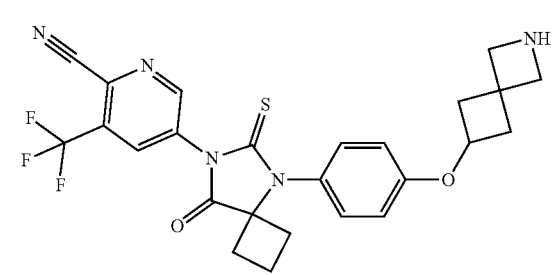 [SMILES: N#Cc1ncc(N2C(=O)C3(CCC3)N(c3ccc(OC4CC5(CNC5)C4)cc3)C2=S)cc1C(F)(F)F] | 86 | 5-[8-[4-(6-azaspiro[3.3]heptan-2-yloxy)phenyl]-5-oxo-7-thioxo-6,8-diazaspiro[3.4]octan-6-yl]-3-(trifluoromethyl)pyridine-2-carbonitrile |
| 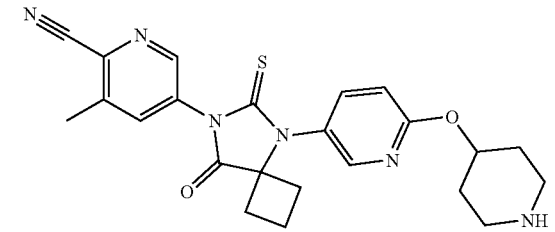 [SMILES: Cc1cc(N2C(=O)C3(CCC3)N(c3ccc(OC4CCNCC4)nc3)C2=S)cnc1C#N] | 87 | 3-methyl-5-[5-oxo-8-[6-(4-piperidyloxy)-3-pyridyl]-7-thioxo-6,8-diazaspiro[3.4]octan-6-yl]pyridine-2-carbonitrile |
| 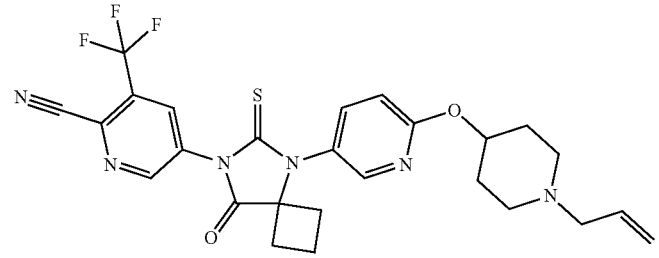 [SMILES: C=CCN1CCC(Oc2ccc(N3C(=S)N(c4cnc(C#N)c(C(F)(F)F)c4)C(=O)C34CCC4)cn2)CC1] | 88 | 5-[8-[6-[(1-allyl-4-piperidyl)oxy]-3-pyridyl]-5-oxo-7-thioxo-6,8-diazaspiro[3.4]octan-6-yl]-3-(trifluoromethyl)pyridine-2-carbonitrile |
| 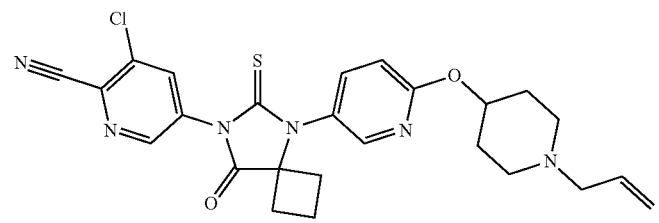 [SMILES: C=CCN1CCC(Oc2ccc(N3C(=S)N(c4cnc(C#N)c(Cl)c4)C(=O)C34CCC4)cn2)CC1] | 89 | 5-[8-[6-[(1-allyl-4-piperidyl)oxy]-3-pyridyl]-5-oxo-7-thioxo-6,8-diazaspiro[3.4]octan-6-yl]-3-chloro-pyridine-2-carbonitrile |

TABLE 1-continued

| Structure | Cpd No. | Cpd Name |
|---|---|---|
| 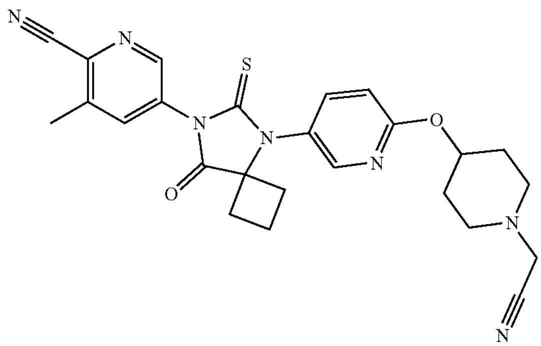 [SMILES: Cc1cc(N2C(=O)C3(CCC3)N(c3ccc(OC4CCN(CC#N)CC4)nc3)C2=S)cnc1C#N] | 90 | 5-[8-[6-[[1-(cyanomethyl)-4-piperidyl]oxy]-3-pyridyl]-5-oxo-7-thioxo-6,8-diazaspiro[3.4]octan-6-yl]-3-methyl-pyridine-2-carbonitrile |
| 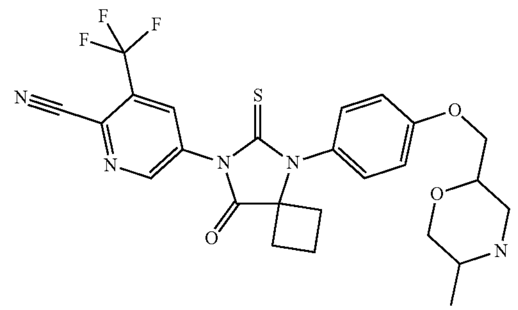 [SMILES: CC1COC(COc2ccc(N3C(=S)N(c4cnc(C#N)c(C(F)(F)F)c4)C(=O)C34CCC4)cc2)CN1] | 91 | 5-[8-[4-[(5-methylmorpholin-2-yl)methoxy]phenyl]-5-oxo-7-thioxo-6,8-diazaspiro[3.4]octan-6-yl]-3-(trifluoromethyl)pyridine-2-carbonitrile |
| 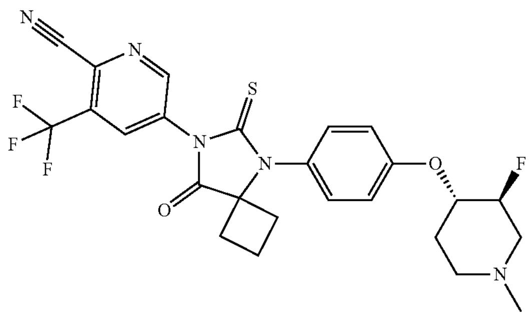 [SMILES: CN1CC[C@H](Oc2ccc(N3C(=S)N(c4cnc(C#N)c(C(F)(F)F)c4)C(=O)C34CCC4)cc2)[C@@H](F)C1] | 92 | 5-[8-[(3SR, 4R)-4-[(3-fluoro-1-methyl-4-piperidyl)oxy]phenyl]-5-oxo-7-thioxo-6,8-diazaspiro[3.4]octan-6-yl]-3-(trifluoromethyl)pyridine-2-carbonitrile |
| 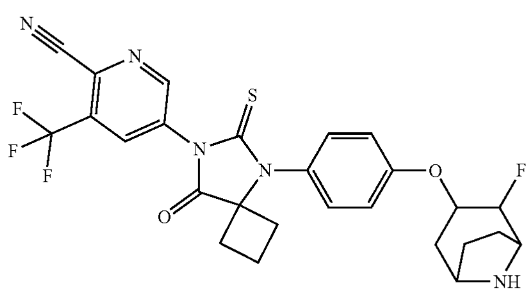 [SMILES: N#Cc1ncc(N2C(=O)C3(CCC3)N(c3ccc(OC4CC5CCC(N5)C4F)cc3)C2=S)cc1C(F)(F)F] | 93 | 5-[8-[4-[(4-fluoro-8-azabicyclo[3.2.1]octan-3-yl)oxy]phenyl]-5-oxo-7-thioxo-6,8-diazaspiro[3.4]octan-6-yl]-3-(trifluoromethyl)pyridine-2-carbonitrile |
| 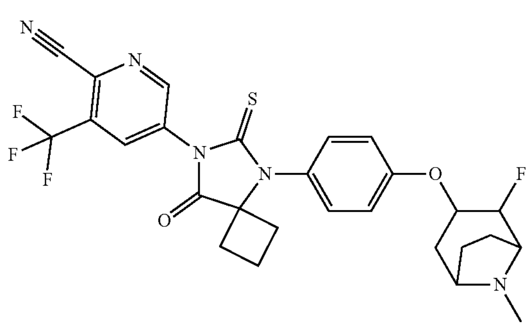 [SMILES: CN1C2CCC1C(F)C(Oc1ccc(N3C(=S)N(c4cnc(C#N)c(C(F)(F)F)c4)C(=O)C34CCC4)cc1)C2] | 94 | 5-[8-[4-[(4-fluoro-8-methyl-8-azabicyclo[3.2.1]octan-3-yl)oxy]phenyl]-5-oxo-7-thioxo-6,8-diazaspiro[3.4]octan-6-yl]-3-(trifluoromethyl)pyridine-2-carbonitrile |

TABLE 1-continued

| Structure | Cpd No. | Cpd Name |
|---|---|---|
| 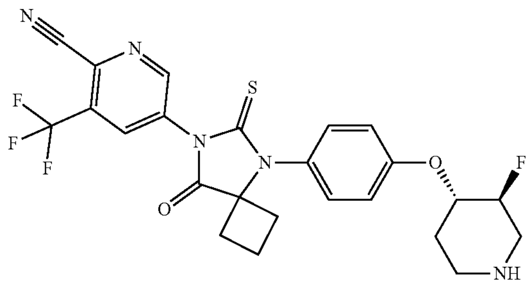 [SMILES: N#Cc1ncc(N2C(=O)C3(CCC3)N(c3ccc(O[C@H]4CCNC[C@@H]4F)cc3)C2=S)cc1C(F)(F)F] | 95 | 5-[8-[(3SR, 4SR)-4-[(3-fluoro-4-piperidyl)oxy]phenyl]-5-oxo-7-thioxo-6,8-diazaspiro[3.4]octan-6-yl]-3-(trifluoromethyl)pyridine-2-carbonitrile |
| 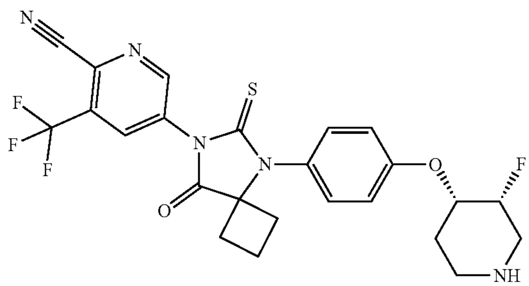 [SMILES: N#Cc1ncc(N2C(=O)C3(CCC3)N(c3ccc(O[C@H]4CCNC[C@H]4F)cc3)C2=S)cc1C(F)(F)F] | 96 | 5-[8-(3RS,4SR)[4-[(3-fluoro-4-piperidyl)oxy]phenyl]-5-oxo-7-thioxo-6,8-diazaspiro[3.4]octan-6-yl]-3-(trifluoromethyl)pyridine-2-carbonitrile |
| 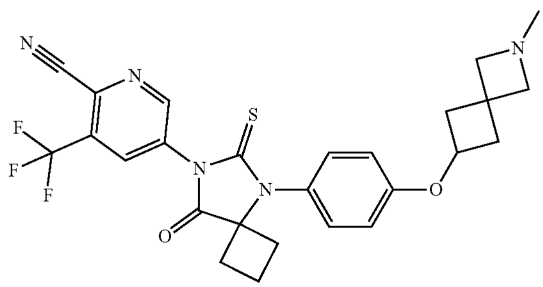 [SMILES: CN1CC2(CC(Oc3ccc(N4C(=S)N(c5cnc(C#N)c(C(F)(F)F)c5)C(=O)C45CCC5)cc3)C2)C1] | 97 | 5-[8-[4-[(6-methyl-6-azaspiro[3.3]heptan-2-yl)oxy]phenyl]-5-oxo-7-thioxo-6,8-diazaspiro[3.4]octan-6-yl]-3-(trifluoromethyl)pyridine-2-carbonitrile |
| 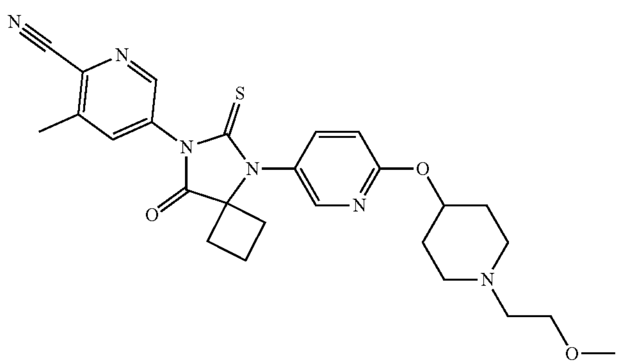 [SMILES: COCCN1CCC(Oc2ccc(N3C(=S)N(c4cnc(C#N)c(C)c4)C(=O)C34CCC4)cn2)CC1] | 98 | 5-[8-[6-[[1-(2-methoxyethyl)-4-piperidyl]oxy]-3-pyridyl]-5-oxo-7-thioxo-6,8-diazaspiro[3.4]octan-6-yl]-3-methyl-pyridine-2-carbonitrile |
| 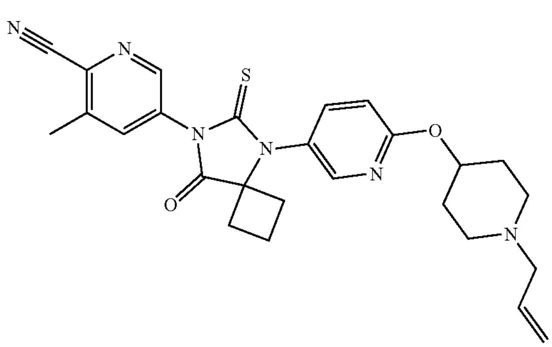 [SMILES: C=CCN1CCC(Oc2ccc(N3C(=S)N(c4cnc(C#N)c(C)c4)C(=O)C34CCC4)cn2)CC1] | 99 | 5-[8-[6-[(1-allyl-4-piperidyl)oxy]-3-pyridyl]-5-oxo-7-thioxo-6,8-diazaspiro[3.4]octan-6-yl]-3-methyl-pyridine-2-carbonitrile |

TABLE 1-continued

| Structure | Cpd No. | Cpd Name |
|---|---|---|
| 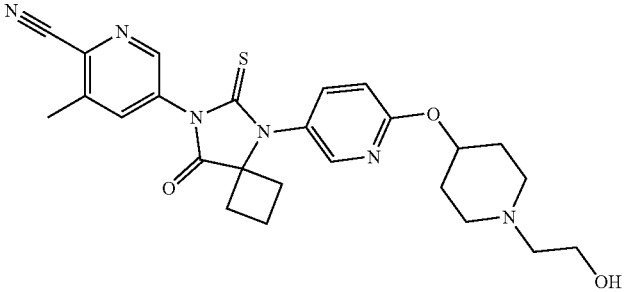 [SMILES: Cc1cc(N2C(=O)C3(CCC3)N(c3ccc(OC4CCN(CCO)CC4)nc3)C2=S)cnc1C#N] | 100 | 5-[8-[6-[[1-(2-hydroxyethyl)-4-piperidyl]oxy]-3-pyridyl]-5-oxo-7-thioxo-6,8-diazaspiro[3.4]octan-6-yl]-3-methyl-pyridine-2-carbonitrile |
| 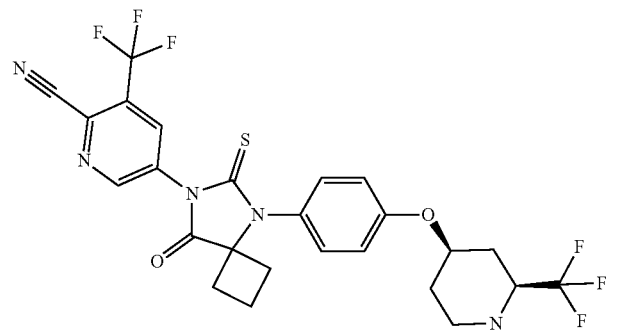 [SMILES: N#Cc1ncc(N2C(=O)C3(CCC3)N(c3ccc(O[C@@H]4CCN[C@H](C(F)(F)F)C4)cc3)C2=S)cc1C(F)(F)F] | 101 | 5-[5-oxo-7-thioxo-8-[4-[[(2SR,4RS)-2-(trifluoromethyl)-4-piperidyl]oxy]phenyl]-6,8-diazaspiro[3.4]octan-6-yl]-3-(trifluoromethyl)pyridine-2-carbonitrile |
| 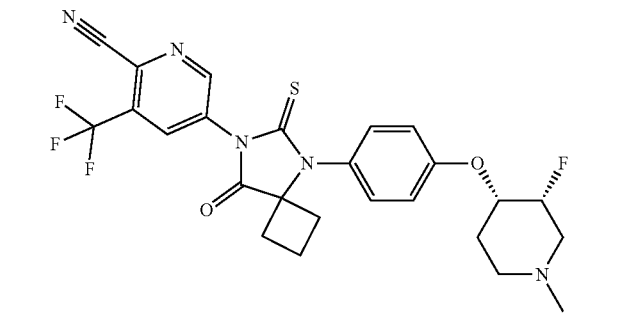 [SMILES: CN1CC[C@H](Oc2ccc(N3C(=S)N(c4cnc(C#N)c(C(F)(F)F)c4)C(=O)C34CCC4)cc2)[C@H](F)C1] | 102 | 5-[8-[(3RS, 4SR) -[4-[(3-fluoro-1-methyl-4-piperidyl)oxy]phenyl]-5-oxo-7-thioxo-6,8-diazaspiro[3.4]octan-6-yl]-3-(trifluoromethyl)pyridine-2-carbonitrile |
| 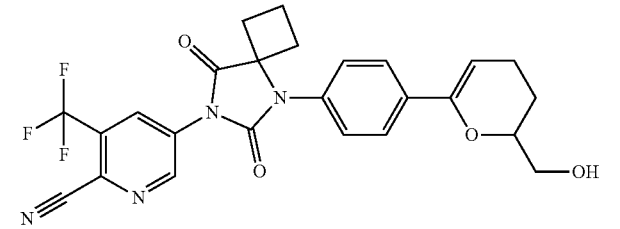 [SMILES: N#Cc1ncc(N2C(=O)N(c3ccc(C4=CCCC(CO)O4)cc3)C3(CCC3)C2=O)cc1C(F)(F)F] | 103 | 5-[8-[4-[2-(hydroxymethyl)-3,4-dihydro-2H-pyran-6-yl]phenyl]-5-oxo-7-thioxo-6,8-diazaspiro[3.4]octan-6-yl]-3-(trifluoromethyl)pyridine-2-carbonitrile |
| 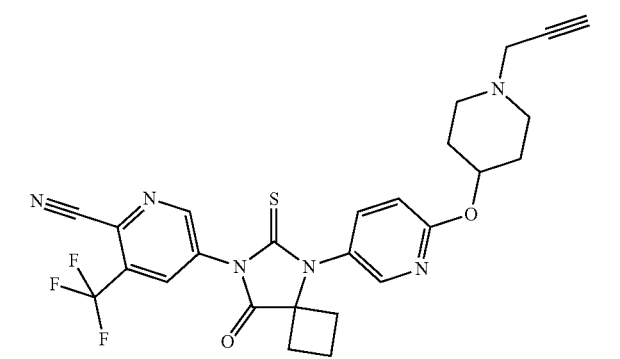 [SMILES: C#CCN1CCC(Oc2ccc(N3C(=S)N(c4cnc(C#N)c(C(F)(F)F)c4)C(=O)C34CCC4)cn2)CC1] | 104 | 5-[5-oxo-8-[6-[(1-prop-2-ynyl-4-piperidyl)oxy]-3-pyridyl]-7-thioxo-6,8-diazaspiro[3.4]octan-6-yl]-3-(trifluoromethyl)pyridine-2-carbonitrile |

TABLE 1-continued

| Structure | Cpd No. | Cpd Name |
|---|---|---|
| 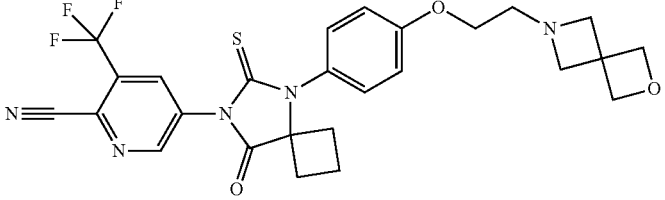 | 105 | 5-[8-[4-[2-(6-oxa-2-azaspiro[3.3]heptan-2-yl)ethoxy]phenyl]-5-oxo-7-thioxo-6,8-diazaspiro[3.4]octan-6-yl]-3-(trifluoromethyl)pyridine-2-carbonitrile |
| 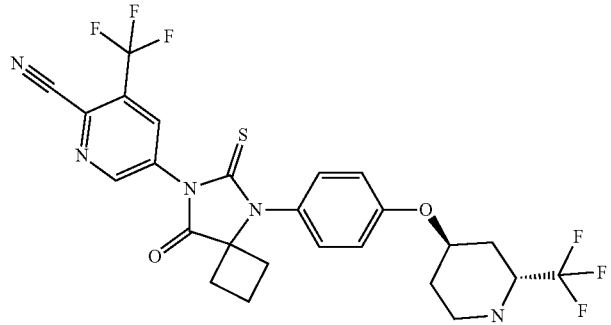 [SMILES: N#Cc1ncc(N2C(=O)C3(CCC3)N(c3ccc(O[C@@H]4CCN[C@@H](C(F)(F)F)C4)cc3)C2=S)cc1C(F)(F)F] | 106 | 5-[5-oxo-7-thioxo-8-[4-[[(2RS,4RS)-2-(trifluoromethyl)-4-piperidyl]oxy]phenyl]-6,8-diazaspiro[3.4]octan-6-yl]-3-(trifluoromethyl)pyridine-2-carbonitrile |
| 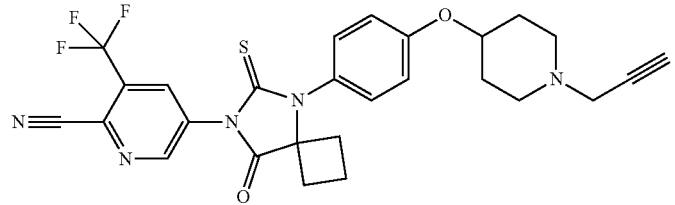 [SMILES: C#CCN1CCC(Oc2ccc(N3C(=S)N(c4cnc(C#N)c(C(F)(F)F)c4)C(=O)C34CCC4)cc2)CC1] | 107 | 5-[5-oxo-8-[4-[(1-prop-2-ynyl-4-piperidyl)oxy]phenyl]-7-thioxo-6,8-diazaspiro[3.4]octan-6-yl]-3-(trifluoromethyl)pyridine-2-carbonitrile |
| 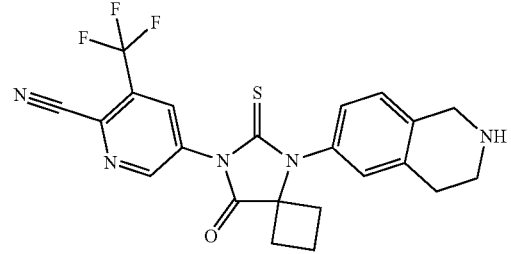 [SMILES: N#Cc1ncc(N2C(=O)C3(CCC3)N(c3ccc4c(c3)CCNC4)C2=S)cc1C(F)(F)F] | 108 | 5-[5-oxo-8-(1,2,3,4-tetrahydroisoquinolin-6-yl)-7-thioxo-6,8-diazaspiro[3.4]octan-6-yl]-3-(trifluoromethyl)pyridine-2-carbonitrile |
| 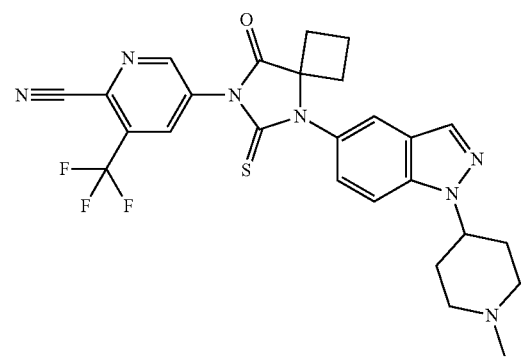 [SMILES: CN1CCC(n2ncc3cc(N4C(=S)N(c5cnc(C#N)c(C(F)(F)F)c5)C(=O)C45CCC5)ccc32)CC1] | 109 | 5-[8-[1-(1-methyl-4-piperidyl)indazol-5-yl]-5-oxo-7-thioxo-6,8-diazaspiro[3.4]octan-6-yl]-3-(trifluoromethyl)pyridine-2-carbonitrile |

TABLE 1-continued

| Structure | Cpd No. | Cpd Name |
|---|---|---|
| 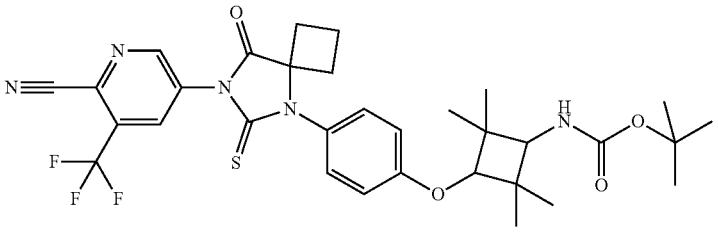 [SMILES: CC(C)(C)OC(=O)NC1C(C)(C)C(Oc2ccc(N3C(=S)N(c4cnc(C#N)c(C(F)(F)F)c4)C(=O)C34CCC4)cc2)C1(C)C] | 110 | tert-butyl N-[3-[4-[6-[6-cyano-5-(trifluoromethyl)-3-pyridyl]-5-oxo-7-thioxo-6,8-diazaspiro[3.4]octan-8-yl]phenoxy]-2,2,4,4-tetramethyl-cyclobutyl]carbamate |
| 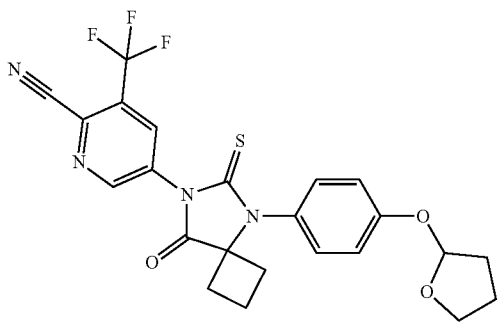 [SMILES: N#Cc1ncc(N2C(=O)C3(CCC3)N(c3ccc(OC4CCCO4)cc3)C2=S)cc1C(F)(F)F] | 111 | 5-[5-oxo-8-(4-tetrahydrofuran-2-yloxyphenyl)-7-thioxo-6,8-diazaspiro[3.4]octan-6-yl]-3-(trifluoromethyl)pyridine-2-carbonitrile |
| 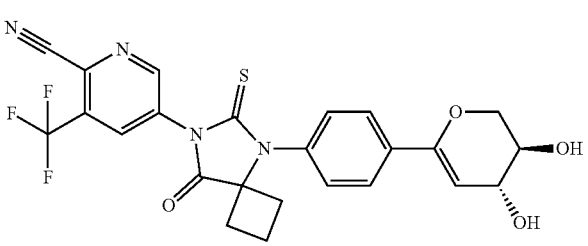 [SMILES: N#Cc1ncc(N2C(=O)C3(CCC3)N(c3ccc(C4=C[C@@H](O)[C@H](O)CO4)cc3)C2=S)cc1C(F)(F)F] | 112 | 5-[8-[4-[(3R,4R)-3,4-dihydroxy-3,4-dihydro-2H-pyran-6-yl]phenyl]-5-oxo-7-thioxo-6,8-diazaspiro[3.4]octan-6-yl]-3-(trifluoromethyl)pyridine-2-carbonitrile |
| 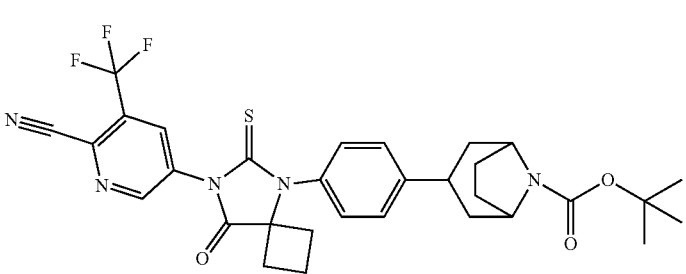 [SMILES: CC(C)(C)OC(=O)N1C2CCC1CC(c1ccc(N3C(=S)N(c4cnc(C#N)c(C(F)(F)F)c4)C(=O)C34CCC4)cc1)C2] | 113 | tert-butyl 3-[4-[6-[6-cyano-5-(trifluoromethyl)-3-pyridyl]-5-oxo-7-thioxo-6,8-diazaspiro[3.4]octan-8-yl]phenyl]-8-azabicyclo[3.2.1]octane-8-carboxylate |
| 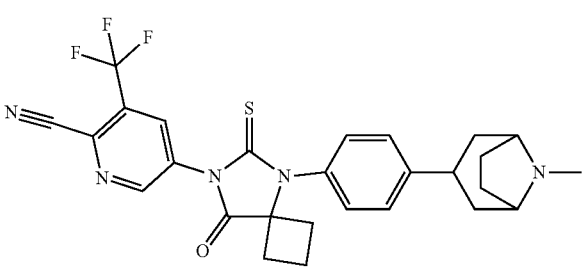 [SMILES: CN1C2CCC1CC(c1ccc(N3C(=S)N(c4cnc(C#N)c(C(F)(F)F)c4)C(=O)C34CCC4)cc1)C2] | 114 | 5-[8-[4-(8-methyl-8-azabicyclo[3.2.1]octan-3-yl)phenyl]-5-oxo-7-thioxo-6,8-diazaspiro[3.4]octan-6-yl]-3-(trifluoromethyl)pyridine-2-carbonitrile |
| 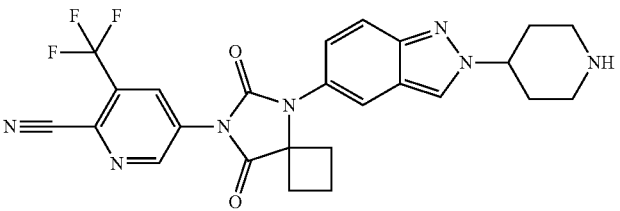 [SMILES: N#Cc1ncc(N2C(=O)N(c3ccc4nn(C5CCNCC5)cc4c3)C3(CCC3)C2=O)cc1C(F)(F)F] | 115 | 5-[5-oxo-8-[2-(4-piperidyl)indazol-5-yl]-7-thioxo-6,8-diazaspiro[3.4]octan-6-yl]-3-(trifluoromethyl)pyridine-2-carbonitrile |

TABLE 1-continued

| Structure | Cpd No. | Cpd Name |
|---|---|---|
| 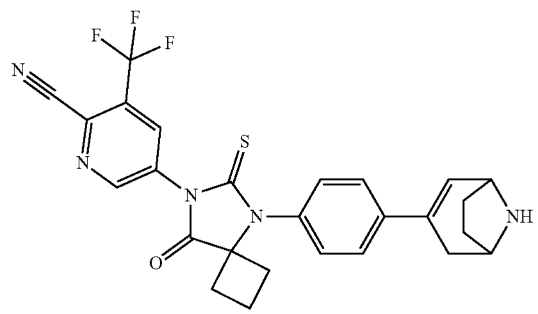 [SMILES: N#Cc1ncc(N2C(=O)C3(CCC3)N(c3ccc(C4=CC5CCC(C4)N5)cc3)C2=S)cc1C(F)(F)F] | 116 | 5-[8-[4-(8-azabicyclo[3.2.1]oct-3-en-3-yl)phenyl]-5-oxo-7-thioxo-6,8-diazaspiro[3.4]octan-6-yl]-3-(trifluoromethyl)pyridine-2-carbonitrile |
| 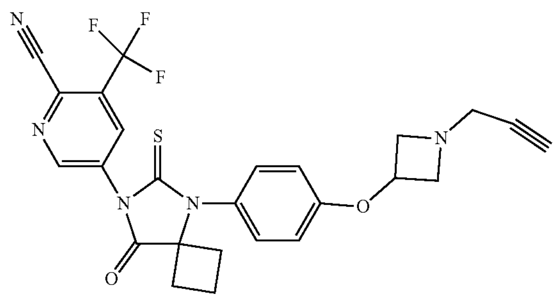 [SMILES: C#CCN1CC(Oc2ccc(N3C(=S)N(c4cnc(C#N)c(C(F)(F)F)c4)C(=O)C34CCC4)cc2)C1] | 117 | 5-[5-oxo-8-[4-(1-prop-2-ynylazetidin-3-yl)oxyphenyl]-7-thioxo-6,8-diazaspiro[3.4]octan-6-yl]-3-(trifluoromethyl)pyridine-2-carbonitrile |
| 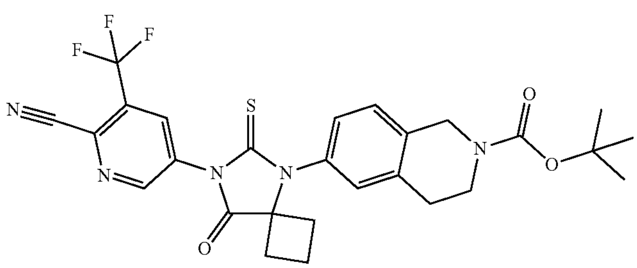 [SMILES: CC(C)(C)OC(=O)N1CCc2cc(N3C(=S)N(c4cnc(C#N)c(C(F)(F)F)c4)C(=O)C34CCC4)ccc2C1] | 118 | tert-butyl 6-[6-[6-cyano-5-(trifluoromethyl)-3-pyridyl]-5-oxo-7-thioxo-6,8-diazaspiro[3.4]octan-8-yl]-3,4-dihydro-1H-isoquinoline-2-carboxylate |
| 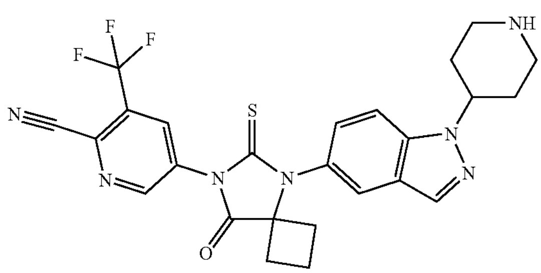 [SMILES: N#Cc1ncc(N2C(=O)C3(CCC3)N(c3ccc4c(cnn4C4CCNCC4)c3)C2=S)cc1C(F)(F)F] | 119 | 5-[5-oxo-8-[1-(4-piperidyl)indazol-5-yl]-7-thioxo-6,8-diazaspiro[3.4]octan-6-yl]-3-(trifluoromethyl)pyridine-2-carbonitrile |
| 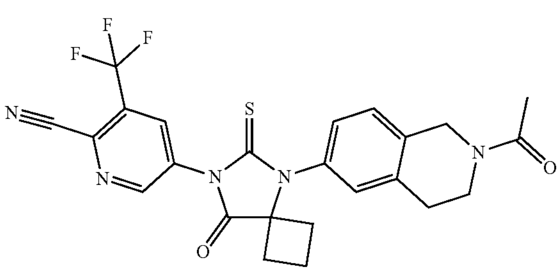 [SMILES: CC(=O)N1CCc2cc(N3C(=S)N(c4cnc(C#N)c(C(F)(F)F)c4)C(=O)C34CCC4)ccc2C1] | 120 | 5-[8-(2-acetyl-3,4-dihydro-1H-isoquinolin-6-yl)-5-oxo-7-thioxo-6,8-diazaspiro[3.4]octan-6-yl]-3-(trifluoromethyl)pyridine-2-carbonitrile |

TABLE 1-continued

| Structure | Cpd No. | Cpd Name |
|---|---|---|
| 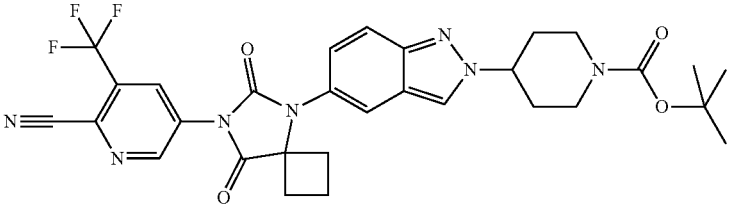 [SMILES: CC(C)(C)OC(=O)N1CCC(n2cc3cc(N4C(=O)N(c5cnc(C#N)c(C(F)(F)F)c5)C(=O)C45CCC5)ccc3n2)CC1] | 121 | tert-butyl 4-[5-[6-[6-cyano-5-(trifluoromethyl)-3-pyridyl]-5-oxo-7-thioxo-6,8-diazaspiro[3.4]octan-8-yl]indazol-2-yl]piperidine-1-carboxylate |
| 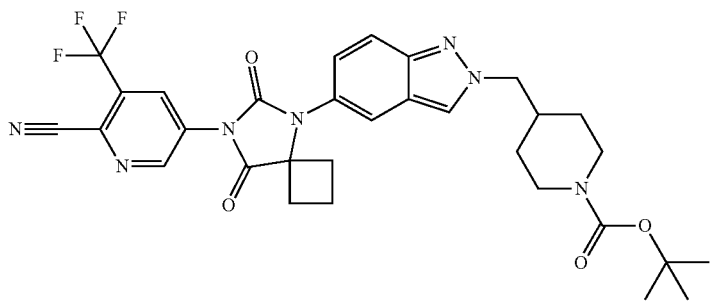 [SMILES: CC(C)(C)OC(=O)N1CCC(Cn2cc3cc(N4C(=O)N(c5cnc(C#N)c(C(F)(F)F)c5)C(=O)C45CCC5)ccc3n2)CC1] | 122 | tert-butyl4-[[5-[6-[6-cyano-5-(trifluoromethyl)-3-pyridyl]-5-oxo-7-thioxo-6,8-diazaspiro[3.4]octan-8-yl]indazol-2-yl]methyl]piperidine-1-carboxylate |
| 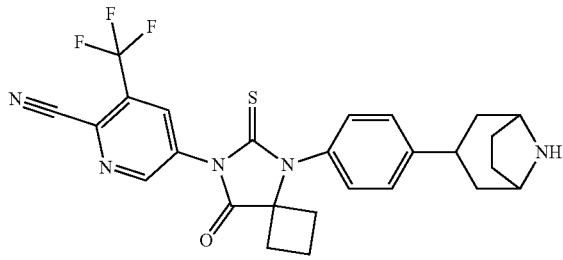 [SMILES: N#Cc1ncc(N2C(=O)C3(CCC3)N(c3ccc(C4CC5CCC(C4)N5)cc3)C2=S)cc1C(F)(F)F] | 123 | 5-[8-[4-(8-azabicyclo[3.2.1]octan-3-yl)phenyl]-5-oxo-7-thioxo-6,8-diazaspiro[3.4]octan-6-yl]-3-(trifluoromethyl)pyridine-2-carbonitrile |
| 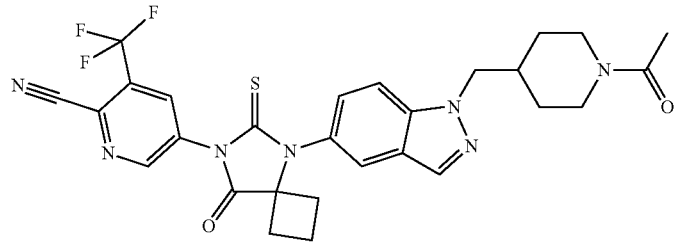 [SMILES: CC(=O)N1CCC(Cn2ncc3cc(N4C(=S)N(c5cnc(C#N)c(C(F)(F)F)c5)C(=O)C45CCC5)ccc32)CC1] | 124 | 5-[8-[1-[(1-acetyl-4-piperidyl)methyl]indazol-5-yl]-5-oxo-7-thioxo-6,8-diazaspiro[3.4]octan-6-yl]-3-(trifluoromethyl)pyridine-2-carbonitrile |
| 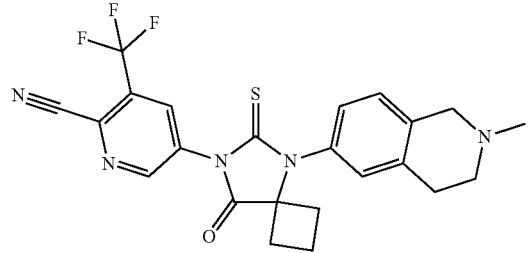 [SMILES: CN1CCc2cc(N3C(=S)N(c4cnc(C#N)c(C(F)(F)F)c4)C(=O)C34CCC4)ccc2C1] | 125 | 5-[8-(2-methyl-3,4-dihydro-1H-isoquinolin-6-yl)-5-oxo-7-thioxo-6,8-diazaspiro[3.4]octan-6-yl]-3-(trifluoromethyl)pyridine-2-carbonitrile |
| 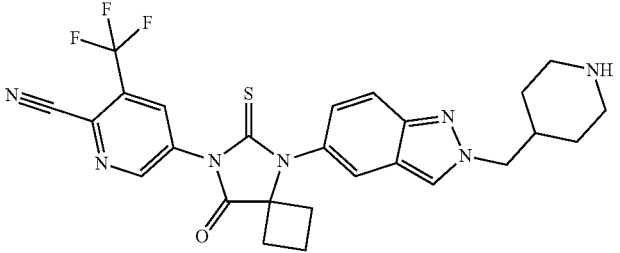 [SMILES: N#Cc1ncc(N2C(=O)C3(CCC3)N(c3ccc4nn(CC5CCNCC5)cc4c3)C2=S)cc1C(F)(F)F] | 126 | 5-[5-oxo-8-[2-(4-piperidylmethyl)indazol-5-yl]-7-thioxo-6,8-diazaspiro[3.4]octan-6-yl]-3-(trifluoromethyl)pyridine-2-carbonitrile |

TABLE 1-continued

| Structure | Cpd No. | Cpd Name |
|---|---|---|
| 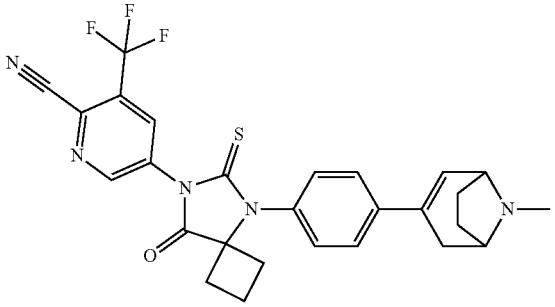 [SMILES: CN1C2C=C(c3ccc(N4C(=S)N(c5cnc(C#N)c(C(F)(F)F)c5)C(=O)C45CCC5)cc3)CC1CC2] | 127 | 5-[8-[4-(8-methyl-8-azabicyclo[3.2.1]oct-3-en-3-yl)phenyl]-5-oxo-7-thioxo-6,8-diazaspiro[3.4]octan-6-yl]-3-(trifluoromethyl)pyridine-2-carbonitrile |
| 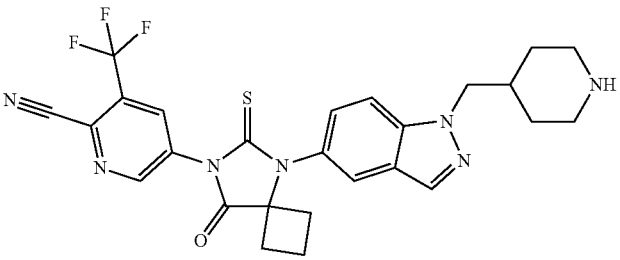 [SMILES: N#Cc1ncc(N2C(=O)C3(CCC3)N(c3ccc4c(cnn4CC4CCNCC4)c3)C2=S)cc1C(F)(F)F] | 128 | 5-[5-oxo-8-[1-(4-piperidylmethyl)indazol-5-yl]-7-thioxo-6,8-diazaspiro[3.4]octan-6-yl]-3-(trifluoromethyl)pyridine-2-carbonitrile |
| 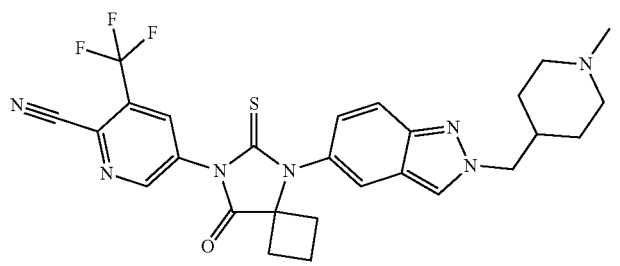 [SMILES: CN1CCC(Cn2cc3cc(N4C(=S)N(c5cnc(C#N)c(C(F)(F)F)c5)C(=O)C45CCC5)ccc3n2)CC1] | 129 | 5-[8-[2-[(1-methyl-4-piperidyl)methyl]indazol-5-yl]-5-oxo-7-thioxo-6,8-diazaspiro[3.4]octan-6-yl]-3-(trifluoromethyl)pyridine-2-carbonitrile |
| 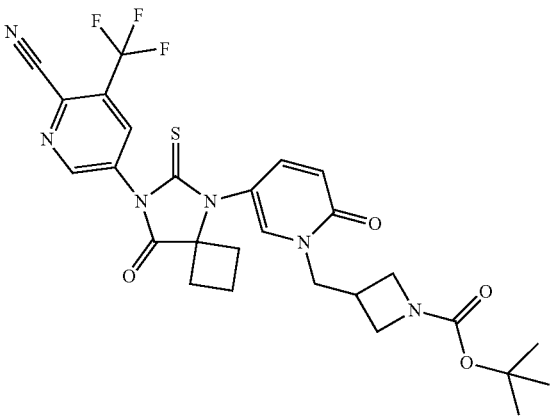 [SMILES: CC(C)(C)OC(=O)N1CC(Cn2cc(N3C(=S)N(c4cnc(C#N)c(C(F)(F)F)c4)C(=O)C34CCC4)ccc2=O)C1] | 130 | tert-butyl 3-[[5-[6-[6-cyano-5-(trifluoromethyl)-3-pyridyl]-5-oxo-7-thioxo-6,8-diazaspiro[3.4]octan-8-yl]-2-oxo-1-pyridyl]methyl]azetidine-1-carboxylate |
| 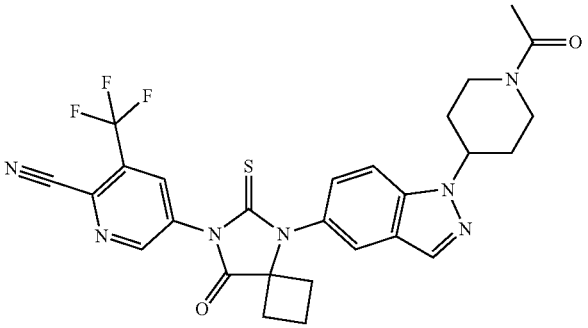 [SMILES: CC(=O)N1CCC(n2ncc3cc(N4C(=S)N(c5cnc(C#N)c(C(F)(F)F)c5)C(=O)C45CCC5)ccc32)CC1] | 131 | 5-[8-[1-(1-acetyl-4-piperidyl)indazol-5-yl]-5-oxo-7-thioxo-6,8-diazaspiro[3.4]octan-6-yl]-3-(trifluoromethyl)pyridine-2-carbonitrile |

TABLE 1-continued

| Structure | Cpd No. | Cpd Name |
|---|---|---|
| 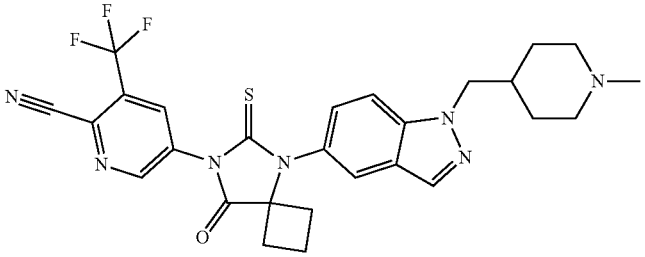 [SMILES: CN1CCC(Cn2ncc3cc(N4C(=S)N(c5cnc(C#N)c(C(F)(F)F)c5)C(=O)C45CCC5)ccc32)CC1] | 132 | 5-[8-[1-[(1-methyl-4-piperidyl)methyl]indazol-5-yl]-5-oxo-7-thioxo-6,8-diazaspiro[3.4]octan-6-yl]-3-(trifluoromethyl)pyridine-2-carbonitrile |
| 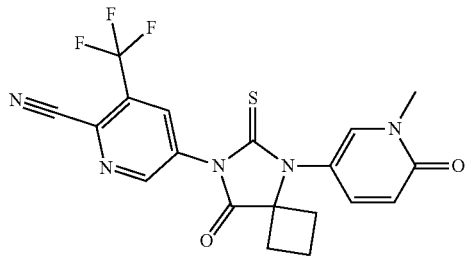 [SMILES: Cn1cc(N2C(=S)N(c3cnc(C#N)c(C(F)(F)F)c3)C(=O)C23CCC3)ccc1=O] | 133 | 5-[8-(1-methyl-6-oxo-3-pyridyl)-5-oxo-7-thioxo-6,8-diazaspiro[3.4]octan-6-yl]-3-(trifluoromethyl)pyridine-2-carbonitrile |
| 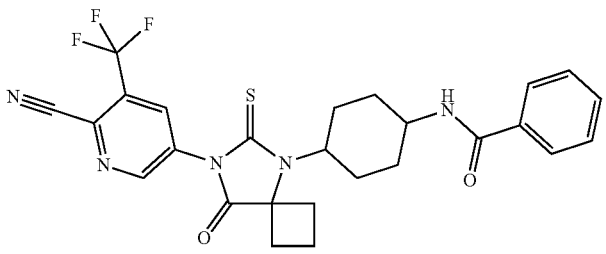 [SMILES: N#Cc1ncc(N2C(=O)C3(CCC3)N(C3CCC(NC(=O)c4ccccc4)CC3)C2=S)cc1C(F)(F)F] | 134 | N-[4-[6-[6-cyano-5-(trifluoromethyl)-3-pyridyl]-5-oxo-7-thioxo-6,8-diazaspiro[3.4]octan-8-yl]cyclohexyl]benzamide |
| 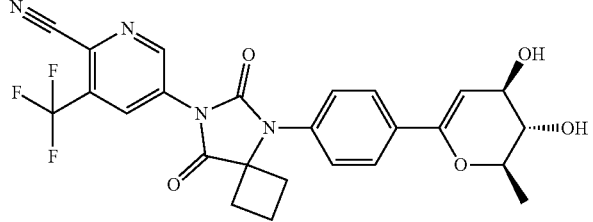 [SMILES: C[C@H]1OC(c2ccc(N3C(=O)N(c4cnc(C#N)c(C(F)(F)F)c4)C(=O)C34CCC4)cc2)=C[C@@H](O)[C@@H]1O] | 135 | 5-[8-[4-[(2S,3R,4S)-3,4-dihydroxy-2-methyl-3,4-dihydro-2H-pyran-6-yl]phenyl]-5-oxo-7-thioxo-6,8-diazaspiro[3.4]octan-6-yl]-3-(trifluoromethyl)pyridine-2-carbonitrile |
| 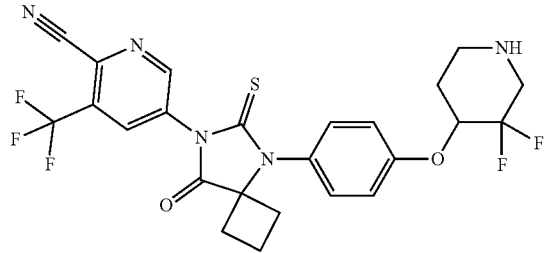 [SMILES: N#Cc1ncc(N2C(=O)C3(CCC3)N(c3ccc(OC4CCNCC4(F)F)cc3)C2=S)cc1C(F)(F)F] | 136 | 5-[8-[4-[(3,3-difluoro-4-piperidyl)oxy]phenyl]-5-oxo-7-thioxo-6,8-diazaspiro[3.4]octan-6-yl]-3-(trifluoromethyl)pyridine-2-carbonitrile |
| 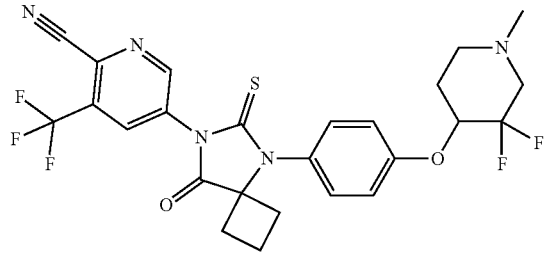 [SMILES: CN1CCC(Oc2ccc(N3C(=S)N(c4cnc(C#N)c(C(F)(F)F)c4)C(=O)C34CCC4)cc2)C(F)(F)C1] | 137 | 5-[8-[4-[(3,3-difluoro-1-methyl-4-piperidyl)oxy]phenyl]-5-oxo-7-thioxo-6,8-diazaspiro[3.4]octan-6-yl]-3-(trifluoromethyl)pyridine-2-carbonitrile |

TABLE 1-continued

| Structure | Cpd No. | Cpd Name |
|---|---|---|
| 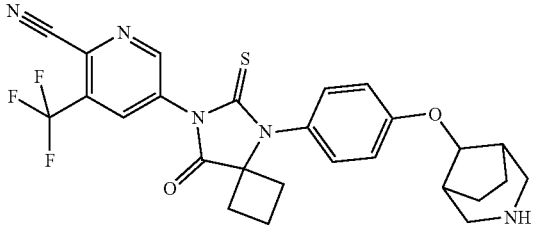 [SMILES: N#Cc1ncc(N2C(=O)C3(CCC3)N(c3ccc(OC4C5CCC4CNC5)cc3)C2=S)cc1C(F)(F)F] | 138 | 5-[8-[4-(3-azabicyclo[3.2.1]octan-8-yloxy)phenyl]-5-oxo-7-thioxo-6,8-diazaspiro[3.4]octan-6-yl]-3-(trifluoromethyl)pyridine-2-carbonitrile |
| 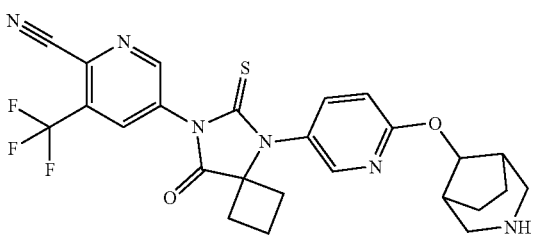 [SMILES: N#Cc1ncc(N2C(=O)C3(CCC3)N(c3ccc(OC4C5CCC4CNC5)nc3)C2=S)cc1C(F)(F)F] | 139 | 5-[8-[6-(3-azabicyclo[3.2.1]octan-8-yloxy)-3-pyridyl]-5-oxo-7-thioxo-6,8-diazaspiro[3.4]octan-6-yl]-3-(trifluoromethyl)pyridine-2-carbonitrile |
| 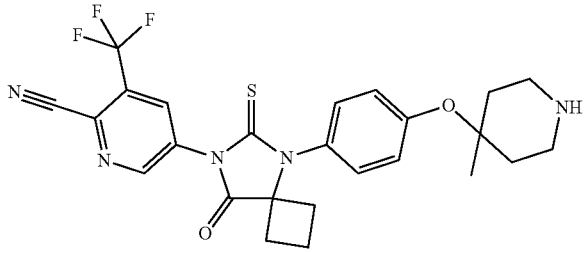 [SMILES: CC1(Oc2ccc(N3C(=S)N(c4cnc(C#N)c(C(F)(F)F)c4)C(=O)C34CCC4)cc2)CCNCC1] | 140 | 5-[8-[4-[(4-methyl-4-piperidyl)oxy]phenyl]-5-oxo-7-thioxo-6,8-diazaspiro[3.4]octan-6-yl]-3-(trifluoromethyl)pyridine-2-carbonitrile |
| 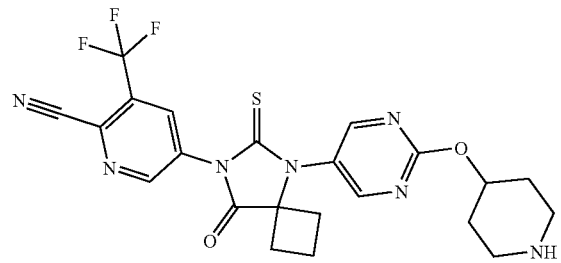 [SMILES: N#Cc1ncc(N2C(=O)C3(CCC3)N(c3cnc(OC4CCNCC4)nc3)C2=S)cc1C(F)(F)F] | 141 | 5-[5-oxo-8-[2-(4-piperidyloxy)pyrimidin-5-yl]-7-thioxo-6,8-diazaspiro[3.4]octan-6-yl]-3-(trifluoromethyl)pyridine-2-carbonitrile |
| 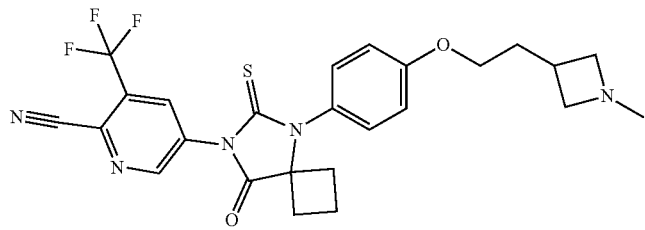 [SMILES: CN1CC(CCOc2ccc(N3C(=S)N(c4cnc(C#N)c(C(F)(F)F)c4)C(=O)C34CCC4)cc2)C1] | 142 | 5-[8-[4-[2-(1-methylazetidin-3-yl)ethoxy]phenyl]-5-oxo-7-thioxo-6,8-diazaspiro[3.4]octan-6-yl]-3-(trifluoromethyl)pyridine-2-carbonitrile |
| 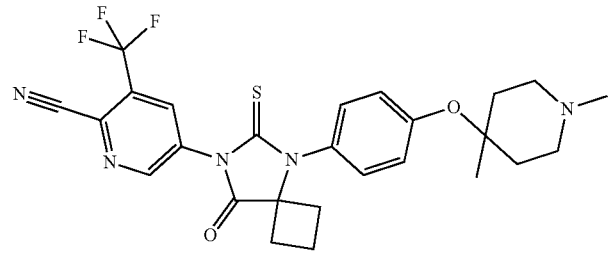 [SMILES: CN1CCC(C)(Oc2ccc(N3C(=S)N(c4cnc(C#N)c(C(F)(F)F)c4)C(=O)C34CCC4)cc2)CC1] | 143 | 5-[8-[4-[(1,4-dimethyl-4-piperidyl)oxy]phenyl]-5-oxo-7-thioxo-6,8-diazaspiro[3.4]octan-6-yl]-3-(trifluoromethyl)pyridine-2-carbonitrile |

TABLE 1-continued

| Structure | Cpd No. | Cpd Name |
|---|---|---|
| 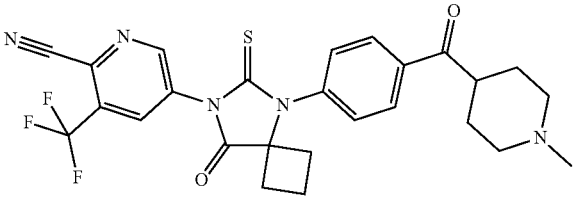 [SMILES: CN1CCC(C(=O)c2ccc(N3C(=S)N(c4cnc(C#N)c(C(F)(F)F)c4)C(=O)C34CCC4)cc2)CC1] | 144 | 5-[8-[4-(1-methylpiperidine-4-carbonyl)phenyl]-5-oxo-7-thioxo-6,8-diazaspiro[3.4]octan-6-yl]-3-(trifluoromethyl)pyridine-2-carbonitrile |
| 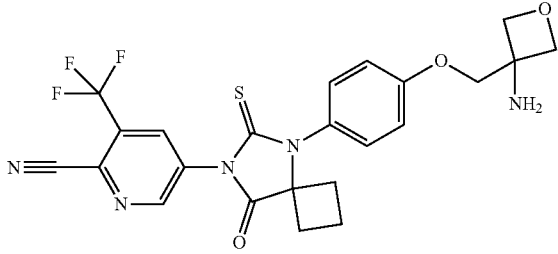 [SMILES: N#Cc1ncc(N2C(=O)C3(CCC3)N(c3ccc(OCC4(N)COC4)cc3)C2=S)cc1C(F)(F)F] | 145 | 5-[8-[4-[(3-aminooxetan-3-yl)methoxy]phenyl]-5-oxo-7-thioxo-6,8-diazaspiro[3.4]octan-6-yl]-3-(trifluoromethyl)pyridine-2-carbonitrile |
| 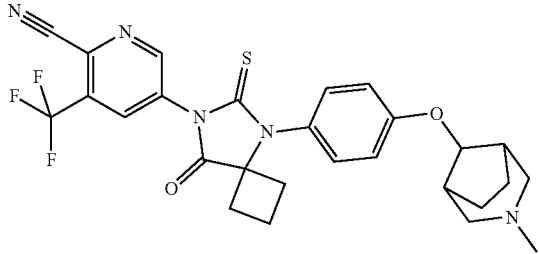 [SMILES: CN1CC2CCC(C1)C2Oc1ccc(N2C(=S)N(c3cnc(C#N)c(C(F)(F)F)c3)C(=O)C23CCC3)cc1] | 146 | 5-[8-[4-[(3-methyl-3-azabicyclo[3.2.1]octan-8-yl)oxy]phenyl]-5-oxo-7-thioxo-6,8-diazaspiro[3.4]octan-6-yl]-3-(trifluoromethyl)pyridine-2-carbonitrile |
| 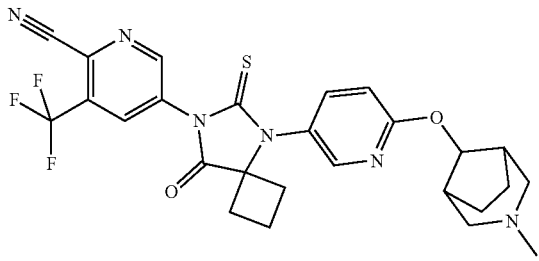 [SMILES: CN1CC2CCC(C1)C2Oc1ccc(N2C(=S)N(c3cnc(C#N)c(C(F)(F)F)c3)C(=O)C23CCC3)cn1] | 147 | 5-[8-[6-[(3-methyl-3-azabicyclo[3.2.1]octan-8-yl)oxy]-3-pyridyl]-5-oxo-7-thioxo-6,8-diazaspiro[3.4]octan-6-yl]-3-(trifluoromethyl)pyridine-2-carbonitrile |
| 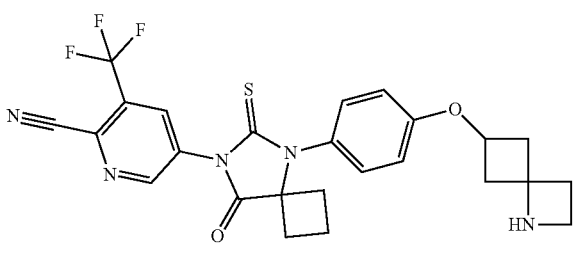 [SMILES: N#Cc1ncc(N2C(=O)C3(CCC3)N(c3ccc(OC4CC5(CCN5)C4)cc3)C2=S)cc1C(F)(F)F] | 148 | 5-[8-[4-(3-azaspiro[3.3]heptan-6-yloxy)phenyl]-5-oxo-7-thioxo-6,8-diazaspiro[3.4]octan-6-yl]-3-(trifluoromethyl)pyridine-2-carbonitrile |
| 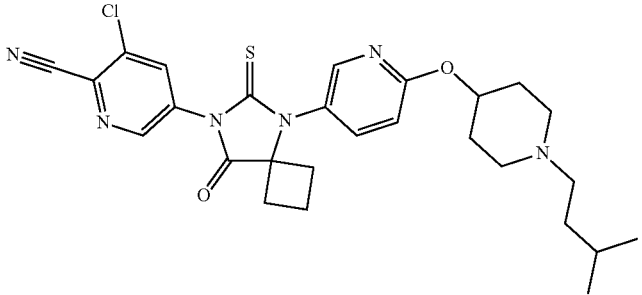 [SMILES: CC(C)CCN1CCC(Oc2ccc(N3C(=S)N(c4cnc(C#N)c(Cl)c4)C(=O)C34CCC4)cn2)CC1] | 149 | 3-chloro-5-[8-[6-[(1-isopentyl-4-piperidyl)oxy]-3-pyridyl]-5-oxo-7-thioxo-6,8-diazaspiro[3.4]octan-6-yl]pyridine-2-carbonitrile |

TABLE 1-continued

| Structure | Cpd No. | Cpd Name |
|---|---|---|
| 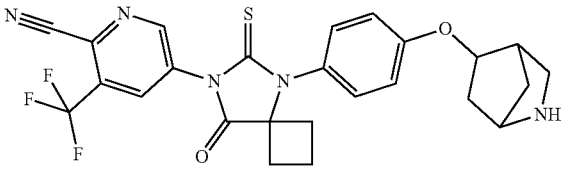 [SMILES: N#Cc1ncc(N2C(=O)C3(CCC3)N(c3ccc(OC4CC5CC4CN5)cc3)C2=S)cc1C(F)(F)F] | 150 | 5-[8-[4-(2-azabicyclo[2.2.1]heptan-5-yloxy)phenyl]-5-oxo-7-thioxo-6,8-diazaspiro[3.4]octan-6-yl]-3-(trifluoromethyl)pyridine-2-carbonitrile |
| 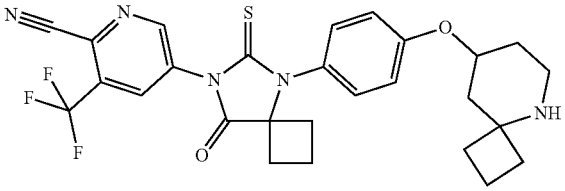 [SMILES: N#Cc1ncc(N2C(=O)C3(CCC3)N(c3ccc(OC4CCNC5(CCC5)C4)cc3)C2=S)cc1C(F)(F)F] | 151 | 5-[8-[4-(9-azaspiro[3.5]nonan-6-yloxy)phenyl]-5-oxo-7-thioxo-6,8-diazaspiro[3.4]octan-6-yl]-3-(trifluoromethyl)pyridine-2-carbonitrile |
| 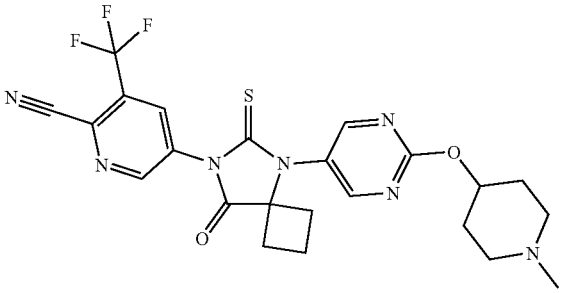 [SMILES: CN1CCC(Oc2ncc(N3C(=S)N(c4cnc(C#N)c(C(F)(F)F)c4)C(=O)C34CCC4)cn2)CC1] | 152 | 5-[8-[2-[(1-methyl-4-piperidyl)oxy]pyrimidin-5-yl]-5-oxo-7-thioxo-6,8-diazaspiro[3.4]octan-6-yl]-3-(trifluoromethyl)pyridine-2-carbonitrile |
| 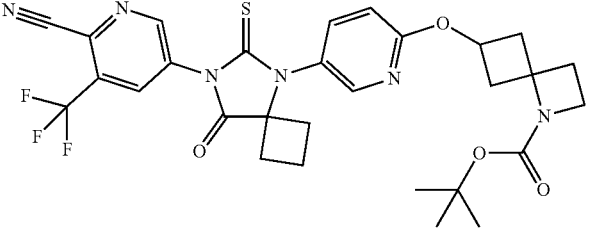 [SMILES: CC(C)(C)OC(=O)N1CCC12CC(Oc1ccc(N3C(=S)N(c4cnc(C#N)c(C(F)(F)F)c4)C(=O)C34CCC4)cn1)C2] | 153 | tert-butyl 6-[[5-[6-[6-cyano-5-(trifluoromethyl)-3-pyridyl]-5-oxo-7-thioxo-6,8-diazaspiro[3.4]octan-8-yl]-2-pyridyl]oxy]-3-azaspiro[3.3]heptane-3-carboxylate |
| 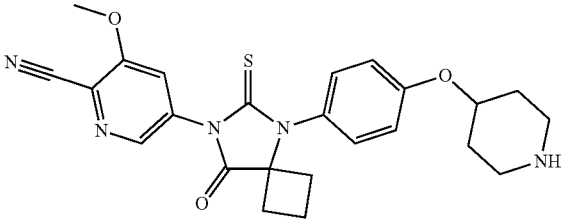 [SMILES: COc1cc(N2C(=O)C3(CCC3)N(c3ccc(OC4CCNCC4)cc3)C2=S)cnc1C#N] | 154 | 3-methoxy-5-[5-oxo-8-[4-(4-piperidyloxy)phenyl]-7-thioxo-6,8-diazaspiro[3.4]octan-6-yl]pyridine-2-carbonitrile |
| 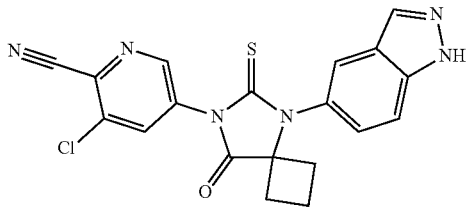 [SMILES: N#Cc1ncc(N2C(=O)C3(CCC3)N(c3ccc4[nH]ncc4c3)C2=S)cc1Cl] | 155 | 3-chloro-5-[8-(1H-indazol-5-yl)-5-oxo-7-thioxo-6,8-diazaspiro[3.4]octan-6-yl]pyridine-2-carbonitrile |

TABLE 1-continued

| Structure | Cpd No. | Cpd Name |
|---|---|---|
| 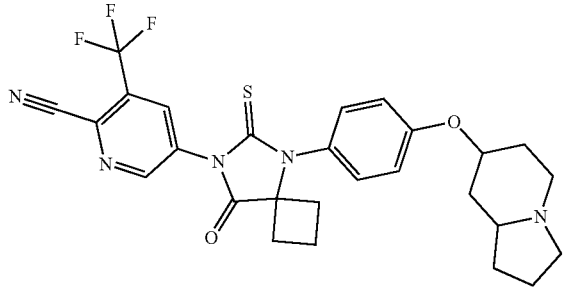 [SMILES: N#Cc1ncc(N2C(=O)C3(CCC3)N(c3ccc(OC4CCN5CCCC5C4)cc3)C2=S)cc1C(F)(F)F] | 156 | 5-[8-[4-(1,2,3,5,6,7,8,8a-octahydroindolizin-7-yloxy)phenyl]-5-oxo-7-thioxo-6,8-diazaspiro[3.4]octan-6-yl]-3-(trifluoromethyl)pyridine-2-carbonitrile |
| 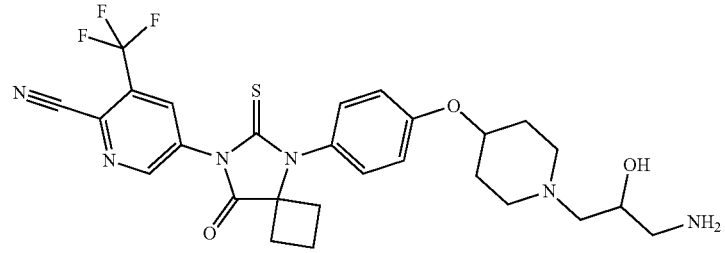 [SMILES: N#Cc1ncc(N2C(=O)C3(CCC3)N(c3ccc(OC4CCN(CC(O)CN)CC4)cc3)C2=S)cc1C(F)(F)F] | 157 | 5-[8-[4-[[1-(3-amino-2-hydroxy-propyl)-4-piperidyl]oxy]phenyl]-5-oxo-7-thioxo-6,8-diazaspiro[3.4]octan-6-yl]-3-(trifluoromethyl)pyridine-2-carbonitrile |
| 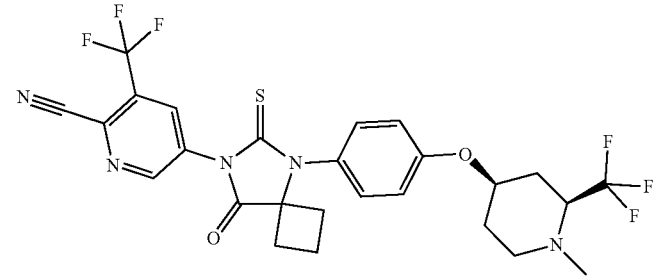 [SMILES: CN1CC[C@@H](Oc2ccc(N3C(=S)N(c4cnc(C#N)c(C(F)(F)F)c4)C(=O)C34CCC4)cc2)C[C@H]1C(F)(F)F] | 158 | 5-[8-[4-[[(2SR, 4RS)-1-methyl-2-(trifluoromethyl)-4-piperidyl]oxy]phenyl]-5-oxo-7-thioxo-6,8-diazaspiro[3.4]octan-6-yl]-3-(trifluoromethyl)pyridine-2-carbonitrile |
| 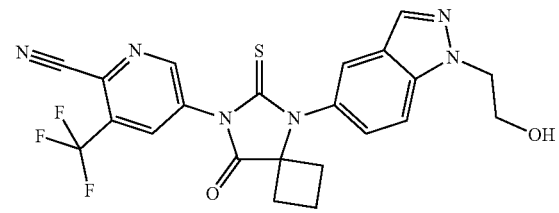 [SMILES: N#Cc1ncc(N2C(=O)C3(CCC3)N(c3ccc4c(cnn4CCO)c3)C2=S)cc1C(F)(F)F] | 159 | 5-[8-[1-(2-hydroxyethyl)indazol-5-yl]-5-oxo-7-thioxo-6,8-diazaspiro[3.4]octan-6-yl]-3-(trifluoromethyl)pyridine-2-carbonitrile |
| 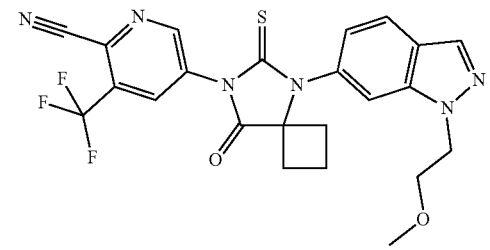 [SMILES: COCCn1ncc2ccc(N3C(=S)N(c4cnc(C#N)c(C(F)(F)F)c4)C(=O)C34CCC4)cc21] | 160 | 5-[8-[1-(2-methoxyethyl)indazol-6-yl]-5-oxo-7-thioxo-6,8-diazaspiro[3.4]octan-6-yl]-3-(trifluoromethyl)pyridine-2-carbonitrile |
| 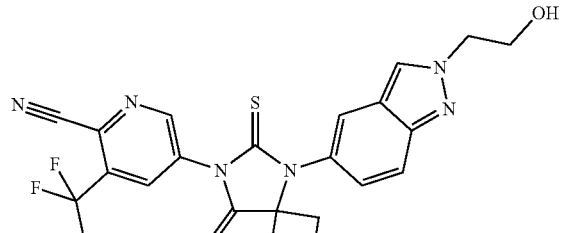 | 161 | 5-[8-[2-(2-hydroxyethyl)indazol-5-yl]-5-oxo-7-thioxo-6,8-diazaspiro[3.4]octan-6-yl]-3-(trifluoromethyl)pyridine-2-carbonitrile |

TABLE 1-continued

| Structure | Cpd No. | Cpd Name |
|---|---|---|
| 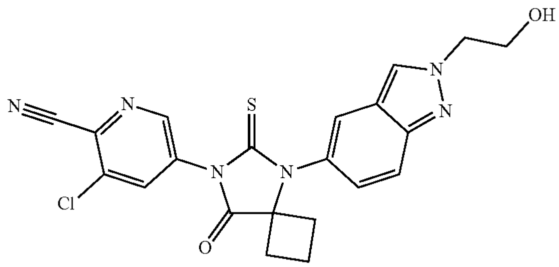 [SMILES: N#Cc1ncc(N2C(=O)C3(CCC3)N(c3ccc4nn(CCO)cc4c3)C2=S)cc1Cl] | 162 | 3-chloro-5-[8-[2-(2-hydroxyethyl)indazol-5-yl]-5-oxo-7-thioxo-6,8-diazaspiro[3.4]octan-6-yl]pyridine-2-carbonitrile |
| 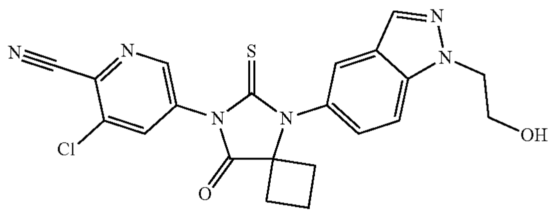 [SMILES: N#Cc1ncc(N2C(=O)C3(CCC3)N(c3ccc4c(cnn4CCO)c3)C2=S)cc1Cl] | 163 | 3-chloro-5-[8-[1-(2-hydroxyethyl)indazol-5-yl]-5-oxo-7-thioxo-6,8-diazaspiro[3.4]octan-6-yl]pyridine-2-carbonitrile |
| 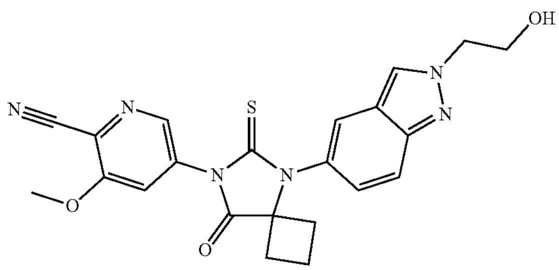 [SMILES: COc1cc(N2C(=O)C3(CCC3)N(c3ccc4nn(CCO)cc4c3)C2=S)cnc1C#N] | 164 | 5-[8-[2-(2-hydroxyethyl)indazol-5-yl]-5-oxo-7-thioxo-6,8-diazaspiro[3.4]octan-6-yl]-3-methoxy-pyridine-2-carbonitrile |
| 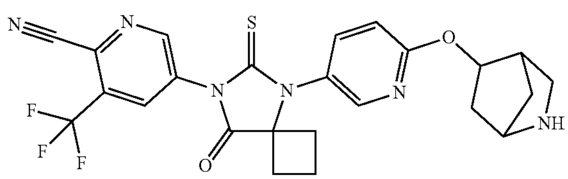 [SMILES: N#Cc1ncc(N2C(=O)C3(CCC3)N(c3ccc(OC4CC5CC4CN5)nc3)C2=S)cc1C(F)(F)F] | 165 | 5-[8-[6-(2-azabicyclo[2.2.1]heptan-5-yloxy)-3-pyridyl]-5-oxo-7-thioxo-6,8-diazaspiro[3.4]octan-6-yl]-3-(trifluoromethyl)pyridine-2-carbonitrile |
| 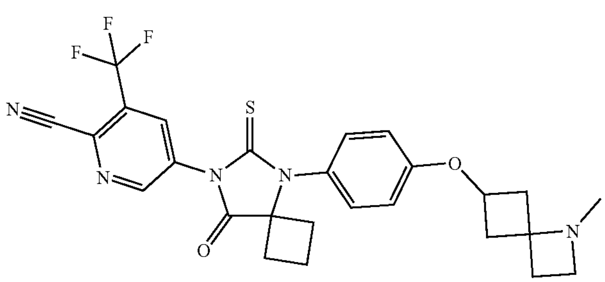 [SMILES: CN1CCC12CC(Oc1ccc(N3C(=S)N(c4cnc(C#N)c(C(F)(F)F)c4)C(=O)C34CCC4)cc1)C2] | 166 | 5-[8-[4-[(3-methyl-3-azaspiro[3.3]heptan-6-yl)oxy]phenyl]-5-oxo-7-thioxo-6,8-diazaspiro[3.4]octan-6-yl]-3-(trifluoromethyl)pyridine-2-carbonitrile |
| 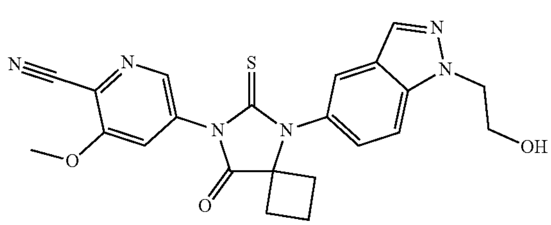 [SMILES: COc1cc(N2C(=O)C3(CCC3)N(c3ccc4c(cnn4CCO)c3)C2=S)cnc1C#N] | 167 | 5-[8-[1-(2-hydroxyethyl)indazol-5-yl]-5-oxo-7-thioxo-6,8-diazaspiro[3.4]octan-6-yl]-3-methoxy-pyridine-2-carbonitrile |

TABLE 1-continued

| Structure | Cpd No. | Cpd Name |
|---|---|---|
| 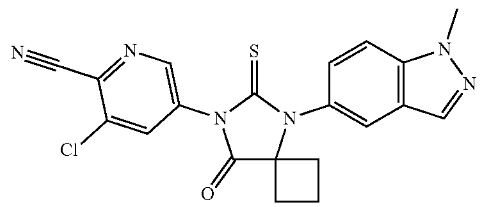 [SMILES: Cn1ncc2cc(N3C(=S)N(c4cnc(C#N)c(Cl)c4)C(=O)C34CCC4)ccc21] | 168 | 3-chloro-5-[8-(1-methylindazol-5-yl)-5-oxo-7-thioxo-6,8-diazaspiro[3.4]octan-6-yl]pyridine-2-carbonitrile |
| 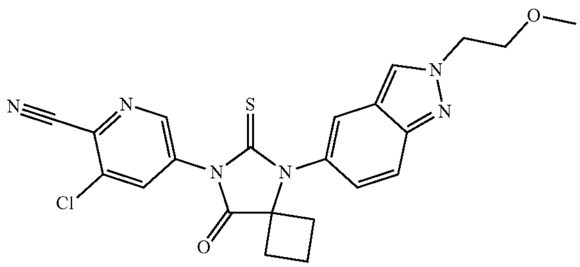 [SMILES: COCCn1cc2cc(N3C(=S)N(c4cnc(C#N)c(Cl)c4)C(=O)C34CCC4)ccc2n1] | 169 | 3-chloro-5-[8-[2-(2-methoxyethyl)indazol-5-yl]-5-oxo-7-thioxo-6,8-diazaspiro[3.4]octan-6-yl]pyridine-2-carbonitrile |
| 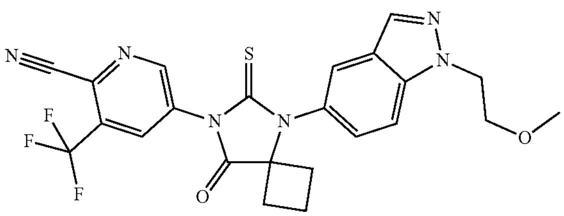 [SMILES: COCCn1ncc2cc(N3C(=S)N(c4cnc(C#N)c(C(F)(F)F)c4)C(=O)C34CCC4)ccc21] | 170 | 5-[8-[1-(2-methoxyethyl)indazol-5-yl]-5-oxo-7-thioxo-6,8-diazaspiro[3.4]octan-6-yl]-3-(trifluoromethyl)pyridine-2-carbonitrile |
| 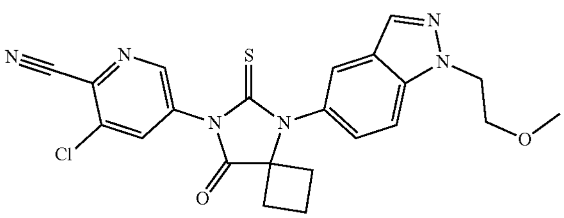 [SMILES: COCCn1ncc2cc(N3C(=S)N(c4cnc(C#N)c(Cl)c4)C(=O)C34CCC4)ccc21] | 171 | 3-chloro-5-[8-[1-(2-methoxyethyl)indazol-5-yl]-5-oxo-7-thioxo-6,8-diazaspiro[3.4]octan-6-yl]pyridine-2-carbonitrile |
| 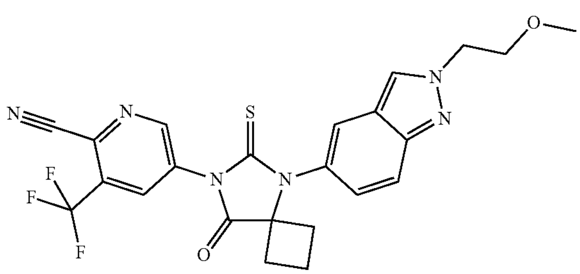 [SMILES: COCCn1cc2cc(N3C(=S)N(c4cnc(C#N)c(C(F)(F)F)c4)C(=O)C34CCC4)ccc2n1] | 172 | 5-[8-[2-(2-methoxyethyl)indazol-5-yl]-5-oxo-7-thioxo-6,8-diazaspiro[3.4]octan-6-yl]-3-(trifluoromethyl)pyridine-2-carbonitrile |
| 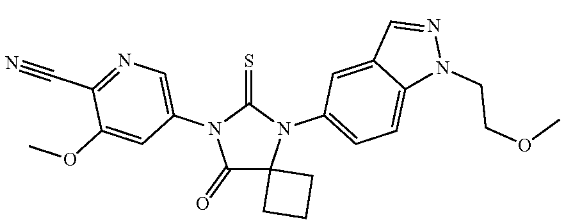 [SMILES: COCCn1ncc2cc(N3C(=S)N(c4cnc(C#N)c(OC)c4)C(=O)C34CCC4)ccc21] | 173 | 3-methoxy-5-[8-[1-(2-methoxyethyl)indazol-5-yl]-5-oxo-7-thioxo-6,8-diazaspiro[3.4]octan-6-yl]pyridine-2-carbonitrile |
| 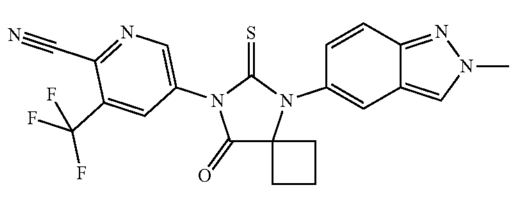 [SMILES: Cn1cc2cc(N3C(=S)N(c4cnc(C#N)c(C(F)(F)F)c4)C(=O)C34CCC4)ccc2n1] | 174 | 5-[8-(2-methylindazol-5-yl)-5-oxo-7-thioxo-6,8-diazaspiro[3.4]octan-6-yl]-3-(trifluoromethyl)pyridine-2-carbonitrile |

TABLE 1-continued

| Structure | Cpd No. | Cpd Name |
|---|---|---|
| 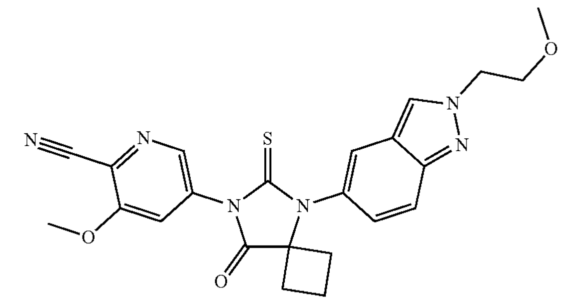 [SMILES: COCCn1cc2cc(N3C(=S)N(c4cnc(C#N)c(OC)c4)C(=O)C34CCC4)ccc2n1] | 175 | 3-methoxy-5-[8-[2-(2-methoxyethyl)indazol-5-yl]-5-oxo-7-thioxo-6,8-diazaspiro[3.4]octan-6-yl]pyridine-2-carbonitrile |
| 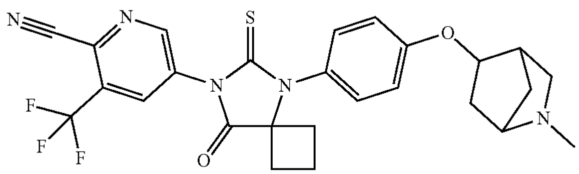 [SMILES: CN1CC2CC1CC2Oc1ccc(N2C(=S)N(c3cnc(C#N)c(C(F)(F)F)c3)C(=O)C23CCC3)cc1] | 176 | 5-[8-[4-[(2-methyl-2-azabicyclo[2.2.1]heptan-5-yl)oxy]phenyl]-5-oxo-7-thioxo-6,8-diazaspiro[3.4]octan-6-yl]-3-(trifluoromethyl)pyridine-2-carbonitrile |
| 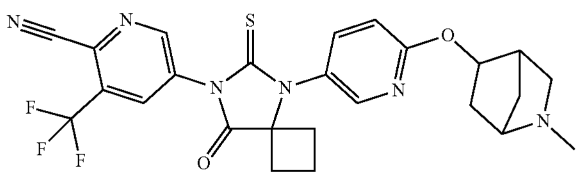 [SMILES: CN1CC2CC1CC2Oc1ccc(N2C(=S)N(c3cnc(C#N)c(C(F)(F)F)c3)C(=O)C23CCC3)cn1] | 177 | 5-[8-[6-[(2-methyl-2-azabicyclo[2.2.1]heptan-5-yl)oxy]-3-pyridyl]-5-oxo-7-thioxo-6,8-diazaspiro[3.4]octan-6-yl]-3-(trifluoromethyl)pyridine-2-carbonitrile |
| 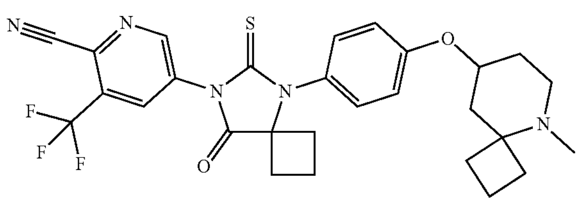 [SMILES: CN1CCC(Oc2ccc(N3C(=S)N(c4cnc(C#N)c(C(F)(F)F)c4)C(=O)C34CCC4)cc2)CC12CCC2] | 178 | 5-[8-[4-[(9-methyl-9-azaspiro[3.5]nonan-6-yl)oxy]phenyl]-5-oxo-7-thioxo-6,8-diazaspiro[3.4]octan-6-yl]-3-(trifluoromethyl)pyridine-2-carbonitrile |
| 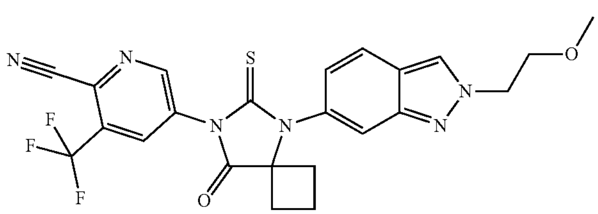 [SMILES: COCCn1cc2ccc(N3C(=S)N(c4cnc(C#N)c(C(F)(F)F)c4)C(=O)C34CCC4)cc2n1] | 179 | 5-[8-[2-(2-methoxyethyl)indazol-6-yl]-5-oxo-7-thioxo-6,8-diazaspiro[3.4]octan-6-yl]-3-(trifluoromethyl)pyridine-2-carbonitrile |
| 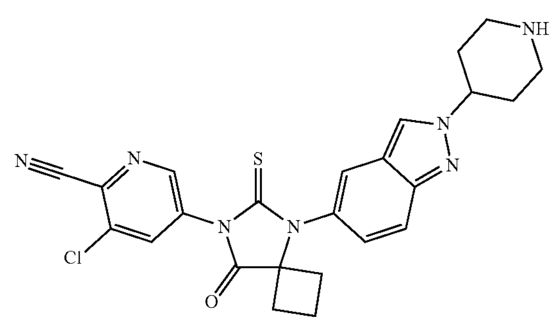 [SMILES: N#Cc1ncc(N2C(=O)C3(CCC3)N(c3ccc4nn(C5CCNCC5)cc4c3)C2=S)cc1Cl] | 180 | 3-chloro-5-[5-oxo-8-[2-(4-piperidyl)indazol-5-yl]-7-thioxo-6,8-diazaspiro[3.4]octan-6-yl]pyridine-2-carbonitrile |

TABLE 1-continued

| Structure | Cpd No. | Cpd Name |
|---|---|---|
| 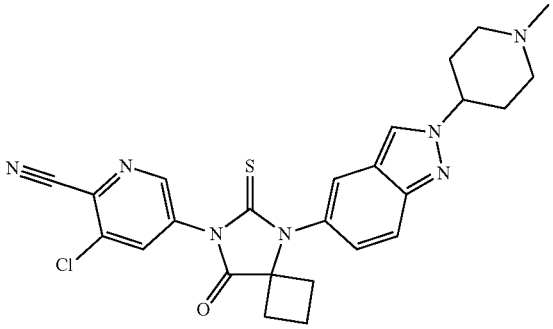 [SMILES: CN1CCC(n2cc3cc(N4C(=S)N(c5cnc(C#N)c(Cl)c5)C(=O)C45CCC5)ccc3n2)CC1] | 181 | 3-chloro-5-[8-[2-(1-methyl-4-piperidyl)indazol-5-yl]-5-oxo-7-thioxo-6,8-diazaspiro[3.4]octan-6-yl]pyridine-2-carbonitrile |
| 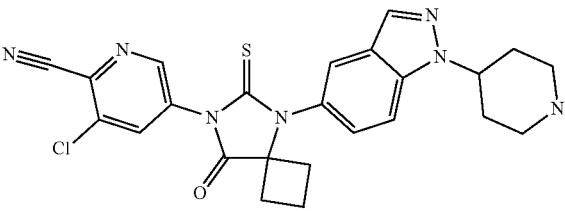 | 182 | 3-chloro-5-[5-oxo-8-[1-(4-piperidyl)indazol-5-yl]-7-thioxo-6,8-diazaspiro[3.4]octan-6-yl]pyridine-2-carbonitrile |
| 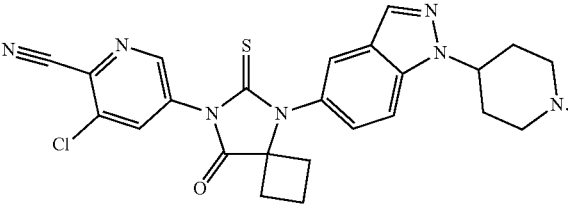 | 183 | 3-chloro-5-[8-[1-(1-methyl-4-piperidyl)indazol-5-yl]-5-oxo-7-thioxo-6,8-diazaspiro[3.4]octan-6-yl]pyridine-2-carbonitrile |
| 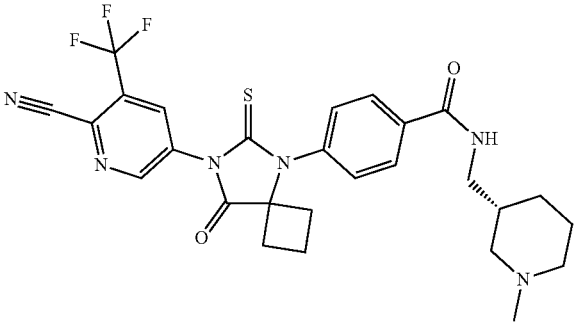 [SMILES: CN1CCC[C@@H](CNC(=O)c2ccc(N3C(=S)N(c4cnc(C#N)c(C(F)(F)F)c4)C(=O)C34CCC4)cc2)C1] | 184 | 4-[6-[6-cyano-5-(trifluoromethyl)-3-pyridyl]-5-oxo-7-thioxo-6,8-diazaspiro[3.4]octan-8-yl]-N-[[(3R)-1-methyl-3-piperidyl]methyl]benzamide |
| 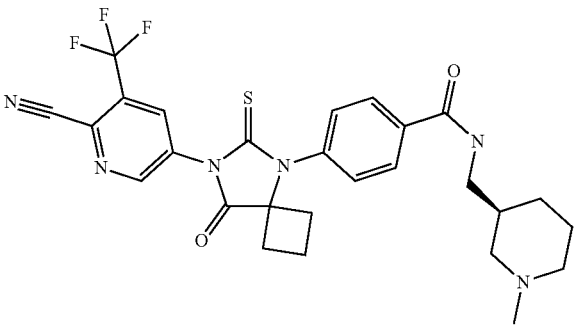 [SMILES: CN1CCC[C@H](CNC(=O)c2ccc(N3C(=S)N(c4cnc(C#N)c(C(F)(F)F)c4)C(=O)C34CCC4)cc2)C1] | 185 | 4-[6-[6-cyano-5-(trifluoromethyl)-3-pyridyl]-5-oxo-7-thioxo-6,8-diazaspiro[3.4]octan-8-yl]-N-[[(3S)-1-methyl-3-piperidyl]methyl]benzamide |

TABLE 1-continued

| Structure | Cpd No. | Cpd Name |
|---|---|---|
| 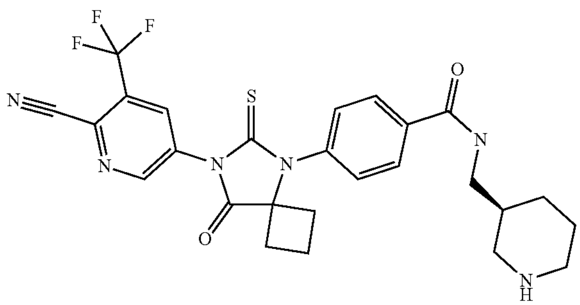 [SMILES: N#Cc1ncc(N2C(=O)C3(CCC3)N(c3ccc(C(=O)NC[C@H]4CCCNC4)cc3)C2=S)cc1C(F)(F)F] | 186 | 4-[6-[6-cyano-5-(trifluoromethyl)-3-pyridyl]-5-oxo-7-thioxo-6,8-diazaspiro[3.4]octan-8-yl]-N-[[(3R)-3-piperidyl]methyl]benzamide |
| 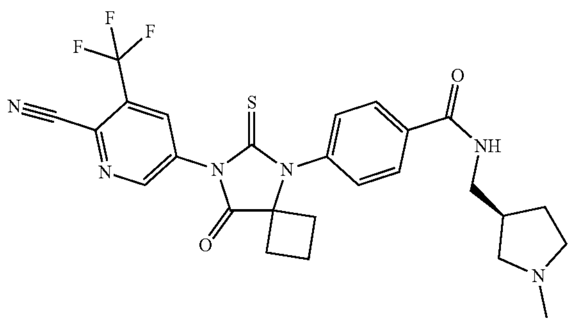 [SMILES: CN1CC[C@H](CNC(=O)c2ccc(N3C(=S)N(c4cnc(C#N)c(C(F)(F)F)c4)C(=O)C34CCC4)cc2)C1] | 187 | 4-[6-[6-cyano-5-(trifluoromethyl)-3-pyridyl]-5-oxo-7-thioxo-6,8-diazaspiro[3.4]octan-8-yl]-N-[[(3S)-1-methylpyrrolidin-3-yl]methyl]benzamide |
| 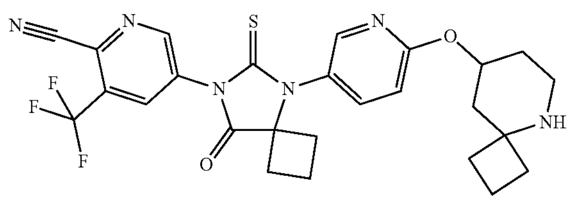 [SMILES: N#Cc1ncc(N2C(=O)C3(CCC3)N(c3ccc(OC4CCNC5(CCC5)C4)nc3)C2=S)cc1C(F)(F)F] | 188 | 5-[8-[6-(9-azaspiro[3.5]nonan-6-yloxy)-3-pyridyl]-5-oxo-7-thioxo-6,8-diazaspiro[3.4]octan-6-yl]-3-(trifluoromethyl)pyridine-2-carbonitrile |
| 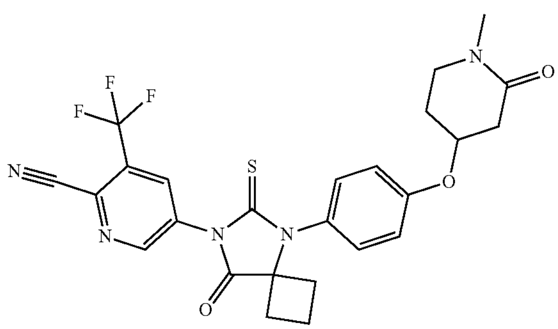 [SMILES: CN1CCC(Oc2ccc(N3C(=S)N(c4cnc(C#N)c(C(F)(F)F)c4)C(=O)C34CCC4)cc2)CC1=O] | 189 | 5-[8-[4-[(1-methyl-2-oxo-4-piperidyl)oxy]phenyl]-5-oxo-7-thioxo-6,8-diazaspiro[3.4]octan-6-yl]-3-(trifluoromethyl)pyridine-2-carbonitrile |
| 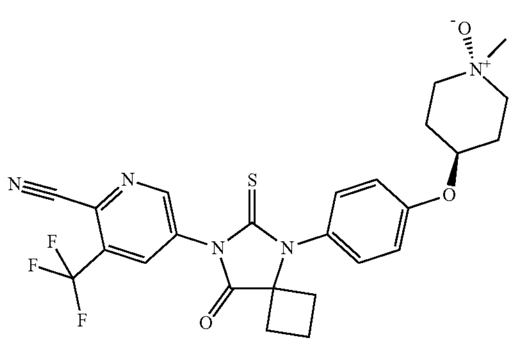 [SMILES: C[N@+]1(O)CC[C@H](Oc2ccc(N3C(=S)N(c4cnc(C#N)c(C(F)(F)F)c4)C(=O)C34CCC4)cc2)CC1] | 190 | 5-[8-[4-(1-methyl-1-oxido-piperidin-1-ium-4-yl)oxyphenyl]-5-oxo-7-thioxo-6,8-diazaspiro[3.4]octan-6-yl]-3-(trifluoromethyl)pyridine-2-carbonitrile |

TABLE 1-continued

| Structure | Cpd No. | Cpd Name |
|---|---|---|
| 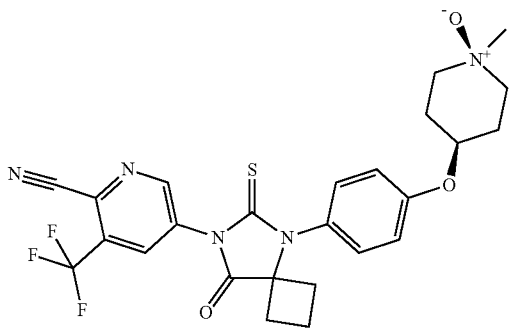 [SMILES: C[N@+]1(O)CC[C@@H](Oc2ccc(N3C(=S)N(c4cnc(C#N)c(C(F)(F)F)c4)C(=O)C34CCC4)cc2)CC1] | 191 | 5-[8-[4-(1-methyl-1-oxido-piperidin-1-ium-4-yl)oxyphenyl]-5-oxo-7-thioxo-6,8-diazaspiro[3.4]octan-6-yl]-3-(trifluoromethyl)pyridine-2-carbonitrile |
| 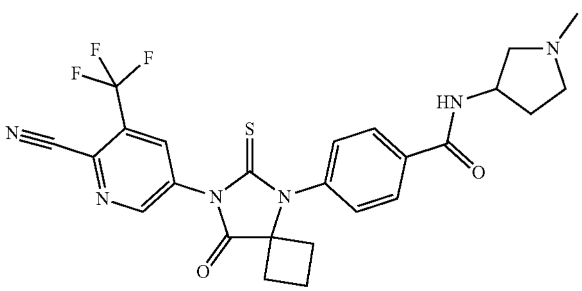 [SMILES: CN1CCC(NC(=O)c2ccc(N3C(=S)N(c4cnc(C#N)c(C(F)(F)F)c4)C(=O)C34CCC4)cc2)C1] | 192 | 4-[6-[6-cyano-5-(trifluoromethyl)-3-pyridyl]-5-oxo-7-thioxo-6,8-diazaspiro[3.4]octan-8-yl]-N-(1-methylpyrrolidin-3-yl)benzamide |
| 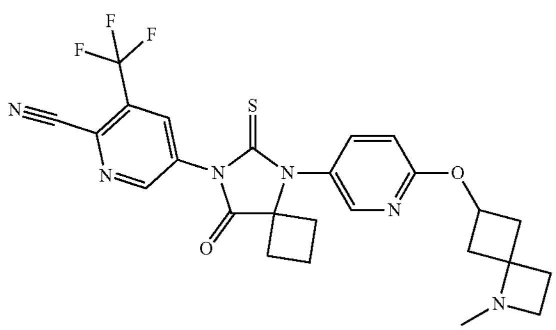 [SMILES: CN1CCC12CC(Oc1ccc(N3C(=S)N(c4cnc(C#N)c(C(F)(F)F)c4)C(=O)C34CCC4)cn1)C2] | 193 | 5-[8-[6-[(3-methyl-3-azaspiro[3.3]heptan-6-yl)oxy]-3-pyridyl]-5-oxo-7-thioxo-6,8-diazaspiro[3.4]octan-6-yl]-3-(trifluoromethyl)pyridine-2-carbonitrile |
| 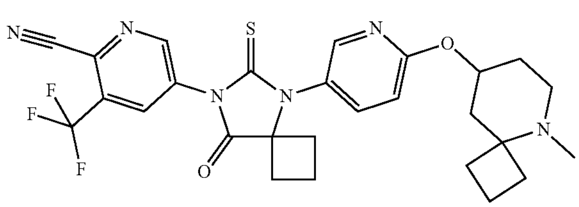 [SMILES: CN1CCC(Oc2ccc(N3C(=S)N(c4cnc(C#N)c(C(F)(F)F)c4)C(=O)C34CCC4)cn2)CC12CCC2] | 194 | 5-[8-[6-[(9-methyl-9-azaspiro[3.5]nonan-6-yl)oxy]-3-pyridyl]-5-oxo-7-thioxo-6,8-diazaspiro[3.4]octan-6-yl]-3-(trifluoromethyl)pyridine-2-carbonitrile |
| 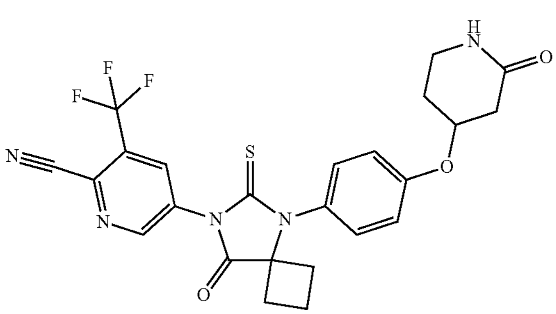 [SMILES: N#Cc1ncc(N2C(=O)C3(CCC3)N(c3ccc(OC4CCNC(=O)C4)cc3)C2=S)cc1C(F)(F)F] | 195 | 5-[5-oxo-8-[4-[(2-oxo-4-piperidyl)oxy]phenyl]-7-thioxo-6,8-diazaspiro[3.4]octan-6-yl]-3-(trifluoromethyl)pyridine-2-carbonitrile |

TABLE 1-continued

| Structure | Cpd No. | Cpd Name |
|---|---|---|
| 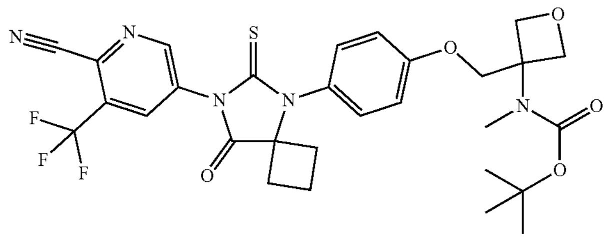 [SMILES: CN(C(=O)OC(C)(C)C)C1(COc2ccc(N3C(=S)N(c4cnc(C#N)c(C(F)(F)F)c4)C(=O)C34CCC4)cc2)COC1] | 196 | tert-butyl N-[3-[[4-[6-[6-cyano-5-(trifluoromethyl)-3-pyridyl]-5-oxo-7-thioxo-6,8-diazaspiro[3.4]octan-8-yl]phenoxy]methyl]oxetan-3-yl]-N-methyl-carbamate |
| 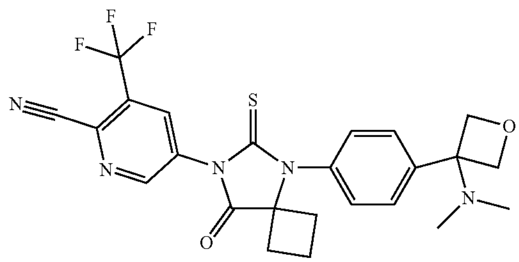 [SMILES: CN(C)C1(c2ccc(N3C(=S)N(c4cnc(C#N)c(C(F)(F)F)c4)C(=O)C34CCC4)cc2)COC1] | 197 | 5-[8-[4-[3-(dimethylamino)oxetan-3-yl]phenyl]-5-oxo-7-thioxo-6,8-diazaspiro[3.4]octan-6-yl]-3-(trifluoromethyl)pyridine-2-carbonitrile |
| 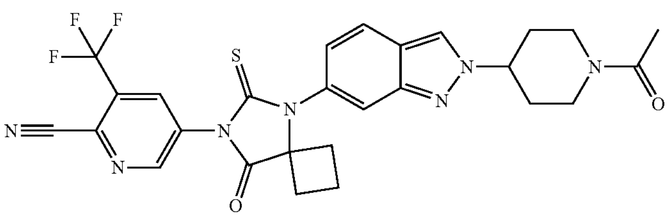 [SMILES: CC(=O)N1CCC(n2cc3ccc(N4C(=S)N(c5cnc(C#N)c(C(F)(F)F)c5)C(=O)C45CCC5)cc3n2)CC1] | 198 | 5-[8-[2-(1-acetyl-4-piperidyl)indazol-6-yl]-5-oxo-7-thioxo-6,8-diazaspiro[3.4]octan-6-yl]-3-(trifluoromethyl)pyridine-2-carbonitrile |
| 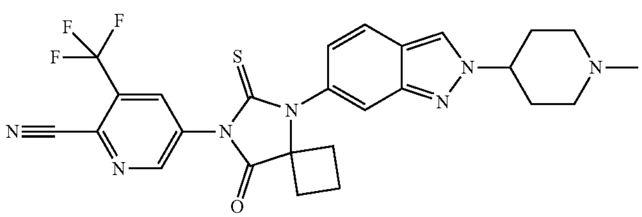 [SMILES: CN1CCC(n2cc3ccc(N4C(=S)N(c5cnc(C#N)c(C(F)(F)F)c5)C(=O)C45CCC5)cc3n2)CC1] | 199 | 5-[8-[2-(1-methyl-4-piperidyl)indazol-6-yl]-5-oxo-7-thioxo-6,8-diazaspiro[3.4]octan-6-yl]-3-(trifluoromethyl)pyridine-2-carbonitrile |
| 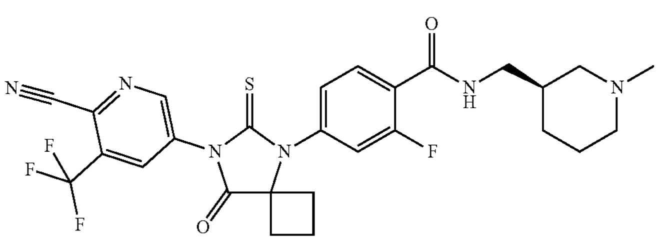 [SMILES: CN1CCC[C@@H](CNC(=O)c2ccc(N3C(=S)N(c4cnc(C#N)c(C(F)(F)F)c4)C(=O)C34CCC4)cc2F)C1] | 200 | 4-[6-[6-cyano-5-(trifluoromethyl)-3-pyridyl]-5-oxo-7-thioxo-6,8-diazaspiro[3.4]octan-8-yl]-2-fluoro-N-[[(3S)-1-methyl-3-piperidyl]methyl]benzamide |
| 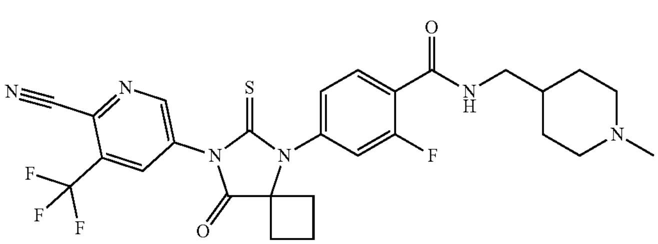 [SMILES: CN1CCC(CNC(=O)c2ccc(N3C(=S)N(c4cnc(C#N)c(C(F)(F)F)c4)C(=O)C34CCC4)cc2F)CC1] | 201 | 4-[6-[6-cyano-5-(trifluoromethyl)-3-pyridyl]-5-oxo-7-thioxo-6,8-diazaspiro[3.4]octan-8-yl]-2-fluoro-N-[(1-methyl-4-piperidyl)methyl]benzamide |

TABLE 1-continued

| Structure | Cpd No. | Cpd Name |
|---|---|---|
| 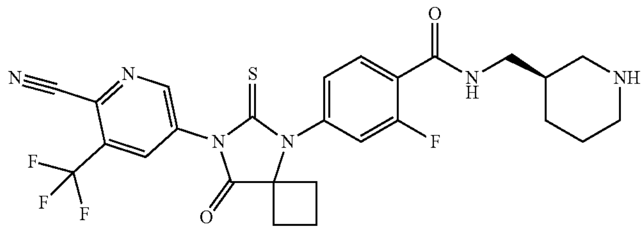 [SMILES: N#Cc1ncc(N2C(=O)C3(CCC3)N(c3ccc(C(=O)NC[C@@H]4CCCNC4)c(F)c3)C2=S)cc1C(F)(F)F] | 202 | 4-[6-[6-cyano-5-(trifluoromethyl)-3-pyridyl]-5-oxo-7-thioxo-6,8-diazaspiro[3.4]octan-8-yl]-2-fluoro-N-[[(3R)-3-piperidyl]methyl]benzamide |
| 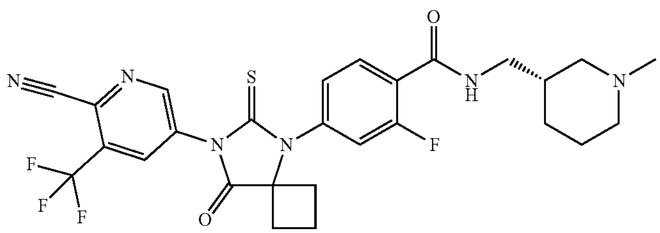 [SMILES: CN1CCC[C@H](CNC(=O)c2ccc(N3C(=S)N(c4cnc(C#N)c(C(F)(F)F)c4)C(=O)C34CCC4)cc2F)C1] | 203 | 4-[6-[6-cyano-5-(trifluoromethyl)-3-pyridyl]-5-oxo-7-thioxo-6,8-diazaspiro[3.4]octan-8-yl]-2-fluoro-N-[[(3R)-1-methyl-3-piperidyl]methyl]benzamide |
| 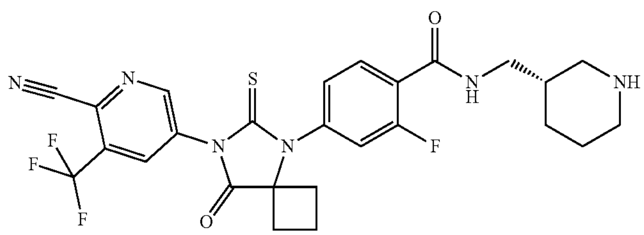 [SMILES: N#Cc1ncc(N2C(=O)C3(CCC3)N(c3ccc(C(=O)NC[C@H]4CCCNC4)c(F)c3)C2=S)cc1C(F)(F)F] | 204 | 4-[6-[6-cyano-5-(trifluoromethyl)-3-pyridyl]-5-oxo-7-thioxo-6,8-diazaspiro[3.4]octan-8-yl]-2-fluoro-N-[[(3S)-3-piperidyl]methyl]benzamide |
| 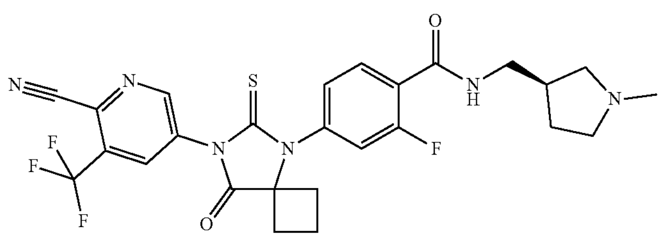 [SMILES: CN1CC[C@@H](CNC(=O)c2ccc(N3C(=S)N(c4cnc(C#N)c(C(F)(F)F)c4)C(=O)C34CCC4)cc2F)C1] | 205 | 4-[6-[6-cyano-5-(trifluoromethyl)-3-pyridyl]-5-oxo-7-thioxo-6,8-diazaspiro[3.4]octan-8-yl]-2-fluoro-N-[[(3S)-1-methylpyrrolidin-3-yl]methyl]benzamide |
| 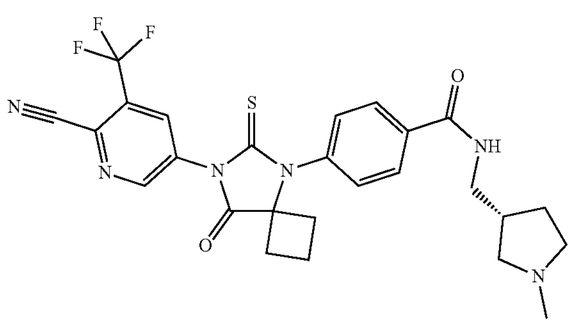 [SMILES: CN1CC[C@@H](CNC(=O)c2ccc(N3C(=S)N(c4cnc(C#N)c(C(F)(F)F)c4)C(=O)C34CCC4)cc2)C1] | 206 | 4-[6-[6-cyano-5-(trifluoromethyl)-3-pyridyl]-5-oxo-7-thioxo-6,8-diazaspiro[3.4]octan-8-yl]-N-[[(3R)-1-methylpyrrolidin-3-yl]methyl]benzamide |
| 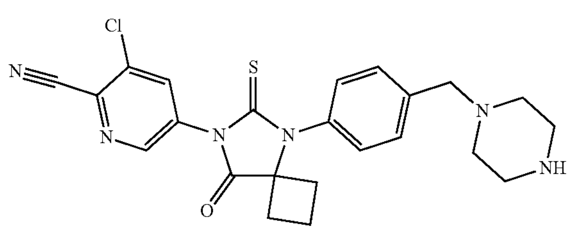 [SMILES: N#Cc1ncc(N2C(=O)C3(CCC3)N(c3ccc(CN4CCNCC4)cc3)C2=S)cc1Cl] | 207 | 3-chloro-5-[5-oxo-8-[4-(piperazin-1-ylmethyl)phenyl]-7-thioxo-6,8-diazaspiro[3.4]octan-6-yl]pyridine-2-carbonitrile |

TABLE 1-continued

| Structure | Cpd No. | Cpd Name |
|---|---|---|
| 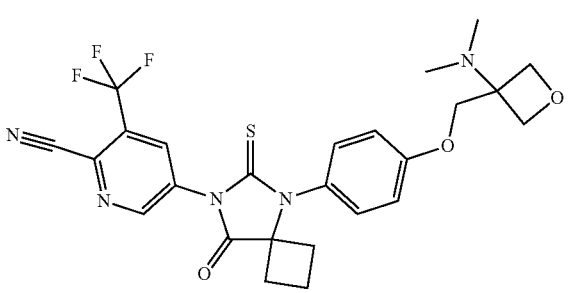 [SMILES: CN(C)C1(COc2ccc(N3C(=S)N(c4cnc(C#N)c(C(F)(F)F)c4)C(=O)C34CCC4)cc2)COC1] | 208 | 5-[8-[4-[[3-(dimethylamino)oxetan-3-yl]methoxy]phenyl]-5-oxo-7-thioxo-6,8-diazaspiro[3.4]octan-6-yl]-3-(trifluoromethyl)pyridine-2-carbonitrile |
| 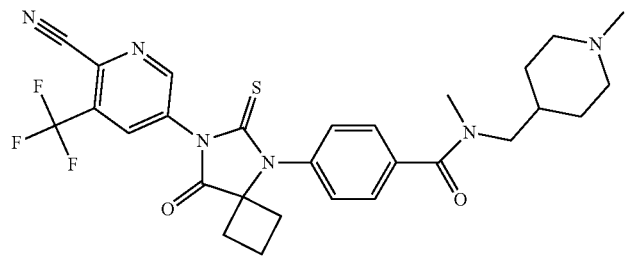 [SMILES: CN1CCC(CN(C)C(=O)c2ccc(N3C(=S)N(c4cnc(C#N)c(C(F)(F)F)c4)C(=O)C34CCC4)cc2)CC1] | 209 | 4-[6-[6-cyano-5-(trifluoromethyl)-3-pyridyl]-5-oxo-7-thioxo-6,8-diazaspiro[3.4]octan-8-yl]-N-methyl-N-[(1-methyl-4-piperidyl)methyl]benzamide |
| 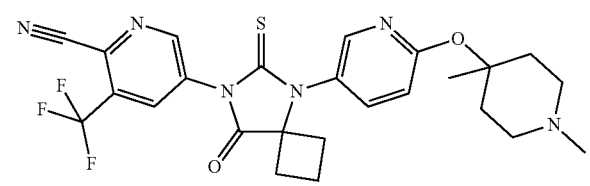 [SMILES: CN1CCC(C)(Oc2ccc(N3C(=S)N(c4cnc(C#N)c(C(F)(F)F)c4)C(=O)C34CCC4)cn2)CC1] | 210 | 5-[8-[6-[(1,4-dimethyl-4-piperidyl)oxy]-3-pyridyl]-5-oxo-7-thioxo-6,8-diazaspiro[3.4]octan-6-yl]-3-(trifluoromethyl)pyridine-2-carbonitrile |
| 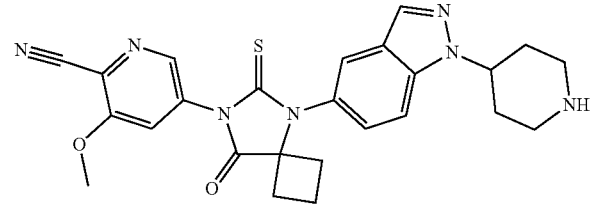 [SMILES: COc1cc(N2C(=O)C3(CCC3)N(c3ccc4c(cnn4C4CCNCC4)c3)C2=S)cnc1C#N] | 211 | 3-methoxy-5-[5-oxo-8-[1-(4-piperidyl)indazol-5-yl]-7-thioxo-6,8-diazaspiro[3.4]octan-6-yl]pyridine-2-carbonitrile |
| 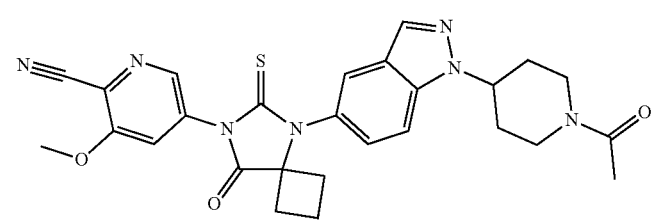 [SMILES: COc1cc(N2C(=O)C3(CCC3)N(c3ccc4c(cnn4C4CCN(C(C)=O)CC4)c3)C2=S)cnc1C#N] | 212 | 5-[8-[1-(1-acetyl-4-piperidyl)indazol-5-yl]-5-oxo-7-thioxo-6,8-diazaspiro[3.4]octan-6-yl]-3-methoxy-pyridine-2-carbonitrile |
| 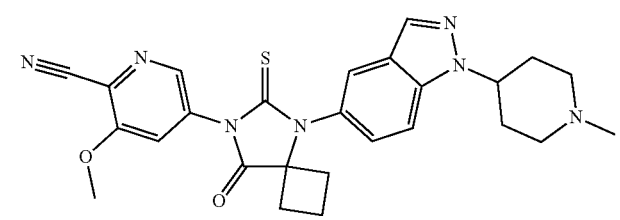 [SMILES: COc1cc(N2C(=O)C3(CCC3)N(c3ccc4c(cnn4C4CCN(C)CC4)c3)C2=S)cnc1C#N] | 213 | 3-methoxy-5-[8-[1-(1-methyl-4-piperidyl)indazol-5-yl]-5-oxo-7-thioxo-6,8-diazaspiro[3.4]octan-6-yl]pyridine-2-carbonitrile |

TABLE 1-continued

| Structure | Cpd No. | Cpd Name |
|---|---|---|
| 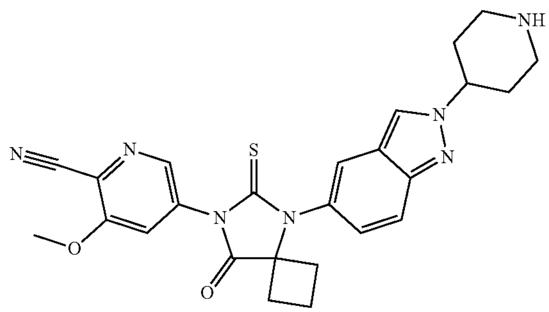 [SMILES: COc1cc(N2C(=O)C3(CCC3)N(c3ccc4nn(C5CCNCC5)cc4c3)C2=S)cnc1C#N] | 214 | 3-methoxy-5-[5-oxo-8-[2-(4-piperidyl)indazol-5-yl]-7-thioxo-6,8-diazaspiro[3.4]octan-6-yl]pyridine-2-carbonitrile |
| 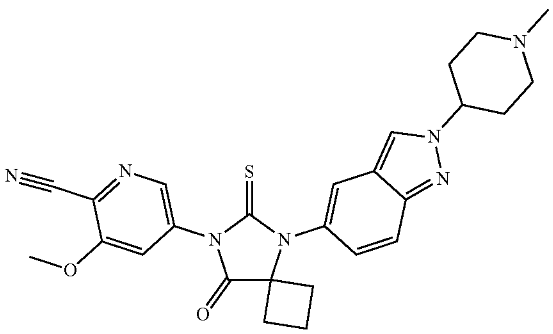 [SMILES: COc1cc(N2C(=O)C3(CCC3)N(c3ccc4nn(C5CCN(C)CC5)cc4c3)C2=S)cnc1C#N] | 215 | 3-methoxy-5-[8-[2-(1-methyl-4-piperidyl)indazol-5-yl]-5-oxo-7-thioxo-6,8-diazaspiro[3.4]octan-6-yl]pyridine-2-carbonitrile |
| 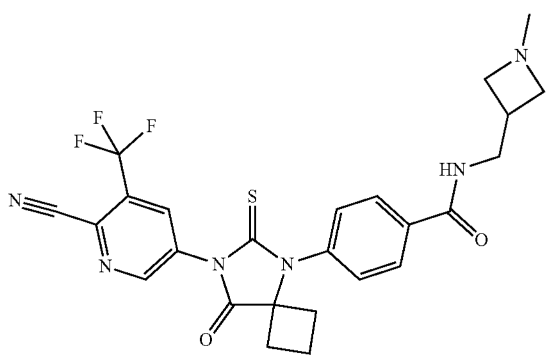 [SMILES: CN1CC(CNC(=O)c2ccc(N3C(=S)N(c4cnc(C#N)c(C(F)(F)F)c4)C(=O)C34CCC4)cc2)C1] | 216 | 4-[6-[6-cyano-5-(trifluoromethyl)-3-pyridyl]-5-oxo-7-thioxo-6,8-diazaspiro[3.4]octan-8-yl]-N-[(1-methylazetidin-3-yl)methyl]benzamide |
| 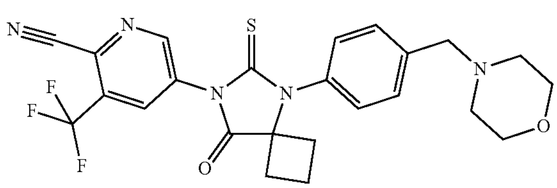 [SMILES: N#Cc1ncc(N2C(=O)C3(CCC3)N(c3ccc(CN4CCOCC4)cc3)C2=S)cc1C(F)(F)F] | 217 | 5-[8-[4-(morpholinomethyl)phenyl]-5-oxo-7-thioxo-6,8-diazaspiro[3.4]octan-6-yl]-3-(trifluoromethyl)pyridine-2-carbonitrile |
| 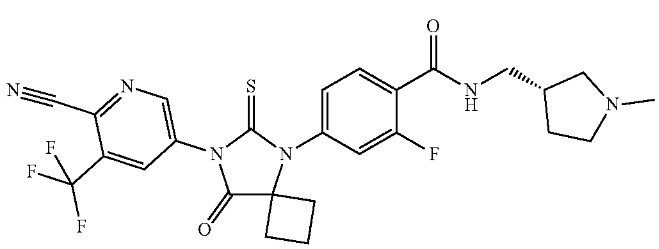 [SMILES: CN1CC[C@H](CNC(=O)c2ccc(N3C(=S)N(c4cnc(C#N)c(C(F)(F)F)c4)C(=O)C34CCC4)cc2F)C1] | 218 | 4-[6-[6-cyano-5-(trifluoromethyl)-3-pyridyl]-5-oxo-7-thioxo-6,8-diazaspiro[3.4]octan-8-yl]-2-fluoro-N-[[(3R)-1-methylpyrrolidin-3-yl]methyl]benzamide |

| Structure | Cpd No. | Cpd Name |
|---|---|---|
| 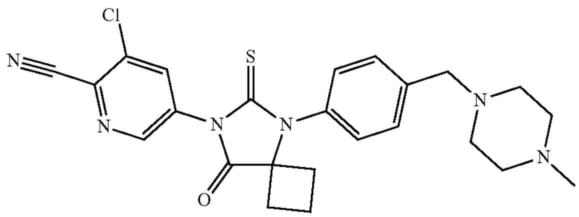 [SMILES: CN1CCN(Cc2ccc(N3C(=S)N(c4cnc(C#N)c(Cl)c4)C(=O)C34CCC4)cc2)CC1] | 219 | 3-chloro-5-[8-[4-[(4-methylpiperazin-1-yl)methyl]phenyl]-5-oxo-7-thioxo-6,8-diazaspiro[3.4]octan-6-yl]pyridine-2-carbonitrile |
| 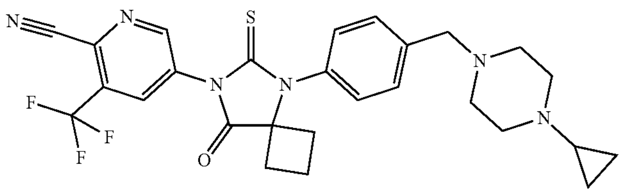 [SMILES: N#Cc1ncc(N2C(=O)C3(CCC3)N(c3ccc(CN4CCN(C5CC5)CC4)cc3)C2=S)cc1C(F)(F)F] | 220 | 5-[8-[4-[(4-cyclopropylpiperazin-1-yl)methyl]phenyl]-5-oxo-7-thioxo-6,8-diazaspiro[3.4]octan-6-yl]-3-(trifluoromethyl)pyridine-2-carbonitrile |
| 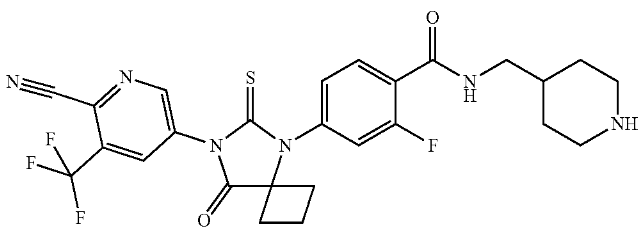 [SMILES: N#Cc1ncc(N2C(=O)C3(CCC3)N(c3ccc(C(=O)NCC4CCNCC4)c(F)c3)C2=S)cc1C(F)(F)F] | 221 | 4-[6-[6-cyano-5-(trifluoromethyl)-3-pyridyl]-5-oxo-7-thioxo-6,8-diazaspiro[3.4]octan-8-yl]-2-fluoro-N-(4-piperidylmethyl)benzamide |
| 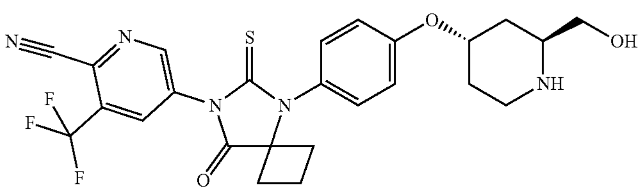 [SMILES: N#Cc1ncc(N2C(=O)C3(CCC3)N(c3ccc(O[C@H]4CCN[C@H](CO)C4)cc3)C2=S)cc1C(F)(F)F] | 222 | 5-[8-(2SR, 4SR) [4-[[2-(hydroxymethyl)-4-piperidyl]oxy]phenyl]-5-oxo-7-thioxo-6,8-diazaspiro[3.4]octan-6-yl]-3-(trifluoromethyl)pyridine-2-carbonitrile |
| 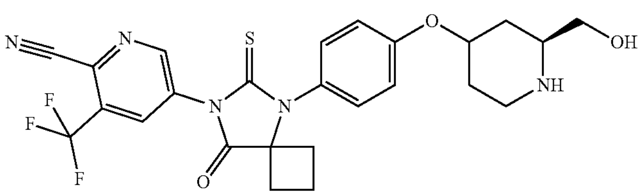 [SMILES: N#Cc1ncc(N2C(=O)C3(CCC3)N(c3ccc(OC4CCN[C@H](CO)C4)cc3)C2=S)cc1C(F)(F)F] | 223 | 5-[8-(2SR, 4RS)[4-[[2-(hydroxymethyl)-4-piperidyl]oxy]phenyl]-5-oxo-7-thioxo-6,8-diazaspiro[3.4]octan-6-yl]-3-(trifluoromethyl)pyridine-2-carbonitrile |
| 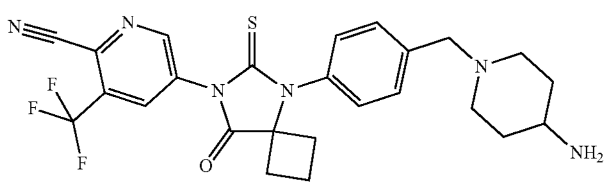 [SMILES: N#Cc1ncc(N2C(=O)C3(CCC3)N(c3ccc(CN4CCC(N)CC4)cc3)C2=S)cc1C(F)(F)F] | 224 | 5-[8-[4-[(4-amino-1-piperidyl)methyl]phenyl]-5-oxo-7-thioxo-6,8-diazaspiro[3.4]octan-6-yl]-3-(trifluoromethyl)pyridine-2-carbonitrile |
| 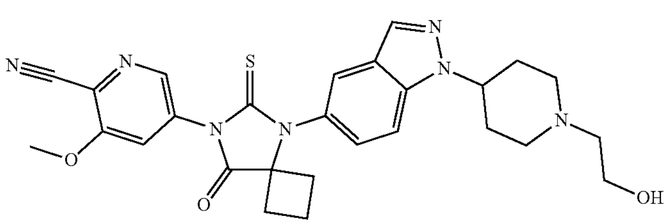 [SMILES: COc1cc(N2C(=O)C3(CCC3)N(c3ccc4c(cnn4C4CCN(CCO)CC4)c3)C2=S)cnc1C#N] | 225 | 5-[8-[1-[1-(2-hydroxyethyl)-4-piperidyl]indazol-5-yl]-5-oxo-7-thioxo-6,8-diazaspiro[3.4]octan-6-yl]-3-methoxy-pyridine-2-carbonitrile |

TABLE 1-continued

| Structure | Cpd No. | Cpd Name |
|---|---|---|
| 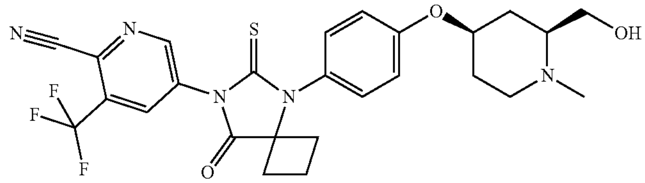 [SMILES: CN1CC[C@@H](Oc2ccc(N3C(=S)N(c4cnc(C#N)c(C(F)(F)F)c4)C(=O)C34CCC4)cc2)C[C@H]1CO] | 226 | 5-[8-(2SR, 4RS)[4-[[2-(hydroxymethyl)-1-methyl-4-piperidyl]oxy]phenyl]-5-oxo-7-thioxo-6,8-diazaspiro[3.4]octan-6-yl]-3-(trifluoromethyl)pyridine-2-carbonitrile |
| 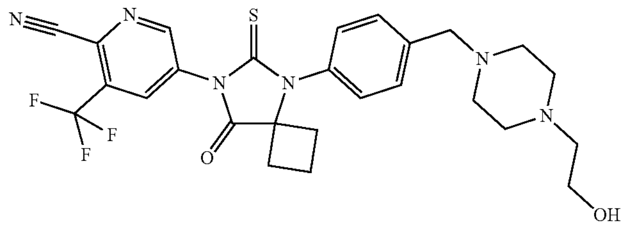 [SMILES: N#Cc1ncc(N2C(=O)C3(CCC3)N(c3ccc(CN4CCN(CCO)CC4)cc3)C2=S)cc1C(F)(F)F] | 227 | 5-[8-[4-[[4-(2-hydroxyethyl)piperazin-1-yl]methyl]phenyl]-5-oxo-7-thioxo-6,8-diazaspiro[3.4]octan-6-yl]-3-(trifluoromethyl)pyridine-2-carbonitrile |
| 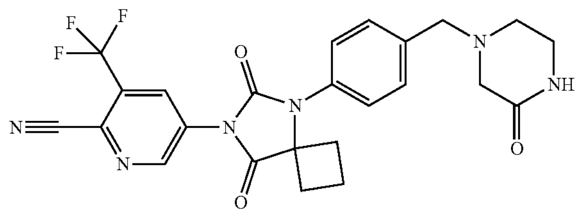 [SMILES: N#Cc1ncc(N2C(=O)N(c3ccc(CN4CCNC(=O)C4)cc3)C3(CCC3)C2=O)cc1C(F)(F)F] | 228 | 5-[5-oxo-8-[4-[(3-oxopiperazin-1-yl)methyl]phenyl]-7-thioxo-6,8-diazaspiro[3.4]octan-6-yl]-3-(trifluoromethyl)pyridine-2-carbonitrile |
| 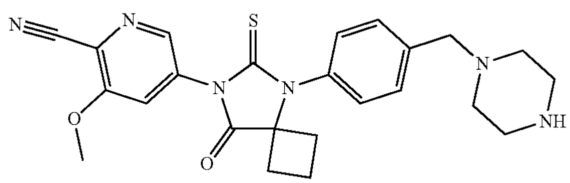 [SMILES: COc1cc(N2C(=O)C3(CCC3)N(c3ccc(CN4CCNCC4)cc3)C2=S)cnc1C#N] | 229 | 3-methoxy-5-[5-oxo-8-[4-(piperazin-1-ylmethyl)phenyl]-7-thioxo-6,8-diazaspiro[3.4]octan-6-yl]pyridine-2-carbonitrile |
| 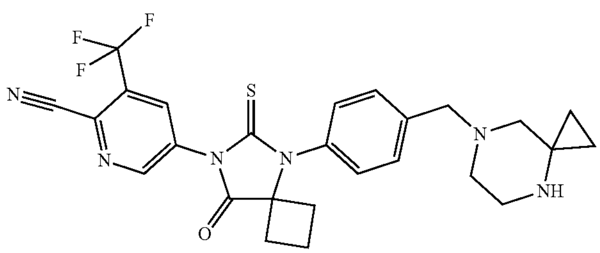 [SMILES: N#Cc1ncc(N2C(=O)C3(CCC3)N(c3ccc(CN4CCNC5(CC5)C4)cc3)C2=S)cc1C(F)(F)F] | 230 | 5-[6-[4-(5,8-diazaspiro[2.5]octan-5-ylmethyl)phenyl]-5-oxo-7-thioxo-6,8-diazaspiro[3.4]octan-8-yl]-3-(trifluoromethyl)pyridine-2-carbonitrile |
| 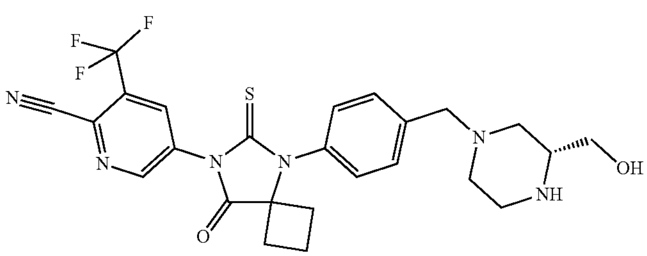 [SMILES: N#Cc1ncc(N2C(=O)C3(CCC3)N(c3ccc(CN4CCN[C@@H](CO)C4)cc3)C2=S)cc1C(F)(F)F] | 231 | 5-[6-[4-[[(3R)-3-(hydroxymethyl)piperazin-1-yl]methyl]phenyl]-5-oxo-7-thioxo-6,8-diazaspiro[3.4]octan-8-yl]-3-(trifluoromethyl)pyridine-2-carbonitrile |
| 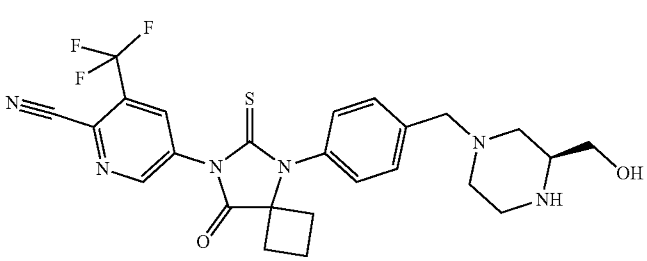 [SMILES: N#Cc1ncc(N2C(=O)C3(CCC3)N(c3ccc(CN4CCN[C@H](CO)C4)cc3)C2=S)cc1C(F)(F)F] | 232 | 5-[6-[4-[[(3S)-3-(hydroxymethyl)piperazin-1-yl]methyl]phenyl]-5-oxo-7-thioxo-6,8-diazaspiro[3.4]octan-8-yl]-3-(trifluoromethyl)pyridine-2-carbonitrile |

TABLE 1-continued

| Structure | Cpd No. | Cpd Name |
|---|---|---|
| 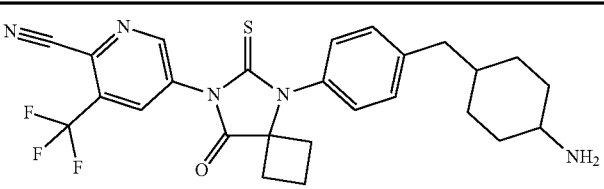 | 233 | 5-[8-[4-[(4-aminocyclohexyl)methyl]phenyl]-5-oxo-7-thioxo-6,8-diazaspiro[3.4]octan-6-yl]-3-(trifluoromethyl)pyridine-2-carbonitrile |
| 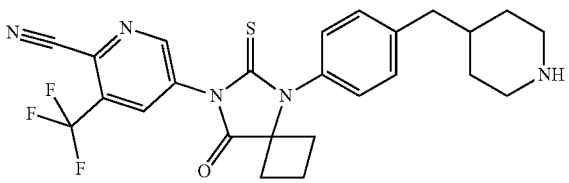 [SMILES: N#Cc1ncc(N2C(=O)C3(CCC3)N(c3ccc(CC4CCNCC4)cc3)C2=S)cc1C(F)(F)F] | 234 | 5-[5-oxo-8-[4-(4-piperidylmethyl)phenyl]-7-thioxo-6,8-diazaspiro[3.4]octan-6-yl]-3-(trifluoromethyl)pyridine-2-carbonitrile |
| 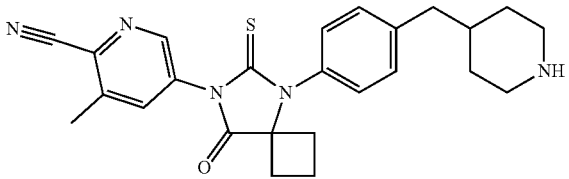 [SMILES: Cc1cc(N2C(=O)C3(CCC3)N(c3ccc(CC4CCNCC4)cc3)C2=S)cnc1C#N] | 235 | 3-methyl-5-[5-oxo-8-[4-(4-piperidylmethyl)phenyl]-7-thioxo-6,8-diazaspiro[3.4]octan-6-yl]pyridine-2-carbonitrile |
| 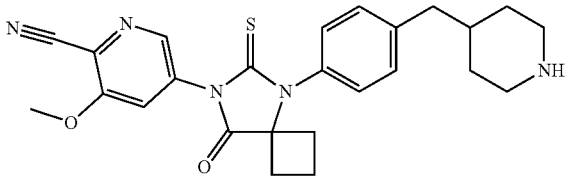 [SMILES: COc1cc(N2C(=O)C3(CCC3)N(c3ccc(CC4CCNCC4)cc3)C2=S)cnc1C#N] | 236 | 3-methoxy-5-[5-oxo-8-[4-(4-piperidylmethyl)phenyl]-7-thioxo-6,8-diazaspiro[3.4]octan-6-yl]pyridine-2-carbonitrile |
| 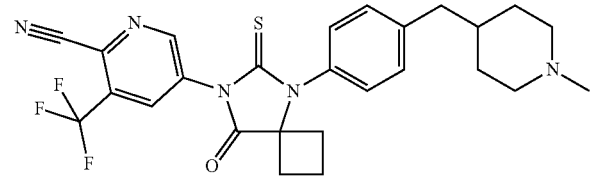 [SMILES: CN1CCC(Cc2ccc(N3C(=S)N(c4cnc(C#N)c(C(F)(F)F)c4)C(=O)C34CCC4)cc2)CC1] | 237 | 5-[8-[4-[(1-methyl-4-piperidyl)methyl]phenyl]-5-oxo-7-thioxo-6,8-diazaspiro[3.4]octan-6-yl]-3-(trifluoromethyl)pyridine-2-carbonitrile |
| 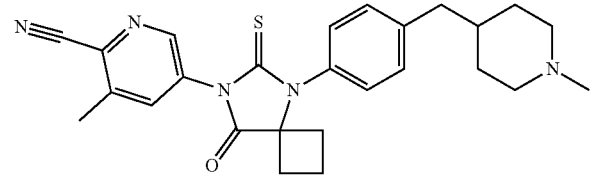 [SMILES: Cc1cc(N2C(=O)C3(CCC3)N(c3ccc(CC4CCN(C)CC4)cc3)C2=S)cnc1C#N] | 238 | 3-methyl-5-[8-[4-[(1-methyl-4-piperidyl)methyl]phenyl]-5-oxo-7-thioxo-6,8-diazaspiro[3.4]octan-6-yl]pyridine-2-carbonitrile |
| 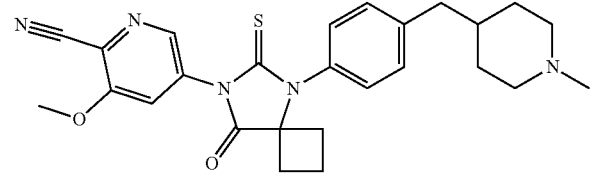 [SMILES: COc1cc(N2C(=O)C3(CCC3)N(c3ccc(CC4CCN(C)CC4)cc3)C2=S)cnc1C#N] | 239 | 3-methoxy-5-[8-[4-[(1-methyl-4-piperidyl)methyl]phenyl]-5-oxo-7-thioxo-6,8-diazaspiro[3.4]octan-6-yl]pyridine-2-carbonitrile |
| 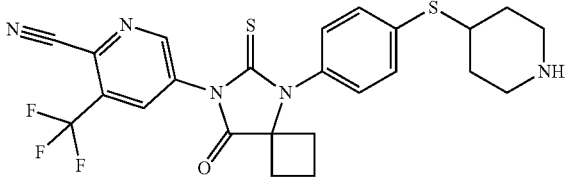 [SMILES: N#Cc1ncc(N2C(=O)C3(CCC3)N(c3ccc(SC4CCNCC4)cc3)C2=S)cc1C(F)(F)F] | 240 | 5-[5-oxo-8-[4-(4-piperidylsulfanyl)phenyl]-7-thioxo-6,8-diazaspiro[3.4]octan-6-yl]-3-(trifluoromethyl)pyridine-2-carbonitrile |

TABLE 1-continued

| Structure | Cpd No. | Cpd Name |
|---|---|---|
| 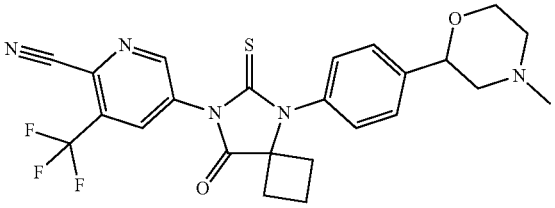 [SMILES: CN1CCOC(c2ccc(N3C(=S)N(c4cnc(C#N)c(C(F)(F)F)c4)C(=O)C34CCC4)cc2)C1] | 241 | 5-[8-[4-(4-methylmorpholin-2-yl)phenyl]-5-oxo-7-thioxo-6,8-diazaspiro[3.4]octan-6-yl]-3-(trifluoromethyl)pyridine-2-carbonitrile |
| 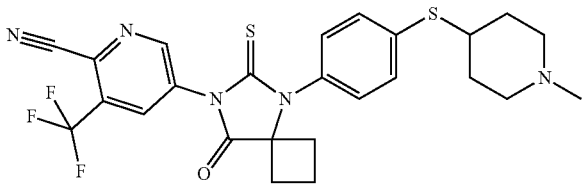 [SMILES: CN1CCC(Sc2ccc(N3C(=S)N(c4cnc(C#N)c(C(F)(F)F)c4)C(=O)C34CCC4)cc2)CC1] | 242 | 5-[8-[4-[(1-methyl-4-piperidyl)sulfanyl]phenyl]-5-oxo-7-thioxo-6,8-diazaspiro[3.4]octan-6-yl]-3-(trifluoromethyl)pyridine-2-carbonitrile |
| 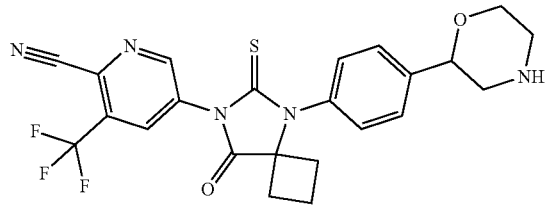 [SMILES: N#Cc1ncc(N2C(=O)C3(CCC3)N(c3ccc(C4CNCCO4)cc3)C2=S)cc1C(F)(F)F] | 243 | 5-[8-(4-morpholin-2-ylphenyl)-5-oxo-7-thioxo-6,8-diazaspiro[3.4]octan-6-yl]-3-(trifluoromethyl)pyridine-2-carbonitrile |
| 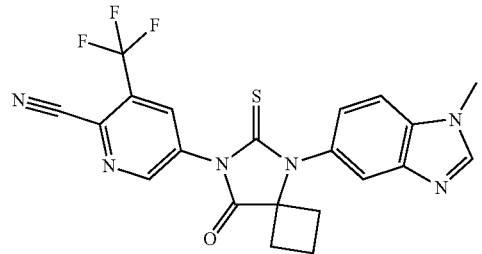 [SMILES: Cn1cnc2cc(N3C(=S)N(c4cnc(C#N)c(C(F)(F)F)c4)C(=O)C34CCC4)ccc21] | 244 | 5-[8-(1-methylbenzimidazol-5-yl)-5-oxo-7-thioxo-6,8-diazaspiro[3.4]octan-6-yl]-3-(trifluoromethyl)pyridine-2-carbonitrile |
| 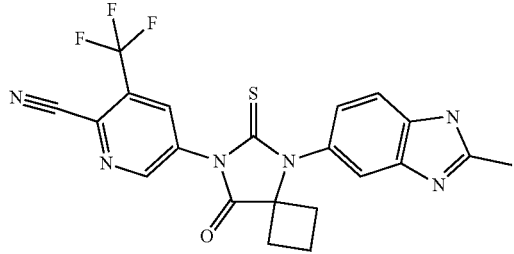 [SMILES: Cc1nc2cc(N3C(=S)N(c4cnc(C#N)c(C(F)(F)F)c4)C(=O)C34CCC4)ccc2[nH]1] | 245 | 5-[8-(2-methyl-1H-benzimidazol-5-yl)-5-oxo-7-thioxo-6,8-diazaspiro[3.4]octan-6-yl]-3-(trifluoromethyl)pyridine-2-carbonitrile |
| 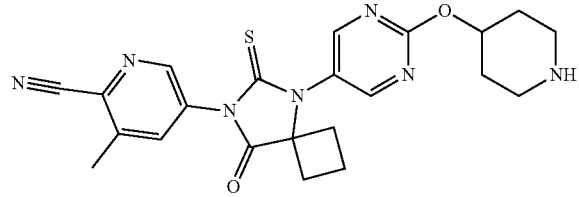 [SMILES: Cc1cc(N2C(=O)C3(CCC3)N(c3cnc(OC4CCNCC4)nc3)C2=S)cnc1C#N] | 246 | 3-methyl-5-[5-oxo-8-[2-(4-piperidyloxy)pyrimidin-5-yl]-7-thioxo-6,8-diazaspiro[3.4]octan-6-yl]pyridine-2-carbonitrile |
| 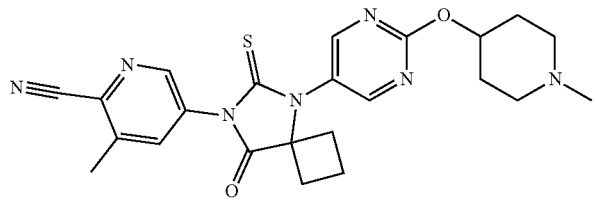 [SMILES: Cc1cc(N2C(=O)C3(CCC3)N(c3cnc(OC4CCN(C)CC4)nc3)C2=S)cnc1C#N] | 247 | 3-methyl-5-[8-[2-[(1-methyl-4-piperidyl)oxy]pyrimidin-5-yl]-5-oxo-7-thioxo-6,8-diazaspiro[3.4]octan-6-yl]pyridine-2-carbonitrile |

TABLE 1-continued

| Structure | Cpd No. | Cpd Name |
|---|---|---|
| 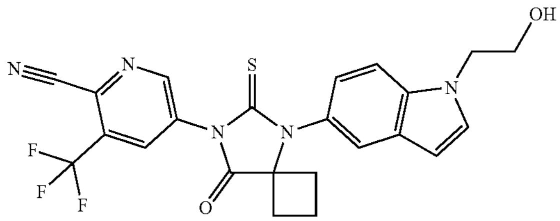 [SMILES: N#Cc1ncc(N2C(=O)C3(CCC3)N(c3ccc4c(ccn4CCO)c3)C2=S)cc1C(F)(F)F] | 248 | 5-[8-[1-(2-hydroxyethyl)indol-5-yl]-5-oxo-7-thioxo-6,8-diazaspiro[3.4]octan-6-yl]-3-(trifluoromethyl)pyridine-2-carbonitrile |
| 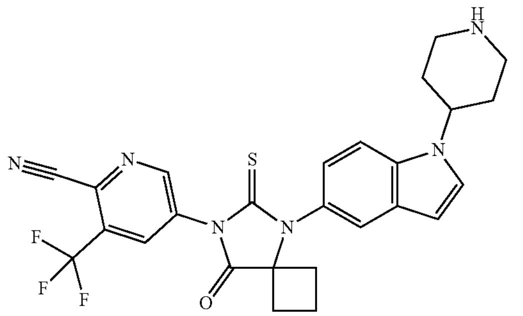 [SMILES: N#Cc1ncc(N2C(=O)C3(CCC3)N(c3ccc4c(ccn4C4CCNCC4)c3)C2=S)cc1C(F)(F)F] | 249 | 5-[5-oxo-8-[1-(4-piperidyl)indol-5-yl]-7-thioxo-6,8-diazaspiro[3.4]octan-6-yl]-3-(trifluoromethyl)pyridine-2-carbonitrile |
| 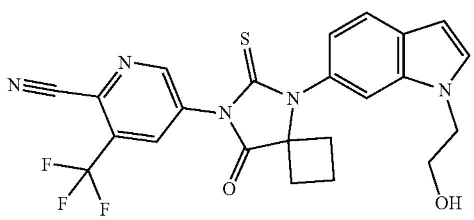 [SMILES: N#Cc1ncc(N2C(=O)C3(CCC3)N(c3ccc4ccn(CCO)c4c3)C2=S)cc1C(F)(F)F] | 250 | 5-[8-[1-(2-hydroxyethyl)indol-6-yl]-5-oxo-7-thioxo-6,8-diazaspiro[3.4]octan-6-yl]-3-(trifluoromethyl)pyridine-2-carbonitrile |
| 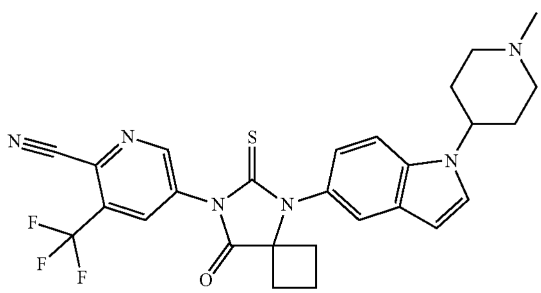 [SMILES: CN1CCC(n2ccc3cc(N4C(=S)N(c5cnc(C#N)c(C(F)(F)F)c5)C(=O)C45CCC5)ccc32)CC1] | 251 | 5-[8-[1-(1-methyl-4-piperidyl)indol-5-yl]-5-oxo-7-thioxo-6,8-diazaspiro[3.4]octan-6-yl]-3-(trifluoromethyl)pyridine-2-carbonitrile |
| 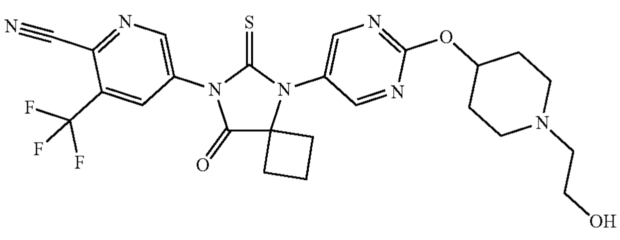 [SMILES: N#Cc1ncc(N2C(=O)C3(CCC3)N(c3cnc(OC4CCN(CCO)CC4)nc3)C2=S)cc1C(F)(F)F] | 252 | 5-[8-[2-[[1-(2-hydroxyethyl)-4-piperidyl]oxy]pyrimidin-5-yl]-5-oxo-7-thioxo-6,8-diazaspiro[3.4]octan-6-yl]-3-(trifluoromethyl)pyridine-2-carbonitrile |
| 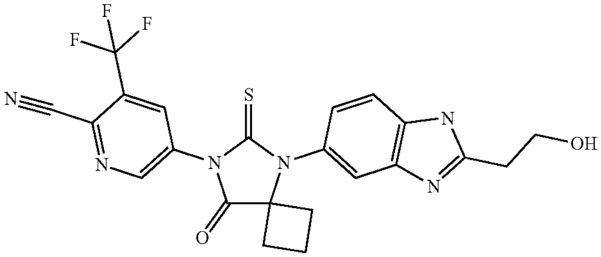 [SMILES: N#Cc1ncc(N2C(=O)C3(CCC3)N(c3ccc4[nH]c(CCO)nc4c3)C2=S)cc1C(F)(F)F] | 253 | 5-[8-[2-(2-hydroxyethyl)-1H-benzimidazol-5-yl]-5-oxo-7-thioxo-6,8-diazaspiro[3.4]octan-6-yl]-3-(trifluoromethyl)pyridine-2-carbonitrile |

| Structure | Cpd No. | Cpd Name |
|---|---|---|
| (structure) | 254 | 5-[8-[2-[[1-(2-hydroxyethyl)-4-piperidyl]oxy]pyrimidin-5-yl]-5-oxo-7-thioxo-6,8-diazaspiro[3.4]octan-6-yl]-3-methyl-pyridine-2-carbonitrile |
| (structure) | 255 | 5-[8-[2-(2-hydroxyethyl)-1-methyl-benzimidazol-5-yl]-5-oxo-7-thioxo-6,8-diazaspiro[3.4]octan-6-yl]-3-(trifluoromethyl)pyridine-2-carbonitrile |
| (structure) | 256 | 5-[8-[2-(1-methyl-4-piperidyl)-1H-benzimidazol-5-yl]-5-oxo-7-thioxo-6,8-diazaspiro[3.4]octan-6-yl]-3-(trifluoromethyl)pyridine-2-carbonitrile |

In a further embodiment, the invention is directed to a compound of Formula (I)

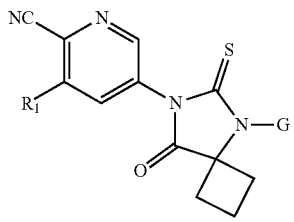

Formula (I)

selected from the group consisting of

Cpd 1, 5-[8-[6-[(1-methyl-4-piperidyl)oxy]-3-pyridyl]-5-oxo-7-thioxo-6,8-diazaspiro[3.4]octan-6-yl]-3-(trifluoromethyl)pyridine-2-carbonitrile;

Cpd 2, 3-methyl-5-[8-[6-[(1-methyl-4-piperidyl)oxy]-3-pyridyl]-5-oxo-7-thioxo-6,8-diazaspiro[3.4]octan-6-yl]pyridine-2-carbonitrile;

Cpd 3, 3-methyl-5-[5-oxo-8-[4-(1H-pyrazol-4-yl)phenyl]-7-thioxo-6,8-diazaspiro[3.4]octan-6-yl]pyridine-2-carbonitrile;

Cpd 4, 3-methyl-5-[5-oxo-8-[4-(1H-pyrazol-3-yl)phenyl]-7-thioxo-6,8-diazaspiro[3.4]octan-6-yl]pyridine-2-carbonitrile;

Cpd 5, 5-[8-[3-methoxy-4-(5-methyl-2-furyl)phenyl]-5-oxo-7-thioxo-6,8-diazaspiro[3.4]octan-6-yl]-3-methyl-pyridine-2-carbonitrile;

Cpd 6, 5-[8-[4-[5-(methoxymethyl)-2-furyl]phenyl]-5-oxo-7-thioxo-6,8-diazaspiro[3.4]octan-6-yl]-3-methyl-pyridine-2-carbonitrile;

Cpd 7, 4-[4-[6-(6-cyano-5-methyl-3-pyridyl)-5-oxo-7-thioxo-6,8-diazaspiro[3.4]octan-8-yl]phenyl]pyrazole-1-carboxamide;

Cpd 8, 2-[4-[6-(6-cyano-5-methyl-3-pyridyl)-5-oxo-7-thioxo-6,8-diazaspiro[3.4]octan-8-yl]phenyl]-N-methyl-acetamide;

Cpd 9, 3-methyl-5-[5-oxo-8-[4-(2-oxoimidazolidin-1-yl)phenyl]-7-thioxo-6,8-diazaspiro[3.4]octan-6-yl]pyridine-2-carbonitrile;

Cpd 10, 4-[4-[6-(6-cyano-5-methyl-3-pyridyl)-5-oxo-7-thioxo-6,8-diazaspiro[3.4]octan-8-yl]phenyl]-N-ethyl-pyrazole-1-carboxamide;

Cpd 11, 4-[6-[6-cyano-5-(trifluoromethyl)-3-pyridyl]-5-oxo-7-thioxo-6,8-diazaspiro[3.4]octan-8-yl]-2-fluoro-N-methyl-benzenecarbothioamide;

Cpd 12, 5-[5-oxo-8-(4-tetrahydrothiopyran-4-yloxyphenyl)-7-thioxo-6,8-diazaspiro[3.4]octan-6-yl]-3-(trifluoromethyl)pyridine-2-carbonitrile;

Cpd 13, 5-[8-[4-(1,1-dioxothian-4-yl)oxyphenyl]-5-oxo-7-thioxo-6,8-diazaspiro[3.4]octan-6-yl]-3-(trifluoromethyl)pyridine-2-carbonitrile;

Cpd 14, 5-[8-[4-[[1-(3-fluoropropyl)-4-piperidyl]oxy]phenyl]-5-oxo-7-thioxo-6,8-diazaspiro[3.4]octan-6-yl]-3-(trifluoromethyl)pyridine-2-carbonitrile;

Cpd 15, 5-[8-(6-methoxy-3-pyridyl)-5-oxo-7-thioxo-6,8-diazaspiro[3.4]octan-6-yl]-3-(trifluoromethyl)pyridine-2-carbonitrile;

Cpd 16, 5-[8-[4-[(3R)-1-methylpyrrolidin-3-yl]oxyphenyl]-5-oxo-7-thioxo-6,8-diazaspiro[3.4]octan-6-yl]-3-(trifluoromethyl)pyridine-2-carbonitrile;

Cpd 17, 5-[8-[4-(azepan-4-yloxy)phenyl]-5-oxo-7-thioxo-6,8-diazaspiro[3.4]octan-6-yl]-3-(trifluoromethyl)pyridine-2-carbonitrile;

Cpd 18, 5-[8-(6-hydroxy-3-pyridyl)-5-oxo-7-thioxo-6,8-diazaspiro[3.4]octan-6-yl]-3-(trifluoromethyl)pyridine-2-carbonitrile;

Cpd 19, 5-[8-[4-(1-methylazepan-4-yl)oxyphenyl]-5-oxo-7-thioxo-6,8-diazaspiro[3.4]octan-6-yl]-3-(trifluoromethyl)pyridine-2-carbonitrile;

Cpd 20, 5-[8-[4-[[(3S)-1-methyl-3-piperidyl]oxy]phenyl]-5-oxo-7-thioxo-6,8-diazaspiro[3.4]octan-6-yl]-3-(trifluoromethyl)pyridine-2-carbonitrile;

Cpd 21, 3-methyl-5-[5-oxo-8-(6-tetrahydrothiopyran-4-yloxy-3-pyridyl)-7-thioxo-6,8-diazaspiro[3.4]octan-6-yl]pyridine-2-carbonitrile;

Cpd 22, 6-[6-[6-cyano-5-(trifluoromethyl)-3-pyridyl]-5-oxo-7-thioxo-6,8-diazaspiro[3.4]octan-8-yl]pyridine-2-sulfonamide;

Cpd 23, 3-methoxy-5-[8-[4-[(1-methyl-4-piperidyl)oxy]phenyl]-5-oxo-7-thioxo-6,8-diazaspiro[3.4]octan-6-yl]pyridine-2-carbonitrile;

Cpd 24, 3-chloro-5-[8-[4-[(1-methyl-4-piperidyl)oxy]phenyl]-5-oxo-7-thioxo-6,8-diazaspiro[3.4]octan-6-yl]pyridine-2-carbonitrile;

Cpd 25, 3-methoxy-5-[8-[6-[(1-methyl-4-piperidyl)oxy]-3-pyridyl]-5-oxo-7-thioxo-6,8-diazaspiro[3.4]octan-6-yl]pyridine-2-carbonitrile;

Cpd 26, 3-chloro-5-[8-[6-[(1-methyl-4-piperidyl)oxy]-3-pyridyl]-5-oxo-7-thioxo-6,8-diazaspiro[3.4]octan-6-yl]pyridine-2-carbonitrile;

Cpd 27, 5-[8-[6-[3-(dimethylamino)propoxy]-3-pyridyl]-5-oxo-7-thioxo-6,8-diazaspiro[3.4]octan-6-yl]-3-methyl-pyridine-2-carbonitrile;

Cpd 28, 5-[8-(4-bromophenyl)-5-oxo-7-thioxo-6,8-diazaspiro[3.4]octan-6-yl]-3-(trifluoromethyl)pyridine-2-carbonitrile;

Cpd 29, 5-[8-[4-[[(1R,3r, 5S)-8-azabicyclo[3.2.1]octan-3-yl]oxy]phenyl]-5-oxo-7-thioxo-6,8-diazaspiro[3.4]octan-6-yl]-3-(trifluoromethyl)pyridine-2-carbonitrile;

Cpd 30, 5-[8-[4-(azepan-4-yloxy)phenyl]-5-oxo-7-thioxo-6,8-diazaspiro[3.4]octan-6-yl]-3-(trifluoromethyl)pyridine-2-carbonitrile;

Cpd 31, ethyl 4-[4-[6-[6-cyano-5-(trifluoromethyl)-3-pyridyl]-5-oxo-7-thioxo-6,8-diazaspiro[3.4]octan-8-yl]benzoyl]piperazine-1-carboxylate;

Cpd 32, tert-butyl 4-[4-[6-[6-cyano-5-(trifluoromethyl)-3-pyridyl]-5-oxo-7-thioxo-6,8-diazaspiro[3.4]octan-8-yl]benzoyl]piperazine-1-carboxylate;

Cpd 33, methyl 2-[4-[4-[6-[6-cyano-5-(trifluoromethyl)-3-pyridyl]-5-oxo-7-thioxo-6,8-diazaspiro[3.4]octan-8-yl]phenoxy]-1-piperidyl]acetate;

Cpd 34, 5-[8-[4-[[1-(3,3-dimethylbutyl)-4-piperidyl]oxy]phenyl]-5-oxo-7-thioxo-6,8-diazaspiro[3.4]octan-6-yl]-3-(trifluoromethyl)pyridine-2-carbonitrile;

Cpd 35, 5-[8-[4-[(1-cyclopropyl-4-piperidyl)oxy]phenyl]-5-oxo-7-thioxo-6,8-diazaspiro[3.4]octan-6-yl]-3-methyl-pyridine-2-carbonitrile;

Cpd 36, 5-[8-[4-[(1-cyclopropyl-4-piperidyl)oxy]phenyl]-5-oxo-7-thioxo-6,8-diazaspiro[3.4]octan-6-yl]-3-(trifluoromethyl)pyridine-2-carbonitrile;

Cpd 37, 5-[8-[4-[[1-(2-methoxyethyl)-4-piperidyl]oxy]phenyl]-5-oxo-7-thioxo-6,8-diazaspiro[3.4]octan-6-yl]-3-methyl-pyridine-2-carbonitrile;

Cpd 38, 5-[8-[4-[[1-(2-methoxyethyl)-4-piperidyl]oxy]phenyl]-5-oxo-7-thioxo-6,8-diazaspiro[3.4]octan-6-yl]-3-(trifluoromethyl)pyridine-2-carbonitrile;

Cpd 39, 5-[8-[4-[[1-(cyanomethyl)-4-piperidyl]oxy]phenyl]-5-oxo-7-thioxo-6,8-diazaspiro[3.4]octan-6-yl]-3-(trifluoromethyl)pyridine-2-carbonitrile;

Cpd 40, 5-[5-oxo-7-thioxo-8-[4-[[1-(2,2,2-trifluoroethyl)-4-piperidyl]oxy]phenyl]-6,8-diazaspiro[3.4]octan-6-yl]-3-(trifluoromethyl)pyridine-2-carbonitrile;

Cpd 41, 3-(difluoromethyl)-5-[8-[4-[(1-methyl-4-piperidyl)oxy]phenyl]-5-oxo-7-thioxo-6,8-diazaspiro[3.4]octan-6-yl]pyridine-2-carbonitrile;

Cpd 42, 5-[5-oxo-8-(4-phenoxycyclohexyl)-7-thioxo-6,8-diazaspiro[3.4]octan-6-yl]-3-(trifluoromethyl)pyridine-2-carbonitrile;

Cpd 43, 5-[5-oxo-8-[6-(4-piperidyloxy)-3-pyridyl]-7-thioxo-6,8-diazaspiro[3.4]octan-6-yl]-3-(trifluoromethyl)pyridine-2-carbonitrile;

Cpd 44, 3-chloro-5-[5-oxo-8-[4-(4-piperidyloxy)phenyl]-7-thioxo-6,8-diazaspiro[3.4]octan-6-yl]pyridine-2-carbonitrile;

Cpd 45, 3-chloro-5-[8-(6-hydroxy-3-pyridyl)-5-oxo-7-thioxo-6,8-diazaspiro[3.4]octan-6-yl]pyridine-2-carbonitrile;

Cpd 46, tert-butyl 4-[[[4-[6-[6-cyano-5-(trifluoromethyl)-3-pyridyl]-5-oxo-7-thioxo-6,8-diazaspiro[3.4]octan-8-yl]benzoyl]amino]methyl]piperidine-1-carboxylate;

Cpd 47, tert-butyl 4-[[4-[6-[6-cyano-5-(trifluoromethyl)-3-pyridyl]-5-oxo-7-thioxo-6,8-diazaspiro[3.4]octan-8-yl]phenyl]methyl]piperazine-1-carboxylate;

Cpd 48, 5-[5-oxo-8-[4-(piperazin-1-ylmethyl)phenyl]-7-thioxo-6,8-diazaspiro[3.4]octan-6-yl]-3-(trifluoromethyl)pyridine-2-carbonitrile;

Cpd 49, ethyl 4-[[[4-[6-[6-cyano-5-(trifluoromethyl)-3-pyridyl]-5-oxo-7-thioxo-6,8-diazaspiro[3.4]octan-8-yl]benzoyl]amino]methyl]piperidine-1-carboxylate;

Cpd 50, 3-chloro-5-[8-[4-[[1-(2-hydroxyethyl)-4-piperidyl]oxy]phenyl]-5-oxo-7-thioxo-6,8-diazaspiro[3.4]octan-6-yl]pyridine-2-carbonitrile;

Cpd 51, 3-chloro-5-[8-[4-[[1-(cyanomethyl)-4-piperidyl]oxy]phenyl]-5-oxo-7-thioxo-6,8-diazaspiro[3.4]octan-6-yl]pyridine-2-carbonitrile;

Cpd 52, 5-[8-[4-[[(1R,3s,5S)-8-methyl-8-azabicyclo[3.2.1]octan-3-yl]oxy]phenyl]-5-oxo-7-thioxo-6,8-diazaspiro[3.4]octan-6-yl]-3-(trifluoromethyl)pyridine-2-carbonitrile;

Cpd 53, 4-[[4-[6-[6-cyano-5-(trifluoromethyl)-3-pyridyl]-5-oxo-7-thioxo-6,8-diazaspiro[3.4]octan-8-yl]phenyl]methyl]-N-methyl-piperazine-1-carboxamide;

Cpd 54, 5-[8-[4-[(4,4-difluoropyrrolidin-2-yl)methoxy]phenyl]-5-oxo-7-thioxo-6,8-diazaspiro[3.4]octan-6-yl]-3-(trifluoromethyl)pyridine-2-carbonitrile;

Cpd 55, ethyl 4-[[4-[6-[6-cyano-5-(trifluoromethyl)-3-pyridyl]-5-oxo-7-thioxo-6,8-diazaspiro[3.4]octan-8-yl]phenyl]methyl]piperazine-1-carboxylate;

Cpd 56, tert-butyl 2-[[4-[6-[6-cyano-5-(trifluoromethyl)-3-pyridyl]-5-oxo-7-thioxo-6,8-diazaspiro[3.4]octan-8-yl]phenoxy]methyl]-4,4-difluoro-pyrrolidine-1-carboxylate;

Cpd 57, methyl 4-[6-[6-cyano-5-(trifluoromethyl)-3-pyridyl]-5-oxo-7-thioxo-6,8-diazaspiro[3.4]octan-8-yl]cyclohexanecarboxylate;

Cpd 58, ethyl 4-[4-[6-[6-cyano-5-(trifluoromethyl)-3-pyridyl]-5-oxo-7-thioxo-6,8-diazaspiro[3.4]octan-8-yl]phenyl]piperazine-1-carboxylate;

Cpd 59, 5-[8-[4-[(1-methylazetidin-3-yl)methoxy]phenyl]-5-oxo-7-thioxo-6,8-diazaspiro[3.4]octan-6-yl]-3-(trifluoromethyl)pyridine-2-carbonitrile;

Cpd 60, 5-[8-[6-[[1-(cyanomethyl)-4-piperidyl]oxy]-3-pyridyl]-5-oxo-7-thioxo-6,8-diazaspiro[3.4]octan-6-yl]-3-(trifluoromethyl)pyridine-2-carbonitrile;

Cpd 61, 5-[8-[6-[[1-(2-methoxyethyl)-4-piperidyl]oxy]-3-pyridyl]-5-oxo-7-thioxo-6,8-diazaspiro[3.4]octan-6-yl]-3-(trifluoromethyl)pyridine-2-carbonitrile;

Cpd 62, 3-methyl-5-[5-oxo-7-thioxo-8-[6-[[1-(2,2,2-trifluoroethyl)-4-piperidyl]oxy]-3-pyridyl]-6,8-diazaspiro[3.4]octan-6-yl]pyridine-2-carbonitrile;

Cpd 63, 5-[8-[6-[[1-(2-hydroxyethyl)-4-piperidyl]oxy]-3-pyridyl]-5-oxo-7-thioxo-6,8-diazaspiro[3.4]octan-6-yl]-3-(trifluoromethyl)pyridine-2-carbonitrile;

Cpd 64, 3-chloro-5-[5-oxo-8-[6-(4-piperidyloxy)-3-pyridyl]-7-thioxo-6,8-diazaspiro[3.4]octan-6-yl]pyridine-2-carbonitrile;

Cpd 65, 3-chloro-5-[8-[6-[[1-(cyanomethyl)-4-piperidyl]oxy]-3-pyridyl]-5-oxo-7-thioxo-6,8-diazaspiro[3.4]octan-6-yl]pyridine-2-carbonitrile;

Cpd 66, 5-[5-oxo-7-thioxo-8-[6-[[1-(2,2,2-trifluoroethyl)-4-piperidyl]oxy]-3-pyridyl]-6,8-diazaspiro[3.4]octan-6-yl]-3-(trifluoromethyl)pyridine-2-carbonitrile;

Cpd 67, 5-[8-[6-[[1-(2-fluoroethyl)-4-piperidyl]oxy]-3-pyridyl]-5-oxo-7-thioxo-6,8-diazaspiro[3.4]octan-6-yl]-3-(trifluoromethyl)pyridine-2-carbonitrile;

Cpd 68, 5-[8-[4-(4-aminocyclohexoxy)phenyl]-5-oxo-7-thioxo-6,8-diazaspiro[3.4]octan-6-yl]-3-(trifluoromethyl)pyridine-2-carbonitrile;

Cpd 69, 5-[8-(4-morpholinophenyl)-5-oxo-7-thioxo-6,8-diazaspiro[3.4]octan-6-yl]-3-(trifluoromethyl)pyridine-2-carbonitrile;

Cpd 70, 3-chloro-5-[8-[6-[[1-(2-methoxyethyl)-4-piperidyl]oxy]-3-pyridyl]-5-oxo-7-thioxo-6,8-diazaspiro[3.4]octan-6-yl]pyridine-2-carbonitrile;

Cpd 71, 5-[8-[4-[(1-acetyl-4,4-difluoro-pyrrolidin-2-yl)methoxy]phenyl]-5-oxo-7-thioxo-6,8-diazaspiro[3.4]octan-6-yl]-3-(trifluoromethyl)pyridine-2-carbonitrile;

Cpd 72, 4-[6-[6-cyano-5-(trifluoromethyl)-3-pyridyl]-5-oxo-7-thioxo-6,8-diazaspiro[3.4]octan-8-yl]-N-[(1-methyl-4-piperidyl)methyl]benzamide;

Cpd 73, 4-[[[4-[6-[6-cyano-5-(trifluoromethyl)-3-pyridyl]-5-oxo-7-thioxo-6,8-diazaspiro[3.4]octan-8-yl]benzoyl]amino]methyl]-N-methyl-piperidine-1-carboxamide;

Cpd 74, 5-[8-[4-(morpholin-2-ylmethoxy)phenyl]-5-oxo-7-thioxo-6,8-diazaspiro[3.4]octan-6-yl]-3-(trifluoromethyl)pyridine-2-carbonitrile;

Cpd 75, 3-methoxy-5-[5-oxo-8-[6-(4-piperidyloxy)-3-pyridyl]-7-thioxo-6,8-diazaspiro[3.4]octan-6-yl]pyridine-2-carbonitrile;

Cpd 76, 5-[5-oxo-8-[4-[4-(pyrrolidine-1-carbonyl)piperazin-1-yl]phenyl]-7-thioxo-6,8-diazaspiro[3.4]octan-6-yl]-3-(trifluoromethyl)pyridine-2-carbonitrile;

Cpd 77, 5-[8-[4-[[1-(2-fluoroethyl)-4-piperidyl]oxy]phenyl]-5-oxo-7-thioxo-6,8-diazaspiro[3.4]octan-6-yl]-3-(trifluoromethyl)pyridine-2-carbonitrile;

Cpd 78, 5-[8-[6-[[1-(2-fluoroethyl)-4-piperidyl]oxy]-3-pyridyl]-5-oxo-7-thioxo-6,8-diazaspiro[3.4]octan-6-yl]-3-methyl-pyridine-2-carbonitrile;

Cpd 79, 3-chloro-5-[8-[6-[[1-(2-hydroxyethyl)-4-piperidyl]oxy]-3-pyridyl]-5-oxo-7-thioxo-6,8-diazaspiro[3.4]octan-6-yl]pyridine-2-carbonitrile;

Cpd 80, 5-[8-[4-[4-(methylamino)cyclohexoxy]phenyl]-5-oxo-7-thioxo-6,8-diazaspiro[3.4]octan-6-yl]-3-(trifluoromethyl)pyridine-2-carbonitrile;

Cpd 81, 5-[8-[4-[4-(dimethylamino)cyclohexoxy]phenyl]-5-oxo-7-thioxo-6,8-diazaspiro[3.4]octan-6-yl]-3-(trifluoromethyl)pyridine-2-carbonitrile;

Cpd 82, 5-[8-[4-[2-(3-oxa-8-azaspiro[4.5]decan-8-yl)ethoxy]phenyl]-5-oxo-7-thioxo-6,8-diazaspiro[3.4]octan-6-yl]-3-(trifluoromethyl)pyridine-2-carbonitrile;

Cpd 83, 5-[8-[4-[2-(2,2-difluoro-6-azaspiro[3.3]heptan-6-yl)ethoxy]phenyl]-5-oxo-7-thioxo-6,8-diazaspiro[3.4]octan-6-yl]-3-(trifluoromethyl)pyridine-2-carbonitrile;

Cpd 84, 5-[8-[4-(1-methylazetidin-3-yl)oxyphenyl]-5-oxo-7-thioxo-6,8-diazaspiro[3.4]octan-6-yl]-3-(trifluoromethyl)pyridine-2-carbonitrile;

Cpd 85, tert-butyl 3-[4-[6-[6-cyano-5-(trifluoromethyl)-3-pyridyl]-5-oxo-7-thioxo-6,8-diazaspiro[3.4]octan-8-yl]phenoxy]-4-fluoro-8-azabicyclo[3.2.1]octane-8-carboxylate;

Cpd 86, 5-[8-[4-(6-azaspiro[3.3]heptan-2-yloxy)phenyl]-5-oxo-7-thioxo-6,8-diazaspiro[3.4]octan-6-yl]-3-(trifluoromethyl)pyridine-2-carbonitrile;

Cpd 87, 3-methyl-5-[5-oxo-8-[6-(4-piperidyloxy)-3-pyridyl]-7-thioxo-6,8-diazaspiro[3.4]octan-6-yl]pyridine-2-carbonitrile;

Cpd 88, 5-[8-[6-[(1-allyl-4-piperidyl)oxy]-3-pyridyl]-5-oxo-7-thioxo-6,8-diazaspiro[3.4]octan-6-yl]-3-(trifluoromethyl)pyridine-2-carbonitrile;

Cpd 89, 5-[8-[6-[(1-allyl-4-piperidyl)oxy]-3-pyridyl]-5-oxo-7-thioxo-6,8-diazaspiro[3.4]octan-6-yl]-3-chloro-pyridine-2-carbonitrile;

Cpd 90, 5-[8-[6-[[1-(cyanomethyl)-4-piperidyl]oxy]-3-pyridyl]-5-oxo-7-thioxo-6,8-diazaspiro[3.4]octan-6-yl]-3-methyl-pyridine-2-carbonitrile;

Cpd 91, 5-[8-[4-[(5-methylmorpholin-2-yl)methoxy]phenyl]-5-oxo-7-thioxo-6,8-diazaspiro[3.4]octan-6-yl]-3-(trifluoromethyl)pyridine-2-carbonitrile;

Cpd 92, 5-[8-[(3SR, 4SR)-4-[(3-fluoro-1-methyl-4-piperidyl)oxy]phenyl]-5-oxo-7-thioxo-6,8-diazaspiro[3.4]octan-6-yl]-3-(trifluoromethyl)pyridine-2-carbonitrile;

Cpd 93, 5-[8-[4-[(4-fluoro-8-azabicyclo[3.2.1]octan-3-yl)oxy]phenyl]-5-oxo-7-thioxo-6,8-diazaspiro[3.4]octan-6-yl]-3-(trifluoromethyl)pyridine-2-carbonitrile;

Cpd 94, 5-[8-[4-[(4-fluoro-8-methyl-8-azabicyclo[3.2.1]octan-3-yl)oxy]phenyl]-5-oxo-7-thioxo-6,8-diazaspiro[3.4]octan-6-yl]-3-(trifluoromethyl)pyridine-2-carbonitrile;

Cpd 95, 5-[8-[(3SR, 4SR)-4-[(3-fluoro-4-piperidyl)oxy]phenyl]-5-oxo-7-thioxo-6,8-diazaspiro[3.4]octan-6-yl]-3-(trifluoromethyl)pyridine-2-carbonitrile;

Cpd 96, 5-[8-(3RS, 4SR) [4-[(3-fluoro-4-piperidyl)oxy]phenyl]-5-oxo-7-thioxo-6,8-diazaspiro[3.4]octan-6-yl]-3-(trifluoromethyl)pyridine-2-carbonitrile;

Cpd 97, 5-[8-[4-[(6-methyl-6-azaspiro[3.3]heptan-2-yl)oxy]phenyl]-5-oxo-7-thioxo-6,8-diazaspiro[3.4]octan-6-yl]-3-(trifluoromethyl)pyridine-2-carbonitrile;

Cpd 98, 5-[8-[6-[[1-(2-methoxyethyl)-4-piperidyl]oxy]-3-pyridyl]-5-oxo-7-thioxo-6,8-diazaspiro[3.4]octan-6-yl]-3-methyl-pyridine-2-carbonitrile;

Cpd 99, 5-[8-[6-[(1-allyl-4-piperidyl)oxy]-3-pyridyl]-5-oxo-7-thioxo-6,8-diazaspiro[3.4]octan-6-yl]-3-methyl-pyridine-2-carbonitrile;

Cpd 100, 5-[8-[6-[[1-(2-hydroxyethyl)-4-piperidyl]oxy]-3-pyridyl]-5-oxo-7-thioxo-6,8-diazaspiro[3.4]octan-6-yl]-3-methyl-pyridine-2-carbonitrile;

Cpd 101, 5-[5-oxo-7-thioxo-8-[4-[[(2SR,4RS)-2-(trifluoromethyl)-4-piperidyl]oxy]phenyl]-6,8-diazaspiro[3.4]octan-6-yl]-3-(trifluoromethyl)pyridine-2-carbonitrile;

Cpd 102, 5-[8-[(3RS, 4SR)-[4-[(3-fluoro-1-methyl-4-piperidyl)oxy]phenyl]-5-oxo-7-thioxo-6,8-diazaspiro[3.4]octan-6-yl]-3-(trifluoromethyl)pyridine-2-carbonitrile;

Cpd 103, 5-[8-[4-[2-(hydroxymethyl)-3,4-dihydro-2H-pyran-6-yl]phenyl]-5-oxo-7-thioxo-6,8-diazaspiro[3.4]octan-6-yl]-3-(trifluoromethyl)pyridine-2-carbonitrile;

Cpd 104, 5-[5-oxo-8-[6-[(1-prop-2-ynyl-4-piperidyl)oxy]-3-pyridyl]-7-thioxo-6,8-diazaspiro[3.4]octan-6-yl]-3-(trifluoromethyl)pyridine-2-carbonitrile;

Cpd 105, 5-[8-[4-[2-(6-oxa-2-azaspiro[3.3]heptan-2-yl)ethoxy]phenyl]-5-oxo-7-thioxo-6,8-diazaspiro[3.4]octan-6-yl]-3-(trifluoromethyl)pyridine-2-carbonitrile;

Cpd 106, 5-[5-oxo-7-thioxo-8-[4-[[(2RS,4RS)-2-(trifluoromethyl)-4-piperidyl]oxy]phenyl]-6,8-diazaspiro[3.4]octan-6-yl]-3-(trifluoromethyl)pyridine-2-carbonitrile;

Cpd 107, 5-[5-oxo-8-[4-[(1-prop-2-ynyl-4-piperidyl)oxy]phenyl]-7-thioxo-6,8-diazaspiro[3.4]octan-6-yl]-3-(trifluoromethyl)pyridine-2-carbonitrile;

Cpd 108, 5-[5-oxo-8-(1,2,3,4-tetrahydroisoquinolin-6-yl)-7-thioxo-6,8-diazaspiro[3.4]octan-6-yl]-3-(trifluoromethyl)pyridine-2-carbonitrile;

Cpd 109, 5-[8-[1-(1-methyl-4-piperidyl)indazol-5-yl]-5-oxo-7-thioxo-6,8-diazaspiro[3.4]octan-6-yl]-3-(trifluoromethyl)pyridine-2-carbonitrile;

Cpd 110, tert-butyl N-[3-[4-[6-[6-cyano-5-(trifluoromethyl)-3-pyridyl]-5-oxo-7-thioxo-6,8-diazaspiro[3.4]octan-8-yl]phenoxy]-2,2,4,4-tetramethyl-cyclobutyl]carbamate;

Cpd 111, 5-[5-oxo-8-(4-tetrahydrofuran-2-yloxyphenyl)-7-thioxo-6,8-diazaspiro[3.4]octan-6-yl]-3-(trifluoromethyl)pyridine-2-carbonitrile;

Cpd 112, 5-[8-[4-[(3R,4R)-3,4-dihydroxy-3,4-dihydro-2H-pyran-6-yl]phenyl]-5-oxo-7-thioxo-6,8-diazaspiro[3.4]octan-6-yl]-3-(trifluoromethyl)pyridine-2-carbonitrile;

Cpd 113, tert-butyl 3-[4-[6-[6-cyano-5-(trifluoromethyl)-3-pyridyl]-5-oxo-7-thioxo-6,8-diazaspiro[3.4]octan-8-yl]phenyl]-8-azabicyclo[3.2.1]octane-8-carboxylate;

Cpd 114, 5-[8-[4-(8-methyl-8-azabicyclo[3.2.1]octan-3-yl)phenyl]-5-oxo-7-thioxo-6,8-diazaspiro[3.4]octan-6-yl]-3-(trifluoromethyl)pyridine-2-carbonitrile;

Cpd 115, 5-[5-oxo-8-[2-(4-piperidyl)indazol-5-yl]-7-thioxo-6,8-diazaspiro[3.4]octan-6-yl]-3-(trifluoromethyl)pyridine-2-carbonitrile;

Cpd 116, 5-[8-[4-(8-azabicyclo[3.2.1]oct-3-en-3-yl)phenyl]-5-oxo-7-thioxo-6,8-diazaspiro[3.4]octan-6-yl]-3-(trifluoromethyl)pyridine-2-carbonitrile;

Cpd 117, 5-[5-oxo-8-[4-(1-prop-2-ynylazetidin-3-yl)oxyphenyl]-7-thioxo-6,8-diazaspiro[3.4]octan-6-yl]-3-(trifluoromethyl)pyridine-2-carbonitrile;

Cpd 118, tert-butyl 6-[6-[6-cyano-5-(trifluoromethyl)-3-pyridyl]-5-oxo-7-thioxo-6,8-diazaspiro[3.4]octan-8-yl]-3,4-dihydro-1H-isoquinoline-2-carboxylate;

Cpd 119, 5-[5-oxo-8-[1-(4-piperidyl)indazol-5-yl]-7-thioxo-6,8-diazaspiro[3.4]octan-6-yl]-3-(trifluoromethyl)pyridine-2-carbonitrile;

Cpd 120, 5-[8-(2-acetyl-3,4-dihydro-1H-isoquinolin-6-yl)-5-oxo-7-thioxo-6,8-diazaspiro[3.4]octan-6-yl]-3-(trifluoromethyl)pyridine-2-carbonitrile;

Cpd 121, tert-butyl 4-[5-[6-[6-cyano-5-(trifluoromethyl)-3-pyridyl]-5-oxo-7-thioxo-6,8-diazaspiro[3.4]octan-8-yl]indazol-2-yl]piperidine-1-carboxylate;

Cpd 122, tert-butyl 4-[[5-[6-[6-cyano-5-(trifluoromethyl)-3-pyridyl]-5-oxo-7-thioxo-6,8-diazaspiro[3.4]octan-8-yl]indazol-2-yl]methyl]piperidine-1-carboxylate Cpd 123, 5-[8-[4-(8-azabicyclo[3.2.1]octan-3-yl)phenyl]-5-oxo-7-thioxo-6,8-diazaspiro[3.4]octan-6-yl]-3-(trifluoromethyl)pyridine-2-carbonitrile;

Cpd 124, 5-[8-[1-[(1-acetyl-4-piperidyl)methyl]indazol-5-yl]-5-oxo-7-thioxo-6,8-diazaspiro[3.4]octan-6-yl]-3-(trifluoromethyl)pyridine-2-carbonitrile;

Cpd 125, 5-[8-(2-methyl-3,4-dihydro-1H-isoquinolin-6-yl)-5-oxo-7-thioxo-6,8-diazaspiro[3.4]octan-6-yl]-3-(trifluoromethyl)pyridine-2-carbonitrile;

Cpd 126, 5-[5-oxo-8-[2-(4-piperidylmethyl)indazol-5-yl]-7-thioxo-6,8-diazaspiro[3.4]octan-6-yl]-3-(trifluoromethyl)pyridine-2-carbonitrile;

Cpd 127, 5-[8-[4-(8-methyl-8-azabicyclo[3.2.1]oct-3-en-3-yl)phenyl]-5-oxo-7-thioxo-6,8-diazaspiro[3.4]octan-6-yl]-3-(trifluoromethyl)pyridine-2-carbonitrile;

Cpd 128, 5-[5-oxo-8-[1-(4-piperidylmethyl)indazol-5-yl]-7-thioxo-6,8-diazaspiro[3.4]octan-6-yl]-3-(trifluoromethyl)pyridine-2-carbonitrile;

Cpd 129, 5-[8-[2-[(1-methyl-4-piperidyl)methyl]indazol-5-yl]-5-oxo-7-thioxo-6,8-diazaspiro[3.4]octan-6-yl]-3-(trifluoromethyl)pyridine-2-carbonitrile;

Cpd 130, tert-butyl 3-[[5-[6-[6-cyano-5-(trifluoromethyl)-3-pyridyl]-5-oxo-7-thioxo-6,8-diazaspiro[3.4]octan-8-yl]-2-oxo-1-pyridyl]methyl]azetidine-1-carboxylate;

Cpd 131, 5-[8-[1-(1-acetyl-4-piperidyl)indazol-5-yl]-5-oxo-7-thioxo-6,8-diazaspiro[3.4]octan-6-yl]-3-(trifluoromethyl)pyridine-2-carbonitrile;

Cpd 132, 5-[8-[1-[(1-methyl-4-piperidyl)methyl]indazol-5-yl]-5-oxo-7-thioxo-6,8-diazaspiro[3.4]octan-6-yl]-3-(trifluoromethyl)pyridine-2-carbonitrile;

Cpd 133, 5-[8-(1-methyl-6-oxo-3-pyridyl)-5-oxo-7-thioxo-6,8-diazaspiro[3.4]octan-6-yl]-3-(trifluoromethyl)pyridine-2-carbonitrile;

Cpd 134, N-[4-[6-[6-cyano-5-(trifluoromethyl)-3-pyridyl]-5-oxo-7-thioxo-6,8-diazaspiro[3.4]octan-8-yl]cyclohexyl]benzamide Cpd 135, 5-[8-[4-[(2S,3R,4S)-3,4-dihydroxy-2-methyl-3,4-dihydro-2H-pyran-6-yl]phenyl]-5-oxo-7-thioxo-6,8-diazaspiro[3.4]octan-6-yl]-3-(trifluoromethyl)pyridine-2-carbonitrile;

Cpd 136, 5-[8-[4-[(3,3-difluoro-4-piperidyl)oxy]phenyl]-5-oxo-7-thioxo-6,8-diazaspiro[3.4]octan-6-yl]-3-(trifluoromethyl)pyridine-2-carbonitrile;

Cpd 137, 5-[8-[4-[(3,3-difluoro-1-methyl-4-piperidyl)oxy]phenyl]-5-oxo-7-thioxo-6,8-diazaspiro[3.4]octan-6-yl]-3-(trifluoromethyl)pyridine-2-carbonitrile;

Cpd 138, 5-[8-[4-(3-azabicyclo[3.2.1]octan-8-yloxy)phenyl]-5-oxo-7-thioxo-6,8-diazaspiro[3.4]octan-6-yl]-3-(trifluoromethyl)pyridine-2-carbonitrile;

Cpd 139, 5-[8-[6-(3-azabicyclo[3.2.1]octan-8-yloxy)-3-pyridyl]-5-oxo-7-thioxo-6,8-diazaspiro[3.4]octan-6-yl]-3-(trifluoromethyl)pyridine-2-carbonitrile;

Cpd 140, 5-[8-[4-[(4-methyl-4-piperidyl)oxy]phenyl]-5-oxo-7-thioxo-6,8-diazaspiro[3.4]octan-6-yl]-3-(trifluoromethyl)pyridine-2-carbonitrile;

Cpd 141, 5-[5-oxo-8-[2-(4-piperidyloxy)pyrimidin-5-yl]-7-thioxo-6,8-diazaspiro[3.4]octan-6-yl]-3-(trifluoromethyl)pyridine-2-carbonitrile;

Cpd 142, 5-[8-[4-[2-(1-methylazetidin-3-yl)ethoxy]phenyl]-5-oxo-7-thioxo-6,8-diazaspiro[3.4]octan-6-yl]-3-(trifluoromethyl)pyridine-2-carbonitrile;

Cpd 143, 5-[8-[4-[(1,4-dimethyl-4-piperidyl)oxy]phenyl]-5-oxo-7-thioxo-6,8-diazaspiro[3.4]octan-6-yl]-3-(trifluoromethyl)pyridine-2-carbonitrile;

Cpd 144, 5-[8-[4-(1-methylpiperidine-4-carbonyl)phenyl]-5-oxo-7-thioxo-6,8-diazaspiro[3.4]octan-6-yl]-3-(trifluoromethyl)pyridine-2-carbonitrile;

Cpd 145, 5-[8-[4-[(3-aminooxetan-3-yl)methoxy]phenyl]-5-oxo-7-thioxo-6,8-diazaspiro[3.4]octan-6-yl]-3-(trifluoromethyl)pyridine-2-carbonitrile;

Cpd 146, 5-[8-[4-[(3-methyl-3-azabicyclo[3.2.1]octan-8-yl)oxy]phenyl]-5-oxo-7-thioxo-6,8-diazaspiro[3.4]octan-6-yl]-3-(trifluoromethyl)pyridine-2-carbonitrile;

Cpd 147, 5-[8-[6-[(3-methyl-3-azabicyclo[3.2.1]octan-8-yl)oxy]-3-pyridyl]-5-oxo-7-thioxo-6,8-diazaspiro[3.4]octan-6-yl]-3-(trifluoromethyl)pyridine-2-carbonitrile;

Cpd 148, 5-[8-[4-(3-azaspiro[3.3]heptan-6-yloxy)phenyl]-5-oxo-7-thioxo-6,8-diazaspiro[3.4]octan-6-yl]-3-(trifluoromethyl)pyridine-2-carbonitrile;

Cpd 149, 3-chloro-5-[8-[6-[(1-isopentyl-4-piperidyl)oxy]-3-pyridyl]-5-oxo-7-thioxo-6,8-diazaspiro[3.4]octan-6-yl]pyridine-2-carbonitrile;

Cpd 150, 5-[8-[4-(2-azabicyclo[2.2.1]heptan-5-yloxy)phenyl]-5-oxo-7-thioxo-6,8-diazaspiro[3.4]octan-6-yl]-3-(trifluoromethyl)pyridine-2-carbonitrile;

Cpd 151, 5-[8-[4-(9-azaspiro[3.5]nonan-6-yloxy)phenyl]-5-oxo-7-thioxo-6,8-diazaspiro[3.4]octan-6-yl]-3-(trifluoromethyl)pyridine-2-carbonitrile;

Cpd 152, 5-[8-[2-[(1-methyl-4-piperidyl)oxy]pyrimidin-5-yl]-5-oxo-7-thioxo-6,8-diazaspiro[3.4]octan-6-yl]-3-(trifluoromethyl)pyridine-2-carbonitrile;

Cpd 153, tert-butyl 6-[[5-[6-[6-cyano-5-(trifluoromethyl)-3-pyridyl]-5-oxo-7-thioxo-6,8-diazaspiro[3.4]octan-8-yl]-2-pyridyl]oxy]-3-azaspiro[3.3]heptane-3-carboxylate;

Cpd 154, 3-methoxy-5-[5-oxo-8-[4-(4-piperidyloxy)phenyl]-7-thioxo-6,8-diazaspiro[3.4]octan-6-yl]pyridine-2-carbonitrile;

Cpd 155, 3-chloro-5-[8-(1H-indazol-5-yl)-5-oxo-7-thioxo-6,8-diazaspiro[3.4]octan-6-yl]pyridine-2-carbonitrile;

Cpd 156, 5-[8-[4-(1,2,3,5,6,7,8,8a-octahydroindolizin-7-yloxy)phenyl]-5-oxo-7-thioxo-6,8-diazaspiro[3.4]octan-6-yl]-3-(trifluoromethyl)pyridine-2-carbonitrile;

Cpd 157, 5-[8-[4-[[1-(3-amino-2-hydroxy-propyl)-4-piperidyl]oxy]phenyl]-5-oxo-7-thioxo-6,8-diazaspiro[3.4]octan-6-yl]-3-(trifluoromethyl)pyridine-2-carbonitrile;

Cpd 158, 5-[8-[4-[[(2SR, 4RS)-1-methyl-2-(trifluoromethyl)-4-piperidyl]oxy]phenyl]-5-oxo-7-thioxo-6,8-diazaspiro[3.4]octan-6-yl]-3-(trifluoromethyl)pyridine-2-carbonitrile;

Cpd 159, 5-[8-[1-(2-hydroxyethyl)indazol-5-yl]-5-oxo-7-thioxo-6,8-diazaspiro[3.4]octan-6-yl]-3-(trifluoromethyl)pyridine-2-carbonitrile;

Cpd 160, 5-[8-[1-(2-methoxyethyl)indazol-6-yl]-5-oxo-7-thioxo-6,8-diazaspiro[3.4]octan-6-yl]-3-(trifluoromethyl)pyridine-2-carbonitrile;

Cpd 161, 5-[8-[2-(2-hydroxyethyl)indazol-5-yl]-5-oxo-7-thioxo-6,8-diazaspiro[3.4]octan-6-yl]-3-(trifluoromethyl)pyridine-2-carbonitrile;

Cpd 162, 3-chloro-5-[8-[2-(2-hydroxyethyl)indazol-5-yl]-5-oxo-7-thioxo-6,8-diazaspiro[3.4]octan-6-yl]pyridine-2-carbonitrile;

Cpd 163, 3-chloro-5-[8-[1-(2-hydroxyethyl)indazol-5-yl]-5-oxo-7-thioxo-6,8-diazaspiro[3.4]octan-6-yl]pyridine-2-carbonitrile;

Cpd 164, 5-[8-[2-(2-hydroxyethyl)indazol-5-yl]-5-oxo-7-thioxo-6,8-diazaspiro[3.4]octan-6-yl]-3-methoxy-pyridine-2-carbonitrile;

Cpd 165, 5-[8-[6-(2-azabicyclo[2.2.1]heptan-5-yloxy)-3-pyridyl]-5-oxo-7-thioxo-6,8-diazaspiro[3.4]octan-6-yl]-3-(trifluoromethyl)pyridine-2-carbonitrile;

Cpd 166, 5-[8-[4-[(3-methyl-3-azaspiro[3.3]heptan-6-yl)oxy]phenyl]-5-oxo-7-thioxo-6,8-diazaspiro[3.4]octan-6-yl]-3-(trifluoromethyl)pyridine-2-carbonitrile;

Cpd 167, 5-[8-[1-(2-hydroxyethyl)indazol-5-yl]-5-oxo-7-thioxo-6,8-diazaspiro[3.4]octan-6-yl]-3-methoxy-pyridine-2-carbonitrile;

Cpd 168, 3-chloro-5-[8-(1-methylindazol-5-yl)-5-oxo-7-thioxo-6,8-diazaspiro[3.4]octan-6-yl]pyridine-2-carbonitrile;

Cpd 169, 3-chloro-5-[8-[2-(2-methoxyethyl)indazol-5-yl]-5-oxo-7-thioxo-6,8-diazaspiro[3.4]octan-6-yl]pyridine-2-carbonitrile;

Cpd 170, 5-[8-[2-(2-methoxyethyl)indazol-5-yl]-5-oxo-7-thioxo-6,8-diazaspiro[3.4]octan-6-yl]-3-(trifluoromethyl)pyridine-2-carbonitrile;

Cpd 171, 3-chloro-5-[8-[1-(2-methoxyethyl)indazol-5-yl]-5-oxo-7-thioxo-6,8-diazaspiro[3.4]octan-6-yl]pyridine-2-carbonitrile;

Cpd 172, 5-[8-[2-(2-methoxyethyl)indazol-5-yl]-5-oxo-7-thioxo-6,8-diazaspiro[3.4]octan-6-yl]-3-(trifluoromethyl)pyridine-2-carbonitrile;

Cpd 173, 3-methoxy-5-[8-[1-(2-methoxyethyl)indazol-5-yl]-5-oxo-7-thioxo-6,8-diazaspiro[3.4]octan-6-yl]pyridine-2-carbonitrile;

Cpd 174, 5-[8-(2-methylindazol-5-yl)-5-oxo-7-thioxo-6,8-diazaspiro[3.4]octan-6-yl]-3-(trifluoromethyl)pyridine-2-carbonitrile;

Cpd 175, 3-methoxy-5-[8-[2-(2-methoxyethyl)indazol-5-yl]-5-oxo-7-thioxo-6,8-diazaspiro[3.4]octan-6-yl]pyridine-2-carbonitrile;

Cpd 176, 5-[8-[4-[(2-methyl-2-azabicyclo[2.2.1]heptan-5-yl)oxy]phenyl]-5-oxo-7-thioxo-6,8-diazaspiro[3.4]octan-6-yl]-3-(trifluoromethyl)pyridine-2-carbonitrile;

Cpd 177, 5-[8-[6-[(2-methyl-2-azabicyclo[2.2.1]heptan-5-yl)oxy]-3-pyridyl]-5-oxo-7-thioxo-6,8-diazaspiro[3.4]octan-6-yl]-3-(trifluoromethyl)pyridine-2-carbonitrile;

Cpd 178, 5-[8-[4-[(9-methyl-9-azaspiro[3.5]nonan-6-yl)oxy]phenyl]-5-oxo-7-thioxo-6,8-diazaspiro[3.4]octan-6-yl]-3-(trifluoromethyl)pyridine-2-carbonitrile;

Cpd 179, 5-[8-[2-(2-methoxyethyl)indazol-6-yl]-5-oxo-7-thioxo-6,8-diazaspiro[3.4]octan-6-yl]-3-(trifluoromethyl)pyridine-2-carbonitrile;

Cpd 180, 3-chloro-5-[5-oxo-8-[2-(4-piperidyl)indazol-5-yl]-7-thioxo-6,8-diazaspiro[3.4]octan-6-yl]pyridine-2-carbonitrile;

Cpd 181, 3-chloro-5-[8-[2-(1-methyl-4-piperidyl)indazol-5-yl]-5-oxo-7-thioxo-6,8-diazaspiro[3.4]octan-6-yl]pyridine-2-carbonitrile;

Cpd 182, 3-chloro-5-[5-oxo-8-[1-(4-piperidyl)indazol-5-yl]-7-thioxo-6,8-diazaspiro[3.4]octan-6-yl]pyridine-2-carbonitrile;

Cpd 183, 3-chloro-5-[8-[1-(1-methyl-4-piperidyl)indazol-5-yl]-5-oxo-7-thioxo-6,8-diazaspiro[3.4]octan-6-yl]pyridine-2-carbonitrile;

Cpd 184, 4-[6-[6-cyano-5-(trifluoromethyl)-3-pyridyl]-5-oxo-7-thioxo-6,8-diazaspiro[3.4]octan-8-yl]-N-[[(3R)-1-methyl-3-piperidyl]methyl]benzamide;

Cpd 185, 4-[6-[6-cyano-5-(trifluoromethyl)-3-pyridyl]-5-oxo-7-thioxo-6,8-diazaspiro[3.4]octan-8-yl]-N-[[(3S)-1-methyl-3-piperidyl]methyl]benzamide;

Cpd 186, 4-[6-[6-cyano-5-(trifluoromethyl)-3-pyridyl]-5-oxo-7-thioxo-6,8-diazaspiro[3.4]octan-8-yl]-N-[[(3R)-3-piperidyl]methyl]benzamide;

Cpd 187, 4-[6-[6-cyano-5-(trifluoromethyl)-3-pyridyl]-5-oxo-7-thioxo-6,8-diazaspiro[3.4]octan-8-yl]-N-[[(3S)-1-methylpyrrolidin-3-yl]methyl]benzamide;

Cpd 188, 5-[8-[6-(9-azaspiro[3.5]nonan-6-yloxy)-3-pyridyl]-5-oxo-7-thioxo-6,8-diazaspiro[3.4]octan-6-yl]-3-(trifluoromethyl)pyridine-2-carbonitrile;

Cpd 189, 5-[8-[4-[(1-methyl-2-oxo-4-piperidyl)oxy]phenyl]-5-oxo-7-thioxo-6,8-diazaspiro[3.4]octan-6-yl]-3-(trifluoromethyl)pyridine-2-carbonitrile;

Cpd 190, 5-[8-[4-(1-methyl-1-oxido-piperidin-1-ium-4-yl)oxyphenyl]-5-oxo-7-thioxo-6,8-diazaspiro[3.4]octan-6-yl]-3-(trifluoromethyl)pyridine-2-carbonitrile;

Cpd 191, 5-[8-[4-(1-methyl-1-oxido-piperidin-1-ium-4-yl)oxyphenyl]-5-oxo-7-thioxo-6,8-diazaspiro[3.4]octan-6-yl]-3-(trifluoromethyl)pyridine-2-carbonitrile;

Cpd 192, 4-[6-[6-cyano-5-(trifluoromethyl)-3-pyridyl]-5-oxo-7-thioxo-6,8-diazaspiro[3.4]octan-8-yl]-N-(1-methylpyrrolidin-3-yl)benzamide;

Cpd 193, 5-[8-[6-[(3-methyl-3-azaspiro[3.3]heptan-6-yl)oxy]-3-pyridyl]-5-oxo-7-thioxo-6,8-diazaspiro[3.4]octan-6-yl]-3-(trifluoromethyl)pyridine-2-carbonitrile;

Cpd 194, 5-[8-[6-[(9-methyl-9-azaspiro[3.5]nonan-6-yl)oxy]-3-pyridyl]-5-oxo-7-thioxo-6,8-diazaspiro[3.4]octan-6-yl]-3-(trifluoromethyl)pyridine-2-carbonitrile;

Cpd 195, 5-[5-oxo-8-[4-[(2-oxo-4-piperidyl)oxy]phenyl]-7-thioxo-6,8-diazaspiro[3.4]octan-6-yl]-3-(trifluoromethyl)pyridine-2-carbonitrile;

Cpd 196, tert-butyl N-[3-[[4-[6-[6-cyano-5-(trifluoromethyl)-3-pyridyl]-5-oxo-7-thioxo-6,8-diazaspiro[3.4]octan-8-yl]phenoxy]methyl]oxetan-3-yl]-N-methyl-carbamate;

Cpd 197, 5-[8-[4-[3-(dimethylamino)oxetan-3-yl]phenyl]-5-oxo-7-thioxo-6,8-diazaspiro[3.4]octan-6-yl]-3-(trifluoromethyl)pyridine-2-carbonitrile;

Cpd 198, 5-[8-[2-(1-acetyl-4-piperidyl)indazol-6-yl]-5-oxo-7-thioxo-6,8-diazaspiro[3.4]octan-6-yl]-3-(trifluoromethyl)pyridine-2-carbonitrile;

Cpd 199, 5-[8-[2-(1-methyl-4-piperidyl)indazol-6-yl]-5-oxo-7-thioxo-6,8-diazaspiro[3.4]octan-6-yl]-3-(trifluoromethyl)pyridine-2-carbonitrile;

Cpd 200, 4-[6-[6-cyano-5-(trifluoromethyl)-3-pyridyl]-5-oxo-7-thioxo-6,8-diazaspiro[3.4]octan-8-yl]-2-fluoro-N-[[(3S)-1-methyl-3-piperidyl]methyl]benzamide;

Cpd 201, 4-[6-[6-cyano-5-(trifluoromethyl)-3-pyridyl]-5-oxo-7-thioxo-6,8-diazaspiro[3.4]octan-8-yl]-2-fluoro-N-[(1-methyl-4-piperidyl)methyl]benzamide;

Cpd 202, 4-[6-[6-cyano-5-(trifluoromethyl)-3-pyridyl]-5-oxo-7-thioxo-6,8-diazaspiro[3.4]octan-8-yl]-2-fluoro-N-[[(3R)-3-piperidyl]methyl]benzamide;

Cpd 203, 4-[6-[6-cyano-5-(trifluoromethyl)-3-pyridyl]-5-oxo-7-thioxo-6,8-diazaspiro[3.4]octan-8-yl]-2-fluoro-N-[[(3R)-1-methyl-3-piperidyl]methyl]benzamide;

Cpd 204, 4-[6-[6-cyano-5-(trifluoromethyl)-3-pyridyl]-5-oxo-7-thioxo-6,8-diazaspiro[3.4]octan-8-yl]-2-fluoro-N-[[(3S)-3-piperidyl]methyl]benzamide;

Cpd 205, 4-[6-[6-cyano-5-(trifluoromethyl)-3-pyridyl]-5-oxo-7-thioxo-6,8-diazaspiro[3.4]octan-8-yl]-2-fluoro-N-[[(3S)-1-methylpyrrolidin-3-yl]methyl]benzamide;

Cpd 206, 4-[6-[6-cyano-5-(trifluoromethyl)-3-pyridyl]-5-oxo-7-thioxo-6,8-diazaspiro[3.4]octan-8-yl]-N-[[(3R)-1-methylpyrrolidin-3-yl]methyl]benzamide;

Cpd 207, 3-chloro-5-[5-oxo-8-[4-(piperazin-1-ylmethyl)phenyl]-7-thioxo-6,8-diazaspiro[3.4]octan-6-yl]pyridine-2-carbonitrile;

Cpd 208, 5-[8-[4-[[3-(dimethylamino)oxetan-3-yl]methoxy]phenyl]-5-oxo-7-thioxo-6,8-diazaspiro[3.4]octan-6-yl]-3-(trifluoromethyl)pyridine-2-carbonitrile;

Cpd 209, 4-[6-[6-cyano-5-(trifluoromethyl)-3-pyridyl]-5-oxo-7-thioxo-6,8-diazaspiro[3.4]octan-8-yl]-N-methyl-N-[(1-methyl-4-piperidyl)methyl]benzamide;

Cpd 210, 5-[8-[6-[(1,4-dimethyl-4-piperidyl)oxy]-3-pyridyl]-5-oxo-7-thioxo-6,8-diazaspiro[3.4]octan-6-yl]-3-(trifluoromethyl)pyridine-2-carbonitrile;

Cpd 211, 3-methoxy-5-[5-oxo-8-[1-(4-piperidyl)indazol-5-yl]-7-thioxo-6,8-diazaspiro[3.4]octan-6-yl]pyridine-2-carbonitrile;

Cpd 212, 5-[8-[1-(1-acetyl-4-piperidyl)indazol-5-yl]-5-oxo-7-thioxo-6,8-diazaspiro[3.4]octan-6-yl]-3-methoxy-pyridine-2-carbonitrile;

Cpd 213, 3-methoxy-5-[8-[1-(1-methyl-4-piperidyl)indazol-5-yl]-5-oxo-7-thioxo-6,8-diazaspiro[3.4]octan-6-yl]pyridine-2-carbonitrile;

Cpd 214, 3-methoxy-5-[5-oxo-8-[2-(4-piperidyl)indazol-5-yl]-7-thioxo-6,8-diazaspiro[3.4]octan-6-yl]pyridine-2-carbonitrile;

Cpd 215, 3-methoxy-5-[8-[2-(1-methyl-4-piperidyl)indazol-5-yl]-5-oxo-7-thioxo-6,8-diazaspiro[3.4]octan-6-yl]pyridine-2-carbonitrile;

Cpd 216, 4-[6-[6-cyano-5-(trifluoromethyl)-3-pyridyl]-5-oxo-7-thioxo-6,8-diazaspiro[3.4]octan-8-yl]-N-[(1-methylazetidin-3-yl)methyl]benzamide;

Cpd 217, 5-[8-[4-(morpholinomethyl)phenyl]-5-oxo-7-thioxo-6,8-diazaspiro[3.4]octan-6-yl]-3-(trifluoromethyl)pyridine-2-carbonitrile;

Cpd 218, 4-[6-[6-cyano-5-(trifluoromethyl)-3-pyridyl]-5-oxo-7-thioxo-6,8-diazaspiro[3.4]octan-8-yl]-2-fluoro-N-[[(3R)-1-methylpyrrolidin-3-yl]methyl]benzamide Cpd 219, 3-chloro-5-[8-[4-[(4-methylpiperazin-1-yl)methyl]phenyl]-5-oxo-7-thioxo-6,8-diazaspiro[3.4]octan-6-yl]pyridine-2-carbonitrile;

Cpd 220, 5-[8-[4-[(4-cyclopropylpiperazin-1-yl)methyl]phenyl]-5-oxo-7-thioxo-6,8-diazaspiro[3.4]octan-6-yl]-3-(trifluoromethyl)pyridine-2-carbonitrile;

Cpd 221, 4-[6-[6-cyano-5-(trifluoromethyl)-3-pyridyl]-5-oxo-7-thioxo-6,8-diazaspiro[3.4]octan-8-yl]-2-fluoro-N-(4-piperidylmethyl)benzamide Cpd 222, 5-[8-(2SR, 4SR) [4-[[2-(hydroxymethyl)-4-piperidyl]oxy]phenyl]-5-oxo-7-thioxo-6,8-diazaspiro[3.4]octan-6-yl]-3-(trifluoromethyl)pyridine-2-carbonitrile;

Cpd 223, 5-[8-(2SR, 4RS)[4-[[2-(hydroxymethyl)-4-piperidyl]oxy]phenyl]-5-oxo-7-thioxo-6,8-diazaspiro[3.4]octan-6-yl]-3-(trifluoromethyl)pyridine-2-carbonitrile;

Cpd 224, 5-[8-[4-[(4-amino-1-piperidyl)methyl]phenyl]-5-oxo-7-thioxo-6,8-diazaspiro[3.4]octan-6-yl]-3-(trifluoromethyl)pyridine-2-carbonitrile;

Cpd 225, 5-[8-[1-[1-(2-hydroxyethyl)-4-piperidyl]indazol-5-yl]-5-oxo-7-thioxo-6,8-diazaspiro[3.4]octan-6-yl]-3-methoxy-pyridine-2-carbonitrile;

Cpd 226, 5-[8-(2SR, 4RS) [4-[[2-(hydroxymethyl)-1-methyl-4-piperidyl]oxy]phenyl]-5-oxo-7-thioxo-6,8-diazaspiro[3.4]octan-6-yl]-3-(trifluoromethyl)pyridine-2-carbonitrile;

Cpd 227, 5-[8-[4-[[4-(2-hydroxyethyl)piperazin-1-yl]methyl]phenyl]-5-oxo-7-thioxo-6,8-diazaspiro[3.4]octan-6-yl]-3-(trifluoromethyl)pyridine-2-carbonitrile;

Cpd 228, 5-[5-oxo-8-[4-[(3-oxopiperazin-1-yl)methyl]phenyl]-7-thioxo-6,8-diazaspiro[3.4]octan-6-yl]-3-(trifluoromethyl)pyridine-2-carbonitrile;

Cpd 229, 3-methoxy-5-[5-oxo-8-[4-(piperazin-1-ylmethyl)phenyl]-7-thioxo-6,8-diazaspiro[3.4]octan-6-yl]pyridine-2-carbonitrile;

Cpd 230, 5-[6-[4-(5,8-diazaspiro[2.5]octan-5-ylmethyl)phenyl]-5-oxo-7-thioxo-6,8-diazaspiro[3.4]octan-8-yl]-3-(trifluoromethyl)pyridine-2-carbonitrile;

Cpd 231, 5-[6-[4-[[(3R)-3-(hydroxymethyl)piperazin-1-yl]methyl]phenyl]-5-oxo-7-thioxo-6,8-diazaspiro[3.4]octan-8-yl]-3-(trifluoromethyl)pyridine-2-carbonitrile;

Cpd 232, 5-[6-[4-[[(3S)-3-(hydroxymethyl)piperazin-1-yl]methyl]phenyl]-5-oxo-7-thioxo-6,8-diazaspiro[3.4]octan-8-yl]-3-(trifluoromethyl)pyridine-2-carbonitrile;

Cpd 233, 5-[8-[4-[(4-aminocyclohexyl)methyl]phenyl]-5-oxo-7-thioxo-6,8-diazaspiro[3.4]octan-6-yl]-3-(trifluoromethyl)pyridine-2-carbonitrile;

Cpd 234, 5-[5-oxo-8-[4-(4-piperidylmethyl)phenyl]-7-thioxo-6,8-diazaspiro[3.4]octan-6-yl]-3-(trifluoromethyl)pyridine-2-carbonitrile;

Cpd 235, 3-methyl-5-[5-oxo-8-[4-(4-piperidylmethyl)phenyl]-7-thioxo-6,8-diazaspiro[3.4]octan-6-yl]pyridine-2-carbonitrile;

Cpd 236, 3-methoxy-5-[5-oxo-8-[4-(4-piperidylmethyl)phenyl]-7-thioxo-6,8-diazaspiro[3.4]octan-6-yl]pyridine-2-carbonitrile;

Cpd 237, 5-[8-[4-[(1-methyl-4-piperidyl)methyl]phenyl]-5-oxo-7-thioxo-6,8-diazaspiro[3.4]octan-6-yl]-3-(trifluoromethyl)pyridine-2-carbonitrile;

Cpd 238, 3-methyl-5-[8-[4-[(1-methyl-4-piperidyl)methyl]phenyl]-5-oxo-7-thioxo-6,8-diazaspiro[3.4]octan-6-yl]pyridine-2-carbonitrile;
Cpd 239, 3-methoxy-5-[8-[4-[(1-methyl-4-piperidyl)methyl]phenyl]-5-oxo-7-thioxo-6,8-diazaspiro[3.4]octan-6-yl]pyridine-2-carbonitrile;
Cpd 240, 5-[5-oxo-8-[4-(4-piperidylsulfanyl)phenyl]-7-thioxo-6,8-diazaspiro[3.4]octan-6-yl]-3-(trifluoromethyl)pyridine-2-carbonitrile;
Cpd 241, 5-[8-[4-(4-methylmorpholin-2-yl)phenyl]-5-oxo-7-thioxo-6,8-diazaspiro[3.4]octan-6-yl]-3-(trifluoromethyl)pyridine-2-carbonitrile;
Cpd 242, 5-[8-[4-[(1-methyl-4-piperidyl)sulfanyl]phenyl]-5-oxo-7-thioxo-6,8-diazaspiro[3.4]octan-6-yl]-3-(trifluoromethyl)pyridine-2-carbonitrile;
Cpd 243, 5-[8-(4-morpholin-2-ylphenyl)-5-oxo-7-thioxo-6,8-diazaspiro[3.4]octan-6-yl]-3-(trifluoromethyl)pyridine-2-carbonitrile;
Cpd 244, 5-[8-(1-methylbenzimidazol-5-yl)-5-oxo-7-thioxo-6,8-diazaspiro[3.4]octan-6-yl]-3-(trifluoromethyl)pyridine-2-carbonitrile;
Cpd 245, 5-[8-(2-methyl-1H-benzimidazol-5-yl)-5-oxo-7-thioxo-6,8-diazaspiro[3.4]octan-6-yl]-3-(trifluoromethyl)pyridine-2-carbonitrile;
Cpd 246, 3-methyl-5-[5-oxo-8-[2-(4-piperidyloxy)pyrimidin-5-yl]-7-thioxo-6,8-diazaspiro[3.4]octan-6-yl]pyridine-2-carbonitrile;
Cpd 247, 3-methyl-5-[8-[2-[(1-methyl-4-piperidyl)oxy]pyrimidin-5-yl]-5-oxo-7-thioxo-6,8-diazaspiro[3.4]octan-6-yl]pyridine-2-carbonitrile;
Cpd 248, 5-[8-[1-(2-hydroxyethyl)indol-5-yl]-5-oxo-7-thioxo-6,8-diazaspiro[3.4]octan-6-yl]-3-(trifluoromethyl)pyridine-2-carbonitrile;
Cpd 249, 5-[5-oxo-8-[1-(4-piperidyl)indol-5-yl]-7-thioxo-6,8-diazaspiro[3.4]octan-6-yl]-3-(trifluoromethyl)pyridine-2-carbonitrile;
Cpd 250, 5-[8-[1-(2-hydroxyethyl)indol-6-yl]-5-oxo-7-thioxo-6,8-diazaspiro[3.4]octan-6-yl]-3-(trifluoromethyl)pyridine-2-carbonitrile;
Cpd 251, 5-[8-[1-(1-methyl-4-piperidyl)indol-5-yl]-5-oxo-7-thioxo-6,8-diazaspiro[3.4]octan-6-yl]-3-(trifluoromethyl)pyridine-2-carbonitrile;
Cpd 252, 5-[8-[2-[[1-(2-hydroxyethyl)-4-piperidyl]oxy]pyrimidin-5-yl]-5-oxo-7-thioxo-6,8-diazaspiro[3.4]octan-6-yl]-3-(trifluoromethyl)pyridine-2-carbonitrile;
Cpd 253, 5-[8-[2-(2-hydroxyethyl)-1H-benzimidazol-5-yl]-5-oxo-7-thioxo-6,8-diazaspiro[3.4]octan-6-yl]-3-(trifluoromethyl)pyridine-2-carbonitrile;
Cpd 254, 5-[8-[2-[[1-(2-hydroxyethyl)-4-piperidyl]oxy]pyrimidin-5-yl]-5-oxo-7-thioxo-6,8-diazaspiro[3.4]octan-6-yl]-3-methyl-pyridine-2-carbonitrile;
Cpd 255, 5-[8-[2-(2-hydroxyethyl)-1-methyl-benzimidazol-5-yl]-5-oxo-7-thioxo-6,8-diazaspiro[3.4]octan-6-yl]-3-(trifluoromethyl)pyridine-2-carbonitrile; and
Cpd 256, 5-[8-[2-(1-methyl-4-piperidyl)-1H-benzimidazol-5-yl]-5-oxo-7-thioxo-6,8-diazaspiro[3.4]octan-6-yl]-3-(trifluoromethyl)pyridine-2-carbonitrile;
or a pharmaceutically acceptable salt form thereof.

A further embodiment of the present invention is directed to an isotopic derivative of a compound of Formula (I). More particularly, the present invention is directed to a deuterated analog of a compound of Formula (I).

An embodiment of the present invention is directed to 5-[5,7-dioxo-8-[6-(4-piperidyloxy)-3-pyridyl]-6,8-diazaspiro[3.4]octan-6-yl]-3-(trifluoromethyl)pyridine-2-carbonitrile (compound H-1)

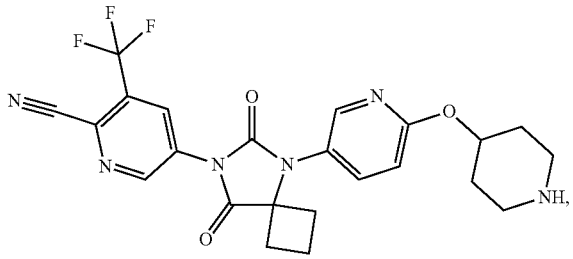

and pharmaceutically acceptable salt forms thereof.

An embodiment of the present invention is directed to 5-[8-[4-[(1-methyl-4-piperidyl)oxy]phenyl]-5,7-dioxo-6,8-diazaspiro[3.4]octan-6-yl]-3-(trifluoromethyl)pyridine-2-carbonitrile (compound H-2)

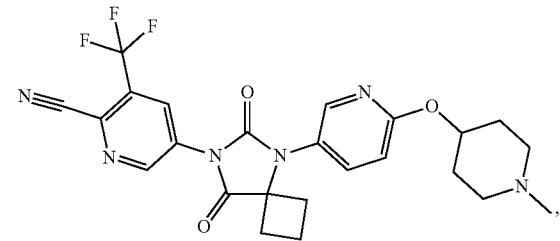

and pharmaceutically acceptable salt forms thereof.

For use in medicine, salts of compounds of Formula (I) refer to non-toxic "pharmaceutically acceptable salts." Other salts may, however, be useful in the preparation of compounds of Formula (I) or of their pharmaceutically acceptable salt forms thereof. Suitable pharmaceutically acceptable salts of compounds of Formula (I) include acid addition salts that can, for example, be formed by mixing a solution of the compound with a solution of a pharmaceutically acceptable acid such as, hydrochloric acid, sulfuric acid, fumaric acid, maleic acid, succinic acid, acetic acid, benzoic acid, citric acid, tartaric acid, carbonic acid or phosphoric acid. Furthermore, where the compounds of Formula (I) carry an acidic moiety, suitable pharmaceutically acceptable salts thereof may include alkali metal salts such as, sodium or potassium salts; alkaline earth metal salts such as, calcium or magnesium salts; and salts formed with suitable organic ligands such as, quaternary ammonium salts. Thus, representative pharmaceutically acceptable salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide, and valerate.

Representative acids and bases that may be used in the preparation of pharmaceutically acceptable salts include acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, a-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine, and zinc hydroxide.

Embodiments of the present invention include prodrugs of compounds of Formula (I). In general, such prodrugs will be functional derivatives of the compounds that are readily convertible in vivo into the required compound. Thus, in the methods of treating or preventing embodiments of the present invention, the term "administering" encompasses the treatment or prevention of the various diseases, conditions, syndromes and disorders described with the compound specifically disclosed or with a compound that may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

Where the compounds according to embodiments of this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include solvated compounds of Formula (I).

Where the processes for the preparation of the compounds according to certain embodiments of the invention give rise to mixture of stereoisomers, these isomers may be separated by conventional techniques such as, preparative chromatography. The compounds may be prepared in racemic form, or individual enantiomers may be prepared either by enantiospecific synthesis or by resolution. The compounds may, for example, be resolved into their component enantiomers by standard techniques such as, the formation of diastereomeric pairs by salt formation with an optically active acid such as, (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

One embodiment of the present invention is directed to a composition, including a pharmaceutical composition, comprising, consisting of, and/or consisting essentially of the (+)-enantiomer of a compound of Formula (I) wherein said composition is substantially free from the (−)-isomer of said compound. In the present context, substantially free means less than about 25%, preferably less than about 10%, more preferably less than about 5%, even more preferably less than about 2% and even more preferably less than about 1% of the (−)-isomer calculated as $$\%(+)\text{-enantiomer} = \frac{(\text{mass}(+)\text{-enantiomer})}{(\text{mass}(+)\text{-enantiomer}) + (\text{mass}(-)\text{-enantiomer})} \times 100.$$

Another embodiment of the present invention is a composition, including a pharmaceutical composition, comprising, consisting of, and consisting essentially of the (−)-enantiomer of a compound of Formula (I) wherein said composition is substantially free from the (+)-isomer of said compound. In the present context, substantially free from means less than about 25%, preferably less than about 10%, more preferably less than about 5%, even more preferably less than about 2% and even more preferably less than about 1% of the (+)-isomer calculated as $$\%(-)\text{-enantiomer} = \frac{(\text{mass}(-)\text{-enantiomer})}{(\text{mass}(+)\text{-enantiomer}) + (\text{mass}(-)\text{-enantiomer})} \times 100.$$

During any of the processes for preparation of the compounds of the various embodiments of the present invention, it may be necessary and/or desirable to protect sensitive or reactive groups on any of the molecules concerned. This may be achieved by means of conventional protecting groups such as those described in *Protective Groups in Organic Chemistry*, Second Edition, J.F.W. McOmie, Plenum Press, 1973; T. W. Greene & P. G. M. Wuts, *Protective Groups in Organic Synthesis*, John Wiley & Sons, 1991; and T. W. Greene & P. G. M. Wuts, *Protective Groups in Organic Synthesis*, Third Edition, John Wiley & Sons, 1999. The protecting groups may be removed at a convenient subsequent stage using methods known from the art.

Even though the compounds of embodiments of the present invention (including their pharmaceutically acceptable salts and pharmaceutically acceptable solvates) can be administered alone, they will generally be administered in admixture with a pharmaceutically acceptable carrier, a pharmaceutically acceptable excipient and/or a pharmaceutically acceptable diluent selected with regard to the intended route of administration and standard pharmaceutical or veterinary practice. Thus, particular embodiments of the present invention are directed to pharmaceutical and veterinary compositions comprising compounds of Formula (I) and at least one pharmaceutically acceptable carrier, pharmaceutically acceptable excipient, and/or pharmaceutically acceptable diluent.

By way of example, in the pharmaceutical compositions of embodiments of the present invention, the compounds of Formula (I) may be admixed with any suitable binder(s), lubricant(s), suspending agent(s), coating agent(s), solubilizing agent(s), and combinations thereof.

Solid oral dosage forms such as, tablets or capsules, containing the compounds of the present invention may be administered in at least one dosage form at a time, as appropriate. It is also possible to administer the compounds in sustained release formulations.

Additional oral forms in which the present inventive compounds may be administered include elixirs, solutions, syrups, and suspensions; each optionally containing flavoring agents and coloring agents.

Alternatively, compounds of Formula (I) can be administered by inhalation (intratracheal or intranasal) or in the form of a suppository or pessary, or they may be applied topically in the form of a lotion, solution, cream, ointment or dusting powder. For example, they can be incorporated into a cream comprising, consisting of, and/or consisting essentially of an aqueous emulsion of polyethylene glycols or liquid paraffin. They can also be incorporated, at a concentration of between about 1% and about 10% by weight of the cream, into an ointment comprising, consisting of, and/or consisting essentially of a wax or soft paraffin base together with any stabilizers and preservatives as may be required. An alternative means of administration includes transdermal administration by using a skin or transdermal patch.

The pharmaceutical compositions of the present invention (as well as the compounds of the present invention alone) can also be injected parenterally, for example, intracavernosally, intravenously, intramuscularly, subcutaneously, intradermally, or intrathecally. In this case, the compositions will also include at least one of a suitable carrier, a suitable excipient, and a suitable diluent.

For parenteral administration, the pharmaceutical compositions of the present invention are best used in the form of a sterile aqueous solution that may contain other substances, for example, enough salts and monosaccharides to make the solution isotonic with blood.

For buccal or sublingual administration, the pharmaceutical compositions of the present invention may be administered in the form of tablets or lozenges, which can be formulated in a conventional manner.

By way of further example, pharmaceutical compositions containing at least one of the compounds of Formula (I) as the active ingredient can be prepared by mixing the compound(s) with a pharmaceutically acceptable carrier, a pharmaceutically acceptable diluent, and/or a pharmaceutically acceptable excipient according to conventional pharmaceutical compounding techniques. The carrier, excipient, and diluent may take a wide variety of forms depending upon the desired route of administration (e.g., oral, parenteral, etc.). Thus, for liquid oral preparations such as, suspensions, syrups, elixirs and solutions, suitable carriers, excipients and diluents include water, glycols, oils, alcohols, flavoring agents, preservatives, stabilizers, coloring agents and the like; for solid oral preparations such as, powders, capsules, and tablets, suitable carriers, excipients and diluents include starches, sugars, diluents, granulating agents, lubricants, binders, disintegrating agents and the like. Solid oral preparations also may be optionally coated with substances such as, sugars, or be enterically coated so as to modulate the major site of absorption and disintegration. For parenteral administration, the carrier, excipient and diluent will usually include sterile water, and other ingredients may be added to increase solubility and preservation of the composition. Injectable suspensions or solutions may also be prepared utilizing aqueous carriers along with appropriate additives such as, solubilizers and preservatives.

A therapeutically effective amount of a compound of Formula (I) or a pharmaceutical composition thereof includes a dose range from about 0.1 mg to about 3000 mg, or any particular amount or range therein, in particular from about 1 mg to about 1000 mg, or any particular amount or range therein, or, more particularly, from about 10 mg to about 500 mg, or any particular amount or range therein, of active ingredient in a regimen of about 1 to about 4 times per day for an average (70 kg) human; although, it is apparent to one skilled in the art that the therapeutically effective amount for a compound of Formula (I) will vary as will the diseases, syndromes, conditions, and disorders being treated.

For oral administration, a pharmaceutical composition is preferably provided in the form of tablets containing about 1.0, about 10, about 50, about 100, about 150, about 200, about 250, and about 500 milligrams of a compound of Formula (I).

An embodiment of the present invention is directed to a pharmaceutical composition for oral administration, comprising a compound of Formula (I) in an amount of from about 25 mg to about 500 mg.

In another embodiment, the pharmaceutical composition for oral administration comprises a compound of Formula (I) in an amount of from about 40 mg to about 95 mg.

Advantageously, a compound of Formula (I) may be administered in a single daily dose, or the total daily dosage may be administered in divided doses of two, three and four times daily.

Optimal dosages of a compound of Formula (I) to be administered may be readily determined and will vary with the particular compound used, the mode of administration, the strength of the preparation and the advancement of the disease, syndrome, condition or disorder. In addition, factors associated with the particular subject being treated, including subject gender, age, weight, diet and time of administration, will result in the need to adjust the dose to achieve an appropriate therapeutic level and desired therapeutic effect. The above dosages are thus exemplary of the average case. There can be, of course, individual instances wherein higher or lower dosage ranges are merited, and such are within the scope of this invention.

Compounds of Formula (I) may be administered in any of the foregoing compositions and dosage regimens or by means of those compositions and dosage regimens established in the art whenever use of a compound of Formula (I) is required for a subject in need thereof.

An embodiment of the present invention is directed to a pharmaceutical composition comprising, consisting of, and/or consisting essentially of, a compound selected from the group consisting of Cpd 1, 5-[8-[6-[(1-methyl-4-piperidyl)oxy]-3-pyridyl]-5-oxo-7-thioxo-6,8-diazaspiro[3.4]octan-6-yl]-3-(trifluoromethyl)pyridine-2-carbonitrile;

Cpd 2, 3-methyl-5-[8-[6-[(1-methyl-4-piperidyl)oxy]-3-pyridyl]-5-oxo-7-thioxo-6,8-diazaspiro[3.4]octan-6-yl]pyridine-2-carbonitrile;

Cpd 23, 3-methoxy-5-[8-[4-[(1-methyl-4-piperidyl)oxy]phenyl]-5-oxo-7-thioxo-6,8-diazaspiro[3.4]octan-6-yl]pyridine-2-carbonitrile;

Cpd 24, 3-chloro-5-[8-[4-[(1-methyl-4-piperidyl)oxy]phenyl]-5-oxo-7-thioxo-6,8-diazaspiro[3.4]octan-6-yl]pyridine-2-carbonitrile;

Cpd 25, 3-methoxy-5-[8-[6-[(1-methyl-4-piperidyl)oxy]-3-pyridyl]-5-oxo-7-thioxo-6,8-diazaspiro[3.4]octan-6-yl]pyridine-2-carbonitrile;

Cpd 26, 3-chloro-5-[8-[6-[(1-methyl-4-piperidyl)oxy]-3-pyridyl]-5-oxo-7-thioxo-6,8-diazaspiro[3.4]octan-6-yl]pyridine-2-carbonitrile;

Cpd 43, 5-[5-oxo-8-[6-(4-piperidyloxy)-3-pyridyl]-7-thioxo-6,8-diazaspiro[3.4]octan-6-yl]-3-(trifluoromethyl)pyridine-2-carbonitrile;

Cpd 44, 3-chloro-5-[5-oxo-8-[4-(4-piperidyloxy)phenyl]-7-thioxo-6,8-diazaspiro[3.4]octan-6-yl]pyridine-2-carbonitrile;

Cpd 64, 3-chloro-5-[5-oxo-8-[6-(4-piperidyloxy)-3-pyridyl]-7-thioxo-6,8-diazaspiro[3.4]octan-6-yl]pyridine-2-carbonitrile;

Cpd 75, 3-methoxy-5-[5-oxo-8-[6-(4-piperidyloxy)-3-pyridyl]-7-thioxo-6,8-diazaspiro[3.4]octan-6-yl]pyridine-2-carbonitrile;

Cpd 87, 3-methyl-5-[5-oxo-8-[6-(4-piperidyloxy)-3-pyridyl]-7-thioxo-6,8-diazaspiro[3.4]octan-6-yl]pyridine-2-carbonitrile; and Cpd 154, 3-methoxy-5-[5-oxo-8-[4-(4-piperidyloxy)phenyl]-7-thioxo-6,8-diazaspiro[3.4]octan-6-yl]pyridine-2-carbonitrile;

and at least one of a pharmaceutically acceptable carrier, a pharmaceutically acceptable excipient, and a pharmaceutically acceptable diluent.

In another embodiment of the present invention, the compounds and compositions, according to the method of the present invention, may be administered using any amount and any route of administration effective for treating a cancer or another proliferative disease, disorder or condition. In some embodiments, the cancer or other proliferative disease, disorder or condition is a prostate cancer.

In some embodiments, the cancer or other proliferative disease, disorder or condition is a castration-resistant prostate cancer (CRPC). In some embodiments, the cancer or other proliferative disease, disorder or condition is a castration-resistant prostate cancer (CRPC) bearing a mutation in AR. In some embodiments, the mutation in AR is a mutation of Phenylalanine (Phe)876.

In some embodiments, the mutation in AR is a mutation of Phe876 to leucine. In some embodiments, the mutation in AR is a mutation of Phe876 to isoleucine. In some embodiments, the mutation in AR is a mutation of Phe876 to valine. In some embodiments, the mutation in AR is a mutation of Phe876 to serine. In some embodiments, the mutation in AR is a mutation of Phe876 to cysteine. In some embodiments, the mutation in AR is a mutation of Phe876 to tyrosine.

In some embodiments, the cancer or other proliferative disease, disorder or condition is a prostate cancer that is resistant to any AR therapy as a consequence of mutation.

In some embodiments, the cancer or other proliferative disease, disorder or condition is a prostate cancer that is resistant to treatment using second-generation AR antagonists, including, but not limited to, Enzalutamide or ARN-509.

The present invention encompasses the recognition that mutations in the AR polypeptide can render the AR polypeptide resistant to anti-androgens or convert anti-androgens to androgen agonists. In some embodiments, the present invention provides compounds that can be used to effect anti-androgenic effects despite the presence of such mutations.

The amino acid sequence of an AR polypeptide described herein can exist in a mutant AR containing, or can be modified to produce an mutant AR polypeptide variant at least one (e.g., 1, 2, 3, 4, 5, 6, 7, 8, 9, 10, or more) additions, substitutions, or deletions of a wild-type amino acid residue.

In some embodiments, the AR polypeptide variants described herein result in a loss of inhibition of AR activity by one or more antiandrogens of 0, 1, 2, 3, 4, 5, 6, 7, 8, 9, 10 up to 100%. In some embodiments, the AR polypeptide variants described herein convert antiandrogens to androgen receptor agonists.

Specific, nonlimiting amino acid residues that can be modified in an AR mutant include, e.g., E566, E589, E669, C687, A700, N772, H777, C785, F877, K911, of the AR polypeptide. These amino acid residues can be substituted with any amino acid or amino acid analog. For example, the substitutions at the recited positions can be made with any of the naturally-occurring amino acids (e.g., alanine, aspartic acid, asparagine, arginine, cysteine, glycine, glutamic acid, glutamine, histidine, leucine, valine, isoleucine, lysine, methionine, proline, threonine, serine, phenylalanine, tryptophan, or tyrosine). In particular instances, an amino acid substitution is E566K, E589K, E669K, C687Y, A700T, N772S, H777Y, C785R, F877C, F877I, F877L, F877S, F877V, F877Y and/or K911E.

In some embodiments, the AR mutants as described herein can include additional modifications of the AR polypeptide previously described in the art, including but not limited to, e.g., A597T, S648G, P683T, D696E, R727H, N728I, I738F, W741L, W741C, W741L, M743V, G751S, A871V, H874Y, T878A, T878S, and P914S.

In some embodiments, the compounds and compositions, according to the method of the present invention, may be administered using any amount and any route of administration effective for treating a bone disease, disorder or condition. In some embodiments, the bone disease, disorder or condition is osteoporosis.

In some embodiments, the present invention is directed to a compound of Formula (I) for use in the treatment of a disease, a syndrome, a condition or a disorder in a subject, including an animal, a mammal and a human in which the disease, the syndrome, the condition or the disorder is affected by the antagonism of the androgen receptor, selected from the group consisting of prostate cancer, castration-resistant prostate cancer, and metastatic castration-resistant prostate cancer.

In certain embodiments, a compound of Formula (I), or a composition thereof, may be administered in combination with another modulator, agonist or antagonist of AR. In some embodiments, the compound of Formula (I), or composition thereof, may be administered in combination with one or more other therapeutic agents.

In some embodiments the AR modulators, agonists or antagonists include, but are not limited to gonadotropin-releasing hormone agonists or antagonists (e.g., Lupron, Zoladex (Goserelin), Degarelix, Ozarelix, ABT-620 (Elagolix), TAK-385 (Relugolix), EP-100 or KLH-2109); non-steroidal antiandrogens, aminoglutethimide, enzalutamide, bicalutamide, nilutamide, flutamide, steroidal antiandrogens, finasteride, dutasteride, bexlosteride, izonsteride, turosteride, episteride, other inhibitors of 5-alphareductase, 3,3'-diindolylmethane (DIM), N-butylbenzene-sulfonamide (NBBS); or a CYP17 inhibitor such as abiraterone acetate, TAK-700 (orteronel), TOK-001 (galeterone) or VT-464.

A further embodiment of the present invention is directed to a pharmaceutical composition comprising, consisting of, and/or consisting essentially of a compound of Formula (I) and a therapeutically effective amount of abiraterone acetate.

A further embodiment of the present invention is directed to a pharmaceutical composition comprising, consisting of, and/or consisting essentially of a compound of Formula (I) and abiraterone acetate and, optionally, prednisone or dexamethasone.

In certain embodiments, a compound of Formula (I), or a pharmaceutical composition thereof, may be administered in combination with a PI3K pathway inhibitor.

In some embodiments the PI3K pathway inhibitors (PI3K, TORC or dual PI3K/TORC inhibitor) include, but are not limited to, everolimus, BEZ-235, BKM120, BGT226, BYL-719, GDC0068, GDC-0980, GDC0941, GDC0032, MK-2206, OSI-027, CC-223, AZD8055, SAR245408, SAR245409, PF04691502, WYE125132, GSK2126458, GSK-2636771, BAY806946, PF-05212384, SF1126, PX866, AMG319, ZSTK474, CalIOl, PWT33597, LY-317615 (enzastaurin hydrochloride), CU-906, or CUDC-907.

In certain embodiments, a compound of Formula (I), or a composition thereof, may be administered in combination with radiation therapy. The term "radiotherapy" or "ionizing radiation" include all forms of radiation, including but not limited to a, (3, and y radiation and ultraviolet light.

In some embodiments radiation therapy includes, but is not limited to, radioactive implants directly inserted in a tumor or body cavity (brachytherapy, interstitial irradiation, and intracavitary irradiation are types of internal radiotherapy), radiopharmaceuticals (e.g. Alpharadin (Radium-223 Chloride), 177Lu-J591 PSMA conjugate), or external beam radiation therapy (including Proton beam).

In certain embodiments, a compound of Formula (I), or a pharmaceutical composition thereof, may be administered in combination with immunotherapy.

In some embodiments the immunotherapy includes, but is not limited to Provenge, Prostvac, Ipilimumab, a CTLA-4 inhibitor or a PD-1 inhibitor.

GENERAL SYNTHETIC METHODS

Representative compounds of the present invention can be synthesized in accordance with the general synthetic methods described below and illustrated in the schemes and examples that follow. Since the schemes are an illustration, the invention should not be construed as being limited by the chemical reactions and conditions described in the schemes and examples. Compounds analogous to the target compounds of these examples can be made according to similar routes. The disclosed compounds are useful as pharmaceutical agents as described herein. The various starting materials used in the schemes and examples are commercially available or may be prepared by methods well within the skill of persons versed in the art.

Abbreviations used in the instant specification, particularly the schemes and examples, are as follows:
ACN acetonitrile
AcOH acetic acid
AIBN 2,2'-azobisisobutyronitrile
Boc tert-butyl carbamate
BOP benzotriazol-1-yloxy)tris(dimethylamino)phosphonium hexfluorophosphate
BuLi butyllithium
Cbz benzyl carbamate
CSS Charcoal Stripped Serum
DIBAL-H diisobutylaluminum hydride
DBU 1.8-diazabicyclo[5.4.0]undec-7-ene
DCC N,N'-dicyclohexylcarbodiimide
DCE 1,2-dichloroethane
DCM dichloromethane
DEAD diethyl azodicarboxylate
DIAD diisopropyl azodicarboxylate
DIPEA diisopropylethylamine
DMA dimethylacetamide
DMAP 4-(dimethylamino)pyridine
DME ethylene glycol dimethyl ether
DMEM Dulbecco's Modified Eagle's Medium
DMF dimethylformamide
DMSO dimethyl sulfoxide
EA ethyl acetate
EDC N-(3-dimethylaminopropyl)-N'-ethylcarbodiimide
EDCI 1-(3-dimethylaminopropyl)-3-ethylcarbodiimide hydrochloride
EMEM Eagle's Minimum Essential Medium
Et ethyl
$Et_2O$ diethyl ether
EtOAc ethyl acetate
EtOH ethyl alcohol
FCS Fetal Calf Serum
h or hr hour(s)
HATU O-(7-azabenzotriazol-1-yl)-N,N,N',N'-tetramethyluronium hexafluorophosphate
HCHO formaldehyde
HCl hydrochloric acid
HCOOH formic acid
HMPA hexamethylphosphoramide
HOBt 1-hydroxybenzotriazole monohydrate
HPLC high performance liquid chromatography
KCN potassium cyanide
LCMS high pressure liquid chromatography with mass spectrometer
LDA lithium diisopropylamide
LiOH lithium hydroxide
LHMDS lithium hexamethyl disilazide
Me methyl
MeCN acetonitrile
MeOH methyl alcohol
mg milligram
min minute
MOM methoxymethyl
NaCN sodium cyanide
NaHMDS sodium hexamethyl disilazide
NaOH sodium hydroxide
NaO$^t$Bu sodium tert-butoxide
NBS N-bromosuccinimide
$NH_4Cl$ ammonium chloride
NMP N-methyl pyrrolidinone
N,N-DMA N, N-dimethylacetamide
PBS Phosphate Buffered Saline
Pd/C palladium on charcoal
$Pd_2(dba)_3$ tris(dibenzylideneacetone)dipalladium
$Pd(dppf)Cl_2$ [1,1'-bis(diphenylphosphino)ferrocene]dichloropalladium
$Pd(OAc)_2$ palladium diacetate
$Pd(PPh_3)_4$ tetrakis(triphenylphosphine)palladium
$PPh_3$ triphenyl phosphine
p-TsOH para-toluenesulfonic acid
RPMI Roswell Park Memorial Institute medium
rt or RT room temperature
SPE solid phase extraction
TBAF tetrabutyl ammonium fluoride
TBDMSCl tert-butyldimethylsilyl chloride
TBTU O-benzotriazol-1-yl-N,N,N',N'-tetramethyluronium hexafluorophosphate
t-Bu tert-butyl
TEMPO 2,2,6,6-tetramethyl-1-piperdinyloxy, free radical
TFA trifluoroacetic acid
THF tetrahydrofuran
TLC thin layer chromatography
TMS-CN trimethylsilyl cyanide
TMSOTf trimethylsilyl trifluoromethanesulfonate Compounds of Formula (I) may be prepared according to the process outlined in Scheme 1, below.

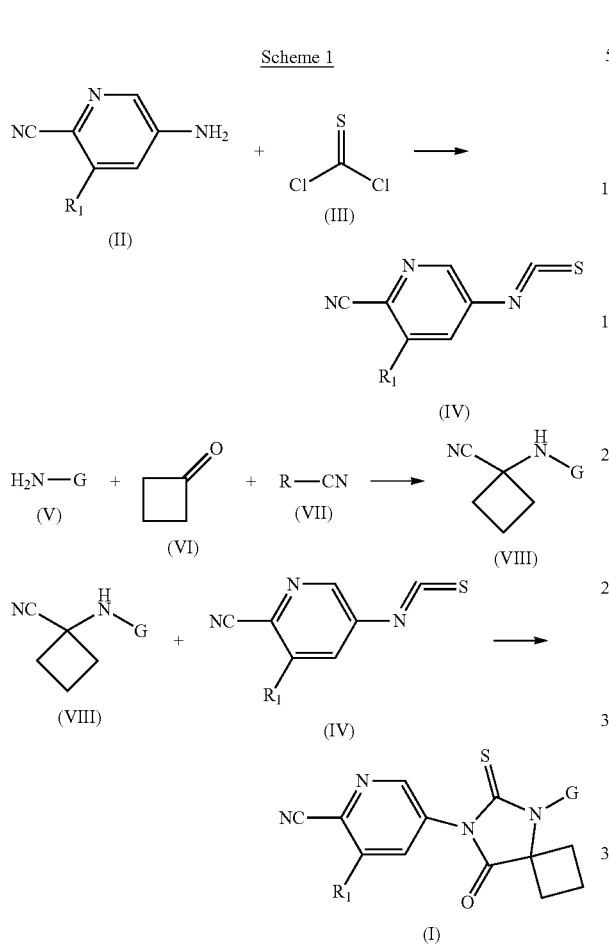

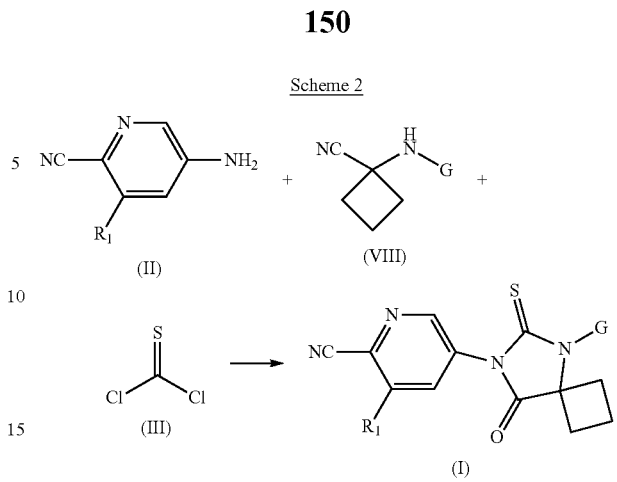

Accordingly, a suitably substituted compound of formula (II), a known compound or compound prepared by known methods, may be reacted with thiophosgene (III) and phenyl chlorothionocarbonate, in the presence of a suitably selected base such as DMAP, K$_2$CO$_3$, Cs$_2$CO$_3$, and the like, in a suitably selected solvent or mixture of solvents such as CHCl$_3$, CH$_2$Cl$_2$, 1,2-dichloroethane, water, THF, toluene, and the like, at a temperature ranging from about 0 to about 130° C., to yield the corresponding compound of formula (IV). A suitably substituted compound of formula (V), a known compound or compound prepared by known methods, may be reacted with cyclobutanone (VI) in the presence of a suitably selected source of cyanide (VII), such as KCN, NaCN, TMS-CN, and the like; in a suitably selected solvent or mixture of solvents such as acetic acid, EtOH, MeOH, and the like, at temperature ranging from about 10 to about 130° C., to yield the corresponding compound of formula (VIII).

The compound of formula (IV) may then be reacted with the compound of formula (VIII) in a suitably selected solvent or mixture of solvents such as DMA, DMF, NMP, DSMO, and the like, at temperature ranging from about 15 to about 180° C., to yield the corresponding compound of formula (I).

Compounds of formula (I) may alternatively be prepared according to the process as outlined in Scheme 2, below.

Alternatively, a suitably substituted compound of formula (II), may be reacted with a compound of formula (VIII), a known compound or compound prepared by known methods, and thiophosgene, in the presence of a Lewis acid such as TMSOTf, AlCl$_3$, ZnCl$_2$, and the like, in a suitably selected solvent or mixture of solvents such as DMA, DMF, NMP, DSMO, and the like, at a temperature ranging from about 0 to about 180° C., to yield the corresponding compound of formula (I).

Compounds of formula (I) may alternatively be prepared according to the process as outlined in Scheme 3, below.

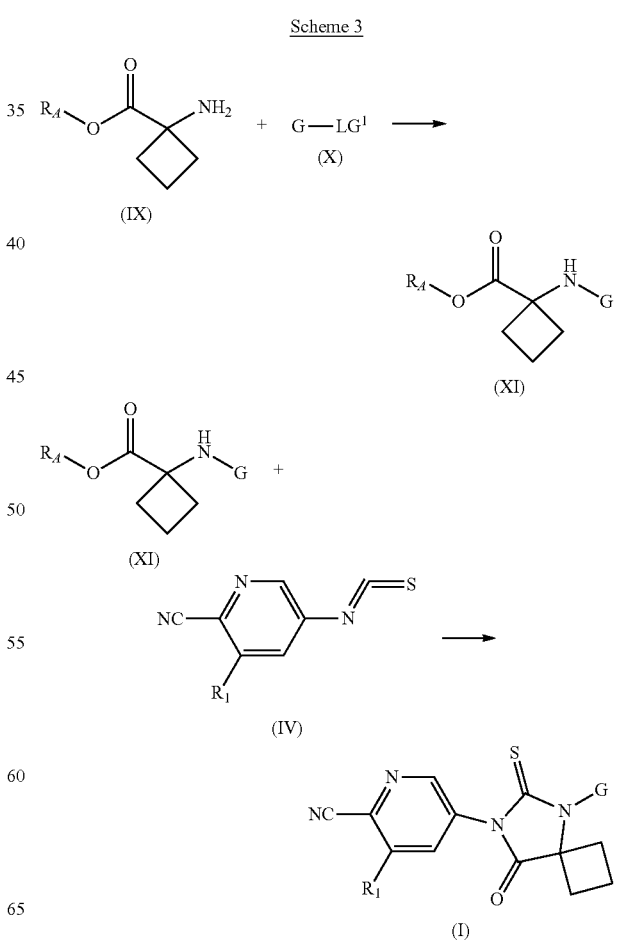

Alternatively, a suitably substituted compound of formula (IX), a known compound or compound prepared by known methods, wherein $R_A$ is H, alkyl, and the like, may be reacted with a compound of formula (X), wherein $LG^1$ is a leaving group such as I, Br, Cl, triflate, and the like, in the presence of a copper catalyst such as CuI, and the like, in the presence of a suitably selected base such as DBU, t-BuOK, and the like; in a suitably selected solvent such as DMA, DMF, NMP, DMSO, and the like; at a temperature ranging from about 15 to about 170° C., under Ullman coupling conditions, to yield the corresponding compound of formula (XI). The compound of formula (XI) is then reacted with the compound of formula (IV) in a suitably selected solvent or mixture of solvents such as THF, 1,4-dioxane, toluene, DMSO, and the like, at temperature ranging from about 15 to about 180° C., to yield the corresponding compound of formula (I).

Compounds of formula (I) may alternatively be prepared according to the process as outlined in Scheme 4, below.

Alternatively, a suitably substituted compound of formula (II) may be reacted with a compound of formula (IX), a known compound or compound prepared by known methods, wherein $R_A$ is H, alkyl, and the like, to yield the corresponding compound of formula (XII). The compound of formula (XII) may then be reacted with the compound of formula (X), wherein $LG^1$ is a leaving group such as I, Br, Cl, triflate, and the like, in the presence of a copper catalyst such as CuI, and the like, in the presence of a suitably selected base such as DBU, t-BuOK, and the like; in a suitably selected solvent such as DMA, DMF, NMP, DMSO, and the like; at temperature ranging from about 15 to about 170° C., under Ullman coupling conditions, to yield the corresponding compound of formula (XIII). The compound of formula (XIII) is then reacted with thiophosgene (III), phenyl chlorothionocarbonate in the presence of a suitably selected base such as DMAP, $K_2CO_3$, $Cs_2CO_3$, and the like, in a suitably selected solvent or mixture of solvents such as $CHCl_3$, $CH_2Cl_2$, 1,2-dichloroethane, water, THF, toluene, and the like, at temperature ranging from about 0 to about 130° C., to yield the corresponding compound of formula (I).

Scheme 5 illustrates the preparation of certain compounds of the present invention wherein G is

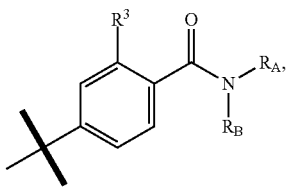

and $R^4$ is an amide.

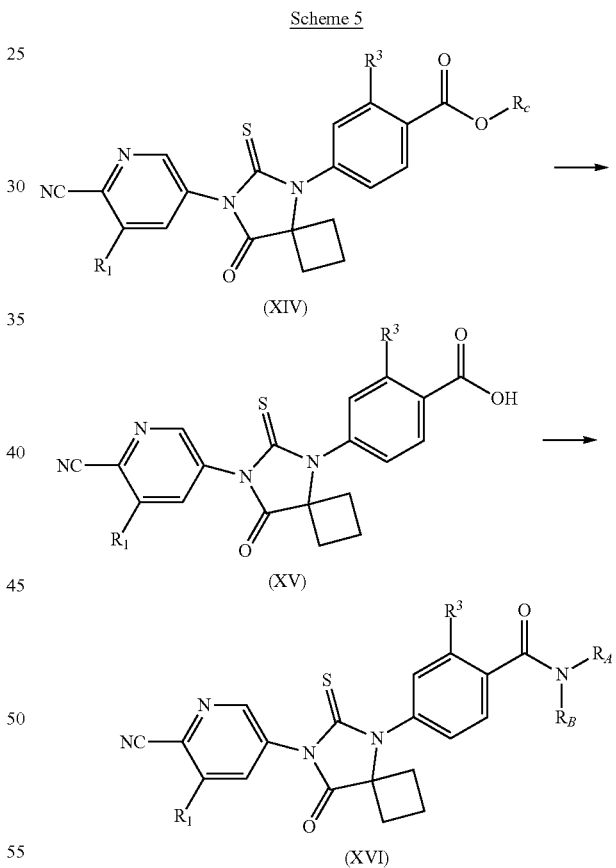

Treatment of a suitably substituted compound of formula (XIV), wherein $R^c$ is $C_{1-6}$alkyl or the like, a known compound or compound prepared by known methods, may be reacted with a suitable base such as NaOH, LiOH, and the like, in a suitably selected solvent or mixture of solvents such as THF, MeOH, water, EtOH, and the like, at a temperature ranging from about 0 to about 60° C., to provide a carboxylic acid of formula (XV). A carboxylic acid of formula (XV) may then be coupled with a variety of agents to provide compounds within the scope of the invention. For example, the carboxylic acid of formula (XV) may be reacted with an appropriately substituted amine of formula H—NR$_A$(R$_B$) in the presence of a coupling reagent such as EDCI, HOBt, DCC, BOP, HATU, and the like, and a base such as trimethylamine, DIPEA, N-methylmorpholine, pyridine, and the like, in a suitably selected solvent or mixture of solvents such as DCM, DCE, THF, DMF, NMP, and the like, at a temperature ranging from about 0 to about 150° C.

Scheme 6 illustrates the preparation of certain compounds of the present invention wherein G is

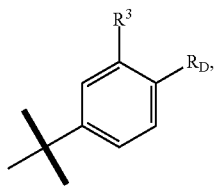

and R$_D$ includes but is not limited to, a heterocyclyl, optionally partially unsaturated pyranyl, or bridged heterocyclyl substituent of the present invention.

Scheme 6

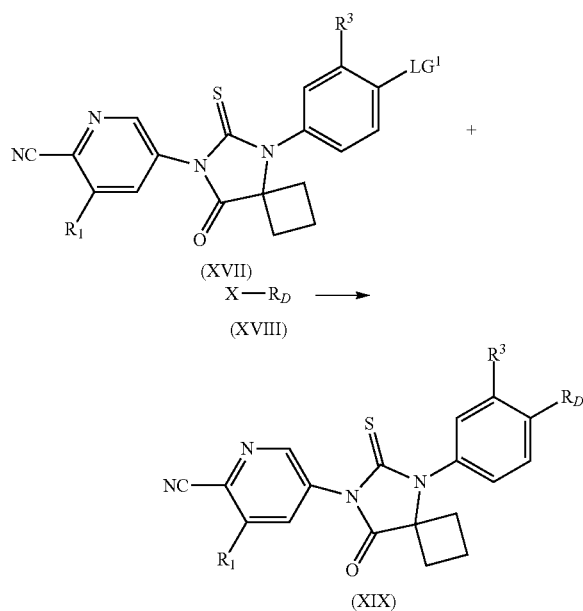

The compound of formula (XVII), wherein LG$^1$ is a suitably selected leaving group such as Cl, Br, OTf, F and the like, is a known compound or compound prepared by known methods. The compound of formula (XVII) may be reacted with a suitably substituted compound of formula (XVIII), wherein X is a suitably selected leaving group such as Cl, Br, OH, triflate, B(OH)$_2$, B(OC$_{1-2}$alkyl)$_2$,

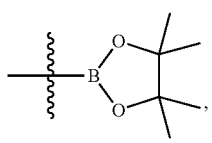 [SMILES: *B1OC(C)(C)C(C)(C)O1]

and the like, a known compound or compound prepared by known methods, under Suzuki coupling conditions. More particularly, such conditions may comprise reaction of a compound of formula (XVII) with a compound of formula (XVIII) in the presence of a suitably selected catalyst or catalyst system, such as Pd(PPh$_3$)$_4$, Pd$_2$(dba)$_3$, Pd(dppf), a mixture of Pd(OAc)$_2$ and PPh$_3$, and the like; in the presence of a suitably selected inorganic base such as K$_2$CO$_3$, Cs$_2$CO$_3$, Na$_2$CO$_3$, and the like; in a suitably selected solvent such as DME, 1,4-dioxane, and the like, preferably mixed with water; to yield the corresponding compound of formula (XIX).

One skilled in the art will recognize that the RD substituent group may alternatively be incorporated into the desired compound of formula (XIX) by reacting a compound of formula (XVIII), wherein the LG$^1$ group is replaced with a group of the formula —B(OR$_D$)$_2$ (wherein the two RD groups are the same in each instance and are selected from hydrogen and C$_{1-2}$alkyl; or the OR$_D$ groups are taken together with the atoms to which they are attached to form

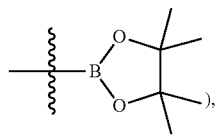 [SMILES: *B1OC(C)(C)C(C)(C)O1]

with a suitably substituted compound of formula (XVIII), wherein the -X substituent may be replaced with a suitably selected leaving group such as Cl, Br, triflate, F, and the like; under Suzuki coupling conditions, more particularly, in the presence of a suitably selected catalysts or catalyst system, such as Pd(PPh$_3$)$_4$, Pd$_2$(dba)$_3$, Pd(dppf), a mixture of Pd(OAc)$_2$ and PPh$_3$, and the like; in the presence of a suitably selected inorganic base such as K$_2$CO$_3$, Cs$_2$CO$_3$, Na$_2$CO$_3$, and the like; in a suitably selected solvent such as DME, 1,4-dioxane, and the like, preferably mixed with water.

Alternatively, certain compounds of the present invention wherein G is

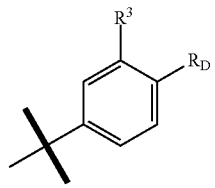

may be prepared according to the process outlined in Scheme 7.

Scheme 7

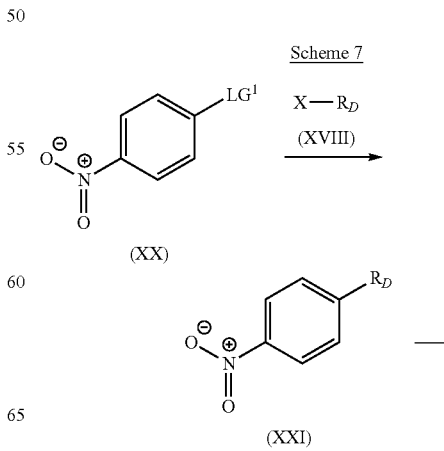

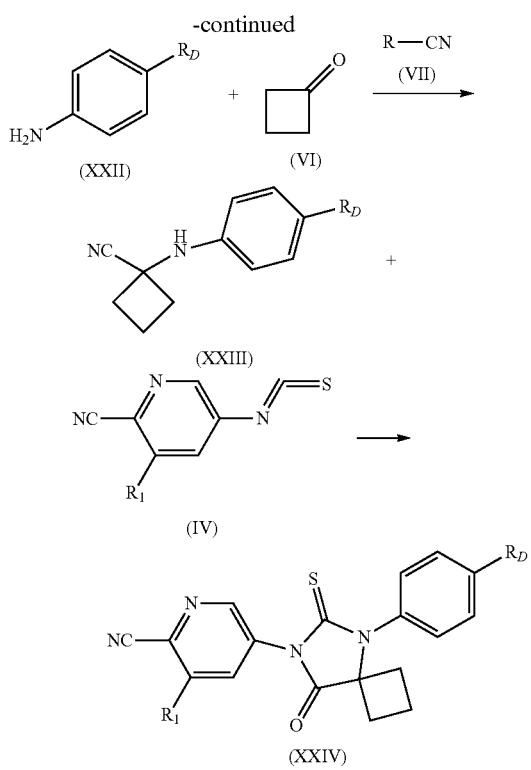

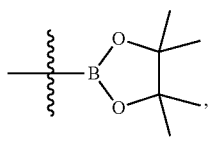 [SMILES: *B1OC(C)(C)C(C)(C)O1]

and the like under Suzuki coupling conditions, more particularly, in the presence of a suitably selected catalyst or catalyst system, such as Pd(PPh$_3$)$_4$, Pd$_2$(dba)$_3$, Pd(dppf), a mixture of Pd(OAc)$_2$ and PPh$_3$, and the like; in the presence of a suitably selected inorganic base such as K$_2$CO$_3$, Cs$_2$CO$_3$, Na$_2$CO$_3$, and the like; in a suitably selected solvent such as DME, 1,4-dioxane, and the like, preferably mixed with water; to yield the corresponding compound of formula (XXI).

The compound of formula (XXI) then may be reacted with a source of hydrogen, under hydrogenation conditions, in the presence of a suitably selected catalyst or catalyst system, such as Pd/C, Pt, and the like, in a suitably selected solvent such as MeOH, EtOAc, and the like, to yield the corresponding compound of formula (XXII). The compound of formula (XXII) then may be reacted with cyclobutanone (VI) in the presence of a suitably selected source of cyanide (VII), such as KCN, NaCN, TMS-CN, and the like; in a suitably selected solvent or mixture of solvents such as acetic acid, EtOH, MeO, and the like; at a temperature ranging from about 10 to about 130° C., to yield the corresponding compound of formula (XXIII).

The compound of formula (XXIII) may be reacted with the compound of formula (IV) in a suitably selected solvent or mixture of solvents such as DMA, DMF, NMP, DSMO, and the like, at a temperature ranging from about 15 to about 180° C., to yield the corresponding compound of formula (XXIV).

One skilled in the art will recognize that when the RD is heterocyclyl, compounds of formula (XVIII) may be prepared as exemplified in Chem. Eur. J. 2014, 20, 4414-4419 or Canadian Journal of Chemistry 1994, 72(5),1262-72.

Certain compounds of the present invention wherein G is

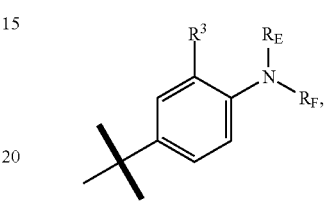

and R$_E$ and R$_F$ may be taken together with the atoms to which they are attached to form a heterocyclyl including, but not limited to, piperidinyl, piperazinyl, thiomorpholinyl, and morpholinyl, may be prepared according to the process outlined in Scheme 8.

Scheme 8

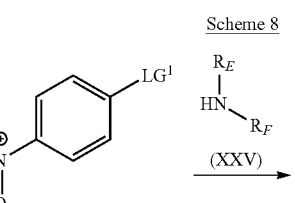

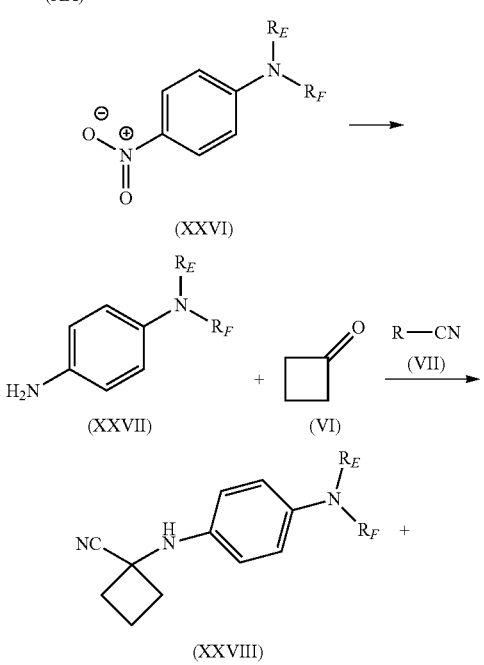

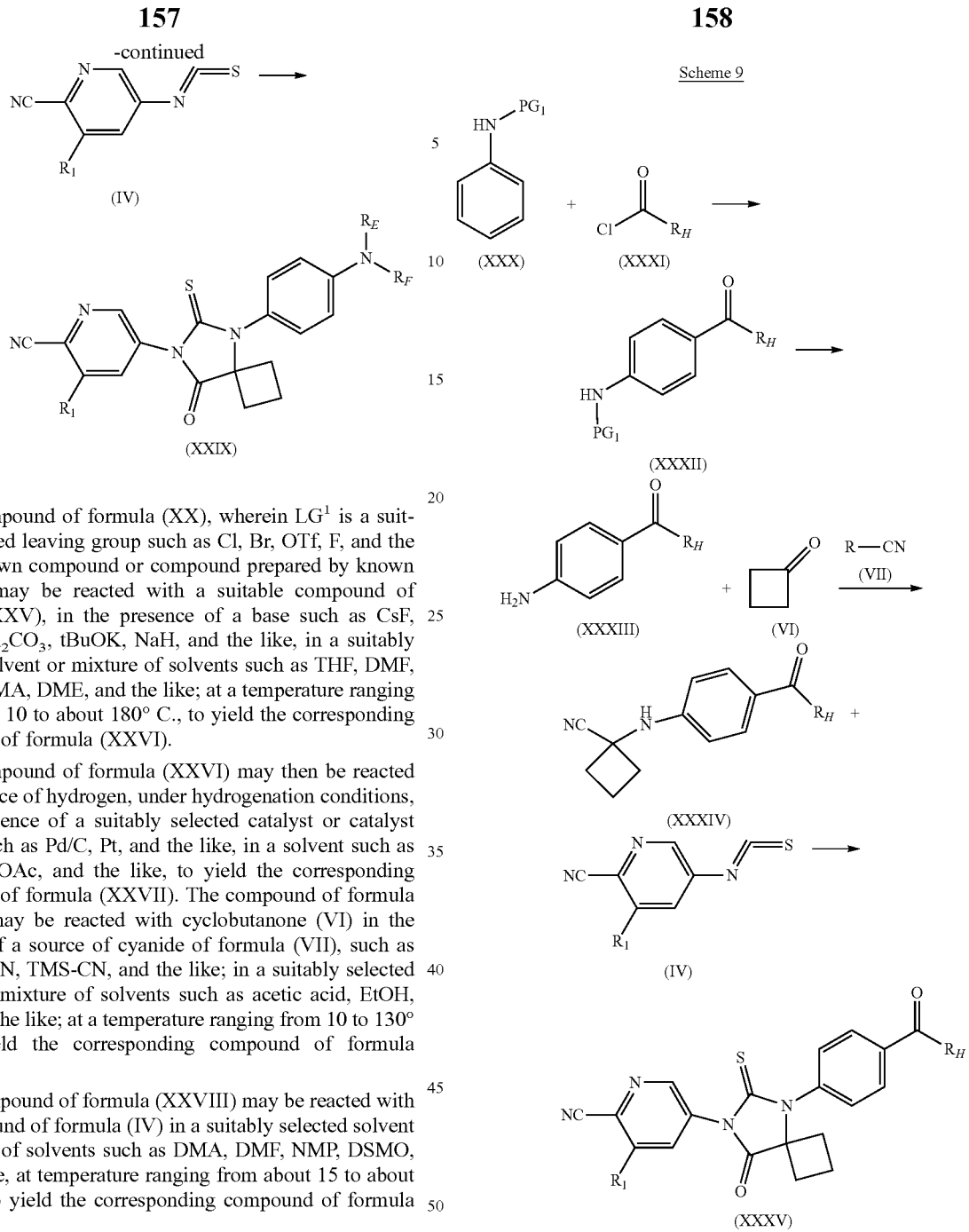

Scheme 9

The compound of formula (XX), wherein LG$^1$ is a suitably selected leaving group such as Cl, Br, OTf, F, and the like, a known compound or compound prepared by known methods, may be reacted with a suitable compound of formula (XXV), in the presence of a base such as CsF, Cs$_2$CO$_2$, K$_2$CO$_3$, tBuOK, NaH, and the like, in a suitably selected solvent or mixture of solvents such as THF, DMF, DMSO, DMA, DME, and the like; at a temperature ranging from about 10 to about 180° C., to yield the corresponding compound of formula (XXVI).

The compound of formula (XXVI) may then be reacted with a source of hydrogen, under hydrogenation conditions, in the presence of a suitably selected catalyst or catalyst system, such as Pd/C, Pt, and the like, in a solvent such as MeOH, EtOAc, and the like, to yield the corresponding compound of formula (XXVII). The compound of formula (XXVII) may be reacted with cyclobutanone (VI) in the presence of a source of cyanide of formula (VII), such as KCN, NaCN, TMS-CN, and the like; in a suitably selected solvent or mixture of solvents such as acetic acid, EtOH, MeO, and the like; at a temperature ranging from 10 to 130° C., to yield the corresponding compound of formula (XXVIII).

The compound of formula (XXVIII) may be reacted with the compound of formula (IV) in a suitably selected solvent or mixture of solvents such as DMA, DMF, NMP, DSMO, and the like, at temperature ranging from about 15 to about 180° C., to yield the corresponding compound of formula (XXIX).

Certain compounds of the present invention wherein G is

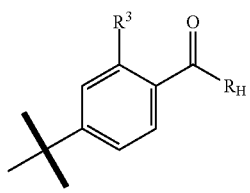

and R$_H$ includes, but is not limited to C$_{1-6}$ alkyl, C$_{3-7}$ cycloalkyl, and heterocyclic substituents of the present invention, may be prepared according to the process outlined in Scheme 9.

The compound of formula (XXX), wherein PG$_1$ is a suitably selected amino protecting group such as —COCH$_3$, -Cbz, and the like, a known compound or compound prepared by known methods, may be reacted with a compound of formula (XXXI), in the presence of a Lewis acid catalyst such as AlCl$_3$, FeCl$_3$, BF$_3$, ZnCl$_2$, and the like, under Friedel Craft acylation conditions, in a suitably selected solvent or mixture of solvents such as DCE, DCM, CH$_3$NO$_2$, and the like, to yield a compound of formula (XXXII). The compound of formula (XXXII) may be deprotected under various conventional reaction conditions, using reagents such as HCl if PG$_1$ is acetyl, or hydrogenolysis if PG$_1$ is carboxybenzyl, and the like, to afford a compound of formula (XXXIII). The compound of formula (XXXIII) may be reacted with cyclobutanone (VI) in the presence of a suitably selected source of cyanide (VII), such as KCN, NaCN, TMS-CN, and the like; in a suitably selected solvent or mixture of solvents such as acetic acid, EtOH, MeOH, and the like; at a temperature ranging from about 10 to about 130° C., to yield the corresponding compound of formula (XXXIV).

The compound of formula (XXXIV) may be reacted with the compound of formula (IV) in a suitably selected solvent or mixture of solvents such as DMA, DMF, NMP, DSMO, and the like, at a temperature ranging from about 15 to about 180° C., to yield the corresponding compound of formula (XXXV).

Certain compounds of the present invention wherein G is substituent i) and $R^4$ is $-Z-(L)_n-R_1$; or wherein G is substituent ii) and R7 is $-Z-(L)_n-R_1$, may be prepared according to the process outlined in Scheme 10. In Scheme 10, Z may be 0 or S, L is $C_{1-3}$alkyl, and $R_1$ is an appropriate substituent of the present invention, including but not limited to, substituted and unsubstituted heterocyclyl substituents, and substituted and unsubstituted bridged heterocyclyl substituents.

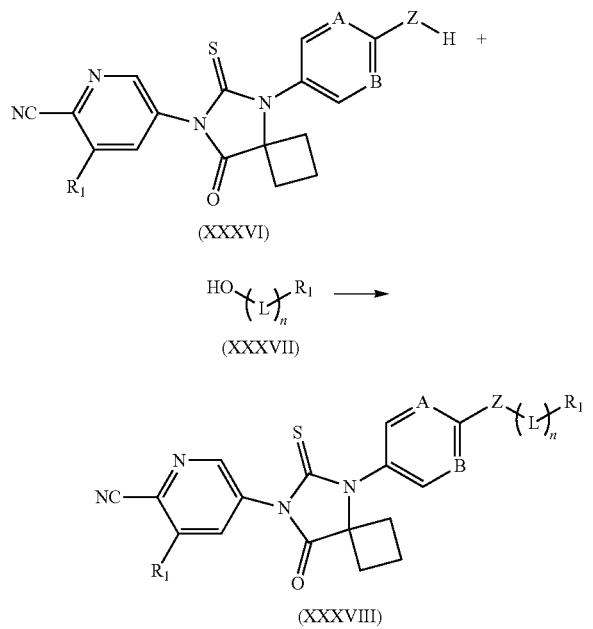

Treatment of a suitably substituted compound of formula (XXXVI), (wherein A is $C(R^3)$ and B is CH; or, A is CH and B is N), a known compound or compound prepared by known methods, may be reacted with a suitably substituted compound of formula (XXXVII), a known compound or compound prepared by known methods, in the presence of DIAD, DEAD, and the like, and PPh$_3$, under Mitsunobu conditions, in a suitably selected solvent or mixture of solvents such as THF, Et$_2$O, and the like; at a temperature ranging from about 0 to about 130° C., to yield the corresponding compound of formula (XXXVIII).

An alternative route for the preparation of certain compounds of formula (XXXVIII), Scheme 10, is shown in Scheme 11. In Scheme 11, A may be CH(R$^3$) when B is N, or A and B may be N.

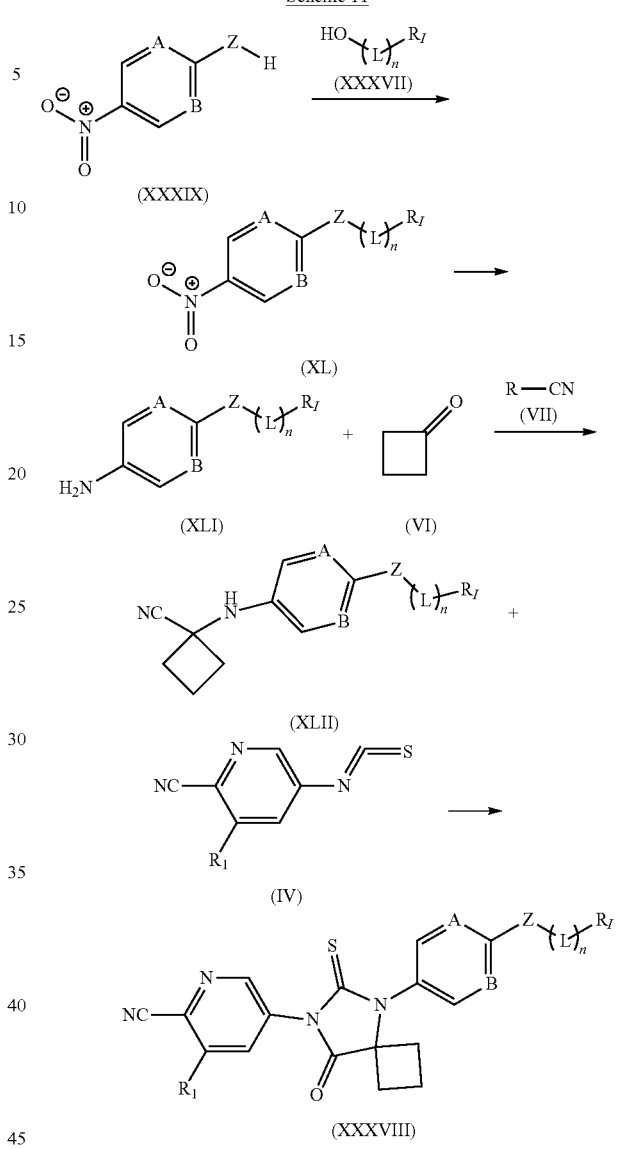

A suitably substituted compound of formula (XXXIX), a known compound or compound prepared by known methods, may be reacted with a suitably substituted compound of formula (XXXVII), a known compound or compound prepared by known methods, in the presence of DIAD, DEAD, and the like, and PPh$_3$, under conventional Mitsunobu conditions, in a suitably selected solvent or mixture of solvents such as THF, Et$_2$O, and the like; at temperature ranging from about 0 to about 130° C., to yield the corresponding compound of formula (XL).

The compound of formula (XL) then may be reacted with a source of hydrogen, under hydrogenation conditions, in the presence of a suitably selected catalyst or catalyst system, such as Pd/C, Pt, and the like, in a suitably selected solvent such as MeOH, EtOAc, and the like, to yield the corresponding compound of formula (XLI). The compound of formula (XLI) may be reacted with cyclobutanone (VI) in the presence of a suitably selected source of cyanide (VII), such as KCN, NaCN, TMS-CN, and the like; in a suitably selected solvent or mixture of solvents such as acetic acid, EtOH, MeO, and the like; at temperature ranging from about 10 to about 130° C., to yield the corresponding compound of formula (XLII).

The compound of formula (XLII) then may be reacted with the compound of formula (IV) in a suitably selected solvent or mixture of solvents such as DMA, DMF, NMP, DSMO, and the like, at temperature ranging from about 15 to about 180° C., to yield the corresponding compound of formula (XXXVIII).

One skilled in the art will recognize that the nitro group in compound of formula (XXXIX) may be substituted with a suitable protecting group, then subsequently deprotected to its corresponding amine subsequent to the Mitsunobu reaction.

Certain compounds of the present invention wherein G is

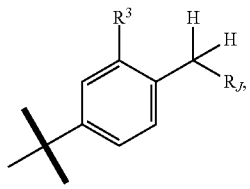

(and $R_J$ includes, but is not limited to, substituted and unsubstituted heterocyclyl, and substituted and unsubstituted cycloalkyl) may be prepared according to the process outlined in Scheme 12.

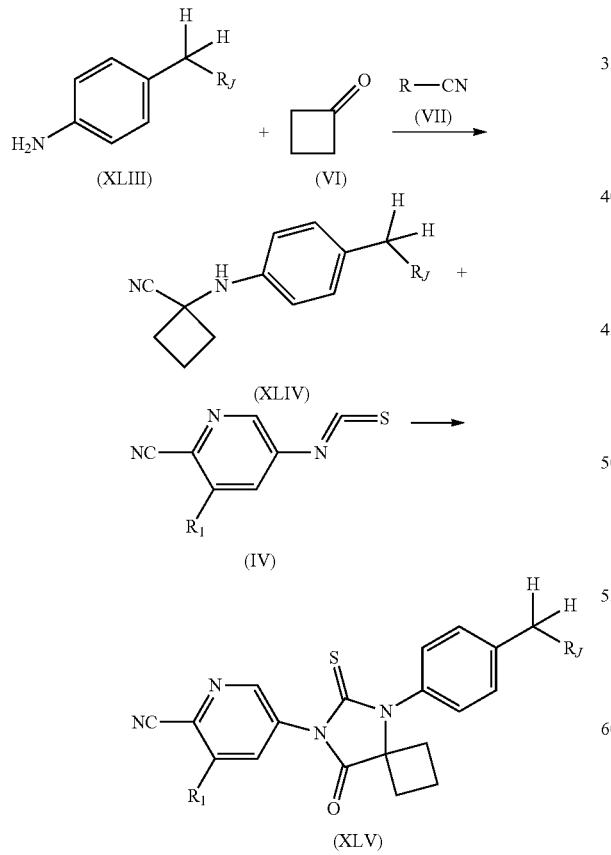

A suitably substituted compound of formula (XLIII), a known compound or compound prepared by known methods, may be treated with cyclobutanone (VI) in the presence of a suitably selected source of cyanide (VII), such as KCN, NaCN, TMS-CN, and the like; in a suitably selected solvent or mixture of solvents such as acetic acid, EtOH, MeO, and the like; at temperature ranging from about 10 to about 130° C., to yield the corresponding compound of formula (XLIV).

The compound of formula (XLIV) may be reacted with the compound of formula (IV) in a suitably selected solvent or mixture of solvents such as DMA, DMF, NMP, DSMO, and the like, at temperature ranging from about 15 to about 180° C., to yield the corresponding compound of formula (XLV).

Certain compounds of the present invention wherein G is

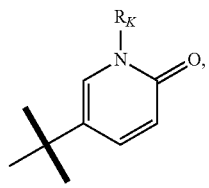

and $R_K$ is methyl or a Boc-protected azetidinylmethyl group, may be prepared according to the process outlined in Scheme 13.

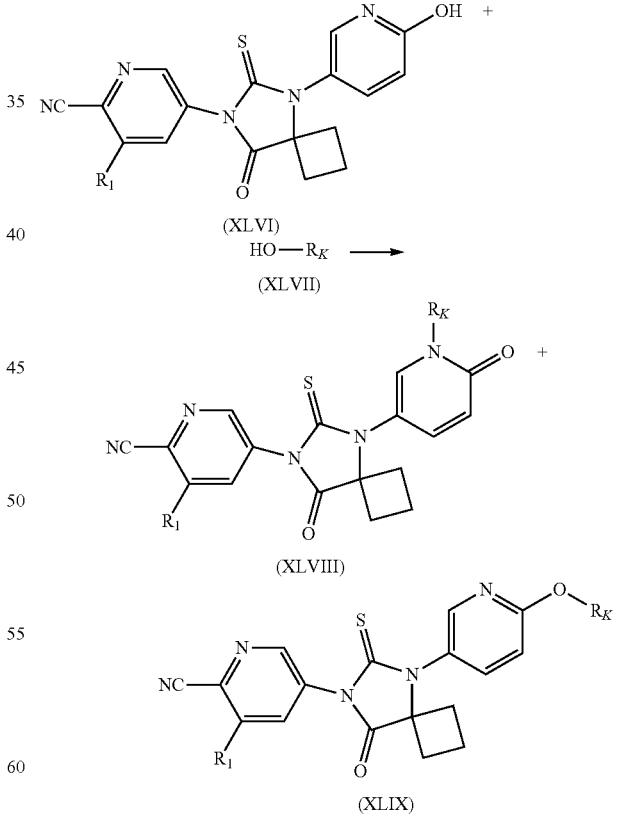

A suitably substituted compound of formula (XLVI), a known compound or compound prepared by known methods, may be treated with a compound of formula (XLVII), a known compound or compound prepared by known methods, in the presence of DIAD, DEAD, and the like, and PPh₃, under Mitsunobu conditions, in a suitably selected solvent or mixture of solvents such as THF, Et₂O, and the like; at a temperature ranging from about 0 to about 130° C., to yield the corresponding compounds of formula (XLVIII) and (XLIX).

Certain compounds of the present invention wherein G is

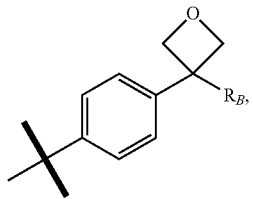

and R_B is amino or dimethylamino, may be prepared according to the process outlined in Scheme 14.

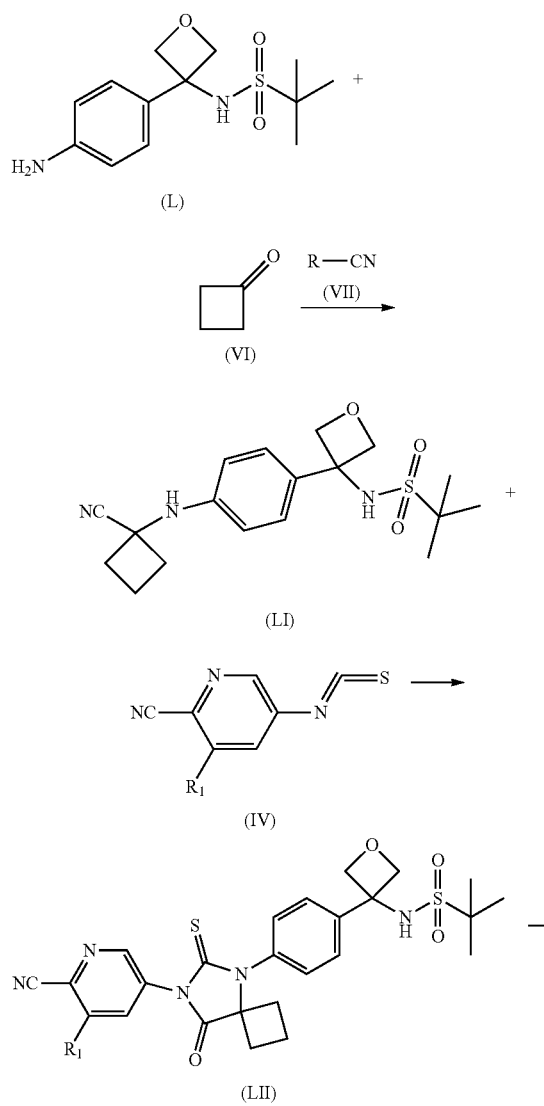

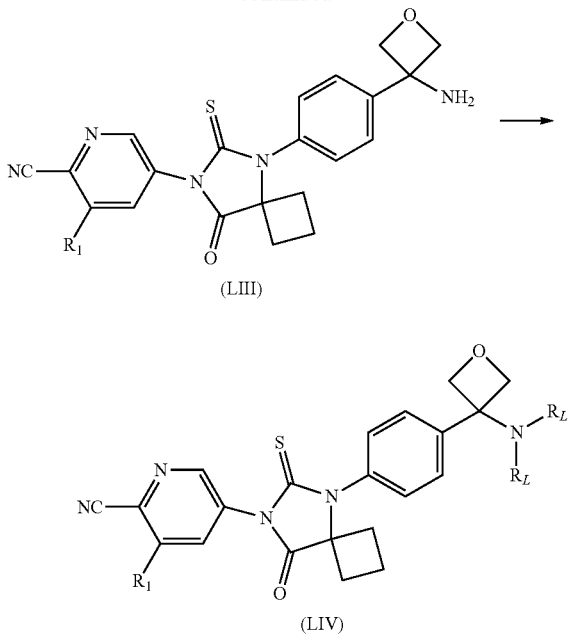

Treatment of a suitably substituted compound of formula (L), a known compound or compound prepared by known methods (wherein R_L is hydrogen or methyl), may be treated with cyclobutanone (VI) in the presence of a suitably selected source of cyanide (VII), such as KCN, NaCN, TMS-CN, and the like; in a suitably selected solvent or mixture of solvents such as acetic acid, EtOH, MeO, and the like; at a temperature ranging from about 10 to about 130° C., to yield the corresponding compound of formula (LI).

The compound of formula (LI) may be reacted with the compound of formula (IV) in a suitably selected solvent or mixture of solvents such as DMA, DMF, NMP, DSMO, and the like, at a temperature ranging from about 15 to about 180° C., to yield the corresponding compound of formula (LII). A compound of formula (LII) may be reacted with an acid such as HCl, TFA, and the like, in a suitably selected solvent or mixture of solvents such as MeOH, EtOH, 1,4-dioxane, water, DCM, and the like; at a temperature ranging from about 0 to about 80° C., to yield the corresponding compound of formula (LIII). A compound of formula LIII may be reacted with R_L-LG¹, wherein is a leaving group such as I, Br, Cl, triflate, and the like, in the presence of a suitably selected base, such as K₂CO₃, Cs₂CO₃, Et₃N, DIPEA, and the like, in the presence of a suitably selected solvent such as THF, DCM, MeCN, DMF, NMP, DMSO, and the like; at a temperature ranging from about 15 to about 170° C., to yield the corresponding compound of formula (LIV). One skilled in the art will recognize that the R_L substituent group may alternatively be incorporated into the desired compound of formula (LIV) by reacting a compound of formula (LIII) with R_L—CHO, in the presence of an acid or not such as AcOH, p-TsOH, in the presence of a reductive agent such as NaBH(AcO)₃, NaCNBH₃, and the like, under reductive amination conditions, in the presence of a suitably selected solvent such as DCM, DCE, THF, MeOH, and the like, at a temperature ranging from about 0 to about 80° C., to yield the corresponding compound of formula (LIV).

SPECIFIC EXAMPLES

Example 1

5-[8-[2-[(1-methyl-4-piperidyl)oxy]pyrimidin-5-yl]-5-oxo-7-thioxo-6,8-diazaspiro[3.4]octan-6-yl]-3-(trifluoromethyl)pyridine-2-carbonitrile Hydrochloride, Cpd 152

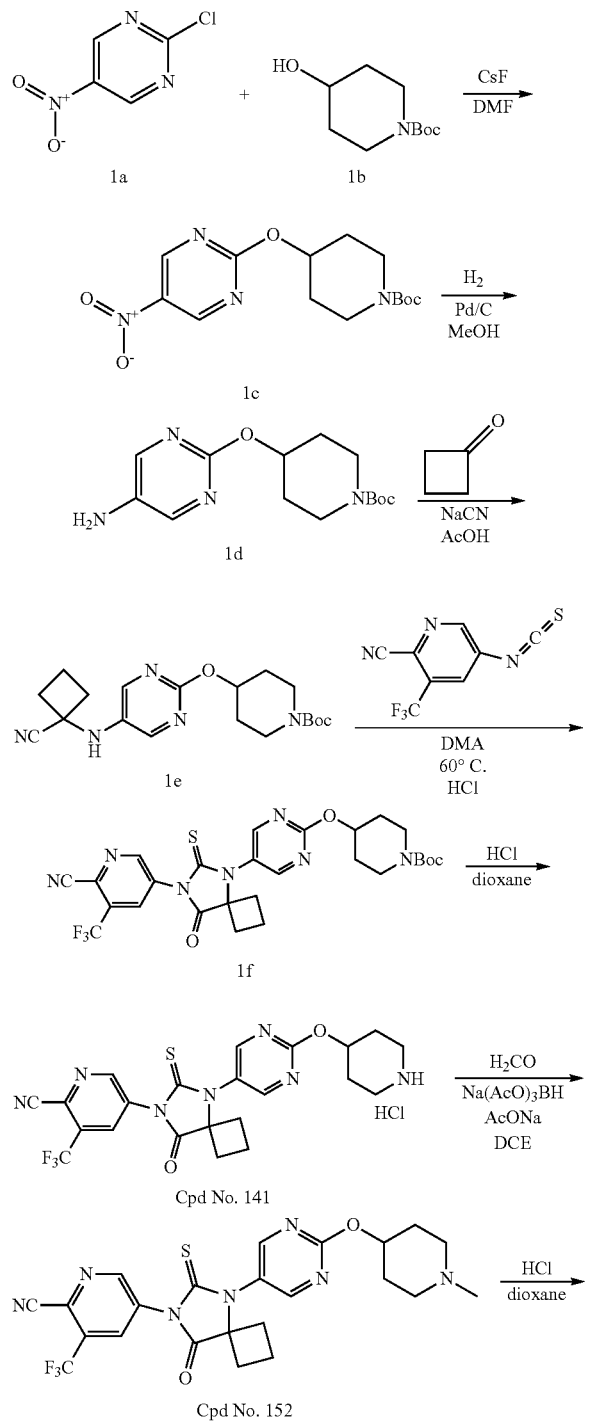

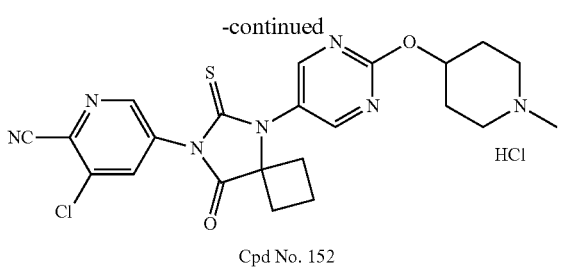

Cpd No. 152

A. 4-(5-Nitro-pyrimidin-2-yloxy)-piperidine-1-carboxylic Acid Tert-Butyl Ester, 1c

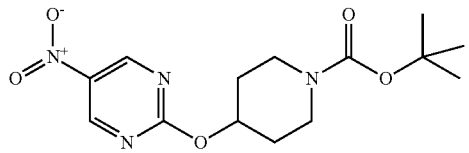 [SMILES: CC(C)(C)OC(=O)N1CCC(Oc2ncc([N+](=O)[O-])cn2)CC1]

Cesium fluoride (5.71 g, 37.6 mmol) was added to a solution of 2-Chloro-5-nitro-pyrimidine (4.0 g, 25.0 mmol) and 4-Hydroxy-piperidine-1-carboxylic acid tert-butyl ester (5.0 g, 25.0 mmol) in DMF (120 mL). The resulting mixture was stirred for 24 h at room temperature. The insolubles were collected by filtration through a short pad of diatomaceous earth. The filtrate was concentrated under reduced pressure. The residue was taken in EA (40 mL) and washed successively with water (40 mL) and brine (20 mL). The organic layer was dried over MgSO₄, filtered, and concentrated to dryness. Chromatography over silica gel (gradient of EA in heptane from 0 to 35%) gave the pure product as a white solid (2.43 g, 30%). $^1$H NMR (300 MHz, Chloroform-d) δ 1.47 (s, 9H), 1.76-1.92 (m, 2H), 1.98-2.13 (m, 2H), 3.21-3.44 (m, 2H), 3.63-4.00 (m, 2H), 5.26-5.50 (m, 1H), 9.29 (s, 2H). MS m/z 269 $C_{14}H_{20}N_4O_5$ (M+H-tBu)⁺.

B. 4-(5-Amino-pyrimidin-2-yloxy)-piperidine-1-carboxylic Acid Tert-Butyl Ester, 1d

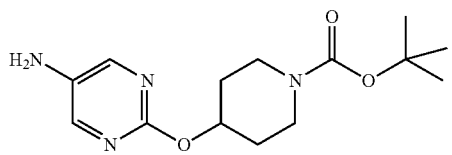 [SMILES: CC(C)(C)OC(=O)N1CCC(Oc2ncc(N)cn2)CC1]

4-(5-Nitro-pyrimidin-2-yloxy)-piperidine-1-carboxylic acid tert-butyl ester (3.0 g, 9.23 mmol) was dissolved in MeOH (40 mL) and cooled in ice/water bath under nitrogen stream. Dry 10% Pd/C (0.6 g) was added to the cold solution. The reaction vessel was connected to a balloon filled with hydrogen. The suspension was then stirred under a hydrogen atmosphere at room temperature during 1 h. The catalyst was removed by filtration through a pad of diatomaceous earth. Removal of solvent gave the crude product that was used without further treatment (2.71 g, 100%). $^1$H NMR (300 MHz, Chloroform-d) δ 1.46 (s, 9H), 1.69-1.86 (m, 2H), 1.89-2.08 (m, 2H), 3.20-3.34 (m, 2H), 3.38 (br s, 2H), 3.65-3.90 (m, 2H), 4.90-5.16 (m, 1H), 8.03 (s, 2H). $C_{14}H_{22}N_4O_3$ MS m/z 295 (M+H)$^+$.

C. 4-[5-(1-Cyano-cyclobutylamino)-pyrimidin-2-yloxy]-piperidine-1-carboxylic Acid Tert-Butyl Ester, 1e

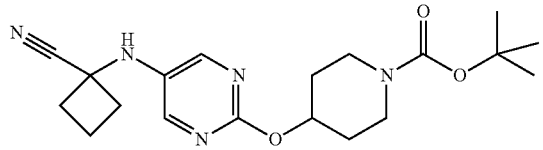 [SMILES: CC(C)(C)OC(=O)N1CCC(Oc2ncc(NC3(C#N)CCC3)cn2)CC1]

Cyclobutanone (1.38 mL, 18.5 mmol) and sodium cyanide (0.90 g, 18.5 mmol) were added successively to a solution of the previous intermediate (2.71 g, 9.23 mmol) in acetic acid (45 mL). The reaction was stirred overnight at room temperature. The solution was then concentrated under reduced pressure in a fume hood. The residue was taken in EA (50 mL) and washed with 1M $Na_2CO_3$ (100 mL) and brine (25 mL). The organic layer was dried over $MgSO_4$, filtered and concentrated to a crude oily residue. Chromatography over silica gel (gradient of EA in heptane from 0 to 60%) gave the pure product (2.47 g, 71%). $^1$H NMR (300 MHz, Chloroform-d) δ 1.47 (s, 9H), 1.72-1.86 (m, 2H), 1.91-2.07 (m, 2H), 2.12-2.31 (m, 2H), 2.31-2.45 (m, 2H), 2.68-2.88 (m, 2H), 3.17-3.37 (m, 2H), 3.70-3.91 (m, 3H), 5.00-5.16 (m, 1H), 8.05 (s, 2H). $C_{19}H_{27}N_5O_3$ MS m/z 374 (M+H)$^+$

D. 4-{5-[7-(6-Cyano-5-trifluoromethyl-pyridin-3-yl)-8-oxo-6-thioxo-5,7-diaza-spiro[3.4]oct-5-yl]-pyrimidin-2-yloxy}-piperidine-1-carboxylic Acid Tert-Butyl Ester, 1f

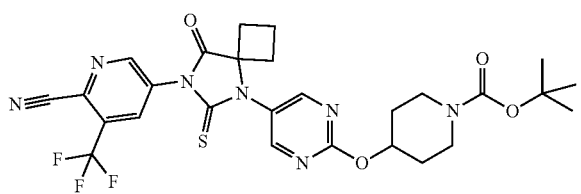 [SMILES: CC(C)(C)OC(=O)N1CCC(Oc2ncc(N3C(=S)N(c4cnc(C#N)c(C(F)(F)F)c4)C(=O)C34CCC4)cn2)CC1]

4-[5-(1-Cyano-cyclobutylamino)-pyrimidin-2-yloxy]-piperidine-1-carboxylic acid tert-butyl ester (2.47 g, 6.61 mmol), and freshly prepared 5-Isothiocyanato-3-trifluoromethyl-pyridine-2-carbonitrile (2.73 g, 11.9 mmol) were heated at 60° C. in DMA (35 mL) during 4 h and then allowed to cool to room temperature. The mixture was diluted with MeOH (7 mL) and 1M HCl (7 mL) was added. The stirring was maintained at room temperature overnight. EA (50 mL) was added and solution washed with water (100 mL), saturated 1M $Na_2CO_3$ (30 mL) and brine (50 mL). The organic layer was dried over $MgSO_4$, filtered and concentrated to dryness. The crude material was purified by chromatography over silica gel (gradient of EA in heptane from 0 to 50%). The fractions with product were collected and concentrated under reduced pressure to yield an amorphous solid (3.40 g, 85%). $^1$H NMR (300 MHz, Chloroform-d) δ 1.48 (s, 10H), 1.73-1.98 (m, 3H), 2.00-2.18 (m, 2H), 2.23-2.40 (m, 1H), 2.42-2.60 (m, 2H), 2.69-2.87 (m, 2H), 3.25-3.44 (m, 2H), 3.76-3.96 (m, 2H), 5.21-5.40 (m, 1H), 8.34 (d, J=2.2 Hz, 1H), 8.50 (s, 2H), 9.08 (d, J=2.2 Hz, 1H). C27H28F3N7O4S MS m/z 548 (M+H-tBu)$^+$.

E. 5-{8-Oxo-5-[2-(piperidin-4-yloxy)-pyrimidin-5-yl]-6-thioxo-5,7-diaza-spiro[3.4]oct-7-yl}-3-trifluoromethyl-pyridine-2-carbonitrilehydrochloride, Cpd 141

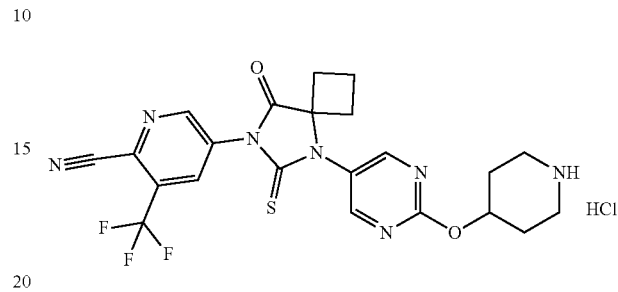

The previous 4-{4-[7-(6-Cyano-5-methoxy-pyridin-3-yl)-8-oxo-6-thioxo-5,7-diaza-spiro[3.4]oct-5-yl]-benzyl}-piperidine-1-carboxylic acid tert-butyl ester (3.40 g, 5.63 mmol) was taken in dioxane (25 mL). Dry 4N HCl in dioxane (14.0 mL, 56.0 mmol) was added with stirring. The mixture was stirred overnight at room temperature and diluted with diethyl ether (150 mL). Triturating during 2 hours gave a white powder that was collected by filtration and dried under high vacuum (2.86 g, 94%). $^1$H NMR (300 MHz, DMSO-d$_6$) δ 1.52-1.75 (m, 1H), 1.92-2.11 (m, 3H), 2.17-2.32 (m, 2H), 2.42-2.59 (m, 2H), 2.58-2.73 (m, 2H), 3.05-3.21 (m, 2H), 3.21-3.35 (m, 2H), 5.17-5.47 (m, 1H), 8.74 (s, 2H), 8.75 (d, J=2.0 Hz, 1H), 9.08 (br s, 2H), 9.21 (d, J=2.0 Hz, 1H). $C_{22}H_{21}ClF_3N_7O_2S$ MS m/z 504 (M+H)$^+$.

5-{8-Oxo-5-[2-(piperidin-4-yloxy)-pyrimidin-5-yl]-6-thioxo-5,7-diaza-spiro[3.4]oct-7-yl}-3-trifluoromethyl-pyridine-2-carbonitrile, Cpd 141

$^1$H NMR (300 MHz, Chloroform-d) δ 1.71-2.30 (m, 7H), 2.42-2.58 (m, 1H), 2.66-2.83 (m, 2H), 2.85-3.01 (m, 2H), 3.18-3.34 (m, 2H), 5.06-5.36 (m, 1H), 8.34 (d, J=2.3 Hz, 1H), 8.50 (s, 2H), 9.08 (d, J=2.3 Hz, 1H). $C_{22}H_{20}F_3N_7O_2S$ MS m/z 504 (M+H)$^+$.

F. 5-[8-[2-[(1-methyl-4-piperidyl)oxy]pyrimidin-5-yl]-5-oxo-7-thioxo-6,8-diazaspiro[3.4]octan-6-yl]-3-(trifluoromethyl)pyridine-2-carbonitrile, Cpd 152

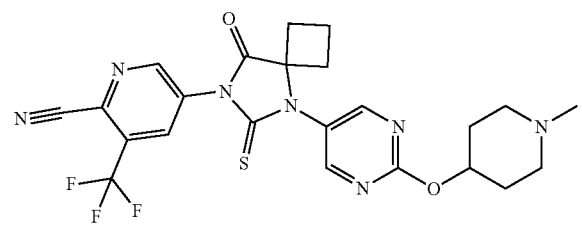 [SMILES: CN1CCC(Oc2ncc(N3C(=S)N(c4cnc(C#N)c(C(F)(F)F)c4)C(=O)C34CCC4)cn2)CC1]

Formaldehyde (37% wt in water, 2.8 mL, 37.2 mmol) was added to a solution of 5-{8-Oxo-5-[2-(piperidin-4-yloxy)-pyrimidin-5-yl]-6-thioxo-5,7-diaza-spiro[3.4]oct-7-yl}-3-trifluoromethyl-pyridine-2-carbonitrile (2.88 g, 5.31 mmol) and sodium acetate (0.436 g, 5.31 mmol) in DCE (15 mL). The mixture was stirred at room temperature for 40 min, before Sodium triacetoxyborohydride (1.78 g, 7.96 mmol) was added in 3 portions within 45 minutes. The reaction was continued 2 h and diluted with DCM (125 mL). The solution was washed successively with 1M $Na_2CO_3$ (100 mL) and water (50 mL). The organic layer was dried over $MgSO_4$, filtered and concentrated to give the crude product. Chromatography over silica gel (gradient of MeOH in DCM from 0 to 15%) gave, upon removal of solvent, a white foam (2.27 g, 82%). $^1$H NMR (300 MHz, Chloroform-d) δ 1.69-1.90 (m, 1H), 1.94-2.09 (m, 2H), 2.09-2.23 (m, 2H), 2.25-2.42 (m, 3H), 2.35 (s, 3H), 2.42-2.59 (m, 2H), 2.69-2.94 (m, 4H), 5.00-5.27 (m, 1H), 8.35 (d, J=2.2 Hz, 1H), 8.50 (s, 2H), 9.09 (d, J=2.2 Hz, 1H). $C_{23}H_{22}F_3N_7O_2S$ MS m/z 518 (M+H)$^+$.

5-[8-[2-[(1-methyl-4-piperidyl)oxy]pyrimidin-5-yl]-5-oxo-7-thioxo-6,8-diazaspiro[3.4]octan-6-yl]-3-(trifluoromethyl)pyridine-2-carbonitrile Hydrochloride Cpd 152, HCl Salt

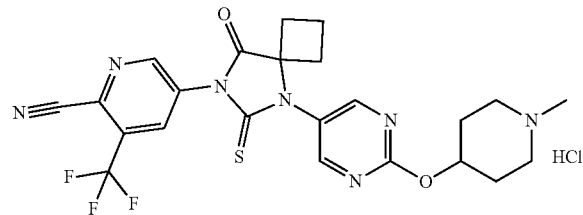 [SMILES: CN1CCC(Oc2ncc(N3C(=S)N(c4cnc(C#N)c(C(F)(F)F)c4)C(=O)C34CCC4)cn2)CC1 ; Cl]

The previous 5-[8-[2-[(1-methyl-4-piperidyl)oxy]pyrimidin-5-yl]-5-oxo-7-thioxo-6,8-diazaspiro[3.4]octan-6-yl]-3-(trifluoromethyl)pyridine-2-carbonitrile (2.27 g, 4.38 mmol) was taken in dioxane (15 mL) and treated with 4N HCl in dioxane (1.26 mL, 5.04 mmol) with stirring. After 1.5 h, diethyl ether (50 mL) was added and the resulting suspension was stirred for another 30 min. The solid was collected by filtration through a sintered funnel and subsequently washed with diethyl ether (2×15 mL). The solid was collected and dried under high vacuum at room temperature to yield the pure title hydrochloride salt (2.24 g, 89%). $^1$H NMR (300 MHz, DMSO-$d_6$) δ 1.48-1.77 (m, 1H), 1.87-2.14 (m, 2H), 2.15-2.29 (m, 2H), 2.29-2.40 (m, 1H), 2.43-2.58 (m, 2H), 2.58-2.71 (m, 2H), 2.78 (dd, J=13.7, 4.2 Hz, 3H), 3.02-3.30 (m, 2H), 3.30-3.44 (m, 2H), 3.44-3.55 (m, 1H), 5.07-5.31 (m, 0.5H), 5.31-5.46 (m, 0.5H), 8.74 (s, 1H), 8.75 (s, 2H); 9.21 (s, 1H), 10.75 (br s, 1H). $C_{23}H_{23}ClF_3N_7O_2S$ MS m/z 518 (M+H)$^+$.

Example 1a. Intermediate Synthesis tert-butyl (3-(4-(4-((1-cyanocyclobutyl)amino)phenoxy)piperidin-1-yl)-2-hydroxypropyl)carbamate

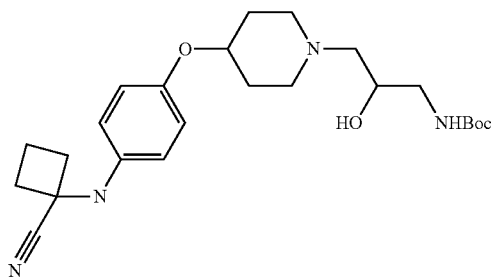 [SMILES: CC(C)(C)OC(=O)NCC(O)CN1CCC(Oc2ccc(NC3(C#N)CCC3)cc2)CC1]

A. To a solution of 4-(4-nitrophenoxy)piperidine (0.845 g, 3.8 mmol) in EtOH (20 mL) was added a solution of sodium methoxide in MeOH ~25% (0.878 mL, 4.68 mmol). After stirring overnight at RT, epichlorohydrin (0.367 mL, 4.68 mmol) was added. After stirring at RT overnight, the mixture was diluted with EtOAc and the organic layer washed with water and brine. The aqueous portion was extracted with EtOAc. The combined organic extracts were dried over $MgSO_4$, filtered and concentrated to give 4-(4-nitrophenoxy)-1-(oxiran-2-ylmethyl)piperidine, directly used in the next step. $^1$H NMR (300 MHz, Chloroform-d) δ 1.81-1.97 (m, 2H), 1.98-2.13 (m, 2H), 2.24-2.36 (m, 1H), 2.36-2.58 (m, 3H), 2.71-2.85 (m, 3H), 2.85-2.96 (m, 1H), 3.05-3.17 (m, 1H), 4.36-4.57 (m, 1H), 6.94 (d, J=9.2 Hz, 2H), 8.19 (d, J=9.2 Hz, 2H); $C_{14}H_{18}N_2O_4$ MS m/z 279 (M+H)$^+$.

B. Aqueous ammonia (8.23 mL, 95.05 mmol) was added to a solution of 4-(4-nitrophenoxy)-1-(oxiran-2-ylmethyl)piperidine in 1,4-dioxane (20 mL). After stirring at 60° C. in a seal tube overnight, the mixture was allowed to cool down to RT and the solvent concentrated. The residue was purified by chromatography over silica gel (gradient of 2.0M ammonia in MeOH in DCM from 0 to 100%) to give 1-amino-3-(4-(4-nitrophenoxy)piperidin-1-yl)propan-2-ol as a yellow oil (1.13 g, 43%). $C_{14}H_{21}N_3O_4$ MS m/z 296 (M+H)$^+$.

C. Di-tert-butyl dicarbonate (0.545 mL, 2.54 mmol) was added to a solution of 1-amino-3-(4-(4-nitrophenoxy)piperidin-1-yl)propan-2-ol (0.716 g, 2.42 mmol) in DCM (10 mL). After stirring overnight at RT, the solvent was concentrated and the residue purified by chromatography over silica gel (gradient of MeOH in DCM from 0 to 30%) to give tert-butyl (2-hydroxy-3-(4-(4-nitrophenoxy)piperidin-1-yl)propyl)carbamate (0.455 g, 75%) as a yellow oil. $^1$H NMR (300 MHz, Chloroform-d) δ 1.44 (s, 9H), 1.78-1.95 (m, 2H), 1.96-2.16 (m, 2H), 2.27-2.46 (m, 3H), 2.53-2.76 (m, 2H), 2.85-2.99 (m, 1H), 2.98-3.15 (m, 1H), 3.24-3.46 (m, 1H), 3.65-3.88 (m, 1H), 4.39-4.58 (m, 1H), 4.99 (br s, 1H), 6.94 (d, J=9.3 Hz, 2H), 8.19 (d, J=9.3 Hz, 2H); $C_{19}H_{29}N_3O_6$ MS m/z 396 (M+H)$^+$.

D. A solution of tert-butyl (2-hydroxy-3-(4-(4-nitrophenoxy)piperidin-1-yl)propyl)carbamate (0.45 g, 1.138 mmol) in MeOH (10 mL) was purged using nitrogen and vacuum. Palladium on charcoal (10% wet, 0.12 g) was added and the mixture was hydrogenated (20 psi) for 16 h. The reaction mixture was filtered through diatomaceous earth, the cake washed with MeOH, and the solvent concentrated under reduced pressure to give tert-butyl (3-(4-(4-aminophenoxy)piperidin-1-yl)-2-hydroxypropyl)carbamate (0.416 g, 93%) as a brown foam used directly into the next step. $^1$H NMR (300 MHz, DMSO-$d_6$) δ 1.37 (s, 9H), 1.52-1.76 (m, 2H), 1.87-2.05 (m, 2H), 2.15-2.39 (m, 4H), 2.63-2.79 (m, 2H), 2.79-2.95 (m, 1H), 2.95-3.12 (m, 1H), 3.52-3.80 (m, 1H), 4.42-4.69 (m, 2H), 6.65 (t, J=5.8 Hz, 1H), 7.16 (d, J=9.3 Hz, 2H), 8.17 (d, J=9.1 Hz, 2H); $C_{19}H_{31}N_3O_4$ MS m/z 366 (M+H)$^+$.

E. Cyclobutanone (0.23 mL, 3.1 mmol) and sodium cyanide (0.152 g, 3.1 mmol) were added successively to a solution of the previous intermediate (0.613 g, 0.738 mmol) in acetic acid (5 mL). The reaction was stirred overnight at room temperature. The solution was then concentrated under reduced pressure. The residue was taken in EtOAc (100 mL) and washed with water (50 mL), aqueous saturated $NaHCO_3$ (50 mL) and brine (50 mL). The organic layer was dried over $MgSO_4$, filtered and concentrated to give a crude residue. Chromatography over silica gel (gradient of MeOH/DCM (1/20) in DCM from 0 to 50%) gave tert-butyl (3-(4-(4-((1- cyanocyclobutyl)amino)phenoxy)piperidin-1-yl)-2-hydroxypropyl)carbamate (0.204 g, 20%); $C_{24}H_{36}N_4O_4$ MS m/z 445 (M+H)$^+$.

Following the procedure described in Example 1, above, selecting and substituting the appropriate reagents, starting materials, and purification methods, and adjusting reaction temperatures, times and other variables or parameters, as needed or desirable, as would be readily recognized by those skilled in the art, the following compounds of Formula (I) of the invention were prepared.

| Cpd No. | Structure | Compound Name & Physical Data |
|---|---|---|
| 254 | 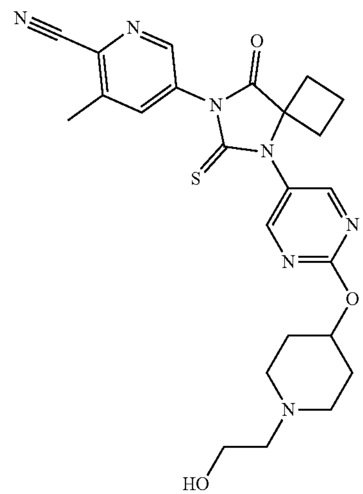 [SMILES: Cc1cc(N2C(=O)C3(CCC3)N(c3cnc(OC4CCN(CCO)CC4)nc3)C2=S)cnc1C#N] | 5-[8-[2-[[1-(2-hydroxyethyl)-4-piperidyl]oxy]pyrimidin-5-yl]-5-oxo-7-thioxo-6,8-diazaspiro[3,4]octan-6-yl]-3-methyl-pyridine-2-carbonitrile. $^1$H NMR (300 MHz, Chloroform-d) δ 1.63-1.90 (m, 1H), 2.22-2.54 (m, 5H), 2.65 (s, 3H), 2.70-2.93 (m, 4H), 3.13-3.40 (m, 4H), 3.58-3.75 (m, 2H), 3.99-4.17 (m, 2H), 5.34-5.72 (m, 1H), 7.82 (d, J = 2.3 Hz, 1H), 8.55 (s, 2H), 8.66 (d, J = 2.3 Hz, 1H), 11.88 (br s, 1H). $C_{24}H_{27}N_7O_3S$. HCl MS m/z 494 (M + H)$^+$. |
| 247 | 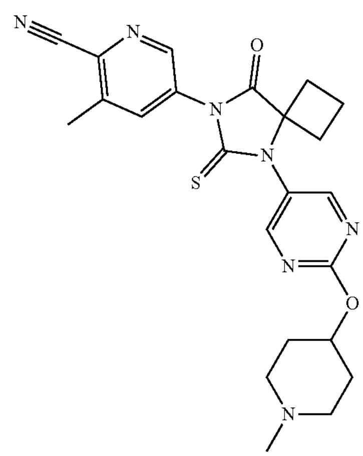 [SMILES: Cc1cc(N2C(=O)C3(CCC3)N(c3cnc(OC4CCN(C)CC4)nc3)C2=S)cnc1C#N] | 3-Methyl-5-[8-[2-[(1-methyl-4-piperidyl)oxy]pyrimidin-5-yl]-5-oxo-7-thioxo-6,8-diazaspiro[3,4]octan-6-yl]pyridine-2-carbonitrile. $^1$H NMR (300 MHz, Chloroform-d) δ 1.69-1.88 (m, 1H), 2.22-2.37 (m, 3H), 2.37-2.54 (m, 2H), 2.64 (s, 3H), 2.68-2.90 (m, 4H), 2.82 (d, J = 4.3 Hz, 3H), 3.15-3.34 (m, 2H), 3.35-3.51 (m, 2H), 5.38-5.64 (s, 1H), 7.82 (d, J = 2.2 Hz, 1H), 8.55 (s, 2H), 8.67 (d, J = 2.1 Hz, 1H), 12.78 (s, 1H). $C_{23}H_{25}N_7O_2S$. HCl MS m/z 464 (M + H)$^+$. |
| 246 | 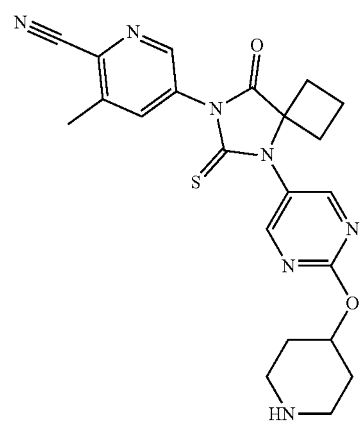 [SMILES: Cc1cc(N2C(=O)C3(CCC3)N(c3cnc(OC4CCNCC4)nc3)C2=S)cnc1C#N] | 3-methyl-5-[5-oxo-8-[2-(4-piperidyloxy)pyrimidin-5-yl]-7-thioxo-6,8-diazaspiro[3.4]octan-6-yl]pyridine-2-carbonitrile. $^1$H NMR (300 MHz, Chloroform-d) δ 1.69-1.87 (m, 1H), 2.23-2.39 (m, 3H), 2.39-2.53 (m, 4H), 2.65 (s, 3H), 2.69-2.85 (m, 2H), 3.24-3.60 (m, 4H), 5.24-5.65 (m, 1H), 7.82 (d, J = 2.2 Hz, 1H), 8.53 (s, 2H), 8.66 (d, J = 2.2 Hz, 1H), 9.83 (br s, 2H). $C_{22}H_{23}N_7O_2S$. HCl MS m/z 450 (M + H)$^+$. |

-continued

| Cpd No. | Structure | Compound Name & Physical Data |
|---|---|---|
| 195 | 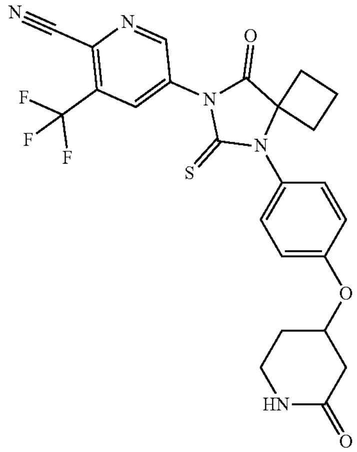 [SMILES: N#Cc1ncc(N2C(=O)C3(CCC3)N(c3ccc(OC4CCNC(=O)C4)cc3)C2=S)cc1C(F)(F)F] | (R,S)-5-[5-oxo-8-[4-[(2-oxo-4-piperidyl)oxy]phenyl]-7-thioxo-6,8-diazaspiro[3.4]octan-6-yl]-3-(trifluoromethyl)pyridine-2-carbonitrile.<br>$^1$H NMR (300 MHz, Chloroform-d) δ 1.62-1.83 (m, 1H), 2.05-2.35 (m, 3H), 2.45-2.80 (m, 6H), 3.29-3.44 (m, 1H), 3.58-3.75 (m, 1H), 4.77-4.93 (m, 1H), 5.86 (br s, 1H), 7.08 (d, J = 8.9 Hz, 2H), 7.24 (d, J = 8.9 Hz, 2H), 8.37 (d, J = 2.2 Hz, 1H), 9.10 (d, J = 2.2 Hz, 1H).<br>$C_{24}H_{20}F_3N_5O_3S$<br>MS m/z 516 (M + H)$^+$. |
| 189 | 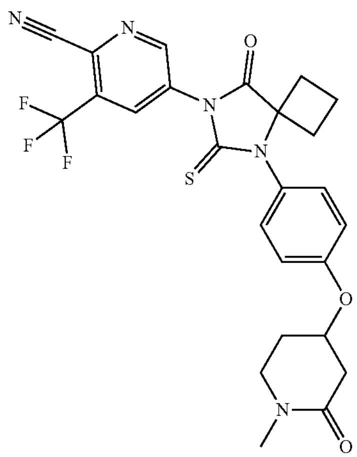 [SMILES: CN1CCC(Oc2ccc(N3C(=S)N(c4cnc(C#N)c(C(F)(F)F)c4)C(=O)C34CCC4)cc2)CC1=O] | (R,S)-5-[8-[4-[(1-methyl-2-oxo-4-piperidyl)oxy]phenyl]-5-oxo-7-thioxo-6,8-diazaspiro[3.4]octan-6-yl]-3-(trifluoromethyl)pyridine-2-carbonitrile<br>$^1$H NMR (300 MHz, Chloroform-d) δ 1.54-1.86 (m, 1H), 2.08-2.37 (m, 3H), 2.43-2.85 (m, 6H), 3.02 (s, 3H), 3.24-3.38 (m, 1H), 3.53-3.76 (m, 1H), 4.71-5.00 (m, 1H), 7.07 (d, J = 8.4 Hz, 2H), 7.23 d, J = 8.4 Hz, 2H), 8.37 (s, 1H), 9.10 (s, 1H).<br>$C_{25}H_{22}F_3N_5O_3S$ MS m/z 530 (M + H)$^+$. |
| 226 | 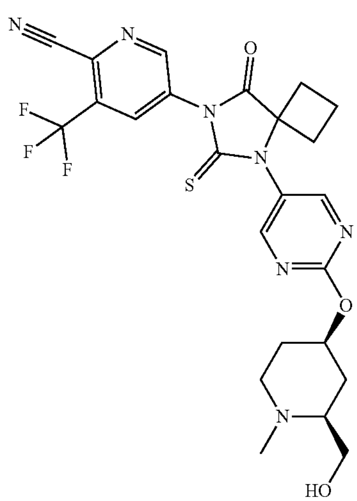 [SMILES: CN1CC[C@@H](Oc2ncc(N3C(=S)N(c4cnc(C#N)c(C(F)(F)F)c4)C(=O)C34CCC4)cn2)C[C@H]1CO] | 5-[8-(2SR,4RS)[4-[[2-(hydroxymethyl)-1-methyl-4-piperidyl]oxy]phenyl]-5-oxo-7-thioxo-6,8-diazaspiro[3.4]octan-6-yl]-3-(trifluoromethyl)pyridine-2-carbonitrile.<br>$^1$H NMR (300 MHz, DMSO-d$_6$) δ 1.36 (q, J = 11.6 Hz, 1H), 1.46-1.69 (m, 2H), 1.89-2.09 (m, 3H), 2.11-2.21 (m, 2H), 2.22 (s, 3H), 2.36-2.48 (m, 2H), 2.54-2.70 (m, 2H), 2.78-2.94 (m, 1H), 3.28-3.44 (m, 1H), 3.49-3.65 (m, 1H), 4.27-4.46 (m, 1H), 4.49 (t, J = 5.5 Hz, 1H), 7.09-7.21 (m, 2H), 7.29 (d, J = 8.7 Hz, 2H), 8.76 (d, J = 2.1 Hz, 1H), 9.22 (d, J= 2.0 Hz, 1H).<br>$C_{26}H_{26}F_3N_5O_3S$ MS m/z 546 (M + H)$^+$. |

| Cpd No. | Structure | Compound Name & Physical Data |
|---|---|---|
| 223 | 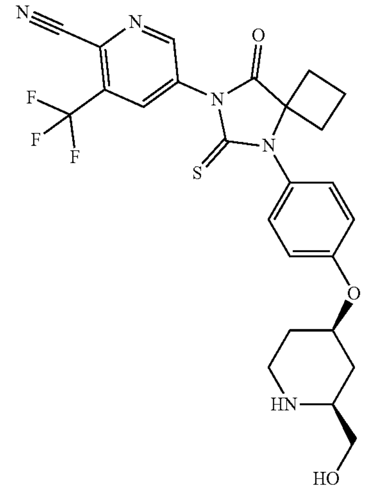 [SMILES: N#Cc1ncc(N2C(=O)C3(CCC3)N(c3ccc(O[C@@H]4CCN[C@H](CO)C4)cc3)C2=S)cc1C(F)(F)F] | 5-[8-(2SR,4RS)[4-[[2-(hydroxymethyl)-4-piperidyl]oxy]phenyl]-5-oxo-7-thioxo-6,8-diazaspiro[3.4]octan-6-yl]-3-(trifluoromethyl)pyridine-2-carbonitrile.<br>$^1$H NMR (300 MHz, DMSO-d$_6$) δ 1.35-1.48 (m, 1H), 1.49-1.63 (m, 1H), 1.64-1.78 (m, 1H), 1.82-2.06 (m, 3H), 2.36-2.47 (m, 2H), 2.55-2.69 (m, 2H), 2.77-3.07 (m, 3H), 3.20-3.39 (m, 3H), 4.74-4.89 (m, 1H), 7.13 (d, J = 8.8 Hz, 2H), 7.30 (d, J = 8.7 Hz, 2H), 8.73 (d, J = 2.1 Hz, 1H), 9.20 (d, J = 2.0 Hz, 1H).<br>$C_{25}H_{24}F_3N_5O_3S$ MS m/z 532 (M + H)$^+$. |
| 222 | 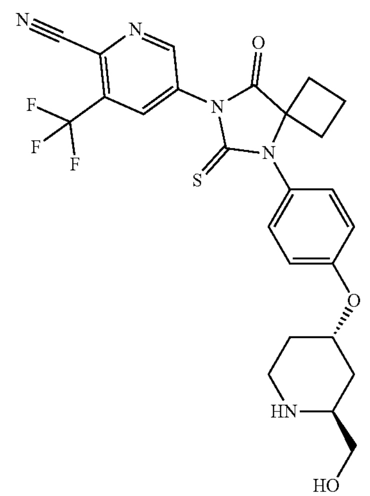 [SMILES: N#Cc1ncc(N2C(=O)C3(CCC3)N(c3ccc(O[C@H]4CCN[C@H](CO)C4)cc3)C2=S)cc1C(F)(F)F] | 5-[8-(2SR,4SR)[4-[[2-(hydroxymethyl)-4-piperidyl]oxy]phenyl]-5-oxo-7-thioxo-6,8-diazaspiro[3.4]octan-6-yl]-3-(trifluoromethyl)pyridine-2-carbonitrile.<br>$^1$H NMR (300 MHz, DMSO-d$_6$) δ 1.10 (q, J = 11.5 Hz, 1H), 1.31-1.65 (m, 2H), 1.89-2.15 (m, 4H), 2.34-2.48 (m, 2H), 2.53-2.76 (m, 4H), 2.98-3.10 (m, 1H), 3.23-3.36 (m, 3H), 4.31-4.55 (m, 1H), 7.14 (d, J = 8.8 Hz, 2H), 7.29 (d, J = 8.7 Hz, 2H), 8.75 (d, J = 2.1 Hz, 1H), 9.21 (d, J = 2.0 Hz, 1H).<br>$C_{25}H_{24}F_3N_5O_3S$ MS m/z 532 (M + H)$^+$. |
| 210 | 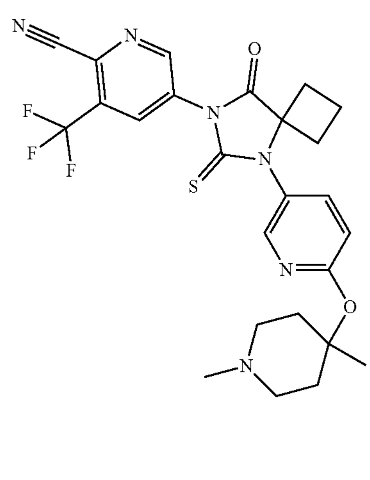 [SMILES: CN1CCC(C)(Oc2ccc(N3C(=S)N(c4cnc(C#N)c(C(F)(F)F)c4)C(=O)C34CCC4)cn2)CC1] | 5-[8-[6-[(1,4-dimethyl-4-piperidyl)oxy]-3-pyridyl]-5-oxo-7-thioxo-6,8-diazaspiro[3.4]octan-6-yl]-3-(trifluoromethyl)pyridine-2-carbonitrile.<br>$^1$H NMR (300 MHz, Chloroform-d) δ 1.26 (s, 3H), 1.56-1.86 (m, 6H), 1.71 (s, 3H), 2.16-2.36 (m, 2H), 2.34-2.44 (m, 2H), 2.47-2.64 (m, 2H), 2.64-2.78 (m, 2H), 6.89 (d, J = 8.8 Hz, 1H), 7.49 (dd, J = 8.8, 2.7 Hz, 1H), 8.05 (d, J = 2.7 Hz, 1H), 8.36 (d, J = 2.2 Hz, 1H), 9.10 (d, J = 2.2 Hz, 1H).<br>$C_{25}H_{25}F_3N_6O_2S$ Ms m/z 531 (M + H)$^+$. |

| Cpd No. | Structure | Compound Name & Physical Data |
|---|---|---|
| 140 | 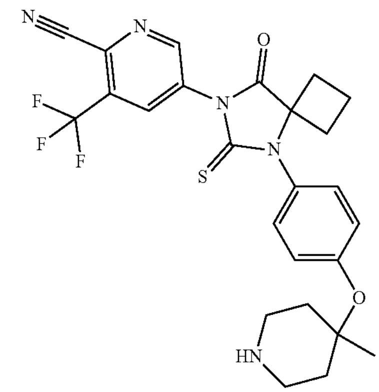 [SMILES: CC1(Oc2ccc(N3C(=S)N(c4cnc(C#N)c(C(F)(F)F)c4)C(=O)C34CCC4)cc2)CCNCC1] | 5-[8-[4-[(4-methyl-4-piperidyl)oxy]phenyl]-5-oxo-7-thioxo-6,8-diazaspiro[3.4]octan-6-yl]-3-(trifluoromethyl)pyridine-2-carbonitrile.<br>$^1$H NMR (300 MHz, Chloroform-d) δ 1.45 (s, 3H), 1.59-1.77 (m, 1H), 1.80-1.97 (m, 3H), 2.06-2.32 (m, 2H), 2.45-2.79 (m, 5H), 3.00-3.14 (m, 2H), 3.14-3.31 (m, 2H), 7.18 (d, J = 8.7 Hz, 2H), 7.22 (d, J = 8.7 Hz, 2H), 8.37 (d, J = 2.3 Hz, 1H), 9.11 (d, J = 2.2 Hz, 1H).<br>$C_{25}H_{24}F_3N_5O_2S$ MS m/z 516 (M + H)$^+$. |
| 143 | 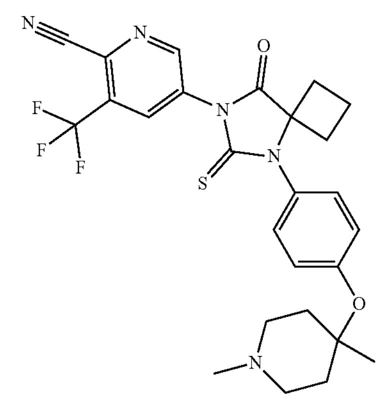 [SMILES: CN1CCC(C)(Oc2ccc(N3C(=S)N(c4cnc(C#N)c(C(F)(F)F)c4)C(=O)C34CCC4)cc2)CC1] | 5-[8-[4-[(1,4-dimethyl-4-piperidyl)oxy]phenyl]-5-oxo-7-thioxo-6,8-diazaspiro[3.4]octan-6-yl]-3-(trifluoromethyl)pyridine-2-carbonitrile.<br>$^1$H NMR (300 MHz, Chloroform-d) δ 1.42 (s, 3H), 1.60-1.77 (m, 2H), 1.77-1.99 (m, 4H), 2.05-2.31 (m, 4H), 2.39 (s, 3H), 2.46-2.82 (m, 4H), 7.06-7.23 (m, 4H), 8.37 (d, J = 2.2 Hz, 1H), 9.11 (d, J = 2.2 Hz, 1H).<br>$C_{26}H_{26}F_3N_5O_2S$ MS m/z 530 (M + H)$^+$. |
| 208 | 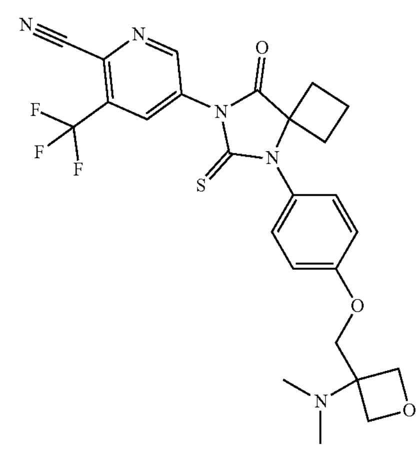 [SMILES: CN(C)C1(COc2ccc(N3C(=S)N(c4cnc(C#N)c(C(F)(F)F)c4)C(=O)C34CCC4)cc2)COC1] | 5-[8-[4-[[3-(dimethylamino)oxetan-3-yl]methoxy]phenyl]-5-oxo-7-thioxo-6,8-diazaspiro[3.4]octan-6-yl]-3-(trifluoromethyl)pyridine-2-carbonitrile.<br>$^1$H NMR (300 MHz, DMSO-d$_6$) δ 1.44-1.68 (m, 1H), 1.85-2.11 (m, 1H), 2.34-2.48 (m, 2H), 2.55-2.71 (m, 2H), 3.32 (s, 3H), 3.35 (s, 3H), 3.86 (s, 2H), 4.55 (d, J = 6.0 Hz, 2H), 4.68 (d, J = 6.0 Hz, 2H), 6.51 (d, J = 8.5 Hz, 2H), 7.15 (d, J = 8.4 Hz, 2H), 8.76 (d, J = 2.2 Hz, 1H), 9.22 (d, J = 2.1 Hz, 1H).<br>$C_{25}H_{24}F_3N_5O_3S$ MS m/z 532 (M + H)$^+$. |

| Cpd No. | Structure | Compound Name & Physical Data |
|---|---|---|
| 196 | 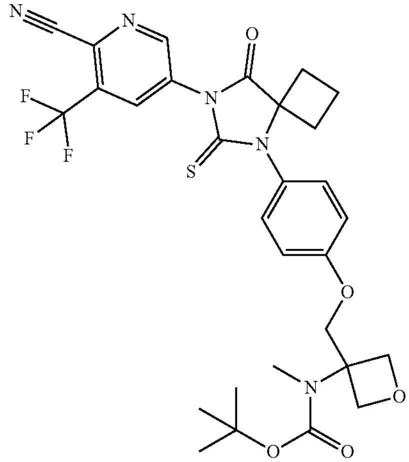 [SMILES: CN(C(=O)OC(C)(C)C)C1(COc2ccc(N3C(=S)N(c4cnc(C#N)c(C(F)(F)F)c4)C(=O)C34CCC4)cc2)COC1] | tert-butyl N-[3-[[4-[6-[6-cyano-5-(trifluoromethyl)-3-pyridyl]-5-oxo-7-thioxo-6,8-diazaspiro[3.4]octan-8-yl]phenoxy]methyl]oxetan-3-yl]-N-methyl-carbamate.<br>$^1$H NMR (300 MHz, DMSO-d$_6$) δ 1.38 (s, 9H), 1.46-1.66 (m, 1H), 1.84-2.08 (m, 1H), 2.36-2.47 (m, 2H), 2.54-2.70 (m, 2H), 2.77 (s, 3H), 4.37 (d, J = 6.5 Hz, 2H), 4.46 (s, 2H), 4.73 (d, J = 6.5 Hz, 2H), 7.22 (d, J = 8.5 Hz, 2H), 7.35 (d, J = 8.5 Hz, 2H), 8.76 (d, J = 2.1 Hz, 1H), 9.22 (d, J = 2.0 Hz, 1H).<br>$C_{29}H_{30}F_3N_5O_5S$ MS m/z 618 (M + H)$^+$. |
| 145 | 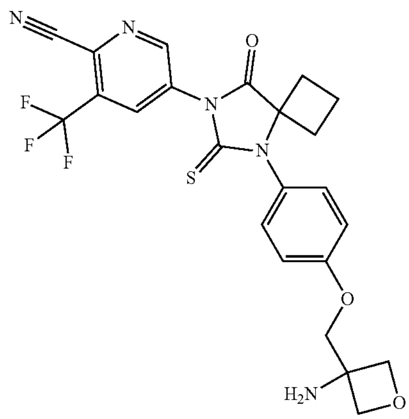 [SMILES: N#Cc1ncc(N2C(=O)C3(CCC3)N(c3ccc(OCC4(N)COC4)cc3)C2=S)cc1C(F)(F)F] | 5-[8-[4-[(3-aminooxetan-3-yl)methoxy]phenyl]-5-oxo-7-thioxo-6,8-diazaspiro[3.4]octan-6-yl]-3-(trifluoromethyl)pyridine-2-carbonitrile.<br>$^1$H NMR (300 MHz, Chloroform-d) δ 1.18 (br s, 2H), 1.46-1.62 (m, 1H), 1.96-2.18 (m, 1H), 2.32-2.63 (m, 4H), 4.35 (s, 2H), 4.55 (d, J = 7.3 Hz, 2H), 4.74 (d, J = 7.4 Hz, 2H), 7.03 (d, J = 8.7 Hz, 2H), 7.13 (d, J = 8.7 Hz, 2H), 8.28 (d, J = 2.2 Hz, 1H), 8.98 (d, J = 2.2 Hz, 1H).<br>$C_{23}H_{20}F_3N_5O_3S$ MS m/z 504 (M + H)$^+$. |
| 194 | 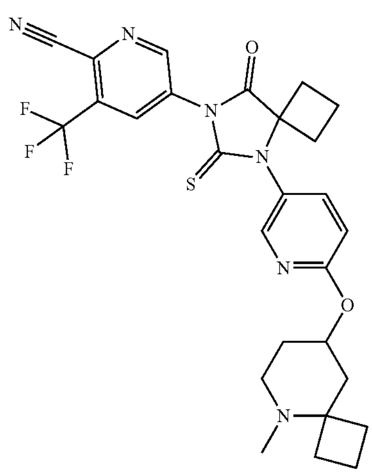 [SMILES: CN1CCC(Oc2ccc(N3C(=S)N(c4cnc(C#N)c(C(F)(F)F)c4)C(=O)C34CCC4)cn2)CC12CCC2] | (R,S)-5-[8-[6-[(9-methyl-9-azaspiro[3.5]nonan-6-yl)oxy]-3-pyridyl]-5-oxo-7-thioxo-6,8-diazaspiro[3.4]octan-6-yl]-3-(trifluoromethyl)pyridine-2-carbonitrile<br>$^1$H NMR (300 MHz, Chloroform-d) δ 1.62-1.93 (m, 7H), 1.99-2.11 (m, 1H), 2.15-2.37 (m, 4H), 2.40 (s, 3H), 2.47-2.66 (m, 3H), 2.66-2.86 (m, 3H), 5.06-5.33 (m, 1H), 6.89 (d, J = 8.8 Hz, 1H), 7.50 (dd, J = 8.8, 2.7 Hz, 1H), 8.10 (d, J = 2.6 Hz, 1H), 8.37 (d, J = 2.2 Hz, 1H), 9.11 (d, J = 2.2 Hz, 1H).<br>$C_{27}H_{27}F_3N_6O_2S$ MS m/z 557 (M + H)$^+$. |

| Cpd No. | Structure | Compound Name & Physical Data |
|---|---|---|
| 188 | 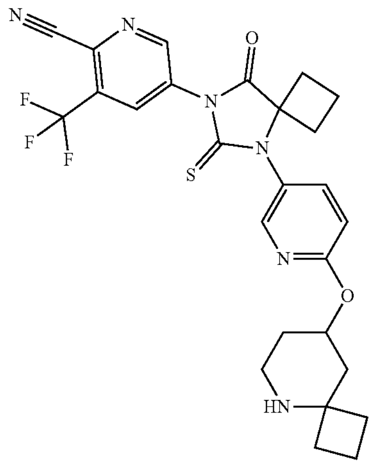 [SMILES: N#Cc1ncc(N2C(=O)C3(CCC3)N(c3ccc(OC4CCNC5(CCC5)C4)nc3)C2=S)cc1C(F)(F)F] | (R,S)-5-[8-[6-(9-azaspiro[3.5]nonan-6-yloxy)-3-pyridyl]-5-oxo-7-thioxo-6,8-diazaspiro[3.4]octan-6-yl]-3-(trifluoromethyl)pyridine-2-carbonitrile.<br>$^1$H NMR (300 MHz, Chloroform-d) δ 1.61-1.80 (m, 3H), 1.80-1.99 (m, 3H), 2.00-2.27 (m, 5H), 2.27-2.40 (m, 2H), 2.46-2.63 (m, 2H), 2.65-2.79 (m, 2H), 2.88 (td, J = 12.5, 11.6, 2.9 Hz, 1H), 3.02-3.16 (m, 1H), 5.13-5.41 (m, 1H), 6.90 (d, J = 8.8 Hz, 1H), 7.51 (dd, J = 8.8, 2.7 Hz, 1H), 8.10 (d, J = 2.6 Hz, 1H), 8.36 (d, J = 2.2 Hz, 1H), 9.10 (d, J = 2.2 Hz, 1H).<br>$C_{26}H_{25}F_3N_6O_2S$ MS m/z 543 (M + H)$^+$. |
| 178 | 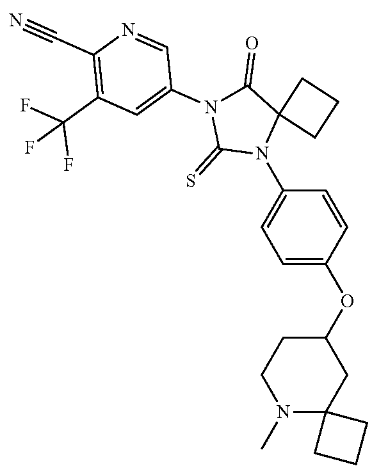 [SMILES: CN1CCC(Oc2ccc(N3C(=S)N(c4cnc(C#N)c(C(F)(F)F)c4)C(=O)C34CCC4)cc2)CC12CCC2] | (R,S)-5-[8-[4-[(9-methyl-9-azaspiro[3.5]nonan-6-yl)oxy]phenyl]-5-oxo-7-thioxo-6,8-diazaspiro[3.4]octan-6-yl]-3-(trifluoromethyl)pyridine-2-carbonitrile.<br>$^1$H NMR (300 MHz, Chloroform-d) δ 1.61-1.92 (m, 7H), 1.94-2.09 (m, 1H), 2.15-2.37 (m, 4H), 2.41 (s, 3H), 2.47-2.75 (m, 5H), 2.74-2.89 (m, 1H), 4.29-4.52 (m, 1H), 7.07 (d, J = 8.9 Hz, 2H), 7.17-7.24 d, J = 8.9 Hz, 2H), 8.37 (d, J = 2.3 Hz, 1H), 9.11 (d, J = 2.2 Hz, 1H).<br>$C_{28}H_{28}F_3N_5O_2S$ MS m/z 556 (M + H)$^+$. |
| 151 | 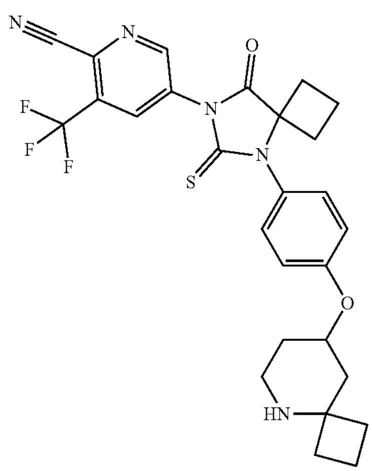 [SMILES: N#Cc1ncc(N2C(=O)C3(CCC3)N(c3ccc(OC4CCNC5(CCC5)C4)cc3)C2=S)cc1C(F)(F)F] | (R,S)-5-[8-[4-(9-azaspiro[3.5]nonan-6-yloxy)phenyl]-5-oxo-7-thioxo-6,8-diazaspiro[3.4]octan-6-yl]-3-(trifluoromethyl)pyridine-2-carbonitrile.<br>$^1$H NMR (300 MHz, Chloroform-d) δ 1.55-1.76 (m, 5H), 1.78-2.02 (m, 3H), 2.02-2.15 (m, 3H), 2.17-2.35 (m, 2H), 2.51-2.74 (m, 4H), 2.74-2.85 (m, 1H), 2.96-3.14 (m, 1H), 4.28-4.53 (m, 1H), 7.07 (d, J = 8.9 Hz, 2H), 7.21 (d, J = 8.9 Hz, 2H), 8.37 (d, J = 2.3 Hz, 1H), 9.11 (d, J = 2.3 Hz, 1H).<br>$C_{27}H_{26}F_3N_5O_2S$ MS m/z 542 (M + H)$^+$. |

| Cpd No. | Structure | Compound Name & Physical Data |
|---|---|---|
| 176 | 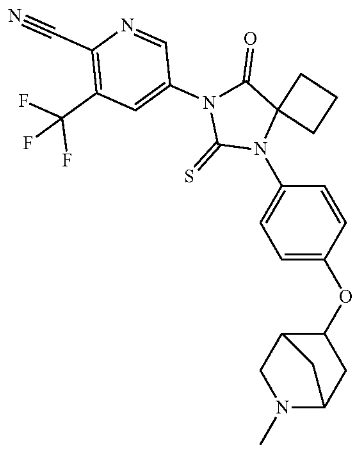 [SMILES: CN1CC2CC1CC2Oc1ccc(N2C(=S)N(c3cnc(C#N)c(C(F)(F)F)c3)C(=O)C23CCC3)cc1] | (R,S)-5-[8-[4-[(2-methyl-2-azabicyclo[2.2.1]heptan-5-yl)oxy]phenyl]-5-oxo-7-thioxo-6,8-diazaspiro[3.4]octan-6-yl]-3-(trifluoromethyl)pyridine-2-carbonitrile.<br>$^1$H NMR (300 MHz, Chloroform-d) δ 1.59-1.80 (m, 4H), 1.95 (dd, J = 13.3, 6.7 Hz, 1H), 2.14-2.34 (m, 1H), 2.48 (s, 3H), 2.55-2.74 (m, 4H), 3.29 (s, 1H), 4.54 (br s, 1H), 7.04 (d, J = 8.9 Hz, 2H), 7.19 (d, J = 8.9 Hz, 2H), 8.37 (d, J = 2.3 Hz, 1H), 9.11 (d, J = 2.2 Hz, 1H).<br>$C_{26}H_{24}F_3N_5O_2S$ MS m/z 528 (M + H)$^+$. |
| 150 | 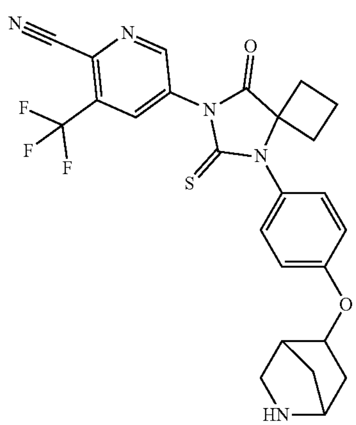 [SMILES: N#Cc1ncc(N2C(=O)C3(CCC3)N(c3ccc(OC4CC5CC4CN5)cc3)C2=S)cc1C(F)(F)F] | (R,S)-5-[8-[4-(2-azabicyclo[2.2.1]heptan-5-yloxy)phenyl]-5-oxo-7-thioxo-6,8-diazaspiro[3.4]octan-6-yl]-3-(trifluoromethyl)pyridine-2-carbonitrile.<br>$^1$H NMR (300 MHz, Chloroform-d) δ 1.46-1.58 (m, 1H), 1.59-1.75 (m, 4H), 1.80 (d, J = 10.2 Hz, 1H), 1.97 (ddd, J = 13.3, 6.7, 2.4 Hz, 1H), 2.14-2.33 (m, 1H), 2.48-2.77 (m, 5H), 2.84-2.97 (m, 1H), 3.60 (s, 1H), 4.30 (d, J = 6.6 Hz, 1H), 7.04 (d, J = 8.9 Hz, 2H), 7.20 (d, J = 8.8 Hz, 2H), 8.37 (d, J = 2.2 Hz, 1H), 9.10 (d, J = 2.2 Hz, 1H).<br>$C_{25}H_{22}F_3N_5O_2S$ Ms m/z 514 (M + H)$^+$. |
| 177 | 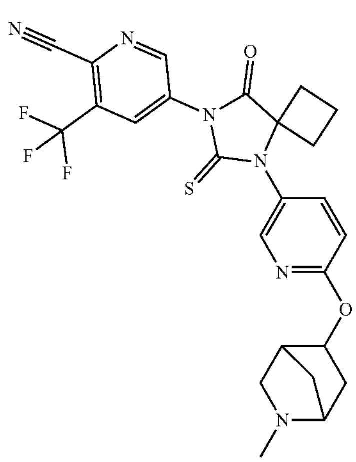 [SMILES: CN1CC2CC1CC2Oc1ccc(N2C(=S)N(c3cnc(C#N)c(C(F)(F)F)c3)C(=O)C23CCC3)cn1] | (R,S)-5-[8-[6-[(2-methyl-2-azabicyclo[2.2.1]heptan-5-yl)oxy]-3-pyridyl]-5-oxo-7-thioxo-6,8-diazaspiro[3.4]octan-6-yl]-3-(trifluoromethyl)pyridine-2-carbonitrile.<br>$^1$H NMR (300 MHz, Chloroform-d) δ 1.61-1.83 (m, 4H), 2.03 (dd, J = 13.8, 7.0 Hz, 1H), 2.18-2.36 (m, 1H), 2.41-2.62 (m, 4H), 2.55 (s, 3H), 2.63-2.79 (m, 3H), 3.44 (s, 1H), 5.29 (d, J = 6.8 Hz, 1H), 6.87 (d, J = 8.7 Hz, 1H), 7.50 (dd, J = 8.7, 2.7 Hz, 1H), 8.13 (d, J = 2.7 Hz, 1H), 8.36 (d, J = 2.3 Hz, 1H), 9.10 (d, J = 2.3 Hz, 1H).<br>$C_{25}H_{23}F_3N_6O_2S$ ms m/z 529 (M + H)$^+$. |

| Cpd No. | Structure | Compound Name & Physical Data |
|---|---|---|
| 165 | 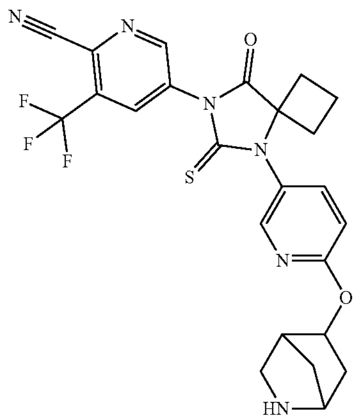 [SMILES: N#Cc1ncc(N2C(=O)C3(CCC3)N(c3ccc(OC4CC5CC4CN5)nc3)C2=S)cc1C(F)(F)F] | (R,S)-5-[8-[6-(2-azabicyclo[2.2.1]heptan-5-yloxy)-3-pyridyl]-5-oxo-7-thioxo-6,8-diazaspiro[3.4]octan-6-yl]-3-(trifluoromethyl)pyridine-2-carbonitrile.<br>$^1$H NMR (300 MHz, Chloroform-d) δ 1.57-1.88 (m, 4H), 2.04 (ddd, J = 13.6, 7.1, 2.4 Hz, 1H), 2.17-2.35 (m, 1H), 2.43-2.78 (m, 7H), 2.89-2.98 (m, 1H), 3.69 (s, 1H), 5.00 (d, J = 6.8 Hz, 1H), 6.88 (d, J = 8.8 Hz, 1H), 7.50 (dd, J = 8.8, 2.7 Hz, 1H), 8.11 (d, J = 2.7 Hz, 1H), 8.36 (d, J = 2.3 Hz, 1H), 9.10 (d, J = 2.3 Hz, 1H).<br>$C_{24}H_{21}F_3N_6O_2S$ MS m/z 515 (M + H)$^+$. |
| 157 | 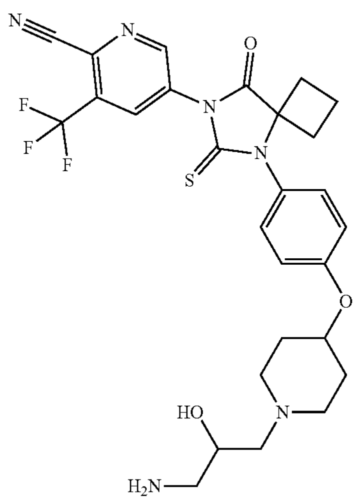 [SMILES: N#Cc1ncc(N2C(=O)C3(CCC3)N(c3ccc(OC4CCN(CC(O)CN)CC4)cc3)C2=S)cc1C(F)(F)F] | 5-[8-[4-[[1-(3-amino-2-hydroxypropyl)-4-piperidyl]oxy]phenyl]-5-oxo-7-thioxo-6,8-diazaspiro[3.4]octan-6-yl]-3-(trifluoromethyl)pyridine-2-carbonitrile.<br>$^1$H NMR (300 MHz, DMSO-d$_6$) δ 1.48-1.58 (m, 1H), 1.60-1.78 (m, 2H), 1.90-2.07 (m, 4H), 2.20-2.70 (m, 9H), 2.72-2.84 (m, 3H), 2.83-2.98 (m, 2H), 3.73-3.91 (m, 2H), 4.39-4.53 (m, 2H), 7.15 (d, J = 8.7 Hz, 2H), 7.29 (d, J = 8.3 Hz, 2H), 8.75 (s, 1H), 9.20 (s, 1H).<br>$C_{27}H_{29}F_3N_6O_3S$ MS m/z 575 (M + H)$^+$. |
| 147 | 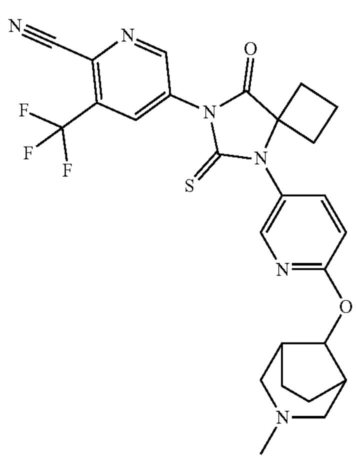 [SMILES: CN1CC2CCC(C1)C2Oc1ccc(N2C(=S)N(c3cnc(C#N)c(C(F)(F)F)c3)C(=O)C23CCC3)cn1] | 5-[8-[6-[(3-methyl-3-azabicyclo[3.2.1]octan-8-yl)oxy]-3-pyridyl]-5-oxo-7-thioxo-6,8-diazaspiro[3.4]octan-6-yl]-3-(trifluoromethyl)pyridine-2-carbonitrile.<br>$^1$H NMR (300 MHz, Chloroform-d) δ 1.50-1.63 (m, 2H), 1.67-1.83 (m, 1H), 1.95-2.09 (m, 2H), 2.21-2.38 (m, 1H), 2.42-2.60 (m, 4H), 2.60-2.77 (m, 2H), 2.81 (s, 3H), 3.15-3.47 (m, 4H), 5.14 (t, J = 5.1 Hz, 1H), 7.04 (d, J = 8.8 Hz, 1H), 7.62 (dd, J = 8.9, 2.6 Hz, 1H), 8.14 (d, J = 2.5 Hz, 1H), 8.35 (d, J = 2.2 Hz, 1H), 9.10 (d, J = 2.2 Hz, 1H).<br>$C_{26}H_{25}F_3N_6O_2S$ MS m/z 543 (M + H)$^+$. |

| Cpd No. | Structure | Compound Name & Physical Data |
|---|---|---|
| 146 | 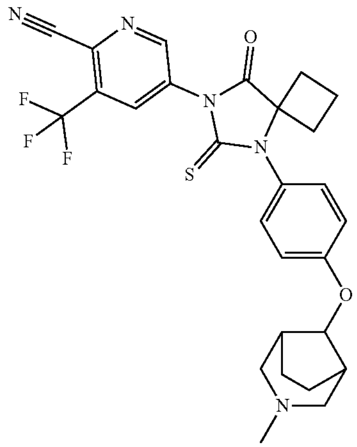 [SMILES: CN1CC2CCC(C1)C2Oc1ccc(N2C(=S)N(c3cnc(C#N)c(C(F)(F)F)c3)C(=O)C23CCC3)cc1] | 5-[8-[4-[(3-methyl-3-azabicyclo[3.2.1]octan-8-yl)oxy]phenyl]-5-oxo-7-thioxo-6,8-diazaspiro[3.4]octan-6-yl]-3-(trifluoromethyl)pyridine-2-carbonitrile.<br>$^1$H NMR (300 MHz, Chloroform-d) δ 1.45-1.63 (m, 2H), 1.63-1.79 (m, 1H), 1.90-2.06 (m, 2H), 2.15-2.36 (m, 1H), 2.45-2.64 (m, 4H), 2.64-2.76 (m, 2H), 2.80 (s, 3H), 3.19-3.42 (m, 4H), 4.52 (t, J = 5.1 Hz, 1H), 7.14 (d, J = 8.5 Hz, 2H), 7.26 (d, J = 8.5 Hz, 2H), 8.36 (s, 1H), 9.10 (s, 1H).<br>$C_{27}H_{26}F_3N_5O_2S$ MS m/z 542 (M + H)$^+$. |
| 139 | 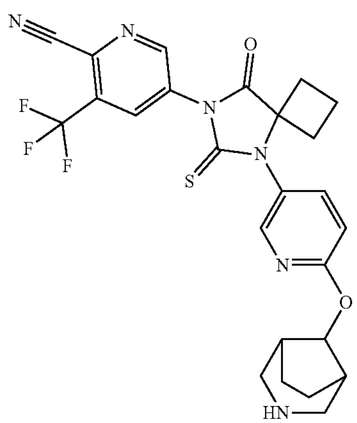 [SMILES: N#Cc1ncc(N2C(=O)C3(CCC3)N(c3ccc(OC4C5CCC4CNC5)nc3)C2=S)cc1C(F)(F)F] | 5-[8-[6-(3-azabicyclo[3.2.1]octan-8-yloxy)-3-pyridyl]-5-oxo-7-thioxo-6,8-diazaspiro[3.4]octan-6-yl]-3-(trifluoromethyl)pyridine-2-carbonitrile.<br>$^1$H NMR (300 MHz, Chloroform-d) δ 1.63-1.87 (m, 3H), 1.96-2.09 (m, 2H), 2.21-2.35 (m, 1H), 2.43 (br s, 1H), 2.46-2.62 (m, 4H), 2.62-2.80 (m, 2H), 3.02 (d, J = 12.5 Hz, 2H), 3.52 (d, J = 12.6 Hz, 2H), 5.01-5.25 (m, 1H), 6.95-7.11 (m, 1H), 7.48-7.63 (m, 1H), 8.12 (s, 1H), 8.36 (s, 1H), 9.11 (s, 1H).<br>$C_{25}H_{23}F_3N_6O_2S$ MS m/z 529 (M + H)$^+$. |
| 138 | 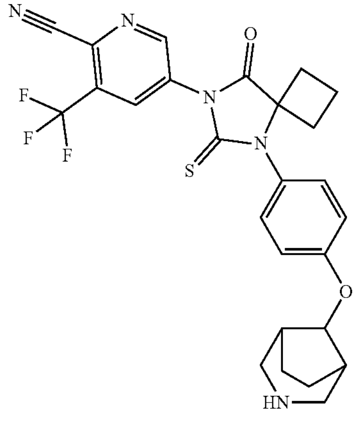 [SMILES: N#Cc1ncc(N2C(=O)C3(CCC3)N(c3ccc(OC4C5CCC4CNC5)cc3)C2=S)cc1C(F)(F)F] | 5-[8-[4-(3-azabicyclo[3.2.1]octan-8-yloxy)phenyl]-5-oxo-7-thioxo-6,8-diazaspiro[3.4]octan-6-yl]-3-(trifluoromethyl)pyridine-2-carbonitrile.<br>$^1$H NMR (300 MHz, Chloroform-d) δ 1.63-1.81 (m, 3H), 1.95-2.06 (m, 2H), 2.13-2.32 (m, 1H), 2.45-2.78 (m, 6H), 3.00 (d, J = 12.6 Hz, 2H), 3.55 (d, J = 12.5 Hz, 2H), 4.51-4.60 (m, 1H), 7.14 (d, J = 8.2 Hz, 2H), 7.26 (d, J = 8.2 Hz, 2H), 8.36 (d, J = 2.2 Hz, 1H), 9.11 (d, J = 2.2 Hz, 1H).<br>$C_{26}H_{24}F_3N_5O_2S$ MS m/z 528 (M + H)$^+$. |

| Cpd No. | Structure | Compound Name & Physical Data |
|---------|-----------|-------------------------------|
| 137 | 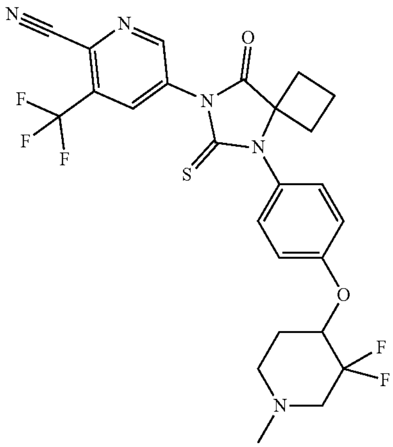 [SMILES: CN1CCC(Oc2ccc(N3C(=S)N(c4cnc(C#N)c(C(F)(F)F)c4)C(=O)C34CCC4)cc2)C(F)(F)C1] | (R,S)-5-[8-[4-[(3,3-difluoro-1-methyl-4-piperidyl)oxy]phenyl]-5-oxo-7-thioxo-6,8-diazaspiro[3.4]octan-6-yl]-3-(trifluoromethyl)pyridine-2-carbonitrile.<br>$^1$H NMR (300 MHz, Chloroform-d) δ 1.62-1.79 (m, 1H), 2.03-2.32 (m, 3H), 2.41 (s, 3H), 2.47-2.73 (m, 6H), 2.75-2.98 (m, 2H), 4.39-4.69 (m, 1H), 7.16 (d, J = 8.9 Hz, 2H), 7.25 (d, J = 9.0 Hz, 3H), 8.36 (d, J = 2.2 Hz, 1H), 9.10 (d, J = 2.2 Hz, 1H).<br>$C_{25}H_{22}F_5N_5O_2S$ MS m/z 552 (M + H)$^+$. |
| 136 | 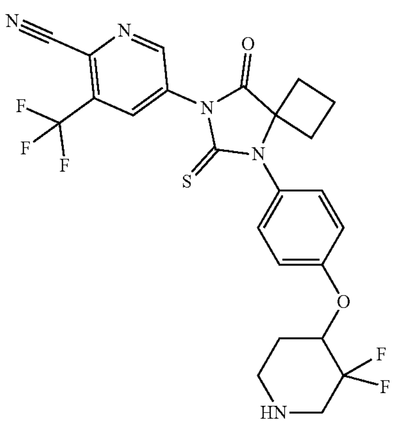 [SMILES: N#Cc1ncc(N2C(=O)C3(CCC3)N(c3ccc(OC4CCNCC4(F)F)cc3)C2=S)cc1C(F)(F)F] | (R,S)-5-[8-[4-[(3,3-difluoro-4-piperidyl)oxy]phenyl]-5-oxo-7-thioxo-6,8-diazaspiro[3.4]octan-6-yl]-3-(trifluoromethyl)pyridine-2-carbonitrile.<br>$^1$H NMR (300 MHz, Chloroform-d) δ 1.64-1.79 (m, 1H), 2.00-2.14 (m, 2H), 2.15-2.33 (m, 2H), 2.48-2.76 (m, 5H), 2.76-2.93 (m, 1H), 2.95-3.17 (m, 2H), 3.23-3.47 (m, 1H), 4.50-4.75 (m, 1H), 7.18 (d, J = 8.6 Hz, 2H), 7.25 (d, J = 8.6 Hz, 2H), 8.36 (d, J = 2.2 Hz, 1H), 9.10 (d, J = 2.2 Hz, 1H).<br>$C_{24}H_{20}F_5N_5O_2S$ MS m/z 538 (M + H)$^+$. |
| 41 | 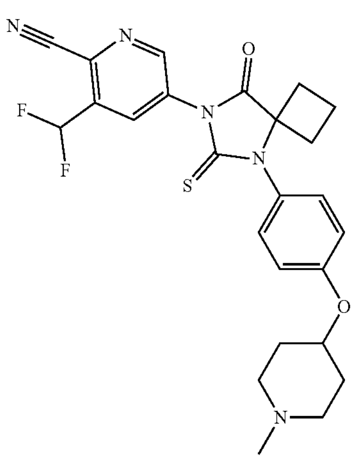 | 3-(difluoromethyl)-5-[8-[4-[(1-methyl-4-piperidyl)oxy]phenyl]-5-oxo-7-thioxo-6,8-diazaspiro[3,4]octan-6-yl]pyridine-2-carbonitrile.<br>$^1$H NMR (300 MHz, Chloroform-d) δ 1.60-1.78 (m, 2H), 1.87-2.06 (m, 3H), 2.06-2.30 (m, 4H), 2.41 (s, 3H), 2.46-2.74 (m, 4H), 2.73-2.90 (m, 2H), 4.36-4.54 (m, 1H), 7.01-7.12 (m, 3H), 7.22 (d, J = 8.8 Hz, 2H), 8.31 (d, J = 2.3 Hz, 1H), 9.02 (d, J = 2.3 Hz, 1H).<br>$C_{25}H_{25}F_2N_5O_2S$ MS m/z 598 (M + H)$^+$. |

| Cpd No. | Structure | Compound Name & Physical Data |
|---|---|---|
| 242 | 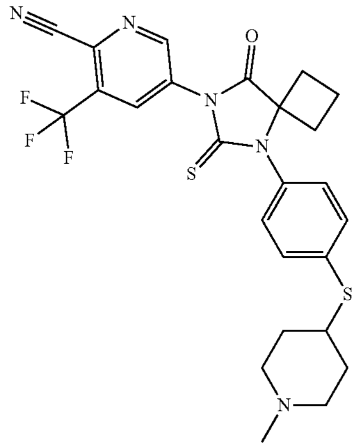 [SMILES: CN1CCC(Sc2ccc(N3C(=S)N(c4cnc(C#N)c(C(F)(F)F)c4)C(=O)C34CCC4)cc2)CC1] | 5-[8-[4-[(1-methyl-4-piperidyl)sulfanyl]phenyl]-5-oxo-7-thioxo-6,8-diazaspiro[3.4]octan-6-yl]-3-(trifluoromethyl)pyridine-2-carbonitrile. $^1$H NMR (300 MHz, DMSO-$d_6$) δ 1.45-1.65 (m, 1H), 1.70-1.88 (m, 2H), 1.89-2.03 (m, 2H), 2.10-2.30 (m, 2H), 2.35-2.47 (m, 2H), 2.56-2.68 (m, 2H), 2.75 (br s, 3H), 2.92-3.10 (m, 2H), 3.42-3.53 (m, 2H), 7.40 (d, J = 8.1 Hz, 2H), 7.62 (d, J = 8.2 Hz, 2H), 8.75 (s, 1H), 9.21 (s, 1H). $C_{25}H_{24}F_3N_5OS_2$•HCl MS m/z 532 (M + H)$^+$. |
| 240 | 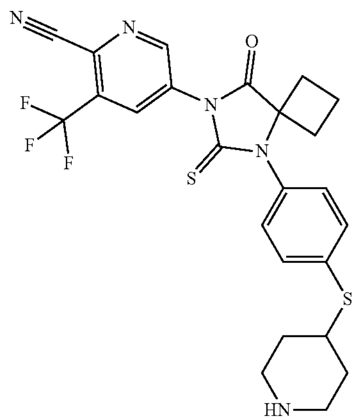 [SMILES: N#Cc1ncc(N2C(=O)C3(CCC3)N(c3ccc(SC4CCNCC4)cc3)C2=S)cc1C(F)(F)F] | 5-[5-oxo-8-[4-(4-piperidylsulfanyl)phenyl]-7-thioxo-6,8-diazaspiro[3.4]octan-6-yl]-3-(trifluoromethyl)pyridine-2-carbonitrile. $^1$H NMR (300 MHz, DMSO-$d_6$) δ 1.47-1.66 (m, 1H), 1.66-1.86 (m, 2H), 1.89-2.05 (m, 1H), 2.07-2.22 (m, 2H), 2.32-2.48 (m, 2H), 2.56-2.71 (m, 2H), 2.90-3.11 (m, 2H), 3.21-3.42 (m, 3H), 3.62-3.79 (m, 1H), 7.39 (d, J = 8.5 Hz, 2H), 7.62 (d, J = 8.5 Hz, 2H), 8.75 (d, J = 2.1 Hz, 1H), 8.91 (br s, 2H), 9.22 (d, J = 2.0 Hz, 1H). $C_{24}H_{22}F_3N_5OS_2$•(HCl)$_2$ MS m/z 518 (M + H)$^+$ |

Example 2

5-[8-[2-[[1-(2-hydroxyethyl)-4-piperidyl]oxy]pyrimidin-5-yl]-5-oxo-7-thioxo-6,8-diazaspiro[3.4]octan-6-yl]-3-(trifluoromethyl)pyridine-2-carbonitrile Cpd 252

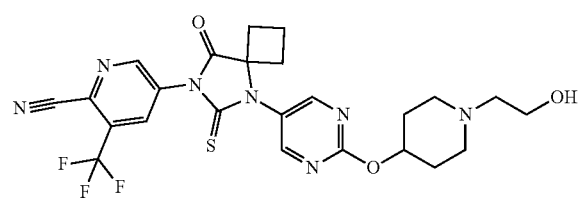 [SMILES: N#Cc1ncc(N2C(=O)C3(CCC3)N(c3cnc(OC4CCN(CCO)CC4)nc3)C2=S)cc1C(F)(F)F]

A mixture of 5-(8-oxo-5-(2-(piperidin-4-yloxy)pyrimidin-5-yl)-6-thioxo-5,7-diazaspiro[3.4]octan-7-yl)-3-(trifluoromethyl)picolinonitrile (0.15 g, 0.298 mmol), (2-Bromoethoxy)-tert-butyldimethylsilane (0.128 mL, 0.596 mmol) and Et$_3$N (0.082 mL, 0.596 mmol) in DMF (5 mL) was stirred at RT overnight. Additional (2-Bromoethoxy)-tert-butyldimethylsilane (0.128 mL, 0.596 mmol) and Et$_3$N (0.082 mL, 0.596 mmol) were added to the mixture and after stirring at 50° C. overnight, the mixture was diluted with EtOAc and aqueous 1.0M Na$_2$CO$_3$. The organic layer was washed with brine, dried over MgSO$_4$, filtered and concentrated. The crude material was purified by chromatography over silica gel (gradient of MeOH in DCM from 0 to 10%). The fractions with product were collected and concentrated under reduced pressure to yield 5-(5-(2-((1-(2-((tert-butyldimethylsilyl)oxy)ethyl)piperidin-4-yl)oxy)pyrimidin-5-yl)-8-oxo-6-thioxo-5,7-diazaspiro[3.4]octan-7-yl)-3-(trifluoromethyl)picolinonitrile (0.06 g, 29%). $C_{30}H_{38}F_3N_7O_3SSi$ MS m/z 661.8 (M+H)$^+$.

TBAF (0.043 g, 0.136 mmol) was added to a solution of 5-(5-(2-((1-(2-((tert-butyldimethylsilyl)oxy)ethyl)piperidin-4-yl)oxy)pyrimidin-5-yl)-8-oxo-6-thioxo-5,7-diazaspiro[3.4]octan-7-yl)-3-(trifluoromethyl)picolinonitrile (0.06, 0.09 mmol) in THF (5 mL). After stirring at RT for 5 days the solvent was removed under reduced pressure. The crude material was purified by chromatography over silica gel (gradient of MeOH in DCM from 10 to 50%). The residue was then purified by preparative reverse phase HPLC chromatography (from 75% aqueous 25 mM NH$_4$CO$_3$/25% ACN to 38% aqueous 25 mM NH$_4$CO$_3$/62% ACN-MeOH) to give 5-(8-oxo-5-(2-(piperidin-4-yloxy)pyrimidin-5-yl)-6-thioxo-5,7-diazaspiro[3.4]octan-7-yl)-3-(trifluoromethyl)picolinonitrile (0.06 g, 12%) as a solid. $^1$H NMR (300 MHz, Chloroform-d) δ 1.70-1.88 (m, 1H), 1.89-2.07 (m, 2H), 2.06-2.20 (m, 2H), 2.22-2.41 (m, 1H), 2.41-2.55 (m, 4H), 2.61 (t, J=5.4 Hz, 2H), 2.68-2.83 (m, 2H), 2.83-2.98 (m, 2H), 3.64 (t, J=5.4 Hz, 2H), 5.05-5.31 (m, 1H), 8.34 (d, J=2.2 Hz, 1H), 8.49 (s, 2H), 9.08 (d, J=2.2 Hz, 1H). $C_{24}H_{24}F_3N_7O_3S$ MS m/z 548 (M+H)$^+$.

Example 3

5-[8-[4-[2-(6-oxa-2-azaspiro[3.3]heptan-2-yl)ethoxy]phenyl]-5-oxo-7-thioxo-6,8-diazaspiro[3.4]octan-6-yl]-3-(trifluoromethyl)pyridine-2-carbonitrile Cpd 105

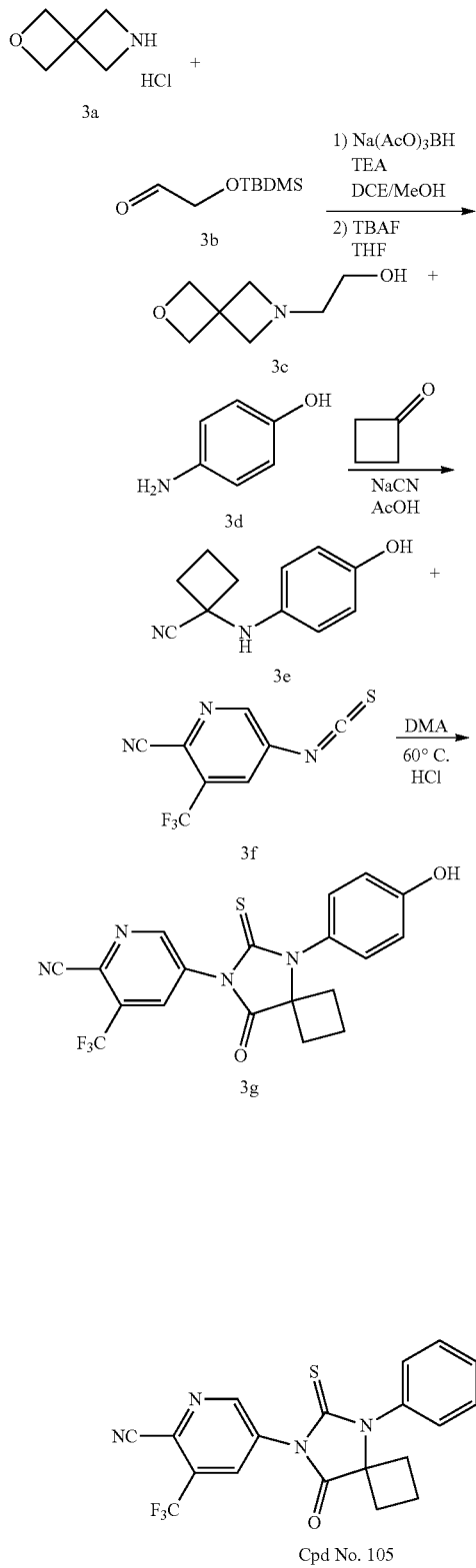

A. 2-(2-Oxa-6-aza-spiro[3.3]hept-6-yl)-ethanol, 3c

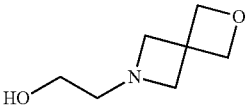

2-Oxa-6-aza-spiro[3.3]heptane hemioxalate (0.30 g, 208 mmol) and triethylamine (0.87 mL, 4.16 mmol) were stirred at room temperature in a mixture of DCE (50 mL) and MeOH (5 mL). To the resulting solution was added (tert-Butyl-dimethyl-silyloxy)-acetaldehyde (0.79 mL, 4.16 mmol) with stirring. Sodium triacetoxyborohydride (0.88 g, 4.16 mmol) was added portion wise over 45 min. Upon reaction completion (2 h), the mixture was diluted with DCM (75 mL) and washed with 1M $Na_2CO_3$ (50 mL). The aqueous layer was extracted with DCM (20 mL). The combined organic layers were dried over $MgSO_4$, filtered and concentrated to yield an oily residue that was used without further treatment (0.536 g, 100%).

The crude oil was taken in THF (30 mL) and treated with TBAF-trihydrate (0.985 g, 3.12 mmol) overnight at room temperature. The solution was then concentrated and product was isolated by preparative LC (gradient of ACN/MeOH 50/50 in 25 mM aqueous $NH_4HCO_3$ from 5 to 37%). The desired fractions were collected and concentrated to an oil (0.298 g, 100%). $^1$H NMR (300 MHz, DMSO-$d_6$) δ 2.59 (t, J=5.8 Hz, 2H), 3.37 (t, J=5.7 Hz, 2H), 3.55 (s, 4H), 4.59 (s, 4H), 8.21 (s, 1H). $C_7H_{13}NO_2$ MS m/z 144 (M+H)$^+$.

B. 1-(4-Hydroxy-phenylamino)-cyclobutanecarbonitrile, 3e

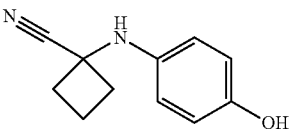 [SMILES: N#CC1(Nc2ccc(O)cc2)CCC1]

Sodium cyanide (1.01 g, 20.6 mmol) was added to a solution of cyclobutanone (5.13 mL, 68.7 mmol) and 4-amino-phenol (5.0 g, 45.8 mmol) in acetic acid (50 mL). The resulting mixture was stirred for 6 h. The solution was concentrated under reduced pressure. The residue was partitioned between EA (500 mL) and 1M $Na_2CO_3$ (250 mL). The organic layer was further washed with saturated $NaHCO_3$ (250 mL), brine (250 mL), dried over $MgSO_4$, filtered and concentrated to dryness. Chromatography over silica gel (gradient of MeOH in DCM from 0 to 3%) gave the pure product as a beige solid (6.94 g, 78%). $^1$H NMR (300 MHz, Chloroform-d) δ 1.79-1.97 (m, 1H), 2.05-2.27 (m, 3H), 2.29-2.46 (m, 2H), 3.80 (br s, 1H), 4.82 (br s, 1H), 6.58 (d, J=8.8 Hz, 2H), 6.75 (d, J=8.6 Hz, 2H). $C_{11}H_{12}N_2O$ MS m/z 189 (M+H)$^+$

C. 5-[5-(4-Hydroxy-phenyl)-8-oxo-6-thioxo-5,7-diaza-spiro[3.4]oct-7-yl]-3-trifluoromethyl-pyridine-2-carbonitrile, 3 g

D. 5-[8-[4-[2-(6-oxa-2-azaspiro[3.3]heptan-2-yl)ethoxy]phenyl]-5-oxo-7-thioxo-6,8-diazaspiro[3.4]octan-6-yl]-3-(trifluoromethyl)pyridine-2-carbonitrile, Cpd 105

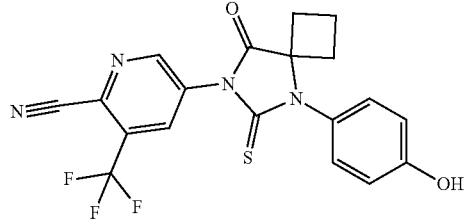 [SMILES: N#Cc1ncc(N2C(=O)C3(CCC3)N(c3ccc(O)cc3)C2=S)cc1C(F)(F)F]

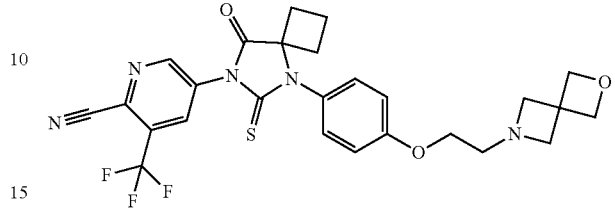

1-(4-Hydroxy-phenylamino)-cyclobutanecarbonitrile (6.93 g, 29.1 mmol) and freshly prepared 5-Isothiocyanato-3-trifluoromethyl-pyridine-2-carbonitrile (6.67 g, 29.1 mmol) were heated overnight at 60° C. in DMA (116 mL) and then allowed to cool to room temperature. The mixture was diluted with MeOH (58 mL) and 1M HCl (58 mL) was added. The stirring was maintained at room temperature for 1 h. EA (500 mL) was added and the solution washed with water (250 mL), saturated NaHCO$_3$ (250 mL) and brine (250 mL). The combined aqueous layers were back extracted with EA (500 mL). The organic layers were dried over MgSO$_4$, filtered and concentrated to dryness. The crude material was purified by chromatography over silica gel (gradient of EA in heptane from 0 to 65%). The fractions with product were collected and concentrated under reduced pressure.

Crystallization from ACN (50 mL) gave a white solid (7.92 g, 63%). $^1$H NMR (300 MHz, DMSO-d$_6$) δ 1.45-1.66 (m, 1H), 1.87-2.07 (m, 1H), 2.35-2.49 (m, 2H), 2.54-2.71 (m, 2H), 6.95 (d, J=8.7 Hz, 2H), 7.18 (d, J=8.7 Hz, 2H), 8.76 (d, J=2.0 Hz, 1H), 9.22 (d, J=2.0 Hz, 1H), 9.92 (s, 1H). C$_{19}$H$_{13}$F$_3$N$_4$O$_2$S MS m/z 419 (M+H)$^+$.

5-[5-(4-Hydroxy-phenyl)-8-oxo-6-thioxo-5,7-diaza-spiro[3.4]oct-7-yl]-3-trifluoromethyl-pyridine-2-carbonitrile (0.57 g, 1.36 mmol), 2-(2-Oxa-6-aza-spiro[3.3]hept-6-yl)-ethanol (0.195 g, 1.36 mmol) and triphenylphosphine (0.71 g, 2.72 mmol) were dissolved in dry THF (15 mL) under nitrogen atmosphere and heated at 65° C. A solution of Diisopropyl azodicarboxylate (DIAD, 0.54 mL, 2.72 mmol) in THF (5 mL) was added dropwise over 15-20 min. Upon completion of the addition, the reaction was continued for 2 h at the same temperature. The mixture was then allowed to cool and concentrate to dryness. The crude residue was chromatographed over silica gel (gradient of MeOH in DCM from 0 to 10%). The pure fractions were concentrated to an amorphous solid. Triturating in diethyl ether gave a white powder (0.0157 g, 21%). $^1$H NMR (300 MHz, Chloroform-d) δ 1.58-1.79 (m, 1H), 2.09-2.34 (m, 1H), 2.46-2.76 (m, 4H), 2.87 (t, J=5.2 Hz, 2H), 3.57 (s, 4H), 4.05 (t, J=5.2 Hz, 2H), 4.77 (s, 4H), 7.07 (d, J=9.0 Hz, 2H), 7.22 (d, J=9.0 Hz, 2H), 8.36 (d, J=2.3 Hz, 1H), 9.10 (d, J=2.3 Hz, 1H). C26H24F3N5O3S MS m/z 544 (M+H)$^+$.

Following the procedure described in Example 3, above, selecting and substituting the appropriate reagents, starting materials, and purification methods, and adjusting reaction temperatures, times and other variables or parameters, as needed or desirable, as would be readily recognized by those skilled in the art, the following compounds of formula (I) of the invention were prepared.

| Cpd No. | Structure | Compound Name & Physical Data |
|---|---|---|
| H-2 | (structure) | 5-[8-[4-[(1-methyl-4-piperidyl)oxy]phenyl]-5,7-dioxo-6,8-diazaspiro[3.4]octan-6-yl]-3-(trifluoromethyl)pyridine-2-carbonitrile. $^1$H NMR (300 MHz, Chloroform-d) δ 1.60-1.82 (m, 1H), 1.84-2.01 (m, 2H), 2.02-2.16 (m, 2H), 2.19-2.32 (m, 2H), 2.36 (s, 3H), 2.44-2.69 (m, 5H), 2.69-2.86 (m, 2H), 4.21-4.65 (m, 1H), 7.04 (d, J = 8.8 Hz, 2H), 7.22 (d, J = 8.8 Hz, 2H), 8.59 (s, 1H), 9.35 (s, 1H). C$_{25}$H$_{24}$F$_3$N$_5$O$_3$ MS m/z 516 (M + H)$^+$ |

| Cpd No. | Structure | Compound Name & Physical Data |
|---|---|---|
| 142 | 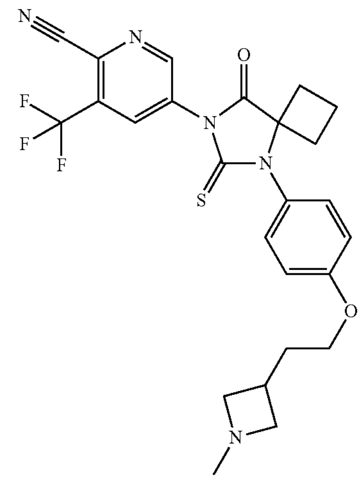 [SMILES: CN1CC(CCOc2ccc(N3C(=S)N(c4cnc(C#N)c(C(F)(F)F)c4)C(=O)C34CCC4)cc2)C1] | 5-[8-[4-[2-(1-methylazetidin-3-yl)ethoxy]phenyl]-5-oxo-7-thioxo-6,8-diazaspiro[3.4]octan-6-yl]-3-(trifluoromethyl)pyridine-2-carbonitrile. <br> $^1$H NMR (300 MHz, Chloroform-d) δ 1.22-1.43 (m, 1H), 1.72-1.90 (m, 3H), 2.13 (s, 3H), 2.16-2.28 (m, 3H), 2.29-2.40 (m, 2H), 2.81-2.90 (m, 2H), 3.31-3.41 (m, 2H), 3.69 (t, J = 5.9 Hz, 2H), 6.71 (d, J = 8.5 Hz, 2H), 6.91 (d, J = 8.6 Hz, 2H), 8.16 (s, 1H), 8.91 (s, 1H). <br> $C_{25}H_{24}F_3N_5O_2S$ <br> MS m/z 516 (M + H)$^+$. |
| 110 | 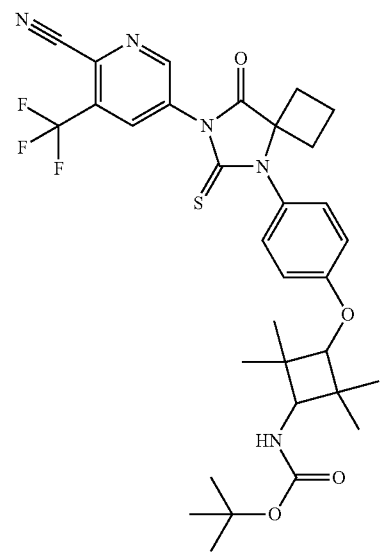 [SMILES: CC(C)(C)OC(=O)NC1C(C)(C)C(Oc2ccc(N3C(=S)N(c4cnc(C#N)c(C(F)(F)F)c4)C(=O)C34CCC4)cc2)C1(C)C] | tert-butyl N-[3-[4-[6-[6-cyano-5-(trifluoromethyl)-3-pyridyl]-5-oxo-7-thioxo-6,8-diazaspiro[3.4]octan-8-yl]phenoxy]-2,2,4,4-tetramethyl-cyclobutyl]carbamate. <br> $^1$H NMR (300 MHz, Chloroform-d) δ 1.17 (s, 6H), 1.45 (s, 9H), 1.62-1.80 (m, 1H), 1.46 (s, 6H), 2.07-2.38 (m, 1H), 2.48-2.78 (m, 4H), 7.03 (d, J = 8.3 Hz, 2H), 7.18 (d, J = 8.3 Hz, 2H), 8.37 (s, 1H), 9.10 (s, 1H). <br> $C_{32}H_{36}F_3N_5O_4S$ <br> MS m/z 644 (M + H)$^+$. |
| 104 | 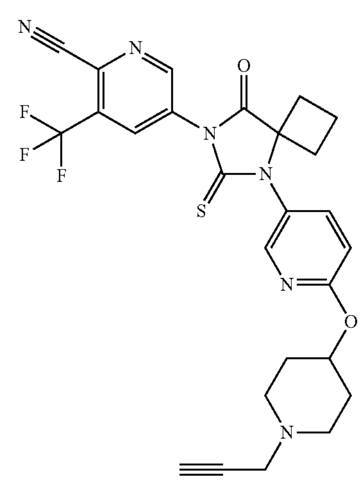 [SMILES: C#CCN1CCC(Oc2ccc(N3C(=S)N(c4cnc(C#N)c(C(F)(F)F)c4)C(=O)C34CCC4)cn2)CC1] | 5-[5-oxo-8-[6-[(1-prop-2-ynyl-4-piperidyl)oxy]-3-pyridyl]-7-thioxo-6,8-diazaspiro[3.4]octan-6-yl]-3-(trifluoromethyl)pyridine-2-carbonitrile. <br> $^1$H NMR (300 MHz, Chloroform-d) δ 1.64-1.83 (m, 1H), 2.19-2.43 (m, 3H), 2.42-2.63 (m, 3H), 2.63-2.82 (m, 4H), 3.22-3.41 (m, 2H), 3.41-3.60 (m, 2H), 3.90 (s, 2H), 5.48-5.54 (m, 1H), 6.98 (d, J = 8.5 Hz, 1H), 7.59 (d, J = 8.5 Hz, 1H), 8.15 (s, 1H), 8.35 (s, 1H), 9.10 (s, 1H) <br> $C_{26}H_{23}F_3N_6O_2S$ <br> MS m/z 541 (M + H)$^+$. |

| Cpd No. | Structure | Compound Name & Physical Data |
|---|---|---|
| 91 | 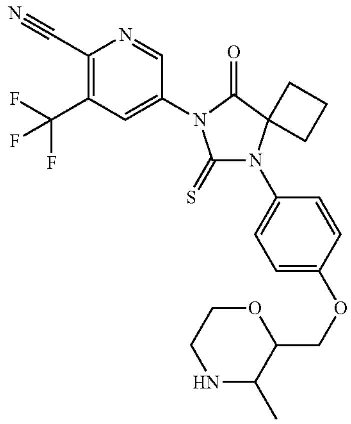 [SMILES: CC1NCCOC1COc1ccc(N2C(=S)N(c3cnc(C#N)c(C(F)(F)F)c3)C(=O)C23CCC3)cc1] | (R,S),(R,S)-5-[8-[4-[(5-methylmorpholin-2-yl)methoxy]phenyl]-5-oxo-7-thioxo-6,8-diazaspiro[3.4]octan-6-yl]-3-(trifluoromethyl)pyridine-2-carbonitrile.<br>¹H NMR (300 MHz, Chloroform-d) δ 1.21 (d, J = 6.7 Hz, 3H), 1.59-1.78 (m, 1H), 2 (br s, 1H) 2.13-2.32 (m, 1H), 2.49-2.76 (m, 4H), 3.00-3.16 (m, 3H), 3.51-3.65 (m, 1H), 3.72-3.83 (m, 1H), 3.95-4.08 (m, 1H), 4.13-4.22 (m, 1H), 4.22-4.34 (m, 1H), 7.12 (d, J = 8.8 Hz, 2H), 7.22 (d, J = 8.8 Hz, 2H), 8.37 (d, J = 2.2 Hz, 1H), 9.10 (d, J = 2.1 Hz, 1H).<br>$C_{25}H_{24}F_3N_5O_3S$<br>MS m/z 532 (M + H)⁺. |
| 87 | 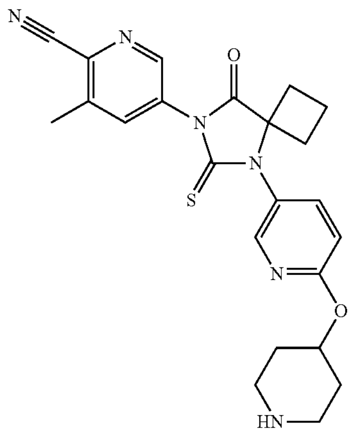 [SMILES: Cc1cc(N2C(=O)C3(CCC3)N(c3ccc(OC4CCNCC4)nc3)C2=S)cnc1C#N] | 3-methyl-5-[5-oxo-8-[6-(4-piperidyloxy)-3-pyridyl]-7-thioxo-6,8-diazaspiro[3.4]octan-6-yl]pyridine-2-carbonitrile.<br>¹H NMR (300 MHz, DMSO-d₆) δ 1.49-1.69 (m, 1H), 1.84-2.06 (m, 3H), 2.11-2.29 (m, 2H), 2.29-2.47 (m, 2H), 2.55-2.70 (m, 2H), 3.02-3.20 (m, 2H), 3.20-3.36 (m, 2H), 5.20-5.40 (m, 1H), 7.07 (d, J = 8.8 Hz, 1H), 7.82 (dd, J = 8.8, 2.6 Hz, 1H), 8.13 (d, J = 2.2 Hz, 1H), 8.23 (d, J = 2.6 Hz, 1H), 8.71 (d, J = 2.1 Hz, 1H), 8.99 (br s, 2H).<br>$C_{23}H_{24}N_6O_2S$•HCl<br>MS m/z 449 (M + H)⁺. |
| 83 | 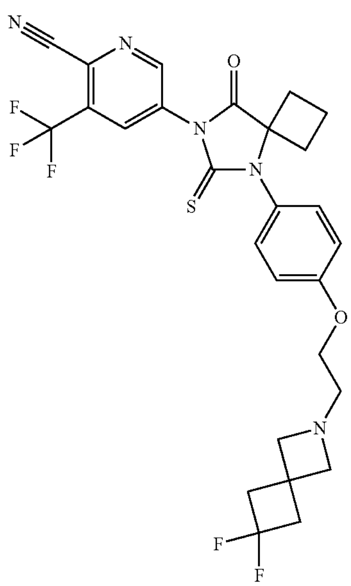 [SMILES: N#Cc1ncc(N2C(=O)C3(CCC3)N(c3ccc(OCCN4CC5(C4)CC(F)(F)C5)cc3)C2=S)cc1C(F)(F)F] | 5-[8-[4-[2-(2,2-difluoro-6-azaspiro[3.3]heptan-6-yl)ethoxy]phenyl]-5-oxo-7-thioxo-6,8-diazaspiro[3.4]octan-6-yl]-3-(trifluoromethyl)pyridine-2-carbonitrile.<br>¹H NMR (300 MHz, Chloroform-d) δ 1.57-1.79 (m, 1H), 2.13-2.38 (m, 1H), 2.49-2.68 (m, 4H), 2.72 (t, J = 12.3 Hz, 4H), 2.91 (t, J = 5.0 Hz, 2H), 3.48 (s, 4H), 4.07 (t, J = 5.1 Hz, 2H), 7.07 (d, J = 8.8 Hz, 2H), 7.22 (d, J = 8.8 Hz, 2H), 8.36 (d, J = 2.2 Hz, 1H), 9.10 (d, J = 2.2 Hz, 1H).<br>$C_{27}H_{24}F_5N_5O_2S$<br>MS m/z 578 (M + H)⁺. |

| Cpd No. | Structure | Compound Name & Physical Data |
|---------|-----------|-------------------------------|
| 82 | 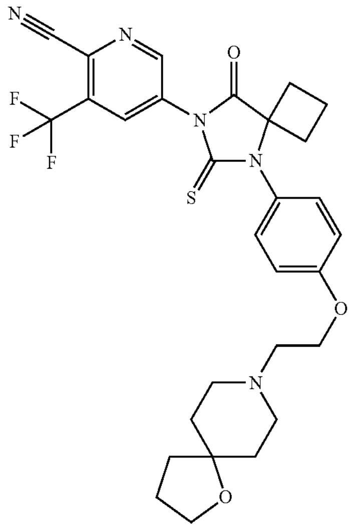 [SMILES: N#Cc1ncc(N2C(=O)C3(CCC3)N(c3ccc(OCCN4CCC5(CCCO5)CC4)cc3)C2=S)cc1C(F)(F)F] | 5-[8-[4-[2-(3-oxa-8-azaspiro[4.5]decan-8-yl)ethoxy]phenyl]-5-oxo-7-thioxo-6,8-diazaspiro[3.4]octan-6-yl]-3-(trifluoromethyl)pyridine-2-carbonitrile.<br>$^1$H NMR (300 MHz, Chloroform-d) δ 1.60-1.90 (m, 8H), 2.14-2.37 (m, 1H), 2.49-2.78 (m, 7H), 2.84-3.10 (m, 2H), 3.57 (s, 2H), 3.86 (t, J = 7.2 Hz, 2H), 4.09-4.50 (m, 2H), 7.10 (d, J = 8.8 Hz, 2H), 7.22 (d, J = 8.8 Hz, 2H), 8.36 (d, J = 2.2 Hz, 1H), 9.10 (d, J = 2.2 Hz, 1H).<br>$C_{29}H_{30}F_3N_5O_3S$<br>MS m/z 586 (M + H)$^+$. |
| 74 | 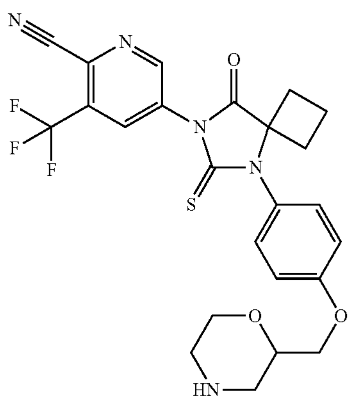 [SMILES: N#Cc1ncc(N2C(=O)C3(CCC3)N(c3ccc(OCC4CNCCO4)cc3)C2=S)cc1C(F)(F)F] | 5-[8-[4-(morpholin-2-ylmethoxy)phenyl]-5-oxo-7-thioxo-6,8-diazaspiro[3.4]octan-6-yl]-3-(trifluoromethyl)pyridine-2-carbonitrile.<br>$^1$H NMR (300 MHz, Chloroform-d) δ 1.58-1.79 (m, 1H), 2.17 (br s, 1H), 2.47-2.75 (m, 5H), 2.76-2.88 (m, 1H), 2.88-3.05 (m, 2H), 3.06-3.20 (m, 1H), 3.68-3.84 (m, 1H), 3.89-4.04 (m, 3H), 4.04-4.13 (m, 1H), 7.10 (d, J = 8.8 Hz, 2H), 7.22 (d, J = 8.7 Hz, 2H), 8.36 (d, J = 2.2 Hz, 1H), 9.10 (d, J = 2.2 Hz, 1H).<br>$C_{24}H_{22}F_3N_5O_3S$<br>MS m/z 518 (M + H)$^+$. |
| 71 | 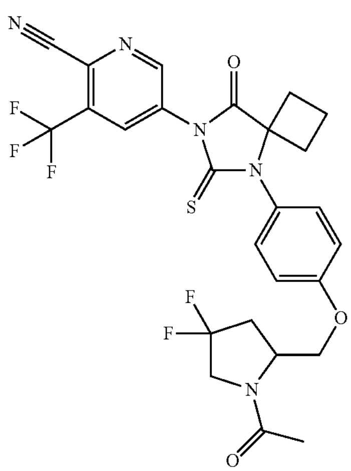 [SMILES: CC(=O)N1CC(F)(F)CC1COc1ccc(N2C(=S)N(c3cnc(C#N)c(C(F)(F)F)c3)C(=O)C23CCC3)cc1] | 5-[8-[4-[(1-acetyl-4,4-difluoro-pyrrolidin-2-yl)methoxy]phenyl]-5-oxo-7-thioxo-6,8-diazaspiro[3.4]octan-6-yl]-3-(trifluoromethyl)pyridine-2-carbonitrile.<br>$^1$H NMR (300 MHz, Chloroform-d) δ 1.62-1.82 (m, 1H), 2.08 (s, 3H), 2.15-2.34 (m, 1H), 2.47-2.84 (m, 6H), 3.90 (t, J = 12.1 Hz, 2H), 4.17-4.34 (m, 2H), 4.63-4.80 (m, 1H), 7.14 (d, J = 8.5 Hz, 2H), 7.23 (d, J = 8.6 Hz, 2H), 8.36 (d, J = 2.2 Hz, 1H), 9.10 (d, J = 2.2 Hz, 1H).<br>$C_{26}H_{22}F_5N_5O_3S$<br>MS m/z 580 (M + H)$^+$. |

| Cpd No. | Structure | Compound Name & Physical Data |
|---|---|---|
| 54 | 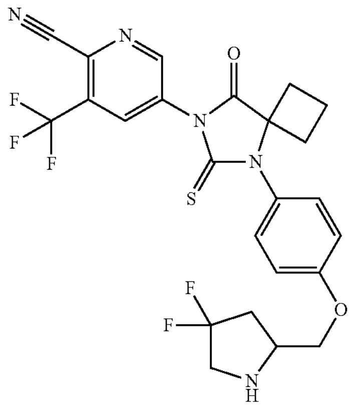 [SMILES: N#Cc1ncc(N2C(=O)C3(CCC3)N(c3ccc(OCC4CC(F)(F)CN4)cc3)C2=S)cc1C(F)(F)F] | 5-[8-[4-[(4,4-difluoropyrrolidin-2-yl)methoxy]phenyl]-5-oxo-7-thioxo-6,8-diazaspiro[3.4]octan-6-yl]-3-(trifluoromethyl)pyridine-2-carbonitrile.<br>¹H NMR (300 MHz, Chloroform-d) δ 1.63-1.77 (m, 1H), 2.10-2.33 (m, 2H), 2.35-2.76 (m, 6H), 3.15-3.45 (m, 2H), 3.71-3.90 (m, 1H), 3.97-4.17 (m, 2H), 7.10 (d, J = 8.7 Hz, 2H), 7.24 (d, J = 6.7 Hz, 2H), 8.37 (d, J = 2.2 Hz, 1H), 9.10 (d, J = 2.1 Hz, 1H).<br>$C_{24}H_{20}F_5N_5O_2S$<br>MS m/z 538 (M + H)⁺. |
| 56 | 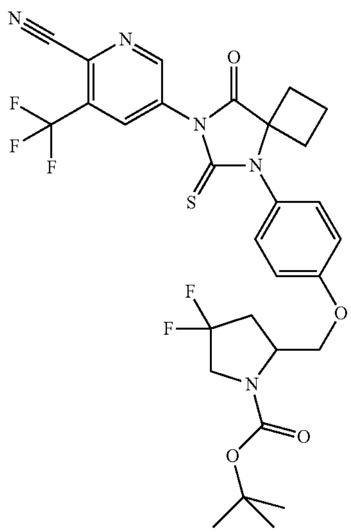 [SMILES: CC(C)(C)OC(=O)N1CC(F)(F)CC1COc1ccc(N2C(=S)N(c3cnc(C#N)c(C(F)(F)F)c3)C(=O)C23CCC3)cc1] | tert-butyl 2-[[4-[6-[6-cyano-5-(trifluoromethyl)-3-pyridyl]-5-oxo-7-thioxo-6,8-diazaspiro[3.4]octan-8-yl]phenoxy]methyl]-4,4-difluoro-pyrrolidine-1-carboxylate.<br>¹H NMR (300 MHz, Chloroform-d) δ 1.49 (s, 9H), 1.60-1.79 (m, 1H), 2.14-2.37 (m, 1H), 2.47-2.77 (m, 6H), 3.71 (q, J = 12.5 Hz, 1H), 3.79-4.02 (m, 1H), 4.03-4.22 (m, 1H), 4.22-4.35 (m, 1H), 4.35-4.56 (m, 1H), 7.13 (d, J = 8.5 Hz, 2H), 7.24 (d, J = 8.4 Hz, 2H), 8.37 (d, J = 2.2 Hz, 1H), 9.10 (d, J = 2.2 Hz, 1H).<br>$C_{29}H_{28}F_5N_5O_4S$<br>MS m/z 638 (M + H)⁺. |
| 63 | 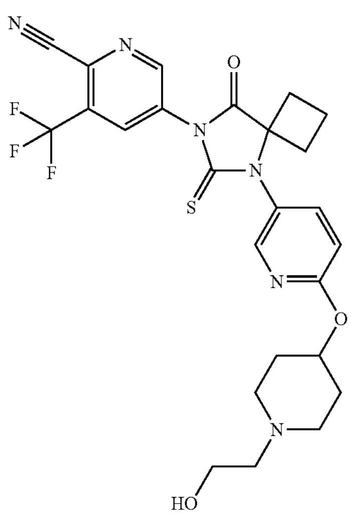 [SMILES: N#Cc1ncc(N2C(=O)C3(CCC3)N(c3ccc(OC4CCN(CCO)CC4)nc3)C2=S)cc1C(F)(F)F] | 5-[8-[6-[[1-(2-hydroxyethyl)-4-piperidyl]oxy]-3-pyridyl]-5-oxo-7-thioxo-6,8-diazaspiro[3.4]octan-6-yl]-3-(trifluoromethyl)pyridine-2-carbonitrile.<br>¹H NMR (300 MHz, DMSO-d₆) δ 1.50-1.71 (m, 1H), 1.88-2.19 (m, 3H), 2.19-2.36 (m, 2H), 2.37-2.49 (m, 2H), 2.57-2.75 (m, 2H), 3.08-3.27 (m, 3H), 3.45 (s, 1H), 3.53-3.69 (m, 2H), 3.74-3.92 (m, 2H), 5.14-5.45 (m, 2H), 7.08 (d, J = 8.8 Hz, 1H), 7.81 (dd, J = 8.9, 2.6 Hz, 1H), 8.23 (d, J = 2.6 Hz, 1H), 8.75 (d, J = 2.1 Hz, 1H), 9.22 (d, J = 2.0 Hz, 1H), 10.33 (br s, 1H).<br>$C_{25}H_{25}F_3N_6O_3S \cdot HCl$<br>MS m/z 547 (M + H)⁺. |

-continued

| Cpd No. | Structure | Compound Name & Physical Data |
|---|---|---|
| 44 | 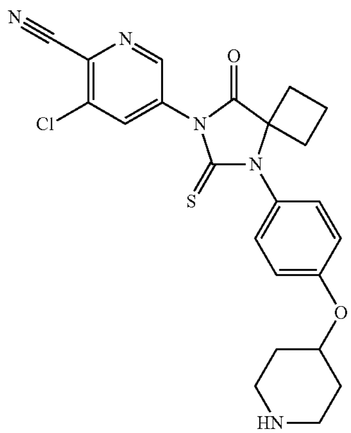 [SMILES: N#Cc1ncc(N2C(=O)C3(CCC3)N(c3ccc(OC4CCNCC4)cc3)C2=S)cc1Cl] | 3-chloro-5-[5-oxo-8-[4-(4-piperidyloxy)phenyl]-7-thioxo-6,8-diazaspiro[3.4]octan-6-yl]pyridine-2-carbonitrile.<br>$^1$H NMR (300 MHz, DMSO-d$_6$) δ 1.45-1.63 (m, 1H), 1.82-2.05 (m, 3H), 2.09-2.25 (m, 2H), 2.34-2.46 (m, 2H), 2.54-2.67 (m, 2H), 3.02-3.17 (m, 2H), 3.20-3.29 (m, 2H), 4.63-4.84 (m, 1H), 7.21 (d, J = 8.5 Hz, 2H), 7.33 (d, J = 8.6 Hz, 2H), 8.53 (d, J = 2.0 Hz, 1H), 8.89 (d, J = 1.9 Hz, 1H), 9.03 (br s, 2H).<br>C$_{23}$H$_{22}$ClN$_5$O$_2$S•HCl<br>MS m/z 468 (M + H)$^+$. |
| 24 | 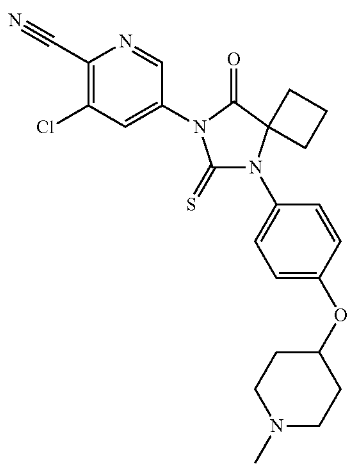 [SMILES: CN1CCC(Oc2ccc(N3C(=S)N(c4cnc(C#N)c(Cl)c4)C(=O)C34CCC4)cc2)CC1] | 3-chloro-5-[8-[4-[(1-methyl-4-piperidyl)oxy]phenyl]-5-oxo-7-thioxo-6,8-diazaspiro[3.4]octan-6-yl]pyridine-2-carbonitrile.<br>$^1$H NMR (300 MHz, DMSO-d$_6$) δ 1.46-1.63 (m, 1H), 1.88-2.35 (m, 5H), 2.35-2.47 (m, 2H), 2.54-2.69 (m, 2H), 2.77 (br s, 3H), 2.98-3.26 (m, 2H), 3.26-3.34 (m, 1H), 3.42-3.54 (m, 1H), 4.42-4.96 (m, 1H), 7.12-7.28 (m, 2H), 7.28-7.46 (m, 2H), 8.54 (d, J = 2.0 Hz, 1H), 8.90 (d, J = 2.0 Hz, 1H), 10.80 (s, 1H).<br>C$_{24}$H$_{24}$ClN$_5$O$_2$S•HCl<br>MS m/z 482 (M + H)$^+$. |
| 25 | 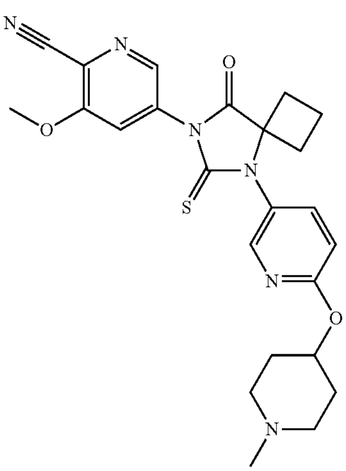 [SMILES: COc1cc(N2C(=O)C3(CCC3)N(c3ccc(OC4CCN(C)CC4)nc3)C2=S)cnc1C#N] | 3-methoxy-5-[8-[6-[(1-methyl-4-piperidyl)oxy]-3-pyridyl]-5-oxo-7-thioxo-6,8-diazaspiro[3.4]octan-6-yl]pyridine-2-carbonitrile.<br>$^1$H NMR (300 MHz, DMSO-d$_6$) δ 1.47-1.70 (m, 1H), 1.86-2.10 (m, 2H), 2.11-2.24 (m, 2H), 2.22-2.37 (m, 1H), 2.37-2.46 (m, 2H), 2.57-2.71 (m, 2H), 2.78 (dd, J = 11.6, 4.6 Hz, 3H), 3.05-3.28 (m, 2H), 3.30-3.42 (m, 1H), 3.42-3.54 (m, 1H), 3.99 (s, 3H), 5.16-5.42 (m, 1H), 7.07 (dd, J = 8.8, 4.1 Hz, 1H), 7.82 (ddd, J = 9.0, 6.6, 2.5 Hz, 1H), 8.04 (d, J = 1.8 Hz, 1H), 8.24 (dd, J = 4.5, 2.5 Hz, 1H), 8.45 (d, J = 1.8 Hz, 1H), 10.62 (br s, 1H).<br>C$_{24}$H$_{26}$N$_6$O$_3$S•HCl<br>MS m/z 479 (M + H)$^+$. |

| Cpd No. | Structure | Compound Name & Physical Data |
|---|---|---|
| 23 | 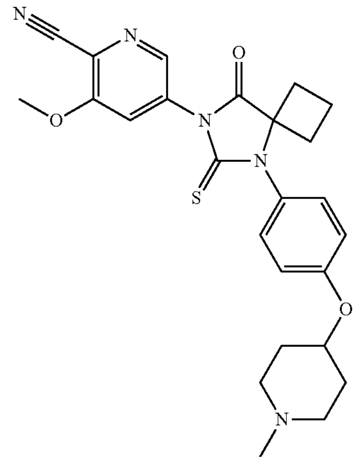 [SMILES: COc1cc(N2C(=O)C3(CCC3)N(c3ccc(OC4CCN(C)CC4)cc3)C2=S)cnc1C#N] | 3-methoxy-5-[8-[4-[(1-methyl-4-piperidyl)oxy]phenyl]-5-oxo-7-thioxo-6,8-diazaspiro[3.4]octan-6-yl]pyridine-2-carbonitrile. $^1$H NMR (300 MHz, DMSO-$d_6$) δ 1.44-1.63 (m, 1H), 1.77-2.04 (m, 2H), 2.04-2.19 (m, 2H), 2.23-2.36 (m, 1H), 2.36-2.46 (m, 2H), 2.56-2.68 (m, 2H), 2.79 (br s, 3H), 3.00-3.27 (m, 2H), 3.29-3.36 (m, 1H), 3.43-3.61 (m, 1H), 3.99 (s, 3H), 4.57-4.90 (m, 1H), 7.21 (d, J = 8.4 Hz, 2H), 7.35 (d, J = 8.4 Hz, 2H), 8.04 (d, J = 1.8 Hz, 1H), 8.45 (d, J = 1.7 Hz, 1H), 10.17 (br s, 1H). $C_{25}H_{27}N_5O_3S$•HCl MS m/z 478 (M + H)$^+$. |
| 18 | 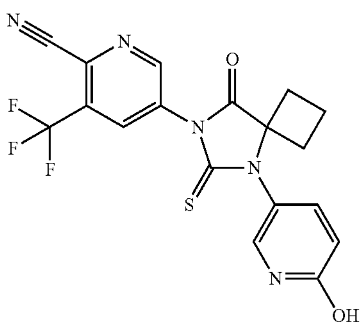 [SMILES: N#Cc1ncc(N2C(=O)C3(CCC3)N(c3ccc(O)nc3)C2=S)cc1C(F)(F)F] | 5-[8-(6-hydroxy-3-pyridyl)-5-oxo-7-thioxo-6,8-diazaspiro[3.4]octan-6-yl]-3-(trifluoromethyl)pyridine-2-carbonitrile. $^1$H NMR (300 MHz, DMSO-$d_6$) δ 1.58-1.81 (m, 1H), 1.87-2.13 (m, 1H), 2.36-2.68 (m, 4H), 6.51 (d, J = 9.6 Hz, 1H), 7.43 (dd, J=9.7, 2.7 Hz, 1H), 7.60 (d, J = 2.8 Hz, 1H), 8.71 (d, J = 2.1 Hz, 1H), 9.18 (d, J = 2.1 Hz, 1H), 11.98 (br s, 1H). $C_{18}H_{12}F_3N_5O_2S$ MS m/z 420 (M + H)$^+$. |

Example 4

5-[5-oxo-8-[4-[(1-prop-2-ynyl-4-piperidyl)oxy]phenyl]-7-thioxo-6,8-diazaspiro[3.4]octan-6-yl]-3-(trifluoromethyl)pyridine-2-carbonitrile

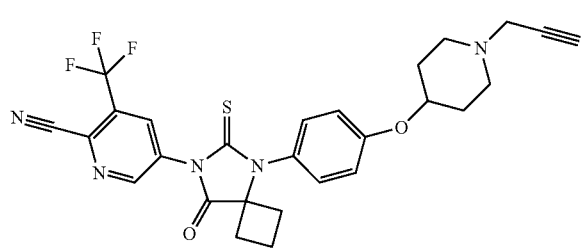 [SMILES: C#CCN1CCC(Oc2ccc(N3C(=S)N(c4cnc(C#N)c(C(F)(F)F)c4)C(=O)C34CCC4)cc2)CC1]

To a solution of 5-(8-oxo-5-(4-(piperidin-4-yloxy)phenyl)-6-thioxo-5,7-diazaspiro[3.4]octan-7-yl)-3-(trifluoromethyl)picolinonitrile (0.3 g, 0.598 mmol) in Et$_3$N (0.125 mL, 0.897 mmol) and MeCN (4 mL) was added propargyl bromide 80% in toluene (0.077 mL, 0.718 mmol). After stirring at RT for 2 h, the solvent was removed under reduced pressure and the residue was diluted with DCM (60 mL) and the organic layer was washed with water and brine. The organic layer was dried over MgSO$_4$, filtered and concentrated. The crude was purified by chromatography over silica gel (gradient of MeOH/DCM (1/50) from 0 to 100%). The fractions with product were collected and concentrated under reduced pressure. The residue was then purified by preparative reverse phase HPLC chromatography (from 70% aqueous 25 mM NH$_4$HCO$_3$/30% ACN to 27% aqueous 25 mM NH$_4$HCO$_3$/73% ACN). Desired fractions were collected, concentrated and aqueous layer extracted with DCM. Combined organic layers were dried over MgSO$_4$, filtered and concentrated to give a solid further triturated with Et$_2$O, filtered and dried to give 5-[5-oxo-8-[4-[(1-prop-2-ynyl-4-piperidyl)oxy]phenyl]-7-thioxo-6,8-diazaspiro[3.4]octan-6-yl]-3-(trifluoromethyl)pyridine-2-carbonitrile (0.138 g, 42%) as a yellow solid. $^1$H NMR (300 MHz, Chloroform-d) δ 1.59-1.85 (m, 2H), 1.85-2.02 (m, 2H), 2.00-2.16 (m, 2H), 2.28 (s, 1H), 2.45-2.76 (m, 6H), 2.76-2.98 (m, 2H), 3.36 (s, 2H), 4.29-4.50 (m, 1H), 7.08 (d, J=8.5 Hz, 2H), 7.21 (d, J=8.4 Hz, 2H), 8.37 (d, J=2.3 Hz, 1H), 9.10 (d, J=2.3 Hz, 1H). $C_{27}H_{24}F_3N_5O_2S$ MS m/z 540 (M+H)$^+$

Example 5

5-[8-[4-(1-methyl-1-oxido-piperidin-1-ium-4-yl)oxyphenyl]-5-oxo-7-thioxo-6,8-diazaspiro[3.4]octan-6-yl]-3-(trifluoromethyl)pyridine-2-carbonitrile Cpd 191

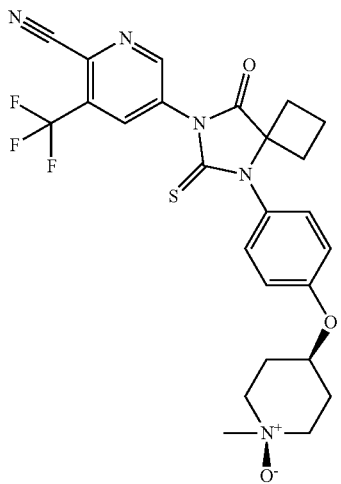 [SMILES: C[N@+]1([O-])CC[C@@H](Oc2ccc(N3C(=S)N(c4cnc(C#N)c(C(F)(F)F)c4)C(=O)C34CCC4)cc2)CC1]

And

5-[8-[4-(1-methyl-1-oxido-piperidin-1-ium-4-yl)oxyphenyl]-5-oxo-7-thioxo-6,8-diazaspiro[3.4]octan-6-yl]-3-(trifluoromethyl)pyridine-2-carbonitrile Cpd 190

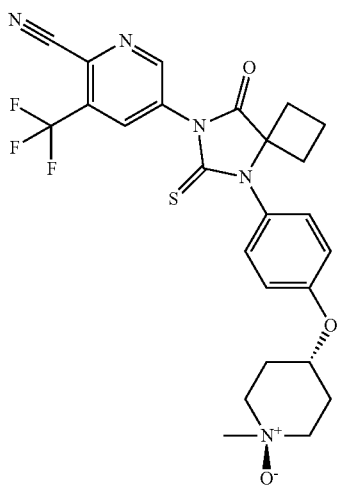 [SMILES: C[N@+]1([O-])CC[C@H](Oc2ccc(N3C(=S)N(c4cnc(C#N)c(C(F)(F)F)c4)C(=O)C34CCC4)cc2)CC1]

To a solution of 5-(5-(4-((1-methylpiperidin-4-yl)oxy)phenyl)-8-oxo-6-thioxo-5,7-diazaspiro[3.4]octan-7-yl)-3-(trifluoromethyl)picolinonitrile (9.29 g, 18.033 mmol) in dry chloroform (250 mL) was added at 0° C. under a nitrogen atmosphere, 3-chloroperbenzoic acid (6.062 g, 27.05 mmol). Upon reaction completion (3 h), the mixture was partitioned between aqueous 1.0M $Na_2CO_3$ and DCM. The aqueous layer was extracted with DCM. The combined organic layers were dried over $MgSO_4$, filtered and concentrated to dryness to give crude cis/trans 5-[8-[4-(1-methyl-1-oxido-piperidin-1-ium-4-yl)oxyphenyl]-5-oxo-7-thioxo-6,8-diazaspiro[3.4]octan-6-yl]-3-(trifluoromethyl)pyridine-2-carbonitrile. The reaction was repeated a second time to generate a total of 13.27 g of crude cis/trans 5-[8-[4-(1-methyl-1-oxido-piperidin-1-ium-4-yl)oxyphenyl]-5-oxo-7-thioxo-6,8-diazaspiro[3.4]octan-6-yl]-3-(trifluoromethyl)pyridine-2-carbonitrile. The crude was purified by reverse phase chromatography (from 81% aqueous 25 mM $NH_4HCO_3$/19% MeCN—MeOH to 45% aqueous 25 mM $NH_4HCO_{3/55}$% MeCN—MeOH). The isomeric mixture was separated by reverse phase chromatography (from 72% aqueous 0.1% HCOOH/28% ACN-MeOH to 36% aqueous 0.1% HCOOH/64% ACN-MeOH) to give first Cpd 191(cis isomer, first product to elute) and then Cpd 190 (trans isomer, second product to elute).

For each set of collected fractions, the aqueous layer was neutralized with solid $Na_2CO_3$, extracted with DCM, dried over $MgSO_4$, filtered, and concentrated to dryness to generate Cpd 191 and Cpd 190 as a foam, each further triturated to generate a yellow solid: Cpd 191, (cis isomer, 2.1 g, 30%) and Cpd 190 (trans isomer, 0.58 g, 8.7%).

Cpd 191: $^1$H NMR (300 MHz, DMSO-$d_6$) δ 1.45-1.64 (m, 1H), 1.78-2.04 (m, 4H), 2.34-2.46 (m, 3H), 2.62 (m, 2H), 3.00-3.12 (m, 2H), 3.20 (s, 3H), 3.49-3.66 (m, 2H), 4.72-4.83 (m, 1H), 7.21 (d, J=8.7 Hz, 2H), 7.34 (d, J=8.6 Hz, 2H), 8.76 (d, J=2.1 Hz, 1H), 9.22 (d, J=2.0 Hz, 1H). C25H24F3N5O3S MS m/z 532 (M+H)$^+$.

Cpd 190: $^1$H NMR (300 MHz, DMSO-$d_6$) δ 1.47-1.64 (m, 1H), 1.88-2.11 (m, 4H), 2.22-2.46 (m, 3H), 2.55-2.72 (m, 2H), 3.17 (s, 3H), 3.19-3.31 (m, 2H), 3.44-3.57 (m, 2H), 4.49-4.66 (m, 1H), 7.19 (d, J=8.6 Hz, 2H), 7.32 (d, J=8.5 Hz, 2H), 8.75 (s, 1H), 9.21 (s, 1H). C25H24F3N5O3S MS m/z 532 (M+H)$^+$.

Example 6

3-chloro-5-[8-[6-[(1-methyl-4-piperidyl)oxy]-3-pyridyl]-5-oxo-7-thioxo-6,8-diazaspiro[3.4]octan-6-yl]pyridine-2-carbonitrile Cpd 26

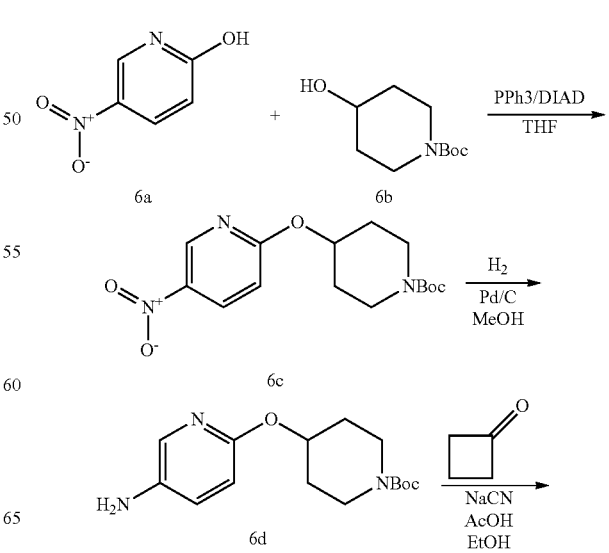

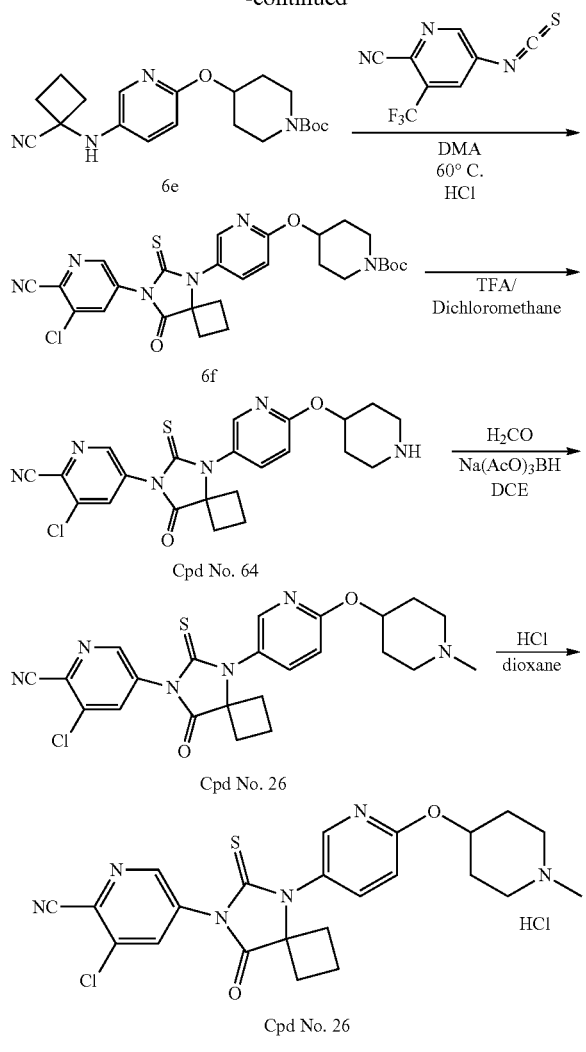

A. 4-(5-Nitro-pyridin-2-yloxy)-piperidine-1-carboxylic acid tert-butyl ester, 6c

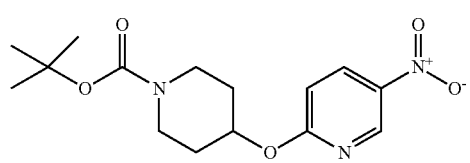 [SMILES: CC(C)(C)OC(=O)N1CCC(Oc2ccc([N+](=O)[O-])cn2)CC1]

To a solution of 2-Hydroxy-5-nitropyridine (10 g, 69.24 mmol) in Tetrahydrofuran (350 mL) at room temperature under nitrogen, 1-Boc-4-hydroxypiperidine (18.67 g, 90 mmol) and Triphenylphosphine (54.5 g, 207.7 mmol) were added. Finally DIAD (40.9 mL, 207.7 mmol) was added dropwise and the mixture was stirred at room temperature overnight. The crude material was poured onto water/NaHCO₃ and extracted with Ethyl acetate. The organic layer was dried over MgSO₄, filtered and concentrated to dryness. The residue was purified by flash chromatography over silica gel (Ethyl acetate-heptane gradient from 5% to 30%).

Pure fractions were combined, concentrated and dried under high vacuum to give the product (22.3 g, 99%). $C_{15}H_{22}N_3O_5$ MS m/z 224.2 (M−100+H)⁺.

B. 4-(5-Amino-pyridin-2-yloxy)-piperidine-1-carboxylic Acid Tert-Butyl Ester, 6d

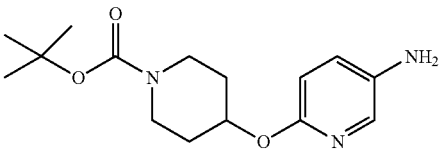 [SMILES: CC(C)(C)OC(=O)N1CCC(Oc2ccc(N)cn2)CC1]

A solution of 4-(5-Nitro-pyridin-2-yloxy)-piperidine-1-carboxylic acid tert-butyl ester (22.4 g, 69.24 mmol) in methanol (210 mL) was purged with nitrogen. Then Pd/C 10% wet catalyst (1.34 g) was added to the solution. The mixture was purged with hydrogen and stirred under a hydrogen atmosphere at room temperature for 14 h. The catalyst was removed by filtration through diatomaceous earth and the solvent evaporated under vacuum to afford the product (20.3 g, 100%). ¹H NMR (300 MHz, Chloroform-d) δ 1.46 (s, 9H), 1.56-1.80 (m, 2H), 1.80-2.11 (m, 2H), 3.06-3.39 (m, 2H), 3.62-3.95 (m, 2H), 5.05 (tt, J=7.8, 3.7 Hz, 1H), 6.53-6.59 (m, 1H), 7.01 (dd, J=8.7, 3.0 Hz, 1H), 7.62 (d, J=2.9 Hz, 1H). $C_{15}H_{23}N_3O_3$ MS m/z 294.2 (M+H)⁺.

C. 4-[5-(1-Cyano-cyclobutylamino)-pyridin-2-yloxy]-piperidine-1-carboxylic Acid Tert-Butyl Ester, 6e

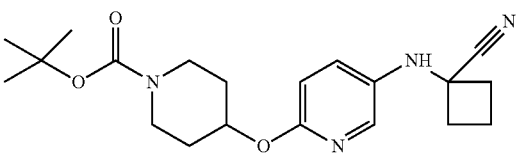 [SMILES: CC(C)(C)OC(=O)N1CCC(Oc2ccc(NC3(C#N)CCC3)cn2)CC1]

To a solution of 4-(5-Amino-pyridin-2-yloxy)-piperidine-1-carboxylic acid tert-butyl ester (20.3 g, 69.2 mmol) and Cyclobutanone (10.35 mL, 138.5 mmol) in Ethanol (56 mL) and Acetic acid (56 mL), sodium cyanide (13.57 g, 276.95 mmol) was added. The mixture was heated to 50° C. and stirred at this temperature for 15 h. The solution was then poured onto water followed by extraction with dichloromethane. The organic layer was separated and washed with brine, then dried over MgSO₄, filtered and concentrated. The product was purified by flash chromatography over silica gel (Methanol-Dichloromethane gradient from 0% to 10%). Fractions were combined and concentrated to dryness. The residue was recrystallized from diisopropyl ether to afford the product as a beige solid (17.75 g, 70%). ¹H NMR (300 MHz, Chloroform-d) δ 1.47 (s, 9H), 1.61-1.81 (m, 2H), 1.89-2.01 (m, 2H), 2.12-2.27 (m, 1H), 2.31-2.45 (m, 2H), 2.76 (ddd, J=11.8, 8.2, 5.7 Hz, 2H), 3.16-3.35 (m, 2H), 3.63-3.85 (m, 3H), 5.10 (dt, J=8.0, 4.1 Hz, 1H), 6.65 (d, J=8.8 Hz, 1H), 7.04 (dd, J=8.8, 2.9 Hz, 1H), 7.62 (d, J=2.9 Hz, 1H). $C_{20}H_{28}N_4O_3$ MS m/z 373.3 (M+H)⁺.

D. 4-{5-[7-(5-Chloro-6-cyano-pyridin-3-yl)-8-oxo-6-thioxo-5,7-diaza-spiro[3.4]oct-5-yl]-pyridin-2-yloxy}-piperidine-1-carboxylic Acid Tert-Butyl Ester, 6f

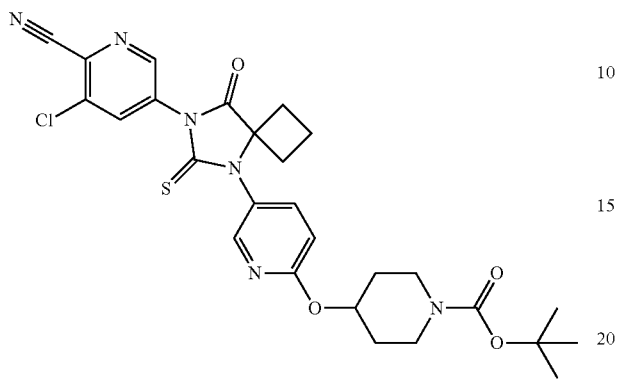

A solution of 4-[5-(1-Cyano-cyclobutylamino)-pyridin-2-yloxy]-piperidine-1-carboxylic acid tert-butyl ester (13.36 g, 35.86 mmol) and 3-Chloro-5-isothiocyanato-pyridine-2-carbonitrile (7.02 g, 35.86 mmol) in N,N-Dimethylacetamide was heated to 60° C. and stirred at that temperature for 15 h. The mixture was allowed to cool to room temperature. Methanol (50 mL) and 1M HCl (50 mL) were added. The mixture was stirred at room temperature for 30 min. The crude reaction mixture was quenched with a NaHCO$_3$ saturated solution and extracted with ethyl acetate. The organic layer was separated and washed with brine, then dried over MgSO$_4$, filtered and concentrated. The product was purified by flash chromatography over silica gel (Ethyl acetate-heptane gradient from 5% to 40%). Fractions were combined and concentrated to dryness to give the product as a foam (17.3 g, 84.9%). C27H29ClN6O4S MS m/z 513.0 (M−55)$^+$.

G. 3-chloro-5-[5-oxo-8-[6-(4-piperidyloxy)-3-pyridyl]-7-thioxo-6,8-diazaspiro[3.4]octan-6-yl]pyridine-2-carbonitrile, Cpd 64

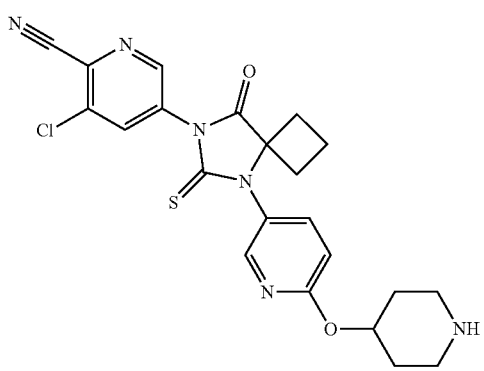 [SMILES: N#Cc1ncc(N2C(=O)C3(CCC3)N(c3ccc(OC4CCNCC4)nc3)C2=S)cc1Cl]

To a solution of 4-{5-[7-(5-Chloro-6-cyano-pyridin-3-yl)-8-oxo-6-thioxo-5,7-diaza-spiro[3.4]oct-5-yl]-pyridin-2-yloxy}-piperidine-1-carboxylic acid tert-butyl ester (17.3 g, 30.4 mmol) in Dichloromethane (90 mL), at 0° C. under Nitrogen, Trifluoroacetic acid (60 mL) was added. The mixture was then stirred at room temperature for 2 h, then evaporated to dryness. The residue was dissolved in dichloromethane, and washed with NaHCO$_3$ saturated solution. The organic layer was dried over MgSO$_4$, filtered and concentrated. The product was purified by flash chromatography over silica gel (Methanol-dichloromethane gradient from 0 to 10%). Product fractions were combined and concentrated to dryness to give the product as a foam (10.2 g, 72%). C22H21ClN6O2S MS m/z 468.9 (M+H)$^+$.

H. 3-chloro-5-[5-oxo-8-[6-(4-piperidyloxy)-3-pyridyl]-7-thioxo-6,8-diazaspiro[3.4]octan-6-yl]pyridine-2-carbonitrile Hydrochloride, Cpd 26

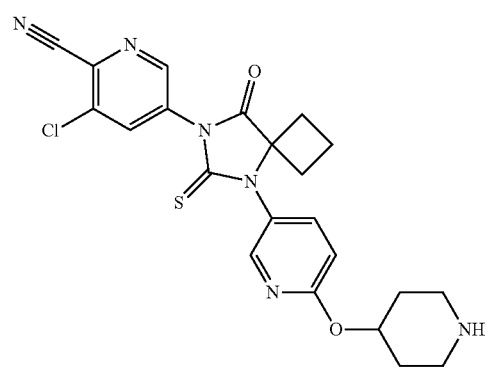 [SMILES: N#Cc1ncc(N2C(=O)C3(CCC3)N(c3ccc(OC4CCNCC4)nc3)C2=S)cc1Cl]

To a solution of 3-chloro-5-[5-oxo-8-[6-(4-piperidyloxy)-3-pyridyl]-7-thioxo-6,8-diazaspiro[3.4]octan-6-yl]pyridine-2-carbonitrile in ethyl acetate, a 4N Hydrogen chloride solution in dioxane was added, followed by evaporation of solvents. The obtained beige solid was suspended in 40 mL of acetonitrile and stirred at 50° C. for 20 min, then cooled to room temperature and collected by filtration. The white solid was then dried under reduced pressure to constant weight (6.4 g, 88%). $^1$H NMR (300 MHz, DMSO-d$_6$) δ 1.59 (d, J=10.7 Hz, 1H), 1.93-2.05 (m, 3H), 2.17-2.31 (m, 2H), 2.39-2.47 (m, 2H), 2.59-2.71 (m, 2H), 3.07-3.31 (m, 4H), 5.28-5.37 (m, 1H), 7.09 (d, J=8.8 Hz, 1H), 7.81 (dd, J=8.8, 2.6 Hz, 1H), 8.24 (d, J=2.6 Hz, 1H), 8.55 (d, J=2.1 Hz, 1H), 8.91 (d, J=2.0 Hz, 1H), 9.23 (s, 2H). C$_{22}$H$_{21}$ClN$_6$O$_2$S MS m/z 468.9 (M+H)$^+$.

I. 3-chloro-5-[8-[6-[(1-methyl-4-piperidyl)oxy]-3-pyridyl]-5-oxo-7-thioxo-6,8-diazaspiro[3.4]octan-6-yl]pyridine-2-carbonitrile Hydrochloride, Cpd 26

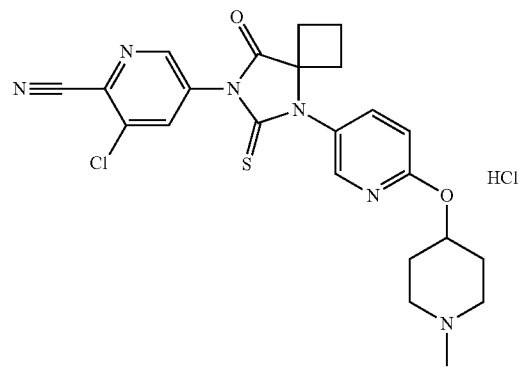 [SMILES: CN1CCC(Oc2ccc(N3C(=S)N(c4cnc(C#N)c(Cl)c4)C(=O)C34CCC4)cn2)CC1 ; Cl]

Formaldehyde (37% wt in water, 0.143 mL, 1.92 mmol) was added to a solution of 3-chloro-5-[5-oxo-8-[6-(4-piperidyloxy)-3-pyridyl]-7-thioxo-6,8-diazaspiro[3.4]octan-6-yl]pyridine-2-carbonitrile (0.300 g, 0.64 mmol) in DCE (8 mL). The mixture was stirred at room temperature for 10 min, then Sodium triacetoxyborohydride (0.407 g, 1.92 mmol) was added. The reaction was stirred for 15 h and diluted with ethyl acetate. The solution was washed successively with saturated NaHCO$_3$ solution, water and brine. The organic layer was dried over MgSO$_4$, filtered and concentrated to give the crude product. The product was purified by flash chromatography over silica gel (Methanol-dichloromethane gradient from 0 to 10%). Pure product fractions were combined and concentrated to dryness. The hydrochloride salt was prepared by addition of 4N Hydrogen chloride solution in dioxane to a solution of product in ethyl acetate followed by evaporation of solvents. The white solid Cpd 26 was then dried under reduced pressure to constant weight (0.176 g, 35%). $^1$H NMR (300 MHz, DMSO-d$_6$) δ 1.43-1.60 (m, 1H), 1.84-2.00 (m, 3H), 2.04-2.16 (m, 2H), 2.19-2.39 (m, 1H), 2.44 (t, J=1.9 Hz, 3H), 2.51-2.61 (m, 1H), 2.64-2.83 (m, 3H), 3.02-3.17 (m, 2H), 3.37-3.46 (m, 1H), 5.04-5.41 (m, 1H), 7.01 (dd, J=8.8, 4.1 Hz, 1H), 7.75 (ddd, J=8.9, 6.4, 2.7 Hz, 1H), 8.17 (dd, J=4.5, 2.6 Hz, 1H), 8.47 (s, OH), 8.83 (d, J=1.9 Hz, 1H), 10.33-10.84 (m, 1H). C$_{23}$H$_{24}$Cl$_2$N$_6$O$_2$S MS m/z 483.0 (M+H)$^+$.

Following the procedure described in Example 6, above, selecting and substituting the appropriate reagents, starting materials, and purification methods, and adjusting reaction temperatures, times and other variables or parameters, as needed or desirable, as would be readily recognized by those skilled in the art, the following compounds of formula (I) of the invention were prepared.

| Cpd No. | Structure | Compound Name & Physical Data |
|---|---|---|
| 153 | 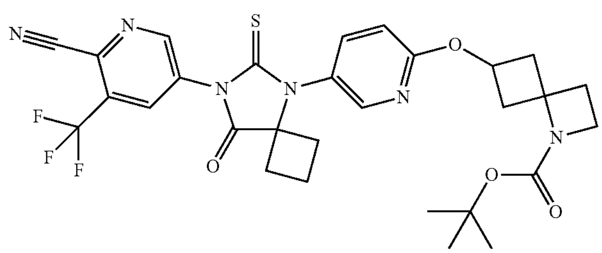 [SMILES: CC(C)(C)OC(=O)N1CCC12CC(Oc1ccc(N3C(=S)N(c4cnc(C#N)c(C(F)(F)F)c4)C(=O)C34CCC4)cn1)C2] | tert-butyl 6-[[5-[6-[6-cyano-5-(trifluoromethyl)-3-pyridyl]-5-oxo-7-thioxo-6,8-diazaspiro[3.4]octan-8-yl]-2-pyridyl]oxy]-3-azaspiro[3.3]heptane-3-carboxylate. $^1$H NMR (300 MHz, Chloroform-d) δ 1.39-1.58 (m, 9H), 1.63-1.77 (m, 1H), 2.10-2.57 (m, 7H), 2.61-2.76 (m, 2H), 3.04-3.33 (m, 2H), 3.77 (t, J = 7.3 Hz, 2H), 5.07-5.84 (m, 1H), 6.86 (d, J = 8.8 Hz, 1H), 7.50 (dd, J = 8.8, 2.7 Hz, 1H), 8.08 (d, J = 2.6 Hz, 1H), 8.35 (d, J = 2.2 Hz, 1H), 9.07 (d, J = 2.2 Hz, 1H). C$_{29}$H$_{29}$F$_3$N$_6$O$_4$S MS m/z 559.0 (M − 55)$^+$. |
| 193 | 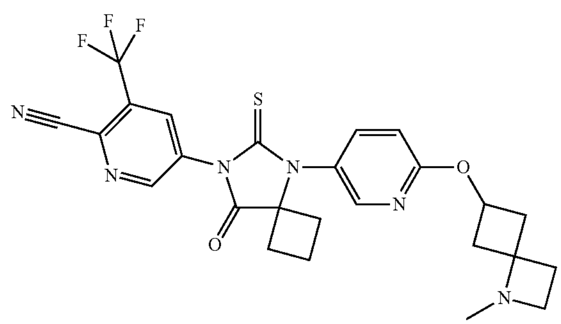 [SMILES: CN1CCC12CC(Oc1ccc(N3C(=S)N(c4cnc(C#N)c(C(F)(F)F)c4)C(=O)C34CCC4)cn1)C2] | 5-[8-[6-[(3-methyl-3-azaspiro[3.3]heptan-6-yl)oxy]-3-pyridyl]-5-oxo-7-thioxo-6,8-diazaspiro[3.4]octan-6-yl]-3-(trifluoromethyl)pyridine-2-carbonitrile. $^1$H NMR (300 MHz, Chloroform-d) δ 1.21-1.35 (m, 2H), 1.64 (dd, J = 62.0, 19.2 Hz, 6H), 2.15-2.36 (m, 1H), 2.41-2.60 (m, 3H), 2.66-2.78 (m, 4H), 3.25-3.54 (m, 1H), 5.17-5.40 (m, 1H), 6.93 (d, J = 8.9 Hz, 1H), 7.55 (dd, J = 8.7, 2.7 Hz, 1H), 8.09 (d, J = 2.4 Hz, 1H), 8.36 (d, J = 2.3 Hz, 1H), 9.10 (d, J = 2.2 Hz, 1H). C$_{25}$H$_{23}$F$_3$N$_6$O$_2$S MS m/z 529.0 (M + H)$^+$ |
| 148 | 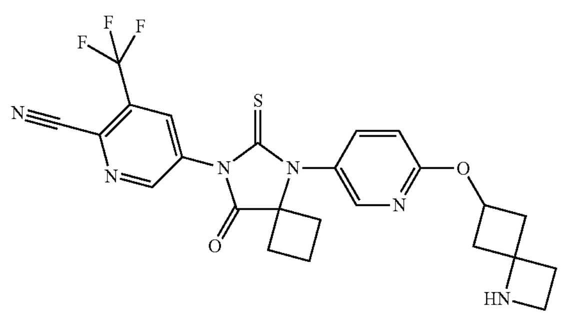 [SMILES: N#Cc1ncc(N2C(=O)C3(CCC3)N(c3ccc(OC4CC5(CCN5)C4)nc3)C2=S)cc1C(F)(F)F] | 5-[8-[4-(3-azaspiro[3.3]heptan-6-yloxy)phenyl]-5-oxo-7-thioxo-6,8-diazaspiro[3.4]octan-6-yl]-3-(trifluoromethyl)pyridine-2-carbonitrile. $^1$H NMR (300 MHz, Chloroform-d) δ 1.57-1.82 (m, 1H), 2.10-2.33 (m, 1H), 2.37-2.77 (m, 8H), 2.85-3.01 (m, 2H), 3.62 (t, J = 7.4 Hz, 2H), 3.75 (s, 2H), 4.33-4.53 (m, 1H), 6.92-6.98 (m, 2H), 7.14-7.24 (m, 2H), 8.36 (d, J = 2.2 Hz, 1H), 9.09 (d, J = 2.2 Hz, 1H). C$_{25}$H$_{22}$F$_3$N$_5$O$_2$S MS m/z 514.0 (M + H)$^+$ |

| Cpd No. | Structure | Compound Name & Physical Data |
|---|---|---|
| 166 | 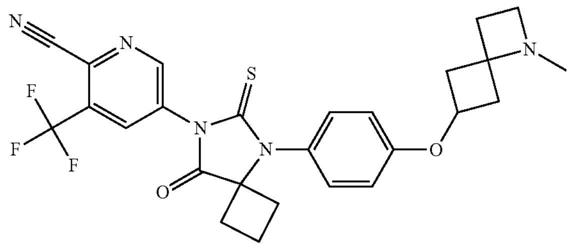 [SMILES: CN1CCC12CC(Oc1ccc(N3C(=S)N(c4cnc(C#N)c(C(F)(F)F)c4)C(=O)C34CCC4)cc1)C2] | 5-[8-[4-[(3-methyl-3-azaspiro[3.3]heptan-6-yl)oxy]phenyl]-5-oxo-7-thioxo-6,8-diazaspiro[3.4]octan-6-yl]-3-(trifluoromethyl)pyridine-2-carbonitrile.<br>$^1$H NMR (300 MHz, Chloroform-d) δ 1.20-1.32 (m, 1H), 1.60-1.79 (m, 1H), 2.14-2.39 (m, 5H), 2.39-2.81 (m, 8H), 3.30 (t, J = 7.0 Hz, 2H), 4.36-4.60 (m, 1H), 6.98 (d, J = 8.7 Hz, 2H), 7.20 (d, J = 8.8 Hz, 2H), 8.37 (d, J = 2.2 Hz, 1H), 9.10 (d, J = 2.2 Hz, 1H).<br>$C_{26}H_{24}F_3N_5O_2S$<br>MS m/z 528.0 (M + H)$^+$ |
| 158 | 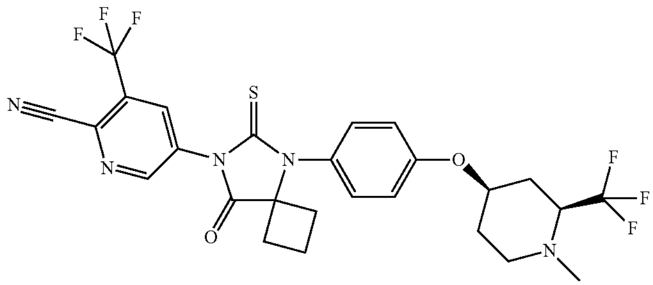 [SMILES: CN1CC[C@@H](Oc2ccc(N3C(=S)N(c4cnc(C#N)c(C(F)(F)F)c4)C(=O)C34CCC4)cc2)C[C@H]1C(F)(F)F] | 5-[8-[4-[[(2SR, 4RS)-1-methyl-2-(trifluoromethyl)-4-piperidyl]oxy]phenyl]-5-oxo-7-thioxo-6,8-diazaspiro[3.4]octan-6-yl]-3-(trifluoromethyl)pyridine-2-carbonitrile.<br>$^1$H NMR (300 MHz, Chloroform-d) δ 1.49-1.64 (m, 1H), 1.66-1.95 (m, 2H), 2.09-2.30 (m, 2H), 2.32-2.44 (m, 2H), 2.47 (s, 3H), 2.51-2.87 (m, 5H), 2.98-3.17 (m, 1H), 4.23-4.41 (m, 1H), 7.07 (d, J = 8.9 Hz, 2H), 7.19-7.25 (m, 2H), 8.37 (d, J = 2.2 Hz, 1H), 9.10 (d, J = 2.2 Hz, 1H).<br>$C_{26}H_{23}F_6N_5O_2S$<br>MS m/z 584.0 (M + H)$^+$ |
| 156 | 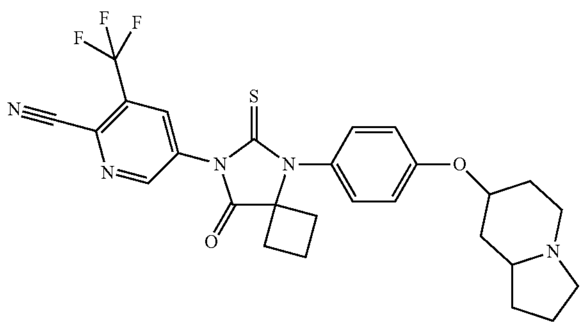 [SMILES: N#Cc1ncc(N2C(=O)C3(CCC3)N(c3ccc(OC4CCN5CCCC5C4)cc3)C2=S)cc1C(F)(F)F] | 5-[8-[4-(1,2,3,5,6,7,8,8a-octahydroindolizin-7-yloxy)phenyl]-5-oxo-7-thioxo-6,8-diazaspiro[3.4]octan-6-yl]-3-(trifluoromethyl)pyridine-2-carbonitrile.<br>$^1$H NMR (300 MHz, Chloroform-d) δ 1.44-1.73 (m, 6H), 1.80-2.06 (m, 2H), 2.10-2.28 (m, 4H), 2.36 (d, J = 12.4 Hz, 1H), 2.51-2.76 (m, 4H), 3.01-3.17 (m, 1H), 3.21 (d, J = 11.6 Hz, 1H), 4.20-4.47 (m, 1H), 7.08 (d, J = 8.9 Hz, 2H), 7.20 (d, J = 8.8 Hz, 2H), 8.37 (d, J = 2.2 Hz, 1H), 9.11 (d, J = 2.2 Hz, 1H).<br>$C_{27}H_{26}F_3N_5O_2S$<br>MS m/z 542.1 (M + H)$^+$ |

Example 7

5-(8-oxo-5-(6-(piperidin-4-yloxy)pyridin-3-yl)-6-thioxo-5,7-diazaspiro[3.4]octan-7-yl)-3-(trifluoromethyl)picolinonitrile, Cpd 43

And 5-(5-(6-((1-methylpiperidin-4-yl)oxy)pyridin-3-yl)-8-oxo-6-thioxo-5,7-diazaspiro[3.4]octan-7-yl)-3-(trifluoromethyl)picolinonitrile, Cpd 1

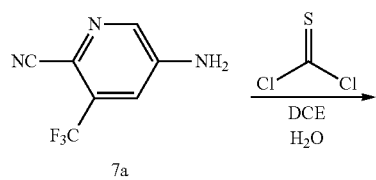

-continued

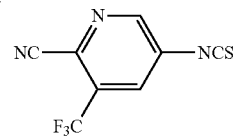

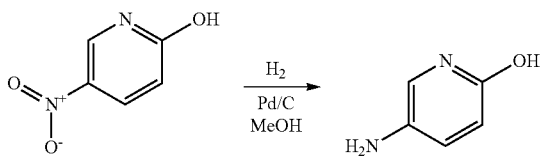

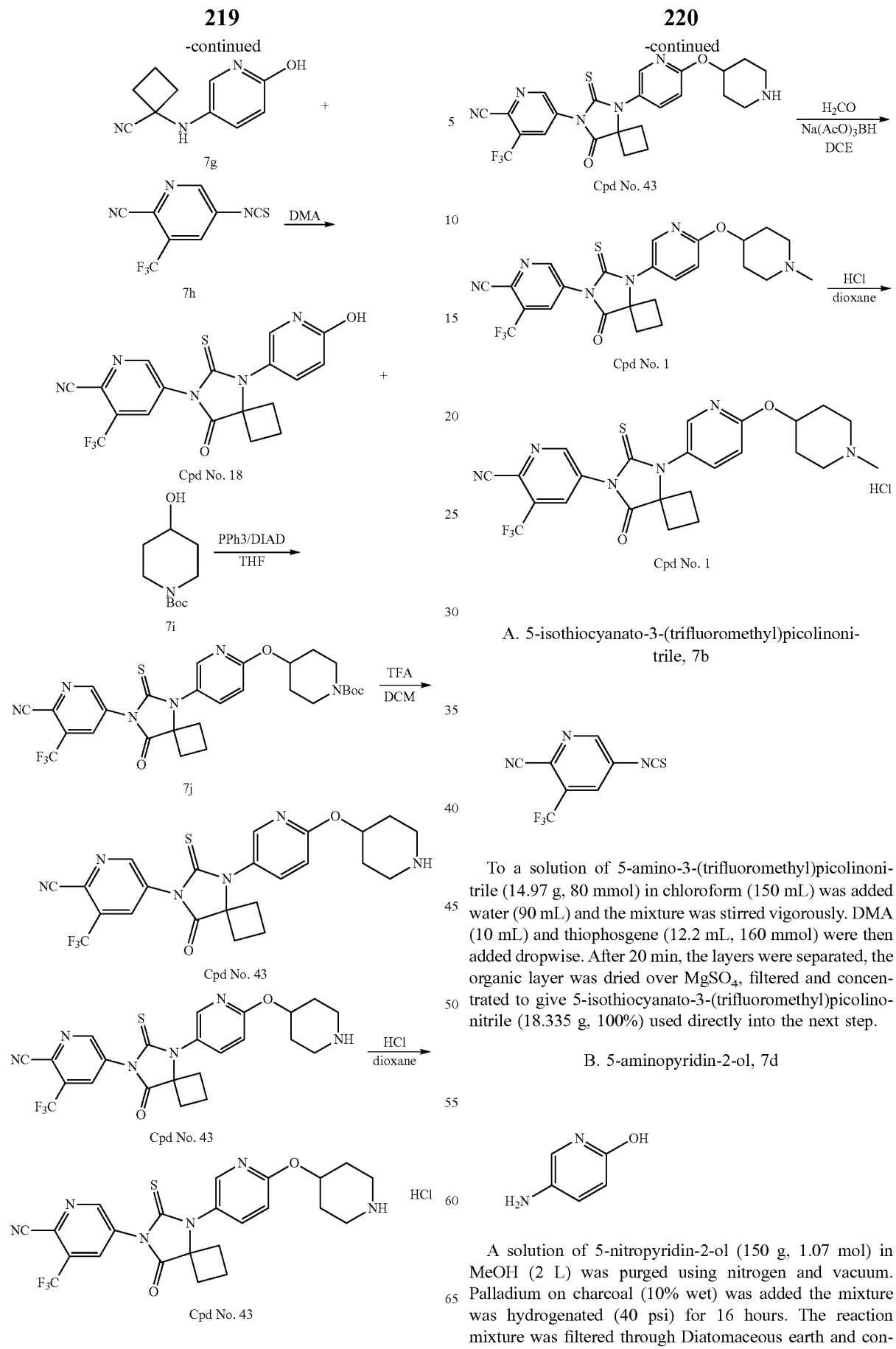

A. 5-isothiocyanato-3-(trifluoromethyl)picolinonitrile, 7b

To a solution of 5-amino-3-(trifluoromethyl)picolinonitrile (14.97 g, 80 mmol) in chloroform (150 mL) was added water (90 mL) and the mixture was stirred vigorously. DMA (10 mL) and thiophosgene (12.2 mL, 160 mmol) were then added dropwise. After 20 min, the layers were separated, the organic layer was dried over MgSO₄, filtered and concentrated to give 5-isothiocyanato-3-(trifluoromethyl)picolinonitrile (18.335 g, 100%) used directly into the next step.

B. 5-aminopyridin-2-ol, 7d

A solution of 5-nitropyridin-2-ol (150 g, 1.07 mol) in MeOH (2 L) was purged using nitrogen and vacuum. Palladium on charcoal (10% wet) was added the mixture was hydrogenated (40 psi) for 16 hours. The reaction mixture was filtered through Diatomaceous earth and concentrated under reduced pressure to give 5-aminopyridin-2-ol as a dark oil used directly into the next step.

C. 1-((6-hydroxypyridin-3-yl)amino)cyclobutanecarbonitrile, 7g

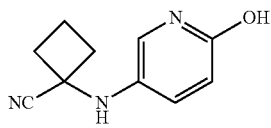

To a solution of 5-aminopyridin-2-ol (60 g, 490.4 mmol) and cyclobutanone (47.65 mL, 637.75 mmol) in MeOH (700 mL) was added zinc iodide (7.8 g, 24.43 mmol) at RT.

Trimethylsilyl cyanide (73 g, 735.8 mmol) was then added in several portions and the mixture was stirred at 50° C. for 16 h, allowed to cool to RT, and then concentrated under reduced pressure. The residue was purified by chromatography over silica gel (gradient of MeOH in DCM from 0 to 8%). The fractions with product were collected and concentrated under reduced pressure to yield 1-((6-hydroxypyridin-3-yl)amino) cyclobutanecarbonitrile as a dark solid (45 g, 48%). $^1$H NMR (300 MHz, Chloroform-d) δ 1.93-2.10 (m, 2H) 2.18-2.32 (m, 2H) 2.55 (br. s., 2H) 5.77-5.92 (m, 1H) 6.26-6.39 (m, 1H) 6.48-6.67 (m, 1H) 6.99-7.19 (m, 1H) 10.81-11.19 (m, 1H) $C_{10}H_{11}N_3O$ MS m/z 190.1 (M+H)$^+$.

D. 5-(5-(6-hydroxypyridin-3-yl)-8-oxo-6-thioxo-5,7-diazaspiro[3.4]octan-7-yl)-3-(trifluoromethyl)picolinonitrile, Cpd 18

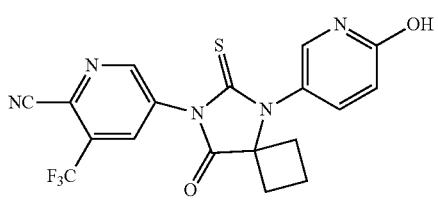 [SMILES: N#Cc1ncc(N2C(=O)C3(CCC3)N(c3ccc(O)nc3)C2=S)cc1C(F)(F)F]

A solution of 5-isothiocyanato-3-(trifluoromethyl)picolinonitrile (13 g, 45.38 mmol) in DMA (60 mL) was added to a solution of 1-((6-hydroxypyridin-3-yl)amino) cyclobutanecarbonitrile (10.416 g, 54.5 mmol) in DMA (60 mL). The mixture was heated at 60° C. for 2 h and then allowed to cool to room temperature. The mixture was treated with MeOH (100 mL) and 2M HCl (100 mL). The resulting suspension stirred at 60° C. for 1 h. The mixture was filtered and the filter cake was washed with water, MeOH, and then dried to give 5-(5-(6-hydroxypyridin-3-yl)-8-oxo-6-thioxo-5,7-diazaspiro[3.4]octan-7-yl)-3-(trifluoromethyl)picolinonitrile as a grey solid (16.7 g, 86%). $^1$H NMR (400 MHz, DMSO-d6) δ 1.60-1.71 (m, 1H) 1.88-2.01 (m, 1H) 2.36-2.44 (m, 2H) 2.53-2.60 (m, 2H) 6.48 (d, J=9.54 Hz, 1H) 7.40 (dd, J=9.66, 2.32 Hz, 1H) 7.58 (br. s., 1H) 8.67 (s, 1H) 9.15 (s, 1H) 12.01 (br. s., 1H). $C_{18}H_{12}F_3N_5O_2S$ MS m/z 420 (M+H)$^+$.

E. 4-{5-[7-(6-Cyano-5-trifluoromethyl-pyridin-3-yl)-8-oxo-6-thioxo-5,7-diaza-spiro[3.4]oct-5-yl]-pyridin-2-yloxy}-piperidine-1-carboxylic Acid Tert-Butyl Ester, 7j

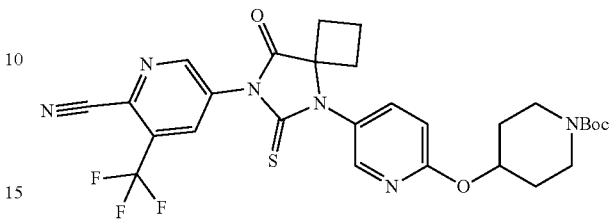

5-[5-(6-Hydroxy-pyridin-3-yl)-8-oxo-6-thioxo-5,7-diaza-spiro[3.4]oct-7-yl]-3-trifluoromethyl-pyridine-2-carbonitrile (16.6 g, 39.6 mmol), 4-Hydroxy-piperidine-1-carboxylic acid tert-butyl ester (8.94 g, 43.5 mmol) and triphenylphosphine (22.8 g, 87.1 mmol) were dissolved in dry THF (150 mL) under a nitrogen atmosphere and heated at 50° C. A solution of Diisopropyl azodicarboxylate (DIAD, 15.6 mL, 79.1 mmol) in THF (50 mL) was added dropwise. Upon completion of the addition, the reaction was continued for 3 h at the same temperature. The mixture was then allowed to cool and concentrated to dryness. The crude residue was purified by column chromatography on silica gel (gradient of Ethyl acetate in heptane from 0 to 30%). The fractions with product were concentrated to an amorphous solid directly used in the next step. $^1$H NMR (300 MHz, Chloroform-d) δ 1.47 (s, 9H), 1.66-1.86 (m, 3H), 1.94-2.10 (m, 2H), 2.15-2.35 (m, 1H), 2.44-2.62 (m, 2H), 2.63-2.80 (m, 2H), 3.22-3.40 (m, 2H), 3.70-3.90 (m, 2H), 5.21-5.35 (m, 1H), 6.91 (d, J=8.8 Hz, 1H), 7.52 (dd, J=8.8, 2.6 Hz, 1H), 8.09 (d, J=2.6 Hz, 1H), 8.36 (d, J=2.2 Hz, 1H), 9.09 (d, J=2.2 Hz, 1H). $C28H_{29}F_3N_6O_4S$ MS m/z 547 (M+H–tBu)$^+$.

F. 5-{8-Oxo-5-[6-(piperidin-4-yloxy)-pyridin-3-yl]-6-thioxo-5,7-diaza-spiro[3.4]oct-7-yl}-3-trifluoromethyl-pyridine-2-carbonitrile, Cpd 43

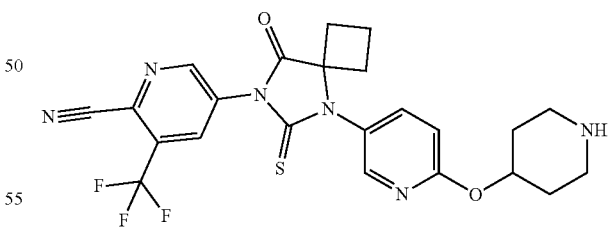

The previous 4-{5-[7-(6-Cyano-5-trifluoromethyl-pyridin-3-yl)-8-oxo-6-thioxo-5,7-diaza-spiro[3.4]oct-5-yl]-pyridin-2-yloxy}-piperidine-1-carboxylic acid tert-butyl ester (43.4 g) was taken in DCM (300 mL). TFA (60 mL) was added with stirring. The mixture was stirred overnight at room temperature and concentrated under reduced pressure. The residue was taken in toluene (150 mL) and again concentrated (3 times). The crude residue was then purified by column chromatography on silica gel (gradient of MeOH in DCM from 0 to 10%) to afford a yellowish amorphous solid (19.8 g). Final purification was performed by preparative LC (gradient of a mixture ACN/MeOH (1/1, v/v) in 0.1% aqueous formic acid from 10 to 54%). The pure fractions were collected and pH brought to 8-9 by addition of solid $Na_2CO_3$. The product was extracted with EA (3×400 mL). The combined organic layers were washed with brine (300 mL), dried over $MgSO_4$, filtered and concentrated to a white foam (9.57 g, 47% for two steps). $^1$H NMR (300 MHz, Chloroform-d) δ 1.45-1.57 (m, 1H), 1.87-2.15 (m, 5H), 2.20-2.41 (m, 2H), 2.42-2.60 (m, 2H), 2.94-3.09 (m, 2H), 3.10-3.30 (m, 2H), 5.15-5.27 (m, 1H), 6.74 (d, J=8.7 Hz, 1H), 7.39 (dd, J=8.7, 2.6 Hz, 1H), 7.90 (d, J=2.6 Hz, 1H), 8.24 (d, J=2.2 Hz, 1H), 8.91 (d, J=2.2 Hz, 1H). $C_{23}H_{21}F_3N_6O_2S$ MS m/z 503 (M+H)$^+$.

G. 5-{8-Oxo-5-[6-(piperidin-4-yloxy)-pyridin-3-yl]-6-thioxo-5,7-diaza-spiro[3.4]oct-7-yl}-3-trifluoromethyl-pyridine-2-carbonitrile Hydrochloride Salt, Cpd 43

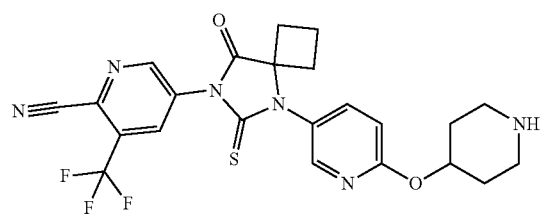 [SMILES: N#Cc1ncc(N2C(=O)C3(CCC3)N(c3ccc(OC4CCNCC4)nc3)C2=S)cc1C(F)(F)F]

The previous 5-{8-Oxo-5-[6-(piperidin-4-yloxy)-pyridin-3-yl]-6-thioxo-5,7-diaza-spiro[3.4]oct-7-yl}-3-trifluoromethyl-pyridine-2-carbonitrile (9.57 g, 19.0 mmol) was taken in dioxane (54 mL) and treated with 4N HCl in dioxane (5.24 mL, 20.9 mmol) with stirring. After 1 h, the mixture was concentrated to dryness under reduced pressure. Diethyl ether (50 mL) was added and the resulting suspension was stirred overnight. The solid was collected on a sintered funnel and washed with diethyl ether (2×15 mL). The solid was dried under high vacuum at room temperature to yield the pure title hydrochloride salt (9.85 g, 93%). $^1$H NMR (300 MHz, DMSO-$d_6$) δ 1.48-1.69 (m, 1H), 1.87-2.04 (m, 3H), 2.12-2.29 (m, 2H), 2.34-2.48 (m, 2H), 2.58-2.73 (m, 2H), 3.04-3.20 (m, 2H), 3.21-3.35 (m, 2H), 5.26-5.40 (m, Hz, 1H), 7.09 (d, J=8.8 Hz, 1H), 7.80 (dd, J=8.8, 2.6 Hz, 1H), 8.22 (d, J=2.6 Hz, 1H), 8.75 (d, J=2.0 Hz, 1H), 8.92 (br s, 2H), 9.21 (d, J=2.0 Hz, 1H). $C_{23}H_{22}ClF_3N_6O_2S$ MS m/z 503 (M+H)$^+$.

H. 5-{5-[6-(1-Methyl-piperidin-4-yloxy)-pyridin-3-yl]-8-oxo-6-thioxo-5,7-diaza-spiro[3.4]oct-7-yl}-3-trifluoromethyl-pyridine-2-carbonitrile, Cpd 1

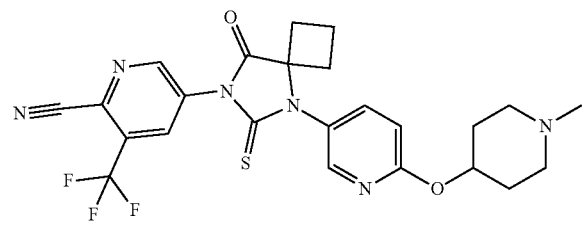 [SMILES: CN1CCC(Oc2ccc(N3C(=S)N(c4cnc(C#N)c(C(F)(F)F)c4)C(=O)C34CCC4)cn2)CC1]

Formaldehyde (37% wt in water, 1.2 mL, 15.2 mmol) was added to a solution of 5-{8-Oxo-5-[6-(piperidin-4-yloxy)-pyridin-3-yl]-6-thioxo-5,7-diaza-spiro[3.4]oct-7-yl}-3-trifluoromethyl-pyridine-2-carbonitrile (4.68 g, 7.13 mmol) in THF (40 mL). The mixture was stirred at room temperature for 30 min, before Sodium triacetoxyborohydride (2.54 g, 11.38 mmol) was added. The reaction was continued overnight and diluted with EA (200 mL). The solution was washed with 1M $Na_2CO_3$ (100 mL). The aqueous layer was back extracted once with EA (100 mL). The combined organic layers were dried over $MgSO_4$, filtered and concentrated to give the crude product. Purification by column chromatography on silica gel (gradient of MeOH in DCM from 0 to 10%) gave, after removal of solvent, a white foam. Preparative LC (gradient from 30 to 73% of a mixture ACN/MeOH (1/1, v/v) in 25 mM aqueous $NH_4HCO_3$) afforded title compound as a white solid (1.57 g, 41%). $^1$H NMR (300 MHz, Chloroform-d) δ 1.64-1.82 (m, 1H), 1.82-1.98 (m, 2H), 2.05-2.19 (m, 2H), 2.19-2.42 (m, 3H), 2.34 (s, 3H), 2.44-2.62 (m, 2H), 2.63-2.84 (m, 4H), 5.00-5.24 (m, 1H), 6.91 (d, J=8.8 Hz, 1H), 7.50 (dd, J=8.8, 2.7 Hz, 1H), 8.09 (d, J=2.6 Hz, 1H), 8.36 (d, J=2.2 Hz, 1H), 9.09 (d, J=2.2 Hz, 1H). $C_{24}H_{23}F_3N_6O_2S$ MS m/z 517 (M+H)$^+$.

I. 5-{5-[6-(1-Methyl-piperidin-4-yloxy)-pyridin-3-yl]-8-oxo-6-thioxo-5,7-diaza-spiro[3.4]oct-7-yl}-3-trifluoromethyl-pyridine-2-carbonitrile Hydrochloride, Cpd 1

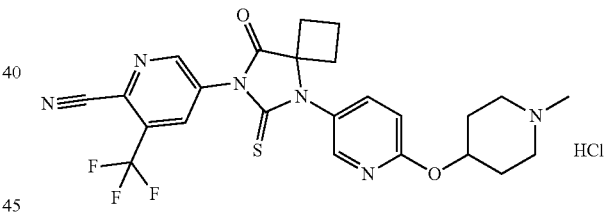

5-{5-[6-(1-Methyl-piperidin-4-yloxy)-pyridin-3-yl]-8-oxo-6-thioxo-5,7-diaza-spiro[3.4]oct-7-yl}-3-trifluoromethyl-pyridine-2-carbonitrile (1.57 g, 3.04 mmol) was taken in dioxane (10 mL) and treated with 4N HCl in dioxane (0.84 mL, 3.37 mmol) with stirring. After 1 h, the mixture was concentrated to dryness under reduced pressure. Diethyl ether (30 mL) was added and the resulting suspension was stirred until a powdered solid was obtained. The solid was collected by filtration on a sintered funnel and washed with diethyl ether (2×15 mL). The solid was dried under high vacuum at room temperature to yield the pure title hydrochloride salt (1.51 g, 90%). $^1$H NMR (300 MHz, DMSO-$d_6$) δ 1.50-1.70 (m, 1H), 1.87-2.36 (m, 5H), 2.37-2.51 (m, 2H), 2.57-2.71 (m, 2H), 2.77 (br s, 3H), 3.04-3.26 (m, 2H), 3.32-3.54 (m, 2H), 5.10-5.51 (m, 1H), 7.08 (d, J=8.8 Hz, 1H), 7.81 (dd, J=8.7, 2.6 Hz, 1H), 8.23 (d, J=2.6 Hz, 1H), 8.75 (d, J=2.1 Hz, 1H), 9.22 (d, J=2.1 Hz, 1H), 10.72 (s, 1H). $C_{24}H_{24}ClF_3N_6O_2S$ MS m/z 517 (M+H)$^+$.

Example 7a—Intermediate Synthesis tert-butyl 2-fluoro-3-hydroxy-8-azabicyclo[3.2.1]octane-8-carboxylate

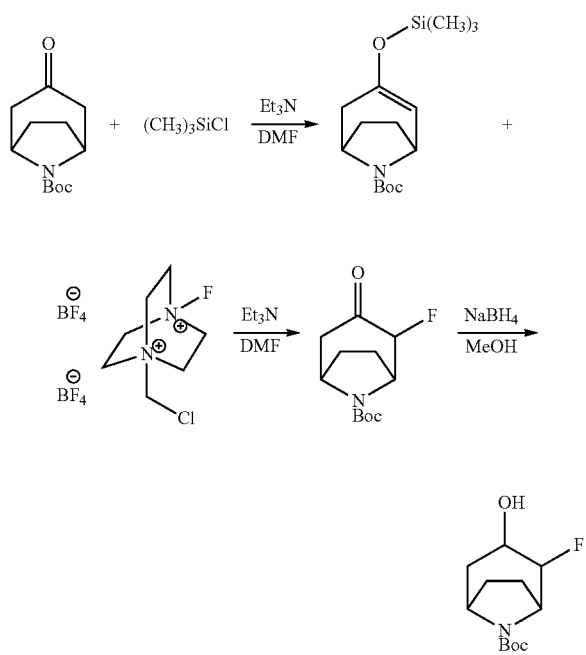

A. To a solution of tert-butyl 3-oxo-8-azabicyclo[3.2.1]octane-8-carboxylate (10 g, 44.38 mmol) and triethylamine (10.8 g, 106.73 mmol) in DMF (100 mL) was added dropwise trimethylsilyl chloride (5.8 g, 53.38 mmol). The mixture was stirred at 100° C. for 16 h, allowed to cool to room temperature, and concentrated under reduced pressure. The crude material was purified by chromatography over silica gel (gradient of EA in heptane from 0 to 100%). The fractions with product were collected and concentrated under reduced pressure to yield tert-butyl 3-((trimethylsilyl)oxy)-8-azabicyclo[3.2.1]oct-3-ene-8-carboxylate as a light yellow oil (8 g, 61%).

B. To a solution of tert-butyl 3-((trimethylsilyl)oxy)-8-azabicyclo[3.2.1]oct-3-ene-8-carboxylate (4 g, 13.44 mmol) in MeCN (50 mL) was added 1-chloromethyl-4-fluoro-1,4-diazoniabicyclo[2.2.2]octane bis(tetrafluoroborate) (5.2 g, 14.67 mmol). The mixture was stirred at RT for 16 h and diluted with water and EtOAc. The organic layer was dried over MgSO$_4$, filtered and concentrated to dryness. The crude material was purified by chromatography over silica gel (gradient of EA in heptane from 0 to 100%). The fractions with product were collected and concentrated under reduced pressure to yield tert-butyl 2-fluoro-3-oxo-8-azabicyclo[3.2.1]octane-8-carboxylate as a white solid (2.5 g, 76%). $C_{12}H_{18}FNO_3$ MS m/z 266.12 (M+Na)$^+$.

C. To a solution of tert-butyl 2-fluoro-3-oxo-8-azabicyclo[3.2.1]octane-8-carboxylate (2.5 g, 10.27 mmol) in MeOH (30 mL) was added sodium borohydride (1.17 g, 30.92 mmol) at 0° C. and stirred at RT for 16 h. The mixture was concentrated under reduced pressure and diluted with water and EtOAc. The organic layer was dried over MgSO$_4$, filtered and concentrated to dryness. The crude material was purified by chromatography over silica gel (gradient of EA in heptane from 0 to 100%). The fractions with product were collected and concentrated under reduced pressure to yield tert-butyl 2-fluoro-3-hydroxy-8-azabicyclo[3.2.1]octane-8-carboxylate as a white solid (0.25 g, 11%). $C_{12}H_{20}FNO_3$ MS m/z 268.13 (M+Na)$^+$.

Following the procedure described in Example 7, above, selecting and substituting the appropriate reagents, starting materials, and purification methods, and adjusting reaction temperatures, times and other variables or parameters, as needed or desirable, as would be readily recognized by those skilled in the art, the following compounds of formula (I) of the invention were prepared.

| Cpd No. | Structure | Compound Name & Physical Data |
|---|---|---|
| 85 | 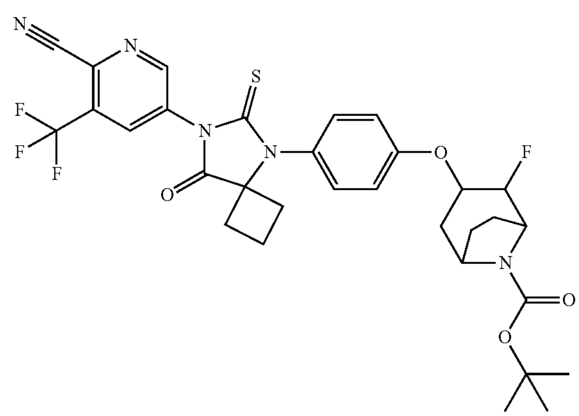 [SMILES: CC(C)(C)OC(=O)N1C2CCC1C(F)C(Oc1ccc(N3C(=S)N(c4cnc(C#N)c(C(F)(F)F)c4)C(=O)C34CCC4)cc1)C2] | tert-butyl 3-[4-[6-[6-cyano-5-(trifluoromethyl)-3-pyridyl]-5-oxo-7-thioxo-6,8-diazaspiro[3.4]octan-8-yl]phenoxy]-4-fluoro-8-azabicyclo[3.2.1]octane-8-carboxylate. $^1$H NMR (400 MHz, Chloroform-d) δ ppm 1.49 (s, 9 H) 1.66 (dd, J = 9.05, 5.14 Hz, 2 H) 1.87 (br. s., 1 H) 1.94-2.15 (m, 3 H) 2.17-2.28 (m, 2 H) 2.50-2.61 (m, 2 H) 2.62-2.70 (m, 2 H) 4.35 (br. s., 2 H) 4.54-4.66 (m, 1.5 H) 4.75 (br. s., 0.5 H) 7.11-7.16 (m, 2 H) 7.18-7.23 (m, 2 H) 8.35 (d, J = 1.71 Hz, 1 H) 9.09 (d, J = 1.96 Hz, 1 H). $C_{31}H_{31}F_4N_5O_4S$ MS m/z 590.1 (M − 55) (M + H)$^+$ |

| Cpd No. | Structure | Compound Name & Physical Data |
|---|---|---|
| 37 | 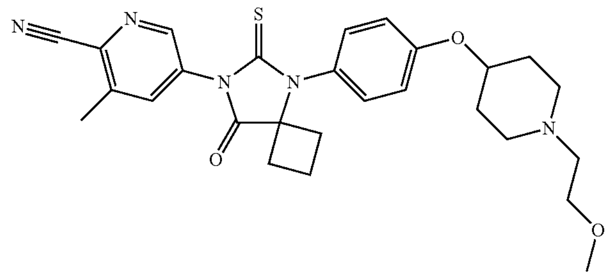 [SMILES: COCCN1CCC(Oc2ccc(N3C(=S)N(c4cnc(C#N)c(C)c4)C(=O)C34CCC4)cc2)CC1] | 5-[8-[4-[[1-(2-methoxyethyl)-4-piperidyl]oxy]phenyl]-5-oxo-7-thioxo-6,8-diazaspiro[3.4]octan-6-yl]-3-methyl-pyridine-2-carbonitrile.<br>$^1$H NMR (400 MHz, DMSO-d6) d ppm 1.45-1.58 (m, 1 H) 1.88-2.01 (m, 2 H) 2.02-2.12 (m, 1 H) 2.15-2.30 (m, 2 H) 2.34-2.46 (m, 2 H) 2.54-2.62 (m, 5 H) 3.08-3.23 (m, 2 H) 3.25-3.33 (m, 6 H) 3.56 (d, J = 11.98 Hz, 1 H) 3.72 (q, J = 4.24 Hz, 2 H) 4.57-4.67 (m, 0.5 H) 4.82 (br. s., 0.5 H) 7.16-7.23 (m, 2 H) 7.30-7.36 (m, 2 H) 8.11 (d, J = 1.47 Hz, 1 H) 8.69 (d, J = 1.71 Hz, 1 H) 10.54 (br. s., 1 H)<br>$C_{27}H_{31}N_5O_3S \cdot HCl$<br>MS m/z 506.2 (M + H)$^+$ |
| 33 | 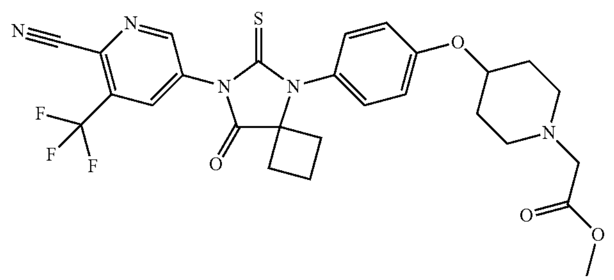 [SMILES: COC(=O)CN1CCC(Oc2ccc(N3C(=S)N(c4cnc(C#N)c(C(F)(F)F)c4)C(=O)C34CCC4)cc2)CC1] | methyl 2-[4-[4-[6-[6-cyano-5-(trifluoromethyl)-3-pyridyl]-5-oxo-7-thioxo-6,8-diazaspiro[3.4]octan-8-yl]phenoxy]-1-piperidyl]acetate<br>$^1$H NMR (400 MHz, Chloroform-d) δ ppm 1.65-1.73 (m, 1 H) 1.88-1.99 (m, 2 H) 2.04-2.14 (m, 2 H) 2.16-2.29 (m, 2 H) 2.51-2.70 (m, 6 H) 2.78-2.87 (m, 2 H) 3.28 (s, 2 H) 3.73 (s, 3 H) 4.38-4.46 (m, 1 H) 7.06 (d, J = 8.80 Hz, 2 H) 7.20 (d, J = 8.80 Hz, 2 H) 8.36 (d, J = 1.96 Hz, 1 H) 9.09 (d, J = 1.96 Hz, 1 H)<br>$C_{27}H_{26}F_3N_5O_4S$<br>MS m/z 574.1 (M + H)$^+$ |
| 98 | 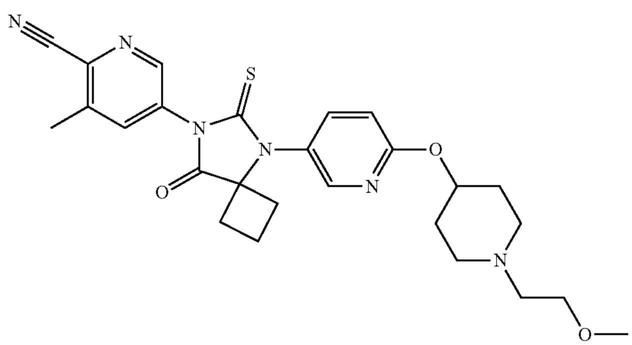 [SMILES: COCCN1CCC(Oc2ccc(N3C(=S)N(c4cnc(C#N)c(C)c4)C(=O)C34CCC4)cn2)CC1] | 5-[8-[6-[[1-(2-methoxyethyl)-4-piperidyl]oxy]-3-pyridyl]-5-oxo-7-thioxo-6,8-diazaspiro[3.4]octan-6-yl]-3-methyl-pyridine-2-carbonitrile.<br>$^1$H NMR (400 MHz, DMSO-d6) d ppm 1.47-1.58 (m, 1 H) 1.66 (q, J = 9.05 Hz, 2 H) 1.86-2.03 (m, 3 H) 2.24 (t, J = 9.41 Hz, 2 H) 2.33-2.43 (m, 2 H) 2.52-2.61 (m, 5 H) 2.70-2.82 (m, 2 H) 3.20 (s, 3 H) 3.32 (br. s., 2 H) 3.47-3.55 (m, 2 H) 5.01 (dt, J = 8.50, 4.43 Hz, 1 H) 6.97 (d, J = 8.56 Hz, 1 H) 7.73 (dd, J = 8.68, 2.57 Hz, 1 H) 8.09 (d, J = 1.71 Hz, 1 H) 8.18 (d, J = 2.45 Hz, 1 H) 8.67 (d, J = 1.96 Hz, 1 H)<br>$C_{26}H_{30}N_6O_3S$<br>MS m/z 507.2 (M + H)$^+$ |
| 77 | 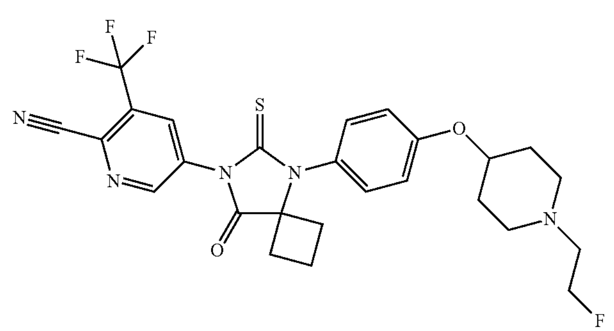 [SMILES: N#Cc1ncc(N2C(=O)C3(CCC3)N(c3ccc(OC4CCN(CCF)CC4)cc3)C2=S)cc1C(F)(F)F] | 5-[8-[4-[[1-(2-fluoroethyl)-4-piperidyl]oxy]phenyl]-5-oxo-7-thioxo-6,8-diazaspiro[3.4]octan-6-yl]-3-(trifluoromethyl)pyridine-2-carbonitrile.<br>$^1$H NMR (400 MHz, Chloroform-d) δ ppm 1.49 (s, 9H) 1.66 (dd, J = 9.05, 5.14 Hz, 2H) 1.87 (br. s., 1 H) 1.94-2.15 (m, 3 H) 2.17-2.28 (m, 2 H) 2.50-2.61 (m, 2 H) 2.62-2.70 (m, 2 H) 4.35 (br. s., 2 H) 4.54-4.66 (m, 1.5 H) 4.75 (br. s., 0.5 H) 7.11-7.16 (m, 2 H) 7.18-7.23 (m, 2 H) 8.35 (d, J = 1.71 Hz, 1 H) 9.09 (d, J = 1.96 Hz, 1 H)<br>$C_{26}H_{25}F_4N_5O_2S \cdot HCl$<br>MS m/z 590.1 (M − 55) (M + H)$^+$ |
| 97 | 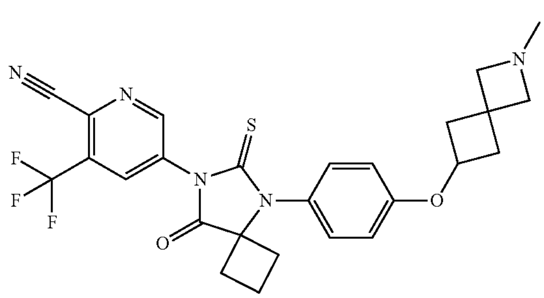 [SMILES: CN1CC2(CC(Oc3ccc(N4C(=S)N(c5cnc(C#N)c(C(F)(F)F)c5)C(=O)C45CCC5)cc3)C2)C1] | 5-[8-[4-[(6-methyl-6-azaspiro[3.3]heptan-2-yl)oxy]phenyl]-5-oxo-7-thioxo-6,8-diazaspiro[3.4]octan-6-yl]-3-(trifluoromethyl)pyridine-2-carbonitrile.<br>$^1$H NMR (400 MHz, DMSO-d6) d ppm 1.51 (d, J = 10.03 Hz, 1 H) 1.86-1.98 (m, 1 H) 2.31 (br. s., 2 H) 2.40 (d, J = 11.49 Hz, 2 H) 2.59 (br. s., 2 H) 2.69 (br. s., 3 H) 2.80 (br. s., 2 H) 3.97 (br. s., 2 H) 4.03 (br. s., 2 H) 4.63-4.74 (m, 1 H) 7.00 (d, J = 8.31 Hz, 2 H) 7.28 (d, J = 8.31 Hz, 2 H) 8.72 (s, 1 H) 9.18 (s, 1 H)<br>$C_{26}H_{24}F_3N_5O_2S \cdot HCl$<br>MS m/z 528.1 (M + H)$^+$ |

| Cpd No. | Structure | Compound Name & Physical Data |
|---|---|---|
| 40 | 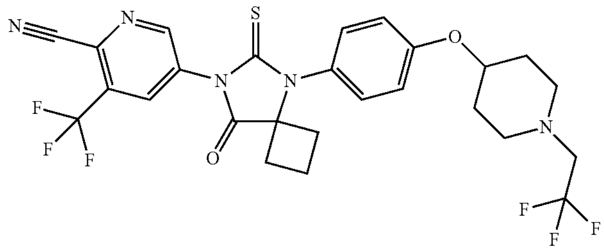 [SMILES: N#Cc1ncc(N2C(=O)C3(CCC3)N(c3ccc(OC4CCN(CC(F)(F)F)CC4)cc3)C2=S)cc1C(F)(F)F] | 5-[5-oxo-7-thioxo-8-[4-[[1-(2,2,2-trifluoroethyl)-4-piperidyl]oxy]phenyl]-6,8-diazaspiro[3.4]octan-6-yl]-3-(trifluoromethyl)pyridine-2-carbonitrile.<br>$^1$H NMR (400 MHz, Chloroform-d) δ ppm 1.69 (d, J = 10.58 Hz, 1 H) 2.15 (br. s., 2 H) 2.24 (dd, J = 19.74, 9.37 Hz, 1 H) 2.41-2.62 (m, 4 H) 2.64-2.72 (m, 2 H) 3.12 (br. s., 2 H) 3.32 (br. s., 2 H) 3.45 (br. s., 2 H) 4.63 (br. s., 1 H) 7.08 (d, J = 8.38 Hz, 2 H) 7.24 (s, 2 H) 8.36 (d, J = 1.76 Hz, 1 H) 9.10 (d, J = 1.76 Hz, 1 H)<br>$C_{26}H_{23}F_6N_5O_2S$<br>MS m/z 584.1 (M + H)$^+$ |
| 100 | 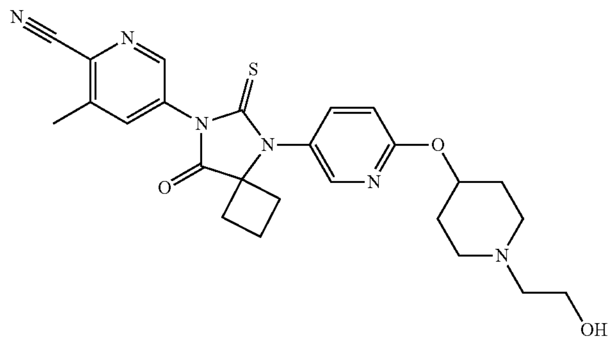 [SMILES: Cc1cc(N2C(=O)C3(CCC3)N(c3ccc(OC4CCN(CCO)CC4)nc3)C2=S)cnc1C#N] | 5-[8-[6-[[1-(2-hydroxyethyl)-4-piperidyl]oxy]-3-pyridyl]-5-oxo-7-thioxo-6,8-diazaspiro[3.4]octan-6-yl]-3-methyl-pyridine-2-carbonitrile.<br>$^1$H NMR (400 MHz, DMSO-d6) d ppm 1.49-1.58 (m, 1 H) 1.68 (q, J = 8.97 Hz, 2 H) 1.88-2.02 (m, 3 H) 2.20-2.31 (m, 2 H) 2.34-2.43 (m, 4 H) 2.53-2.61 (m, 5 H) 2.78 (d, J = 11.25 Hz, 2 H) 3.48 (t, J = 5.75 Hz, 2 H) 4.42 (br. s., 1 H) 5.02 (dt, J = 8.68, 4.46 Hz, 1 H) 6.98 (d, J = 8.80 Hz, 1 H) 7.73 (dd, J = 8.80, 2.69 Hz, 1 H) 8.10 (d, J = 1.47 Hz, 1 H) 8.18 (d, J = 2.45 Hz, 1 H) 8.68 (d, J = 1.96 Hz, 1 H)<br>$C_{25}H_{28}N_6O_3S$<br>MS m/z 493.1 (M + H)$^+$ |
| 78 | 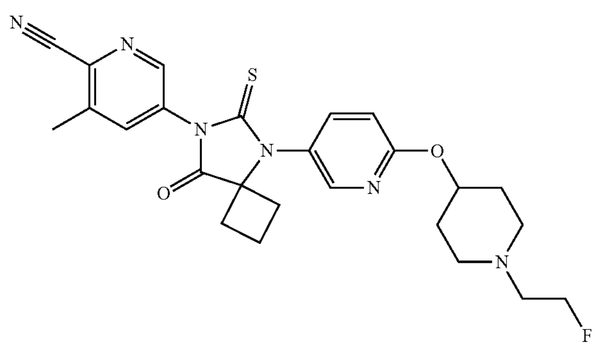 [SMILES: Cc1cc(N2C(=O)C3(CCC3)N(c3ccc(OC4CCN(CCF)CC4)nc3)C2=S)cnc1C#N] | 5-[8-[6-[[1-(2-fluoroethyl)-4-piperidyl]oxy]-3-pyridyl]-5-oxo-7-thioxo-6,8-diazaspiro[3.4]octan-6-yl]-3-methyl-pyridine-2-carbonitrile.<br>$^1$H NMR (400 MHz, DMSO-d6) d ppm 1.49-1.60 (m, 1 H) 1.71 (d, J = 8.07 Hz, 2 H) 1.86-2.07 (m, 4 H) 2.30-2.44 (m, 3 H) 2.53-2.66 (m, 6 H) 2.83 (br. s., 2 H) 3.39 (br. s., 2 H) 4.48 (br. s., 1 H) 4.60 (br. s., 1 H) 5.04 (br. s., 1 H) 6.98 (d, J = 8.80 Hz, 1 H) 7.73-7.77 (m, 1 H) 8.10 (d, J = 1.47 Hz, 1 H) 8.18 (d, J = 2.69 Hz, 1 H) 8.68 (d, J = 1.96 Hz, 1 H)<br>$C_{25}H_{27}FN_6O_2S$<br>MS m/z 495.1 (M + H)$^+$ |
| 90 | 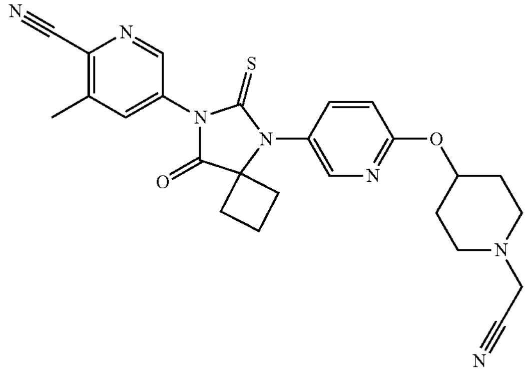 [SMILES: Cc1cc(N2C(=O)C3(CCC3)N(c3ccc(OC4CCN(CC#N)CC4)nc3)C2=S)cnc1C#N] | 5-[8-[6-[[1-(cyanomethyl)-4-piperidyl]oxy]-3-pyridyl]-5-oxo-7-thioxo-6,8-diazaspiro[3.4]octan-6-yl]-3-methyl-pyridine-2-carbonitrile.<br>$^1$H NMR (400 MHz, DMSO-d6) d ppm 1.48-1.60 (m, 1 H) 1.85-1.97 (m, 3 H) 2.14 (br. s., 2 H) 2.33-2.43 (m, 2 H) 2.53-2.63 (m, 5 H) 2.84 (br. s., 2 H) 3.06 (br. s., 2 H) 4.11 (br. s., 2 H) 5.16 (br. s., 1 H) 7.01 (d, J = 8.80 Hz, 1 H) 7.77 (dd, J = 8.80, 2.45 Hz, 1 H) 8.10 (s, 1 H) 8.20 (d, J = 2.20 Hz, 1 H) 8.68 (d, J = 1.47 Hz, 1 H)<br>$C_{25}H_{25}N_7O_2S$<br>MS m/z 488.1 (M + H)$^+$ |

| Cpd No. | Structure | Compound Name & Physical Data |
|---|---|---|
| 62 | 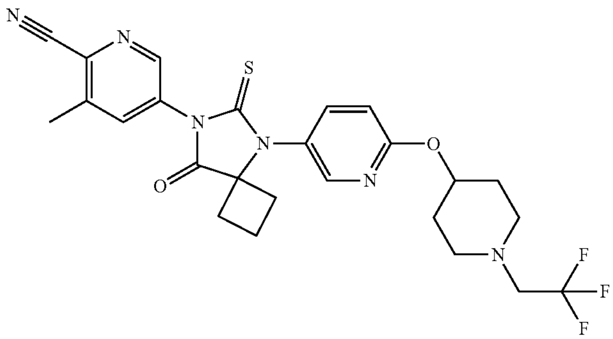 [SMILES: Cc1cc(N2C(=O)C3(CCC3)N(c3ccc(OC4CCN(CC(F)(F)F)CC4)nc3)C2=S)cnc1C#N] | 3-methyl-5-[5-oxo-7-thioxo-8-[6-[[1-(2,2,2-trifluoroethyl)-4-piperidyl]oxy]-3-pyridyl]-6,8-diazaspiro[3.4]octan-6-yl]pyridine-2-carbonitrile.<br>$^1$H NMR (400 MHz, DMSO-d6) d ppm 1.49-1.61 (m, 1 H) 1.64-1.75 (m, 2 H) 1.89-2.03 (m, 3 H) 2.33-2.44 (m, 2 H) 2.52-2.62 (m, 7 H) 2.84-2.92 (m, 2 H) 3.18 (q, J = 10.27 Hz, 2 H) 5.05 (dt, J = 8.25, 4.31 Hz, 1 H) 6.98 (d, J = 8.80 Hz, 1 H) 7.74 (dd, J = 8.80, 2.69 Hz, 1 H) 8.10 (d, J = 1.47 Hz, 1 H) 8.18 (d, J = 2.45 Hz, 1 H) 8.68 (d, J = 1.96 Hz, 1 H)<br>$C_{25}H_{25}F_3N_6O_2S$<br>MS m/z 531.0 (M + H)$^+$ |
| 30 | 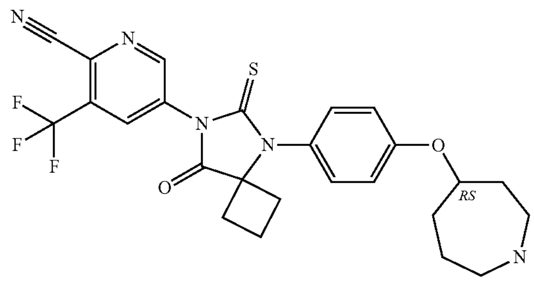 [SMILES: N#Cc1ncc(N2C(=O)C3(CCC3)N(c3ccc(OC4CCCNCC4)cc3)C2=S)cc1C(F)(F)F] | 5-[8-[4-(azepan-4-yloxy)phenyl]-5-oxo-7-thioxo-6,8-diazaspiro[3.4]octan-6-yl]-3-(trifluoromethyl)pyridine-2-carbonitrile<br>$^1$H NMR (400 MHz, Chloroform-d) δ ppm ppm 1.59-1.69 (m, 2 H) 1.95-2.08 (m, 4 H) 2.11-2.23 (m, 2 H) 2.45-2.66 (m, 4 H) 2.86-3.12 (m, 4 H) 4.57-4.65 (m, 1 H) 6.98 (d, J = 8.80 Hz, 2 H) 7.14 (d, J = 8.80 Hz, 2 H) 8.30 (d, J = 1.71 Hz, 1 H) 9.04 (d, J = 1.71 Hz, 1 H)<br>$C_{25}H_{24}F_3N_5O_2S•HCl$<br>MS m/z 508.1 (M + H)+ |
| 92 | 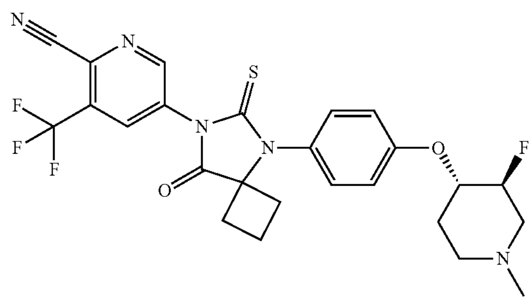 [SMILES: CN1CC[C@H](Oc2ccc(N3C(=S)N(c4cnc(C#N)c(C(F)(F)F)c4)C(=O)C34CCC4)cc2)[C@@H](F)C1] | 5-[8-[(3SR, 4SR)-4-[(3-fluoro-1-methyl-4-piperidyl)oxy]phenyl]-5-oxo-7-thioxo-6,8-diazaspiro[3.4]octan-6-yl]-3-(trifluoromethyl)pyridine-2-carbonitrile<br>$^1$H NMR (400 MHz, Chloroform-d) δ ppm 1.61-1.73 (m, 1 H) 1.79-1.92 (m, 1 H) 2.15-2.30 (m, 3 H) 2.35 (s, 3 H) 2.40-2.48 (m, 1 H) 2.51-2.61 (m, 2 H) 2.61-2.77 (m, 3 H) 2.99-3.10 (m, 1 H) 4.32-4.43 (m, 1 H) 4.67 (td, J = 7.39, 4.41 Hz, 0.5 H) 4.79 (td, J = 7.39, 4.41 Hz, 0.5 H) 7.09-7.16 (m, 2 H) 7.18-7.24 (m, 2 H) 8.36 (d, J = 1.76 Hz, 1 H) 9.09 (d, J = 1.76 Hz, 1 H)<br>$C_{25}H_{23}F_4N_5O_2S$<br>MS m/z 534.1 (M + H)$^+$ |
| 51 | 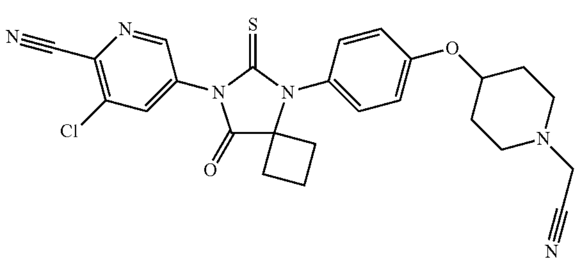 [SMILES: N#CCN1CCC(Oc2ccc(N3C(=S)N(c4cnc(C#N)c(Cl)c4)C(=O)C34CCC4)cc2)CC1] | 3-chloro-5-[8-[4-[[1-(cyanomethyl)-4-piperidyl]oxy]phenyl]-5-oxo-7-thioxo-6,8-diazaspiro[3.4]octan-6-yl]pyridine-2-carbonitrile.<br>$^1$H NMR (400 MHz, Chloroform-d) δ ppm 1.70 (br. s., 1 H) 2.18-2.37 (m, 3 H) 2.49-2.61 (m, 3 H) 2.66 (d, J = 9.48 Hz, 3 H) 3.30-3.56 (m, 4 H) 4.12 (br. s., 2 H) 4.75 (br. s., 1 H) 7.11 (d, J = 7.50 Hz, 2 H) 7.26-7.32 (m, 2 H) 8.11 (s, 1 H) 8.80 (s, 1 H)<br>$C_{25}H_{23}ClN_6O_2S•HCl$<br>MS m/z 507.1 (M + H)$^+$ |
| 86 | 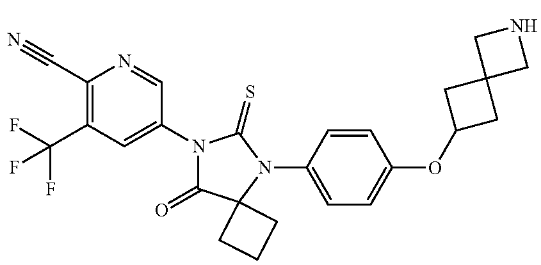 [SMILES: N#Cc1ncc(N2C(=O)C3(CCC3)N(c3ccc(OC4CC5(CNC5)C4)cc3)C2=S)cc1C(F)(F)F] | 5-[8-[4-(6-azaspiro[3.3]heptan-2-yloxy)phenyl]-5-oxo-7-thioxo-6,8-diazaspiro[3.4]octan-6-yl]-3-(trifluoromethyl)pyridine-2-carbonitrile.<br>$^1$H NMR (400 MHz, DMSO-d$_6$) d ppm 1.52 (d, J = 10.36 Hz, 1 H) 1.89-1.98 (m, 1 H) 2.26-2.33 (m, 2 H) 2.37-2.44 (m, 2 H) 2.58 (d, J = 9.04 Hz, 2 H) 2.77-2.86 (m, 2 H) 3.94 (br. s., 2 H) 4.01 (br. s., 2 H) 4.62-4.70 (m, 1 H) 7.01 (d, J = 8.60 Hz, 2 H) 7.28 (d, J = 8.60 Hz, 2 H) 8.73 (s, 1 H) 8.98 (br. s., 1 H) 9.19 (s, 1 H)<br>$C_{25}H_{22}F_3N_5O_2S•HCl$<br>MS m/z 514.1 (M + H)$^+$ |

| Cpd No. | Structure | Compound Name & Physical Data |
|---|---|---|
| 95 | 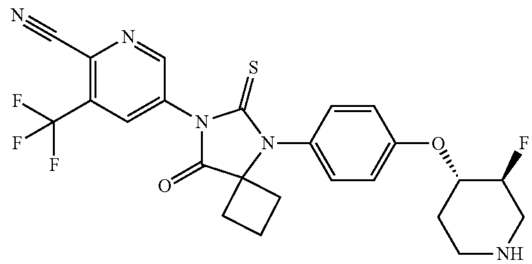 [SMILES: N#Cc1ncc(N2C(=O)C3(CCC3)N(c3ccc(O[C@H]4CCNC[C@@H]4F)cc3)C2=S)cc1C(F)(F)F] | 5-[8-[(3SR, 4SR)-4-[(3-fluoro-4-piperidyl)oxy]phenyl]-5-oxo-7-thioxo-6,8-diazaspiro[3.4]octan-6-yl]-3-(trifluoromethyl)pyridine-2-carbonitrile.<br>$^1$H NMR (400 MHz, DMSO-d6) d ppm 1.51 (d, J = 9.54 Hz, 1 H) 1.93 (d, J = 8.80 Hz, 2 H) 2.24 (br. s., 1 H) 2.34-2.44 (m, 2 H) 2.59 (br. s., 2 H) 3.08 (br. s., 2 H) 3.21 (d, J = 9.05 Hz, 3 H) 4.84-5.10 (m, 2 H) 7.19-7.27 (m, 2 H) 7.28-7.36 (m, 2 H) 8.73 (s, 1 H) 9.18 (s, 1 H)<br>$C_{24}H_{21}F_4N_5O_2S \cdot HCl$<br>MS m/z 520.1 (M + H)$^+$ |
| 45 | 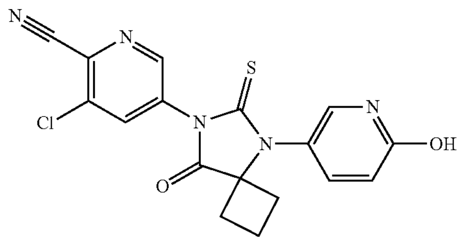 [SMILES: N#Cc1ncc(N2C(=O)C3(CCC3)N(c3ccc(O)nc3)C2=S)cc1Cl] | 3-chloro-5-[8-(6-hydroxy-3-pyridyl)-5-oxo-7-thioxo-6,8-diazaspiro[3.4]octan-6-yl]pyridine-2-carbonitrile.<br>$^1$H NMR (400 MHz, DMSO-d6) d ppm 1.59-1.72 (m, 1 H) 1.89-1.99 (m, 1 H) 2.37-2.45 (m, 2 H) 2.51-2.60 (m, 2 H) 6.47 (d, J = 9.78 Hz, 1 H) 7.39 (dd, J = 9.66, 2.81 Hz, 1 H) 7.58 (d, J = 2.45 Hz, 1 H) 8.47 (d, J = 1.96 Hz, 1 H) 8.83 (d, J = 1.96 Hz, 1 H) 11.96 (br. s., 1 H)<br>$C_{17}H_{12}ClN_5O_2S$<br>MS m/z 386.0 (M + H)$^+$ |
| 96 | 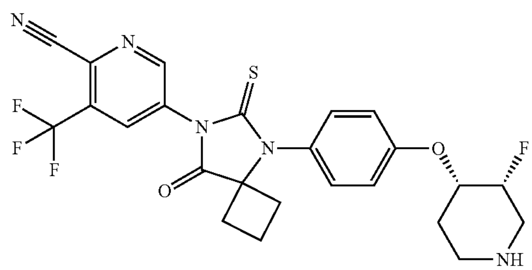 [SMILES: N#Cc1ncc(N2C(=O)C3(CCC3)N(c3ccc(O[C@H]4CCNC[C@H]4F)cc3)C2=S)cc1C(F)(F)F] | 5-[8-(3RS, 4SR) [4-[(3-fluoro-4-piperidyl)oxy]phenyl]-5-oxo-7-thioxo-6,8-diazaspiro[3.4]octan-6-yl]-3-(trifluoromethyl)pyridine-2-carbonitrile<br>$^1$H NMR (400 MHz, DMSO-d6) d ppm 1.53 (d, J = 10.36 Hz, 1 H) 1.95 (dd, J = 19.29, 8.93 Hz, 1 H) 2.01-2.20 (m, 2 H) 2.52-2.67 (m, 4 H) 3.02-3.18 (m, 2 H) 3.57-3.75 (m, 2 H) 4.83 (d, J = 6.39 Hz, 1 H) 4.90 (d, J = 8.60 Hz, 1 H) 5.16 (br. s., 1 H) 5.28 (br. s., 1 H) 7.24 (d, J = 9.04 Hz, 2 H) 7.28-7.40 (m, 2 H) 8.73 (d, J = 1.76 Hz, 1 H) 9.19 (d, J = 1.54 Hz, 1 H)<br>$C_{24}H_{21}F_4N_5O_2S \cdot HCl$<br>MS m/z 520.1 (M + H)$^+$ |
| 61 | 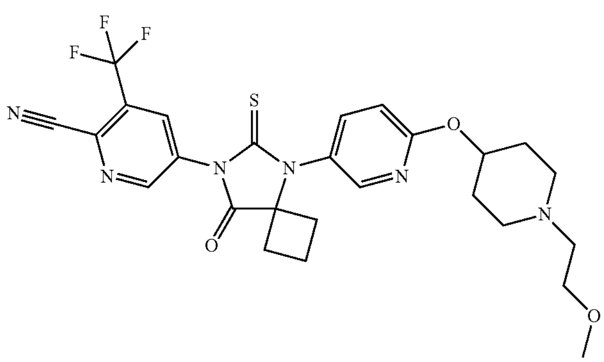 [SMILES: COCCN1CCC(Oc2ccc(N3C(=S)N(c4cnc(C#N)c(C(F)(F)F)c4)C(=O)C34CCC4)cn2)CC1] | 5-[8-[6-[[1-(2-methoxyethyl)-4-piperidyl]oxy]-3-pyridyl]-5-oxo-7-thioxo-6,8-diazaspiro[3.4]octan-6-yl]-3-(trifluoromethyl)pyridine-2-carbonitrile.<br>$^1$H NMR (400 MHz, DMSO-d6) d ppm 1.52-1.65 (m, 1 H) 1.90-2.03 (m, 1 H) 2.04-2.19 (m, 2 H) 2.20-2.35 (m, 2 H) 2.38-2.48 (m, 2 H) 2.60-2.69 (m, 2 H) 3.11-3.26 (m, 2 H) 3.28-3.37 (m, 5 H) 3.57 (d, J = 12.30 Hz, 1 H) 3.68-3.80 (m, 2 H) 5.18-5.40 (m, 1 H) 7.09 (dd, J = 8.78, 3.76 Hz, 1 H) 7.72-7.89 (m, 1 H) 8.23 (dd, J = 6.02, 2.51 Hz, 1 H) 8.67-8.80 (m, 1 H) 9.22 (s, 1 H) 10.51-10.72 (m, 1 H)<br>$C_{26}H_{27}F_3N_6O_3S \cdot HCl$<br>MS m/z 561.2 (M + H)$^+$ |
| 52 | 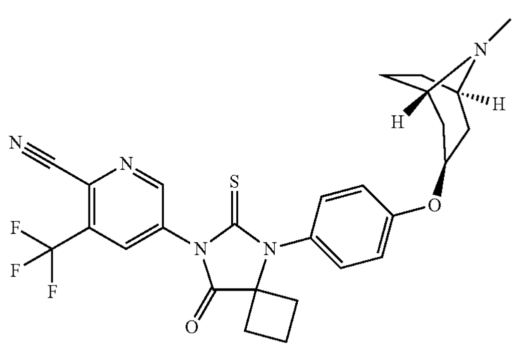 [SMILES: CN1[C@@H]2CC[C@H]1C[C@H](Oc1ccc(N3C(=S)N(c4cnc(C#N)c(C(F)(F)F)c4)C(=O)C34CCC4)cc1)C2] | 5-[8-[4-[[(1R,3s,5S)-8-methyl-8-azabicyclo[3.2.1]octan-3-yl]oxy]phenyl]-5-oxo-7-thioxo-6,8-diazaspiro[3.4]octan-6-yl]-3-(trifluoromethyl)pyridine-2-carbonitrile.<br>$^1$H NMR (400 MHz, DMSO-d6) d ppm 1.51 (d, J = 9.78 Hz, 1 H) 1.89-1.99 (m, 1 H) 2.00-2.25 (m, 6 H) 2.27-2.44 (m, 4 H) 2.59 (d, J = 9.29 Hz, 2 H) 2.65 (d, J = 3.67 Hz, 3 H) 3.94 (br. s., 2 H) 4.78-4.90 (m, 1 H) 7.18-7.24 (m, 2 H) 7.25-7.33 (m, 2 H) 8.73 (s, 1 H) 9.18 (d, J = 1.96 Hz, 1 H)<br>$C_{27}H_{26}F_3N_5O_2S \cdot HCl$<br>MS m/z 542.1 (M + H)$^+$ |

-continued

| Cpd No. | Structure | Compound Name & Physical Data |
|---|---|---|
| 75 | 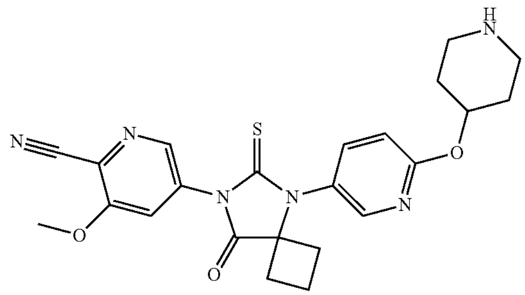 [SMILES: COc1cc(N2C(=O)C3(CCC3)N(c3ccc(OC4CCNCC4)nc3)C2=S)cnc1C#N] | 3-methoxy-5-[5-oxo-8-[6-(4-piperidyloxy)-3-pyridyl]-7-thioxo-6,8-diazaspiro[3.4]octan-6-yl]pyridine-2-carbonitrile.<br>$^1$H NMR (400 MHz, DMSO-d6) d ppm 1.48-1.61 (m, 1 H) 1.85-2.02 (m, 3 H) 2.11-2.22 (m, 2 H) 2.32-2.43 (m, 2 H) 2.56-2.66 (m, 2 H) 3.09 (d, J = 4.16 Hz, 2 H) 3.22 (br. s., 2 H) 3.95 (br. s., 3 H) 5.27 (dt, J = 7.58, 4.03 Hz, 1 H) 7.04 (d, J = 8.80 Hz, 1 H) 7.78 (dd, J = 8.68, 2.57 Hz, 1 H) 8.01 (d, J = 1.22 Hz, 1 H) 8.20 (d, J = 2.45 Hz, 1 H) 8.41 (d, J = 1.47 Hz, 1 H) 9.08 (br. s., 2 H).<br>$C_{23}H_{24}N_6O_3S \cdot HCl$<br>MS m/z 465.1 (M + H)$^+$ |
| 154 | 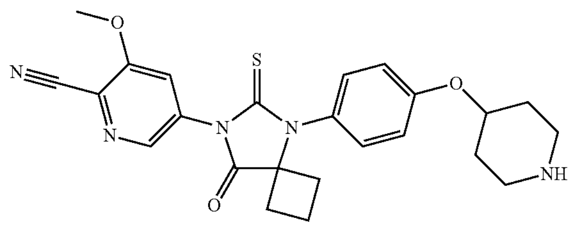 [SMILES: COc1cc(N2C(=O)C3(CCC3)N(c3ccc(OC4CCNCC4)cc3)C2=S)cnc1C#N] | 3-methoxy-5-[5-oxo-8-[4-(4-piperidyloxy)phenyl]-7-thioxo-6,8-diazaspiro[3.4]octan-6-yl]pyridine-2-carbonitrile.<br>$^1$H NMR (400 MHz, DMSO-d6) d ppm 1.48-1.59 (m, 1 H) 1.82-2.04 (m, 3 H) 2.16 (br. s., 2 H) 2.36-2.48 (m, 2 H) 2.56-2.66 (m, 2 H) 3.10 (br. s., 2 H) 3.25 (br. s., 2 H) 3.99 (s, 3 H) 4.74 (br. s., 1 H) 7.20 (d, J = 9.03 Hz, 2 H) 7.34 (d, J = 8.78 Hz, 2 H) 8.05 (d, J = 1.51 Hz, 1 H) 8.45 (d, J = 1.51 Hz, 1 H) 8.94-9.12 (m, 2 H)<br>$C_{24}H_{25}N_5O_3S \cdot HCl$<br>MS m/z 464.2 (M + H)$^+$ |
| 68 | 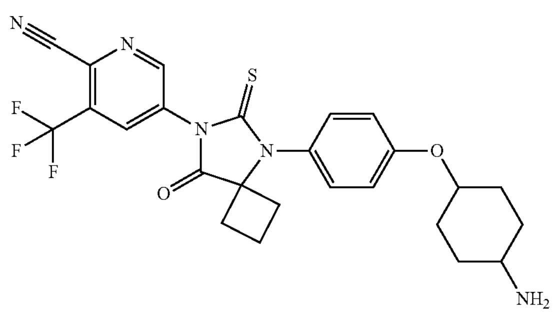 [SMILES: N#Cc1ncc(N2C(=O)C3(CCC3)N(c3ccc(OC4CCC(N)CC4)cc3)C2=S)cc1C(F)(F)F] | 5-[8-[4-(4-aminocyclohexoxy)phenyl]-5-oxo-7-thioxo-6,8-diazaspiro[3.4]octan-6-yl]-3-(trifluoromethyl)pyridine-2-carbonitrile<br>$^1$H NMR (400 MHz, DMSO-d6) d ppm 1.43-1.60 (m, 1H), 1.61-1.83 (m, 6H), 1.84-2.10 (m, 3H), 2.34-2.45 (m, 3H), 2.49-2.66 (m, 3H), 3.06-3.29 (br s, 1H), 4.64 (br s, 1H), 7.12 (d, 2H, J = 8.8 Hz), 7.29 (d, 2H, J = 8.8 Hz), 8.73 (d, 1H, J = 2.0 Hz), 9.19 (d, 1H, J = 2.0 Hz).<br>$C_{25}H_{24}F_3N_5O_2S \cdot HCl$<br>MS m/z 516.0 (M + H)$^+$ |
| 80 | 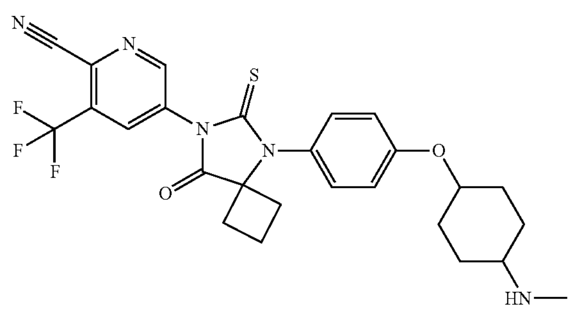 [SMILES: CNC1CCC(Oc2ccc(N3C(=S)N(c4cnc(C#N)c(C(F)(F)F)c4)C(=O)C34CCC4)cc2)CC1] | 5-[8-[4-[4-(methylamino)cyclohexoxy]phenyl]-5-oxo-7-thioxo-6,8-diazaspiro[3.4]octan-6-yl]-3-(trifluoromethyl)pyridine-2-carbonitrile.<br>$^1$H NMR (400 MHz, DMSO-d6) d ppm 1.47-1.57 (m, 1 H) 1.58-1.77 (m, 4 H) 1.83-2.05 (m, 5 H) 2.35-2.44 (m, 2 H) 2.49-2.54 (m, 3 H) 2.55-2.65 (m, 2 H) 3.04 (br. s., 1 H) 4.65 (br. s., 1 H) 7.13 (d, J = 8.80 Hz, 2 H) 7.29 (d, J = 8.80 Hz, 2 H) 8.73 (d, J = 1.71 Hz, 1 H) 8.88 (br. s., 1 H) 9.19 (d, J = 1.71 Hz, 1 H).<br>$C_{26}H_{26}F_3N_5O_2S \cdot HCl$<br>MS m/z 530.2 (M + H)$^+$ |
| 50 | 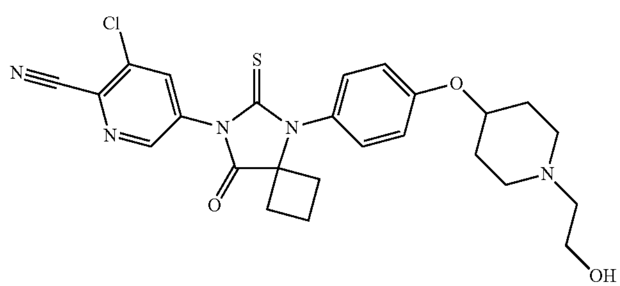 [SMILES: N#Cc1ncc(N2C(=O)C3(CCC3)N(c3ccc(OC4CCN(CCO)CC4)cc3)C2=S)cc1Cl] | 3-chloro-5-[8-[4-[[1-(2-hydroxyethyl)-4-piperidyl]oxy]phenyl]-5-oxo-7-thioxo-6,8-diazaspiro[3.4]octan-6-yl]pyridine-2-carbonitrile.<br>$^1$H NMR (400 MHz, DMSO-d6) d ppm 1.42-1.60 (m, 1H, M01), 1.84-2.13 (m, 1H), 2.30 (br s, 1H, M04), 2.40-2.44 (m, 2H), 2.51-2.55 (m, 2H), 3.20 (br s, 1H), 3.35-3.58 (m, XH), 3.83 (br s, 2H), 4.07 (br t, 2H, J = 9.7 Hz), 4.20 (br s, 2H), 7.17 (br d, 2H, J = 8.8 Hz), 7.33 (br d, 2H, J = 8.6 Hz), 8.63-8.82 (m, 1H), 9.10-9.37 (m, 1H).<br>$C_{25}H_{26}ClN_5O_3S \cdot HCl$<br>MS m/z 512.1 (M + H)$^+$ |

-continued

| Cpd No. | Structure | Compound Name & Physical Data |
|---|---|---|
| 79 | 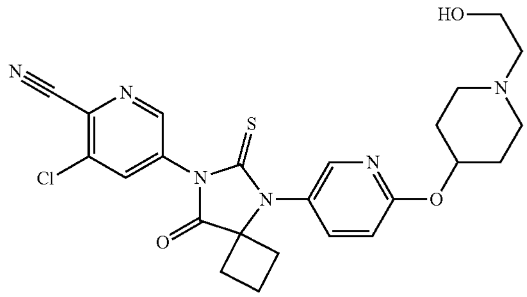 [SMILES: N#Cc1ncc(N2C(=O)C3(CCC3)N(c3ccc(OC4CCN(CCO)CC4)nc3)C2=S)cc1Cl] | 3-chloro-5-[8-[6-[[1-(2-hydroxyethyl)-4-piperidyl]oxy]-3-pyridyl]-5-oxo-7-thioxo-6,8-diazaspiro[3.4]octan-6-yl]pyridine-2-carbonitrile.<br>$^1$H NMR (400 MHz, Chloroform-d) δ ppm 1.81-2.01 (m, 3 H) 2.05-2.34 (m, 4 H) 2.40-2.54 (m, 3 H) 2.56-2.72 (m, 4 H) 2.83 (br. s., 2 H) 3.62 (t, J = 5.18 Hz, 2 H) 5.14 (br. s., 1 H) 6.85 (d, J = 8.82 Hz, 1 H) 7.44 (dd, J = 8.60, 2.65 Hz, 1 H) 8.03 (dd, J = 8.38, 2.21 Hz, 2 H) 8.73 (d, J = 1.98 Hz, 1 H).<br>$C_{24}H_{25}ClN_6O_3S$<br>MS m/z 513.1 (M + H)$^+$ |
| 39 | 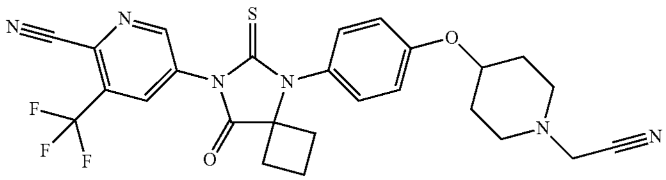 [SMILES: N#CCN1CCC(Oc2ccc(N3C(=S)N(c4cnc(C#N)c(C(F)(F)F)c4)C(=O)C34CCC4)cc2)CC1] | 5-[8-[4-[[1-(cyanomethyl)-4-piperidyl]oxy]phenyl]-5-oxo-7-thioxo-6,8-diazaspiro[3.4]octan-6-yl]-3-(trifluoromethyl)pyridine-2-carbonitrile.<br>$^1$H NMR (400 MHz, Chloroform-d) δ ppm ppm 1.81-2.00 (m, 3H, M01), 2.02-2.23 (m, 4H, M02), 2.44-2.68 (m, 7H, M03), 2.79 (br d, 1H, J = 4.6 Hz, M04), 2.88 (br s, 2H, M05), 3.58 (s, 2H, M06), 4.42 (br s, 1H, M07), 7.02 (d, 2H, J = 9.0 Hz, M08), 7.16 (d, 2H, J = 7.9 Hz, M09), 8.30 (d, 1H, J = 2.2 Hz, M10), 9.04 (d, 1H, J = 2.0 Hz, M11).<br>$C_{26}H_{23}F_3N_6O_2S \cdot HCl$<br>MS m/z 541.1 (M + H)$^+$ |
| 81 | 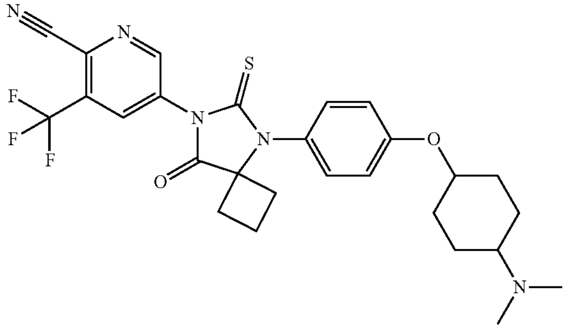 [SMILES: CN(C)C1CCC(Oc2ccc(N3C(=S)N(c4cnc(C#N)c(C(F)(F)F)c4)C(=O)C34CCC4)cc2)CC1] | 5-[8-[4-[4-(dimethylamino)cyclohexoxy]phenyl]-5-oxo-7-thioxo-6,8-diazaspiro[3.4]octan-6-yl]-3-(trifluoromethyl)pyridine-2-carbonitrile.<br>$^1$H NMR (400 MHz, Chloroform-d) δ ppm 1.71 (br. s., 3 H) 2.00 (br. s., 2 H) 2.10-2.28 (m, 3 H) 2.33 (br. s., 2 H) 2.58 (d, J = 9.48 Hz, 2 H) 2.67 (br. s., 2 H) 2.79 (br. s., 6 H) 3.23 (br. s., 1 H) 4.65 (br. s., 1 H) 7.08 (d, J = 6.62 Hz, 2 H) 7.23 (d, J = 7.50 Hz, 2 H) 8.36 (s, 1 H) 9.10 (s, 1 H) 12.44 (br. s., 1 H).<br>$C_{27}H_{28}F_3N_5O_2S \cdot HCl$<br>MS m/z 544.1 (M + H)$^+$ |
| 93 | 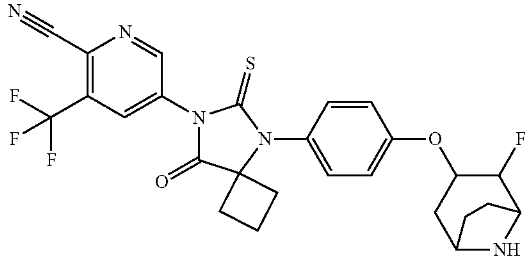 [SMILES: N#Cc1ncc(N2C(=O)C3(CCC3)N(c3ccc(OC4CC5CCC(N5)C4F)cc3)C2=S)cc1C(F)(F)F] | 5-[8-[4-[(4-fluoro-8-azabicyclo[3.2.1]octan-3-yl)oxy]phenyl]-5-oxo-7-thioxo-6,8-diazaspiro[3.4]octan-6-yl]-3-(trifluoromethyl)pyridine-2-carbonitrile<br>$^1$H NMR (400 MHz, Chloroform-d) δ ppm 1.70 (br. s., 1 H) 1.95 (d, J = 5.51 Hz, 1 H) 2.16-2.47 (m, 6 H) 2.49-2.59 (m, 2 H) 2.62-2.72 (m, 2 H) 4.25 (br. s., 1 H) 4.33 (br. s., 1 H) 4.59 (dd, J = 15.66, 8.16 Hz, 1 H) 5.24 (d, J = 4.19 Hz, 0.5 H) 5.35 (d, J = 4.63 Hz, 0.5 H) 7.11-7.20 (m, 2 H) 7.24 (d, J = 9.04 Hz, 2 H) 8.35 (d, J = 1.98 Hz, 1 H) 9.09 (d, J = 1.98 Hz, 1 H) 10.39 (br. s., 2 H).<br>$C_{26}H_{23}F_4N_5O_2S \cdot HCl$<br>MS m/z 546.1 (M + H)$^+$ |
| 102 | 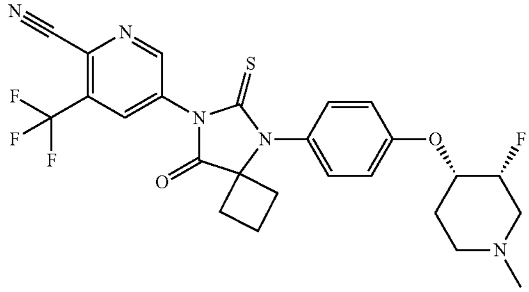 [SMILES: CN1CC[C@H](Oc2ccc(N3C(=S)N(c4cnc(C#N)c(C(F)(F)F)c4)C(=O)C34CCC4)cc2)[C@H](F)C1] | 5-[8-[(3RS, 4SR)-[4-[(3-fluoro-1-methyl-4-piperidyl)oxy]phenyl]-5-oxo-7-thioxo-6,8-diazaspiro[3.4]octan-6-yl]-3-(trifluoromethyl)pyridine-2-carbonitrile<br>$^1$H NMR (400 MHz, Chloroform-d) δ ppm 1.68-1.75 (m, 1 H) 2.19-2.39 (m, 2 H) 2.50-2.62 (m, 2 H) 2.68 (d, J = 8.78 Hz, 3 H) 2.93 (d, J = 3.26 Hz, 3 H) 3.16 (d, J = 8.28 Hz, 1 H) 3.28-3.46 (m, 2 H) 3.63 (d, J = 9.03 Hz, 1 H) 5.00 (br. s., 1 H) 5.51 (d, J = 9.79 Hz, 1 H) 5.62 (d, J = 9.29 Hz, 1 H) 7.18 (d, J = 8.53 Hz, 2 H) 7.29 (s, 2 H) 8.36 (d, J = 2.01 Hz, 1 H) 9.10 (d, J = 2.01 Hz, 1 H) 13.32 (br. s., 1 H)<br>$C_{25}H_{23}F_4N_5O_2S \cdot HCl$<br>MS m/z 534.1 (M + H)$^+$ |

-continued

| Cpd No. | Structure | Compound Name & Physical Data |
|---|---|---|
| 65 | 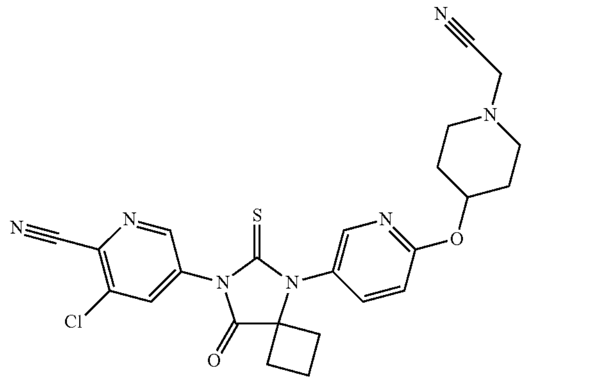 [SMILES: N#CCN1CCC(Oc2ccc(N3C(=S)N(c4cnc(C#N)c(Cl)c4)C(=O)C34CCC4)cn2)CC1] | 3-chloro-5-[8-[6-[[1-(cyanomethyl)-4-piperidyl]oxy]-3-pyridyl]-5-oxo-7-thioxo-6,8-diazaspiro[3.4]octan-6-yl]pyridine-2-carbonitrile.<br>$^1$H NMR (400 MHz, Chloroform-d) δ ppm 1.66 (d, J = 6.85 Hz, 1 H) 2.22 (br. s., 3 H) 2.46 (br. s., 4 H) 2.65 (br. s., 2 H) 3.15-3.58 (m, 4 H) 4.05 (d, J = 7.09 Hz, 2 H) 5.38 (br. s., 1 H) 6.93 (br. s., 1 H) 7.44-7.61 (m, 1 H) 8.05 (br. s., 2 H) 8.67-8.81 (m, 1 H).<br>$C_{24}H_{22}ClN_7O_2S$•HCl<br>MS m/z 508.1 (M + H)$^+$ |
| 38 | 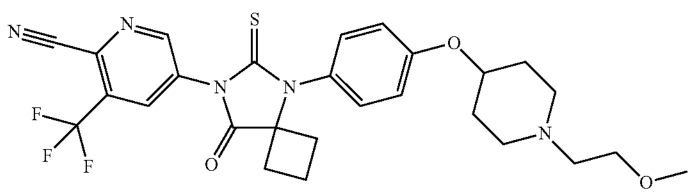 [SMILES: COCCN1CCC(Oc2ccc(N3C(=S)N(c4cnc(C#N)c(C(F)(F)F)c4)C(=O)C34CCC4)cc2)CC1] | 5-[8-[4-[[1-(2-methoxyethyl)-4-piperidyl]oxy]phenyl]-5-oxo-7-thioxo-6,8-diazaspiro[3.4]octan-6-yl]-3-(trifluoromethyl)pyridine-2-carbonitrile<br>$^1$H NMR (400 MHz, Chloroform-d) δ ppm 1.59-1.67 (m, 1 H) 1.85-1.95 (m, 2 H) 2.04-2.24 (m, 3 H) 2.38-2.56 (m, 4 H) 2.56-2.67 (m, 4 H) 2.80 (br. s., 2 H) 3.31 (s, 3 H) 3.48-3.56 (m, 2 H) 4.37 (br. s., 1 H) 7.00 (d, J = 8.82 Hz, 2 H) 7.14 (d, J = 8.82 Hz, 2 H) 8.30 (d, J = 1.98 Hz, 1 H) 9.04 (d, J = 1.98 Hz, 1 H).<br>$C_{27}H_{28}F_3N_5O_3S$•HCl<br>MS m/z 560.2 (M + H)$^+$ |
| 94 | 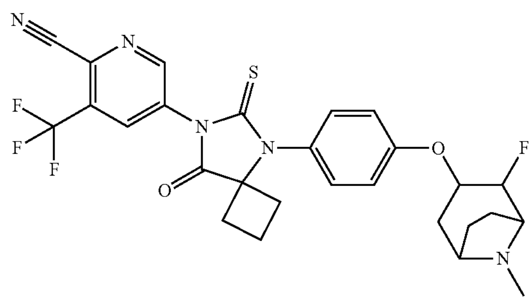 [SMILES: CN1C2CCC1C(F)C(Oc1ccc(N3C(=S)N(c4cnc(C#N)c(C(F)(F)F)c4)C(=O)C34CCC4)cc1)C2] | 5-[8-[4-[(4-fluoro-8-methyl-8-azabicyclo[3.2.1]octan-3-yl)oxy]phenyl]-5-oxo-7-thioxo-6,8-diazaspiro[3.4]octan-6-yl]-3-(trifluoromethyl)pyridine-2-carbonitrile.<br>$^1$H NMR (400 MHz, Chloroform-d) δ ppm 1.54-1.69 (m, 3H), 1.74-1.87 (m, 2H), 1.82-2.00 (m, 2H), 2.03-2.20 (m, 2H), 2.31 (s, 3H), 2.47-2.63 (m, 3H), 3.16 (br d, 1H, J = 3.1 Hz), 3.33-3.37 (m, 1H), 4.31-4.42 (m, 1H), 4.62-4.65 (m, 0.5H), 4.75-4.78 (m, 0.5H), 7.05-7.08 (m, 2H), 7.12-7.15 (m, 2H), 8.30 (d, 1H, J = 2.2 Hz), 9.04 (d, 1H, J = 2.4 Hz)<br>$C_{27}H_{25}F_4N_5O_2S$<br>MS m/z 560.1 (M + H)$^+$ |
| 35 | 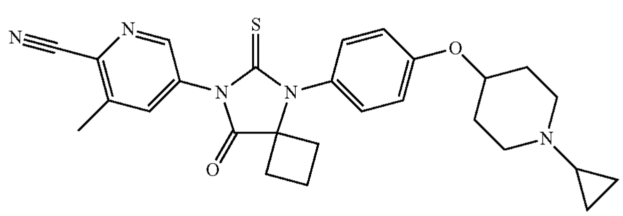 [SMILES: Cc1cc(N2C(=O)C3(CCC3)N(c3ccc(OC4CCN(C5CC5)CC4)cc3)C2=S)cnc1C#N] | 5-[8-[4-[(1-cyclopropyl-4-piperidyl)oxy]phenyl]-5-oxo-7-thioxo-6,8-diazaspiro[3.4]octan-6-yl]-3-methyl-pyridine-2-carbonitrile<br>$^1$H NMR (400 MHz, Chloroform-d) δ ppm 0.53 (br. s., 4 H) 1.67 (br. s., 2 H) 1.88 (br. s., 2 H) 2.06 (d, J = 17.12 Hz, 2 H) 2.17-2.25 (m, 1 H) 2.48-2.71 (m, 9 H) 2.97 (br. s., 2 H) 4.43 (br. s., 1 H) 7.03-7.09 (m, 2 H) 7.21 (d, J = 8.80 Hz, 2 H) 7.83 (d, J = 1.71 Hz, 1 H) 8.67 (d, J = 2.20 Hz, 1 H).<br>$C_{27}H_{29}N_5O_2S$<br>MS m/z 488.1 (M + H)$^+$ |
| 36 | 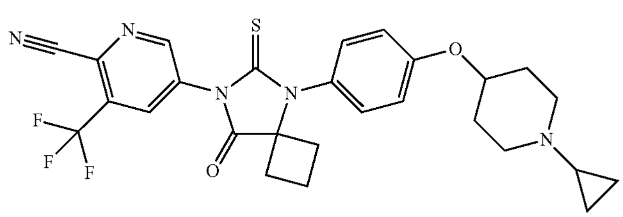 [SMILES: N#Cc1ncc(N2C(=O)C3(CCC3)N(c3ccc(OC4CCN(C5CC5)CC4)cc3)C2=S)cc1C(F)(F)F] | 5-[8-[4-[(1-cyclopropyl-4-piperidyl)oxy]phenyl]-5-oxo-7-thioxo-6,8-diazaspiro[3.4]octan-6-yl]-3-(trifluoromethyl)pyridine-2-carbonitrile<br>$^1$H NMR (400 MHz, Chloroform-d) δ ppm 0.50 (br. s., 4 H) 1.66-1.71 (m, 2 H) 1.86 (br. s., 2 H) 2.03 (br. s., 2 H) 2.18-2.27 (m, 1 H) 2.48-2.72 (m, 6 H) 2.95 (br. s., 2 H) 4.41 (br. s., 1 H) 7.04-7.10 (m, 2 H) 7.17-7.22 (m, 2 H) 8.36 (d, J = 1.96 Hz, 1 H) 9.10 (d, J = 1.96 Hz, 1 H).<br>$C_{27}H_{26}F_3N_5O_2S$<br>MS m/z 542.0 (M + H)$^+$ |

| Cpd No. | Structure | Compound Name & Physical Data |
|---|---|---|
| 89 | 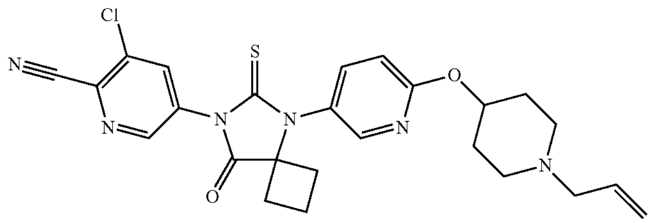 [SMILES: C=CCN1CCC(Oc2ccc(N3C(=S)N(c4cnc(C#N)c(Cl)c4)C(=O)C34CCC4)cn2)CC1] | 5-[8-[6-[(1-allyl-4-piperidyl)oxy]-3-pyridyl]-5-oxo-7-thioxo-6,8-diazaspiro[3.4]octan-6-yl]-3-chloro-pyridine-2-carbonitrile. $^1$H NMR (400 MHz, Chloroform-d) δ ppm ppm 1.71 (m, 2H), 2.17-2.37 (m, 3H), 2.42-2.55 (m, 3H), 2.61-2.75 (m, 3H), 3.08 (br s, 2H), 3.41 (br s, 2H), 3.57 (br s, 2H), 5.39-5.60 (m, 2H), 6.11-6.29 (m, 1H), 6.92 (d, 1H, J = 8.8 Hz), 7.54 (dd, 1H, J = 8.8, 2.7 Hz), 8.09 (d, 2H, J = 2.0 Hz), 8.78 (d, 1H, J = 2.0 Hz). $C_{25}H_{25}ClN_6O_2S$•HCl MS m/z 509.0 (M + H)$^+$ |
| 70 | 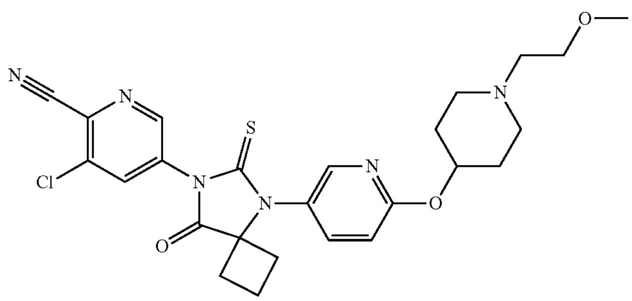 [SMILES: COCCN1CCC(Oc2ccc(N3C(=S)N(c4cnc(C#N)c(Cl)c4)C(=O)C34CCC4)cn2)CC1] | 3-chloro-5-[8-[6-[[1-(2-methoxyethyl)-4-piperidyl]oxy]-3-pyridyl]-5-oxo-7-thioxo-6,8-diazaspiro[3.4]octan-6-yl]pyridine-2-carbonitrile. $^1$H NMR (400 MHz, Chloroform-d) δ ppm 1.71 (d, J = 10.27 Hz, 1 H) 1.95 (br. s., 2 H) 2.07-2.33 (m, 3 H) 2.34-2.55 (m, 4 H) 2.57-2.76 (m, 4 H) 2.89 (br. s., 2 H) 3.36 (s, 3 H) 3.49-3.67 (m, 2 H) 5.15 (br. s., 1 H) 6.90 (d, J = 8.80 Hz, 1 H) 7.43-7.55 (m, 1 H) 8.08 (dd, J = 9.54, 2.20 Hz, 2 H) 8.79 (d, J = 1.96 Hz, 1 H) $C_{25}H_{27}ClN_6O_3S$ MS m/z 527.1 (M + H)$^+$ |
| 14 | 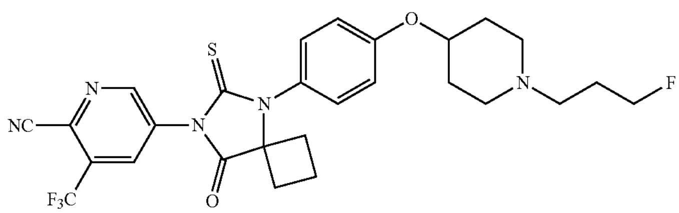 [SMILES: N#Cc1ncc(N2C(=O)C3(CCC3)N(c3ccc(OC4CCN(CCCF)CC4)cc3)C2=S)cc1C(F)(F)F] | 5-(5-(4-((1-(3-fluoropropyl)piperidin-4-yl)oxy)phenyl)-8-oxo-6-thioxo-5,7-diazaspiro[3.4]octan-7-yl)-3-(trifluoromethyl)picolinonitrile. $^1$H NMR (500 MHz, DMSO-d6) δ ppm 1.55-1.58 (m, 1H), 1.64-1.71 (m, 2H), 1.79-1.97 (m, 2H), 1.98-2.03 (m, 3H), 2.22-2.26 (m, 2H), 2.37-2.48 (m, 4H), 2.60-2.65 (m, 2H), 2.72-2.75 (m, 2H), 4.44-4.47 (m, 2H), 4.55 (t, 1H, J = 6.1 Hz), 7.16 (d, 2H, J = 8.8 Hz), 7.30 (d, 2H, J = 8.8 Hz), 8.77 (d, 1H, J = 1.9 Hz), 9.23 (d, 1H, J = 2.2 Hz) $C_{27}H_{27}F_4N_5O_2S$ MS m/z 562.1 (M + H)$^+$ |
| 17 | 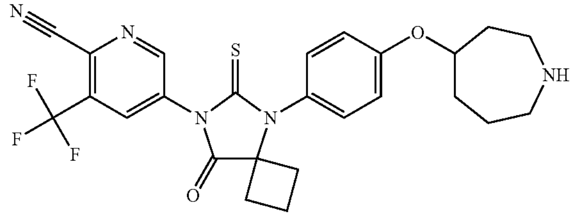 [SMILES: N#Cc1ncc(N2C(=O)C3(CCC3)N(c3ccc(OC4CCCNCC4)cc3)C2=S)cc1C(F)(F)F] | 5-[8-(4-azaperhydroepin-4-yloxyphenyl)-5-oxo-7-thioxo-6,8-diazaspiro[3.4]oct-6-yl]-3-(trifluoromethyl)pyridine-2-carbonitrile $C_{25}H_{24}F_3N_5O_2S$•HCl MS m/z 516.1 (M + H)$^+$ |
| 19 | 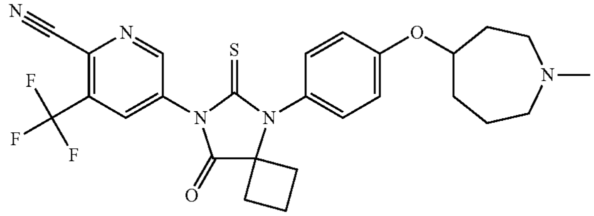 [SMILES: CN1CCCC(Oc2ccc(N3C(=S)N(c4cnc(C#N)c(C(F)(F)F)c4)C(=O)C34CCC4)cc2)CC1] | 5-{8-[4-(1-methylazaperhydroepin-4-yloxy)phenyl]-5-oxo-7-thioxo-6,8-diazaspiro[3.4]oct-6-yl}-3-(trifluoromethyl)pyridine-2-carbonitrile. $^1$H NMR (500 MHz, DMSO-d6) δ ppm 1.54-1.57 (m, 1H), 1.75-1.90 (m, 1H), 1.92-2.01 (m, 3H), 2.06-2.13 (m, 2H), 2.19-2.26 (m, 2H), 2.37 (br s, 1H), 2.41-2.48 (m, 3H), 2.61-2.65 (m, 1H), 2.83 (t, 2H, J = 5.7 Hz), 3.15-3.19 (m, 1H), 3.44-3.51 (m, 2H), 4.78-4.84 (m, 1H), 7.15-7.18 (m, 2H), 7.32-7.34 (m, 2H), 8.76 (d, 1H, J = 1.9 Hz), 9.22 (d, 1H, J = 1.9 Hz). $C_{26}H_{26}F_3N_5O_2S$•HCl MS m/z 530.2 (M + H)$^+$ |

-continued

| Cpd No. | Structure | Compound Name & Physical Data |
|---|---|---|
| 20 | 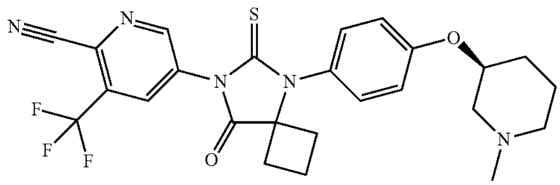 [SMILES: CN1CCC[C@H](Oc2ccc(N3C(=S)N(c4cnc(C#N)c(C(F)(F)F)c4)C(=O)C34CCC4)cc2)C1] | 5-{8-[4-((3S)-1-methyl(3-piperidyloxy))phenyl]-5-oxo-7-thioxo-6,8-diazaspiro[3.4]oct-6-yl}-3-(trifluoromethyl)pyridine-2-carbonitrile.<br>$^1$H NMR (500 MHz, DMSO-d$_6$) δ ppm 1.42 (br s, 1H), 1.53-1.63 (m, 2H), 1.75 (br dd, 1H, J = 8.7, 3.9 Hz), 1.93-2.07 (m, 3H), 2.13 (br s, 1H), 2.23 (br s, 3H), 2.41-2.49 (m, 2H), 2.55-2.65 (m, 3H), 2.92 (br d, 1H, J = 8.8 Hz), 4.49 (br s, 1H), 7.14-7.18 (m, 2H, J = 8.8 Hz), 7.29-7.32 (m, 2H, J = 8.8 Hz), 8.77 (d, 1H, J = 1.9 Hz), 9.23 (d, 1H, J = 1.9 Hz)<br>$C_{25}H_{24}F_3N_5O_2S$<br>MS m/z 516.2 (M + H)$^+$ |
| 12 | 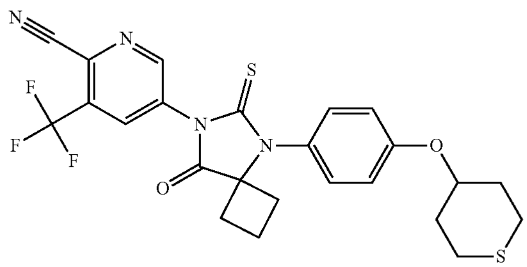 [SMILES: N#Cc1ncc(N2C(=O)C3(CCC3)N(c3ccc(OC4CCSCC4)cc3)C2=S)cc1C(F)(F)F] | 5-[5-oxo-8-(4-thian-4-yloxyphenyl)-7-thioxo-6,8-diazaspiro[3.4]oct-6-yl]-3-(trifluoromethyl)pyridine-2-carbonitrile<br>$^1$H NMR (500 MHz, DMSO-d$_6$) δ ppm 1.53-1.60 (m, 1H), 1.81-1.85 (m, 2H), 1.98 (br d, 1H, J = 10.4 Hz), 2.25 (ddd, 2H, J = 9.7, 6.4, 3.5 Hz), 2.34-2.46 (m, 2H), 2.62 (br t, 2H, J = 9.8 Hz), 2.72 (dd, 2H, J = 9.9, 2.7 Hz), 2.78-2.82 (m, 2H), 4.51-4.55 (m, 1H), 7.18 (d, 2H, J = 8.8 Hz), 7.31 (d, 2H, J = 8.8 Hz), 8.77 (d, 1H, J = 1.9 Hz), 9.22 (s, 1H)<br>$C_{24}H_{21}F_3N_4O_2S_2$<br>MS m/z 519.1 (M + H)$^+$ |
| 13 | 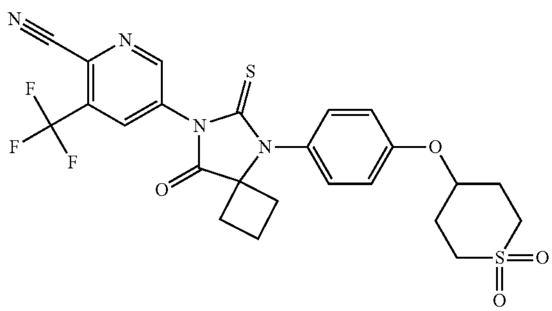 [SMILES: N#Cc1ncc(N2C(=O)C3(CCC3)N(c3ccc(OC4CCS(=O)(=O)CC4)cc3)C2=S)cc1C(F)(F)F] | 5-{8-[4-(1,1-dioxothian-4-yloxy)phenyl]-5-oxo-7-thioxo-6,8-diazaspiro[3.4]oct-6-yl}-3-(trifluoromethyl)pyridine-2-carbonitrile<br>$^1$H NMR (500 MHz, DMSO-d$_6$) δ ppm 1.53-1.60 (m, 1H), 1.95-2.01 (m, 1H), 2.21-2.34 (m, 4H), 2.41-2.48-2.49 (m, 1H), 2.60-2.66 (m, 2H), 3.21-3.31 (m, 1H), 3.21-3.31 (m, 4H), 4.82 (dt, 1H, J = 6.5, 3.4 Hz), 7.25 (d, 2H, J = 9.1 Hz), 7.35 (d, 2H, J = 8.8 Hz), 8.76 (d, 1H, J = 1.9 Hz), 9.22-9.24 (m, 1H)<br>$C_{24}H_{21}F_3N_4O_4S_2$<br>MS m/z 551.1 (M + H)$^+$ |
| 2 | 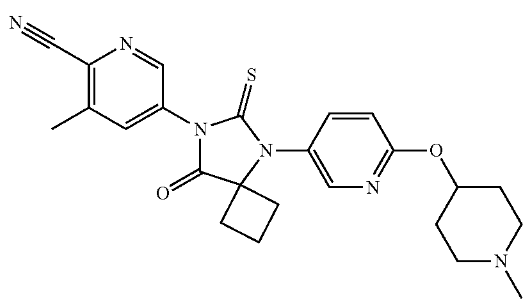 [SMILES: Cc1cc(N2C(=O)C3(CCC3)N(c3ccc(OC4CCN(C)CC4)nc3)C2=S)cnc1C#N] | 3-methyl-5-{8-[6-(1-methyl(4-piperidyloxy))(3-pyridyl)]-5-oxo-7-thioxo-6,8-diazaspiro[3.4]oct-6-yl}pyridine-2-carbonitrile.<br>$^1$H NMR (500 MHz, DMSO-d$_6$) δ ppm 1.54-1.65 (m, 1H), 1.67-1.77 (m, 2H), 1.91-2.10 (m, 3H), 2.14-2.24 (m, 2H), 2.20 (s, 3H), 2.37-2.49 (m, 3H), 2.59 (s, 3H), 2.54-2.72 (m, 3H), 5.05 (tt, 1H, J = 8.6, 4.1 Hz), 7.01 (d, 1H, J = 8.8 Hz), 7.77 (dd, 1H, J = 8.8, 2.8 Hz), 8.14 (d, 1H, J = 2.2 Hz), 8.22 (d, 1H, J = 2.8 Hz), 8.72 (d, 1H, J = 2.2 Hz)<br>$C_{24}H_{26}N_6O_2S$<br>MS m/z 463.2 (M + H)$^+$ |
| 21 | 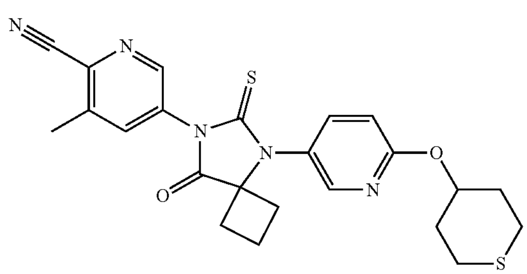 [SMILES: Cc1cc(N2C(=O)C3(CCC3)N(c3ccc(OC4CCSCC4)nc3)C2=S)cnc1C#N] | 3-methyl-5-[5-oxo-8-(6-thian-4-yloxy(3-pyridyl))-7-thioxo-6,8-diazaspiro[3.4]oct-6-yl]pyridine-2-carbonitrile<br>$^1$H NMR (500 MHz, DMSO-d$_6$) δ ppm 1.55-1.63 (m, 1H), 1.84-2.02 (m, 3H), 2.28 (ddd, 2H, J = 9.6, 6.5, 3.2 Hz), 2.37-2.48 (m, 2H), 2.55-2.74 (m, 4H), 2.59 (s, 3H), 2.77-2.84 (m, 2H), 5.13-5.19 (m, 1H), 7.04 (d, 1H, J = 8.8 Hz), 7.79 (dd, 1H, J = 8.7, 2.7 Hz), 8.14 (d, 1H, J = 2.2 Hz), 8.22 (d, 1H, J = 2.5 Hz), 8.72 (d, 1H, J = 1.9 Hz)<br>$C_{23}H_{23}N_5O_2S_2$<br>MS m/z 466.1 (M + H)$^+$ |

Example 8

5-[5-oxo-7-thioxo-8-[6-[[1-(2,2,2-trifluoroethyl)-4-piperidyl]oxy]-3-pyridyl]-6,8-diazaspiro[3.4]octan-6-yl]-3-(trifluoromethyl)pyridine-2-carbonitrile, Cpd 66

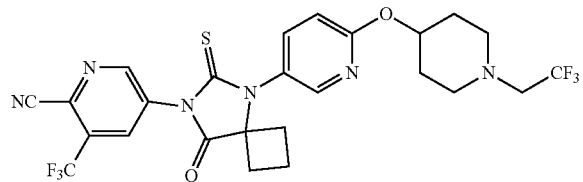 [SMILES: N#Cc1ncc(N2C(=O)C3(CCC3)N(c3ccc(OC4CCN(CC(F)(F)F)CC4)nc3)C2=S)cc1C(F)(F)F]

To a solution of 5-(8-oxo-5-(6-(piperidin-4-yloxy)pyridin-3-yl)-6-thioxo-5,7-diazaspiro[3.4]octan-7-yl)-3-(trifluoromethyl)picolinonitrile (0.246 g, 0.4 mmol), DIEA (0.206 g, 1.6 mmol) in THF (5 mL) was added 2,2,2-trifluoroethyl trifluoromethanesulfonate (0.185 g, 0.8 mmol). The mixture was heated at 80° C. for 12 h, cooled down to RT and concentrated under reduced pressure. The residue was purified by preparative reverse phase HPLC (Column: Gemini C18 150*25 mm*10 μm, Flow rate: 25 mL/min, Mobile Phase A: Purified water (containing 0.1% HCl), Mobile Phase B: acetonitrile, Gradient: 36-66(% B) from 0-15 min) to afford 5-[5-oxo-7-thioxo-8-[6-[[1-(2,2,2-trifluoroethyl)-4-piperidyl]oxy]-3-pyridyl]-6,8-diazaspiro[3.4]octan-6-yl]-3-(trifluoromethyl)pyridine-2-carbonitrile hydrochloride salt (0.0562 g, 23%). $^1$H NMR (400 MHz, DMSO-d$_6$) δ ppm 1.53-1.64 (m, 1H) 1.83-2.02 (m, 3H) 2.16 (br. s., 2H) 2.38-2.47 (m, 2H) 2.64 (t, J=10.16 Hz, 2H) 2.97 (br. s., 2H) 3.18 (br. s., 2H) 3.65-3.81 (m, 2H) 5.19 (br. s., 1H) 7.06 (d, J=8.78 Hz, 1H) 7.78 (dd, J=8.53, 2.76 Hz, 1H) 8.22 (d, J=2.51 Hz, 1H) 8.75 (d, J=2.01 Hz, 1H) 9.21 (d, J=1.76 Hz, 1H) C$_{25}$H$_{22}$F$_6$N$_6$O$_2$S. HCl MS m/z 585.1 (M+H)$^+$.

Example 9

5-[8-[6-[[1-(cyanomethyl)-4-piperidyl]oxy]-3-pyridyl]-5-oxo-7-thioxo-6,8-diazaspiro[3.4]octan-6-yl]-3-(trifluoromethyl)pyridine-2-carbonitrile, Cpd 60

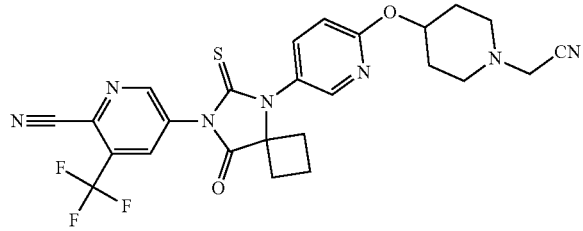 [SMILES: N#CCN1CCC(Oc2ccc(N3C(=S)N(c4cnc(C#N)c(C(F)(F)F)c4)C(=O)C34CCC4)cn2)CC1]

To a solution of 5-(8-oxo-5-(6-(piperidin-4-yloxy)pyridin-3-yl)-6-thioxo-5,7-diazaspiro[3.4]octan-7-yl)-3-(trifluoromethyl)picolinonitrile (0.154 g, 0.25 mmol), DIEA (0.129 g, 1 mmol) in DMF (3 mL) was added 1-fluoro-2-iodoethane (0.087 g, 0.5 mmol). The mixture was heated at 80° C. for 12 h, cooled down to RT and concentrated under reduced pressure. The residue was purified by preparative reverse phase HPLC ((Column: Gemini C18 150*25 mm*10 μm, Flow rate: 25 mL/min, Mobile Phase A: Purified water (containing 0.1% HCl), Mobile Phase B: acetonitrile, Gradient: 15-45(% B) from 0-15 min) to afford 5-[8-[6-[[1-(cyanomethyl)-4-piperidyl]oxy]-3-pyridyl]-5-oxo-7-thioxo-6,8-diazaspiro[3.4]octan-6-yl]-3-(trifluoromethyl)pyridine-2-carbonitrile hydrochloride salt (0.075 g, 50%). $^1$H NMR (400 MHz, DMSO-d$_6$) δ ppm 1.52-1.65 (m, 1H) 1.90-2.02 (m, 1H) 2.09 (br. s., 2H) 2.22-2.34 (m, 2H) 2.38-2.49 (m, 2H) 2.64 (t, J=9.79 Hz, 2H) 3.16 (br. s., 2H) 3.30 (br. s., 2H) 4.41 (br. s., 2H) 5.28 (br. s., 1H) 7.05-7.10 (m, 1H) 7.80 (dd, J=8.78, 2.51 Hz, 1H) 8.24 (d, J=2.51 Hz, 1H) 8.76 (d, J=2.01 Hz, 1H) 9.22 (d, J=1.76 Hz, 1H). C$_{25}$H$_{22}$F$_3$N$_7$O$_2$S. HCl MS m/z 542.2 (M+H)$^+$.

Example 10

5-[8-[6-[[1-(2-fluoroethyl)-4-piperidyl]oxy]-3-pyridyl]-5-oxo-7-thioxo-6,8-diazaspiro[3.4]octan-6-yl]-3-(trifluoromethyl)pyridine-2-carbonitrile, Cpd 67

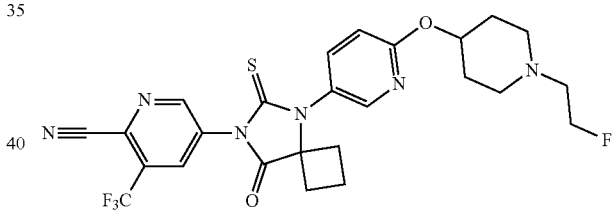

To a solution of 5-(8-oxo-5-(6-(piperidin-4-yloxy)pyridin-3-yl)-6-thioxo-5,7-diazaspiro[3.4]octan-7-yl)-3-(trifluoromethyl)picolinonitrile (0.154 g, 0.25 mmol), DIEA (0.129 g, 1 mmol) in DMF (3 mL) was added 2-chloroacetonitrile (0.038 g, 0.5 mmol). The mixture was heated at 80° C. for 12 h, cooled down to RT and concentrated under reduced pressure. The residue was purified by preparative reverse phase HPLC ((Column: Gemini C18 150*25 mm*10 μm, Flow rate: 25 mL/min, Mobile Phase A: Purified water (containing 0.1% HCl), Mobile Phase B: acetonitrile, Gradient: 15-45(% B) from 0-15 min) to afford 5-[8-[6-[[1-(2-fluoroethyl)-4-piperidyl]oxy]-3-pyridyl]-5-oxo-7-thioxo-6,8-diazaspiro[3.4]octan-6-yl]-3-(trifluoromethyl)pyridine-2-carbonitrile hydrochloride salt (0.078 g, 53%). $^1$H NMR (400 MHz, DMSO-d$_6$) δ ppm 1.51-1.67 (m, 1H) 1.90-2.13 (m, 2H) 2.15-2.37 (m, 3H) 2.39-2.48 (m, 2H) 2.65 (t, J=9.79 Hz, 2H) 3.18-3.28 (m, 2H) 3.45-3.64 (m, 4H) 4.78-5.02 (m, 2H) 5.19-5.43 (m, 1H) 7.09 (d, J=8.78 Hz, 1H) 7.81 (d, J=6.78 Hz, 1H) 8.24 (br. s., 1H) 8.75 (d, J=2.01 Hz, 1H) 9.22 (d, J=2.01 Hz, 1H) 10.83 (br. s., 1H). C$_{25}$H$_{24}$F$_4$N$_6$O$_2$S. HCl MS m/z 549.1 (M+H)$^+$.

Example 11

5-(5-(4-((1-(3,3-dimethylbutyl)piperidin-4-yl)oxy)phenyl)-8-oxo-6-thioxo-5,7-diazaspiro[3.4]octan-7-yl)-3-(trifluoromethyl)picolinonitrile, Cpd 34

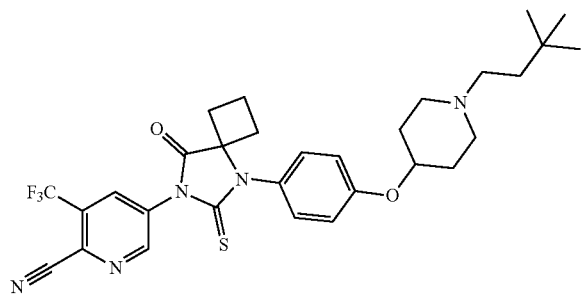 [SMILES: CC(C)(C)CCN1CCC(Oc2ccc(N3C(=S)N(c4cnc(C#N)c(C(F)(F)F)c4)C(=O)C34CCC4)cc2)CC1]

3,3-Dimethylbutanal (0.032 g, 0.32 mmol) was added to a solution of 5-(8-oxo-5-(4-(piperidin-4-yloxy)phenyl)-6-thioxo-5,7-diazaspiro[3.4]octan-7-yl)-3-(trifluoromethyl)picolinonitrile (0.1 g, 0.164 mmol), acetic acid (0.009 g, 0.162 mmol) in DCE (3 mL). The mixture was stirred at RT for 30 min, before Sodium triacetoxyborohydride (0.069 g, 0.324 mmol) was added. The reaction was stirred at RT overnight, washed with aqueous saturated NaHCO$_3$ and extracted with EtOAc. The organic layer was washed successively with water, brine, dried over MgSO$_4$, filtered and concentrated to give the crude product. The residue was purified by preparative reverse phase HPLC (Column: Gemini 150*25 mm*5 µm, Flow rate: 25 mL/min, Mobile Phase A: Purified water (containing 0.1% HCl), Mobile Phase B: acetonitrile, Gradient: 30-60(% B) from 0-10 min). Desired fractions were collected, concentrated under reduced pressure, neutralized with aqueous saturated NaHCO$_3$ and extracted with DCM. The organic layer was dried over MgSO$_4$, filtered and concentrated to afford 5-(5-(4-((1-(3,3-dimethylbutyl)piperidin-4-yl)oxy)phenyl)-8-oxo-6-thioxo-5,7-diazaspiro[3.4]octan-7-yl)-3-(trifluoromethyl)picolinonitrile (0.048 g, 50%). $^1$H NMR (400 MHz, DMSO-d$_6$) δ ppm 0.88 (s, 9H) 1.34 (d, J=12.57 Hz, 2H) 1.49-1.71 (m, 3H) 1.97 (br. s., 2H) 2.19 (br. s., 2H) 2.24-2.35 (m, 2H) 2.42 (br. s., 2H) 2.56-2.67 (m, 3H) 2.72 (br. s., 2H) 4.44 (br. s., 1H) 7.14 (d, J=8.60 Hz, 2H) 7.28 (d, J=8.60 Hz, 2H) 8.75 (s, 1H) 9.21 (s, 1H). C$_{30}$H$_{34}$F$_3$N$_5$O$_2$S MS m/z 586.1 (M+H)$^+$.

Example 12

5-[8-[4-[(3R)-1-methylpyrrolidin-3-yl]oxyphenyl]-5-oxo-7-thioxo-6,8-diazaspiro[3.4]octan-6-yl]-3-(trifluoromethyl)pyridine-2-carbonitrile, Cpd 16

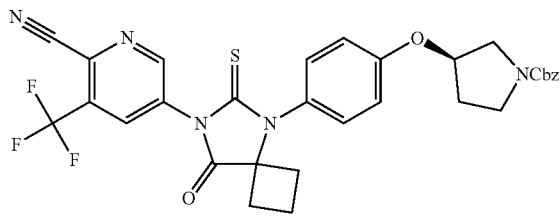 [SMILES: N#Cc1ncc(N2C(=O)C3(CCC3)N(c3ccc(O[C@@H]4CCN(C(=O)OCc5ccccc5)C4)cc3)C2=S)cc1C(F)(F)F]

A. To a solution of 5-(5-(4-hydroxyphenyl)-8-oxo-6-thioxo-5,7-diazaspiro[3.4]octan-7-yl)-3-(trifluoromethyl)picolinonitrile (0.21 g, 0.5 mmol), (R)-benzyl 3-hydroxypyrrolidine-1-carboxylate (0.124 g, 0.6 mmol) and triphenylphosphine (0.2 g, 0.75 mmol) in dry THF (6 mL) was added DIAD (0.15 g, 0.75 mmol) under a nitrogen atmosphere. After stirring at RT overnight the mixture was diluted with water and extracted with EtOAc. The organic layer was then washed with water, brine, dried over Na$_2$SO$_4$, filtered and concentrated to dryness. Chromatography over silica gel (gradient of EA in heptane from 0 to 50%) gave (R)-benzyl 3-(4-(7-(6-cyano-5-(trifluoromethyl)pyridin-3-yl)-8-oxo-6-thioxo-5,7-diazaspiro[3.4]octan-5-yl)phenoxy)pyrrolidine-1-carboxylate as a pale yellow solid (0.22 g, 71%).

B. (R)-5-(8-oxo-5-(4-(pyrrolidin-3-yloxy)phenyl)-6-thioxo-5,7-diazaspiro[3.4]octan-7-yl)-3-(trifluoromethyl)picolinonitrile

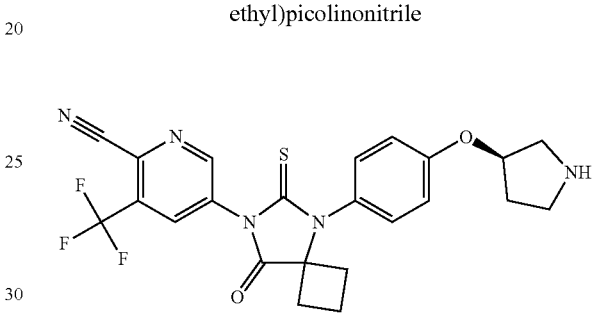

To a solution of (R)-benzyl 3-(4-(7-(6-cyano-5-(trifluoromethyl)pyridin-3-yl)-8-oxo-6-thioxo-5,7-diazaspiro[3.4]octan-5-yl)phenoxy)pyrrolidine-1-carboxylate (0.2 g, 0.32 mmol) in DCM (6.4 mL) was added borane dimethyl sulfide complex (0.41 g, 3.2 mmol). The mixture was stirred at room temperature 4 h, then poured into water/aqueous saturated NaHCO$_3$ and extracted with DCM. The organic layer was then washed with water, brine, dried over Na$_2$SO$_4$, filtered and concentrated to dryness. Chromatography over silica gel (gradient of MeOH in DCM from 0 to 10%) gave (R)-5-(8-oxo-5-(4-(pyrrolidin-3-yloxy)phenyl)-6-thioxo-5,7-diazaspiro[3.4]octan-7-yl)-3-(trifluoromethyl) picolinonitrile as an off-white solid (0.08 g, 82%).

C. 5-[8-[4-[(3R)-1-methylpyrrolidin-3-yl]oxyphenyl]-5-oxo-7-thioxo-6,8-diazaspiro[3.4]octan-6-yl]-3-(trifluoromethyl)pyridine-2-carbonitrile

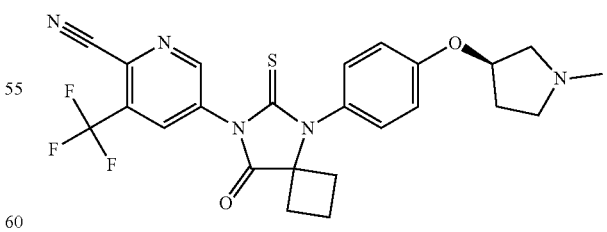

Formaldehyde (37% wt in water, 36 µl, 0.49 mmol) was added at 0° C. to a solution of (R)-5-(8-oxo-5-(4-(pyrrolidin-3-yloxy)phenyl)-6-thioxo-5,7-diazaspiro[3.4]octan-7-yl)-3-(trifluoromethyl)picolinonitrile (0.08 g, 0.16 mmol) and AcOH (46 µL, 0.8 mmol) in MeOH (3.2 mL). The mixture was stirred at room temperature overnight, then diluted with water and aqueous saturated NaHCO₃ and extracted with EtOAc. The organic layer was washed with water, brine, dried over Na₂SO₄, filtered and concentrated to dryness. The resulting material was purified by preparative reverse phase HPLC (C18 column using gradient of a mixture MeCN/0/1% aqueous TFA from 30 to 70%). The pure fractions were collected, concentrated to dryness, redissolved in EtOAc, and treated with aqueous 2.0M HCl in Et₂O at 0° C., then concentrated to give 5-[8-[4-[(3R)-1-methylpyrrolidin-3-yl]oxyphenyl]-5-oxo-7-thioxo-6,8-diazaspiro[3.4]octan-6-yl]-3-(trifluoromethyl)pyridine-2-carbonitrile HCl as a pale yellow solid (0.036 g, 42%). ¹H NMR (500 MHz, DMSO-d₆) δ ppm 1.54-1.62 (m, 1H), 1.98-2.05 (m, 1H), 2.15-2.26 (m, 1H), 2.31 (dtd, 1H, J=14.2, 9.4, 4.9 Hz), 2.39-2.51 (m, 3H), 2.67 (br t, 3H, J=9.5 Hz), 2.93 (br s, 1H), 3.44-3.56 (m, 1H), 3.75-3.83 (m, 1H), 5.26 (br s, 1H), 7.22 (br d, 2H, J=8.8 Hz), 7.40 (d, 2H, J=7.9 Hz), 8.79 (d, 1H, J=1.9 Hz), 9.25 (d, 2H, J=1.6 Hz) C₂₄H₂₂F₃N₅O₂S. HCl MS m/z 502.1 (M+H)⁺.

Example 13

5-[8-[4-[[(1R,3r, 5S)-8-azabicyclo[3.2.1]octan-3-yl]oxy]phenyl]-5-oxo-7-thioxo-6,8-diazaspiro[3.4]octan-6-yl]-3-(trifluoromethyl)pyridine-2-carbonitrile, Cpd 29

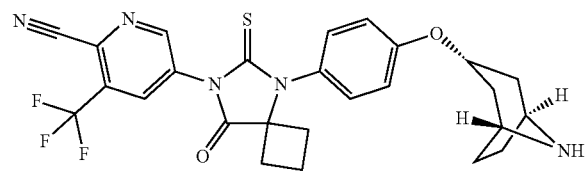 [SMILES: N#Cc1ncc(N2C(=O)C3(CCC3)N(c3ccc(O[C@H]4C[C@H]5CC[C@@H](C4)N5)cc3)C2=S)cc1C(F)(F)F]

Cyanomethylenetributylphosphorane (0.181 g, 0.75 mmol) was added to a solution of 5-(5-(4-hydroxyphenyl)-8-oxo-6-thioxo-5,7-diazaspiro[3.4]octan-7-yl)-3-(trifluoromethyl) picolinonitrile (0.209 g, 0.5 mmol) and tert-butyl (1S,5R)-3-hydroxy-8-azabicyclo[3.2.1]octane-8-carboxylate (0.17 g, 0.75 mmol) in THF (10 mL). The solution was stirred at 80° C. for 10 h, allowed to cool to RT and concentrated under reduced pressure. The residue was purified by chromatography over silica gel (petroleum ether: EtOAc=2:1) to yield (1R,3r,5S)-tert-butyl 3-(4-(7-(6-cyano-5-(trifluoromethyl)pyridin-3-yl)-8-oxo-6-thioxo-5,7-diazaspiro[3.4]octan-5-yl)phenoxy)-8-azabicyclo[3.2.1]octane-8-carboxylate (0.2 g, 45%), directly used into the next step.

TFA (2 mL, 26 mmol) was added to a solution of (1R,3r,5S)-tert-butyl 3-(4-(7-(6-cyano-5-(trifluoromethyl)pyridin-3-yl)-8-oxo-6-thioxo-5,7-diazaspiro[3.4]octan-5-yl)phenoxy)-8-azabicyclo[3.2.1]octane-8-carboxylate (0.2 g, 0.223 mmol) in DCM (10 mL). The mixture was stirred for 2 h at RT and then concentrated under reduced pressure. The residue was purified by preparative reverse phase HPLC ((Column: Synergi 150*25 mm*10 μm, Flow rate: 30 mL/min, Mobile Phase A: Purified water (containing 0.1% HCl), Mobile Phase B: acetonitrile, Gradient: 40-70(% B) from 0-15 min) to afford 5-[8-[4-[[(1R,3r, 5S)-8-azabicyclo[3.2.1]octan-3-yl]oxy]phenyl]-5-oxo-7-thioxo-6,8-diazaspiro[3.4]octan-6-yl]-3-(trifluoromethyl)pyridine-2-carbonitrile (0.057 g, 46%) as a TFA salt. ¹H NMR (400 MHz, CHLOROFORM-d) δ ppm 1.69 (br. s., 1H) 2.01 (br. s., 2H) 2.24 (d, J=9.54 Hz, 1H) 2.30-2.52 (m, 6H) 2.57 (d, J=10.79 Hz, 2H) 2.68 (br. s., 2H) 4.25 (br. s., 2H) 4.71 (br. s., 1H) 7.08 (d, J=7.03 Hz, 2H) 7.23 (d, J=8.03 Hz, 2H) 8.36 (d, J=1.76 Hz, 1H) 9.10 (s, 1H) 9.92 (s, 1H). C₂₆H₂₄F₃N₅O₂S MS m/z 528.1 (M+H)⁺.

Example 14

3-methoxy-5-[8-[4-[(1-methyl-4-piperidyl)methyl]phenyl]-5-oxo-7-thioxo-6,8-diazaspiro[3.4]octan-6-yl]pyridine-2-carbonitrile hydrochloride, Cpd 239

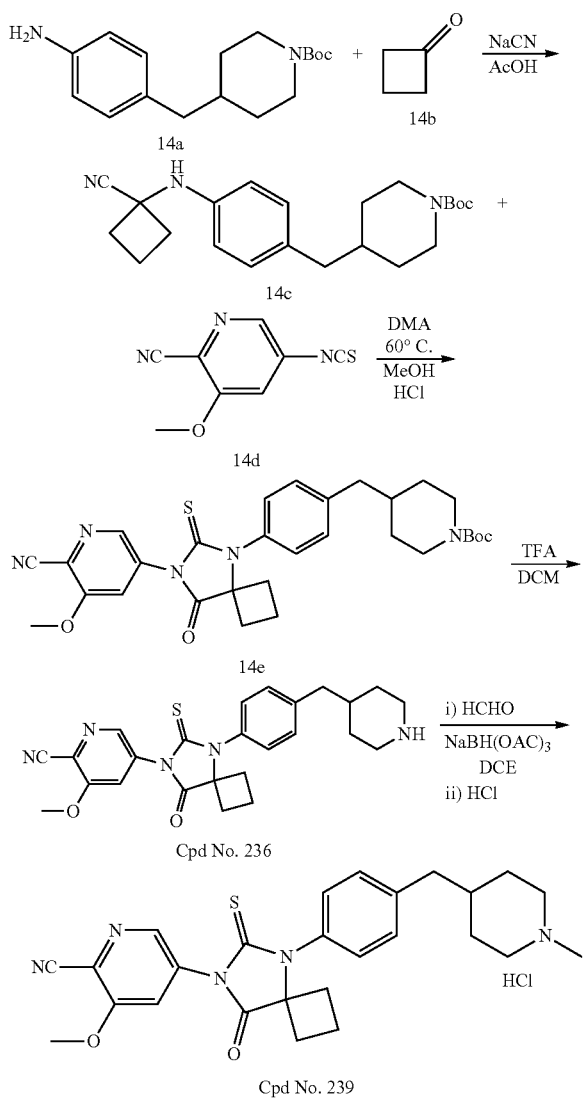

A. 4-[4-(1-Cyano-cyclobutylamino)-benzyl]-piperidine-1-carboxylic Acid Tert-Butyl Ester, 14c

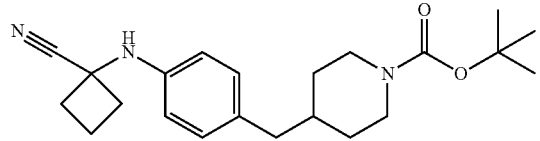 [SMILES: CC(C)(C)OC(=O)N1CCC(Cc2ccc(NC3(C#N)CCC3)cc2)CC1]

Cyclobutanone (1.54 mL, 20.6 mmol) was added to a solution of 4-(4-Amino-benzyl)-piperidine-1-carboxylic acid tert-butyl ester (3.0 g, 10.3 mmol) in Acetic acid (50 mL). The solution was stirred for 15 min at room temperature before Sodium cyanide (1.01 g, 20.6 mmol) was added and the reaction stirred for 4 h. The solution was concentrated under reduced pressure. The resultant residue was partitioned between EA (75 mL) and 1M Na$_2$CO$_3$ (125 mL). The organic layer was further washed with brine (50 mL), dried over MgSO$_4$, filtered and concentrated to dryness. Purification by chromatography over silica gel (gradient of EA in heptane from 0 to 50%) gave the pure product as an oily residue (2.82 g, 74%). $^1$H NMR (300 MHz, Chloroform-d) δ 0.73-0.97 (m, 1H), 1.00-1.19 (m, 2H), 1.20-1.34 (m, 1H), 1.45 (s, 9H), 1.61 (d, J=11.4 Hz, 2H), 2.09-2.31 (m, 2H), 2.31-2.41 (m, 2H), 2.44 (d, J=6.8 Hz, 2H), 2.63 (t, J=12.7 Hz, 2H), 2.72-2.89 (m, 2H), 6.58 (d, J=8.3 Hz, 2H), 7.00 (d, J=8.3 Hz, 2H). C$_{22}$H$_{31}$N$_3$O$_2$ MS m/z 270 (M+H-Boc)$^+$.

B. 4-{4-[7-(6-Cyano-5-methoxy-pyridin-3-yl)-8-oxo-6-thioxo-5,7-diaza-spiro[3.4]oct-5-yl]-benzyl}-piperidine-1-carboxylic Acid Tert-Butyl Ester, 14e

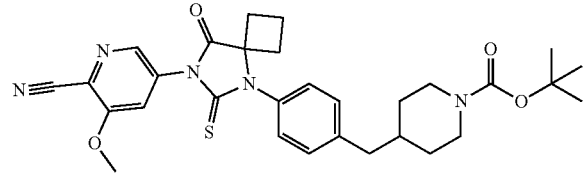 [SMILES: COc1cc(N2C(=O)C3(CCC3)N(c3ccc(CC4CCN(C(=O)OC(C)(C)C)CC4)cc3)C2=S)cnc1C#N]

4-[4-(1-Cyano-cyclobutylamino)-benzyl]-piperidine-1-carboxylic acid tert-butyl ester (0.484 g, 1.24 mmol) and freshly prepared 5-Isothiocyanato-3-methoxy-pyridine-2-carbonitrile (0.59 g, 3.08 mmol) were mixed in DMA (12 mL). The resulting solution was stirred at 60° C. for 4 hours and then allowed to cool to room temperature. The mixture was diluted with MeOH (2.5 mL) and 1M HCl (2.5 mL) was added. The stirring was maintained overnight. EA (35 mL) was added and solution washed with 1M Na$_2$CO$_3$ (150 mL) and brine (25 mL). The organic layer was dried over MgSO$_4$, filtered and concentrated to dryness. The crude was purified by chromatography over silica gel (gradient of EA in heptane from 0 to 60%) to yield pure product (0.744 g, 53%). $^1$H NMR (300 MHz, Chloroform-d) δ 1.08-1.30 (m, 3H), 1.45 (s, 9H), 1.62-1.84 (m, 4H), 2.12-2.34 (m, 1H), 2.48-2.77 (m, 9H), 4.00 (s, 3H), 7.23 (d, J=8.2 Hz, 2H), 7.35 (d, J=8.0 Hz, 2H), 7.57 (d, J=1.9 Hz, 1H), 8.43 (d, J=1.8 Hz, 1H). C$_{30}$H$_{35}$N$_5$O$_4$S MS m/z 506 (M+H-tBu)$^+$.

C. 3-Methoxy-5-[8-oxo-5-(4-piperidin-4-ylmethyl-phenyl)-6-thioxo-5,7-diaza-spiro[3.4]oct-7-yl]-pyridine-2-carbonitrile, Cpd 236

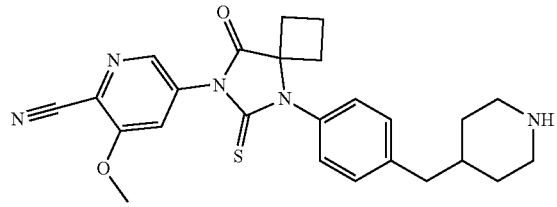 [SMILES: COc1cc(N2C(=O)C3(CCC3)N(c3ccc(CC4CCNCC4)cc3)C2=S)cnc1C#N]

The previous 4-{4-[7-(6-Cyano-5-methoxy-pyridin-3-yl)-8-oxo-6-thioxo-5,7-diaza-spiro[3.4]oct-5-yl]-benzyl}-piperidine-1-carboxylic acid tert-butyl ester (0.744 g, 1.32 mmol) was taken in DCM (15 mL). Trifluoroacetic acid (2.65 mL, 35.6 mmol) was added with stirring. The mixture was concentrated to dryness after 30 min at room temperature. Preparative LC (gradient of ACN in 25 mM aqueous NH$_4$HCO$_3$ from 19 to 55%) afforded the desired pure product. Trituration in diethyl ether gave 3-Methoxy-5-[8-oxo-5-(4-piperidin-4-ylmethyl-phenyl)-6-thioxo-5,7-diaza-spiro[3.4]oct-7-yl]-pyridine-2-carbonitrile as a white powder (0.30 g, 96%). $^1$H NMR (300 MHz, Chloroform-d) δ 1.42-1.73 (m, 3H), 1.81 (d, J=12.4 Hz, 2H), 2.13-2.34 (m, 1H), 2.48-2.82 (m, 9H), 3.32 (d, J=12.3 Hz, 2H), 4.00 (s, 3H), 7.23 (d, J=7.8 Hz, 2H), 7.35 (d, J=8.0 Hz, 2H), 7.56 (d, J=1.9 Hz, 1H), 8.43 (d, J=1.9 Hz, 1H). C$_{25}$H$_{27}$N$_5$O$_2$S MS m/z 462 (M+H)$^+$.

D. 3-methoxy-5-[8-[4-[(1-methyl-4-piperidyl)methyl]phenyl]-5-oxo-7-thioxo-6,8-diazaspiro[3.4]octan-6-yl]pyridine-2-carbonitrile, Cpd 239

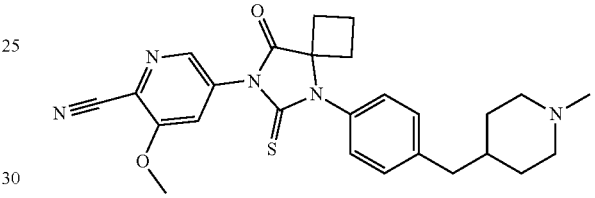

Formaldehyde (37% wt in water, 0.34 mL, 4.55 mmol) was added to a solution of 3-Methoxy-5-[8-oxo-5-(4-piperidin-4-ylmethyl-phenyl)-6-thioxo-5,7-diaza-spiro[3.4]oct-7-yl]-pyridine-2-carbonitrile (0.30 g, 0.65 mmol) in DCE (3 mL). The mixture was stirred at room temperature for 30 min, before Sodium triacetoxyborohydride (0.22 g, 0.97 mmol) was added in 2 portions within 30 min. The reaction was continued for 1 h and diluted with DCM (75 mL). The solution was washed successively with 1M Na$_2$CO$_3$ (40 mL) and water (15 mL). The organic layer was dried over MgSO$_4$, filtered and concentrated to give the crude product. Preparative LC (gradient of ACN in 25 mM aqueous NH$_4$HCO$_3$ from 25 to 62%), upon removal of solvent, gave the pure product as a white solid (0.20 g, 64%). $^1$H NMR (300 MHz, Chloroform-d) δ 1.32-1.52 (m, 2H), 1.64-1.75 (m, 3H), 1.95 (t, J=11.6 Hz, 2H), 2.14-2.28 (m, 1H), 2.30 (s, 3H), 2.50-2.75 (m, 7H), 2.90 (d, J=11.3 Hz, 2H), 4.00 (s, 3H), 7.22 (d, J=8.2 Hz, 2H), 7.36 (d, J=8.0 Hz, 2H), 7.57 (d, J=1.9 Hz, 1H), 8.44 (d, J=1.9 Hz, 1H). C$_{26}$H$_{29}$N$_5$O$_2$S MS m/z 476 (M+H)$^+$.

E. 3-methoxy-5-[8-[4-[(1-methyl-4-piperidyl)methyl]phenyl]-5-oxo-7-thioxo-6,8-diazaspiro[3.4]octan-6-yl]pyridine-2-carbonitrile Hydrochloride, Cpd 239

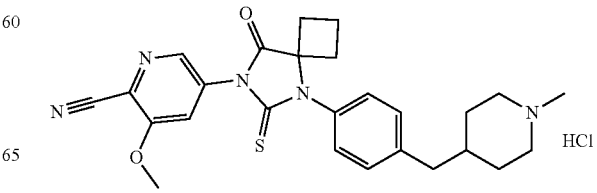

The previous intermediate (0.20 g, 0.421 mmol) was taken in dioxane (5 mL) and treated with 4N HCl in dioxane (0.126 mL, 0.505 mmol) with stirring. After 2.5 h, diethyl ether (40 mL) was added and the resulting suspension was stirred for another 30 min. The solid was collected on a sintered funnel and washed with diethyl ether (2×10 mL). The solid was dried under high vacuum at room temperature to yield the pure title hydrochloride salt (0.214 g, 97%). $^1$H NMR (300 MHz, DMSO-$d_6$) δ 1.43-1.65 (m, 3H), 1.71-1.86 (m, 3H), 1.89-2.06 (m, 1H), 2.34-2.47 (m, 2H), 2.55-2.66 (m, 4H), 2.69 (s, 3H), 2.79-3.00 (m, 2H), 3.33-3.44 (m, 2H), 3.99 (s, 3H), 7.35 (d, J=8.0 Hz, 2H), 7.43 (d, J=8.1 Hz, 2H), 8.06 (d, J=1.8 Hz, 1H), 8.46 (d, J=1.8 Hz, 1H), 10.27 (br s, 1H). $C_{26}H_{29}N_5O_2S$. HCl MS m/z 476 (M+H)$^+$.

Example 14a—Intermediate Synthesis tert-butyl (4-(4-((1-cyanocyclobutyl)amino)benzyl)cyclohexyl)carbamate

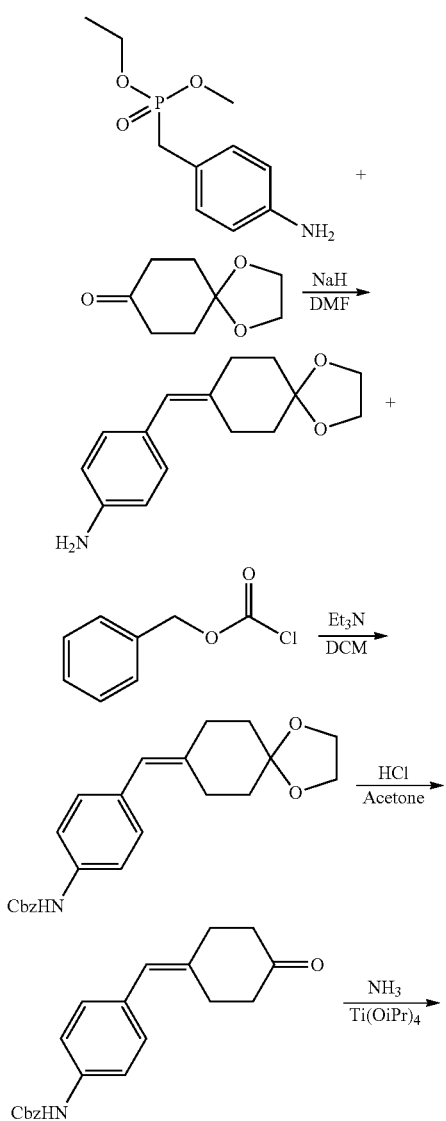

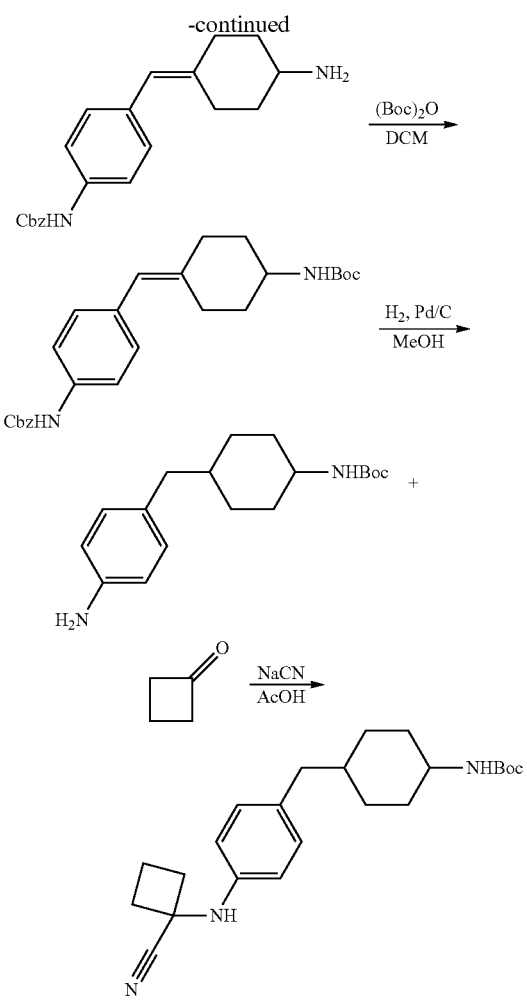

A. Sodium hydride (60% in oil, 0.7 g, 17.51 mmol) was added to a solution of 1,4-dioxaspiro[4.5]decan-8-one (2 g, 12.81 mmol) and diethyl 4-aminobenzylphosphonate (3.5 g, 14.397 mmol) in dry DMF (15 mL). The mixture was stirred at RT overnight, diluted with water and the solution extracted with Et$_2$O. The organic layer was dried over MgSO$_4$, filtered and concentrated to give 4-(1,4-dioxaspiro[4.5]decan-8-ylidenemethyl)aniline directly used into the next step (3.01 g, 77%). $^1$H NMR (300 MHz, DMSO-$d_6$) δ 1.50-1.73 (m, 4H), 2.23-2.31 (m, 2H), 2.36-2.46 (m, 2H), 3.89 (s, 4H), 5.03 (br s, 2H), 6.10 (s, 1H), 6.50 (d, J=8.1 Hz, 2H), 6.87 (d, J=8.1 Hz, 2H). $C_{15}H_{19}NO_2$ MS m/z 246 (M+H)$^+$.

B. Benzyl chloroformate (1.77 mL, 11.79 mmol) was added to a solution of 4-(1,4-dioxaspiro[4.5]decan-8-ylidenemethyl)aniline (3.01 g, 9.82 mmol) in DCM (35 mL) and Et$_3$N (2.73 mL, 19.65 mmol). The mixture was stirred at RT overnight and concentrated under reduced pressure. The residue was diluted with DCM and aqueous 1.0M Na$_2$CO$_3$. The organic layer was washed with aqueous 1.0M Na$_2$CO$_3$, dried over MgSO$_4$, filtered, concentrated and the crude material was purified by chromatography over silica gel (gradient of EA in heptane from 0 to 40%) to yield benzyl (4-(1,4-dioxaspiro[4.5]decan-8-ylidenemethyl)phenyl)carbamate as a white solid (1.05 g, 28%). $^1$H NMR (300 MHz, Chloroform-d) δ 1.61-1.73 (m, 2H), 1.72-1.84 (m, 2H), 2.35-2.46 (m, 2H), 2.46-2.60 (m, 2H), 3.98 (s, 4H), 5.20 (s, 2H), 6.25 (s, 1H), 6.64 (br s, 1H), 7.14 (d, J=8.5 Hz, 2H), 7.28-7.47 (m, 7H). C23H25N04 MS m/z 380 (M+H)+.

C. Aqueous 1.0M HCl (8.35 mL, 8.35 mmol) was added to a solution of benzyl (4-(1,4-dioxaspiro[4.5]decan-8-ylidenemethyl)phenyl)carbamate (2.64 g, 6.96 mmol) in acetone (17 mL). After stirring at RT overnight, the mixture was filtered and the solid washed with water and dried to give benzyl (4-((4-oxocyclohexylidene)methyl) phenyl)carbamate as a white solid) (1.57 g, 67%). The mother waters were extracted with EtOAc. The organic layers were dried over MgSO₄, filtered, concentrated to generate more benzyl (4-((4-oxocyclohexylidene)methyl)phenyl)carbamate (0.65 g, 24%). $^1$H NMR (300 MHz, DMSO-d₆) δ 2.39 (m, 4H), 2.61 (t, J=6.9 Hz, 2H), 2.70 (t, J=7.1 Hz, 2H), 5.15 (s, 2H), 6.38 (s, 1H), 7.20 (d, J=8.2 Hz, 2H), 7.28-7.53 (m, 7H), 9.79 (s, 1H). $C_{21}H_{21}NO_3$ MS m/z 336 (M+H)+.

D. Titanium (IV) isopropoxide (2.47 mL, 8.11 mmol) was added to a solution of benzyl (4-((4-oxocyclohexylidene)methyl)phenyl)carbamate (1.36 g, 4.06 mmol) in 7.0M ammonia in MeOH (34 mL). After stirring at RT for 6 h, sodium borohydride (0.232 g, 6.12 mmol) was added to the previous mixture. The reaction was stirred at RT overnight, diluted with aqueous 1.0M Na₂CO₃, and extracted with EtOAc. The organic layers were combined, dried over MgSO₄, filtered, concentrated to give benzyl (4-((4-aminocyclohexylidene)methyl)phenyl)carbamate as a foam (1.23 g, 90%), used directly into the next step. $^1$H NMR (300 MHz, Chloroform-d) δ 1.06-1.41 (m, 2H), 1.59 (br s, 2H), 1.83-2.11 (m, 3H), 2.16-2.30 (m, 1H), 2.30-2.47 (m, 1H), 2.72-3.00 (m, 2H), 5.20 (s, 2H), 6.20 (s, 1H), 6.71 (s, 1H), 7.13 (d, J=8.2 Hz, 2H), 7.28-7.45 (m, 7H). $C_{21}H_{24}N_2O_2$ MS m/z 337 (M+H)+.

E. Di-tert-butyl dicarbonate (1.01 g, 4.63 mmol) was added to a solution of benzyl (4-((4-aminocyclohexylidene)methyl)phenyl)carbamate (1.41 g, 4.209 mmol) in DCM (20 mL). The mixture was stirred at RT for 1 h, concentrated and the residue purified by chromatography over silica gel (gradient of EA in heptane from 0 to 40%) to yield tert-butyl N-[4-[[4-(benzyloxycarbonylamino)phenyl]methylene]cyclohexyl]carbamate (1.024 g, 55%) as a white solid. $^1$H NMR (300 MHz, DMSO-d₆) δ 1.07-1.34 (m, 2H), 1.38 (s, 9H), 1.70-1.90 (m, 2H), 1.90-2.08 (m, 1H), 2.09-2.24 (m, 1H), 2.24-2.40 (m, 1H), 2.62-2.82 (m, 1H), 3.35-3.57 (m, 1H), 5.14 (s, 2H), 6.16 (s, 1H), 6.76 (d, J=8.0 Hz, 1H), 7.10 (d, J=8.4 Hz, 2H), 7.27-7.53 (m, 7H), 9.75 (s, 1H). $C_{26}H_{32}N_2O_4$ MS m/z 459 (M+Na)+.

F. To a solution of tert-butyl N-[4-[[4-(benzyloxycarbonylamino)phenyl]methylene]cyclohexyl]carbamate (1.28 g, 2.93 mmol) in MeOH (15 mL) was added, at 0° C., Palladium on charcoal (10% wet, 0.15 g, 1.41 mmol) under a hydrogen atmosphere for 20 h at RT. The reaction mixture was filtered through diatomaceous earth and concentrated under reduced pressure to give tert-butyl (4-(4-aminobenzyl)cyclohexyl)carbamate (0.805 g, 90%), directly used into the next step. $^1$H NMR (300 MHz, Chloroform-d) δ 0.93-1.06 (m, 1H), 1.05-1.26 (m, 2H), 1.44 (s, 9H), 1.45-1.61 (m, 4H), 1.61-1.78 (m, 2H), 1.96 (m, 1H), 2.39 (dd, J=15.7, 6.9 Hz, 2H), 3.54 (br s, 2H), 4.16-4.82 (m, 1H), 6.62 (d, J=8.2 Hz, 2H), 6.91 (d, J=8.2 Hz, 2H). $C_{18}H_{28}N_2O_2$ MS m/z 305 (M+H)+.

G. Cyclobutanone (0.395 mL, 5.28 mmol) was added to a solution of tert-butyl (4-(4-aminobenzyl)cyclohexyl)carbamate (0.805 g, 2.64 mmol) in Acetic acid (15 mL). The solution was stirred for 15 min at room temperature before Sodium cyanide (0.267 g, 5.28 mmol) was added and the reaction stirred for 3 h. The solution was concentrated under reduced pressure, and the resulting material residue was partitioned between EA and 1M Na₂CO₃. The organic layer was further washed with brine, dried over MgSO₄, filtered and concentrated to yield tert-butyl (4-(4-((1-cyanocyclobutyl)amino)benzyl)cyclohexyl) carbamate as a foam (1.014 g, 90%), used directly in the next step without further purification. $^1$H NMR (300 MHz, Chloroform-d) δ 0.92-1.08 (m, 1H), 1.08-1.23 (m, 2H), 1.44 (s, 9H), 1.48-1.62 (m, 4H), 1.61-1.80 (m, 2H), 1.88-2.03 (m, 1H), 2.09-2.29 (m, 2H), 2.29-2.50 (m, 4H), 2.69-2.88 (m, 2H), 3.72 (br s, 1H), 4.64 (br s, 1H), 6.59 (d, J=8.2 Hz, 2H), 7.00 (d, J=8.2 Hz, 2H). $C_{23}H_{33}N_3O_2$ MS m/z 406 (M+Na)+.

Following the procedure described in Example 14, above, selecting and substituting the appropriate reagents, starting materials, and purification methods, and adjusting reaction temperatures, times and other variables or parameters, as needed or desirable, as would be readily recognized by those skilled in the art, the following compounds of Formula (I) of the invention were prepared.

| Cpd No. | Structure | Compound Name & Physical Data |
|---|---|---|
| 238 | 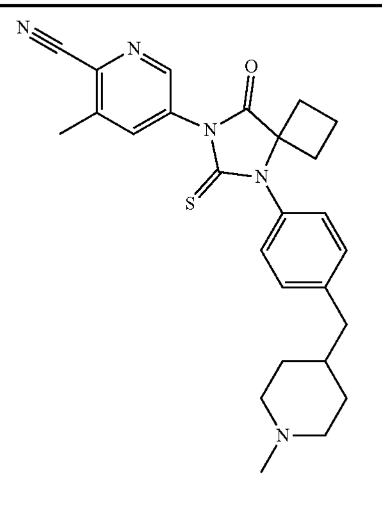 | 3-methyl-5-[8-[4-[(1-methyl-4-piperidyl)methyl]phenyl]-5-oxo-7-thioxo-6,8-diazaspiro[3.4]octan-6-yl]pyridine-2-carbonitrile. $^1$H NMR (300 MHz, DMSO-d₆) δ 1.39-1.64 (m, 3H), 1.69-1.86 (m, 3H), 1.89-2.08 (m, 1H), 2.30-2.46 (m, 2H), 2.58 (s, 3H), 2.60-2.67 (m, 4H), 2.69 (s, 3H), 2.77-3.02 (m, 2H), 3.32-3.45 (m, 2H), 7.35 (d, J = 8.0 Hz, 2H), 7.42 (d, J = 8.1 Hz, 2H), 8.14 (d, J = 2.1 Hz, 1H), 8.71 (d, J = 2.1 Hz, 1H), 10.15 (br s, 1H). $C_{26}H_{29}N_5OS$•HCl MS m/z 560 (M + H)+ |

| Cpd No. | Structure | Compound Name & Physical Data |
|---|---|---|
| 237 | 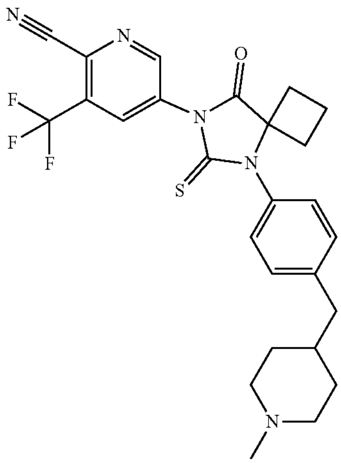 [SMILES: CN1CCC(Cc2ccc(N3C(=S)N(c4cnc(C#N)c(C(F)(F)F)c4)C(=O)C34CCC4)cc2)CC1] | 5-[8-[4-[(1-methyl-4-piperidyl)methyl]phenyl]-5-oxo-7-thioxo-6,8-diazaspiro[3.4]octan-6-yl]-3-(trifluoromethyl)pyridine-2-carbonitrile.<br>$^1$H NMR (300 MHz, Chloroform-d) δ 1.29-1.47 (m, 2H), 1.61-1.77 (m, 5H), 1.83-1.99 (m, 2H), 2.27 (s, 3H), 2.52-2.74 (m, 6H), 2.80-2.93 (m, 2H), 7.21 (d, J = 8.2 Hz, 2H), 7.36 (d, J = 8.1 Hz, 2H), 8.37 (d, J = 2.2 Hz, 1H), 9.11 (d, J = 2.2 Hz, 1H).<br>$C_{26}H_{26}F_3N_5OS$<br>MS m/z 514 (M + H)$^+$ |
| 236 | 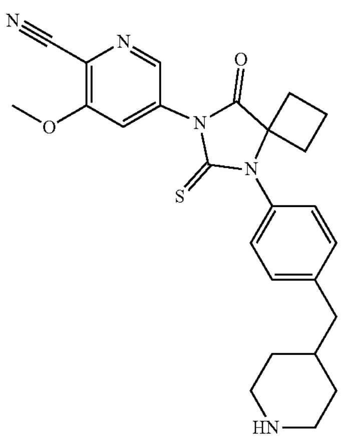 [SMILES: COc1cc(N2C(=O)C3(CCC3)N(c3ccc(CC4CCNCC4)cc3)C2=S)cnc1C#N] | 3-methoxy-5-[5-oxo-8-[4-(4-piperidylmethyl)phenyl]-7-thioxo-6,8-diazaspiro[3.4]octan-6-yl]pyridine-2-carbonitrile.<br>$^1$H NMR (300 MHz, Chloroform-d) δ 1.55-1.75 (m, 3H), 1.78-1.94 (m, 2H), 2.14-2.35 (m, 1H), 2.48-2.76 (m, 7H), 2.76-2.87 (m, 2H), 3.33-3.46 (m, 2H), 4.01 (s, 3H), 7.25 (d, J = 8.2 Hz, 2H), 7.35 (d, J = 8.0 Hz, 2H), 7.56 (d, J = 2.0 Hz, 1H), 8.43 (d, J = 1.9 Hz, 1H).<br>$C_{25}H_{27}N_5O_2S$<br>MS m/z 462 (M + H)$^+$ |
| 235 | 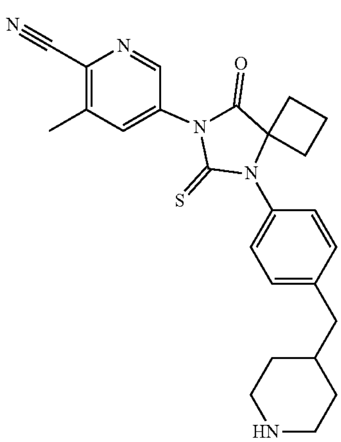 [SMILES: Cc1cc(N2C(=O)C3(CCC3)N(c3ccc(CC4CCNCC4)cc3)C2=S)cnc1C#N] | 3-methyl-5-[5-oxo-8-[4-(4-piperidylmethyl)phenyl]-7-thioxo-6,8-diazaspiro[3 4]octan-6-yl]pyridine-2-carbonitrile.<br>$^1$H NMR (300 MHz, DMSO-d$_6$) δ 1.30-1.62 (m, 3H), 1.68-1.81 (m, 2H), 1.82-2.04 (m, 2H), 2.33-2.47 (m, 2H), 2.58 (s, 3H), 2.59-2.69 (m, 4H), 2.73-2.94 (m, 2H), 3.16-3.31 (m, 2H), 7.35 (d, J = 8.0 Hz, 2H), 7.42 (d, J = 8.1 Hz, 2H), 8.14 (d, J = 2.2 Hz, 1H), 8.63 br (s, 1H), 8.71 (d, J = 2.1 Hz, 1H), 8.85 (br s, 1H).<br>$C_{25}H_{27}N_5OS$•HCl<br>MS m/z 446 (M + H)$^+$ |

| Cpd No. | Structure | Compound Name & Physical Data |
|---|---|---|
| 234 | 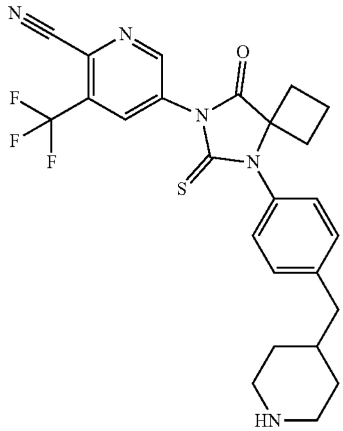 [SMILES: N#Cc1ncc(N2C(=O)C3(CCC3)N(c3ccc(CC4CCNCC4)cc3)C2=S)cc1C(F)(F)F] | 5-[5-oxo-8-[4-(4-piperidylmethyl)phenyl]-7-thioxo-6,8-diazaspiro[3.4]octan-6-yl]-3-(trifluoromethyl)pyridine-2-carbonitrile.<br>$^1$H NMR (300 MHz, Chloroform-d) δ 1.61-1.96 (m, 6H), 2.14-2.36 (m, 1H), 2.49-2.76 (m, 5H), 2.76-2.93 (m, 2H), 3.42-3.58 (m, 4H), 7.25 (d, J = 8.1 Hz, 2H), 7.36 (d, J = 8.1 Hz, 2H), 8.36 (d, J = 2.2 Hz, 1H), 9.10 (d, J = 2.2 Hz, 1H).<br>$C_{25}H_{24}F_3N_5OS$ MS m/z 500 (M + H)$^+$ |
| 233 | 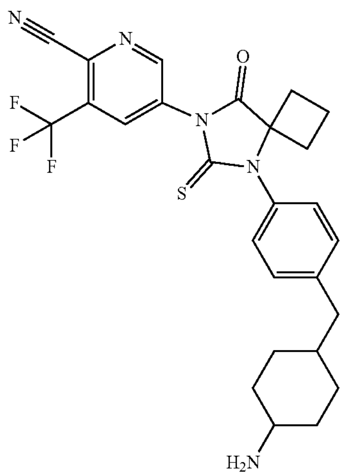 [SMILES: N#Cc1ncc(N2C(=O)C3(CCC3)N(c3ccc(CC4CCC(N)CC4)cc3)C2=S)cc1C(F)(F)F] | 5-[8-[4-[(4-aminocyclohexyl)methyl]phenyl]-5-oxo-7-thioxo-6,8-diazaspiro[3.4]octan-6-yl]-3-(trifluoromethyl)pyridine-2-carbonitrile.<br>$^1$H NMR (300 MHz, DMSO-d$_6$) δ 1.19-2.05 (m, 15H), 2.36-2.47 (m, 2H), 2.55-2.73 (m, 1H), 7.23-7.51 (m, 4H), 7.97 (br s, 3H), 8.77 (s, 1H), 9.22 (s, 1H).<br>$C_{26}H_{26}F_3N_5OS$•HCl MS m/z 514 (M + H)$^+$ |
| 232 | 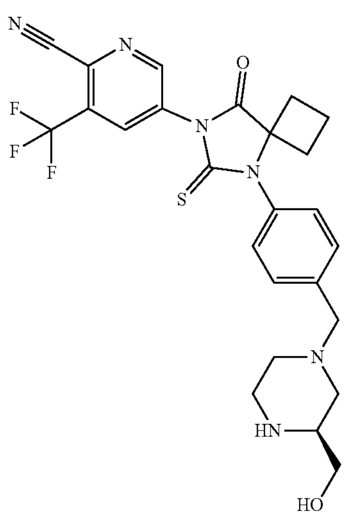 [SMILES: N#Cc1ncc(N2C(=O)C3(CCC3)N(c3ccc(CN4CCN[C@H](CO)C4)cc3)C2=S)cc1C(F)(F)F] | 5-[6-[4-[[(3S)-3-(hydroxymethyl)piperazin-1-yl]methyl]phenyl]-5-oxo-7-thioxo-6,8-diazaspiro[3.4]octan-8-yl]-3-(trifluoromethyl)pyridine-2-carbonitrile.<br>$^1$H NMR (300 MHz, DMSO-d$_6$) δ 1.40-1.63 (m, 1H), 1.86-2.09 (m, 1H), 2.18-2.34 (m, 1H), 2.33-2.46 (m, 2H), 2.57-2.70 (m, 2H), 2.82-3.13 (m, 4H), 3.13-3.30 (m, 2H), 3.52-3.63 (m, 2H), 3.67 (s, 2H), 5.40 (t, J = 4.9 Hz, 1H), 7.39 (d, J = 8.0 Hz, 2H), 7.56 (d, J = 8.0 Hz, 2H), 8.60 (br s, 1H), 8.76 (d, J = 2.1 Hz, 1H), 9.05 (br s, 1H), 9.22 (d, J = 2.0 Hz, 1H).<br>$C_{25}H_{25}F_3N_6O_2S$•HCl MS m/z 531 (M + H)$^+$ |

-continued

| Cpd No. | Structure | Compound Name & Physical Data |
|---|---|---|
| 231 | 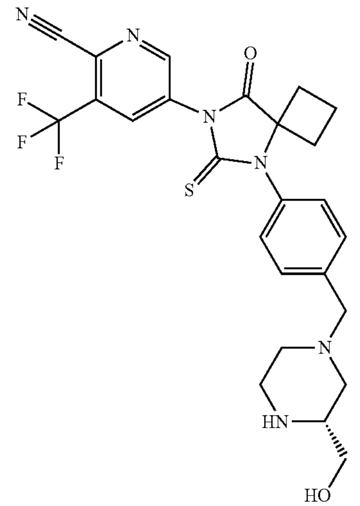 [SMILES: N#Cc1ncc(N2C(=O)C3(CCC3)N(c3ccc(CN4CCN[C@@H](CO)C4)cc3)C2=S)cc1C(F)(F)F] | 5-[6-[4-[[(3R)-3-(hydroxymethyl)piperazin-1-yl]methyl]phenyl]-5-oxo-7-thioxo-6,8-diazaspiro[3.4]octan-8-yl]-3-(trifluoromethyl)pyridine-2-carbonitrile.<br>$^1$H NMR (300 MHz, DMSO-d$_6$) δ 1.42-1.65 (m, 1H), 1.88-2.08 (m, 1H), 2.21-2.35 (m, 1H), 2.35-2.46 (m, 2H), 2.57-2.73 (m, 2H), 2.81-3.13 (m, 4H), 3.14-3.31 (m, 2H), 3.51-3.64 (m, 2H), 3.67 (s, 2H), 5.40 (t, J = 4.8 Hz, 1H), 7.39 (d, J = 7.9 Hz, 2H), 7.56 (d, J = 8.0 Hz, 2H), 8.66 (br s, 1H), 8.77 (d, J = 2.0 Hz, 1H), 9.10 (br s, 1H), 9.22 (d, J = 2.0 Hz, 1H).<br>$C_{25}H_{25}F_3N_6O_2S$•HCl MS m/z 531 (M + H)$^+$ |
| 230 | 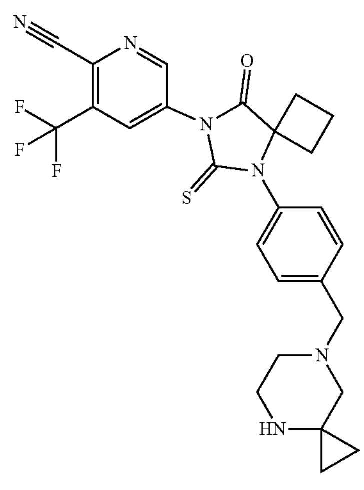 [SMILES: N#Cc1ncc(N2C(=O)C3(CCC3)N(c3ccc(CN4CCNC5(CC5)C4)cc3)C2=S)cc1C(F)(F)F] | 5-[6-[4-(5,8-diazaspiro[2.5]octan-5-ylmethyl)phenyl]-5-oxo-7-thioxo-6,8-diazaspiro[3.4]octan-8-yl]-3-(trifluoromethyl)pyridine-2-carbonitrile.<br>$^1$H NMR (300 MHz, DMSO-d$_6$) δ 0.87-1.03 (m, 2H), 1.09-1.26 (m, 2H), 1.45-1.65 (m, 1H), 1.88-2.07 (m, 1H), 2.34-2.49 (m, 2H), 2.57-2.72 (m, 2H), 3.31-3.45 (m, 2H), 3.45-3.62 (m, 6H), 7.47 (d, J = 7.8 Hz, 2H), 7.74 (d, J = 7.8 Hz, 2H), 8.77 (d, J = 2.1 Hz, 1H), 9.23 (d, J = 2.0 Hz, 1H), 9.81 (br s, 2H).<br>$C_{26}H_{25}F_3N_6OS$•HCl MS m/z 527 (M + H)$^+$ |
| 229 | 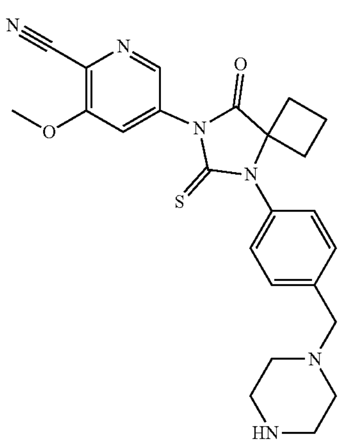 [SMILES: COc1cc(N2C(=O)C3(CCC3)N(c3ccc(CN4CCNCC4)cc3)C2=S)cnc1C#N] | 3-methoxy-5-[5-oxo-8-[4-(piperazin-1-ylmethyl)phenyl]-7-thioxo-6,8-diazaspiro[3.4]octan-6-yl]pyridine-2-carbonitrile.<br>$^1$H NMR (300 MHz, DMSO-d$_6$) δ 1.42-1.61 (m, 1H), 1.90-2.06 (m, 1H), 2.36-2.46 (m, 2H), 2.56-2.68 (m, 2H), 3.06-3.19 (m, 4H), 3.52-3.60 (m, 4H), 3.56 (s, 2H), 3.98 (s, 3H), 7.39 (d, J = 7.9 Hz, 2H), 7.54 (d, J = 8.0 Hz, 2H), 8.04 (s, 1H), 8.45 (s, 1H), 8.56 (br s, 1H).<br>$C_{24}H_{26}N_6O_2S$ MS m/z 463 (M + H)$^+$ |

| Cpd No. | Structure | Compound Name & Physical Data |
|---|---|---|
| 228 | 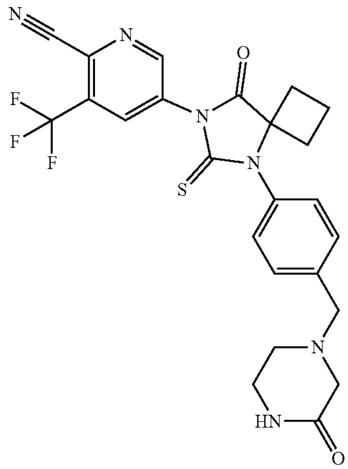 [SMILES: N#Cc1ncc(N2C(=O)C3(CCC3)N(c3ccc(CN4CCNC(=O)C4)cc3)C2=S)cc1C(F)(F)F] | 5-[5-oxo-8-[4-[(3-oxopiperazin-1-yl)methyl]phenyl]-7-thioxo-6,8-diazaspiro[3.4]octan-6-yl]-3-(trifluoromethyl)pyridine-2-carbonitrile.<br>$^1$H NMR (300 MHz, DMSO-d$_6$, free base) δ 1.46-1.69 (m, 1H), 1.87-2.11 (m, 1H), 2.34-2.50 (m, 2H), 2.55-2.72 (m, 4H), 2.95 (s, 2H), 3.13-3.28 (m, 2H), 3.66 (s, 2H), 7.38 (d, J = 7.9 Hz, 2H), 7.56 (d, J = 7.9 Hz, 2H), 7.79 (br s, 1H), 8.77 (d, J = 2.1 Hz, 1H), 9.22 (d, J = 2.1 Hz, 1H).<br>$C_{24}H_{21}F_3N_6O_2S$•HCl MS m/z 515 (M + H)$^+$ |
| 227 | 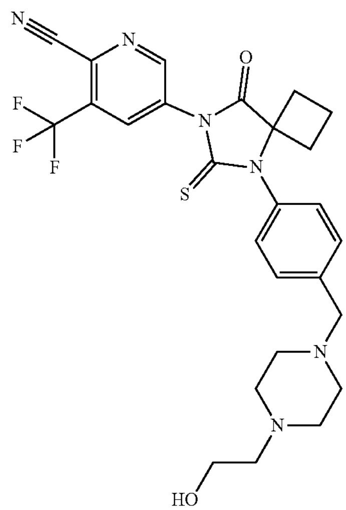 [SMILES: N#Cc1ncc(N2C(=O)C3(CCC3)N(c3ccc(CN4CCN(CCO)CC4)cc3)C2=S)cc1C(F)(F)F] | 5-[8-[4-[[4-(2-hydroxyethyl)piperazin-1-yl]methyl]phenyl]-5-oxo-7-thioxo-6,8-diazaspiro[3.4]octan-6-yl]-3-(trifluoromethyl)pyridine-2-carbonitrile.<br>$^1$H NMR (300 MHz, Chloroform-d) δ 1.64-1.80 (m, 1H), 2.25 (q, J = 9.4 Hz, 1H), 2.58 (q, J = 10.5 Hz, 2H), 2.65-2.78 (m, 2H), 2.89-3.23 (m, 8H), 3.56-3.72 (m, 2H), 3.95-4.14 (m, 2H), 4.65 (s, 1H), 7.30 (d, J = 7.7 Hz, 2H), 7.54 (d, J = 7.8 Hz, 2H), 8.36 (d, J = 2.2 Hz, 1H), 9.11 (d, J = 2.2 Hz, 1H), 12.02 (br s, 1H).<br>$C_{26}H_{27}F_3N_6O_2S$•HCl MS m/z 545 (M + H)$^+$ |
| 224 | 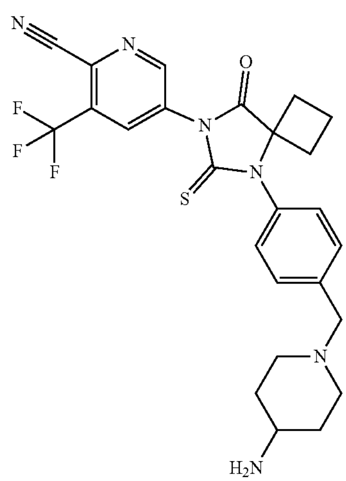 | 5-[8-[4-[(4-amino-1-piperidyl)methyl]phenyl]-5-oxo-7-thioxo-6,8-diazaspiro[3.4]octan-6-yl]-3-(trifluoromethyl)pyridine-2-carbonitrile.<br>$^1$H NMR (300 MHz, DMSO-d$_6$) δ 1.15-1.39 (m, 2H), 1.43-1.61 (m, 1H), 1.63-1.77 (m, 2H), 1.87-2.11 (m, 3H), 2.33-2.48 (m, 3H), 2.53-2.69 (m, 4H), 2.70-2.86 (m, 2H), 3.53 (s, 2H), 7.35 (d, J = 7.9 Hz, 2H), 7.52 (d, J = 8.0 Hz, 2H), 8.77 (s, 1H), 9.23 (s, 1H).<br>$C_{25}H_{25}F_3N_6OS$ MS m/z 515 (M + H)$^+$ |

| Cpd No. | Structure | Compound Name & Physical Data |
|---|---|---|
| 220 | 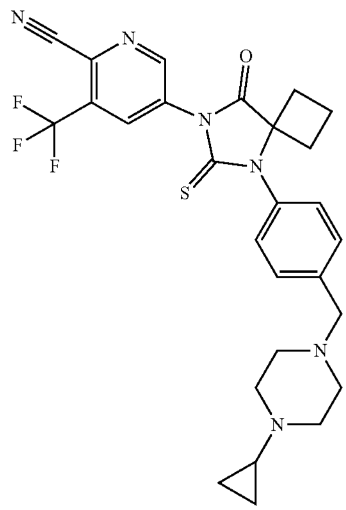 [SMILES: N#Cc1ncc(N2C(=O)C3(CCC3)N(c3ccc(CN4CCN(C5CC5)CC4)cc3)C2=S)cc1C(F)(F)F] | 5-[8-[4-[(4-cyclopropylpiperazin-1-yl)methyl]phenyl]-5-oxo-7-thioxo-6,8-diazaspiro[3.4]octan-6-yl]-3-(trifluoromethyl)pyridine-2-carbonitrile.<br>$^1$H NMR (300 MHz, Chloroform-d) δ 0.86 (s, 2H), 1.47-1.78 (m, 3H), 2.18-2.44 (m, 2H), 2.47-2.64 (m, 2H), 2.64-2.76 (m, 2H), 2.76-3.00 (m, 4H), 2.98-3.31 (m, 4H), 3.70 (s, 2H), 7.28 (d, J = 7.8 Hz, 2H), 7.54 (d, J = 7.8 Hz, 1H), 8.01 (br s, 1H), 8.37 (d, J = 2.2 Hz, 1H), 9.11 (d, J = 2.3 Hz, 1H).<br>$C_{27}H_{27}F_3N_6OS\cdot HCl$ MS m/z 541 (M + H)$^+$ |
| 219 | 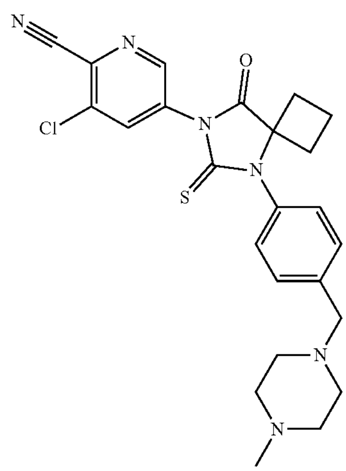 [SMILES: CN1CCN(Cc2ccc(N3C(=S)N(c4cnc(C#N)c(Cl)c4)C(=O)C34CCC4)cc2)CC1] | 3-chloro-5-[8-[4-[(4-methylpiperazin-1-yl)methyl]phenyl]-5-oxo-7-thioxo-6,8-diazaspiro[3 4]octan-6-yl]pyridine-2-carbonitrile.<br>$^1$H NMR (300 MHz, DMSO-d$_6$) δ 1.45-1.63 (m, 1H), 1.87-2.07 (m, 1H), 2.35-2.45 (m, 2H), 2.55-2.69 (m, 2H), 2.75 (s, 3H), 2.87-3.13 (m, 4H), 3.30-3.45 (m, 4H), 3.67 (s, 2H), 7.39 (d, J = 7.8 Hz, 2H), 7.55 (d, J = 7.9 Hz, 2H), 8.55 (s, 1H), 8.90 (s, 1H), 10.48 (br s, 1H).<br>$C_{24}H_{25}ClN_6OS\cdot HCl$ MS m/z 481 (M + H)$^+$ |
| 217 | 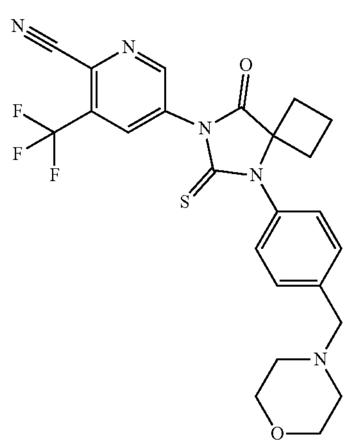 [SMILES: N#Cc1ncc(N2C(=O)C3(CCC3)N(c3ccc(CN4CCOCC4)cc3)C2=S)cc1C(F)(F)F] | 5-[8-[4-(morpholinomethyl)phenyl]-5-oxo-7-thioxo-6,8-diazaspiro[3.4]octan-6-yl]-3-(trifluoromethyl)pyridine-2-carbonitrile.<br>$^1$H NMR (300 MHz, DMSO-d$_6$) δ 1.43-1.67 (m, 1H), 1.87-2.10 (m, 1H), 2.33-2.48 (m, 6H), 2.57-2.71 (m, 2H), 3.57 (s, 2H), 3.59-3.68 (m, 4H), 7.37 (d, J = 8.0 Hz, 2H), 7.55 (d, J = 8.1 Hz, 2H), 8.77 (d, J = 2.1 Hz, 1H), 9.22 (d, J = 2.0 Hz, 1H).<br>$C_{24}H_{22}F_3N_5O_2S$ MS m/z 502 (M + H)$^+$ |

| Cpd No. | Structure | Compound Name & Physical Data |
|---|---|---|
| 207 | 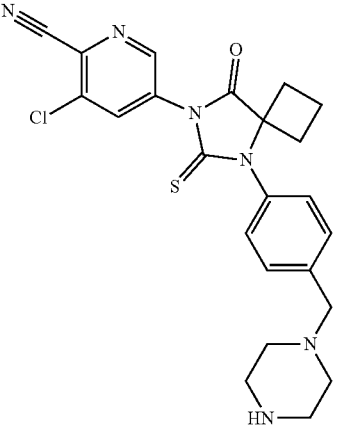 [SMILES: N#Cc1ncc(N2C(=O)C3(CCC3)N(c3ccc(CN4CCNCC4)cc3)C2=S)cc1Cl] | 3-chloro-5-[5-oxo-8-[4-(piperazin-1-ylmethyl)phenyl]-7-thioxo-6,8-diazaspiro[3.4]octan-6-yl]pyridine-2-carbonitrile.<br>$^1$H NMR (300 MHz, Chloroform-d) δ 1.48-1.71 (m, 1H), 2.04-2.28 (m, 1H), 2.40-2.70 (m, 4H), 2.72-2.91 (m, 4H), 3.30-3.45 (m, 4H), 3.67 (s, 2H), 7.26 (d, J = 7.9 Hz, 2H), 7.52 (d, J = 7.9 Hz, 2H), 8.08 (s, 1H), 8.72 (s, 1H).<br>$C_{23}H_{23}ClN_6OS \cdot HCl$ MS m/z 467 $(M + H)^+$ |
| 55 | 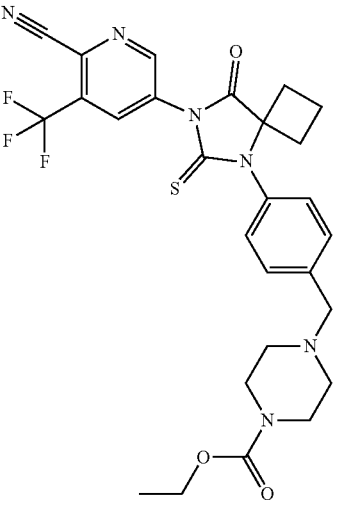 [SMILES: CCOC(=O)N1CCN(Cc2ccc(N3C(=S)N(c4cnc(C#N)c(C(F)(F)F)c4)C(=O)C34CCC4)cc2)CC1] | Ethyl 4-[[4-[6-[6-cyano-5-(trifluoromethyl)-3-pyridyl]-5-oxo-7-thioxo-6,8-diazaspiro[3.4]octan-8-yl]phenyl]methyl]piperazine-1-carboxylate.<br>$^1$H NMR (300 MHz, Chloroform-d) δ 1.26 (t, J = 7.2 Hz, 3H), 1.52-1.81 (m, 1H), 2.13-2.36 (m, 1H), 2.38-2.54 (m, 4H), 2.54-2.83 (m, 4H), 3.38-3.60 (m, 4H), 3.63 (s, 2H), 4.14 (q, J = 7.2 Hz, 2H), 7.27 (d, J = 8.2 Hz, 2H), 7.58 (d, J = 7.9 Hz, 2H), 8.37 (s, 1H), 9.10 (s, 1H).<br>$C_{27}H_{27}F_3N_6O_3S$ MS m/z 573 $(M + H)^+$ |
| 53 | 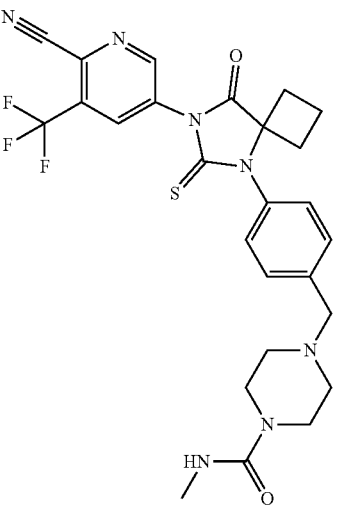 [SMILES: CNC(=O)N1CCN(Cc2ccc(N3C(=S)N(c4cnc(C#N)c(C(F)(F)F)c4)C(=O)C34CCC4)cc2)CC1] | 4-[[4-[6-[6-cyano-5-(trifluoromethyl)-3-pyridyl]-5-oxo-7-thioxo-6,8-diazaspiro[3.4]octan-8-yl]phenyl]methyl]-N-methyl-piperazine-1-carboxamide.<br>$^1$H NMR (300 MHz, Chloroform-d) δ 1.62-1.81 (m, 1H), 2.13-2.36 (m, 1H), 2.42-2.56 (m, 4H), 2.56-2.77 (m, 4H), 2.82 (d, J = 4.5 Hz, 3H), 3.30-3.45 (m, 4H), 3.61 (s, 2H), 4.45 (q, J = 4.7 Hz, 1H), 7.27 (d, J = 7.3 Hz, 2H), 7.56 (d, J = 7.9 Hz, 2H), 8.37 (d, J = 2.2 Hz, 1H), 9.11 (d, J = 2.2 Hz, 1H).<br>$C_{26}H_{26}F_3N_7O_2S$ MS m/z 558 $(M + H)^+$ |

| Cpd No. | Structure | Compound Name & Physical Data |
|---|---|---|
| 48 | 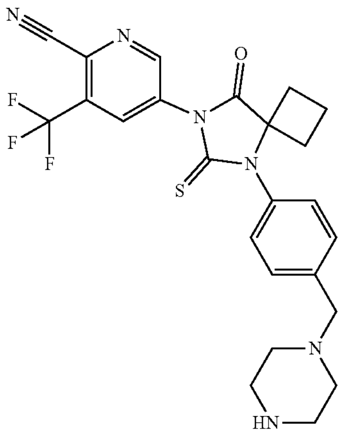 [SMILES: N#Cc1ncc(N2C(=O)C3(CCC3)N(c3ccc(CN4CCNCC4)cc3)C2=S)cc1C(F)(F)F] | 5-[5-oxo-8-[4-(piperazin-1-ylmethyl)phenyl]-7-thioxo-6,8-diazaspiro[3.4]octan-6-yl]-3-(trifluoromethyl)pyridine-2-carbonitrile.<br>$^1$H NMR (300 MHz, Chloroform-d) 1.59-1.80 (m, 1H), 2.16-2.35 (m, 1H), 2.40-2.51 (m, 4H), 2.52-2.81 (m, 4H), 3.38-3.56 (m, 4H), 3.61 (s, 2H), 7.27 (d, J = 7.1 Hz, 2H), 7.57 (d, J = 7.9 Hz, 2H), 8.37 (d, J = 2.3 Hz, 1H), 9.11 (d, J = 2.3 Hz, 1H).<br>$C_{24}H_{23}F_3N_6OS$ MS m/z 501 $(M + H)^+$ |
| 47 | 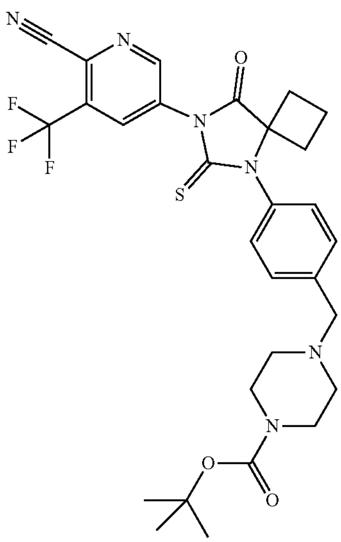 [SMILES: CC(C)(C)OC(=O)N1CCN(Cc2ccc(N3C(=S)N(c4cnc(C#N)c(C(F)(F)F)c4)C(=O)C34CCC4)cc2)CC1] | tert-butyl 4-[[4-[6-[6-cyano-5-(trifluoromethyl)-3-pyridyl]-5-oxo-7-thioxo-6,8-diazaspiro[3.4]octan-8-yl]phenyl]methyl]piperazine-1-carboxylate.<br>$^1$H NMR (300 MHz, Chloroform-J) δ 1.46 (s, 9H), 1.59-1.80 (m, 1H), 2.16-2.35 (m, 1H), 2.40-2.51 (m, 4H), 2.52-2.81 (m, 4H), 3.38-3.56 (m, 4H), 3.61 (s, 2H), 7.27 (d, J = 7.1 Hz, 2H), 7.57 (d, J = 7.9 Hz, 2H), 8.37 (d, J = 2.3 Hz, 1H), 9.11 (d, J = 2.3 Hz, 1H).<br>$C_{29}H_{31}F_3N_6O_3S$ MS m/z 601 $(M + H)^+$ |
| 243 | 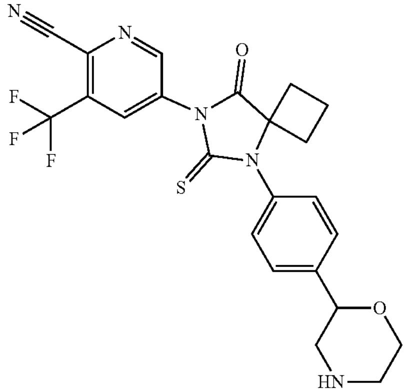 [SMILES: N#Cc1ncc(N2C(=O)C3(CCC3)N(c3ccc(C4CNCCO4)cc3)C2=S)cc1C(F)(F)F] | 5-[8-(4-morpholin-2-ylphenyl)-5-oxo-7-thioxo-6,8-diazaspiro[3.4]octan-6-yl]-3-(trifluoromethyl)pyridine-2-carbonitrile.<br>$^1$H NMR (300 MHz, Chloroform-d) δ 1.57-1.77 (m, 1H), 2.19-2.36 (m, 1H), 2.47-2.62 (m, 2H), 2.63-2.78 (m, 2H), 3.01-3.17 (m, 1H), 3.17-3.37 (m, 1H), 3.41-3.57 (m, 1H), 3.55-3.76 (m, 1H), 4.28 (d, J = 7.6 Hz, 2H), 5.12 (d, J = 10.7 Hz, 1H), 7.37 (d, J = 8.1 Hz, 2H), 7.62 (d, J = 8.1 Hz, 2H), 8.35 (d, J = 2.2 Hz, 1H), 9.09 (d, J = 2.2 Hz, 1H), 10.32 (br s, 2H).<br>$C_{23}H_{20}F_3N_5O_2S \cdot HCl$ MS m/z 488 $(M + H)^+$ |

| Cpd No. | Structure | Compound Name & Physical Data |
|---|---|---|
| 241 | 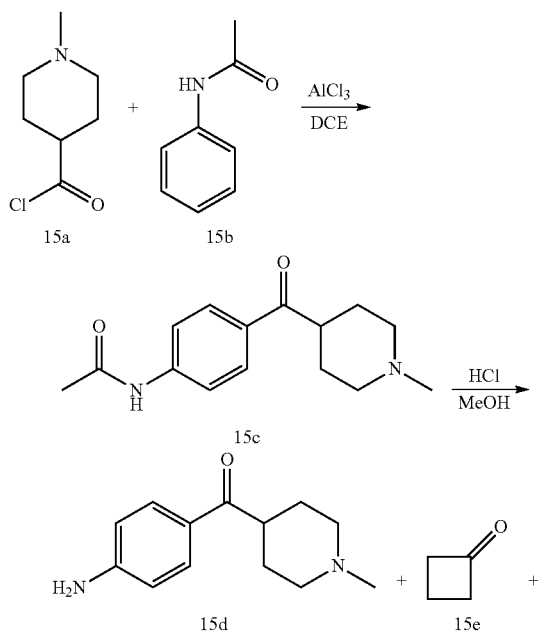 | 5-[8-[4-(4-methylmorpholin-2-yl)phenyl]-5-oxo-7-thioxo-6,8-diazaspiro[3.4]octan-6-yl]-3-(trifluoromethyl)pyridine-2-carbonitrile. <br> $^1$H NMR (300 MHz, Chloroform-d) δ 1.62-1.79 (m, 1H), 2.15-2.36 (m, 1H), 2.54 (q, J = 10.7 Hz, 2H), 2.62-2.83 (m, 3H), 2.87 (s, 3H), 2.91-3.09 (m, 1H), 3.44-3.58 (m, 1H), 3.57-3.69 (m, 1H), 4.19-4.34 (m, 1H), 4.56 (t, J = 12.5 Hz, 1H), 5.41 (d, J = 10.8 Hz, 1H), 7.37 (d, J = 7.9 Hz, 2H), 7.64 (d, J = 7.9 Hz, 2H), 8.36 (d, J = 2.2 Hz, 1H), 9.10 (d, J = 2.2 Hz, 1H). <br> $C_{24}H_{22}F_3N_5O_2S$•HCl MS m/z 502 (M + H)$^+$ |
| 8 | 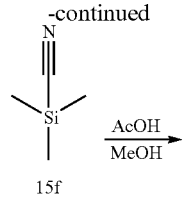 | 2-{4-[7-(6-cyano-5-methyl(3-pyridyl))-8-oxo-6-thioxo-5,7-diazaspiro[3.4]oct-5-yl]phenyl}-N-methylacetamide. <br> $^1$H NMR (500 MHz, DMSO-d$_6$) δ ppm 1.54-1.56 (m, 1H), 1.96-2.0 (m, 1H), 2.40-2.45 (m, 3H), 2.58-2.63 (m, 7H), 3.51 (s, 2H), 7.34-7.36 (m, 2H, J = 8 2 Hz), 7.47-7.49 (m, 2H, J = 8.2 Hz), 8.15 (d, 1H, J = 1.6 Hz), 8.73 (d, 1H, J = 2.2 Hz) <br> $C_{22}H_{21}N_5O_2S$ MS m/z 420.2 (M + H)$^+$ |

Example 15

5-[8-[4-(1-methylpiperidine-4-carbonyl)phenyl]-5-oxo-7-thioxo-6,8-diazaspiro[3.4]octan-6-yl]-3-(trifluoromethyl)pyridine-2-carbonitrile Cpd 144

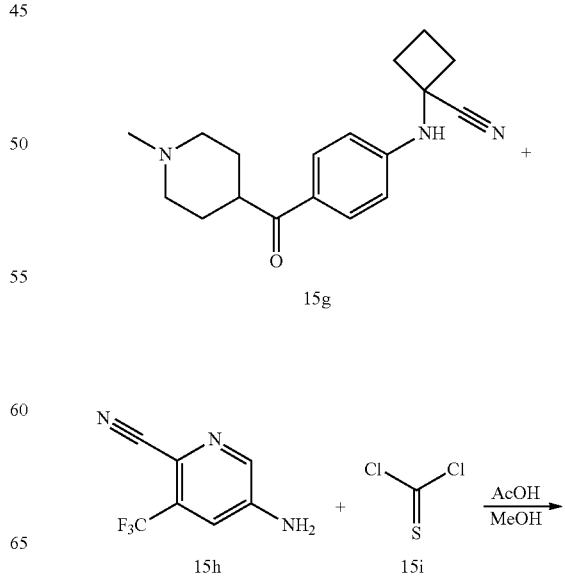

3.24 (m, 1H), 4.11 (br s, 2H), 6.65 (d, J=8.6 Hz, 2H), 7.80 (d, J=8.7 Hz, 2H). $C_{13}H_{18}N_2O$ MS m/z 219 (M+H)⁺.

C. 1-((4-(1-methylpiperidine-4-carbonyl)phenyl) amino)cyclobutanecarbonitrile, 15g

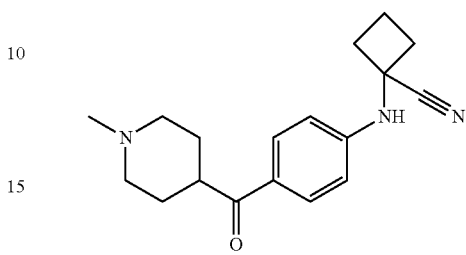

Cyclobutanone (0.435 mL, 5.77 mmol) was added to a solution of (4-aminophenyl)(1-methylpiperidin-4-yl)methanone (0.84 g, 3.84 mmol) in Acetic acid (2.5 mL) and MeOH (25 mL). The solution was stirred for 15 min at room temperature before trimethylsilyl cyanide (0.963 mL, 7.698 mmol) was added dropwise. After stirring at RT overnight, aqueous 1.0M $Na_2CO_3$ (100 mL) was added carefully and the solution was extracted with DCM. The organic layers were dried over $MgSO_4$, filtered and concentrated to dryness. Chromatography over silica gel (gradient of MeOH:DCM 1:9 in DCM from 0 to 100%) gave 1-((4-(1-methylpiperidine-4-carbonyl)phenyl)amino)cyclobutanecarbonitrile (0.5 g, 44%) as a yellow solid. ¹H NMR (300 MHz, Chloroform-d) δ 1.76-1.95 (m, 4H), 2.00-2.13 (m, 2H), 2.13-2.27 (m, 2H), 2.29 (s, 3H), 2.32-2.47 (m, 2H), 2.77-2.88 (m, 2H), 2.88-2.97 (m, 2H), 3.03-3.24 (m, 1H), 4.67 (br s, 1H), 6.64 (d, J=8.7 Hz, 2H), 7.87 (d, J=8.7 Hz, 2H). $C_{18}H_{23}N_3O$ MS m/z 298 (M+H)⁺.

D. 5-[8-[4-(1-methylpiperidine-4-carbonyl)phenyl]-5-oxo-7-thioxo-6,8-diazaspiro[3.4]octan-6-yl]-3-(trifluoromethyl)pyridine-2-carbonitrile, Cpd 144

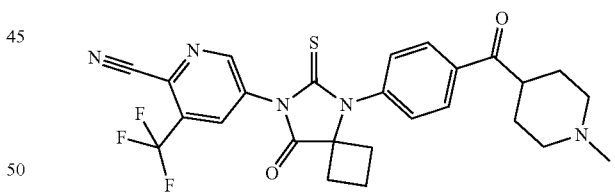

A mixture of 5-amino-3-(trifluoromethyl)picolinonitrile (0.28 g, 1.496 mmol), 1-((4-(1-methylpiperidine-4-carbonyl)phenyl)amino)cyclobutanecarbonitrile (0.444 g, 1.493 mmol) and thiophosgene (0.172 mL, 2.244 mmol) in MeOH (15 mL) was stirred at 65° C. overnight. The mixture was allowed to cool down to RT, poured into water/ice and extracted with DCM. The organic layers were dried over $MgSO_4$, filtered and concentrated to dryness. Chromatography over silica gel (gradient of MeOH:DCM 1:9 in DCM from 0 to 100%) gave a residue further triturated with $Et_2O$ to yield 5-(5-(4-(1-methylpiperidine-4-carbonyl)phenyl)-8-oxo-6-thioxo-5,7-diazaspiro[3.4]octan-7-yl)-3-(trifluoromethyl) picolinonitrile (0.202 g, 26%) as a solid. ¹H NMR (300 MHz, Chloroform-d) δ 1.57-1.85 (m, 1H), 2.04-2.22 (m, 3H), 2.21-2.39 (m, 3H), 2.62 (s, 3H), 2.69-3.08 (m, 4H),

---

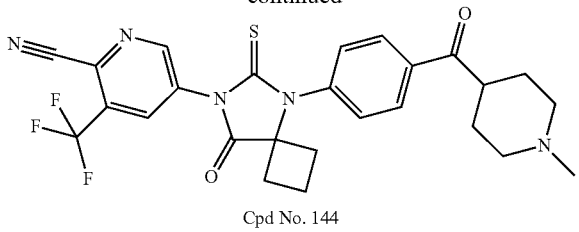

Cpd No. 144

A. N-(4-(1-methylpiperidine-4-carbonyl)phenyl) acetamide, 15c

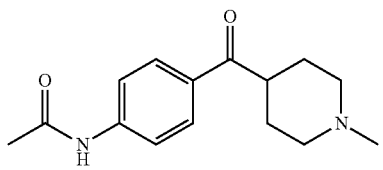 [SMILES: CC(=O)Nc1ccc(C(=O)C2CCN(C)CC2)cc1]

Aluminium Chloride (4.23 g, 31.77 mmol) was added portionwise under a nitrogen atmosphere to a mixture of 1-methylpiperidine-4-carbonyl chloride (1.71 g, 10.58 mmol) and N-phenylacetamide (1.71 g, 12.71 mmol) in DCE (35 mL) at 0° C. The mixture was stirred at 85° C. overnight, allowed to cool to RT and poured into ice and aqueous 6.0M NaOH. The solution was basified to pH 10 to 11 and the aqueous layer extracted with DCM. The organic layers were combined, dried over $MgSO_4$, filtered, concentrated and the residue purified by chromatography over silica gel (gradient of MeOH:DCM 1:9 in DCM from 0 to 100%) to give N-(4-(1-methylpiperidine-4-carbonyl)phenyl)acetamide (1.21 g, 47%) as a solid. ¹H NMR (300 MHz, Chloroform-d) δ 1.78-1.90 (m, 4H), 2.00-2.13 (m, 2H), 2.20 (s, 3H), 2.29 (s, 3H), 2.83-2.98 (m, 2H), 3.08-3.28 (m, 1H), 7.62 (d, J=8.3 Hz, 2H), 7.81 (br s, 1H), 7.90 (d, J=8.5 Hz, 2H). $C_{15}H_{20}N_2O_2$ MS m/z 261 (M+H)⁺.

B. (4-aminophenyl)(1-methylpiperidin-4-yl)methanone, 15d

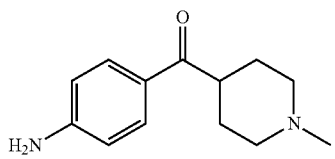 [SMILES: CN1CCC(C(=O)c2ccc(N)cc2)CC1]

Aqueous 2.0N HCl (15.37 mL, 30.74 mmol) was added to a solution of N-(4-(1-methylpiperidine-4-carbonyl)phenyl) acetamide (1.2 g, 4.61 mmol) in MeOH (8 mL). The mixture was refluxed for 2 h, allowed to cool to RT, and the mixture was basified to pH 9 to 10 with aqueous 10.0M NaOH and extracted with DCM. The organic layers were combined, dried over $MgSO_4$, filtered, and concentrated under reduced pressure to give (4-aminophenyl)(1-methylpiperidin-4-yl) methanone (0.848 g, 84%), directly used into the next step. ¹H NMR (300 MHz, Chloroform-d) δ 1.77-1.92 (m, 4H), 2.01-2.17 (m, 2H), 2.31 (s, 3H), 2.85-2.98 (m, 2H), 3.05-

3.07-3.39 (m, 2H), 3.32-3.81 (m, 2H), 7.48 (d, J=8.0 Hz, 2H), 8.16 (d, J=8.0 Hz, 2H), 8.37 (s, 1H), 9.11 (s, 1H). $C_{26}H_{24}F_3N_5O_2S$ MS m/z 528 (M+H)$^+$.

Example 16

5-[8-[1-(1-methyl-4-piperidyl)indol-5-yl]-5-oxo-7-thioxo-6,8-diazaspiro[3.4]octan-6-yl]-3-(trifluoromethyl)pyridine-2-carbonitrile, Cpd 251

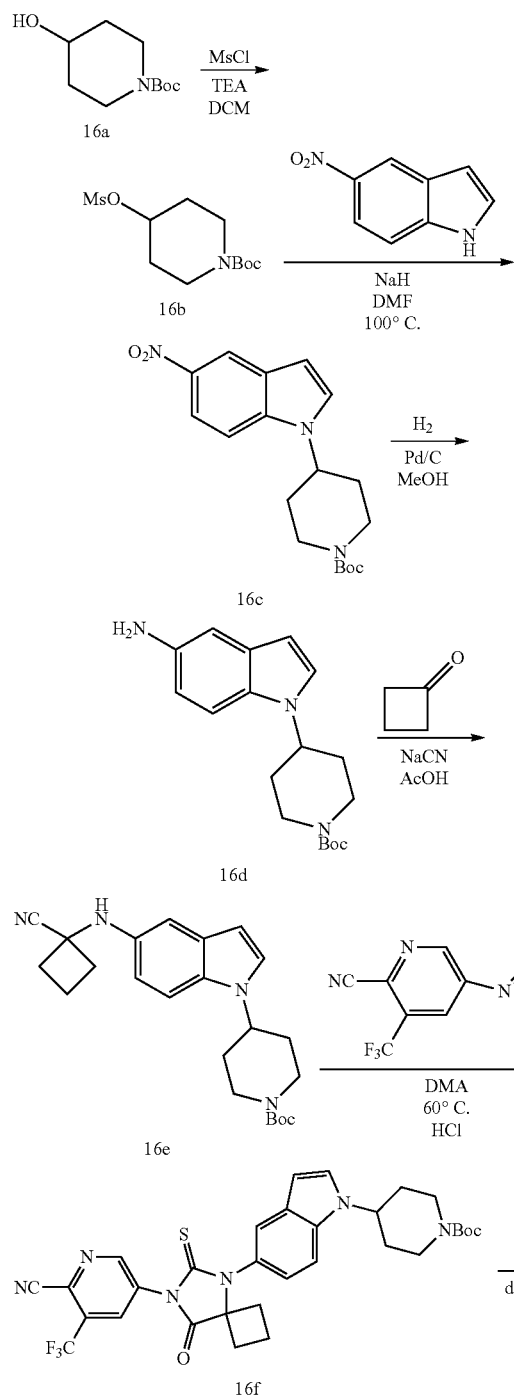

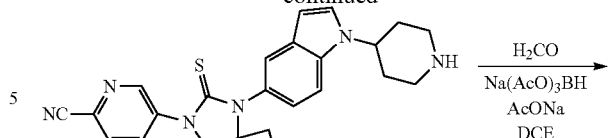

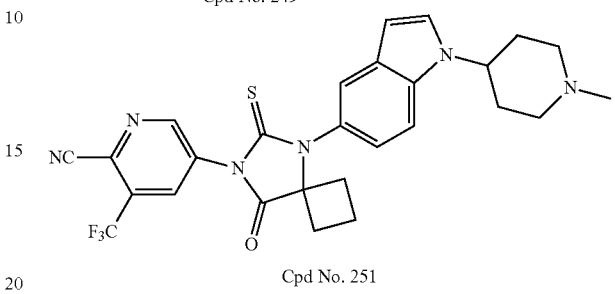

A. 4-Methanesulfonyloxy-piperidine-1-carboxylic Acid Tert-Butyl Ester, 16b

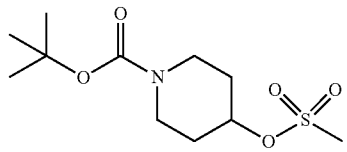 [SMILES: CC(C)(C)OC(=O)N1CCC(OS(C)(=O)=O)CC1]

A 250 mL round-bottom flask equipped with a stirring bar, addition funnel and a nitrogen inlet, was charged with 4-Hydroxy-piperidine-1-carboxylic acid tert-butyl ester (8 g, 39.7 mmol) and triethyl amine (6.08 mL, 43.7 mmol) in DCM (125 mL) and cooled in an ice bath under light nitrogen steam. Methanesulfonyl chloride (3.7 mL, 47.7 mmol) was added dropwise over 10-15 min. The mixture was allowed to come to room temperature and stirred for 1.5 h. The solution was washed with water (70 mL), dried over MgSO$_4$, filtered and concentrated to yield the crude product as an oil (11.1 g, 100%). $C_{11}H_{21}NO_5S$ MS m/z 280 (M+H)$^+$.

B. 4-(5-Nitro-indol-1-yl)-piperidine-1-carboxylic Acid Tert-Butyl Ester, 16c

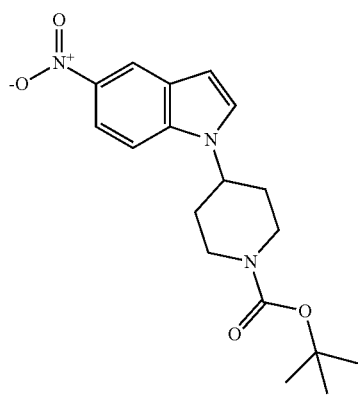

5-Nitro-1H-indole (2 g, 12.3 mmol) was dissolved in DMF (30 mL) and cooled in an ice bath under a nitrogen atmosphere. Sodium hydride (60% in mineral oil, 0.543 g, 13.5 mmol) was added in one portion. The mixture was stirred for 30 min while allowed to come to room temperature. The solution was then heated at 100° C. before a solution of 4-Methanesulfonyloxy-piperidine-1-carboxylic acid tert-butyl ester (4.14 g, 16.7 mmol) in DMF (40 mL) was added dropwise in two portions at 30 min intervals. The reaction was continued for 4 h at 100° C. and then allowed to cool to room temperature. The mixture was recharged with sodium hydride (60% in mineral oil, 0.543 g, 13.5 mmol) and after 30 min, a solution of 4-Methanesulfonyloxy-piperidine-1-carboxylic acid tert-butyl ester (4.14 g, 16.7 mmol) in DMF (40 mL) was also added dropwise. The reaction was continued for another 4 h at room temperature and quenched with water (200 mL). The organic mixture was extracted with EA (2×40 mL). The combined organic extracts were dried over MgSO$_4$, filtered, and concentrated to dryness. Chromatography over silica gel (gradient of DCM in heptane from 0 to 60% and then of EA in heptane from 0 to 35%) afforded the title compound (1.58 g, 37%). $^1$H NMR (300 MHz, Chloroform-d) δ 1.50 (s, 9H), 1.93 (qd, J=12.4, 4.4 Hz, 2H), 2.03-2.18 (m, 2H), 2.94 (t, J=13.3 Hz, 2H), 4.26-4.51 (m, 3H), 6.72 (d, J=3.4 Hz, 1H), 7.33 (d, J=3.4 Hz, 1H), 7.40 (d, J=9.1 Hz, 1H), 8.11 (dd, J=9.1, 2.3 Hz, 1H), 8.59 (d, J=2.2 Hz, 1H). C$_{18}$H$_{23}$N$_3$O$_4$ MS m/z 290 (M+H−tBu)$^+$.

C. 4-(5-Amino-indol-1-yl)-piperidine-1-carboxylic Acid Tert-Butyl Ester, 16d

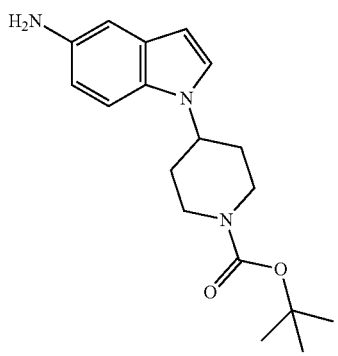 [SMILES: CC(C)(C)OC(=O)N1CCC(n2ccc3cc(N)ccc32)CC1]

4-(5-Nitro-indol-1-yl)-piperidine-1-carboxylic acid tert-butyl ester (1.58 g, 4.57 mmol) was dissolved in MeOH (50 mL) and cooled to 0-5° C. under nitrogen stream. 10% Pd/C (0.316 g) was added. The reaction vessel was connected to a balloon filled with hydrogen. The reaction was evacuated and placed under an atmosphere of hydrogen (3 times) and finally stirred at room temperature for 1 h under hydrogen. The catalyst was removed by filtration through a short pad of diatomaceous earth, then rinsed with MeOH (2×10 mL). The filtrate was concentrated to give the crude 4-(5-Amino-indol-1-yl)-piperidine-1-carboxylic acid tert-butyl ester (1.40 g, 97%). $^1$H NMR (300 MHz, Chloroform-d) δ 1.49 (s, 9H), 1.87 (qd, J=12.5, 4.4 Hz, 2H), 2.07 (d, J=10.5 Hz, 2H), 2.90 (t, J=13.0 Hz, 2H), 3.49 (br s, 2H), 4.18-4.42 (m, 3H), 6.33 (d, J=3.2 Hz, 1H), 6.68 (dd, J=8.7, 2.2 Hz, 1H), 6.94 (d, J=2.1 Hz, 1H), 7.09 (d, J=3.2 Hz, 1H), 7.17 (d, J=8.7 Hz, 1H). C$_{18}$H$_{25}$N$_3$O$_2$ MS m/z 316 (M+H)$^+$.

D. 4-[5-(1-Cyano-cyclobutylamino)-indol-1-yl]-piperidine-1-carboxylic Acid Tert-Butyl Ester, 16e

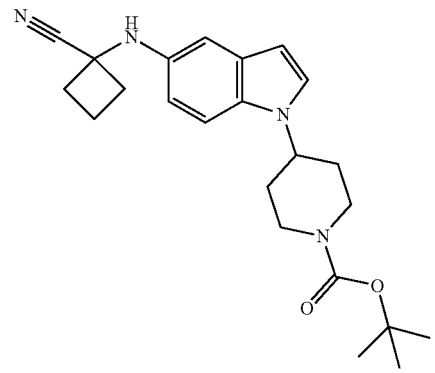 [SMILES: CC(C)(C)OC(=O)N1CCC(n2ccc3cc(NC4(C#N)CCC4)ccc32)CC1]

Cyclobutanone (0.432 mL, 4.78 mmol) was added to a solution of the previous intermediate (1.40 g, 4.44 mmol) and Acetic acid (5 mL) in MeoH (50 mL). The solution was stirred 15 min at room temperature before Trimethylsilyl cyanide (1.11 mL, 8.89 mmol) was added dropwise. Upon completion of the addition, the reaction was continued overnight. The solution was diluted with EA (100 mL) and washed with 1M Na$_2$CO$_3$ (70 mL). The organic layer was dried over MgSO$_4$, filtered and concentrated to a crude oily residue. Chromatography over silica gel (gradient of EA in heptane from 0 to 35%) gave the pure product (0.488 g, 28%). $^1$E1 Wit (300 MHz, Chloroform-d) δ 1.50 (s, 9H), 1.88 (qd, J=12.4, 4.4 Hz, 2H), 2.07 (d, J=13.4, 3.4 Hz, 2H), 2.13-2.33 (m, 2H), 2.42 (ddd, J=12.1, 9.4, 7.1 Hz, 2H), 2.73-3.02 (m, 4H), 3.87 (br s, 1H), 4.20-4.48 (m, 3H), 6.41 (d, J=3.1 Hz, 1H), 6.67 (dd, J=8.8, 2.3 Hz, 1H), 6.91 (d, J=2.2 Hz, 1H), 7.12 (d, J=3.2 Hz, 1H), 7.25 (d, J=8.8 Hz, 1H). C$_{23}$H$_{30}$N$_4$O$_2$ MS m/z 395 (M+H)$^+$.

E. 4-{5-[7-(6-Cyano-5-trifluoromethyl-pyridin-3-yl)-8-oxo-6-thioxo-5,7-diaza-spiro[3.4]oct-5-yl]-indol-1-yl}-piperidine-1-carboxylic Acid Tert-Butyl Ester, 16f

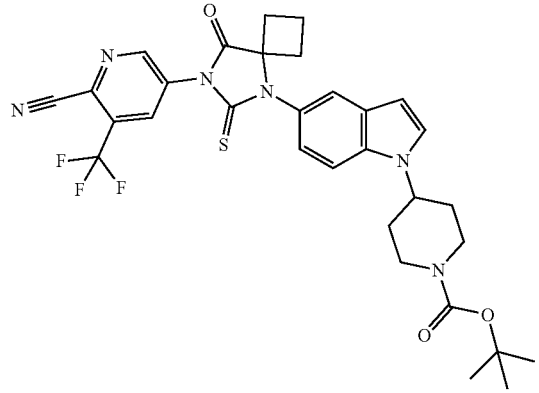 [SMILES: CC(C)(C)OC(=O)N1CCC(n2ccc3cc(N4C(=S)N(c5cnc(C#N)c(C(F)(F)F)c5)C(=O)C45CCC5)ccc32)CC1]

4-[5-(1-Cyano-cyclobutylamino)-indol-1-yl]-piperidine-1-carboxylic acid tert-butyl ester (0.488 g, 1.24 mmol) and freshly prepared 5-Isothiocyanato-3-trifluoromethyl-pyridine-2-carbonitrile (0.510 g, 2.23 mmol) were mixed in DMA (5 mL). The resulting solution was stirred at 60° C. for 4 h and then allowed to cool to room temperature. The mixture was diluted with MeOH (1.5 mL) and 1M HCl (1.5 mL) was added. The stirring was maintained overnight. EA (25 mL) was added and the solution washed with 1M $Na_2CO_3$ (10 mL) and brine (5 mL). The organic layer was dried over $MgSO_4$, filtered and concentrated to dryness. The crude material was purified by chromatography over silica gel (gradient of EA in heptane from 0 to 50%) to yield pure product (0.693 g, 89%). $^1$H NMR (300 MHz, Chloroform-d) δ 1.51 (s, 9H), 1.56-1.76 (m, 1H), 1.96 (qd, J=12.4, 4.4 Hz, 2H), 2.07-2.31 (m, 3H), 2.68 (dd, J=9.1, 7.0 Hz, 4H), 2.95 (t, J=12.8 Hz, 2H), 4.25-4.55 (m, 3H), 6.65 (d, J=3.2 Hz, 1H), 7.10 (dd, J=8.7, 2.0 Hz, 1H), 7.33 (d, J=3.3 Hz, 1H), 7.50-7.62 (m, 2H), 8.40 (d, J=2.2 Hz, 1H), 9.14 (d, J=2.2 Hz, 1H). $C_{31}H_{31}F_3N_6O_3S$ MS m/z 569 (M+H-tBu)$^+$.

F. 5-[8-Oxo-5-(1-piperidin-4-yl-1H-indol-5-yl)-6-thioxo-5,7-diaza-spiro[3.4]oct-7-yl]-3-trifluoromethyl-pyridine-2-carbonitrile, Cpd 249

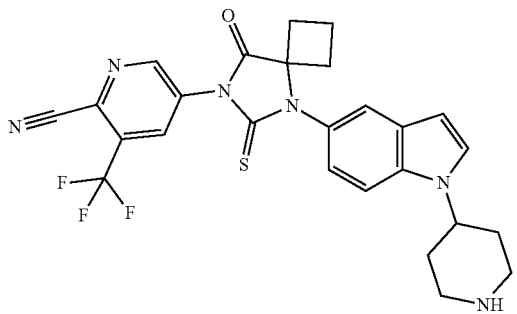 [SMILES: N#Cc1ncc(N2C(=O)C3(CCC3)N(c3ccc4c(ccn4C4CCNCC4)c3)C2=S)cc1C(F)(F)F]

The previous 4-{5-[7-(6-Cyano-5-trifluoromethyl-pyridin-3-yl)-8-oxo-6-thioxo-5,7-diaza-spiro[3.4]oct-5-yl]-indol-1-yl}-piperidine-1-carboxylic acid tert-butyl ester (0.693 g, 1.11 mmol) was taken in dioxane (5 mL). 4N HCl in dioxane (2.5 mL, 10 mmol) was added with stirring for 3 h at room temperature. Diethyl ether (40 mL) was added and the resulting precipitate was stirred for 15 min and collected by filtration on a sintered funnel. The solid was washed with diethyl ether (10 mL). The solid was re-dissolved in DCM (40 mL). The solution was washed with 1M $Na_2CO_3$ (10 mL), water (20 mL). The organic layer was dried over $MgSO_4$, filtered and concentrated to dryness to yield 0.598 g (103%) of the crude product. Half of the yielded product was purified by preparative LC (gradient of ACN in 25 mM aqueous $NH_4HCO_3$ from 30 to 73%). The pure fractions were collected and concentrated to afford the desired product 0.100 g (17%). $^1$H NMR (300 MHz, Chloroform-d) δ 1.53-1.75 (m, 1H), 1.99-2.36 (m, 7H), 2.61-2.73 (m, 5H), 2.85-2.99 (m, 2H), 3.40 (d, J=12.6 Hz, 2H), 4.32-4.51 (m, 1H), 6.65 (d, J=3.2 Hz, 1H), 7.09 (dd, J=8.7, 2.0 Hz, 1H), 7.38 (d, J=3.4 Hz, 1H), 7.53-7.63 (m, 2H), 8.40 (d, J=2.2 Hz, 1H), 9.14 (d, J=2.1 Hz, 1H). $C_{26}H_{23}F_3N_6OS$ MS m/z 525 (M+H)$^+$.

G. 5-[8-[1-(1-methyl-4-piperidyl)indol-5-yl]-5-oxo-7-thioxo-6,8-diazaspiro[3.4]octan-6-yl]-3-(trifluoromethyl)pyridine-2-carbonitrile, Cpd 251

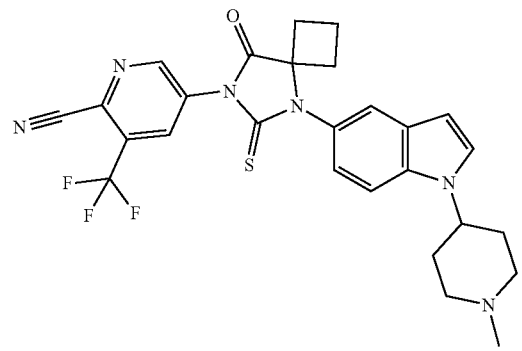 [SMILES: CN1CCC(n2ccc3cc(N4C(=S)N(c5cnc(C#N)c(C(F)(F)F)c5)C(=O)C45CCC5)ccc32)CC1]

Formaldehyde (37% wt in water, 0.30 mL, 4.00 mmol) was added to a solution of 5-[8-Oxo-5-(1-piperidin-4-yl-1H-indol-5-yl)-6-thioxo-5,7-diaza-spiro[3.4]oct-7-yl]-3-trifluoromethyl-pyridine-2-carbonitrile (0.30 g, 0.572 mmol) in DCE (2.25 mL). The mixture was stirred at room temperature for 40 min, before Sodium triacetoxyborohydride (0.30 g, 1.41 mmol) was added in 3 portions over 45 min. The reaction was continued overnight and diluted with DCM (50 mL). The solution was washed successively with 1M $Na_2CO_3$ (25 mL) and water (30 mL). The organic layer was dried over $MgSO_4$, filtered and concentrated to give the crude product. Preparative LC (gradient of ACN in 25 mM aqueous $NH_4HCO_3$ from 41 to 83%) gave, upon removal of solvent, the pure product as a sticky solid. Triturating in diethyl ether (2 mL) afford a white powder (0.056 g, 18%). $^1$H NMR (300 MHz, Chloroform-d) δ 1.48-1.77 (m, 1H), 2.03-2.31 (m, 7H), 2.41 (s, 3H), 2.68-2.75 (m, 4H), 3.09 (m, 2H), 4.16-4.38 (m, 1H), 6.64 (d, J=3.2 Hz, 1H), 7.08 (dd, J=8.7, 1.9 Hz, 1H), 7.37 (d, J=3.3 Hz, 1H), 7.56 (m, 2H), 8.40 (d, J=2.2 Hz, 1H), 9.14 (d, J=2.2 Hz, 1H). $C_{27}H_{25}F_3N_6OS$ MS m/z 539 (M+H)$^+$.

Following the procedure described in Example 16, above, selecting and substituting the appropriate reagents, starting materials, and purification methods, and adjusting reaction temperatures, times and other variables or parameters, as needed or desirable, as would be readily recognized by those skilled in the art, the following compounds of formula (I) of the invention were prepared.

| Cpd No. | Structure | Compound Name & Physical Data |
|---|---|---|
| 255 | 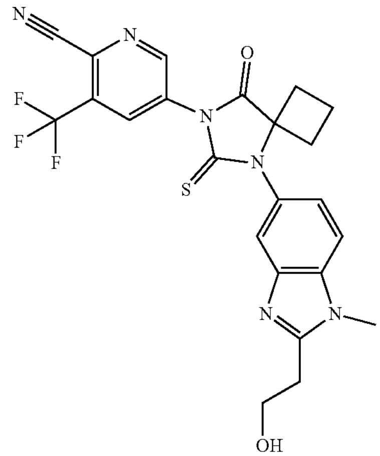 [SMILES: Cn1c(CCO)nc2cc(N3C(=S)N(c4cnc(C#N)c(C(F)(F)F)c4)C(=O)C34CCC4)ccc21] | 5-[8-[2-(2-hydroxyethyl)-1-methyl-benzimidazol-5-yl]-5-oxo-7-thioxo-6,8-diazaspiro[3.4]octan-6-yl]-3-(trifluoromethyl)pyridine-2-carbonitrile.<br>$^1$H NMR (300 MHz, DMSO-d$_6$) δ 1.38-1.60 (m, 1H), 1.88-2.04 (m, 1H), 2.40-2.59 (m, 2H), 2.60-2.74 (m, 2H), 3.08 (t, J = 6.6 Hz, 2H), 3.35 (d, J = 13.8 Hz, 3H), 3.82 (s, 3H), 3.86 (1, J = 6.6 Hz, 5H), 4.89 (br s, 1H), 7.22 (d, J = 8.5 Hz, 1H), 7.59 (s, 1H), 7.72 (d, J = 8.5 Hz, 1H), 8.79 (s, 1H), 9.25 (s, 1H).<br>$C_{23}H_{19}F_3N_6O_2S$ MS m/z 501 (M + H)$^+$ |
| 253 | 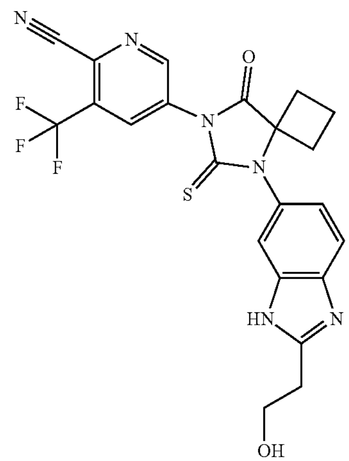 [SMILES: N#Cc1ncc(N2C(=O)C3(CCC3)N(c3ccc4nc(CCO)[nH]c4c3)C2=S)cc1C(F)(F)F] | 5-[8-[2-[[1-(2-hydroxyethyl)-4-piperidyl]oxy]pyrimidin-5-yl]-5-oxo-7-thioxo-6,8-diazaspiro[3.4]octan-6-yl]-3-methyl-pyridine-2-carbonitrile.<br>$^1$H NMR (300 MHz, DMSO-d$_6$) δ 1.40-1.61 (m, 1H), 1.96 (m, 1H), 2.42-2.57 (m, 2H), 2.60-2.73 (m, 2H), 3.01 (t, J = 6.7 Hz, 2H), 3.86 (m, 2H), 4.89 (m, 1H), 7.09-7.15 (m, 1H), 7.46-7.72 (m, 2H), 8.78 (s, 1H), 9.25 (s, 1H), 12.45 (s, 0.5H), 12.50 (s, 0.5H)<br>$C_{22}H_{17}F_3N_6O_2S$ MS m/z 487 (M + H)$^+$ |
| 250 | 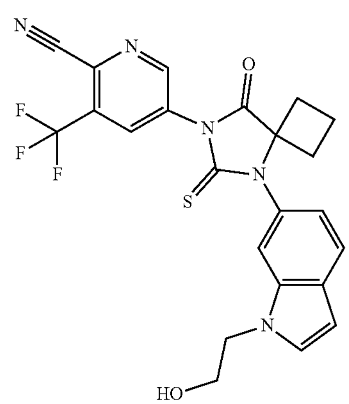 [SMILES: N#Cc1ncc(N2C(=O)C3(CCC3)N(c3ccc4ccn(CCO)c4c3)C2=S)cc1C(F)(F)F] | 5-[8-[1-(2-hydroxyethyl)indol-6-yl]-5-oxo-7-thioxo-6,8-diazaspiro[3.4]octan-6-yl]-3-(trifluoromethyl)pyridine-2-carbonitrile.<br>$^1$H NMR (300 MHz, Chloroform-d) δ 1.48-1.74 (m, 2H), 2.13-2.33 (m, 1H), 2.68 (dd, J = 9.1, 7.0 Hz, 4H), 4.00 (t, J = 5.1 Hz, 2H), 4.33 (t, J = 5.2 Hz, 2H), 6.64 (dd, J = 3.3, 0.9 Hz, 1H), 7.01 (dd, J = 8.3, 1.8 Hz, 1H), 7.33 (d, J = 3.2 Hz, 1H), 7.35-7.45 (m, 1H), 7.81 (d, J = 8.3 Hz, 1H), 8.39 (d, J = 2.2 Hz, 1H), 9.12 (d, J = 2.2 Hz, 1H).<br>$C_{23}H_{18}F_3N_5O_2S$ MS m/z 486 (M + H)$^+$ |

-continued

| Cpd No. | Structure | Compound Name & Physical Data |
|---|---|---|
| 249 | 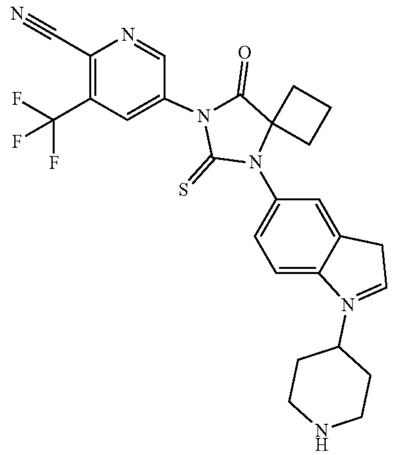 | 5-[5-oxo-8-[1-(4-piperidyl)indol-5-yl]-7-thioxo-6,8-diazaspiro[3.4]octan-6-yl]-3-(trifluoromethyl)pyridine-2-carbonitrile.<br>$^1$H NMR (300 MHz, Chloroform-d) δ 1.56-1.70 (m, 1H), 2.08-2.31 (m, 5H), 2.68 (dd, J = 9.1, 7.0 Hz, 4H), 2.92-3.01 (m, 2H), 3.36-3.59 (m, 2H), 4.43 (p, J = 8.0 Hz, 1H), 6.66 (d, J = 3.2 Hz, 1H), 7.10 (dd, J = 8.6, 2.0 Hz, 1H), 7.39 (d, J = 3.3 Hz, 1H), 7.51-7.66 (m, 2H), 8.40 (d, J = 2.2 Hz, 1H), 9.14 (d, J = 2.2 Hz, 1H).<br>$C_{26}H_{23}F_3N_6OS$ MS m/z 525 (M + H)$^+$ |
| 248 | 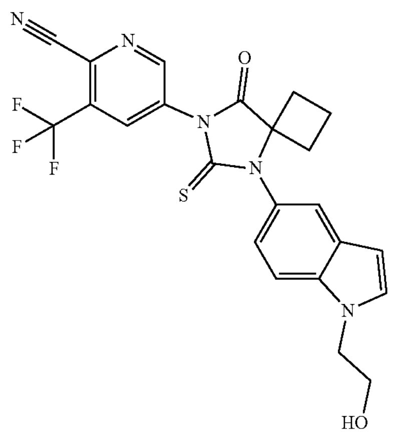 [SMILES: N#Cc1ncc(N2C(=O)C3(CCC3)N(c3ccc4c(ccn4CCO)c3)C2=S)cc1C(F)(F)F] | 5-[8-[1-(2-hydroxyethyl)indol-5-yl]-5-oxo-7-thioxo-6,8-diazaspiro[3.4]octan-6-yl]-3-(trifluoromethyl)pyridine-2-carbonitrile.<br>$^1$H NMR (300 MHz, Chloroform-d) δ 1.56-1.84 (m, 2H), 2.17-2.30 (m, 1H), 2.62-2.74 (m, 4H), 4.04 (q, J = 5.3 Hz, 2H), 4.35 (t, J = 5.2 Hz, 2H), 6.64 (d, J = 3.1 Hz, 1H), 7.10 (dd, J = 8.7, 2.0 Hz, 1H), 7.32 (d, J = 3.2, 2.0 Hz, 1H), 7.46-7.76 (m, 2H), 8.41 (d, J = 2.2 Hz, 1H), 9.14 (d, J = 2.2 Hz, 1H).<br>$C_{23}H_{18}F_3N_5O_2S$ MS m/z 486 (M + H)$^+$ |
| 245 | 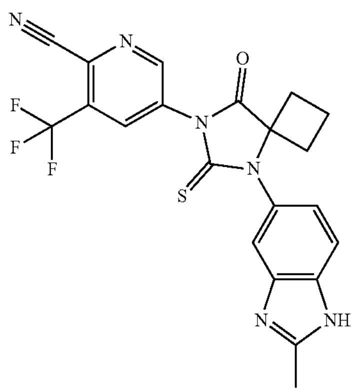 [SMILES: Cc1nc2cc(N3C(=S)N(c4cnc(C#N)c(C(F)(F)F)c4)C(=O)C34CCC4)ccc2[nH]1] | 5-[8-(2-methyl-1H-benzimidazol-5-yl)-5-oxo-7-thioxo-6,8-diazaspiro[3.4]octan-6-yl]-3-(trifluoromethyl)pyridine-2-carbonitrile.<br>$^1$H NMR (300 MHz, DMSO-d$_6$) δ 1.40-1.58 (m, 1H), 1.97 (p, J = 9.3 Hz, 1H), 2.35-2.57 (m, 2H), 2.54 (s, 3H), 2.57-2.75 (m, 2H), 3.32 (s, 1H), 7.11 (dd, 7 = 8.4, 1.9 Hz, 1H), 7.49 (m, 1H), 7.63 (m, 1H), 8.78 (d, J = 2.1 Hz, 1H), 9.24 (d, J = 2.0 Hz, 1H), 12.50 (s, 1H).<br>$C_{21}H_{15}F_3N_6OS$ MS m/z 457 (M + H)$^+$ |

| Cpd No. | Structure | Compound Name & Physical Data |
|---|---|---|
| 244 | 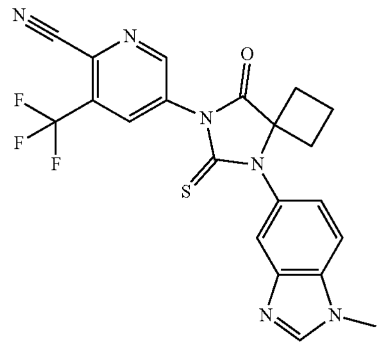 [SMILES: Cn1cnc2cc(N3C(=S)N(c4cnc(C#N)c(C(F)(F)F)c4)C(=O)C34CCC4)ccc21] | 5-[8-(1-methylbenzimidazol-5-yl)-5-oxo-7-thioxo-6,8-diazaspiro[3.4]octan-6-yl]-3-(trifluoromethyl)pyridine-2-carbonitrile.<br>$^1$H NMR (300 MHz, DMSO-d$_6$) δ 1.42-1.57 (m, 1H), 1.91-2.05 (m, 1H), 2.42-2.58 (m, 2H), 2.59-2.74 (m, 2H), 3.92 (s, 3H), 7.29 (dd, J = 8.5, 1.9 Hz, 1H), 7.70 (d, J = 1.8 Hz, 1H), 7.79 (d, J = 8.5 Hz, 1H), 8.35 (s, 1H), 8.79 (d, J = 2.1 Hz, 1H), 9.25 (d, 7 = 2.1 Hz, 1H).<br>C$_{21}$H$_{15}$F$_3$N$_6$OS MS m/z 457 (M + H)$^+$ |
| 225 | 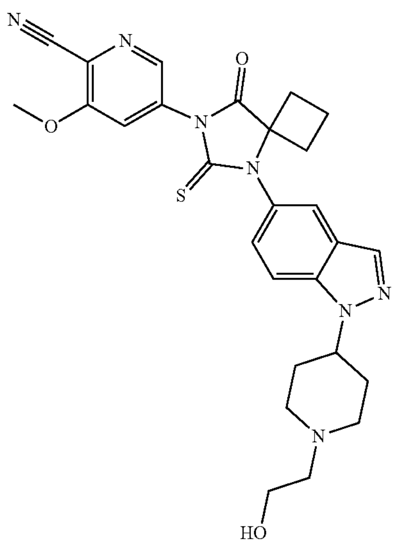 [SMILES: COc1cc(N2C(=O)C3(CCC3)N(c3ccc4c(cnn4C4CCN(CCO)CC4)c3)C2=S)cnc1C#N] | 5-[8-[1-[1-(2-hydroxyethyl)-4-piperidyl]indazol-5-yl]-5-oxo-7-thioxo-6,8-diazaspiro[3.4]octan-6-yl]-3-methoxy-pyridine-2-carbonitrile.<br>$^1$H NMR (300 MHz, Chloroform-d) δ 1.56-1.78 (m, 1H), 2.05-2.53 (m, 7H), 2.57-2.78 (m, 6H), 3.16 (t, J = 5.1 Hz, 2H), 3.50 (m, 1H), 3.69 (t, 5.1 Hz, 2H), 3.94-4.03 (s, 3H), 4.45-4.68 (m, 1H), 7.16-7.39 (m, 2H), 7.55-7.82 (m, 3H), 8.06-8.21 (m, 1H), 8.38-8.57 (m, 1H).<br>C$_{27}$H$_{29}$N$_7$O$_3$S MS m/z 532 (M + H)$^+$ |
| 215 | 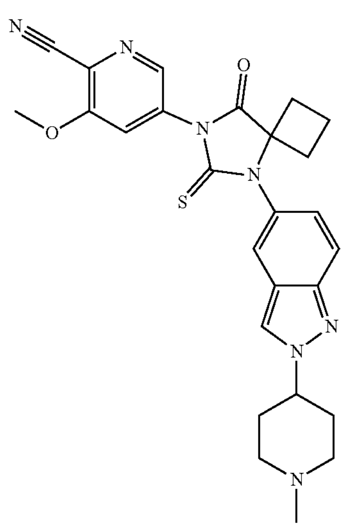 [SMILES: COc1cc(N2C(=O)C3(CCC3)N(c3ccc4nn(C5CCN(C)CC5)cc4c3)C2=S)cnc1C#N] | 3-methoxy-5-[8-[2-(1-methyl-4-piperidyl)indazol-5-yl]-5-oxo-7-thioxo-6,8-diazaspiro[3.4]octan-6-yl]pyridine-2-carbonitrile.<br>$^1$H NMR (300 MHz, DMSO-d$_6$) δ 1.45-1.62 (m, 1H), 1.90-2.05 (m, 1H), 2.07-2.20 (m, 5H), 2.24 (s, 3H), 2.42-2.57 (m, 2H), 2.58-2.70 (m, 2H), 2.87-2.98 (m, 2H), 4.00 (s, 3H), 4.40-4.62 (m, 1H), 7.18 (dd, J = 9.1, 1.9 Hz, 1H), 7.76-7.84 (m, 2H), 8.07 (d, J = 1.9 Hz, 1H), 8.48 (d, J = 1.8 Hz, 1H), 8.61 (s, 1H).<br>C$_{26}$H$_{27}$N$_7$O$_2$S MS m/z 502 (M + H)$^+$ |

| Cpd No. | Structure | Compound Name & Physical Data |
|---|---|---|
| 214 | 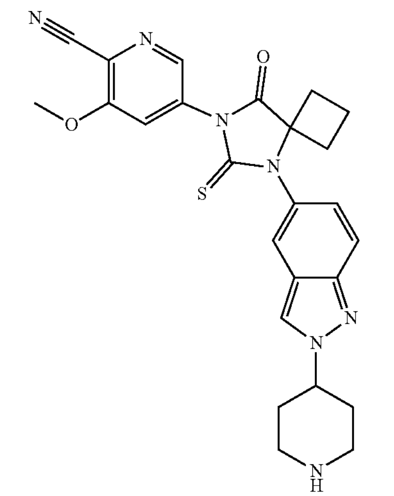 [SMILES: COc1cc(N2C(=O)C3(CCC3)N(c3ccc4nn(C5CCNCC5)cc4c3)C2=S)cnc1C#N] | 3-methoxy-5-[5-oxo-8-[2-(4-piperidyl)indazol-5-yl]-7-thioxo-6,8-diazaspiro[3.4]octan-6-yl]pyridine-2-carbonitrile.<br>$^1$H NMR (300 MHz, DMSO-$d_6$) δ 1.46-1.62 (m, 1H), 1.90-2.22 (m, 5H), 2.44-2.57 (m, 2H), 2.58-2.82 (m, 4H), 3.10-3.19 (m, 2H), 3.10-3.21 (m, 2H), 4.00 (s, 3H), 4.56-4.70 (m, 1H), 7.18 (dd, J = 9.1, 1.9 Hz, 1H), 7.79 (d, J = 8.3 Hz, 1H), 7.81 (s, 1H, 8.07 (d, J = 1.8 Hz, 1H), 8.48 (d, J = 1.8 Hz, 1H), 8.58 (s, 1H).<br>$C_{25}H_{25}N_7O_2S$ MS m/z 488 (M + H)$^+$ |
| 213 | 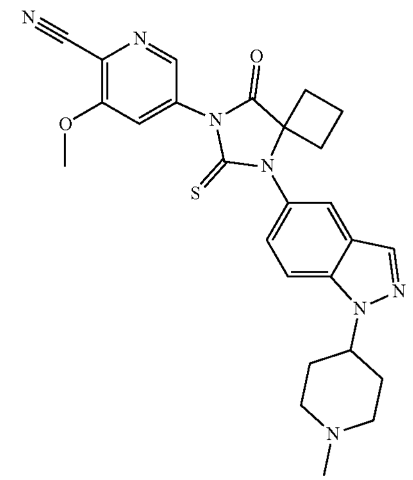 [SMILES: COc1cc(N2C(=O)C3(CCC3)N(c3ccc4c(cnn4C4CCN(C)CC4)c3)C2=S)cnc1C#N] | 3-methoxy-5-[8-[1-(1-methyl-4-piperidyl)indazol-5-yl]-5-oxo-7-thioxo-6,8-diazaspiro[3.4]octan-6-yl]pyridine-2-carbonitrile.<br>$^1$H NMR (300 MHz, DMSO-$d_6$) δ 1.42-1.60 (m, 1H), 1.90-2.02 (m, 3H), 2.12-2.20 (m, 4H), 2.25 (s, 3H), 2.41-2.56 (m, 2H), 2.58-2.69 (m, 2H), 2.88-2.97 (m, 2H), 4.00 (s, 3H), 4.59-4.73 (m, 1H), 7.36 (dd, J = 8.9, 1.9 Hz, 1H), 7.85 (d, J = 1.8 Hz, 1H), 7.95 (d, J = 8.9 Hz, 1H), 8.06 (d, J = 1.9 Hz, 1H), 8.23 (s, 1H), 8.48 (d, J = 1.8 Hz, 1H).<br>$C_{26}H_{27}N_7O_2S$ MS m/z 502 (M + H)$^+$ |
| 212 | 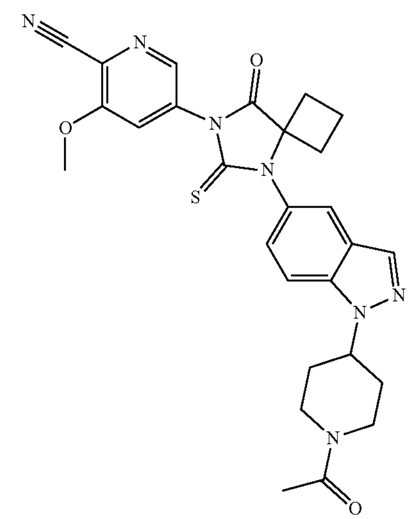 [SMILES: COc1cc(N2C(=O)C3(CCC3)N(c3ccc4c(cnn4C4CCN(C(C)=O)CC4)c3)C2=S)cnc1C#N] | 5-[8-[1-(1-acetyl-4-piperidyl)indazol-5-yl]-5-oxo-7-thioxo-6,8-diazaspiro[3.4]octan-6-yl]-3-methoxy-pyridine-2-carbonitrile.<br>$^1$H NMR (300 MHz, DMSO-$d_6$) δ 1.44-1.62 (m, 1H), 1.86-2.14 (m, 5H), 2.08 (s, 3H), 2.42-2.56 (m, 2H), 2.58-2.72 (m, 2H), 2.75-2.88 (m, 1H), 4.00 (s, 3H), 4.49-4.61 (m, 1H), 4.93-5.08 (m, 1H), 7.39 (dd, J = 8.9, 1.9 Hz, 1H), 7.86 (d, J = 1.9 Hz, 1H), 7.97 (d, J = 8.9 Hz, 1H), 8.06 (d, J = 1.9 Hz, 1H), 8.24 (s, 1H), 8.48 (d, J = 1.8 Hz, 1H).<br>$C_{27}H_{27}N_7O_3S$ MS m/z 530 (M + H)$^+$ |

| Cpd No. | Structure | Compound Name & Physical Data |
|---|---|---|
| 211 | 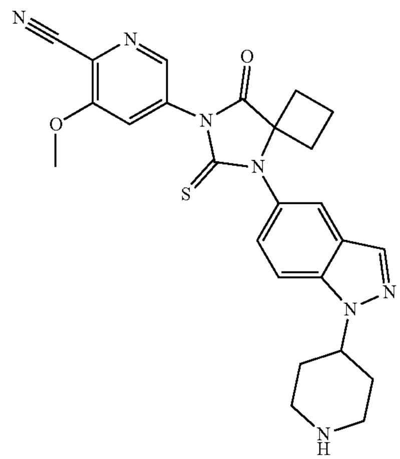 [SMILES: COc1cc(N2C(=O)C3(CCC3)N(c3ccc4c(cnn4C4CCNCC4)c3)C2=S)cnc1C#N] | 3-methoxy-5-[5-oxo-8-[1-(4-piperidyl)indazol-5-yl]-7-thioxo-6,8-diazaspiro[3.4]octan-6-yl]pyridine-2-carbonitrile.<br>$^1$H NMR (300 MHz, DMSO-d$_6$) δ 1.44-1.61 (m, 1H), 1.90-2.30 (m, 5H), 2.40-2.55 (m, 2H), 2.58-2.71 (m, 2H), 2.73-2.90 (m, 2H), 3.14-3.24 (m, 2H), 4.00 (s, 4H), 4.74-4.84 (m, 1H), 7.37 (dd, J = 8.9, 1.9 Hz, 1H), 7.85 (d, J = 1.9 Hz, 1H), 7.95 (d, J = 8.8 Hz, 1H), 8.06 (d, J = 1.9 Hz, 1H), 8.24 (s, 1H), 8.48 (d, J = 1.8 Hz, 1H). $C_{25}H_{25}N_7O_2S$ MS m/z 488 (M + H)$^+$ |
| 199 | 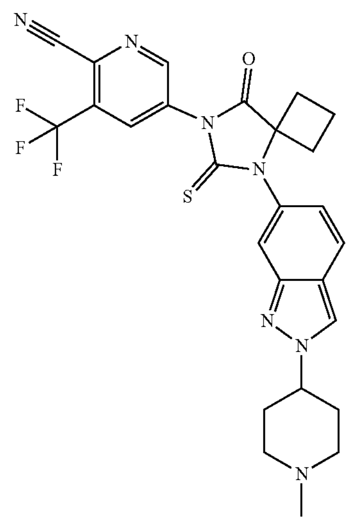 [SMILES: CN1CCC(n2cc3ccc(N4C(=S)N(c5cnc(C#N)c(C(F)(F)F)c5)C(=O)C45CCC5)cc3n2)CC1] | 5-[8-[2-(1-methyl-4-piperidyl)indazol-6-yl]-5-oxo-7-thioxo-6,8-diazaspiro[3.4]octan-6-yl]-3-(trifluoromethyl)pyridine-2-carbonitrile.<br>$^1$H NMR (300 MHz, DMSO-d$_6$) δ 1.43-1.71 (m, 1H), 1.85-2.05 (m, 1H), 2.06-2.36 (m, 6H), 2.24 (s, 3H), 2.40-2.77 (m, 4H), 2.92 (m, 2H), 4.42-4.65 (m, 1H), 6.99 (d, J = 8.7 Hz, 1H), 7.72 (s, 1H), 7.90 (d, J = 8.7 Hz, 1H), 8.59 (s, 1H), 8.79 (s, 1H), 9.25 (s, 1H). $C_{26}H_{24}F_3N_7OS$ MS m/z 540 (M+H)$^+$ |
| 198 | 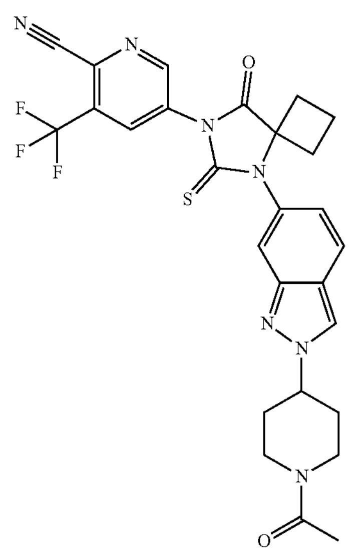 [SMILES: CC(=O)N1CCC(n2cc3ccc(N4C(=S)N(c5cnc(C#N)c(C(F)(F)F)c5)C(=O)C45CCC5)cc3n2)CC1] | 5-[8-[2-(1-acetyl-4-piperidyl)indazol-6-yl]-5-oxo-7-thioxo-6,8-diazaspiro[3.4]octan-6-yl]-3-(trifluoromethyl)pyridine-2-carbonitrile.<br>$^1$H NMR (300 MHz, DMSO-d$_6$) δ 1.45-1.65 (m, 1H), 1.86-2.04 (m, 1H), 2.07 (s, 3H), 2.08-2.28 (m, 4H), 2.41-2.72 (m, 4H), 2.70-2.85 (m, 2H), 3.92-4.08 (m, 1H), 4.46-4.64 (m, 1H), 4.76-4.84 (m, 1H), 7.00 (d, J = 8.8 Hz, 1H), 7.71 (s, 1H), 7.91 (d, J = 8.7 Hz, 1H), 8.60 (s, 1H), 8.79 (s, 1H), 9.25 (s, 1H). $C_{27}H_{24}F_3N_7O_2S$ MS m/z 568 (M + H)$^+$ |

| Cpd No. | Structure | Compound Name & Physical Data |
|---|---|---|
| 183 | 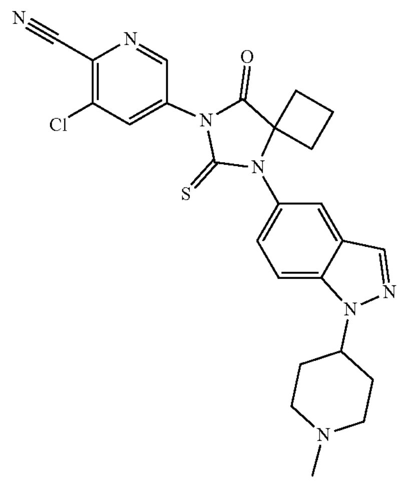 [SMILES: CN1CCC(n2ncc3cc(N4C(=S)N(c5cnc(C#N)c(Cl)c5)C(=O)C45CCC5)ccc32)CC1] | 3-chloro-5-[8-[1-(1-methyl-4-piperidyl)indazol-5-yl]-5-oxo-7-thioxo-6,8-diazaspiro[3.4]octan-6-yl]pyridine-2-carbonitrile. $^1$H NMR (300 MHz, DMSO-d$_6$) δ 1.44-1.65 (m, 1H), 1.88-2.05 (m, 3H), 2.12-2.24 (m, 4H), 2.26 (s, 3H), 2.40-2.55 (m, 2H), 2.57-2.70 (m, 2H), 2.87-3.00 (m, 2H), 4.55-4.75 (m, 1H), 7.35 (d, J = 8.9 Hz, 1H), 7.84 (s, 1H), 7.95 (d, J = 8.9 Hz, 1H), 8.23 (s, 1H), 8.56 (s, 1H), 8.92 (s, 1H). C$_{25}$H$_{24}$ClN$_7$OS MS m/z 506 (M + H)$^+$ |
| 182 | 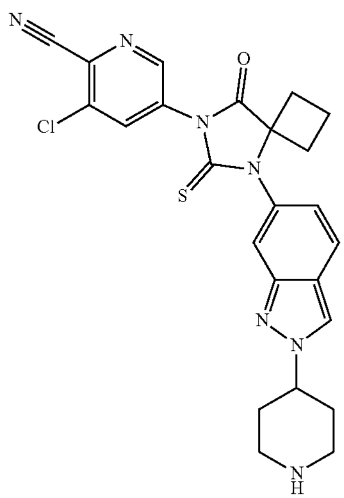 [SMILES: N#Cc1ncc(N2C(=O)C3(CCC3)N(c3ccc4cn(C5CCNCC5)nc4c3)C2=S)cc1Cl] | 3-chloro-5-[5-oxo-8-[1-(4-piperidyl)indazol-5-yl]-7-thioxo-6,8-diazaspiro[3.4]octan-6-yl]pyridine-2-carbonitrile. $^1$H NMR (300 MHz, DMSO-d$_6$) δ 1.40-1.66 (m, 1H), 1.82-2.14 (m, 5H), 2.40-2.56 (m, 2H), 2.58-2.66 (m, 2H), 2.68-2.82 (m, 2H), 3.06-3.18 (m, 2H), 4.68-4.85 (m, 2H), 7.35 (d, J = 8.9 Hz, 1H), 7.84 (s, 1H), 7.95 (d, J = 8.9 Hz, 1H), 8.23 (s, 1H), 8.56 (s, 1H), 8.92 (s, 1H). C$_{24}$H$_{22}$ClN$_7$OS MS m/z 492 (M + H)$^+$ |
| 181 | 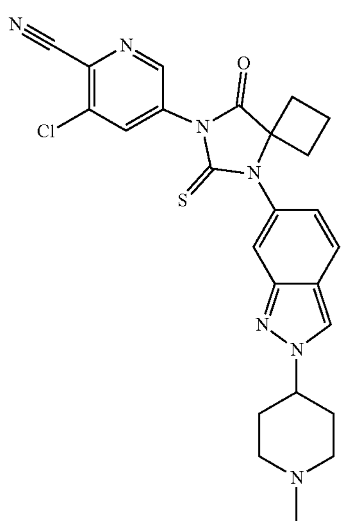 [SMILES: CN1CCC(n2cc3ccc(N4C(=S)N(c5cnc(C#N)c(Cl)c5)C(=O)C45CCC5)cc3n2)CC1] | 3-chloro-5-[8-[2-(1-methyl-4-piperidyl)indazol-5-yl]-5-oxo-7-thioxo-6,8-diazaspiro[3.4]octan-6-yl]pyridine-2-carbonitrile. $^1$H NMR (300 MHz, DMSO-d$_6$) δ 1.36-1.55(s, 1H), 1.80-1.95 (m, 1H), 1.97-2.14 (m, 4H), 2.16 (s, 3H), 2.33-2.47 (m, 2H), 2.49-2.63 (m, 2H), 2.75-2.90 (m, 2H), 4.34-4.56 (m, 1H), 7.08 (d, J = 9.1 Hz, 1H), 7.72 (m, 2H), 8.51 (m, 2H), 8.85 (s, 1H). C$_{25}$H$_{24}$ClN$_7$OS MS m/z 506 (M + H)$^+$ |

| Cpd No. | Structure | Compound Name & Physical Data |
|---|---|---|
| 180 | 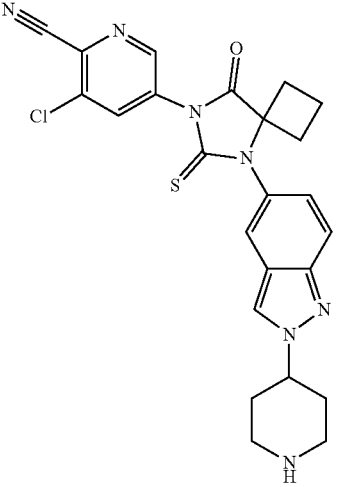 [SMILES: N#Cc1ncc(N2C(=O)C3(CCC3)N(c3ccc4nn(C5CCNCC5)cc4c3)C2=S)cc1Cl] | 3-chloro-5-[5-oxo-8-[2-(4-piperidyl)indazol-5-yl]-7-thioxo-6,8-diazaspiro[3.4]octan-6-yl]pyridine-2-carbonitrile.<br>$^1$H NMR (300 MHz, DMSO-$d_6$) δ 1.44-1.62 (m, 1H), 1.85-2.05 (m, 5H), 2.42-2.56 (m, 2H), 2.58-2.79 (m, 4H), 2.99-3.19 (m, 2H), 4.52-4.68 (m, 1H), 7.16 (dd, J = 9.0, 1.9 Hz, 1H), 7.79 (m, 2H), 8.45-8.72 (m, 2H), 8.93 (d, J = 2.0 Hz, 1H).<br>$C_{24}H_{22}ClN_7OS$ MS m/z 492 (M + H)$^+$ |
| 179 | 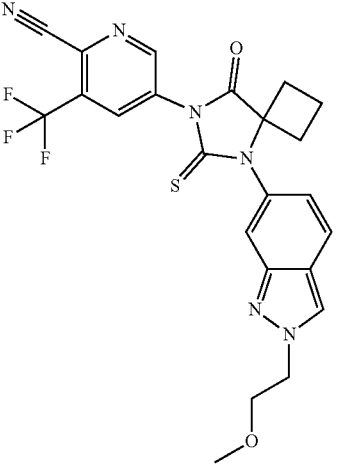 [SMILES: COCCn1cc2ccc(N3C(=S)N(c4cnc(C#N)c(C(F)(F)F)c4)C(=O)C34CCC4)cc2n1] | 5-[8-[2-(2-methoxyethyl)indazol-6-yl]-5-oxo-7-thioxo-6,8-diazaspiro[3.4]octan-6-yl]-3-(trifluoromethyl)pyridine-2-carbonitrile.<br>$^1$H NMR (300 MHz, Chloroform-d) δ 1.59-1.80 (m, 1H), 2.23 (dt, J = 10.8, 8.9 Hz, 1H), 2.70 (dd, J = 9.0, 7.1 Hz, 4H), 3.38 (s, 3H), 3.91 (t, J = 5.0 Hz, 2H), 4.64 (t, J = 5.0 Hz, 2H), 6.95 (dd, J = 8.8, 1.8 Hz, 1H), 7.65-7.78 (s, 1H), 7.87 (dd, J = 8.8, 1.8 Hz, 1H), 8.16 (s, 1H), 8.41 (d, J = 2.2 Hz, 1H), 9.15 (d, J = 2.2 Hz, 1H).<br>$C_{23}H_{19}F_3N_6O_2S$ MS m/z 501 (M + H)$^+$ |
| 175 | 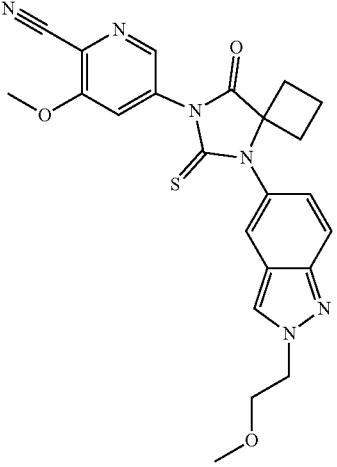 [SMILES: COCCn1cc2cc(N3C(=S)N(c4cnc(C#N)c(OC)c4)C(=O)C34CCC4)ccc2n1] | 3-methoxy-5-[8-[2-(2-methoxyethyl)indazol-5-yl]-5-oxo-7-thioxo-6,8-diazaspiro[3.4]octan-6-yl]pyridine-2-carbonitrile.<br>$^1$H NMR (300 MHz, DMSO-$d_6$) δ 1.42-1.68 (m, 1H), 1.97 (m, 1H), 2.41-2.58 (m, 2H), 2.59-2.70 (m, 2H), 3.26 (s, 3H), 3.86 (t, J = 5.1 Hz, 2H), 4.00 (s, 3H), 4.65 (t, J = 5.1 Hz, 2H), 7.19 (dd, J = 9.1, 2.0 Hz, 1H), 7.69-7.92 (m, 2H), 8.07 (d, J = 1.9 Hz, 1H), 8.48 (s, 1H), 8.53 (s, 1H).<br>$C_{23}H_{22}N_6O_3S$ MS m/z 463 (M + H)$^+$ |

| Cpd No. | Structure | Compound Name & Physical Data |
|---|---|---|
| 174 | 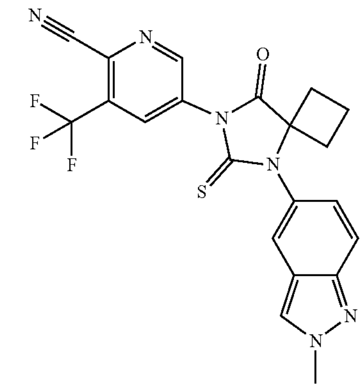 [SMILES: Cn1cc2cc(N3C(=S)N(c4cnc(C#N)c(C(F)(F)F)c4)C(=O)C34CCC4)ccc2n1] | 5-[8-(2-methylindazol-5-yl)-5-oxo-7-thioxo-6,8-diazaspiro[3.4]octan-6-yl]-3-(trifluoromethyl)pyridine-2-carbonitrile.<br>$^1$H NMR (300 MHz, Chloroform-d) δ 1.60-1.75 (m, 1H), 2.10-2.38 (m, 1H), 2.60-2.76 (m, 2H), 4.29 (s, 3H), 7.13 (dd, J = 9.0, 2.0 Hz, 1H), 7.65 (d, J = 2.0 Hz, 1H), 7.89 (d, J = 9.0 Hz, 1H), 8.06 (s, 1H), 8.40 (s, 1H).<br>$C_{21}H_{15}F_3N_6OS$ MS m/z 457 (M + H)$^+$ |
| 173 | 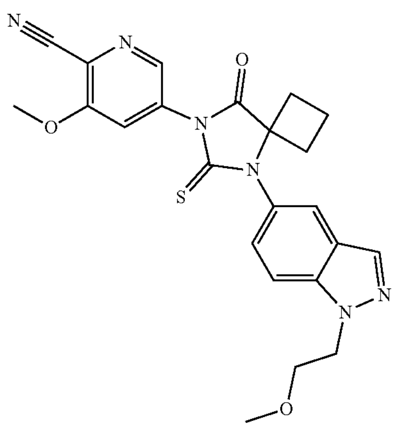 [SMILES: COCCn1ncc2cc(N3C(=S)N(c4cnc(C#N)c(OC)c4)C(=O)C34CCC4)ccc21] | 3-methoxy-5-[8-[1-(2-methoxyethyl)indazol-5-yl]-5-oxo-7-thioxo-6,8-diazaspiro[3.4]octan-6-yl]pyridine-2-carbonitrile.<br>$^1$H NMR (300 MHz, DMSO-d$_6$) δ 1.42-1.62 (m, 1H), 1.87-2.10 (m, 1H), 2.40-2.57 (m, 2H), 2.58-2.72 (m, 2H), 3.24 (s, 3H), 3.82 (t, J = 5.2 Hz, 2H), 4.00 (s, 3H), 4.63 (t, J = 5.2 Hz, 2H), 7.36 (dd, J = 9.0, 1.9 Hz, 1H), 7.75-7.97 (m, 2H), 8.07 (d, J = 1.9 Hz, 1H), 8.23 (s, 1H), 8.48 (d, J = 1.8 Hz, 1H).<br>$C_{23}H_{22}N_6O_3S$ MS m/z 463 (M + H)$^+$ |
| 172 | 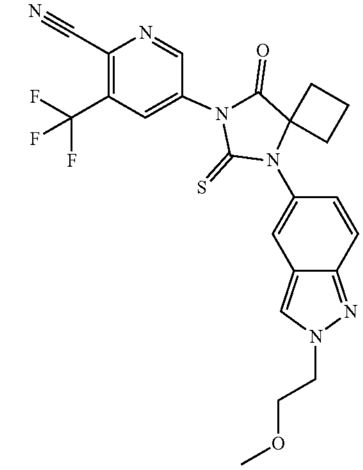 [SMILES: COCCn1cc2cc(N3C(=S)N(c4cnc(C#N)c(C(F)(F)F)c4)C(=O)C34CCC4)ccc2n1] | 5-[8-[2-(2-methoxyethyl)indazol-5-yl]-5-oxo-7-thioxo-6,8-diazaspiro[3.4]octan-6-yl]-3-(trifluoromethyl)pyridine-2-carbonitrile.<br>$^1$H NMR (300 MHz, DMSO-d$_6$) δ 1.41-1.68 (m, 1H), 1.87-2.05 (m, 1H), 2.44-2.57 (m, 2H), 2.60-2.68 (m, 1H), 3.26 (s, 4H), 3.86 (t, J = 5.1 Hz, 2H), 4.65 (t, J = 5.1 Hz, 2H), 7.18 (dd, J = 9.1, 2.0 Hz, 1H), 7.66-7.96 (m, 2H), 8.54 (s, 1H), 8.79 (d, J = 2.1 Hz, 1H), 9.25 (d, J = 2.1 Hz, 1H).<br>$C_{23}H_{19}F_3N_6O_2S$ MS m/z 501 (M + H)$^+$ |

| Cpd No. | Structure | Compound Name & Physical Data |
|---|---|---|
| 171 | 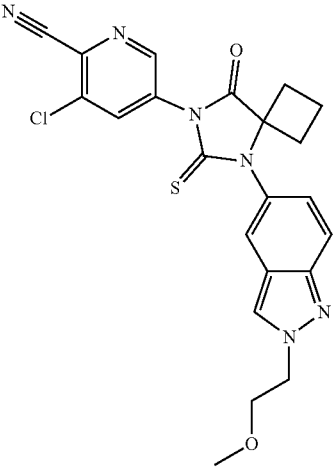 [SMILES: COCCn1cc2cc(N3C(=S)N(c4cnc(C#N)c(Cl)c4)C(=O)C34CCC4)ccc2n1] | 3-chloro-5-[8-[1-(2-methoxyethyl)indazol-5-yl]-5-oxo-7-thioxo-6,8-diazaspiro[3.4]octan-6-yl]pyridine-2-carbonitrile.<br>$^1$H NMR (300 MHz, DMSO-$d_6$) δ 1.44-1.60 (m, 1H), 1.88-2.05 (m, 1H), 2.41-2.56 (m, 2H), 2.58-2.72 (m, 2H), 3.24 (s, 3H), 3.82 (t, J = 5.2 Hz, 2H), 4.63 (t, J = 5.2 Hz, 2H), 7.35 (dd, J = 8.8, 1.9 Hz, 1H), 7.83 (d, J = 1.9 Hz, 1H), 7.88 (d, J = 8.9 Hz, 1H), 8.23 (s, 1H), 8.57 (d, J = 2.0 Hz, 1H), 8.93 (d, J = 2.0 Hz, 1H).<br>$C_{22}H_{19}ClN_6O_2S$ MS m/z 467 (M + H)$^+$ |
| 170 | 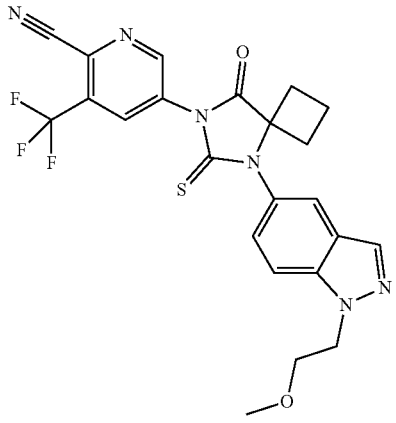 [SMILES: COCCn1ncc2cc(N3C(=S)N(c4cnc(C#N)c(C(F)(F)F)c4)C(=O)C34CCC4)ccc21] | 5-[8-[1-(2-methoxyethyl)indazol-5-yl]-5-oxo-7-thioxo-6,8-diazaspiro[3.4]octan-6-yl]-3-(trifluoromethyl)pyridine-2-carbonitrile.<br>$^1$H NMR (300 MHz, DMSO-$d_6$) δ 1.44-1.62 (m, 1H), 1.90-2.05 (m, 1H), 2.42-2.57 (m, 2H),, 2.60-2.72 (m, 2H), 3.24 (s, 3H), 3.82 (t, J = 5.2 Hz, 2H), 4.63 (t, J = 5.2 Hz, 2H), 7.35 (dd, J = 8.8, 1.9 Hz, 1H), 7.84 (d, J = 1.9 Hz, 1H), 7.89 (d, J = 8.9 Hz, 1H), 8.24 (s, 1H), 8.79 (d, J = 2.1 Hz, 1H), 9.25 (d, J = 2.1 Hz, 1H).<br>$C_{23}H_{19}F_3N_6O_2S$ MS m/z 501 (M + H)$^+$ |
| 169 | 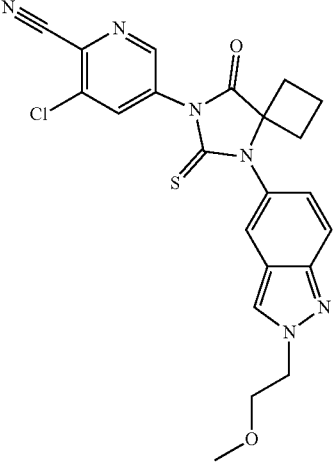 [SMILES: COCCn1cc2cc(N3C(=S)N(c4cnc(C#N)c(Cl)c4)C(=O)C34CCC4)ccc2n1] | 3-chloro-5-[8-[2-(2-methoxyethyl)indazol-5-yl]-5-oxo-7-thioxo-6,8-diazaspiro[3.4]octan-6-yl]pyridine-2-carbonitrile.<br>$^1$H NMR (300 MHz, DMSO-$d_6$) δ 1.43-1.69 (m, 1H), 1.91-2.05 (m, 1H), 2.44-2.58 (m, 2H), 2.58-2.68 (m, 2H), 3.26 (s, 3H), 3.86 (t, J = 5.1 Hz, 2H), 4.65 (t, J = 5.1 Hz, 2H), 7.17 (dd, J = 9.0, 2.0 Hz, 1H), 7.64-7.91 (m, 2H), 8.46-8.67 (m, 2H), 8.93 (d, J = 2.0 Hz, 1H).<br>$C_{22}H_{19}ClN_6O_2S$ MS m/z 467 (M + H)$^+$ |

| Cpd No. | Structure | Compound Name & Physical Data |
|---|---|---|
| 168 | 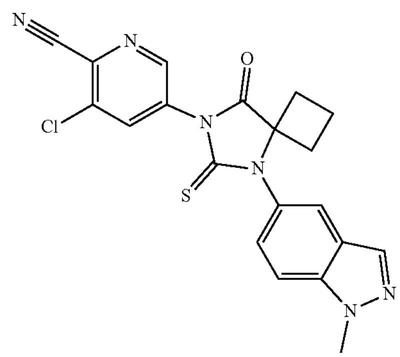 [SMILES: Cn1ncc2cc(N3C(=S)N(c4cnc(C#N)c(Cl)c4)C(=O)C34CCC4)ccc21] | 3-chloro-5-[8-(1-methylindazol-5-yl)-5-oxo-7-thioxo-6,8-diazaspiro[3.4]octan-6-yl]pyridine-2-carbonitrile.<br>$^1$H NMR (300 MHz, Chloroform-d) δ 1.59-1.71 (m, 1H), 2.13-2.35 (m, 1H), 2.53-2.77 (m, 4H), 4.16 (s, 3H), 7.28 (dd, J = 8.8 Hz, 2H), 7.61 (d, J = 8.8, 1.9 Hz, 1H), 7.70 (d, J = 1 9 Hz, 1H), 8.10 (s, 1H), 8.14 (d, J = 2.1 Hz, 1H), 8.83 (d, J = 2.1 Hz, 1H).<br>$C_{20}H_{15}ClN_6OS$ MS m/z 423 (M + H)$^+$ |
| 167 | 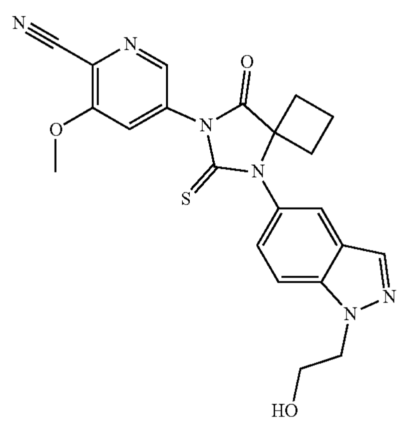 [SMILES: COc1cc(N2C(=O)C3(CCC3)N(c3ccc4c(cnn4CCO)c3)C2=S)cnc1C#N] | 5-[8-[1-(2-hydroxyethyl)indazol-5-yl]-5-oxo-7-thioxo-6,8-diazaspiro[3.4]octan-6-yl]-3-methoxy-pyridine-2-carbonitrile.<br>$^1$H NMR (300 MHz, DMSO-d$_6$) δ 1.42-1.62 (m, 1H), 1.90-2.05 (m, 1H), 2.40-2.57 (m, 2H), 2.58-2.70 (m, 2H), 3.86 (dt, J = 5.4, 5.3 Hz, 2H), 4.00 (s, 3H), 4.51 (t, J = 5.4 Hz, 2H), 4.95 (t, J = 5.3 Hz, 1H), 7.35 (dd, J = 8.8, 1.9 Hz, 1H), 7.74-7.95 (m, 2H), 8.07 (d, J = 1.9 Hz, 1H), 8.22 (s, 1H), 8.48 (d, J = 1.8 Hz, 1H).<br>$C_{22}H_{20}N_6O_3S$ MS m/z 449 (M + H)$^+$ |
| 164 | 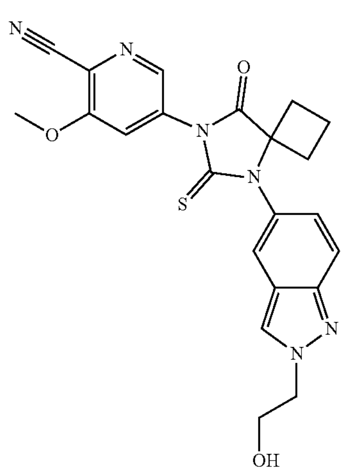 [SMILES: COc1cc(N2C(=O)C3(CCC3)N(c3ccc4nn(CCO)cc4c3)C2=S)cnc1C#N] | 5-[8-[2-(2-hydroxyethyl)indazol-5-yl]-5-oxo-7-thioxo-6,8-diazaspiro[3.4]octan-6-yl]-3-methoxy-pyridine-2-carbonitrile.<br>$^1$H NMR (300 MHz, DMSO-d$_6$) δ 1.42-1.62 (m, 1H), 1.87-2.07 (m, 1H), 2.41-2.57 (m, 2H), 2.58-2.71 (m, 2H), 3.91 (t, J = 5.3 Hz, 2H), 4.00 (s, 3H), 4.51 (t, J = 5.3 Hz, 2H), 5.03 (br s, 1H), 7.18 (dd, J = 9.2, 2.0 Hz, 1H), 7.78 (d, J = 9.1 Hz, 1H), 7.82 (s, 1H), 8.07 (d, J = 1.9 Hz, 1H), 8.48 (s, 1H), 8.52 (s, 1H).<br>$C_{22}H_{20}N_6O_3S$ MS m/z 449 (M + H)$^+$ |

| Cpd No. | Structure | Compound Name & Physical Data |
|---|---|---|
| 163 | 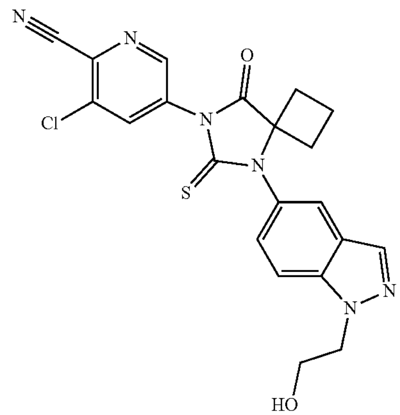 [SMILES: N#Cc1ncc(N2C(=O)C3(CCC3)N(c3ccc4c(cnn4CCO)c3)C2=S)cc1Cl] | 3-chloro-5-[8-[1-(2-hydroxyethyl)indazol-5-yl]-5-oxo-7-thioxo-6,8-diazaspiro[3.4]octan-6-yl]pyridine-2-carbonitrile.<br>$^1$H NMR (300 MHz, DMSO-d$_6$) δ 1.43-1.62 (m, 1H), 1.85-2.15 (m, 1H), 2.40-2.57 (m, 2H), 2.58-2.72 (m, 2H), 3.86 (t, J = 5.3 Hz, 2H), 4.51 (t, J = 5.3 Hz, 2H), 4.95 (br s, 1H), 7.34 (d, J = 9.0 Hz, 1H), 7.70-8.00 (m, 2H), 8.22 (s, 1H), 8.57 (d, J = 2.1 Hz, 1H), 8.93 (d, J = 2.1 Hz, 1H).<br>C$_{21}$H$_{17}$ClN$_6$O$_2$S MS m/z 453 (M + H)$^+$ |
| 162 | 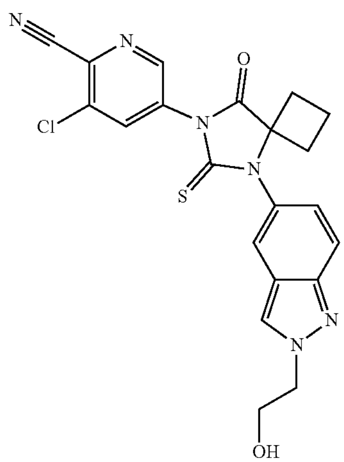 [SMILES: N#Cc1ncc(N2C(=O)C3(CCC3)N(c3ccc4nn(CCO)cc4c3)C2=S)cc1Cl] | 3-chloro-5-[8-[2-(2-hydroxyethyl)indazol-5-yl]-5-oxo-7-thioxo-6,8-diazaspiro[3.4]octan-6-yl]pyridine-2-carbonitrile.<br>$^1$H NMR (300 MHz, DMSO-d$_6$) δ 1.45-1.62 (m, 1H), 1.87-2.07 (m, 1H), 2.43-2.57 (m, 2H), 2.58-2.70 (m, 2H), 3.90 (m, 2H), 4.51 (m, 2H), 5.02 (br s, 1H), 7.17 (dd, J = 9.0, 2.1 Hz, 1H), 7.67-7.95 (m, 2H), 8.52 (s, 1H), 8.56 (d, J = 2.1 Hz, 1H), 8.93 (d, J = 2.1 Hz, 1H).<br>C$_{21}$H$_{17}$ClN$_6$O$_2$S MS m/z 453 (M + H)$^+$ |
| 161 | 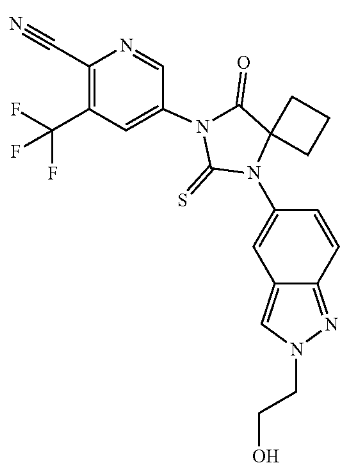 [SMILES: N#Cc1ncc(N2C(=O)C3(CCC3)N(c3ccc4nn(CCO)cc4c3)C2=S)cc1C(F)(F)F] | 5-[8-[2-(2-hydroxyethyl)indazol-5-yl]-5-oxo-7-thioxo-6,8-diazaspiro[3.4]octan-6-yl]-3-(trifluoromethyl)pyridine-2-carbonitrile.<br>$^1$H NMR (300 MHz, DMSO-d$_6$) δ 1.45-1.65 (m, 1H), 1.90-2.05 (m, 1H), 2.42-2.59 (m, 2H), 2.59-2.72 (m, 2H), 3.90 (t, J = 5.4 Hz, 2H), 4.52 (t, J = 5.3 Hz, 2H), 5.03 (br s, 1H), 7.17 (dd, J = 9.0, 2.0 Hz, 1H), 7.67-7.96 (m, 2H), 8.53 (s, 1H), 8.79 (d, J = 2.1 Hz, 1H), 9.25 (d, J = 2.1 Hz, 1H).<br>C$_{22}$H$_{17}$F$_3$N$_6$O$_2$S MS m/z 487 (M + H)$^+$ |

| Cpd No. | Structure | Compound Name & Physical Data |
|---|---|---|
| 160 | 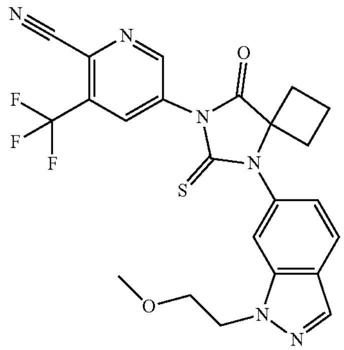 [SMILES: COCCn1ncc2ccc(N3C(=S)N(c4cnc(C#N)c(C(F)(F)F)c4)C(=O)C34CCC4)cc21] | 5-[8-[1-(2-methoxyethyl)indazol-6-yl]-5-oxo-7-thioxo-6,8-diazaspiro[3.4]octan-6-yl]-3-(trifluoromethyl)pyridine-2-carbonitrile.<br>$^1$H NMR (300 MHz, Chloroform-d) δ 1.58-1.75 (m, 1H), 2.12-2.37 (m, 1H), 2.54-2.86 (m, 4H), 3.27 (s, 3H), 3.82 (t, J = 5.0 Hz, 2H), 4.61 (t, J = 5.0 Hz, 2H), 7.04 (d, J = 8.4 Hz, 1H), 7.55 (s, 1H), 7.91 (d, J = 8.4 Hz, 1H), 8.12 (s, 1H), 8.40 (d, J = 2.3 Hz, 1H), 9.13 (d, J = 2.3 Hz, 1H).<br>$C_{23}H_{19}F_3N_6O_2S$ MS m/z 501 (M + H)$^+$ |
| 159 | 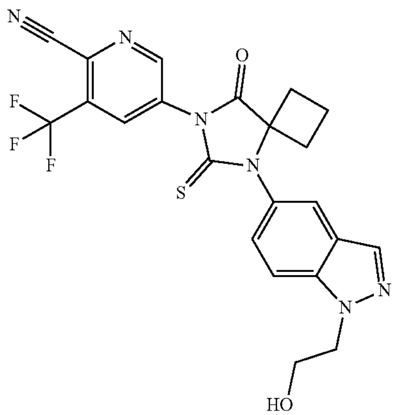 [SMILES: N#Cc1ncc(N2C(=O)C3(CCC3)N(c3ccc4c(cnn4CCO)c3)C2=S)cc1C(F)(F)F] | 5-[8-[1-(2-hydroxyethyl)indazol-5-yl]-5-oxo-7-thioxo-6,8-diazaspiro[3.4]octan-6-yl]-3-(trifluoromethyl)pyridine-2-carbonitrile.<br>$^1$H NMR (300 MHz, DMSO-d$_6$) δ 1.40-1.67 (m, 1H), 1.86-2.15 (m, 1H), 2.38-2.58 (m, 2H), 2.58-2.77 (m, 2H), 3.86 (t, J = 5.5 Hz, 2H), 4.51 (t, J = 5.4 Hz, 2H), 4.96 (t, J = 5.2 Hz, 1H), 7.34 (dd, J = 8.8, 2.0 Hz, 1H), 7.83 (d, J = 1.9 Hz, 1H), 7.87 (d, J = 8.9 Hz, 1H), 8.23 (s, 1H), 8.79 (d, J = 2.2 Hz, 1H), 9.25 (d, J = 2.1 Hz, 1H).<br>$C_{22}H_{17}F_3N_6O_2S$ MS m/z 487 (M + H)$^+$ |
| 155 | 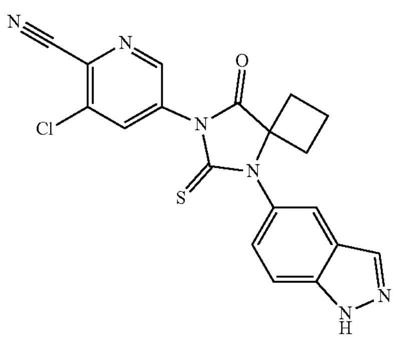 [SMILES: N#Cc1ncc(N2C(=O)C3(CCC3)N(c3ccc4[nH]ncc4c3)C2=S)cc1Cl] | 3-chloro-5-[8-(1H-indazol-5-yl)-5-oxo-7-thioxo-6,8-diazaspiro[3.4]octan-6-yl]pyridine-2-carbonitrile.<br>$^1$H NMR (300 MHz, DMSO-d$_6$) δ 1.40-1.58 (m, 1H), 1.82-2.07 (m, 1H), 2.38-2.56 (m, 2H), 2.57-2.70 (m, 2H), 7.32 (dd, J = 8.7, 2.0 Hz, 1H), 7.75 (d, J = 8.8 Hz, 1H), 7.85 (d, J = 1.9 Hz, 1H), 8.23 (s, 1H), 8.57 (d, J = 2.0 Hz, 1H), 8.93 (d, J = 2.0 Hz, 1H).<br>$C_{19}H_{13}ClN_6OS$ MS m/z 409 (M + H)$^+$ |
| 121 | 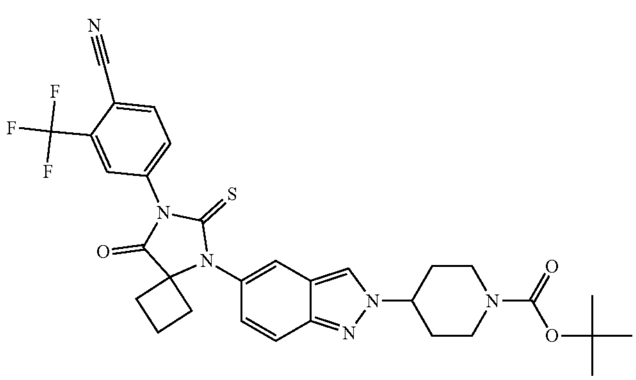 | tert-butyl 4-[5-[6-[6-cyano-5-(trifluoromethyl)-3-pyridyl]-5-oxo-7-thioxo-6,8-diazaspiro[3.4]octan-8-yl]indazol-2-yl]piperidine-1-carboxylate.<br>$^1$H NMR (300 MHz, Chloroform-d) δ 1.50 (s, 9H), 1.57-1.75 (m, 1H), 1.99-2.37 (m, 5H), 2.53-2.79 (m, 4H), 2.85-3.13 (m, 2H), 4.26-4.44 (m, 2H), 4.53-4.70 (m, 1H), 7.13 (dd, J = 9.1, 2.0 Hz, 1H), 7.67 (d, J = 1.9 Hz, 1H), 7.90 (d, J = 9.1 Hz, 1H), 8.11 (s, 1H), 8.39 (d, J = 2.2 Hz, 1H), 9.13 (d, J = 2.2 Hz, 1H).<br>$C_{30}H_{30}F_3N_7O_3S$ MS m/z 569.9 (M + H)$^+$ |

| Cpd No. | Structure | Compound Name & Physical Data |
|---|---|---|
| 115 | 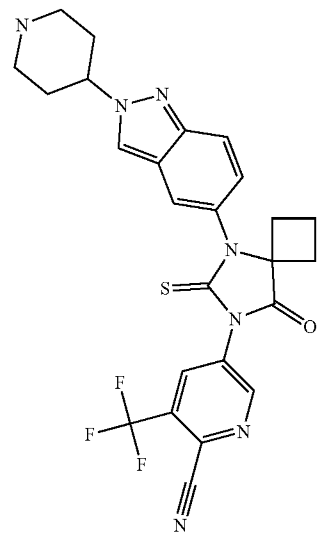 [SMILES: N#Cc1ncc(N2C(=O)C3(CCC3)N(c3ccc4nn(C5CCNCC5)cc4c3)C2=S)cc1C(F)(F)F] | 5-[5-oxo-8-[2-(4-piperidyl)indazol-5-yl]-7-thioxo-6,8-diazaspiro[3.4]octan-6-yl]-3-(trifluoromethyl)pyridine-2-carbonitrile.<br>$^1$H NMR (300 MHz, Chloroform-d) δ 1.56-1.78 (m, 1H), 2.04-2.45 (m, 5H), 2.57-2.80 (m, 4H), 2.83-3.02 (m, 2H), 3.41 (d, J = 12.9 Hz, 2H), 4.55-4.73 (m, 1H), 7.13 (dd, J = 9.0, 1.9 Hz, 1H), 7.67 (d, J = 1.9 Hz, 1H), 7.90 (d, J = 9.1 Hz, 1H), 8.14 (s, 1H), 8.40 (d, J = 2.2 Hz, 1H), 9.13 (d, J = 2.2 Hz, 1H).<br>$C_{25}H_{22}F_3N_7OS$ MS m/z 526.0 (M + H)$^+$ |
| 119 | 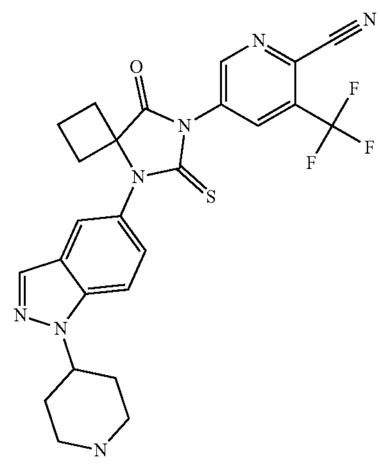 [SMILES: N#Cc1ncc(N2C(=O)C3(CCC3)N(c3ccc4c(cnn4C4CCNCC4)c3)C2=S)cc1C(F)(F)F] | 5-[5-oxo-8-[1-(4-piperidyl)indazol-5-yl]-7-thioxo-6,8-diazaspiro[3.4]octan-6-yl]-3-(trifluoromethyl)pyridine-2-carbonitrile.<br>$^1$H NMR (300 MHz, Chloroform-d) δ 1.58-1.76 (m, 1H), 2.09-2.46 (m, 5H), 2.54-2.80 (m, 4H), 2.88-3.06 (m, 2H), 3.43 (d, J = 12.9 Hz, 2H), 4.52-4.80 (m, 1H), 7.23-7.32 (m, 1H), 7.65-7.75 (m, 2H), 8.13 (s, 1H), 8.39 (d, J = 2 2 Hz, 1H), 9.13 (d, J = 2.2 Hz, 1H).<br>$C_{25}H_{22}F_3N_7OS$ MS m/z 526.0 (M + H)$^+$ |
| 131 | 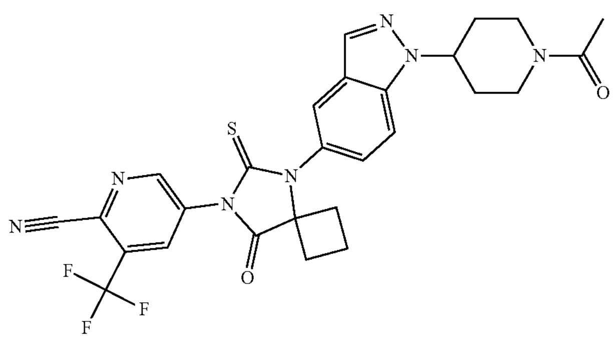 [SMILES: CC(=O)N1CCC(n2ncc3cc(N4C(=S)N(c5cnc(C#N)c(C(F)(F)F)c5)C(=O)C45CCC5)ccc32)CC1] | 5-[8-[1-(1-acetyl-4-piperidyl)indazol-5-yl]-5-oxo-7-thioxo-6,8-diazaspiro[3.4]octan-6-yl]-3-(trifluoromethyl)pyridine-2-carbonitrile.<br>$^1$H NMR (300 MHz, Chloroform-d) δ 1.48-1.84 (m, 4H), 2.06-2.48 (m, 6H), 2.55-2.80 (m, 4H), 2.90 (t, J = 12.6 Hz, 1H), 3.35 (t, J = 12.6 Hz, 1H), 4.08 (d, J = 14.0 Hz, 1H), 4.59-4.93 (m, 1H), 7.26-7.32 (m, 1H), 7.65 (d, J = 8.9 Hz, 1H), 7.72 (d, J = 1.9 Hz, 1H), 8.13 (s, 1H), 8.39 (d, J = 2.2 Hz, 1H), 9.13 (d, J = 2.2 Hz, 1H).<br>$C_{27}H_{24}F_3N_7O_2S$ MS m/z 568.2 (M + H)$^+$ |

| Cpd No. | Structure | Compound Name & Physical Data |
|---|---|---|
| 109 | 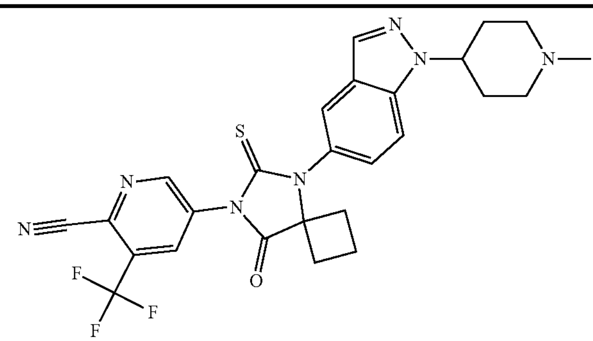 | 5-[8-[1-(1-methyl-4-piperidyl)indazol-5-yl]-5-oxo-7-thioxo-6,8-diazaspiro[3.4]octan-6-yl]-3-(trifluoromethyl)pyridine-2-carbonitrile. <br> $^1$H NMR (300 MHz, Chloroform-d) δ 1.54-1.73 (m, 1H), 2.03-2.14 (m, 2H), 2.17-2.29 (m, 3H), 2.39 (s, 3H), 2.41-2.51 (m, 2H), 2.56-2.80 (m, 4H), 3.08 (d, J = 11.6 Hz, 2H), 4.35-4.65 (m, 1H), 7.22-7.27 (m, 1H), 7.62-7.73 (m, 2H), 8.11 (s, 1H), 8.39 (d, J = 2 2 Hz, 1H), 9.13 (d, J = 2.2 Hz, 1H). <br> $C_{26}H_{24}F_3N_7OS$ MS m/z 540.0 $(M + H)^+$ |

Example 17

4-[6-[6-cyano-5-(trifluoromethyl)-3-pyridyl]-5-oxo-7-thioxo-6,8-diazaspiro[3.4]octan-8-yl]-2-fluoro-N-(4-piperidylmethyl)benzamide, Cpd 221

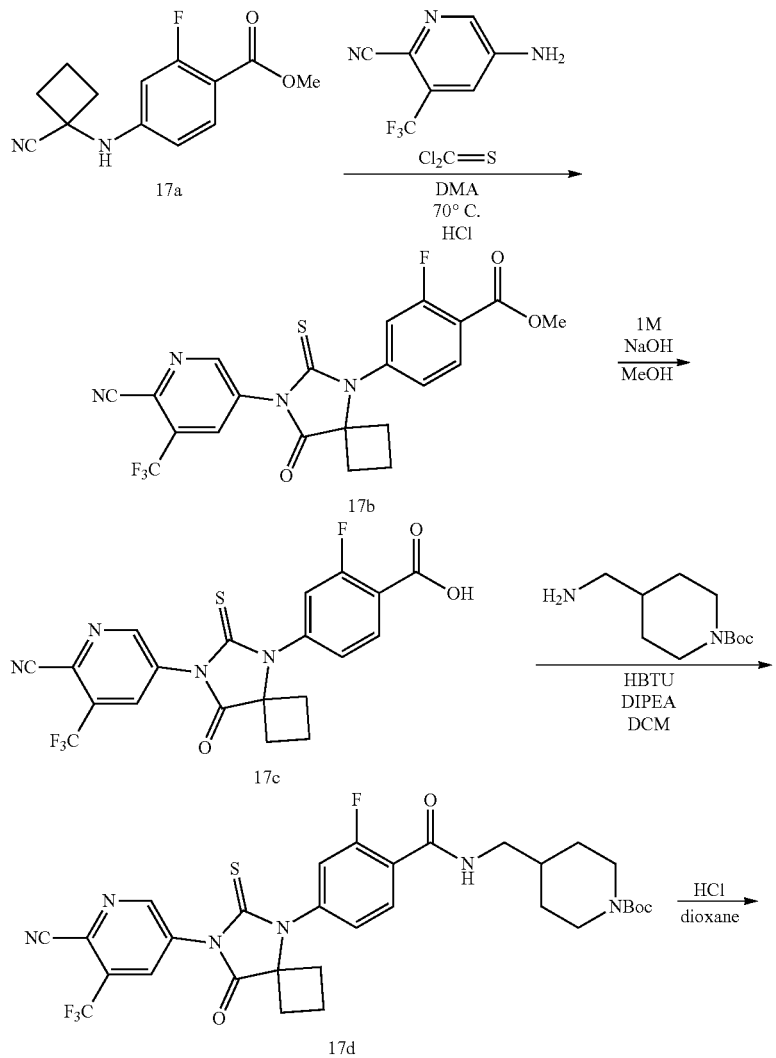

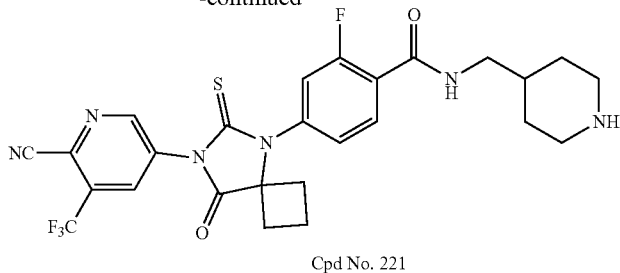

Cpd No. 221

A. Methyl 4-(7-(6-cyano-5-(trifluoromethyl)pyridin-3-yl)-8-oxo-6-thioxo-5,7-diazaspiro[3.4]octan-5-yl)-2-fluorobenzoate, 17b

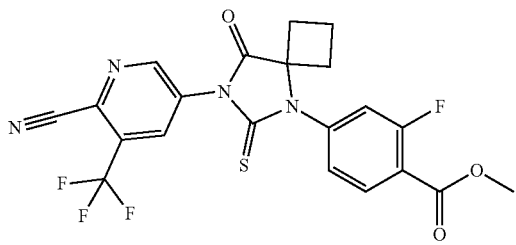 [SMILES: COC(=O)c1ccc(N2C(=S)N(c3cnc(C#N)c(C(F)(F)F)c3)C(=O)C23CCC3)cc1F]

4-(1-Cyano-cyclobutylamino)-2-fluoro-benzoic acid methyl ester (2.0 g, 8.05 mmol) and 5-Amino-3-trifluoromethyl-pyridine-2-carbonitrile (1.96 g, 10.5 mmol) were mixed in DMA (35 mL). Thiophosgene (0.92 mL, 12.1 mmol) was added via syringe. The resulting solution was stirred at 70° C. overnight and then allowed to cool to room temperature. The mixture was diluted with MeOH (8.0 mL) and 1M HCl (8.0 mL) was added. The stirring was maintained for 2 h. EA (100 mL) was added and the solution was washed with 1M Na$_2$CO$_3$ (100 mL) and brine (50 mL). The organic layer was dried over MgSO$_4$, filtered and concentrated to dryness. The crude material was purified by chromatography over silica gel (gradient of EA in heptane from 0 to 35%) to yield the desired product. Triturating in diethyl ether (20 mL) afforded 4-[7-(6-Cyano-5-trifluoromethyl-pyridin-3-yl)-8-oxo-6-thioxo-5,7-diaza-spiro[3.4]oct-5-yl]-2-fluoro-benzoic acid methyl ester as a white solid (1.49 g, 39%). $^1$H NMR (300 MHz, Chloroform-d) δ 1.64-1.85 (m, 1H), 2.16-2.38 (m, 1H), 2.48-2.66 (m, 2H), 2.66-2.83 (m, 2H), 3.99 (s, 3H), 7.14-7.25 (m, 2H), 8.18 (t, J=8.0 Hz, 1H), 8.35 (d, J=2.2 Hz, 1H), 9.09 (d, J=2.2 Hz, 1H). C$_{21}$H$_{14}$F$_4$N$_4$O$_3$S MS m/z 479 (M+H)$^+$.

B. 4-[7-(6-Cyano-5-trifluoromethyl-pyridin-3-yl)-8-oxo-6-thioxo-5,7-diaza-spiro[3.4]oct-5-yl]-2-fluoro-benzoic Acid, 17c

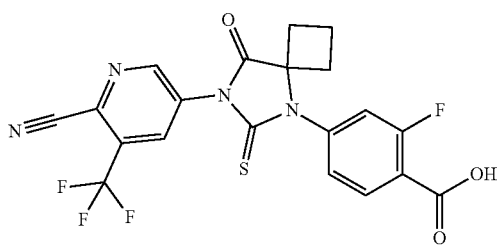 [SMILES: N#Cc1ncc(N2C(=O)C3(CCC3)N(c3ccc(C(=O)O)c(F)c3)C2=S)cc1C(F)(F)F]

4-[7-(6-Cyano-5-trifluoromethyl-pyridin-3-yl)-8-oxo-6-thioxo-5,7-diaza-spiro[3.4]oct-5-yl]-2-fluoro-benzoic acid methyl ester (1.49 g, 3.11 mmol) was taken in MeOH (15 mL). 1M NaOH (15 mL, 15.0 mmol) was added at room temperature. The pH of the reaction mixture was brought to 2-3 by addition of 1M HCl (ca. 48 mL). A resulting precipitate was collected by filtration and washed with water (50 mL). 4-[7-(6-Cyano-5-trifluoromethyl-pyridin-3-yl)-8-oxo-6-thioxo-5,7-diaza-spiro[3.4]oct-5-yl]-2-fluoro-benzoic acid was collected as a solid and dried under high vacuum (2.93 g, 94%). $^1$H NMR (300 MHz, DMSO-d$_6$) δ 1.48-1.74 (m, 1H), 1.85-2.11 (m, 1H), 2.38-2.58 (m, 2H), 2.59-2.74 (m, 2H), 7.41 (dd, J=8.3, 1.9 Hz, 1H), 7.49 (dd, J=10.9, 1.9 Hz, 1H), 8.10 (t, J=8.2 Hz, 1H), 8.75 (d, J=2.1 Hz, 1H), 9.21 (d, J=2.0 Hz, 1H), 13.56 (br s, 1H). C$_{20}$H$_{12}$F$_4$N$_4$O$_3$S MS m/z 465 (M+H)$^+$.

C. 4-({4-[7-(6-Cyano-5-trifluoromethyl-pyridin-3-yl)-8-oxo-6-thioxo-5,7-diaza-spiro[3.4]oct-5-yl]-2-fluoro-benzoylamino}-methyl)-piperidine-1-carboxylic Acid Tert-Butyl Ester, 17d

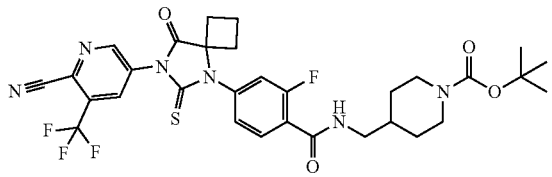 [SMILES: CC(C)(C)OC(=O)N1CCC(CNC(=O)c2ccc(N3C(=S)N(c4cnc(C#N)c(C(F)(F)F)c4)C(=O)C34CCC4)cc2F)CC1]

O-(benzotriazol-1-yl)-N,N,N'-N'-tetramethyluronium hexafluorophosphate (HBTU), (0.306 g, 0.808 mmol) was added at room temperature to a stirred solution of 4-[7-(6-Cyano-5-trifluoromethyl-pyridin-3-yl)-8-oxo-6-thioxo-5,7-diaza-spiro[3.4]oct-5-yl]-2-fluoro-benzoic acid (0.25 g, 0.538 mmol), 4-Aminomethyl-piperidine-1-carboxylic acid tert-butyl ester (0.138 g, 0.646 mmol) and Diisopropylethylamine (0.275 mL, 1.615 mmol) in DCM (12 mL). The reaction was continued for 1 h and then concentrated under reduced pressure. The residue was taken in EA (40 mL) and washed with 1M Na$_2$CO$_3$ (25 mL). The organic layer was dried over MgSO$_4$, filtered and concentrated to dryness. The crude material was purified by flash column chromatography over silica gel (gradient of EA in heptanes from 0 to 60%) to give a white solid (0.251 g, 70%). $^1$H NMR (300 MHz, Chloroform-d) δ 1.17-1.31 (m, 3H), 1.46 (s, 9H), 1.65-1.91 (m, 5H), 2.18-2.40 (m, 1H), 2.46-2.64 (m, 2H), 2.64-2.78 (m, 4H), 3.35-3.54 (m, 2H), 6.79 (dt, J=11.9, 5.9 Hz, 1H), 7.18 (dd, J=11.5, 1.9 Hz, 1H), 7.28 (d, J=9.3 Hz, 1H), 8.31 (d, J=8.4 Hz, 1H), 8.35 (d, J=2.0 Hz, 1H), 9.09 (d, J=2.2 Hz, 1H). C31H$_{32}$F$_4$N$_6$O$_4$S MS m/z 561 (M+H-Boc)$^+$.

D. 4-[6-[6-cyano-5-(trifluoromethyl)-3-pyridyl]-5-oxo-7-thioxo-6,8-diazaspiro[3.4]octan-8-yl]-2-fluoro-N-(4-piperidylmethyl)benzamide, Cpd 221

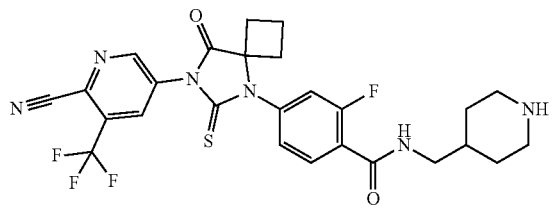 [SMILES: N#Cc1ncc(N2C(=O)C3(CCC3)N(c3ccc(C(=O)NCC4CCNCC4)c(F)c3)C2=S)cc1C(F)(F)F]

The previous intermediate (0.211 g, 0.291 mmol) was taken in dioxane (5 mL) and treated with 4N HCl in dioxane (1.45 mL, 5.81 mmol) with stirring. After 16 h, the reaction mixture was concentrated to a gummy residue. Preparative LC (gradient of ACN in 25 mM aqueous $NH_4HCO_3$ from 19 to 55%) gave, upon removal of solvent, the pure product as a white solid (0.112 g, 65%). $^1$H NMR (300 MHz, DMSO-$d_6$) δ 1.13-1.30 (m, 2H), 1.49-1.65 (m, 1H), 1.65-1.81 (m, 3H), 1.91-2.07 (m, 1H), 2.39-2.56 (m, 2H), 2.55-2.75 (m, 4H), 3.10 (d, J=12.3 Hz, 2H), 3.17 (t, J=6.1 Hz, 2H), 7.38 (dd, J=8.1, 2.0 Hz, 1H), 7.46 (dd, J=10.3, 1.9 Hz, 1H), 7.80 (t, J=8.0 Hz, 1H), 8.60 (t, J=6.1 Hz, 1H), 8.75 (d, J=2.1 Hz, 1H), 9.21 (d, J=2.1 Hz, 1H). $C_{26}H_{24}F_4N_6O_2S$ MS m/z 561 $(M+H)^+$.

Following the procedure described in Example 17, above, selecting and substituting the appropriate reagents, starting materials, and purification methods, and adjusting reaction temperatures, times and other variables or parameters, as needed or desirable, as would be readily recognized by those skilled in the art, the following compounds of formula (I) of the invention were prepared.

| Cpd No. | Structure | Compound Name & Physical Data |
|---|---|---|
| 201 | 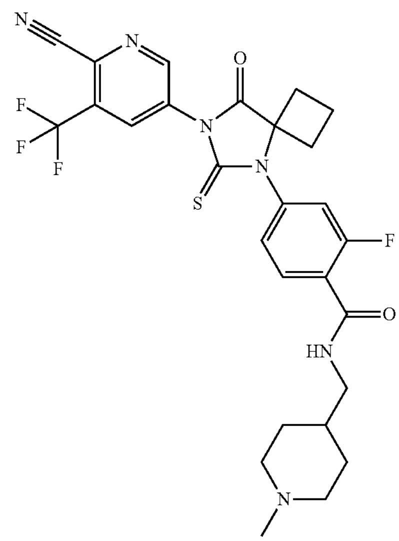 [SMILES: CN1CCC(CNC(=O)c2ccc(N3C(=S)N(c4cnc(C#N)c(C(F)(F)F)c4)C(=O)C34CCC4)cc2F)CC1] | 4-[6-[6-cyano-5-(trifluoromethyl)-3-pyridyl]-5-oxo-7-thioxo-6,8-diazaspiro[3.4]octan-8-yl]-2-fluoro-N-[(1-methyl-4-piperidyl)methyl]benzamide. $^1$H NMR (300 MHz, Chloroform-d) δ 1.31-1.51 (m, 2H), 1.57-1.69 (m, 1H), 1.72-1.82 (m, 3H), 1.89-2.03 (m, 3H), 2.19-2.37 (m, 1H), 2.28 (s, 3H), 2.47-2.65 (m, 2H), 2.66-2.81 (m, 2H), 2.83-2.97 (m, 2H), 3.43 (t, J = 6.2 Hz, 2H), 6.63-6.88 (m, 1H), 7.17 (dd, J = 11.5, 2.0 Hz, 1H), 7.27 (d, J = 8.3 Hz, 1H), 8.30 (d, J = 8.3 Hz, 1H), 8.35 (d, J = 2.2 Hz, 1H), 9.09 (d, J = 2.2 Hz, 1H). $C_{27}H_{26}F_4N_6O_2S$ MS m/z 575 $(M + H)^+$ |
| 218 | 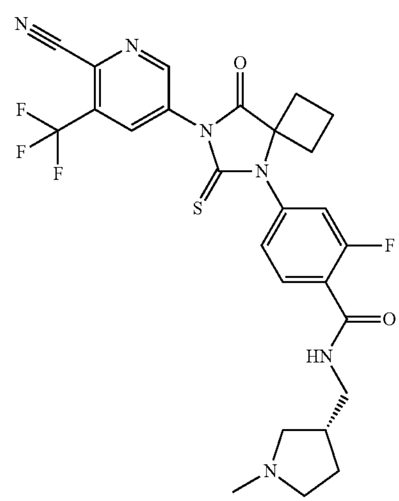 [SMILES: CN1CC[C@@H](CNC(=O)c2ccc(N3C(=S)N(c4cnc(C#N)c(C(F)(F)F)c4)C(=O)C34CCC4)cc2F)C1] | 4-[6-[6-cyano-5-(trifluoromethyl)-3-pyridyl]-5-oxo-7-thioxo-6,8-diazaspiro[3.4]octan-8-yl]-2-fluoro-N-[[(3R)-1-methylpyrrolidin-3-yl]methyl]benzamide. $^1$H NMR (300 MHz, DMSO-$d_6$) δ 1.46-1.72 (m, 2H), 1.90-2.09 (m, 2H), 2.35 (s, 3H), 2.40-2.81 (m, 9H), 3.20-3.32 (m, 2H), 7.38 (d, J = 8.0 Hz, 1H), 7.46 (d, J = 10.2 Hz, 1H), 7.80 (t, J = 8.0 Hz, 1H), 8.66 (t, J = 5.7 Hz, 1H), 8.75 (d, J = 2.0 Hz, 1H), 9.21 (d, J = 2.0 Hz, 1H). $C_{26}H_{24}F_4N_6O_2S$ MS m/z 561 $(M + H)^+$ |

| Cpd No. | Structure | Compound Name & Physical Data |
|---|---|---|
| 205 | 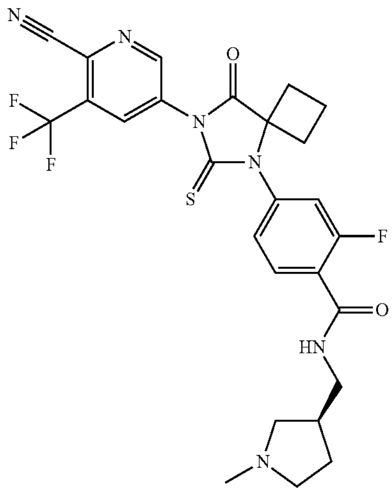 [SMILES: CN1CC[C@H](CNC(=O)c2ccc(N3C(=S)N(c4cnc(C#N)c(C(F)(F)F)c4)C(=O)C34CCC4)cc2F)C1] | 4-[6-[6-cyano-5-(trifluoromethyl)-3-pyridyl]-5-oxo-7-thioxo-6,8-diazaspiro[3.4]octan-8-yl]-2-fluoro-N-[[(3S)-1-methylpyrrolidin-3-yl]methyl]benzamide.<br>$^1$H NMR (300 MHz, Chloroform-d) δ 1.53-1.79 (m, 2H), 1.96-2.14 (m, 1H), 2.14-2.31 (m, 1H), 2.41 (s, 3H), 2.45-2.75 (m, 9H), 3.45 (d, J = 6.0 Hz, 2H), 7.14 (dd, J = 11.0, 1.9 Hz, 1H), 7.21 (dd, J = 8.3, 1.9 Hz, 1H), 8.14 (t, J = 8.2 Hz, 1H), 8.33 (d, J = 2.2 Hz, 1H), 9.05 (d, J = 2.2 Hz, 1H).<br>$C_{26}H_{24}F_4N_6O_2S$<br>MS m/z 561 (M + H)$^+$ |
| 216 | 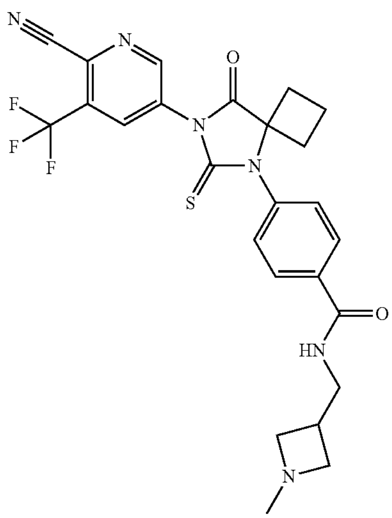 [SMILES: CN1CC(CNC(=O)c2ccc(N3C(=S)N(c4cnc(C#N)c(C(F)(F)F)c4)C(=O)C34CCC4)cc2)C1] | 4-[6-[6-cyano-5-(trifluoromethyl)-3-pyridyl]-5-oxo-7-thioxo-6,8-diazaspiro[3.4]octan-8-yl]-N-[(1-methylazetidin-3-yl)methyl]benzamide.<br>$^1$H NMR (300 MHz, DMSO-d$_6$) δ 1.43-1.66 (m, 1H), 1.86-2.06 (m, 1H), 2.33-2.46 (m, 2H), 2.56-2.74 (m, 2H), 2.80 (dd, J = 11.4, 5.0 Hz, 3H), 2.92-3.10 (m, 1H), 3.46-3.62 (m, 2H), 3.72-3.87 (m, 1H), 3.88-4.00 (m, 1H), 4.01-4.12 (m, 1H), 4.12-4.26 (m, 1H), 7.55 (d, J = 8.2 Hz, 2H), 8.09 (d, J = 8.2 Hz, 2H), 8.77 (d, J = 2.0 Hz, 1H), 8.91 (dt, J = 19.8, 5.6 Hz, 1H), 9.23 (d, J = 2.0 Hz, 1H), 10.24 (br s, 1H).<br>$C_{25}H_{23}F_3N_6O_2S$•HCl<br>MS m/z 529 (M + H)$^+$ |
| 206 | 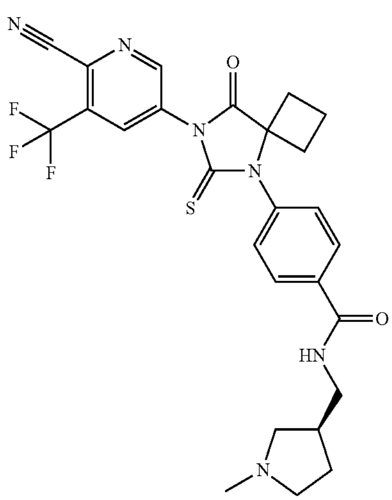 [SMILES: CN1CC[C@H](CNC(=O)c2ccc(N3C(=S)N(c4cnc(C#N)c(C(F)(F)F)c4)C(=O)C34CCC4)cc2)C1] | 4-[6-[6-cyano-5-(trifluoromethyl)-3-pyridyl]-5-oxo-7-thioxo-6,8-diazaspiro[3.4]octan-8-yl]-N-[[(3R)-1-methylpyrrolidin-3-yl]methyl]benzamide.<br>$^1$H NMR (300 MHz, DMSO-d$_6$) δ 1.40-1.64 (m, 2H), 1.80-2.07 (m, 2H), 2.24 (s, 3H), 2.28-2.47 (m, 6H), 2.59-2.75 (m, 3H), 3.26 (t, J = 6.3 Hz, 2H), 7.52 (d, J = 8.1 Hz, 2H), 8.04 (d, J = 8.0 Hz, 2H), 8.70 (t, J = 5.7 Hz, 1H), 8.77 (d, J = 2.1 Hz, 1H), 9.23 (d, J = 2.1 Hz, 1H).<br>$C_{26}H_{25}F_3N_6O_2S$<br>MS m/z 543 (M + H)$^+$ |

-continued

| Cpd No. | Structure | Compound Name & Physical Data |
|---|---|---|
| 204 | 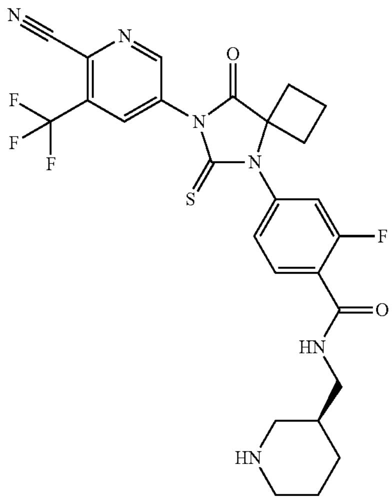 [SMILES: N#Cc1ncc(N2C(=O)C3(CCC3)N(c3ccc(C(=O)NC[C@H]4CCCNC4)c(F)c3)C2=S)cc1C(F)(F)F] | 4-[6-[6-cyano-5-(trifluoromethyl)-3-pyridyl]-5-oxo-7-thioxo-6,8-diazaspiro[3.4]octan-8-yl]-2-fluoro-N-[[(3S)-3-piperidyl]methyl]benzamide. <br> $^1$H NMR (300 MHz, DMSO-d$_6$) δ 1.33-1.52 (m, 1H), 1.52-1.72 (m, 2H), 1.72-1.86 (m, 2H), 1.92-2.11 (m, 1H), 2.30-2.45 (m, 1H), 2.45-2.58 (m, 2H), 2.58-2.74 (m, 4H), 2.98 (d, J = 12.2 Hz, 1H), 3.07 (d, J = 11.8 Hz, 1H), 3.18 (t, J = 6.7 Hz, 2H), 3.4 (br s, 1H), 7.38 (d, J = 8.1 Hz, 1H), 7.47 (d, J = 10.3 Hz, 1H), 7.80 (t, J = 7.9 Hz, 1H), 8.61 (t, J = 6.1 Hz, 1H), 8.75 (d, J = 2.1 Hz, 1H), 9.21 (d, J = 2.0 Hz, 1H). <br> $C_{26}H_{24}F_4N_6O_2S$ <br> MS m/z 561 (M + H)$^+$ |
| 203 | 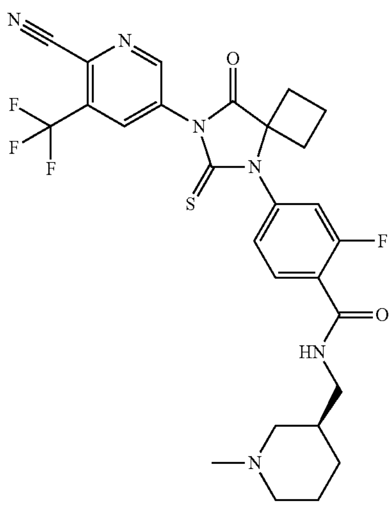 [SMILES: CN1CCC[C@H](CNC(=O)c2ccc(N3C(=S)N(c4cnc(C#N)c(C(F)(F)F)c4)C(=O)C34CCC4)cc2F)C1] | 4-[6-[6-cyano-5-(trifluoromethyl)-3-pyridyl]-5-oxo-7-thioxo-6,8-diazaspiro[3.4]octan-8-yl]-2-fluoro-N-[[(3R)-1-methyl-3-piperidyl]methyl]benzamide. <br> $^1$H NMR (300 MHz, DMSO-d$_6$) δ 0.78-1.05 (m, 1H), 1.34-1.52 (m, 1H), 1.54-1.74 (m, 4H), 1.74-1.92 (m, 2H), 1.92-2.08 (m, 1H), 2.15 (s, 3H), 2.39-2.58 (m, 2H), 2.58-2.81 (m, 4H), 3.08-3.26 (m, 2H), 7.37 (dd, J = 8.2, 1.9 Hz, 1H), 7.46 (dd, J = 10.4, 1.9 Hz, 1H), 7.80 (t, J = 8.0 Hz, 1H), 8.58 (t, J = 5.9 Hz, 1H), 8.75 (d, J = 2.1 Hz, 1H), 9.22 (d, J = 2.0 Hz, 1H). <br> $C_{27}H_{26}F_4N_6O_2S$ <br> MS m/z 575 (M + H)$^+$ |
| 202 | 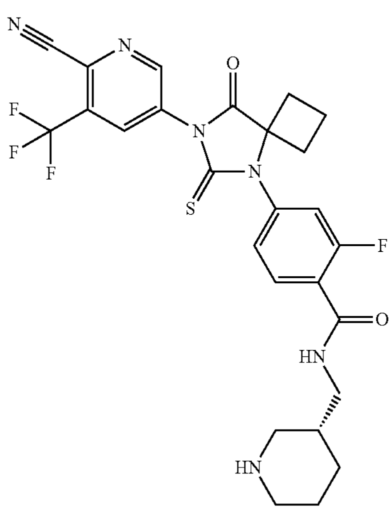 [SMILES: N#Cc1ncc(N2C(=O)C3(CCC3)N(c3ccc(C(=O)NC[C@@H]4CCCNC4)c(F)c3)C2=S)cc1C(F)(F)F] | 4-[6-[6-cyano-5-(trifluoromethyl)-3-pyridyl]-5-oxo-7-thioxo-6,8-diazaspiro[3.4]octan-8-yl]-2-fluoro-N-[[(3R)-3-piperidyl]methyl]benzamide. <br> $^1$H NMR (300 MHz, DMSO-d$_6$) δ 1.34-1.52 (m, 1H), 1.60 (d, J = 19.2 Hz, 2H), 1.72-1.84 (m, 2H), 1.93-2.06 (m, 1H), 2.30-2.42 (m, 1H), 2.43-2.58 (m, 4H), 2.58-2.75 (m, 2H), 2.98 (d, J = 12.3 Hz, 1H), 3.07 (d, J = 12.6 Hz, 1H), 3.16 (t, J = 6.5 Hz, 2H), 3.4 (br s, 1H), 7.38 (d, J = 8.2 Hz, 1H), 7.46 (d, J = 10.3 Hz, 1H), 7.80 (t, J = 7.9 Hz, 1H), 8.62 (t, J = 6.1 Hz, 1H), 8.75 (s, 1H), 9.21 (s, 1H). <br> $C_{26}H_{24}F_4N_6O_2S$ <br> MS m/z 560 (M + H)$^+$ |

| Cpd No. | Structure | Compound Name & Physical Data |
|---|---|---|
| 200 | 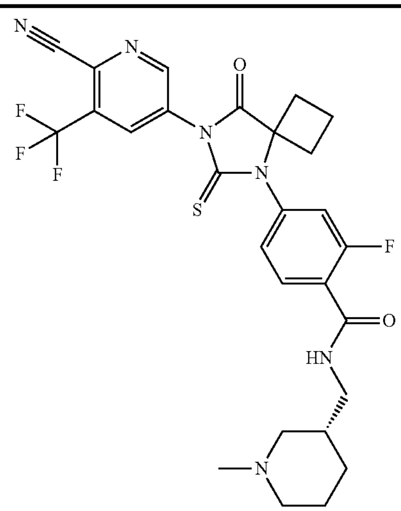 | 4-[6-[6-cyano-5-(trifluoromethyl)-3-pyridyl]-5-oxo-7-thioxo-6,8-diazaspiro[3.4]octan-8-yl]-2-fluoro-N-[[(3S)-1-methyl-3-piperidyl]methyl]benzamide.<br>$^1$H NMR (300 MHz, Chloroform-d) δ 0.99-1.19 (m, 1H), 1.54-2.11 (m, 6H), 2.18-2.37 (m, 2H), 2.29 (s, 3H), 2.48-2.65 (m, 2H), 2.66-2.80 (m, 3H), 2.80-2.92 (m, 1H), 3.41-3.53 (m, 2H), 6.91 (br s, 1H), 7.17 (d, J = 11.5, 2.0 Hz, 1H), 7.27 (d, J = 8.4 Hz, 1H), 8.30 (d, J = 8.4 Hz, 1H), 8.35 (d, J = 2.2 Hz, 1H), 9.09 (d, J = 2.2 Hz, 1H).<br>$C_{27}H_{26}F_4N_6O_2S$<br>MS m/z 575 (M + H)$^+$ |
| 192 | 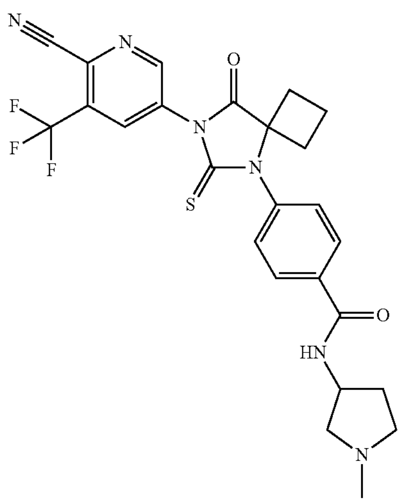 [SMILES: CN1CCC(NC(=O)c2ccc(N3C(=S)N(c4cnc(C#N)c(C(F)(F)F)c4)C(=O)C34CCC4)cc2)C1] | 4-[6-[6-cyano-5-(trifluoromethyl)-3-pyridyl]-5-oxo-7-thioxo-6,8-diazaspiro[3.4]octan-8-yl]-N-(1-methylpyrrolidin-3-yl)benzamide.<br>$^1$H NMR (300 MHz, DMSO-d$_6$) δ 1.44-1.66 (m, 1H), 1.71-1.88 (m, 1H), 1.92-2.08 (m, 1H), 2.10-2.25 (m, 1H), 2.30 (s, 3H), 2.38-2.47 (m, 2H), 2.58-2.74 (m, 4H), 2.74-2.84 (m, 1H), 3.31-3.44 (m, 1H), 4.33-4.54 (m, 1H), 7.51 (d, J = 8.0 Hz, 2H), 8.06 (d, J = 8.0 Hz, 2H), 8.67 (d, J = 7.0 Hz, 1H), 8.77 (s, 1H), 9.23 (s, 1H).<br>$C_{25}H_{23}F_3N_6O_2S$<br>MS m/z 529 (M + H)$^+$ |
| 187 | 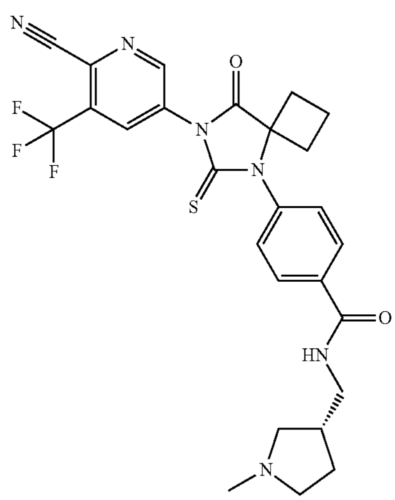 [SMILES: CN1CC[C@@H](CNC(=O)c2ccc(N3C(=S)N(c4cnc(C#N)c(C(F)(F)F)c4)C(=O)C34CCC4)cc2)C1] | 4-[6-[6-cyano-5-(trifluoromethyl)-3-pyridyl]-5-oxo-7-thioxo-6,8-diazaspiro[3.4]octan-8-yl]-N-[[(3S)-1-methylpyrrolidin-3-yl]methyl]benzamide.<br>$^1$H NMR (300 MHz, DMSO-d$_6$) δ 1.41-1.64 (m, 2H), 1.82-2.07 (m, 2H), 2.24 (s, 3H), 2.28-2.48 (m, 6H), 2.59-2.75 (m, 3H), 3.26 (t, J = 6.3 Hz, 2H), 7.53 (d, J = 8.1 Hz, 2H), 8.04 (d, J = 8.1 Hz, 3H), 8.70 (t, J = 5.7 Hz, 1H), 8.77 (d, J = 2.1 Hz, 1H), 9.23 (d, J = 2.2 Hz, 1H).<br>$C_{26}H_{25}F_3N_6O_2S$<br>MS m/z 543 (M + H)$^+$ |

| Cpd No. | Structure | Compound Name & Physical Data |
|---|---|---|
| 186 | 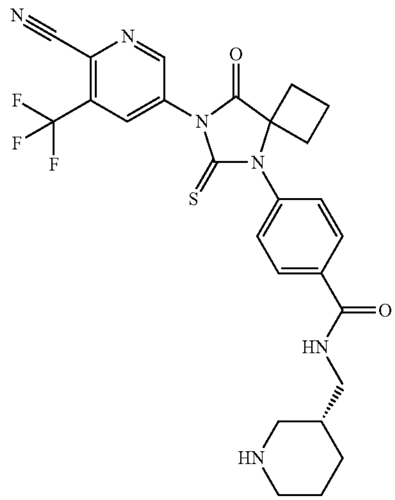 [SMILES: N#Cc1ncc(N2C(=O)C3(CCC3)N(c3ccc(C(=O)NC[C@@H]4CCCNC4)cc3)C2=S)cc1C(F)(F)F] | 4-[6-[6-cyano-5-(trifluoromethyl)-3-pyridyl]-5-oxo-7-thioxo-6,8-diazaspiro[3.4]octan-8-yl]-N-[[(3R)-3-piperidyl]methyl]benzamide. $^1$H NMR (300 MHz, DMSO-d$_6$) δ 1.14-1.31 (m, 1H), 1.46-1.66 (m, 2H), 1.66-1.87 (m, 2H), 1.86-2.06 (m, 3H), 2.38-2.57 (m, 3H), 2.58-2.76 (m, 4H), 3.08 (d, J = 12.2 Hz, 1H), 3.16 (d, J = 11.8 Hz, 2H), 3.21 (t, J = 6.7 Hz, 2H), 3.4 (br s, 1H), 7.53 (d, J = 8.1 Hz, 2H), 8.08 (d, J = 8.1 Hz, 2H), 8.72-8.87 (m, 2H), 9.23 (s, 1H). C$_{26}$H$_{25}$F$_3$N$_6$O$_2$S MS m/z 543 (M + H)$^+$ |
| 185 | 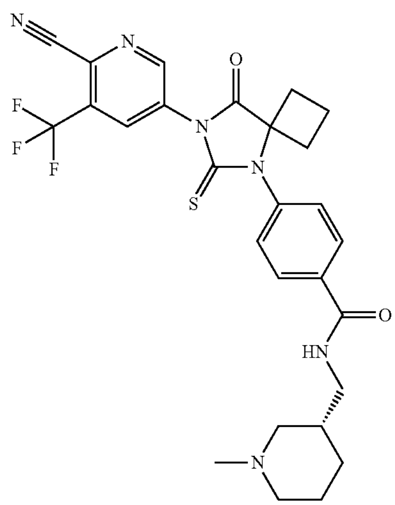 [SMILES: CN1CCC[C@@H](CNC(=O)c2ccc(N3C(=S)N(c4cnc(C#N)c(C(F)(F)F)c4)C(=O)C34CCC4)cc2)C1] | 4-[6-[6-cyano-5-(trifluoromethyl)-3-pyridyl]-5-oxo-7-thioxo-6,8-diazaspiro[3.4]octan-8-yl]-N-[[(3S)-1-methyl-3-piperidyl]methyl]benzamide. $^1$H NMR (300 MHz, DMSO-d$_6$) δ 0.83-1.04 (m, 1H), 1.39-1.74 (m, 5H), 1.75-1.91 (m, 2H), 1.91-2.06 (m, 1H), 2.13 (s, 3H), 2.34-2.56 (m, 2H), 2.56-2.78 (m, 4H), 3.06-3.27 (m, 2H), 7.52 (d, J = 8.3 Hz, 2H), 8.05 (d, J = 8.3 Hz, 2H), 8.64 (t, J = 5.8 Hz, 1H), 8.77 (d, J = 2.1 Hz, 1H), 9.23 (d, J = 2.1 Hz, 1H). C$_{27}$H$_{27}$F$_3$N$_6$O$_2$S MS m/z 557 (M + H)$^+$ |
| 184 | 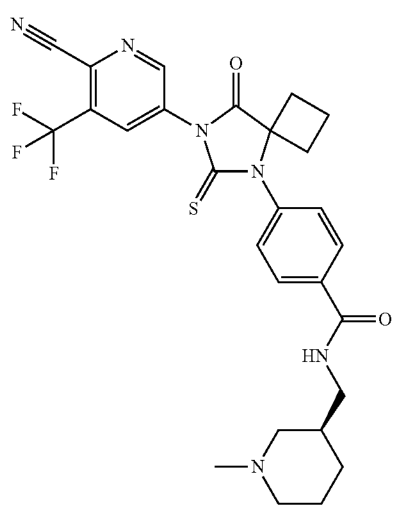 [SMILES: CN1CCC[C@H](CNC(=O)c2ccc(N3C(=S)N(c4cnc(C#N)c(C(F)(F)F)c4)C(=O)C34CCC4)cc2)C1] | 4-[6-[6-cyano-5-(trifluoromethyl)-3-pyridyl]-5-oxo-7-thioxo-6,8-diazaspiro[3.4]octan-8-yl]-N-[[(3R)-1-methyl-3-piperidyl]methyl]benzamide. $^1$H NMR (300 MHz, DMSO-d$_6$) δ 0.79-1.05 (m, 1H), 1.35-1.75 (m, 5H), 1.75-1.91 (m, 2H), 1.91-2.04 (m, 1H), 2.14 (s, 3H), 2.38-2.48 (m, 2H), 2.56-2.80 (m, 4H), 3.09-3.26 (m, 2H), 7.52 (d, J = 8.3 Hz, 2H), 8.05 (d, J = 8.3 Hz, 2H), 8.64 (t, J = 5.8 Hz, 1H), 8.77 (d, J = 2.1 Hz, 1H), 9.23 (d, J = 2.1 Hz, 1H). C$_{27}$H$_{27}$F$_3$N$_6$O$_2$S MS m/z 557 (M + H)$^+$ |

| Cpd No. | Structure | Compound Name & Physical Data |
|---|---|---|
| 73 | 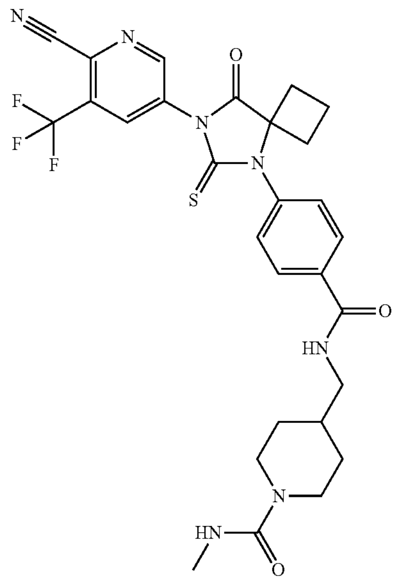 [SMILES: CNC(=O)N1CCC(CNC(=O)c2ccc(N3C(=S)N(c4cnc(C#N)c(C(F)(F)F)c4)C(=O)C34CCC4)cc2)CC1] | 4-[[[4-[6-[6-cyano-5-(trifluoromethyl)-3-pyridyl]-5-oxo-7-thioxo-6,8-diazaspiro[3.4]octan-8-yl]benzoyl]amino]methyl]-N-methyl-piperidine-1-carboxamide. <br> $^1$H NMR (300 MHz, Chloroform-d) δ 1.12-1.33 (m, 2H), 1.64-1.93 (m, 4H), 2.13-2.37 (m, 1H), 2.47-2.62 (m, 2H), 2.63-2.81 (m, 4H), 2.72 (s, 3H), 3.25-3.42 (m, 2H), 3.78-4.00 (m, 2H), 6.65 (br s, 1H), 7.41 (d, J = 8.3 Hz, 2H), 7.98 (d, J = 8.3 Hz, 2H), 8.36 (d, J = 2.2 Hz, 1H), 9.10 (d, J = 2.2 Hz, 1H). <br> $C_{28}H_{28}F_3N_7O_3S$ MS m/z 600 $(M + H)^+$ |
| 72 | 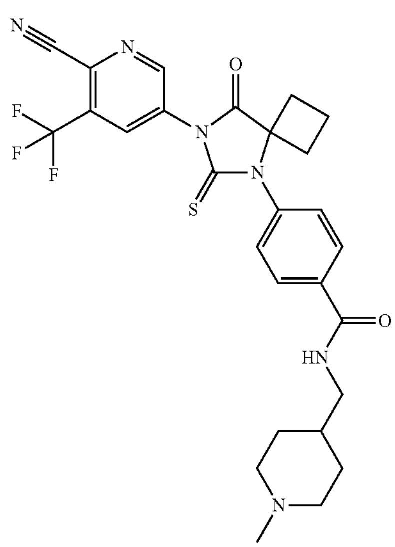 [SMILES: CN1CCC(CNC(=O)c2ccc(N3C(=S)N(c4cnc(C#N)c(C(F)(F)F)c4)C(=O)C34CCC4)cc2)CC1] | 4-[6-[6-cyano-5-(trifluoromethyl)-3-pyridyl]-5-oxo-7-thioxo-6,8-diazaspiro[3.4]octan-8-yl]-N-[(1-methyl-4-piperidyl)methyl]benzamide. <br> $^1$H NMR (300 MHz, Chloroform-d) δ 1.53-1.73 (m, 3H), 1.79-1.94 (m, 3H), 2.15-2.31 (m, 3H), 2.43 (s, 3H), 2.47-2.63 (m, 2H), 2.63-2.78 (m, 2H), 2.98-3.13 (m, 2H), 3.41 (t, J = 6.0 Hz, 2H), 6.99 (t, J = 6.1 Hz, 1H), 7.40 (d, J = 8.1 Hz, 2H), 8.07 (d, J = 8.1 Hz, 2H), 8.36 (d, J = 2.2 Hz, 1H), 9.09 (d, J = 2.2 Hz, 1H). <br> $C_{27}H_{27}F_3N_6O_2S$ <br> MS m/z 557 $(M + H)^+$ |

| Cpd No. | Structure | Compound Name & Physical Data |
|---|---|---|
| 49 | 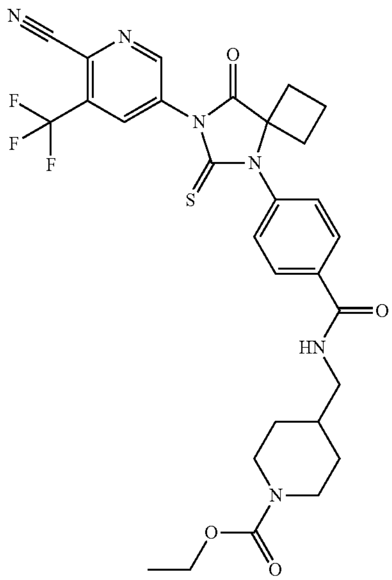 [SMILES: CCOC(=O)N1CCC(CNC(=O)c2ccc(N3C(=S)N(c4cnc(C#N)c(C(F)(F)F)c4)C(=O)C34CCC4)cc2)CC1] | ethyl 4-[[[4-[6-[6-cyano-5-(trifluoromethyl)-3-pyridyl]-5-oxo-7-thioxo-6,8-diazaspiro[3.4]octan-8-yl]benzoyl]amino]methyl]piperidine-1-carboxylate.<br>$^1$H NMR (300 MHz, Chloroform-d) δ 1.12-1.33 (m, 5H), 1.64-1.93 (m, 4H), 2.13-2.37 (m, 1H), 2.47-2.62 (m, 2H), 2.63-2.81 (m, 4H), 3.34-3.46 (m, 2H), 4.02-4.30 (m, 4H), 6.34 (t, J = 6.1 Hz, 1H), 7.41 (d, J = 8.3 Hz, 2H), 7.98 (d, J = 8.3 Hz, 2H), 8.36 (d, J = 2.2 Hz, 1H), 9.10 (d, J = 2.2 Hz, 1H).<br>$C_{29}H_{29}F_3N_6O_4S$<br>MS m/z 615 (M + H)$^+$ |
| 46 | 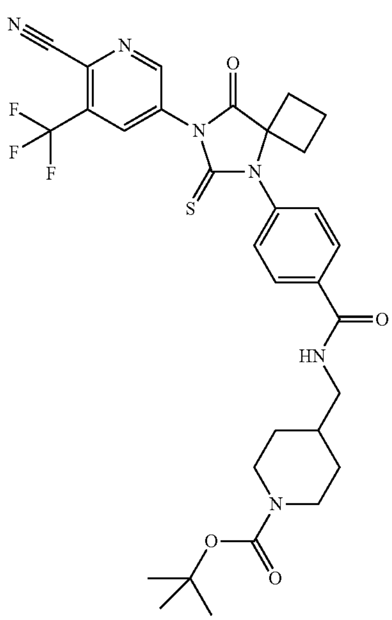 [SMILES: CC(C)(C)OC(=O)N1CCC(CNC(=O)c2ccc(N3C(=S)N(c4cnc(C#N)c(C(F)(F)F)c4)C(=O)C34CCC4)cc2)CC1] | tert-butyl 4-[[[4-[6-[6-cyano-5-(trifluoromethyl)-3-pyridyl]-5-oxo-7-thioxo-6,8-diazaspiro[3.4]octan-8-yl]benzoyl]amino]methyl]piperidine-1-carboxylate.<br>$^1$H NMR (300 MHz, Chloroform-d) δ 1.12-1.33 (m, 2H), 1.45 (s, 9H), 1.64-1.93 (m, 4H), 2.13-2.37 (m, 1H), 2.47-2.62 (m, 2H), 2.63-2.81 (m, 4H), 3.34-3.46 (m, 2H), 4.02-4.30 (m, 2H), 6.34 (t, J = 6.1 Hz, 1H), 7.41 (d, J = 8.3 Hz, 2H), 7.98 (d, J = 8.3 Hz, 2H), 8.36 (d, J = 2.2 Hz, 1H), 9.10 (d, J = 2.2 Hz, 1H).<br>$C_{31}H_{33}F_3N_6O_4S$<br>MS m/z 643 (M + H)$^+$ |

-continued

| Cpd No. | Structure | Compound Name & Physical Data |
|---|---|---|
| 32 | 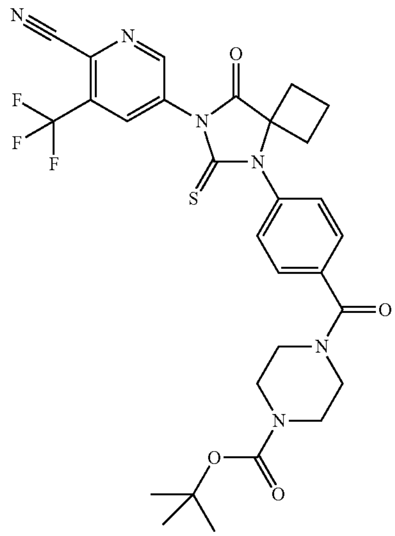 [SMILES: CC(C)(C)OC(=O)N1CCN(C(=O)c2ccc(N3C(=S)N(c4cnc(C#N)c(C(F)(F)F)c4)C(=O)C34CCC4)cc2)CC1] | tert-butyl 4-[4-[6-[6-cyano-5-(trifluoromethyl)-3-pyridyl]-5-oxo-7-thioxo-6,8-diazaspiro[3.4]octan-8-yl]benzoyl]piperazine-1-carboxylate.<br>$^1$H NMR (300 MHz, DMSO-d$_6$) δ 1.45 (s, 9H), 1.52-1.72 (m, 1H), 1.93-2.25 (m, 1H), 2.30-2.53 (m, 2H), 2.62-2.80 (m, 2H), 3.39-3.77 (m, 8H), 7.54 (d, J = 7.9 Hz, 2H), 7.70 (d, J = 7.9 Hz, 2H), 8.81 (s, 1H), 9.27 (s, 1H). C$_{29}$H$_{29}$F$_3$N$_6$O$_4$S MS m/z 615 (M + H)$^+$ |
| 31 | 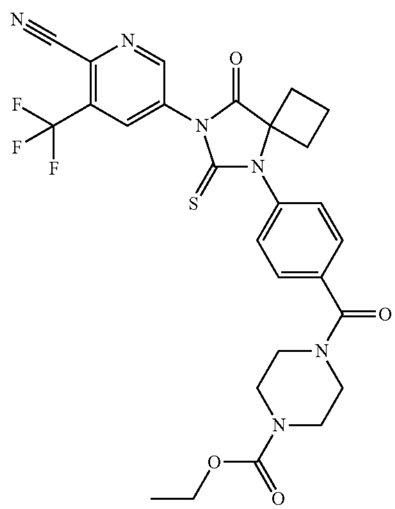 [SMILES: CCOC(=O)N1CCN(C(=O)c2ccc(N3C(=S)N(c4cnc(C#N)c(C(F)(F)F)c4)C(=O)C34CCC4)cc2)CC1] | ethyl 4-[4-[6-[6-cyano-5-(trifluoromethyl)-3-pyridyl]-5-oxo-7-thioxo-6,8-diazaspiro[3.4]octan-8-yl]benzoyl]piperazine-1-carboxylate.<br>$^1$H NMR (300 MHz, DMSO-d$_6$) δ 1.20 (t, J = 7.1 Hz, 3H), 1.48-1.71 (m, 1H), 1.90-2.06 (m, 1H), 2.38-2.50 (m, 2H), 2.59-2.78 (m, 2H), 3.38-3.70 (m, 8H), 4.07 (q, J = 7.1 Hz, 3H), 7.51 (d, J = 8.0 Hz, 2H), 7.66 (d, J = 7.9 Hz, 2H), 8.77 (d, J = 2.0 Hz, 1H), 9.23 (d, J = 2.0 Hz, 1H). C$_{27}$H$_{25}$F$_3$N$_6$O$_4$S MS m/z 587 (M + H)$^+$ |
| 209 | 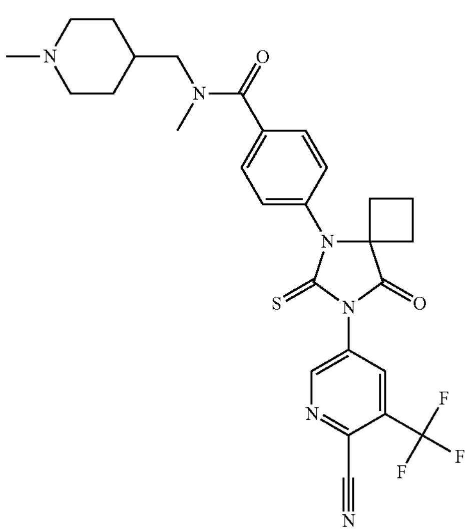 [SMILES: CN1CCC(CN(C)C(=O)c2ccc(N3C(=S)N(c4cnc(C#N)c(C(F)(F)F)c4)C(=O)C34CCC4)cc2)CC1] | $^1$H NMR (400 MHz, Chloroform-d) δ ppm ppm 1.67-1.94 (m, 6 H) 2.07-2.24 (m, 3 H) 2.34 (br. s., 2 H) 2.43-2.56 (m, 2 H) 2.61 (d, J = 9.04 Hz, 2 H) 2.75 (d, J = 13.89 Hz, 1 H) 3.01 (br. s., 3 H) 3.19 (br. s., 2 H) 3.44 (d, J = 6.17 Hz, 2 H) 7.30 (d, J = 7.28 Hz, 2 H) 7.47-7.62 (m, 2 H) 8.31 (s, 1 H) 9.05 (s, 1 H). C$_{28}$H$_{29}$F$_3$N$_6$O$_2$S HCl MS m/z 571.2 (M + H)$^+$ |

Example 18

4-(7-(6-cyano-5-(trifluoromethyl)pyridin-3-yl)-8-oxo-6-thioxo-5,7-diazaspiro[3.4]octan-5-yl)-2-fluoro-N-methylbenzothioamide, Cpd 11

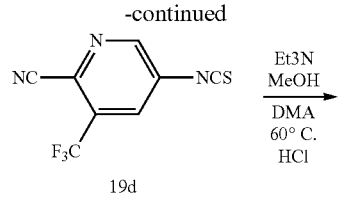

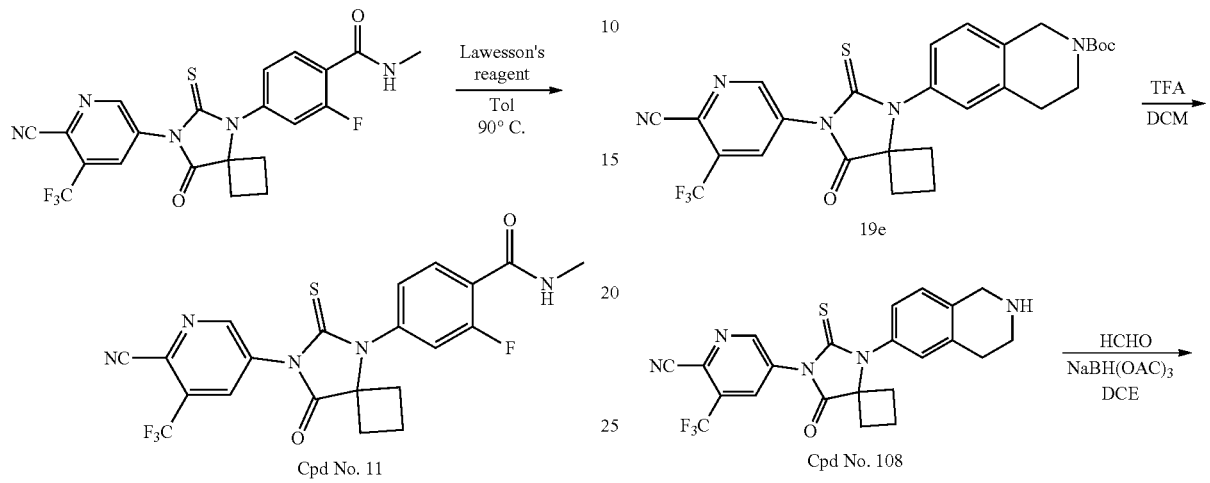

A mixture of 4-(7-(6-cyano-5-(trifluoromethyl)pyridin-3-yl)-8-oxo-6-thioxo-5,7-diazaspiro[3.4]octan-5-yl)-2-fluoro-N-methylbenzamide (0.4 g, 0.83 mmol) and Lawesson's reagent (0.34 g, 0.83 mmol) in toluene (4 mL) was stirred at 90° C. overnight. The mixture was cooled to RT and concentrated under reduced pressure. The residue was purified by chromatography over silica gel (gradient of EA in heptane from 0 to 3%) to yield 4-(7-(6-cyano-5-(trifluoromethyl)pyridin-3-yl)-8-oxo-6-thioxo-5,7-diazaspiro[3.4]octan-5-yl)-2-fluoro-N-methylbenzothioamide as a yellow solid (0.094 g, 23%). $^1$H NMR (500 MHz, DMSO-$d_6$) δ ppm 1.59-1.62 (m, 1H), 1.95-2.01 (m, 1H), 2.48-2.5 (m, 2H), 2.64-2.67 (m, 2H), 3.92 (s, 3H), 7.46 (d, 1H, J=1.6 Hz), 7.48 (d, 1H, J=1.6 Hz), 7.55 (d, 1H, J=1.6 Hz), 8.13-8.15 (m, 1H), 8.75 (d, 1H, J=1.6 Hz), 9.22 (d, 1H, J=1.6 Hz). $C_{21}H_{15}F_4N_5OS_2$ MS m/z 478.2 (M+H)$^+$.

Example 19

5-[8-(2-methyl-3,4-dihydro-1H-isoquinolin-6-yl)-5-oxo-7-thioxo-6,8-diazaspiro[3.4]octan-6-yl]-3-(trifluoromethyl)pyridine-2-carbonitrile, Cpd 125

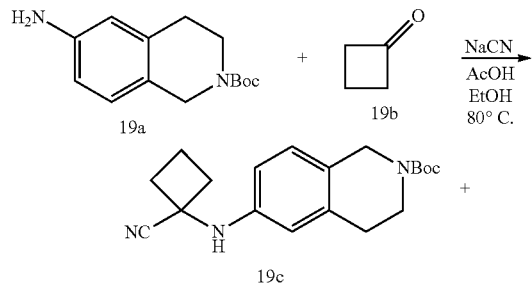

A. tert-butyl 6-((1-cyanocyclobutyl)amino)-3,4-dihydroisoquinoline-2(1H)-carboxylate, 19c

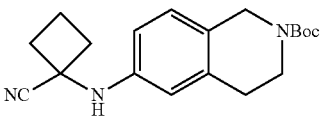 [SMILES: CC(C)(C)OC(=O)N1CCc2cc(NC3(C#N)CCC3)ccc2C1]

Tert-butyl 6-amino-3,4-dihydroisoquinoline-2(1H)-carboxylate (2.5 g, 10.1 mmol) and cyclobutanone (1.51 mL, 20.1 mmol) were mixed in acetic acid (8 mL) and ethanol (8 mL). Sodium cyanide (1.97 g, 40.3 mmol) was added and the mixture was stirred at 80° C. overnight and then allowed to cool to room temperature. The mixture was then poured into water and extracted with DCM. The organic layer was dried over MgSO$_4$, filtered and concentrated to dryness. The crude material was purified by chromatography over silica gel (gradient of EA in heptane from 0 to 50%). The fractions with product were collected and concentrated under reduced pressure to yield tert-butyl 6-((1-cyanocyclobutyl)amino)-3,4-dihydroisoquinoline-2(1H)-carboxylate as an amorphous solid (2.66 g, 81%). $C_{19}H_{25}N_3O_2$ MS m/z 328.2 (M+H)$^+$.

B. tert-butyl 6-(7-(6-cyano-5-(trifluoromethyl)pyridin-3-yl)-8-oxo-6-thioxo-5,7-diaza-spiro[3.4]octan-5-yl)-3,4-dihydroisoquinoline-2(1H)-carboxylate, 19e

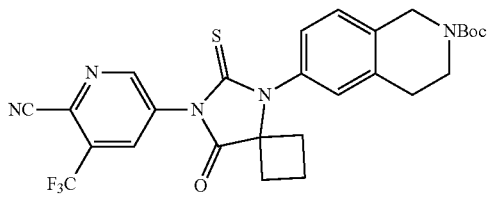 [SMILES: CC(C)(C)OC(=O)N1CCc2cc(N3C(=S)N(c4cnc(C#N)c(C(F)(F)F)c4)C(=O)C34CCC4)ccc2C1]

Tert-butyl 6-((1-cyanocyclobutyl)amino)-3,4-dihydroisoquinoline-2(1H)-carboxylate (1 g, 3.054 mmol), and freshly prepared 5-Isothiocyanato-3-trifluoromethyl-pyridine-2-carbonitrile (0.84 g, 3.66 mmol) were heated at 60° C. in DMA (12 mL) overnight and then allowed to cool to room temperature. The mixture was diluted with MeOH (88 mL) and 1M HCl (88 mL) and stirred at RT for 30 minutes. EA (100 mL) was added and the solution was washed with water, saturated NaHCO$_3$, and brine. The organic layer was dried over MgSO$_4$, filtered and concentrated to dryness. The crude material was purified by chromatography over silica gel (gradient of EA in heptane from 0 to 50%). The fractions with product were collected and concentrated under reduced pressure to yield tert-butyl 6-(7-(6-cyano-5-(trifluoromethyl)pyridin-3-yl)-8-oxo-6-thioxo-5,7-diazaspiro[3.4]octan-5-yl)-3,4-dihydroisoquinoline-2(1H)-carboxylate as a white solid (0.92 g, 54%). $^1$H NMR (300 MHz, Chloroform-d) δ 1.51 (s, 9H), 1.63-1.78 (m, 1H), 2.25 (d, J=9.9 Hz, 1H), 2.48-2.78 (m, 4H), 2.93 (t, J=6.0 Hz, 2H), 3.72 (t, J=5.9 Hz, 2H), 4.68 (s, 2H), 7.04-7.17 (m, 2H), 7.34 (d, J=8.1 Hz, 1H), 8.36 (d, J=2.2 Hz, 1H), 9.10 (d, J=2.2 Hz, 1H). C$_{27}$H$_{26}$F$_3$N$_5$O$_3$S MS m/z 501.9 (M−55)$^+$.

C. 5-(8-oxo-5-(1,2,3,4-tetrahydroisoquinolin-6-yl)-6-thioxo-5,7-diazaspiro[3.4]octan-7-yl)-3-(trifluoromethyl)picolinonitrile, Cpd 108

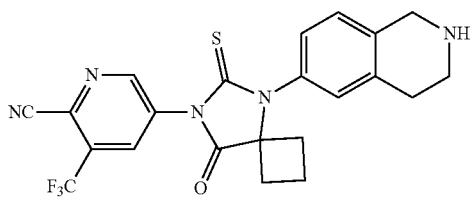 [SMILES: N#Cc1ncc(N2C(=O)C3(CCC3)N(c3ccc4c(c3)CCNC4)C2=S)cc1C(F)(F)F]

To a solution of tert-butyl 6-(7-(6-cyano-5-(trifluoromethyl)pyridin-3-yl)-8-oxo-6-thioxo-5,7-diazaspiro[3.4]octan-5-yl)-3,4-dihydroisoquinoline-2(1H)-carboxylate (0.77 g, 1.38 mmol) in DCM (8.5 mL) was added TFA (5.5 mL). After stirring at RT for 3 h the reaction mixture was concentrated and diluted with EtOAc. The solution was washed with aqueous saturated NaHCO$_3$(3x) and brine (1x). The organic layer was dried over MgSO$_4$, filtered and concentrated to dryness. The crude was purified by chromatography over silica gel (gradient of EA in heptane from 0 to 35%) to yield 5-[5-oxo-8-(1,2,3,4-tetrahydroisoquinolin-6-yl)-7-thioxo-6,8-diazaspiro[3.4]octan-6-yl]-3-(trifluoromethyl) pyridine-2-carbonitrile as a yellow pale solid (0.36 g, 57%). $^1$H NMR (300 MHz, Chloroform-d) δ 1.60-1.78 (m, 1H), 2.11-2.35 (m, 1H), 2.43-2.75 (m, 4H), 2.96 (t, J=5.9 Hz, 2H), 3.26 (t, J=6.0 Hz, 2H), 4.17 (s, 2H), 7.02-7.13 (m, 2H), 7.26 (s, 1H), 8.36 (d, J=2.2 Hz, 1H), 9.10 (d, J=2.2 Hz, 1H). C$_{22}$H$_{18}$F$_3$N$_5$OS MS m/z 458.0 (M+H)$^+$.

D. 5-(5-(2-methyl-1,2,3,4-tetrahydroisoquinolin-6-yl)-8-oxo-6-thioxo-5,7-diazaspiro[3.4]octan-7-yl)-3-(trifluoromethyl)picolinonitrile, Cpd 125

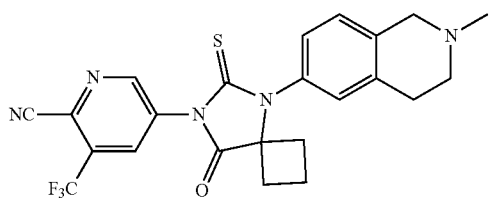 [SMILES: CN1CCc2cc(N3C(=S)N(c4cnc(C#N)c(C(F)(F)F)c4)C(=O)C34CCC4)ccc2C1]

Formaldehyde (37% wt in water, 0.06 mL, 0.81 mmol) was added to a solution of 5-[5-oxo-8-(1,2,3,4-tetrahydroisoquinolin-6-yl)-7-thioxo-6,8-diazaspiro[3.4]octan-6-yl]-3-(trifluoromethyl) pyridine-2-carbonitrile (0.124 g, 0.27 mmol) in DCE (5 mL). The mixture was stirred at room temperature for 5 min, before Sodium triacetoxyborohydride (0.172 g, 0.81 mmol) was added. The reaction was stirred at RT overnight and diluted with EtOAc (125 mL). The solution was washed successively with aqueous saturated NaHCO$_3$. The organic layer was dried over MgSO$_4$, filtered and concentrated to give the crude product. Chromatography over silica gel (gradient of MeOH in DCM from 0 to 10%) gave, upon removal of solvent, 5-[8-(2-methyl-3,4-dihydro-1H-isoquinolin-6-yl)-5-oxo-7-thioxo-6,8-diazaspiro[3.4]octan-6-yl]-3-(trifluoromethyl)pyridine-2-carbonitrile as a pale yellow solid (0.082 g, 83%). $^1$H NMR (300 MHz, Chloroform-d) δ 1.62-1.79 (m, 3H), 2.05-2.34 (m, 1H), 2.42-2.71 (m, 6H), 2.77 (s, 2H), 3.03 (d, J=6.1 Hz, 2H), 3.69 (s, 2H), 7.07 (s, 2H), 7.24 (s, 1H), 8.36 (d, J=2.2 Hz, 1H), 9.10 (d, J=2.2 Hz, 1H). C$_{23}$H$_{20}$F$_3$N$_5$OS MS m/z 472.0 (M+H)$^+$.

E. 5-(5-(2-acetyl-1,2,3,4-tetrahydroisoquinolin-6-yl)-8-oxo-6-thioxo-5,7-diazaspiro[3.4]octan-7-yl)-3-(trifluoromethyl)picolinonitrile, Cpd 120

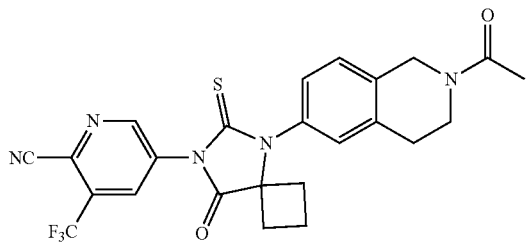 [SMILES: CC(=O)N1CCc2cc(N3C(=S)N(c4cnc(C#N)c(C(F)(F)F)c4)C(=O)C34CCC4)ccc2C1]

5-[5-oxo-8-(1,2,3,4-tetrahydroisoquinolin-6-yl)-7-thioxo-6,8-diazaspiro[3.4]octan-6-yl]-3-(trifluoromethyl)pyridine-2-carbonitrile (0.121 g, 0.26 mmol) was combined with acetic anhydride (2 mL). After stirring at RT overnight, the reaction mixture was concentrated and diluted with DCM. The solution was washed with aqueous saturated NaHCO$_3$(3x) and brine (1x). The organic layer was dried over MgSO$_4$, filtered and concentrated to dryness. The crude material was purified by chromatography over silica gel (gradient of EA in heptane from 5 to 40%) to yield impure desired product which was further purified by reverse phase preparative HPLC (0.072 g, 55%).

The raw material was purified by using a GILSON Semi-Preparative System, operated by Trilution software, equipped with a Phenomenex Gemini C18 100A column (100 mm long×30 mm I.D.; 5 µm particles) at 25° C., with a flow rate of 40 mL/min. A gradient elution was performed from 70% of a 0.1% HCOOH aqueous solution (pH 3)/30% Acetonitrile to 73% of a 0.1% HCOOH aqueous solution (pH3)/27% Acetonitrile in 20 min. The injection volume was 8000 µL. Acquisition frequency was set to 254 nm for the UV-Dual detector. $^1$H NMR (300 MHz, Chloroform-d) δ 1.36-1.71 (m, 4H), 2.07-2.26 (m, 2H), 2.40-2.70 (m, 3H), 2.79-3.01 (m, 2H), 3.65-3.87 (m, 2H), 4.57-4.84 (m, 2H), 7.00-7.13 (m, 2H), 7.24-7.35 (m, 1H), 8.29 (d, J=2.2 Hz, 1H), 9.03 (d, J=2.2 Hz, 1H). C$_{24}$H$_{20}$F$_3$N$_5$O$_2$S MS m/z 500 (M+H)$^+$.

Example 20

3-chloro-5-[8-[6-[(1-isopentyl-4-piperidyl)oxy]-3-pyridyl]-5-oxo-7-thioxo-6,8-diazaspiro[3.4]octan-6-yl]pyridine-2-carbonitrile, Cpd 149

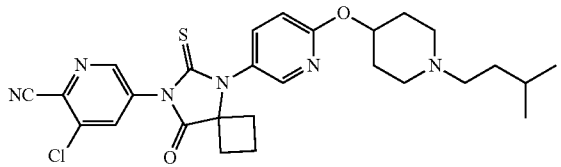 [SMILES: CC(C)CCN1CCC(Oc2ccc(N3C(=S)N(c4cnc(C#N)c(Cl)c4)C(=O)C34CCC4)cn2)CC1]

3-Methylbutyraldehyde (0.103 mL, 0.96 mmol) was added to a solution of 3-chloro-5-(8-oxo-5-(6-(piperidin-4-yloxy)pyridin-3-yl)-6-thioxo-5,7-diazaspiro[3.4]octan-7-yl)picolinonitrile (0.15 g, 0.32 mmol) in DCE (4.8 mL). The mixture was stirred at RT for 10 min, before Sodium triacetoxyborohydride (0.203 g, 0.96 mmol) was added. The reaction was stirred at RT overnight, washed with aqueous saturated NaHCO$_3$ and extracted with EtOAc. The organic layer was washed successively with water, brine, dried over MgSO$_4$, filtered and concentrated to give the crude product. Chromatography was performed over silica gel (gradient of MeOH in DCM from 0 to 10%). The pure fractions were concentrated to give a residue which was further purified by reverse phase preparative HPLC to afford 3-chloro-5-(5-(6-((1-isopentylpiperidin-4-yl)oxy)pyridin-3-yl)-8-oxo-6-thioxo-5,7-diazaspiro[3.4]octan-7-yl)picolinonitrile as a solid (0.014 g, 8%). $^1$H NMR (300 MHz, Chloroform-d) δ 0.91 (d, J=6.5 Hz, 6H), 1.37-1.52 (m, 2H), 1.54-1.78 (m, 1H), 1.84-1.99 (m, 2H), 2.05-2.31 (m, 4H), 2.34-2.58 (m, 6H), 2.63-2.74 (m, 2H), 2.78-2.94 (m, 2H), 5.01-5.25 (m, 1H), 6.90 (d, J=8.8 Hz, 1H), 7.50 (dd, J=8.7, 2.8 Hz, 1H), 8.08 (d, J=2.7 Hz, 1H), 8.11 (d, J=2.2 Hz, 1H), 8.79 (d, J=2.1 Hz, 1H). C$_{27}$H$_{31}$ClN$_6$O$_2$S MS m/z 539.1 (M+H)$^+$.

Example 21

5-(5-(1-methyl-6-oxo-1,6-dihydropyridin-3-yl)-8-oxo-6-thioxo-5,7-diazaspiro[3.4]octan-7-yl)-3-(trifluoromethyl)picolinonitrile, Cpd 133

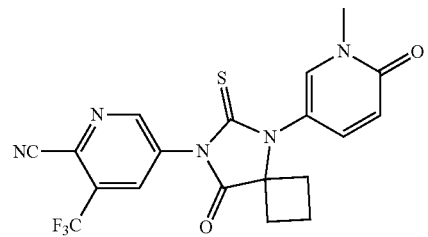 [SMILES: Cn1cc(N2C(=S)N(c3cnc(C#N)c(C(F)(F)F)c3)C(=O)C23CCC3)ccc1=O]

5-(5-(6-hydroxypyridin-3-yl)-8-oxo-6-thioxo-5,7-diazaspiro[3.4]octan-7-yl)-3-(trifluoromethyl)picolinonitrile (0.84 g, 2 mmol), methanol (0.089 mL, 2.2 mmol) and triphenylphosphine (1.154 g, 4.4 mmol) were dissolved in dry DMF (2 mL) and dry THF (14 mL) under a nitrogen atmosphere and heated at 50° C. A solution of Diisopropyl azodicarboxylate (DIAD, 0.788 mL, 4 mmol) in THF (6 mL) was added dropwise. Once the addition was complete, the reaction was continued for 3 h at the same temperature. The mixture was allowed to cool and then diluted with EtOAc. The organic layer was washed with aqueous saturated NaHCO$_3$, brine, dried over MgSO$_4$, filtered and concentrated to dryness. The crude residue was chromatographed over silica gel (gradient of EtOAc in heptane from 5 to 30%). The pure fractions were concentrated to give a residue which was further purified by reverse phase preparative HPLC to afford 5-(5-(1-methyl-6-oxo-1,6-dihydropyridin-3-yl)-8-oxo-6-thioxo-5,7-diazaspiro[3.4]octan-7-yl)-3-(trifluoromethyl)picolinonitrile as a solid (0.23 g, 27%).

The raw material was purified by using a GILSON Semi-Preparative System, operated by Trilution software, equipped with a Phenomenex Gemini C18 100A column (100 mm long×30 mm I.D.; 5 µm particles) at 25° C., with a flow rate of 40 mL/min. A gradient elution was performed from 59% of a 0.1% HCOOH aqueous solution (pH 3)/41% Acetonitrile to 17% of a 0.1% HCOOH aqueous solution (pH 3)/83% Acetonitrile in 20 min. The injection volume was 8000 µL. Acquisition frequency was set to 254 nm for the UV-Dual detector. $^1$H NMR (300 MHz, Chloroform-d) δ 1.75-1.98 (m, 1H), 2.20-2.42 (m, 1H), 2.44-2.63 (m, 2H), 2.63-2.77 (m, 2H), 3.63 (s, 3H), 6.72 (d, J=9.7 Hz, 1H), 7.19-7.28 (m, 1H), 7.40 (d, J=2.8 Hz, 1H), 8.32 (d, J=2.2 Hz, 1H), 9.06 (d, J=2.2 Hz, 1H). C$_{19}$H$_{14}$F$_3$N$_5$O$_2$S MS m/z 433.9 (M+H)$^+$.

Example 22 tert-Butyl 3-{5-[7-(6-Cyano-5-trifluoromethyl-pyridin-3-yl)-8-oxo-6-thioxo-5,7-diaza-spiro[3.4]oct-5-yl]-pyridin-2-yloxymethyl}-azetidine-1-carboxylate And tert-Butyl 3-[[5-[6-[6-cyano-5-(trifluoromethyl)-3-pyridyl]-5-oxo-7-thioxo-6,8-diazaspiro[3.4]octan-8-yl]-2-oxo-1-pyridyl]methyl]azetidine-1-carboxylate, as a Mixture, Cpd 130

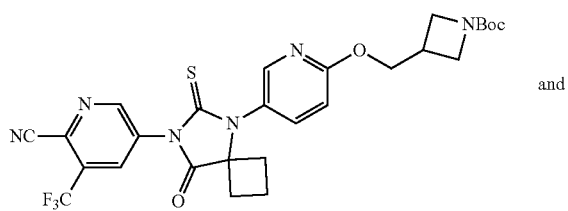

and

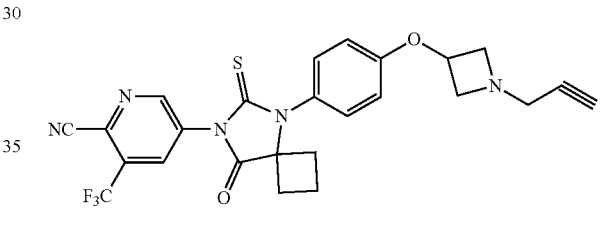

Cpd 130

A mixture of of 5-[5-(6-Hydroxy-pyridin-3-yl)-8-oxo-6-thioxo-5,7-diaza-spiro[3.4]oct-7-yl]-3-trifluoromethyl-pyridine-2-carbonitrile and 1-Boc-3-hydroxymethylazetidine in a freshly prepared 0.36M solution of 2-(tributylphosphoranylidene)-acetonitrile in heptane under a nitrogen atmosphere was heated to 110° C. for 16 h. The crude material was poured onto water/NaHCO$_3$ and extracted with Ethyl acetate. The organic layer was dried over MgSO$_4$, filtered and concentrated to dryness. The residue was purified by flash chromatography over silica gel (Ethyl acetate-heptane gradient from 5% to 30%). Two products were isolated. Pure fractions were combined and concentrated to dryness under high vacuum to give the mixture as Cpd 130.

tert-Butyl 3-{5-[7-(6-Cyano-5-trifluoromethyl-pyridin-3-yl)-8-oxo-6-thioxo-5,7-diaza-spiro[3.4]oct-5-yl]-pyridin-2-yloxymethyl}-azetidine-1-carboxylate (405 mg, 34%). $^1$H NMR (300 MHz, Chloroform-d) δ 1.44 (s, 9H), 1.65-1.83 (m, 1H), 2.15-2.35 (m, 1H), 2.44-2.61 (m, 2H), 2.63-2.78 (m, 2H), 2.92-3.12 (m, 1H), 3.73-3.89 (m, 2H), 4.02-4.16 (m, 2H), 4.51 (d, J=6.7 Hz, 2H), 6.95 (d, J=8.7 Hz, 1H), 7.54 (dd, J=8.8, 2.6 Hz, 1H), 8.11 (d, J=2.6 Hz, 1H), 8.36 (d, J=2.3 Hz, 1H), 9.09 (d, J=2.2 Hz, 1H). $C_{27}H_{27}F_3N_6O_4S$ MS m/z 588.9 (M+H)$^+$.

tert-Butyl 3-[[5-[6-[6-cyano-5-(trifluoromethyl)-3-pyridyl]-5-oxo-7-thioxo-6,8-diazaspiro[3.4]octan-8-yl]-2-oxo-1-pyridyl]methyl]azetidine-1-carboxylate (215 mg, 18%). $^1$H NMR (300 MHz, Chloroform-d) δ 1.35 (s, 9H), 1.67-1.85 (m, 1H), 2.12-2.34 (m, 1H), 2.35-2.53 (m, 2H), 2.56-2.77 (m, 2H), 2.95-3.15 (m, 1H), 3.56-3.71 (m, 2H), 3.94-4.01 (m, 2H), 4.09-4.19 (m, 2H), 6.64 (d, J=9.7 Hz, 1H), 7.10-7.29 (m, 1H), 7.38 (d, J=2.7 Hz, 1H), 8.26 (d, J=2.2 Hz, 1H), 8.98 (d, J=2.2 Hz, 1H). $C_{27}H_{27}F_3N_6O_4S$ MS m/z 588.8 (M+H)$^+$.

Example 23

5-(8-oxo-5-(4-((1-(prop-2-yn-1-yl)azetidin-3-yl)oxy)phenyl)-6-thioxo-5,7-diazaspiro[3.4]octan-7-yl)-3-(trifluoromethyl)picolinonitrile, Cpd 117

To a solution of 5-(5-(4-(azetidin-3-yloxy)phenyl)-8-oxo-6-thioxo-5,7-diazaspiro[3.4]octan-7-yl)-3-(trifluoromethyl)picolinonitrile (0.11 g, 0.232 mmol) and DIPEA (0.0121 mL, 0.696 mmol) in MeCN (3 mL) was added propargyl bromide (0.024 mL, 0.186 mmol). After stirring at RT for 15 h, dimethyl amine (0.024 mL, 0.232 mmol) was added and the solution stirred for another 30 min. The mixture was poured onto ice and aqueous saturated NaHCO$_3$ and diluted with EtOAc. The organic layer was washed with aqueous saturated NaHCO$_3$, brine, dried over MgSO$_4$, filtered and concentrated to give 5-(8-oxo-5-(4-((1-(prop-2-yn-1-yl)azetidin-3-yl)oxy)phenyl)-6-thioxo-5,7-diazaspiro[3.4]octan-7-yl)-3-(trifluoromethyl)picolinonitrile (0.004 g, 3%). $^1$H NMR (300 MHz, Chloroform-d) δ 1.59-1.82 (m, 1H), 2.20-2.29 (m, 1H), 2.30-2.35 (m, 1H), 2.50-2.60 (m, 2H), 2.61-2.75 (m, 2H), 3.40 (d, J=2.4 Hz, 2H), 3.43-3.50 (m, 2H), 3.75-3.93 (m, 2H), 4.70-4.95 (m, 1H), 6.96 (d, J=8.9 Hz, 2H), 7.21 (d, J=8.8 Hz, 1H), 8.36 (d, J=2.3 Hz, 1H), 9.10 (d, J=2.3 Hz, 1H). $C_{25}H_{20}F_3N_5O_2S$ MS m/z 512.0 (M+H)$^+$.

Following the procedure described in Example 23, above, selecting and substituting the appropriate reagents, starting materials, and purification methods, and adjusting reaction temperatures, times and other variables or parameters, as needed or desirable, as would be readily recognized by those skilled in the art, the following compounds of formula (I) of the invention were prepared.

| Cpd No. | Structure | Compound Name & Physical Data |
|---|---|---|
| 88 | 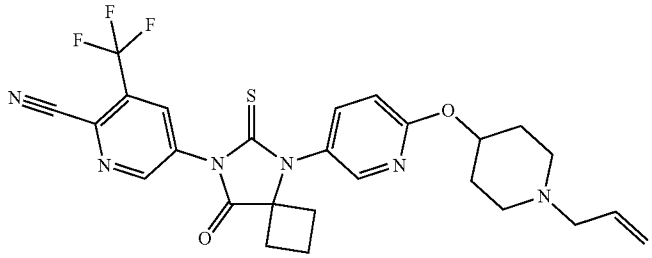 [SMILES: C=CCN1CCC(Oc2ccc(N3C(=S)N(c4cnc(C#N)c(C(F)(F)F)c4)C(=O)C34CCC4)cn2)CC1] | 5-[8-[6-[(1-allyl-4-piperidyl)oxy]-3-pyridyl]-5-oxo-7-thioxo-6,8-diazaspiro[3.4]octan-6-yl]-3-(trifluoromethyl)pyridine-2-carbonitrile. $^1$H NMR (300 MHz, Chloroform-d) δ ppm 1.65-1.79 (m, 1 H) 1.87-1.97 (m, 2 H) 2.14 (br. s., 2 H) 2.20-2.32 (m, 1 H) 2.35-2.59 (m, 4 H) 2.69 (t, J = 9.41 Hz, 2 H) 2.83 (br. s., 2 H) 3.09 (d, J = 6.36 Hz, 2 H) 5.10-5.28 (m, 3 H) 5.92 (ddt, J = 16.96, 10.18, 6.60, 6.60 Hz, 1 H) 6.90 (d, J = 8.80 Hz, 1 H) 7.49 (dd, J = 8.80, 2.69 Hz, 1 H) 8.08 (d, J = 2.45 Hz, 1 H) 8.35 (d, J = 1.96 Hz, 1 H) 9.09 (d, J = 1.96 Hz, 1 H). $C_{26}H_{25}F_3N_6O_2S$ MS m/z 543.1 $(M + H)^+$ |
| 99 | 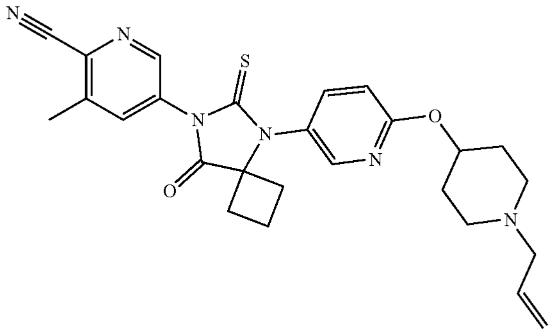 [SMILES: C=CCN1CCC(Oc2ccc(N3C(=S)N(c4cnc(C#N)c(C)c4)C(=O)C34CCC4)cn2)CC1] | 5-[8-[6-[(1-allyl-4-piperidyl)oxy]-3-pyridyl]-5-oxo-7-thioxo-6,8-diazaspiro[3.4]octan-6-yl]-3-methyl-pyridine-2-carbonitrile. $^1$H NMR (400 MHz, DMSO-$d_6$) δ ppm 1.48-1.60 (m, 1 H) 1.68 (q, J = 9.13 Hz, 2 H) 1.86-2.04 (m, 3 H) 2.18 (t, J = 9.54 Hz, 2 H) 2.34-2.44 (m, 2 H) 2.53-2.62 (m, 5 H) 2.67-2.77 (m, 2 H) 2.94 (d, J = 6.36 Hz, 2 H) 5.03 (dt, J = 8.50, 4.43 Hz, 1 H) 5.07-5.19 (m, 2 H) 5.81 (ddt, J = 17.00, 10.39, 6.36, 6.36 Hz, 1 H) 6.97 (d, J = 8.80 Hz, 1 H) 7.73 (dd, J = 8.80, 2.45 Hz, 1 H) 8.10 (d, J = 1.47 Hz, 1 H) 8.18 (d, J = 2.45 Hz, 1 H) 8.68 (d, J = 1.71 Hz, 1 H). $C_{26}H_{28}N_6O_2S$ MS m/z 489.2 $(M + H)^+$ |

Example 24

5-(5-(1-((1-methylpiperidin-4-yl)methyl)-1H-indazol-5-yl)-8-oxo-6-thioxo-5,7-diazaspiro[3.4]octan-7-yl)-3-(trifluoromethyl)picolinonitrile, Cpd 132

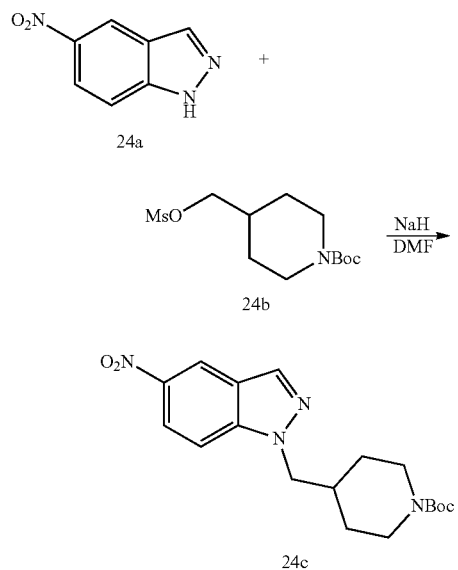

-continued

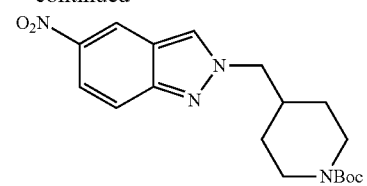

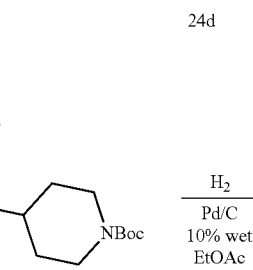

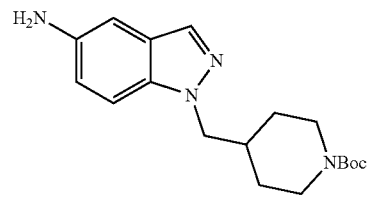

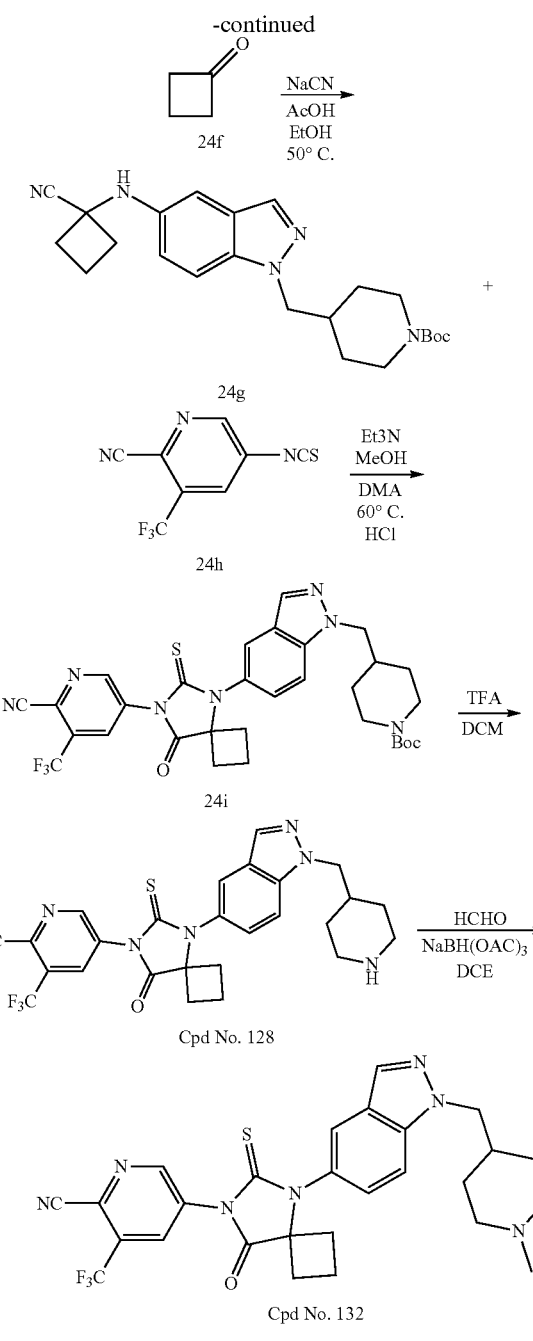

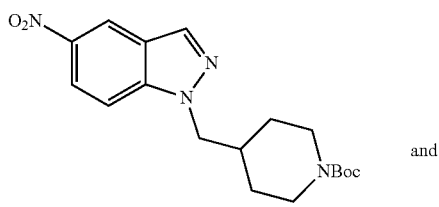

A. tert-Butyl 4-((5-nitro-1H-indazol-1-yl)methyl)piperidine-1-carboxylate and tert-butyl 4-((5-nitro-2H-indazol-2-yl)methyl)piperidine-1-carboxylate, 24c and 24d

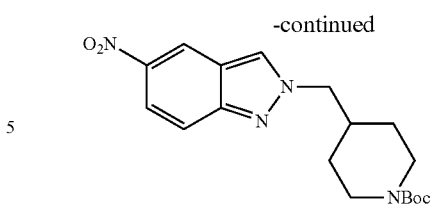

A solution of 5-nitro-1H-indazole (1.19 g, 7.3 mmol) in DMF (12 mL) was added to a suspension of sodium hydride (0.321 g, 13.37 mmol) in DMF (1 mL). After stirring the mixture at RT for 30 min and at 100° C. for 15 min, a solution of tert-butyl 4-(((methylsulfonyl)oxy)methyl)piperidine-1-carboxylate (2.14 g, 7.3 mmol) (*J. Med. Chem.* 2012, 55, 2416-2426) in DMF (13 mL) was added dropwise in two portions at the same temperature. The reaction mixture was stirred at 100° C. overnight, allowed to cool to RT and diluted with aqueous saturated NaHCO$_3$ and extracted with EtOAc. The organic layer was washed with aqueous saturated NaHCO$_3$, brine, was dried over MgSO$_4$, filtered and concentrated to dryness. The crude residue was chromatographed over silica gel (gradient of EtOAc in heptane from 30 to 100%) to give, upon removal of solvent, tert-butyl 4-((5-nitro-1H-indazol-1-yl)methyl)piperidine-1-carboxylate (0.855 g, 33%) and tert-butyl 44(5-nitro-2H-indazol-2-yl)methyl)piperidine-1-carboxylate (0.495 g, 19%) as a mixed fraction (1.09 g).

tert-Butyl 4-((5-nitro-1H-indazol-1-yl)methyl)piperidine-1-carboxylate $^1$H NMR (300 MHz, DMSO-d$_6$) δ 1.00-1.25 (m, 2H), 1.29-1.43 (m, 11H), 1.96-2.17 (m, 1H), 2.54-2.71 (m, 2H), 3.74-4.07 (m, 2H), 4.39 (d, J=7.0 Hz, 2H), 7.93 (d, J=9.3 Hz, 1H), 8.20 (dd, J=9.3, 2.1 Hz, 1H), 8.40 (s, 1H), 8.80 (d, J=2.1 Hz, 1H). C$_{18}$H$_{24}$N$_4$O$_4$ MS m/z 305.1 (M−55)$^+$.

tert-Butyl 4-((5-nitro-2H-indazol-2-yl)methyl)piperidine-1-carboxylate $^1$H NMR (300 MHz, DMSO-d$_6$) δ 1.03-1.26 (m, 2H), 1.31-1.54 (m, 11H), 2.18 (td, J=7.4, 3.7 Hz, 1H), 2.67 (s, 2H), 3.91 (d, J=13.1 Hz, 2H), 4.42 (d, J=7.2 Hz, 2H), 7.77 (d, J=9.5 Hz, 1H), 8.00 (dd, J=9.4, 2.2 Hz, 1H), 8.78 (s, 1H), 8.88 (d, J=2.2 Hz, 1H). C$_{18}$H$_{24}$N$_4$O$_4$ MS m/z 305.1 (M−55)$^+$ B. tert-butyl 4-((5-amino-1H-indazol-1-yl)methyl)piperidine-1-carboxylate, 24e

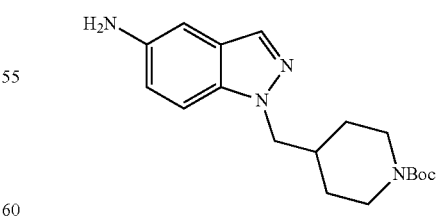

A solution of tert-butyl 4-((5-nitro-1H-indazol-1-yl)methyl)piperidine-1-carboxylate (0.622 g, 1.72 mmol) in EtOAc (7 mL) was purged using nitrogen and vacuum. Palladium on charcoal (10% wet) was added the mixture was hydrogenated for 2 h. The reaction mixture was filtered through diatomaceous earth and the filtrate was concentrated C. tert-Butyl 4-((5-((1-cyanocyclobutyl)amino)-1H-indazol-1-yl)methyl) piperidine-1-carboxylate, 24g

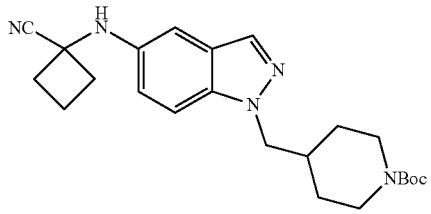 [SMILES: CC(C)(C)OC(=O)N1CCC(Cn2ncc3cc(NC4(C#N)CCC4)ccc32)CC1]

tert-Butyl 4-((5-amino-1H-indazol-1-yl)methyl)piperidine-1-carboxylate (0.54 g, 1.63 mmol) and cyclobutanone (0.244 mL, 3.268 mmol) were mixed in acetic acid (1.3 mL) and ethanol (1.3 mL). Sodium cyanide (0.32 g, 6.53 mmol) was added and the mixture was stirred at 50° C. overnight and then allowed to cool to room temperature. The mixture was then poured into water and extracted with DCM. The organic layer was dried over MgSO$_4$, filtered and concentrated to dryness. The crude material was purified by chromatography over silica gel (gradient of MeOH in DCM from 0 to 10%). The fractions with product were collected and concentrated under reduced pressure to yield tert-butyl 4-((5-((1-cyanocyclobutyl)amino)-1H-indazol-1-yl)methyl)piperidine-1-carboxylate as an amorphous solid (0.4 g, 60%). $C_{23}H_{31}N_5O_2$ MS m/z 354.2 (M−55)$^+$.

D. tert-butyl 4-((5-(7-(6-cyano-5-(trifluoromethyl)pyridin-3-yl)-8-oxo-6-thioxo-5,7-diazaspiro[3.4]octan-5-yl)-1H-indazol-1-yl)methyl)piperidine-1-carboxylate, 24i

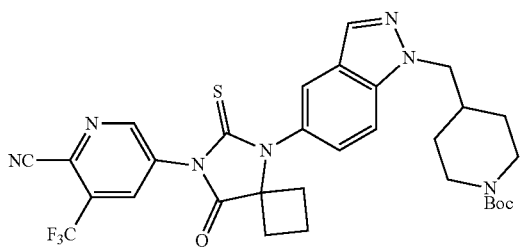 [SMILES: CC(C)(C)OC(=O)N1CCC(Cn2ncc3cc(N4C(=S)N(c5cnc(C#N)c(C(F)(F)F)c5)C(=O)C45CCC5)ccc32)CC1]

tert-Butyl 4-((5-((1-cyanocyclobutyl)amino)-1H-indazol-1-yl)methyl)piperidine-1-carboxylate (0.4 g, 0.977 mmol), and freshly prepared 5-Isothiocyanato-3-trifluoromethyl-pyridine-2-carbonitrile (0.224 g, 0.977 mmol) were heated at 60° C. in DMA (3.9 mL) overnight and then allowed to cool to room temperature. The mixture was diluted with MeOH (1.95 mL) and 1M HCl (1.95 mL) and stirred at RT for 30 min. EA (20 mL) was added and the solution washed with water, aqueous saturated NaHCO$_3$ and brine. The organic layer was dried over MgSO$_4$, filtered and concentrated to dryness. The crude material was purified by chromatography over silica gel (gradient of EA in heptane from 5 to 40%). The fractions with product were collected and concentrated under reduced pressure to yield tert-butyl 4-((5-(7-(6-cyano-5-(trifluoromethyl)pyridin-3-yl)-8-oxo-6-thioxo-5,7-diazaspiro[3.4]octan-5-yl)-1H-indazol-1-yl)methyl)piperidine-1-carboxylate as a foam (0.501 g, 80%). $C_{31}H_{32}F_3N_7O_3S$ MS m/z 540.2 (M-Boc)$^+$.

E. 5-(8-Oxo-5-(1-(piperidin-4-ylmethyl)-1H-indazol-5-yl)-6-thioxo-5,7-diazaspiro[3.4]octan-7-yl)-3-(trifluoromethyl)picolinonitrile, Cpd 128

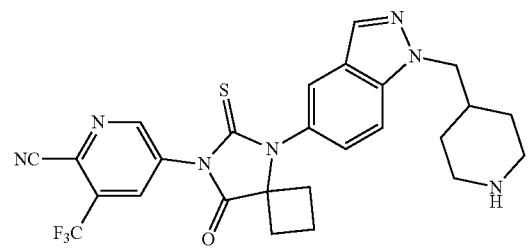 [SMILES: N#Cc1ncc(N2C(=O)C3(CCC3)N(c3ccc4c(cnn4CC4CCNCC4)c3)C2=S)cc1C(F)(F)F]

To a solution of tert-butyl 4-((5-(7-(6-cyano-5-(trifluoromethyl)pyridin-3-yl)-8-oxo-6-thioxo-5,7-diazaspiro[3.4]octan-5-yl)-1H-indazol-1-yl)methyl)piperidine-1-carboxylate (0.501 g, 0.783 mmol) in DCM (4.7 mL) was added TFA (3.13 mL). After stirring at RT for 3 h the reaction mixture was concentrated and diluted with DCM. The solution was washed with aqueous saturated NaHCO$_3$, water and brine. The organic layer was dried over MgSO$_4$, filtered and concentrated to dryness. The crude material was purified by chromatography over silica gel (gradient of MeOH in DCM from 0 to 10%) to yield 5-(8-oxo-5-(1-(piperidin-4-ylmethyl)-1H-indazol-5-yl)-6-thioxo-5,7-diazaspiro[3.4]octan-7-yl)-3-(trifluoromethyl)picolinonitrile as a solid (0.19 g, 44%). $^1$H NMR (300 MHz, Chloroform-d) δ 1.59-1.97 (m, 5H), 2.14-2.34 (m, 1H), 2.34-2.52 (m, 1H), 2.55-2.78 (m, 4H), 2.85-3.07 (m, 2H), 3.38-3.62 (m, 2H), 4.39 (d, J=7.0 Hz, 2H), 7.34 (dd, J=8.9, 1.9 Hz, 1H), 7.63 (d, J=8.9 Hz, 1H), 7.74 (d, J=1.9 Hz, 1H), 8.18 (s, 1H), 8.40 (d, J=2.2 Hz, 1H), 9.12 (d, J=2.2 Hz, 1H). C26H24F3N7OS MS m/z 540.0 (M+H)$^+$.

F. 5-(5-(1-((1-methylpiperidin-4-yl)methyl)-1H-indazol-5-yl)-8-oxo-6-thioxo-5,7-diazaspiro[3.4]octan-7-yl)-3-(trifluoromethyl)picolinonitrile, Cpd 132

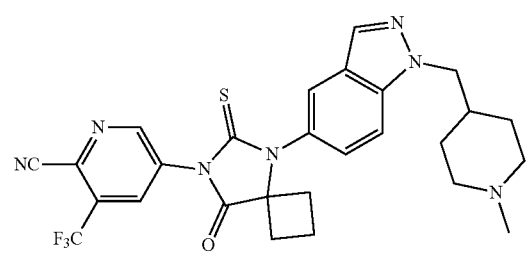 [SMILES: CN1CCC(Cn2ncc3cc(N4C(=S)N(c5cnc(C#N)c(C(F)(F)F)c5)C(=O)C45CCC5)ccc32)CC1]

Formaldehyde (37% wt in water, 0.095 mL, 1.28 mmol) was added to a solution of 5-(8-oxo-5-(1-(piperidin-4-ylmethyl)-1H-indazol-5-yl)-6-thioxo-5,7-diazaspiro[3.4]octan-7-yl)-3-(trifluoromethyl)picolinonitrile (0.231 g, 0.428 mmol) in DCE (6 mL). The mixture was stirred at room temperature for 5 min, before Sodium triacetoxyborohydride (0.272 g, 1.28 mmol) was added. The reaction was stirred at RT overnight and diluted with aqueous saturated NaHCO$_3$. The solution was extracted with EtOAc and the organic layer was washed successively with water, brine, dried over MgSO$_4$, filtered and concentrated to give 5-(5-(1-(1-methylpiperidin-4-yl)methyl)-1H-indazol-5-yl)-8-oxo-6-thioxo-5,7-diazaspiro[3.4]octan-7-yl)-3-(trifluoromethyl)picolinonitrile as a solid (0.163 g, 67%). $^1$H NMR (300 MHz, Chloroform-d) δ 1.47-1.62 (m, 2H), 1.69 (d, J=11.5 Hz, 3H), 1.94-2.17 (m, 2H), 2.18-2.28 (m, 1H), 2.31 (s, 3H), 2.52-2.80 (m, 4H), 2.93 (d, J=11.5 Hz, 2H), 4.32 (d, J=6.9 Hz, 2H), 7.22-7.30 (m, 1H), 7.58 (d, J=8.9 Hz, 1H), 7.70 (d, J=1.9 Hz, 1H), 8.12 (s, 1H), 8.39 (d, J=2.2 Hz, 1H), 9.13 (d, J=2.2 Hz, 1H). $C_{27}H_{26}F_3N_7OS$ MS m/z 554.0 (M+H)$^+$.

Following the procedure described in Example 24, above, selecting and substituting the appropriate reagents, starting materials, and purification methods, and adjusting reaction temperatures, times and other variables or parameters, as needed or desirable, as would be readily recognized by those skilled in the art, the following compounds of Formula (I) of the invention were prepared.

| Cpd No. | Structure | Compound Name & Physical Data |
|---|---|---|
| 122 | 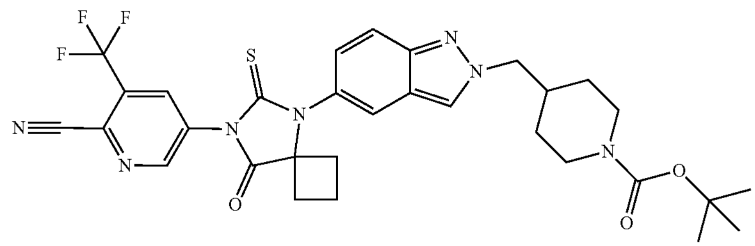 [SMILES: CC(C)(C)OC(=O)N1CCC(Cn2cc3cc(N4C(=S)N(c5cnc(C#N)c(C(F)(F)F)c5)C(=O)C45CCC5)ccc3n2)CC1] | tert-Butyl 4-[[5-[6-[6-cyano-5-(trifluoromethyl)-3-pyridyl]-5-oxo-7-thioxo-6,8-diazaspiro[3.4]octan-8-yl]indazol-2-yl]methyl]piperidine-1-carboxylate.<br>$^1$H NMR (300 MHz, Chloroform-d) δ 1.15-1.37 (m, 2H), 1.45 (s, 9H), 1.56-1.75 (m, 3H), 2.14-2.41 (m, 2H), 2.54-2.84 (m, 6H), 4.14 (d, J = 13.0 Hz, 2H), 4.34 (d, J = 7.1 Hz, 2H), 7.13 (dd, J = 9.1, 2.0 Hz, 1H), 7.65 (d, J = 1.9 Hz, 1H), 7.89 (d, J = 9.1 Hz, 1H), 8.03 (s, 1H), 8.40 (d, J = 2.2 Hz, 1H), 9.13 (d, J = 2.2 Hz, 1H). $C_{31}H_{32}F_3N_7O_3S$ MS m/z 540.0 (M − 100 + H)$^+$ |
| 126 | 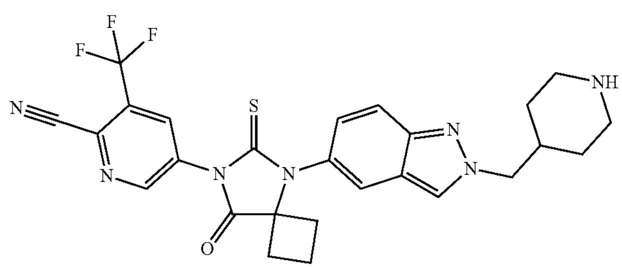 [SMILES: N#Cc1ncc(N2C(=O)C3(CCC3)N(c3ccc4nn(CC5CCNCC5)cc4c3)C2=S)cc1C(F)(F)F] | 5-[5-oxo-8-[2-(4-piperidylmethyl)indazol-5-yl]-7-thioxo-6,8-diazaspiro[3.4]octan-6-yl]-3-(trifluoromethyl)pyridine-2-carbonitrile.<br>$^1$H NMR (300 MHz, Chloroform-d) δ 1.60-1.72 (m, 1H), 1.73-1.90 (m, 4H), 2.14-2.34 (m, 1H), 2.38-2.52 (m, 0H), 2.57-2.74 (m, 4H), 2.76-2.98 (m, 2H), 3.46 (d, J = 12.7 Hz, 2H), 4.38 (d, J = 7.2 Hz, 2H), 7.13 (dd, J = 9.1, 2.0 Hz, 1H), 7.61-7.68 (m, 1H), 7.85 (d, J = 9.1 Hz, 1H), 8.07 (s, 1H), 8.39 (d, J = 2.3 Hz, 1H), 9.12 (d, J = 2.2 Hz, 1H).<br>$C_{26}H_{24}F_3N_7OS$ MS m/z 539.9 (M + H)+ |
| 129 | 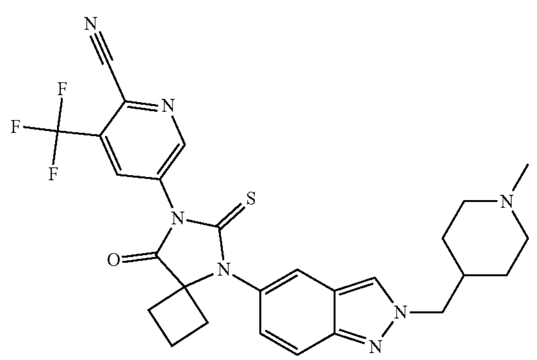 [SMILES: CN1CCC(Cn2cc3cc(N4C(=S)N(c5cnc(C#N)c(C(F)(F)F)c5)C(=O)C45CCC5)ccc3n2)CC1] | 5-[8-[2-[(1-methyl-4-piperidyl)methyl]indazol-5-yl]-5-oxo-7-thioxo-6,8-diazaspiro[3.4]octan-6-yl]-3-(trifluoromethyl)pyridine-2-carbonitrile.<br>$^1$H NMR (300 MHz, Chloroform-d) δ 1.34-1.57 (m, 2H), 1.59-1.69 (m, 3H), 1.91-2.06 (m, 3H), 2.17-2.26 (m, 1H), 2.29 (s, 3H), 2.54-2.74 (m, 4H), 2.90 (d, J = 11.2 Hz, 2H), 4.34 (d, J = 7.1 Hz, 2H), 7.12 (dd, J = 9.1, 2.0 Hz, 1H), 7.65 (d, J = 1.9 Hz, 1H), 7.88 (d, J = 9.1 Hz, 1H), 8.04 (s, 1H), 8.40 (d, J = 2.2 Hz, 1H), 9.13 (d, J = 2.2 Hz, 1H).<br>$C_{27}H_{26}F_3N_7OS$ MS m/z 554.0 (M + H)+ |

Example 25

5-[8-[1-[(1-acetyl-4-piperidyl)methyl]indazol-5-yl]-5-oxo-7-thioxo-6,8-diazaspiro[3.4]octan-6-yl]-3-(trifluoromethyl)pyridine-2-carbonitrile, Cpd 124

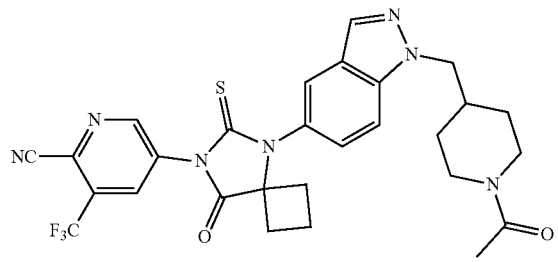 [SMILES: CC(=O)N1CCC(Cn2ncc3cc(N4C(=S)N(c5cnc(C#N)c(C(F)(F)F)c5)C(=O)C45CCC5)ccc32)CC1]

To a mixture of 5-(8-oxo-5-(1-(piperidin-4-ylmethyl)-1H-indazol-5-yl)-6-thioxo-5,7-diazaspiro[3.4]octan-7-yl)-3-(trifluoromethyl)picolinonitrile (0.134 g, 0.248 mmol), Et$_3$N (0.052 mL, 0.372 mmol) and DMAP (3 mg) in DCM (0.62 mL) was added acetic anhydride (0.028 mL, 0.298 mmol). After stirring at RT overnight the reaction mixture was concentrated and diluted with DCM. The solution was washed with aqueous saturated NaHCO$_3$ and brine. The organic layer was dried over MgSO$_4$, filtered and concentrated to dryness. The crude material was purified by chromatography over silica gel (gradient of MeOH in DCM from 0 to 10%) to yield 5-(5-(1-(1-acetylpiperidin-4-yl)methyl)-1H-indazol-5-yl)-8-oxo-6-thioxo-5,7-diazaspiro[3.4]octan-7-yl)-3-(trifluoromethyl)picolinonitrile as a solid (0.087 g, 60%). $^1$H NMR (300 MHz, Chloroform-d) δ 1.32 (ddd, J=17.7, 12.6, 4.6 Hz, 2H), 1.63-1.85 (m, 3H), 2.10 (s, 3H), 2.21-2.41 (m, 2H), 2.46-2.81 (m, 5H), 2.97-3.14 (m, 1H), 3.86 (d, J=13.6 Hz, 1H), 4.34 (d, J=6.9 Hz, 2H), 4.67 (d, J=13.4 Hz, 1H), 7.21-7.34 (m, 1H), 7.59 (d, J=8.9 Hz, 1H), 7.73 (d, J=1.9 Hz, 1H), 8.14 (s, 1H), 8.41 (d, J=2.2 Hz, 1H), 9.14 (d, J=2.2 Hz, 1H). C$_{28}$H$_{26}$F$_3$N$_7$O$_2$S MS m/z 581.9 (M+H)$^+$.

Example 26

5-(5-(4-(3-(dimethylamino)oxetan-3-yl)phenyl)-8-oxo-6-thioxo-5,7-diazaspiro[3.4]octan-7-yl)-3-(trifluoromethyl)picolinonitrile, Cpd 197

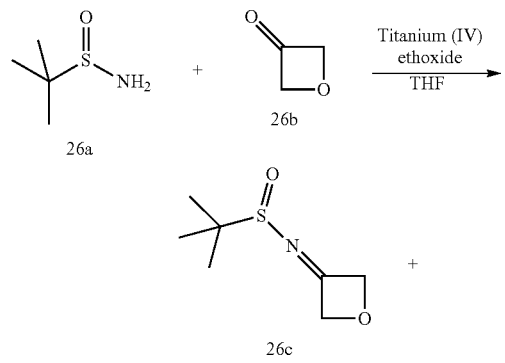

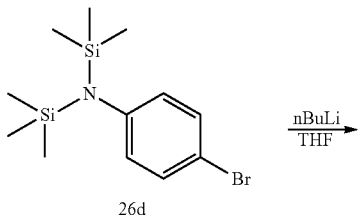

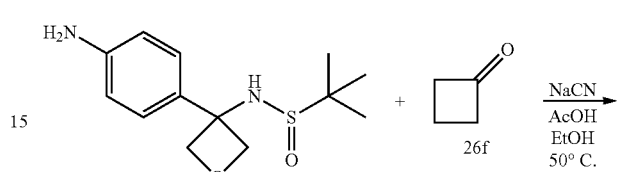

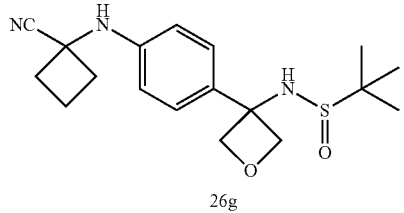

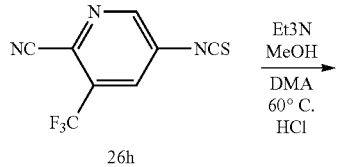

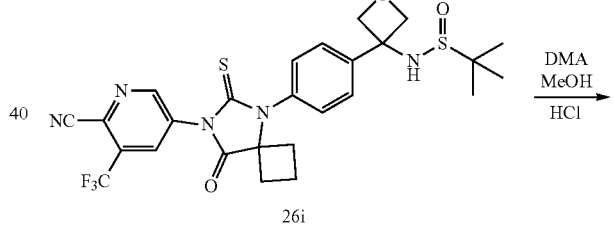

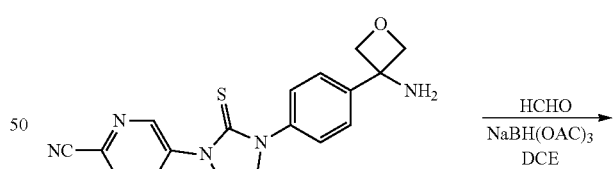

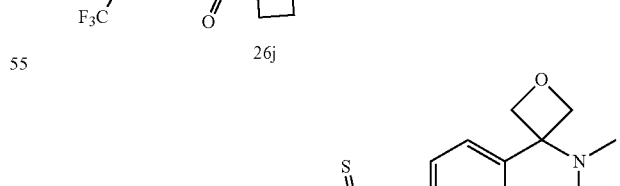

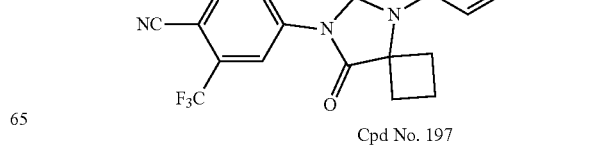

Cpd No. 197

A. 2-methyl-N-(oxetan-3-ylidene)propane-2-sulfinamide, 26e

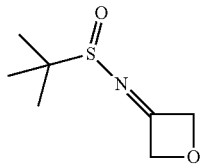

To a solution of 2-methylpropane-2-sulfinamide (2.424 g, 20 mmol) and oxetan-3-one (1.41 mL, 24 mmol) in THF (40 mL) was added dropwise over 15 min Titanium (IV) ethoxide (8.38 mL, 40 mmol) under a nitrogen atmosphere at RT and the mixture was stirred at 60° C. overnight. The reaction mixture was allowed to cool to RT. The mixture was quenched with chilled aqueous saturated NaHCO$_3$ and diluted with EtOAc. The suspension was filtered through diatomaceous earth and the organic layer was washed with aqueous saturated NaHCO$_3$, brine, dried over MgSO$_4$, filtered and concentrated to dryness. The crude material was purified by chromatography over silica gel (gradient of EA in heptane from 10 to 100%). The fractions with product were collected and concentrated under reduced pressure to yield 2-methyl-N-(oxetan-3-ylidene)propane-2-sulfinamide (1 g, 29%). $^1$H NMR (300 MHz, Chloroform-d) δ 1.28 (s, 9H), 5.37-5.58 (m, 2H), 5.61-5.87 (m, 2H). C$_7$H$_{13}$NO$_2$S MS m/z 176.1 (M+H)$^+$.

B. N-(3-(4-aminophenyl)oxetan-3-yl)-2-methylpropane-2-sulfinamide, 26e

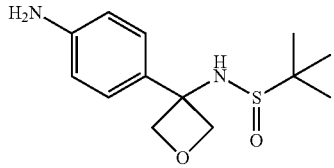 [SMILES: CC(C)(C)S(=O)NC1(c2ccc(N)cc2)COC1]

n-Butyl lithium (1.65M in hexanes, 3.29 mL, 5.27 mmol) was added to a solution of 4-Bromo-N,N-bis(trimethylsilyl)aniline (1.488 mL, 5.27 mmol) in THF (18 mL) at −78° C. under nitrogen. After stirring at −78° C. for 1 h, a solution of 2-methyl-N-(oxetan-3-ylidene)propane-2-sulfinamide (0.77 g, 4.39 mmol) was added over 15 min at −78° C. under nitrogen. After stirring at −78° C. for 1 h, the mixture was allowed to warm to RT and stirred at RT overnight. The mixture was poured into chilled aqueous saturated NaHCO$_3$ and extracted with EtOAc. The organic layer was acidified with acetic acid and oxalic acid then the mixture was basified with NaHCO$_3$ and Na$_2$CO$_3$. The organic layer was dried over MgSO$_4$, filtered and concentrated under high vacuum to yield N-(3-(4-aminophenyl)oxetan-3-yl)-2-methylpropane-2-sulfinamide (0.76 g, 64%) used directly into the next step. $^1$H NMR (300 MHz, Chloroform-d) δ 1.20 (s, 9H), 4.95-5.05 (m, 4H), 5.11-5.19 (m, 1H), 6.70 (d, J=8.5 Hz, 2H), 7.13 (d, J=8.5 Hz, 2H). C$_{13}$H$_{20}$N$_2$O$_2$S MS m/z 269.2 (M+H)$^+$.

C. N-(3-(4-((1-cyanocyclobutyl)amino)phenyl)oxetan-3-yl)-2-methylpropane-2-sulfinamide, 26g

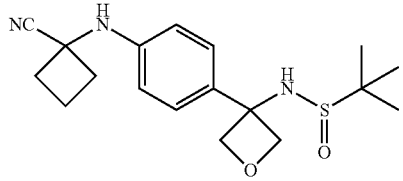 [SMILES: CC(C)(C)S(=O)NC1(c2ccc(NC3(C#N)CCC3)cc2)COC1]

N-(3-(4-aminophenyl)oxetan-3-yl)-2-methylpropane-2-sulfinamide (0.76 g, 2.83 mmol) and cyclobutanone (0.423 mL, 5.664 mmol) were mixed in acetic acid (2.3 mL) and ethanol (2.3 mL). Sodium cyanide (0.555 g, 11.328 mmol) was added and the mixture was stirred at 50° C. overnight and then allowed to cool to room temperature. The mixture was then poured into water and extracted with DCM. The organic layer was dried over MgSO$_4$, filtered and concentrated to dryness. The crude material was purified by chromatography over silica gel (gradient of MeOH in DCM from 0 to 10%). The fractions with product were collected and concentrated under reduced pressure to yield N-(3-(4-((1-cyanocyclobutyl)amino)phenyl)oxetan-3-yl)-2-methylpropane-2-sulfinamide as a solid (0.785 g, 80%). C$_{18}$H$_{25}$N$_3$O$_2$S MS m/z 348.2 (M+H)$^+$.

D. N-(3-(4-(7-(6-cyano-5-(trifluoromethyl)pyridin-3-yl)-8-oxo-6-thioxo-5,7-diazaspiro[3.4]octan-5-yl)phenyl)oxetan-3-yl)-2-methylpropane-2-sulfinamide and 5-(5-(4-(3-aminooxetan-3-yl)phenyl)-8-oxo-6-thioxo-5,7-diazaspiro[3.4]octan-7-yl)-3-(trifluoromethyl)picolinonitrile, 26i and 26j

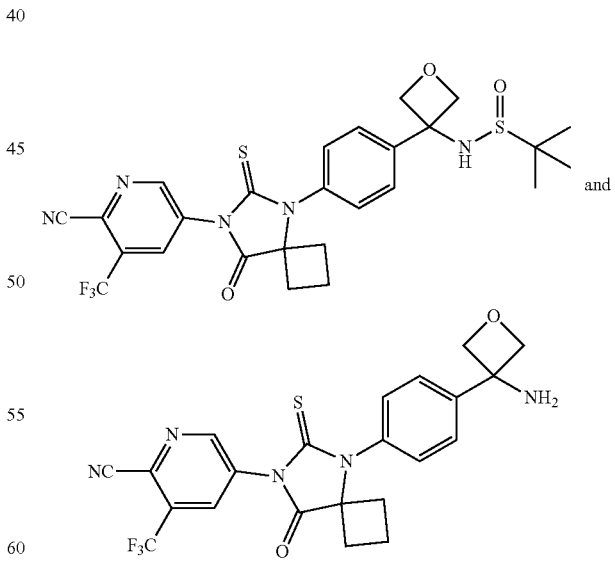

N-(3-(4-((1-cyanocyclobutyl)amino)phenyl)oxetan-3-yl)-2-methylpropane-2-sulfinamide (0.353 g, 1.016 mmol), and freshly prepared 5-Isothiocyanato-3-trifluoromethyl-pyridine-2-carbonitrile (0.379 g, 1.125 mmol) were heated at 60° C. in DMA (4.1 mL) overnight and then allowed to cool to room temperature. The mixture was diluted with MeOH (5.12 mL) and 1M HCl (2.03 mL) and stirred at RT for 30 min. EA was added and the solution washed with water, aqueous saturated NaHCO$_3$ and brine. The organic layer was dried over MgSO$_4$, filtered and concentrated to dryness. The crude material was purified by chromatography over silica gel (gradient of EA in heptane from 0 to 100%). The fractions with products were collected and concentrated under reduced pressure. The raw material was purified by using a GILSON Semi-Preparative System, operated by Trilution software, equipped with a Phenomenex Gemini C18 100A column (100 mm long×30 mm I.D.; 5 μm particles) at 25° C., with a flow rate of 40 mL/min. A gradient elution was performed from 70% of a 65 mM aqueous solution of Ammonium acetate (pH 7)/30% Acetonitrile to 73% of a 65 mM aqueous solution of Ammonium acetate (pH 7)/27% Acetonitrile in 20 min. Pure fractions were combined, neutralized with NaHCO$_3$ solution and extracted with dichloromethane. The organic layer was washed with brine, dried over MgSO$_4$ and concentrated to afford pure N-(3-(4-(7-(6-cyano-5-(trifluoromethyl)pyridin-3-yl)-8-oxo-6-thioxo-5,7-diazaspiro[3.4]octan-5-yl)phenyl) oxetan-3-yl)-2-methylpropane-2-sulfinamide (0.192 g, 33%) and pure 5-(5-(4-(3-aminooxetan-3-yl)phenyl)-8-oxo-6-thioxo-5,7-diazaspiro[3.4]octan-7-yl)-3-(trifluoromethyl) picolinonitrile (0.041 g, 9%)

5-(5-(4-(3-aminooxetan-3-yl)phenyl)-8-oxo-6-thioxo-5,7-diazaspiro[3.4]octan-7-yl)-3-(trifluoromethyl)picolinonitrile, 26j $^1$H NMR (300 MHz, Chloroform-d) δ 1.63-1.80 (m, 1H), 2.15-2.37 (m, 1H), 2.51-2.84 (m, 4H), 4.80 (d, J=6.5 Hz, 2H), 5.02 (d, J=6.5 Hz, 2H), 7.37 (d, J=8.5 Hz, 1H), 7.85 (d, J=8.5 Hz, 2H), 8.37 (d, J=2.3 Hz, 1H), 9.11 (d, J=2.3 Hz, 1H). C$_{22}$H$_{18}$F$_3$N$_5$O$_2$S MS m/z 473.9 (M+H)$^+$.

Isolation of Additional 5-(5-(4-(3-aminooxetan-3-yl) phenyl)-8-oxo-6-thioxo-5,7-diazaspiro[3.4]octan-7-yl)-3-(trifluoromethyl)picolinonitrile, 26j

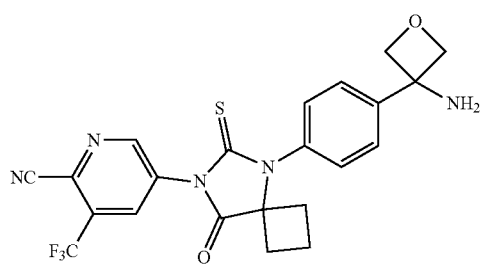 [SMILES: N#Cc1ncc(N2C(=O)C3(CCC3)N(c3ccc(C4(N)COC4)cc3)C2=S)cc1C(F)(F)F]

To a solution of N-(3-(4-(7-(6-cyano-5-(trifluoromethyl) pyridin-3-yl)-8-oxo-6-thioxo-5,7-diazaspiro[3.4]octan-5-yl) phenyl)oxetan-3-yl)-2-methylpropane-2-sulfinamide (0.168 g, 0.157 mmol) in DMA (3.5 mL) and MeOH (3.5 mL) was added aqueous 2.0M HCl (0.7 mL, 1.4 mmol). The mixture was stirred for 30 min at RT; additional aqueous 2.0M HCl (0.2 mL, 0.4 mmol) was added. After stirring at RT for 1 day the mixture was poured onto ice and diluted with EtOAc. The organic layer was washed with water, aqueous saturated NaHCO$_3$, brine, dried over MgSO$_4$, filtered and concentrated to dryness to yield 5-(5-(4-(3-aminooxetan-3-yl)phenyl)-8-oxo-6-thioxo-5,7-diazaspiro[3.4]octan-7-yl)-3-(trifluoromethyl)picolinonitrile as a solid (0.074 g, 100%). $^1$H NMR (300 MHz, Chloroform-d) δ 1.63-1.80 (m, 1H), 2.15-2.37 (m, 1H), 2.51-2.84 (m, 4H), 4.80 (d, J=6.5 Hz, 2H), 5.02 (d, J=6.5 Hz, 2H), 7.37 (d, J=8.5 Hz, 1H), 7.85 (d, J=8.5 Hz, 2H), 8.37 (d, J=2.3 Hz, 1H), 9.11 (d, J=2.3 Hz, 1H). C$_{22}$H$_{18}$F$_3$N$_5$O$_2$S MS m/z 473.9 (M+H)$^+$.

E. 5-(5-(4-(3-(dimethylamino)oxetan-3-yl)phenyl)-8-oxo-6-thioxo-5,7-diazaspiro[3.4]octan-7-yl)-3-(trifluoromethyl)picolinonitrile, Cpd 197

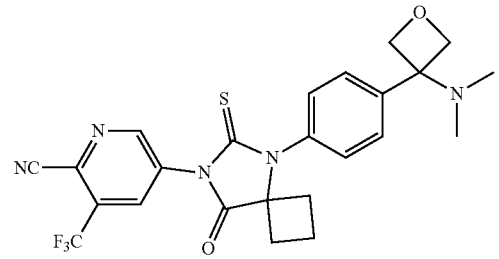 [SMILES: CN(C)C1(c2ccc(N3C(=S)N(c4cnc(C#N)c(C(F)(F)F)c4)C(=O)C34CCC4)cc2)COC1]

Formaldehyde (37% wt in water, 0.013 mL, 0.471 mmol) was added to a solution of yield 5-(5-(4-(3-aminooxetan-3-yl)phenyl)-8-oxo-6-thioxo-5,7-diazaspiro[3.4]octan-7-yl)-3-(trifluoromethyl)picolinonitrile (0.074 g, 0.157 mmol) in DCE (3 mL). The mixture was stirred at room temperature for 5 min, before Sodium triacetoxyborohydride (0.099 g, 0.471 mmol) was added. The reaction was stirred at RT overnight and diluted with aqueous saturated NaHCO$_3$. The solution was extracted with DCM and the organic layer was dried over MgSO$_4$, filtered and concentrated to give a residue The raw material was purified by using a GILSON Semi-Preparative System, operated by Trilution software, equipped with a Phenomenex Gemini C18 100A column (100 mm long×30 mm I.D.; 5 1.μm particles) at 25° C., with a flow rate of 40 mL/min. A gradient elution was performed from 70% of a 25 mM aqueous solution of Ammonium bicarbonate (pH 8)/30% Acetonitrile-Methanol (1:1 mixture) to 73% of a 25 mM aqueous solution of Ammonium bicarbonate (pH 8)/27% Acetonitrile-Methanol (1:1 mixture) in 20 min. Pure fractions were combined and extracted with dichloromethane. The organic layer was washed with brine, dried over MgSO$_4$ and concentrated to afford pure 5-(5-(4-(3-(dimethylamino)oxetan-3-yl)phenyl)-8-oxo-6-thioxo-5,7-diazaspiro[3.4]octan-7-yl)-3-(trifluoromethyl)picolinonitrile as a pale yellow solid (0.048 g, 61%). $^1$H NMR (300 MHz, Chloroform-d) δ 1.62-1.80 (m, 1H), 2.15 (s, 6H), 2.18-2.37 (m, 1H), 2.50-2.78 (m, 4H), 4.79-5.11 (m, 4H), 7.29-7.41 (m, 4H), 8.38 (d, J=2.2 Hz, 1H), 9.11 (d, J=2.2 Hz, 1H). C$_{24}$H$_{22}$F$_3$N$_5$O$_2$S MS m/z 502.1 (M+H)$^+$.

Following the procedure described in Example 26, above, selecting and substituting the appropriate reagents, starting materials, and purification methods, and adjusting reaction temperatures, times and other variables or parameters, as needed or desirable, as would be readily recognized by those skilled in the art, the following compound of Formula (I) of the invention was prepared.

| Cpd No. | Structure | Compound Name & Physical Data |
|---|---|---|
| 196 | 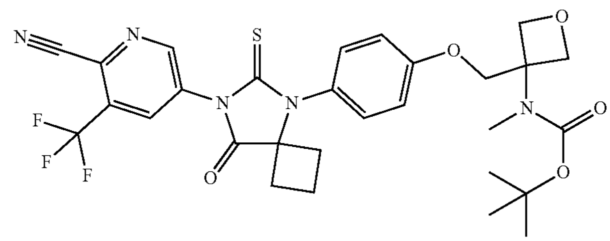 [SMILES: CN(C(=O)OC(C)(C)C)C1(COc2ccc(N3C(=S)N(c4cnc(C#N)c(C(F)(F)F)c4)C(=O)C34CCC4)cc2)COC1] | tert-butyl N-[3-[[4-[6-[6-cyano-5-(trifluoromethyl)-3-pyridyl]-5-oxo-7-thioxo-6,8-diazaspiro[3.4]octan-8-yl]phenoxy]methyl]oxetan-3-yl]-N-methyl-carbamate. $^1$H NMR (300 MHz, DMSO-$d_6$) δ 1.38 (s, 9H), 1.45-1.65 (m, 1H), 1.86-2.07 (m, 1H), 2.36-2.48 (m, 2H), 2.55-2.68 (m, 2H), 2.77 (s, 3H), 4.31-4.42 (m, 2H), 4.46 (s, 2H), 4.67-4.81 (m, 2H), 7.22 (d, J = 8.5 Hz, 2H), 7.35 (d, J = 8.5 Hz, 2H), 8.76 (d, J = 2.1 Hz, 1H), 9.22 (d, J = 2.0 Hz, 1H). $C_{29}H_{30}F_3N_5O_5S$ MS m/z 640 (M + Na)$^+$ |

Example 27

5-[8-(4-bromophenyl)-5-oxo-7-thioxo-6,8-diazaspiro[3.4]octan-6-yl]-3-(trifluoromethyl)pyridine-2-carbonitrile, Cpd 28

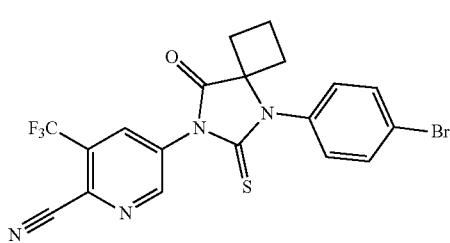 [SMILES: N#Cc1ncc(N2C(=O)C3(CCC3)N(c3ccc(Br)cc3)C2=S)cc1C(F)(F)F]

1-((4-bromophenyl)amino)cyclobutanecarbonitrile (9.79 g, 39 mmol), and freshly prepared 5-Isothiocyanato-3-trifluoromethyl-pyridine-2-carbonitrile (9.3 g, 32.46 mmol) were heated at 60° C. in DMA (50 mL) for 2 h and then allowed to cool to room temperature. The mixture was diluted with MeOH (50 mL) and 2M HCl (50 mL) and stirred at 60° C. for another 2 h. EA was added and the organic layer was dried over MgSO$_4$, filtered and concentrated under reduced pressure. The crude material was purified by reverse phase preparative HPLC (Column: SYNERGI, Flow rate: 80 mL/min, Mobile Phase A: Purified water (containing 0.1% TFA), Mobile Phase B: acetonitrile, Gradient: 55-98(% B) from 0-35 min). The desired fractions were collected and the pH adjusted to 8 using 10% aqueous NaHCO$_3$. The solution was concentrated under reduced pressure and extracted with EtOAc. The organic layers were washed with brine, dried over MgSO$_4$, filtered and concentrated under reduced pressure to yield 5-(5-(4-bromophenyl)-8-oxo-6-thioxo-5,7-diazaspiro[3.4]octan-7-yl)-3-(trifluoromethyl)picolinonitrile as a solid (5 g, 32%). $^1$H NMR (400 MHz, Chloroform-d) δ ppm ppm 1.68-1.78 (m, 1H) 2.18-2.34 (m, 1H) 2.49-2.62 (m, 2H) 2.66-2.77 (m, 2H) 7.18-7.24 (m, 2H) 7.72-7.79 (m, 2H) 8.36 (d, J=2.26 Hz, 1H) 9.10 (d, J=2.26 Hz, 1H). $C_{19}H_{12}BrF_3N_4OS$ MS m/z 483 (M+H)$^+$.

Example 28

5-(5-(4-(8-methyl-8-azabicyclo[3.2.1]octan-3-yl)phenyl)-8-oxo-6-thioxo-5,7-diazaspiro[3.4]octan-7-yl)-3-(trifluoromethyl)picolinonitrile, Cpd 114

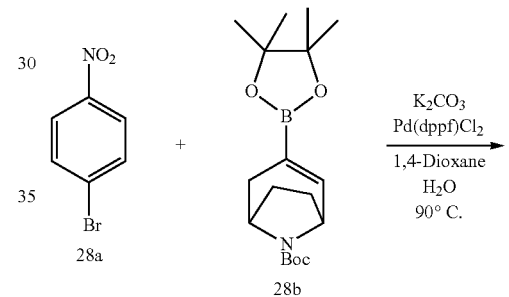

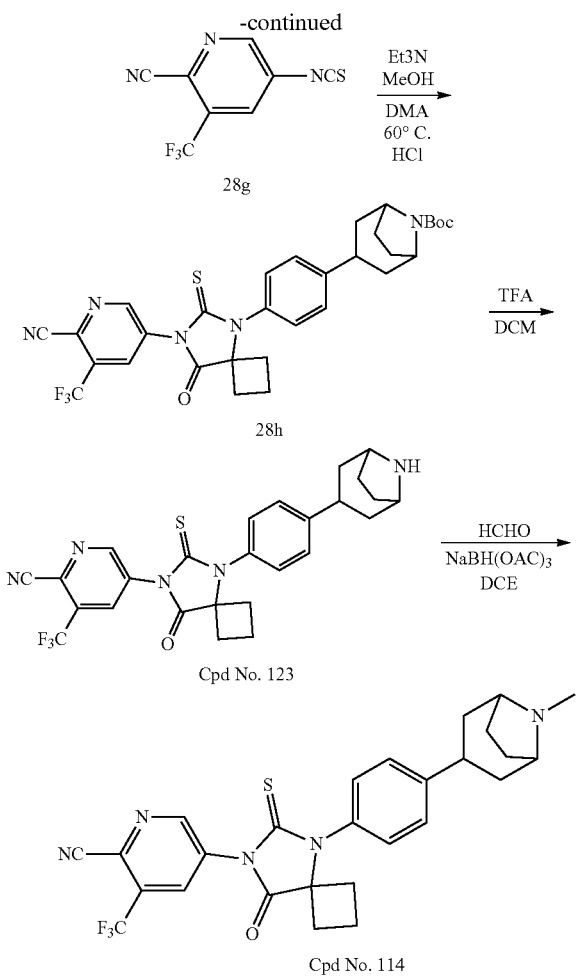

Cpd No. 123

Cpd No. 114

A. tert-Butyl 3-(4-nitrophenyl)-8-azabicyclo[3.2.1]oct-3-ene-8-carboxylate, 28c

A mixture of 1-bromo-4-nitrobenzene (0.3 g, 1.485 mmol), tert-butyl 3-(4,4,5,5-tetramethyl-1,3,2-dioxaborolan-2-yl)-8-azabicyclo[3.2.1]oct-2-ene-8-carboxylate (0.647 g, 1.931 mmol), potassium carbonate (0.616 g, 4.455 mmol), Pd(dppf)Cl2 (0.121 g, 0.148 mmol) in 1,4-Dioxane (6 mL) and water (3 mL) was stirred at 90° C. overnight then allowed to cool to RT. The mixture was filtered through diatomaceous earth; the organic layer was washed with water, brine, dried over MgSO4, filtered and concentrated to dryness. The crude material was purified by chromatography over silica gel (gradient of MeOH in DCM from 0 to 10%). The fractions with products were collected and concentrated under reduced pressure to yield tert-butyl 3-(4-nitrophenyl)-8-azabicyclo[3.2.1]oct-3-ene-8-carboxylate as a solid (0.490 g, 100%). $C_{18}H_{22}N_2O_4$ MS m/z 275.1 $(M-55)^+$.

B. tert-Butyl 3-(4-aminophenyl)-8-azabicyclo[3.2.1]octane-8-carboxylate, 28d

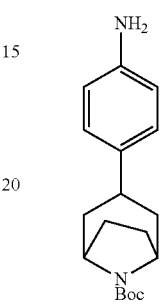

A solution of tert-butyl 3-(4-nitrophenyl)-8-azabicyclo[3.2.1]oct-3-ene-8-carboxylate (0.491 g, 1.485 mmol) in EtOAc 4.5 mL) was purged using nitrogen and reduced pressure. Palladium on charcoal (10% wet) was added and the mixture was hydrogenated overnight. The reaction mixture was filtered through diatomaceous earth and concentrated under reduced pressure to give tert-butyl 4-((5-amino-1H-indazol-1-yl)methyl)piperidine-1-carboxylate used directly into the next step. $C_{18}H_{26}N_2O_2$ MS m/z 303.2 $(M+H)^+$.

C. (tert-Butyl 3-(4-((1-cyanocyclobutyl)amino)phenyl)-8-azabicyclo[3.2.1]octane-8-carboxylate, 28f

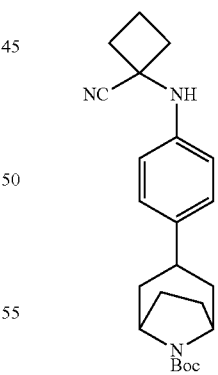

tert-Butyl 4-((5-amino-1H-indazol-1-yl)methyl)piperidine-1-carboxylate (0.449 g, 1.485 mmol) and cyclobutanone (0.222 mL, 2.97 mmol) were mixed in acetic acid (1.2 mL) and ethanol (1.2 mL). Sodium cyanide (0.291 g, 5.94 mmol) was added and the mixture was stirred at 50° C. overnight and then allowed to cool to room temperature. The mixture was then poured into water and extracted with DCM. The organic layer was dried over MgSO4, filtered and

353 concentrated to dryness. The crude material was purified by chromatography over silica gel (gradient of EtOAc in Heptane from 5 to 80%). The fractions with product were collected and concentrated under reduced pressure to yield tert-butyl 3-(4-((1-cyanocyclobutyl)amino)phenyl)-8-azabicyclo[3.2.1]octane-8-carboxylate as a solid (0.486 g, 86%). $C_{23}H_{31}N_3O_2$ MS m/z 382.3 $(M+H)^+$.

D. tert-Butyl 3-(4-(7-(6-cyano-5-(trifluoromethyl)pyridin-3-yl)-8-oxo-6-thioxo-5,7-diazaspiro[3.4]octan-5-yl)phenyl)-8-azabicyclo[3.2.1]octane-8-carboxylate, 28h

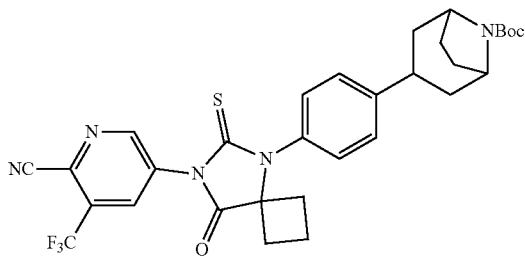 [SMILES: CC(C)(C)OC(=O)N1C2CCC1CC(c1ccc(N3C(=S)N(c4cnc(C#N)c(C(F)(F)F)c4)C(=O)C34CCC4)cc1)C2]

tert-Butyl 3-(4-((1-cyanocyclobutyl)amino)phenyl)-8-azabicyclo[3.2.1]octane-8-carboxylate (0.53 g, 1.39 mmol), and freshly prepared 5-Isothiocyanato-3-trifluoromethyl-pyridine-2-carbonitrile (0.516 g, 1.53 mmol) were heated at 60° C. in DMA (4.06 mL) overnight and then allowed to cool to room temperature. The mixture was diluted with MeOH (3 mL) and 1M HCl (3 mL) and stirred at RT for 30 min. EA was added and the solution was washed with water, aqueous saturated $NaHCO_3$ and brine. The organic layer was dried over $MgSO_4$, filtered and concentrated to dryness. The crude material was purified by chromatography over silica gel (gradient of EA in heptane from 5 to 40%). The fractions with product were collected and concentrated under reduced pressure to yield tert-butyl 3-(4-(7-(6-cyano-5-(trifluoromethyl)pyridin-3-yl)-8-oxo-6-thioxo-5,7-diazaspiro[3.4]octan-5-yl)phenyl)-8-azabicyclo[3.2.1]octane-8-carboxylate as a yellow solid (0.445 g, 52%). Another aliquot (0.073 g) was purified by reverse phase preparative HPLC to yield titled product as a yellow solid (0.038 g).

HPLC Conditions: GILSON Semi-Prepeparative System, operated by Trilution software, equipped with a Phenomenex Gemini C18 100A column (100 mm long×30 mm I.D.; 5 µm particles) at 25° C., with a flow rate of 40 mL/min. A gradient elution was performed from 49% of a 0.1% HCOOH aqueous solution (pH 3)/51% Acetonitrile to 6% of a 0.1% HCOOH aqueous solution (pH 3)/94% Acetonitrile in 20 min. The injection volume was 8000 µL. Acquisition frequency was set to 254 nm for the UV-Dual detector. $^1$H NMR (300 MHz, Chloroform-d) δ 1.51 (s, 9H), 1.53-1.56 (m, 4H), 1.59-1.74 (m, 1H), 1.75-1.89 (m, 1H), 1.96-2.15 (m, 2H), 2.15-2.34 (m, 1H), 2.62 (dq, J=20.8, 10.6, 10.1 Hz, 6H), 4.21-4.51 (m, 2H), 7.20-7.28 (m, 2H), 7.43 (t, J=8.3 Hz, 2H), 8.37 (d, J=2.2 Hz, 1H), 9.11 (d, J=2.2 Hz, 1H). $C_{31}H_{32}F_3N_5O_3S$ MS m/z 512.1 $(M-100+H)^+$.

354

E. 5-(5-(4-(8-azabicyclo[3.2.1]octan-3-yl)phenyl)-8-oxo-6-thioxo-5,7-diazaspiro[3.4]octan-7-yl)-3-(trifluoromethyl)picolinonitrile, Cpd 123

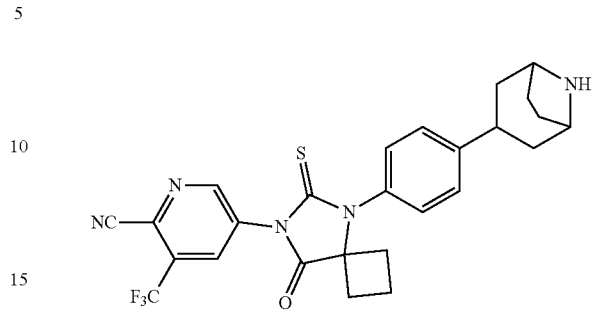

To a solution of tert-butyl 3-(4-(7-(6-cyano-5-(trifluoromethyl)pyridin-3-yl)-8-oxo-6-thioxo-5,7-diazaspiro[3.4]octan-5-yl)phenyl)-8-azabicyclo[3.2.1]octane-8-carboxylate (0.445 g, 0.728 mmol) in DCM (6 mL) was added TFA (4 mL). After stirring at RT for 3 h the reaction mixture was concentrated and evaporated with toluene. The mixture was poured into aqueous saturated $NaHCO_3$ and extracted with EtOAc. The organic layer was washed with water, brine, dried over $MgSO_4$, filtered and concentrated to dryness. The crude material was purified by chromatography over silica gel (gradient of 2 M $NH_3$/MeOH in DCM from 0 to 10%) to yield 5-(5-(4-(8-azabicyclo[3.2.1]octan-3-yl)phenyl)-8-oxo-6-thioxo-5,7-diazaspiro[3.4]octan-7-yl)-3-(trifluoromethyl)picolinonitrile as a solid (0.195 g, 52%). Another aliquot (0.087 g) was purified by reverse phase preparative HPLC to yield the title product as a yellow solid (0.068 g).

HPLC Conditions: GILSON Semi-Prepeparative System, operated by Trilution software, equipped with a Phenomenex Gemini C18 100A column (100 mm long×30 mm I.D.; 5 µm particles) at 25° C., with a flow rate of 40 mL/min. A gradient elution was performed from 70% of a 0.1% HCOOH aqueous solution (pH 3)/30% Acetonitrile to 73% of a 0.1% HCOOH aqueous solution (pH 3)/27% Acetonitrile in 20 min. The injection volume was 8000 µL. Acquisition frequency was set to 254 nm for the UV-Dual detector. $^1$H NMR (300 MHz, Chloroform-d) δ 1.58-1.77 (m, 4H), 1.83-2.00 (m, 1H), 2.07-2.30 (m, 1H), 2.34-2.80 (m, 10H), 3.71-3.97 (m, 2H), 7.21-7.29 (m, 2H), 7.46-7.54 (m, 2H), 8.37 (d, J=2.2 Hz, 1H), 9.11 (d, J=2.2 Hz, 1H). $C_{26}H_{24}F_3N_5OS$ MS m/z 512.0 $(M+H)^+$.

F. 5-(5-(4-(8-methyl-8-azabicyclo[3.2.1]octan-3-yl)phenyl)-8-oxo-6-thioxo-5,7-diazaspiro[3.4]octan-7-yl)-3-(trifluoromethyl)picolinonitrile, Cpd 114

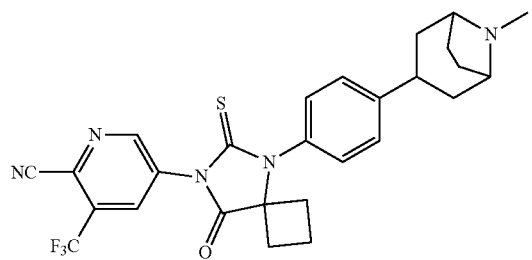 [SMILES: CN1C2CCC1CC(c1ccc(N3C(=S)N(c4cnc(C#N)c(C(F)(F)F)c4)C(=O)C34CCC4)cc1)C2]

Formaldehyde (37% wt in water, 0.047 mL, 0.633 mmol) was added to a solution of 5-(5-(4-(8-azabicyclo[3.2.1]octan-3-yl)phenyl)-8-oxo-6-thioxo-5,7-diazaspiro[3.4]octan-7-yl)-3-(trifluoromethyl)picolinonitrile (0.108 g, 0.211 mmol) in DCE (5 mL). The mixture was stirred at room temperature for 5 min, before Sodium triacetoxyborohydride (0.134 g, 0.633 mmol) was added. The reaction was stirred at RT overnight and diluted with aqueous saturated NaHCO$_3$. The solution was extracted with DCM and the organic layer was washed, dried over MgSO$_4$, filtered and concentrated to give a residue that was then purified by chromatography over silica gel (gradient of MeOH in DCM from 0 to 10%) to yield 5-(5-(4-(8-methyl-8-azabicyclo[3.2.1]octan-3-yl)phenyl)-8-oxo-6-thioxo-5,7-diazaspiro[3.4]octan-7-yl)-3-(trifluoromethyl)picolinonitrile as a beige solid (0.05 g, 45%). $^1$H NMR (300 MHz, Chloroform-d) δ 1.60-1.76 (m, 1H), 1.78-1.97 (m, 1H), 2.02-2.18 (m, 4H), 2.21-2.40 (m, 2H), 2.49-2.81 (m, 8H), 2.87-3.17 (m, 1H), 3.38-3.51 (m, 1H), 3.72-3.91 (m, 2H), 7.20-7.34 (m, 2H), 7.51-7.66 (m, 2H), 8.36 (d, J=2.3 Hz, 1H), 9.11 (d, J=2.3 Hz, 1H). C$_{27}$H$_{26}$F$_3$N$_5$OS MS m/z 526.0 (M+H)$^+$.

Following the procedure described in Example 28, above, selecting and substituting the appropriate reagents, starting materials, and purification methods, and adjusting reaction temperatures, times and other variables or parameters, as needed or desirable, as would be readily recognized by those skilled in the art, the following compounds of Formula (I) of the invention were prepared.

| Cpd No. | Structure | Compound Name & Physical Data |
|---|---|---|
| 116 | 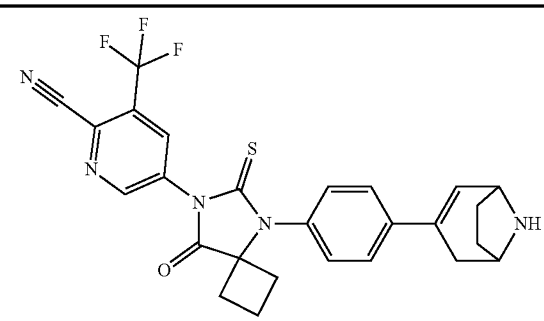 | 5-[8-[4-(8-azabicyclo[3.2.1]oct-3-en-3-yl)phenyl]-5-oxo-7-thioxo-6,8-diazaspiro[3.4]octan-6-yl]-3-(trifluoromethyl)pyridine-2-carbonitrile. $^1$H NMR (300 MHz, Chloroform-d) δ 1.62-1.74 (m, 2H), 1.75-1.93 (m, 1H), 2.10-2.33 (m, 4H), 2.39-2.61 (m, 2H), 2.62-2.79 (m, 2H), 3.33 (d, J = 17.6 Hz, 1H), 4.16-4.30 (m, 2H), 6.48 (d, J = 5.6 Hz, 1H), 7.19-7.35 (m, 2H), 7.59 (d, J = 8.2 Hz, 2H), 8.36 (d, J = 2.3 Hz, 1H), 9.10 (d, J = 2.3 Hz, 1H). C$_{26}$H$_{22}$F$_3$N$_5$OS MS m/z 510.1 (M + H)+ |
| 127 | 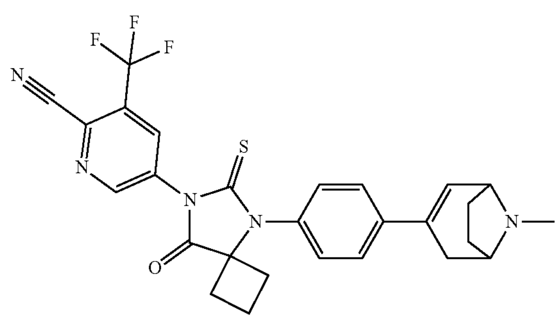 [SMILES: CN1C2C=C(c3ccc(N4C(=S)N(c5cnc(C#N)c(C(F)(F)F)c5)C(=O)C45CCC5)cc3)CC1CC2] | 5-[8-[4-(8-methyl-8-azabicyclo[3.2.1]oct-3-en-3-yl)phenyl]-5-oxo-7-thioxo-6,8-diazaspiro[3.4]octan-6-yl]-3-(trifluoromethyl)pyridine-2-carbonitrile. $^1$H NMR (300 MHz, DMSO-d$_6$) δ 1.49-1.62 (m, 1H), 1.91-2.05 (m, 2H), 2.13-2.47 (m, 5H), 2.58-2.73 (m, 2H), 2.78 (s, 3H), 3.06-3.28 (m, 1H), 3.46-3.71 (m, 1H), 4.03-4.36 (m, 2H), 6.45-6.71 (m, 1H), 7.44 (d, J = 8.3 Hz, 2H), 7.73 (d, J = 8.1 Hz, 2H), 8.76 (d, J = 2.1 Hz, 1H), 9.22 (d, J = 2.1 Hz, 1H). C$_{27}$H$_{24}$F$_3$N$_5$OS MS m/z 524.0 (M + H)+ |

Example 29

5-(8-oxo-5-(4-(4-(pyrrolidine-1-carbonyl)piperazin-1-yl)phenyl)-6-thioxo-5,7-diazaspiro[3.4]octan-7-yl)-3-(trifluoromethyl)picolinonitrile, Cpd 76

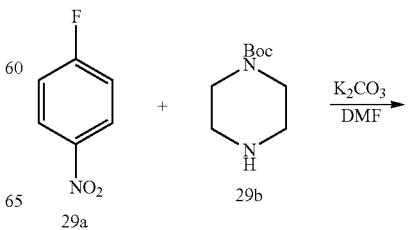

357
-continued

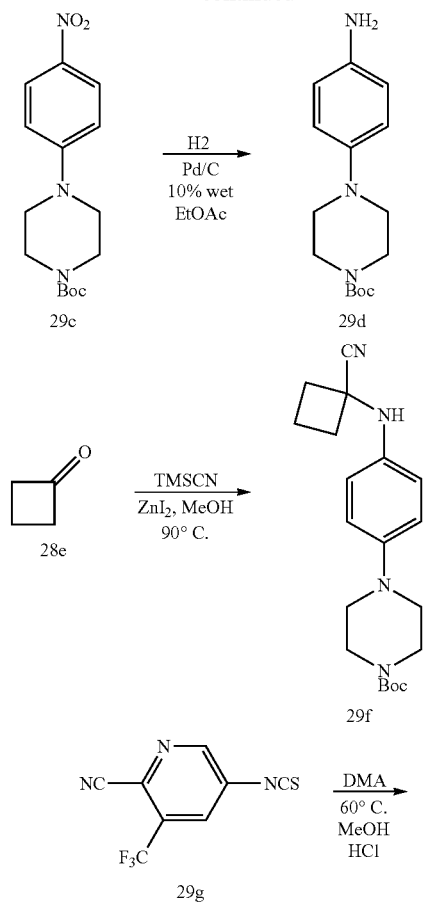

358

A. tert-Butyl 4-(4-nitrophenyl)piperazine-1-carboxylate, 29c

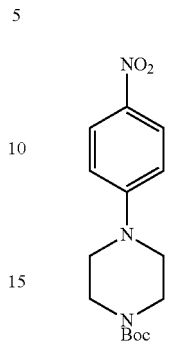

To a solution of 1-fluoro-4-nitrobenzene (5 g, 35.43 mmol) and tert-butyl piperazine-1-carboxylate (6.6 g, 35.43 mmol) in DMF (100 mL) was added potassium carbonate (14.7 g, 106.36 mmol) and the mixture was stirred at 50° C. for 18 h, then allowed to cool to room temperature and concentrated under reduced pressure. The oily residue was washed with diethyl ether (3x) to give tert-butyl 4-(4-nitrophenyl)piperazine-1-carboxylate as a yellow solid (8.2 g, 95%). $^1$H NMR (400 MHz, Chloroform-d) δ ppm 1.48 (s, 9H) 3.38-3.45 (m, 4H) 3.56-3.63 (m, 4H) 6.75-6.86 (m, 2H) 8.07-8.20 (m, 2H). $C_{15}H_{21}N_3O_4$ MS m/z 308.1 (M+H)$^+$

B. tert-Butyl 4-(4-aminophenyl)piperazine-1-carboxylate, 29d

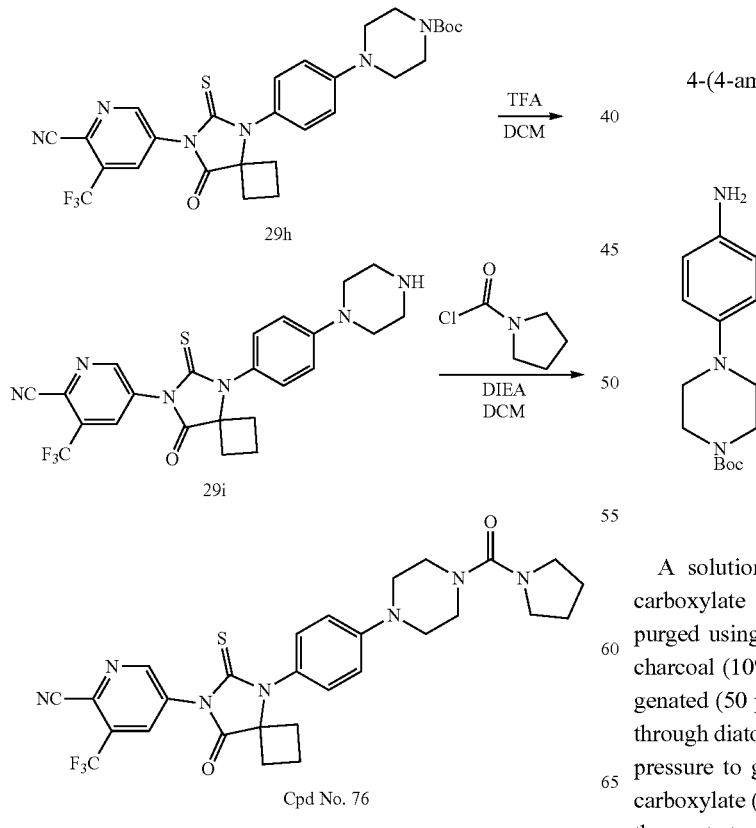

A solution of tert-butyl 4-(4-nitrophenyl)piperazine-1-carboxylate (8.2 g, 26.68 mmol) in MeOH (100 mL) was purged using nitrogen and reduced pressure. Palladium on charcoal (10% wet) was added and the mixture was hydrogenated (50 psi) for 16 h. The reaction mixture was filtered through diatomaceous earth and concentrated under reduced pressure to give tert-butyl 4-(4-aminophenyl)piperazine-1-carboxylate (7.4 g, 97%) as a dark blue oil used directly into the next step. $C_{15}H_{23}N_3O_2$ MS m/z 277.9 (M+H)$^+$.

C. tert-Butyl 4-(4-((1-cyanocyclobutyl)amino)phe-
nyl)piperazine-1-carboxylate, 29f

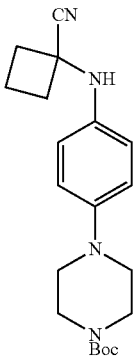 [SMILES: CC(C)(C)OC(=O)N1CCN(c2ccc(NC3(C#N)CCC3)cc2)CC1]

To a solution of tert-butyl 4-(4-aminophenyl)piperazine-1-carboxylate (7.6 g, 27.4 mmol) and cyclobutanone (3.06 mL, 40.94 mmol) in MeOH (50 mL) was added zinc iodide (0.44 g, 1.378 mmol) at RT. Trimethylsilyl cyanide (4.1 g, 41.328 mmol) was then added and the mixture was stirred at 90° C. for 16 h and then allowed to cool down to RT and concentrated under reduced pressure. The residue was partitioned between water and EtOAc. The organic layer was concentrated under reduced pressure to give a dark oil, then the oil was further washed with diethyl ether to afford tert-butyl 4-(4-((1-cyanocyclobutyl)amino)phenyl)piperazine-1-carboxylate as a purple solid (7.4 g, 56%). $C_{20}H_{28}N_4O_2$ MS m/z 356.9 (M+H)$^+$.

D. tert-Butyl 4-(4-(7-(6-cyano-5-(trifluoromethyl)
pyridin-3-yl)-8-oxo-6-thioxo-5,7-diazaspiro[3.4]
octan-5-yl)phenyl)piperazine-1-carboxylate, 29h

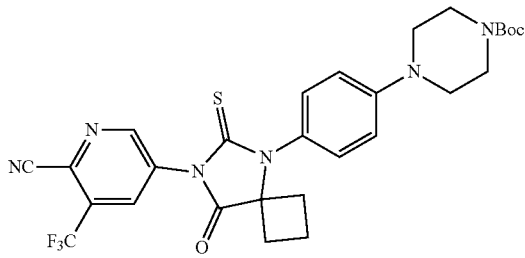 [SMILES: CC(C)(C)OC(=O)N1CCN(c2ccc(N3C(=S)N(c4cnc(C#N)c(C(F)(F)F)c4)C(=O)C34CCC4)cc2)CC1]

A solution of of 5-isothiocyanato-3-(trifluoromethyl)picolinonitrile (0.4 g, 1.75 mmol) in DMA (5 mL) was added to a solution of tert-butyl 4-(4-((1-cyanocyclobutyl) amino) phenyl)piperazine-1-carboxylate (0.518 g, 1.45 mmol) in DMA (5 mL). The mixture was heated at 60° C. for 2 h and then allowed to cool to room temperature. The mixture was treated with MeOH (5 mL) and 2M HCl (5 mL). The resulting suspension stirred at 60° C. for 2 h and poured into water. The precipitate was collected by filtration, washed with water and dried to give tert-butyl 4-(4-(7-(6-cyano-5-(trifluoromethyl)pyridin-3-yl)-8-oxo-6-thioxo-5,7-diazaspiro[3.4]octan-5-yl)phenyl)piperazine-1-carboxylate (0.8 g, 94%) as a grey solid. The compound was directly used into the next step without purification.

E. 5-(8-oxo-5-(4-(piperazin-1-yl)phenyl)-6-thioxo-5,7-diazaspiro[3.4]octan-7-yl)-3-(trifluoromethyl)picolinonitrile, 29i

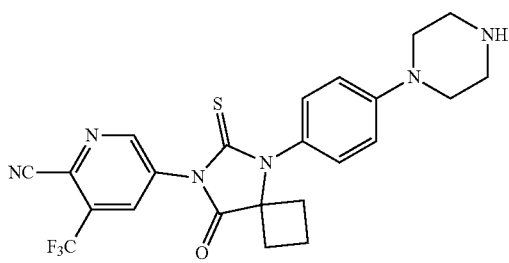 [SMILES: N#Cc1ncc(N2C(=O)C3(CCC3)N(c3ccc(N4CCNCC4)cc3)C2=S)cc1C(F)(F)F]

To a solution of tert-butyl 4-(4-(7-(6-cyano-5-(trifluoromethyl)pyridin-3-yl)-8-oxo-6-thioxo-5,7-diazaspiro[3.4]octan-5-yl)phenyl)piperazine-1-carboxylate (0.8 g, 1.36 mmol) in DCM (30 mL) was added TFA (1.55 g, 13.64 mmol). After stirring at RT for 18 h the reaction mixture was concentrated to give the title compound as an oil (0.74 g, 90%). A portion of the crude material was purified by preparative reverse phase HPLC (column:Synergi Max-RP 150×30 mm×4u, mobile phase:32-52% $CH_3CN/H_2O(HCl)$) to yield 5-(8-oxo-5-(4-(piperazin-1-yl)phenyl)-6-thioxo-5,7-diazaspiro[3.4]octan-7-yl)-3-(trifluoromethyl) picolinonitrile as a solid. $^1$H NMR (400 MHz, Chloroform-d) δ ppm 1.67-1.76 (m, 1H) 2.17-2.33 (m, 1H) 2.51-2.63 (m, 2H) 2.64-2.74 (m, 2H) 3.42-3.54 (m, 4H) 3.60-3.76 (m, 4H) 7.11-7.18 (m, 2H) 7.24-7.26 (m, 2H) 8.34-8.38 (m, 1H) 9.07-9.14 (m, 1H). $C_{23}H_{21}F_3N_6OS$, HCl MS m/z 487.1 (M+H)$^+$.

F. 5-(8-oxo-5-(4-(4-(pyrrolidine-1-carbonyl)piperazin-1-yl)phenyl)-6-thioxo-5,7-diazaspiro[3.4]octan-7-yl)-3-(trifluoromethyl)picolinonitrile, Cpd 76

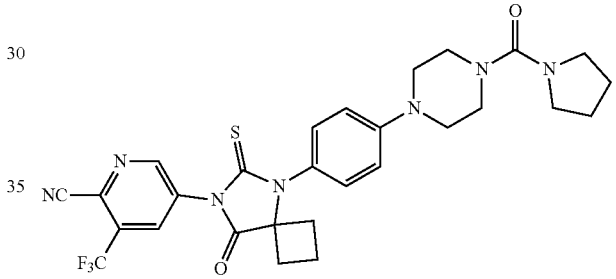

To a mixture of 5-(8-oxo-5-(4-(piperazin-1-yl)phenyl)-6-thioxo-5,7-diazaspiro[3.4]octan-7-yl)-3-(trifluoromethyl) picolinonitrile (0.22 g, 0.452 mmol), DIEA (0.233 g, 1.808 mmol) in DCM (8 mL) was added 1-Pyrrolidinecarbonyl chloride (0.120 g, 0.904 mmol). After stirring at RT overnight the reaction mixture was concentrated to afford the title compound as an oil. The crude oil was purified by reverse phase preparative HPLC (column:Synergi Max-RP 150*30 mm*4u, mobile phase:54-84% $CH_3CN/H_2O$ (HCl)) to give 5-(8-oxo-5-(4-(4-(pyrrolidine-1-carbonyl)piperazin-1-yl) phenyl)-6-thioxo-5,7-diazaspiro[3.4]octan-7-yl)-3-(trifluoromethyl)picolinonitrile as a light yellow solid (0.089 g, 32%). $^1$H NMR (400 MHz, Chloroform-d) δ ppm ppm 1.88 (br. s., 4H) 2.26 (br. s., 2H) 2.54 (br. s., 2H) 2.70 (br. s., 2H) 3.42 (br. s., 4H) 3.51 (br. s., 4H) 3.89 (br. s., 4H) 7.40 (br. s., 2H) 7.80 (br. s., 2H) 8.35 (s, 1H) 9.08 (s, 1H). $C_{24}H_{28}F_3N_7O_2S$. HCl MS m/z 584.2 (M+H)$^+$.

Following the procedure described in Example 29, above, selecting and substituting the appropriate reagents, starting materials, and purification methods, and adjusting reaction temperatures, times and other variables or parameters, as needed or desirable, as would be readily recognized by those skilled in the art, the following compounds of formula (I) of the invention were prepared.

| Cpd No. | Structure | Compound Name & Physical Data |
|---|---|---|
| 58 | 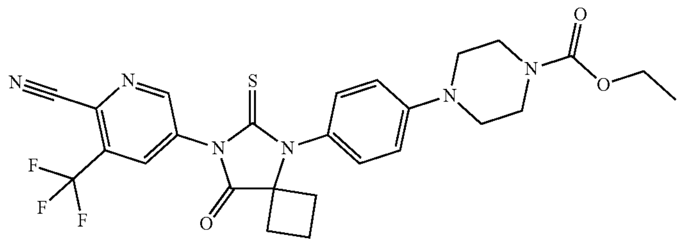 [SMILES: CCOC(=O)N1CCN(c2ccc(N3C(=S)N(c4cnc(C#N)c(C(F)(F)F)c4)C(=O)C34CCC4)cc2)CC1] | Ethyl 4-[4-[6-[6-cyano-5-(trifluoromethyl)-3-pyridyl]-5-oxo-7-thioxo-6,8-diazaspiro[3.4]octan-8-yl]phenyl]piperazine-1-carboxylate. <br> $^1$H NMR (400 MHz, Chloroform-d) δ ppm ppm 1.30 (t, J = 7.06 Hz, 3 H) 1.70 (br. s., 1 H) 2.25 (br. s., 1 H) 2.51-2.72 (m, 4 H) 3.34 (br. s., 4 H) 3.76 (br. s., 4 H) 4.19 (q, J = 7.06 Hz, 2 H) 7.21-7.26 (m, 4 H) 8.36 (s, 1 H) 9.10 (s, 1 H) $C_{26}H_{25}F_3N_6O_3S$•HCl <br> MS m/z 559.1 (M + H)$^+$ |
| 69 | 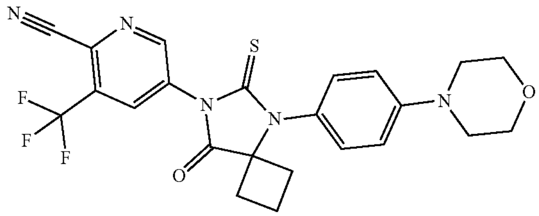 [SMILES: N#Cc1ncc(N2C(=O)C3(CCC3)N(c3ccc(N4CCOCC4)cc3)C2=S)cc1C(F)(F)F] | 5-[8-(4-Morpholinophenyl)-5-oxo-7-thioxo-6,8-diazaspiro[3.4]octan-6-yl]-3-(trifluoromethyl)pyridine-2-carbonitrile. <br> $^1$H NMR (400 MHz, Chloroform-d) δ ppm ppm 1.61-1.74 (m, 1 H) 2.14-2.32 (m, 1 H) 2.50-2.74 (m, 4 H) 3.25-3.37 (m, 4 H) 3.89-3.96 (m, 4 H) 7.09-7.16 (m, 2 H) 7.19-7.23 (m, 2 H) 8.35 (d, J = 1.96 Hz, 1 H) 9.09 (d, J = 1.96 Hz, 1 H) <br> $C_{23}H_{20}F_3N_5O_2S$•HCl MS m/z 448.1 (M + H)$^+$ |
| 9 | 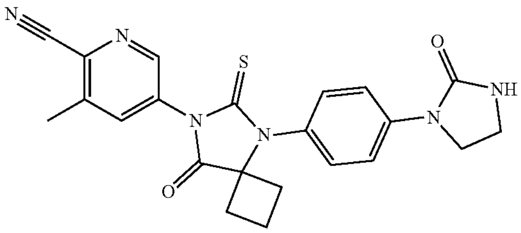 [SMILES: Cc1cc(N2C(=O)C3(CCC3)N(c3ccc(N4CCNC4=O)cc3)C2=S)cnc1C#N] | 3-Methyl-5-{5-oxo-8-[4-(2-oxoimidazolidinyl)phenyl]-7-thioxo-6,8-diazaspiro[3.4]oct-6-yl}pyridine-2-carbonitrile. <br> $^1$H NMR (500 MHz, DMSO-d$_6$) δ ppm 1.59-1.62 (m, 1H), 2.01-2.03 (m, 1H), 2.49-2.55 (m, 2H), 2.64 (s, 3H), 2.64-2.70 (m, 2H), 3.51 (t, 2H, J = 8.0 Hz), 3.97-4.01 (t, 2H, J = 8.8 Hz), 7.18 (s, 1H), 7.40-7.43 (m, 2H, J = 8.8 Hz), 7.81-7.84 (m, 2H, J = 8.8 Hz), 8.21 (d, 1H, J = 1.9 Hz), 8.78 (d, 1H, J = 2.2 Hz) <br> $C_{22}H_{20}N_6O_2S$ MS m/z 433.1 (M + H)+ |

Example 30

5-(5-(4-(2-(hydroxymethyl)-3,4-dihydro-2H-pyran-6-yl)phenyl)-8-oxo-6-thioxo-5,7-diazaspiro[3.4]octan-7-yl)-3-(trifluoromethyl)picolinonitrile, Cpd 103

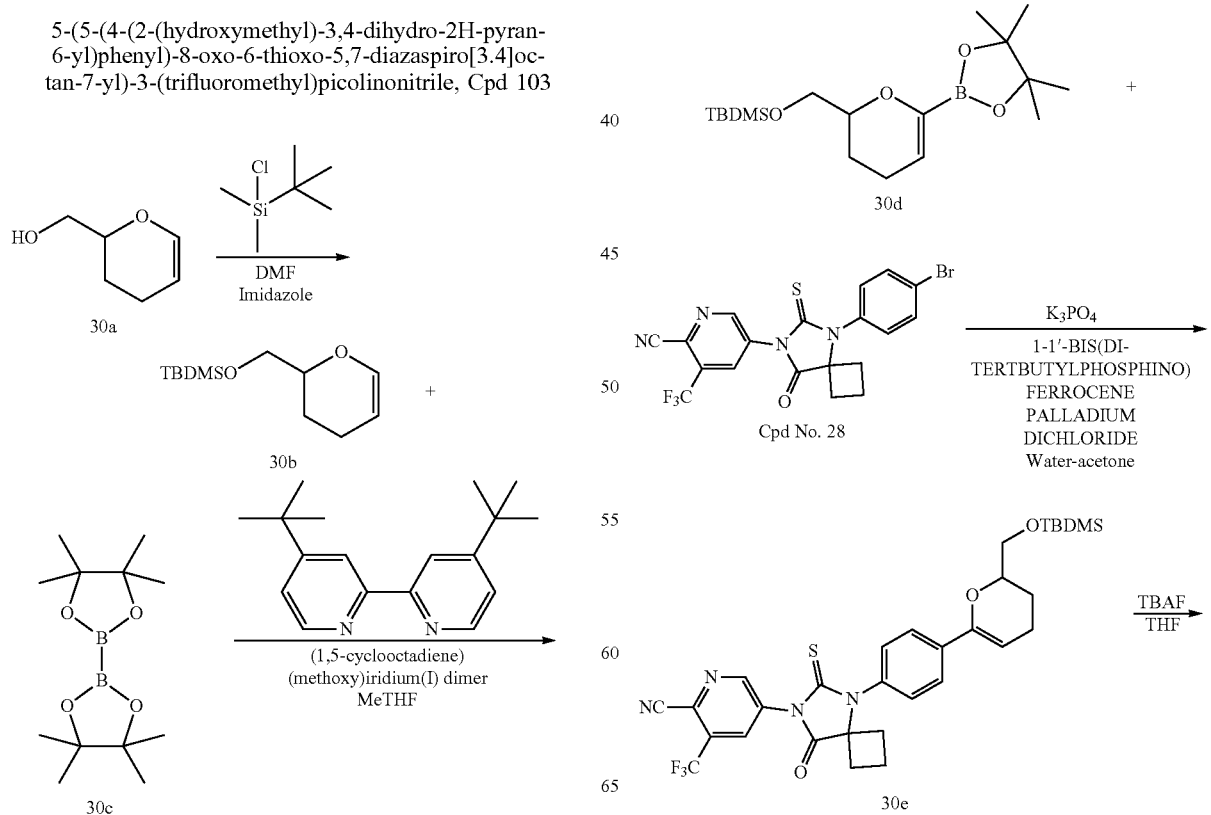

-continued

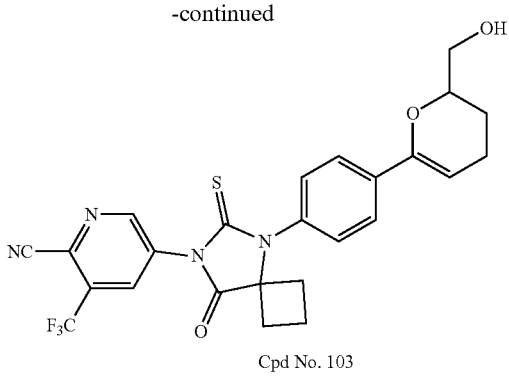

Cpd No. 103

A. tert-butyl((3,4-dihydro-2H-pyran-2-yl)methoxy)dimethylsilane, 30b

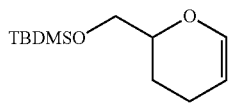

To a solution of (3,4-dihydro-2H-pyran-2-yl)methanol (5.00 mL, 46.9 mmol) in dry DMF (18 mL) was added imidazole (7.98 g, 117 mmol). The solution was cooled to 0° C., TBDMSCl (8.48 g, 56.2 mmol) was added and the reaction mixture was stirred at room temperature for 24 h. The reaction mixture was diluted with Et$_2$O and washed with brine (3x). The combined organic layers were dried over MgSO$_4$, filtered and concentrated in vacuo to give tert-butyl((3,4-dihydro-2H-pyran-2-yl)methoxy)dimethylsilane as an oil (9.6 g, 90%).

B. tert-Butyldimethyl((6-(4,4,5,5-tetramethyl-1,3,2-dioxaborolan-2-yl)-3,4-dihydro-2H-pyran-2-yl)methoxy)silane, 30d

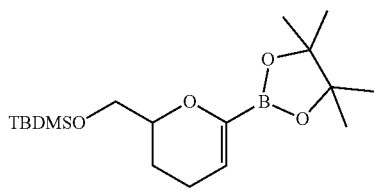 [SMILES: CC1(C)OB(C2=CCCC(CO[Si](C)(C)C(C)(C)C)O2)OC1(C)C]

In a Schlenk tube, 2-methyltetrahydrofuran (5 mL) was carefully degassed in vacuo and back-filled with N$_2$, then, bis(pinacolato)diboron (0.695 g, 2.74 mmol), bis(1,5-cyclooctadiene)di-μ-methoxydiiridium (I) (22 mg, 32.8 μmol) and 4,4'-di-tert-butyl-2,2'-bipyridine (18 mg, 0.066 mmol) were added. The brown mixture was stirred for 10 min. In another flask, a solution of tert-butyl ((3,4-dihydro-2H-pyran-2-yl)methoxy) dimethylsilane (0.5 g, 2.19 mmol) in 2-Me-THF (5 mL) was degassed and transferred via cannula to the Schlenk tube. The reaction was heated at 80° C. for 2 h then bis(1,5-cyclooctadiene)di-μ-methoxydiiridium (I) (22 mg, 32.8 μmol) was added, and the reaction mixture was degassed and back-filled with N2 and stirred at 80° C. for 24 h to give tert-butyldimethyl(((6-(4,4,5,5-tetramethyl-1,3,2-dioxaborolan-2-yl)-3,4-dihydro-2H-pyran-2-yl)methoxy)silane in solution in 2-Me-THF used as such into the next step.

C. 5-(5-(4-(2-((((tert-butyldimethylsilyl)oxy)methyl)-3,4-dihydro-2H-pyran-6-yl)phenyl)-8-oxo-6-thioxo-5,7-diazaspiro[3.4]octan-7-yl)-3-(trifluoromethyl)picolinonitrile, 30e

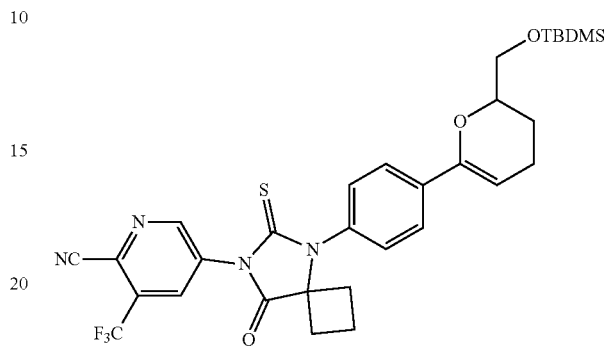

A mixture of tert-butyldimethyl(((6-(4,4,5,5-tetramethyl-1,3,2-dioxaborolan-2-yl)-3,4-dihydro-2H-pyran-2-yl)methoxy)silane (155 mg, 0.437 mmol), water (200 μL), acetone (3 mL, 40.6 mmol) and K$_3$PO$_4$ (247 mg, 1.17 mmol) was purged with N2 and stirred at room temperature for 2 min. Then 5-(5-(4-bromophenyl)-8-oxo-6-thioxo-5,7-diazaspiro[3.4]octan-7-yl)-3-(trifluoromethyl)picolinonitrile (140 mg, 0.292 mmol) and Pd(dppf)$_2$Cl$_2$ (19 mg, 29.2 μmol) were added. The mixture was purged again with N2 and stirred at room temperature for 90 min. The mixture was diluted with EtOAc and water, the layers were separated and the organic layer was dried over MgSO$_4$, filtered and the solvent was removed under reduced pressure to give 5-(5-(4-(2-((((tert-butyldimethylsilyl)oxy)methyl)-3,4-dihydro-2H-pyran-6-yl)phenyl)-8-oxo-6-thioxo-5,7-diazaspiro[3.4]octan-7-yl)-3-(trifluoromethyl) picolinonitrile as a brown oil, used as such in the next step.

D. 5-(5-(4-(2-(hydroxymethyl)-3,4-dihydro-2H-pyran-6-yl)phenyl)-8-oxo-6-thioxo-5,7-diazaspiro[3.4]octan-7-yl)-3-(trifluoromethyl)picolinonitrile, Cpd 103

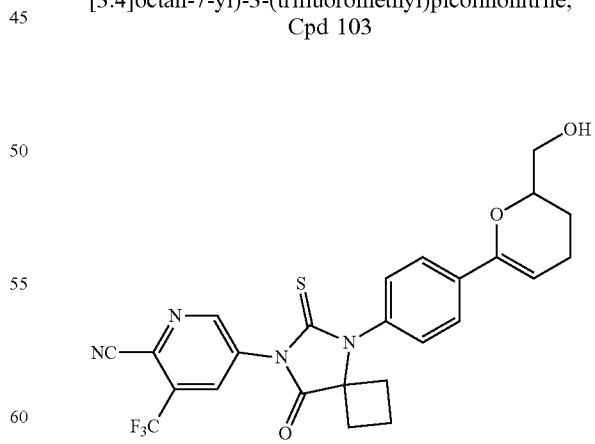

To a solution of 5-(5-(4-(2-((((tert-butyldimethylsilyl)oxy)methyl)-3,4-dihydro-2H-pyran-6-yl)phenyl)-8-oxo-6-thioxo-5,7-diazaspiro[3.4]octan-7-yl)-3-(trifluoromethyl)picolinonitrile (267 mg, 0.425 mmol) in THF (2 mL) was added TBAF (0.51 mL, 0.510 mmol). The mixture was stirred at room temperature for 24 h. Silica was added and the mixture was concentrated in vacuo to give a dry load which was purified by preparative LC (irregular SiOH 15-40 μm, 12 g Grace, dry loading, mobile phase (gradient of MeOH in DCM from 0 to 20%) to give a crude residue further purified by achiral SFC (Stationary phase: Cyano 6 μm 150×21.2 mm, mobile phase: 80% $CO_2$, 20% MeOH) to yield 5-(5-(4-(2-(hydroxymethyl)-3,4-dihydro-2H-pyran-6-yl)phenyl)-8-oxo-6-thioxo-5,7-diazaspiro[3.4]octan-7-yl)-3-(trifluoromethyl)picolinonitrile as a white solid (0.018 g, 8%). $^1$H NMR (400 MHz, DMSO-$d_6$) δ ppm 1.50-1.65 (m, 2H) 1.89-2.00 (m, 2H) 2.16-2.34 (m, 2H) 2.41-2.50 (m, 2H) 2.60-2.68 (m, 2H) 3.55-3.68 (m, 2H) 3.93-4.06 (m, 1H) 4.86 (t, J=5.8 Hz, 1H) 5.59 (t, J=4.0 Hz, 1H) 7.38 (d, J=8.6 Hz, 2H) 7.80 (d, J=8.1 Hz, 2H) 8.77 (d, J=2.0 Hz, 1H) 9.22 (d, J=2.0 Hz, 1H). $C_{25}H_{21}F_3N_4O_3S$ MS m/z 515.2 (M+H)$^+$ Intermediate Synthesis-30a (((3R,4R)-6-(4,4,5,5-tetramethyl-1,3,2-dioxaborolan-2-yl)-3,4-dihydro-2H-pyran-3,4-diyl)bis(oxy))bis(trimethylsilane

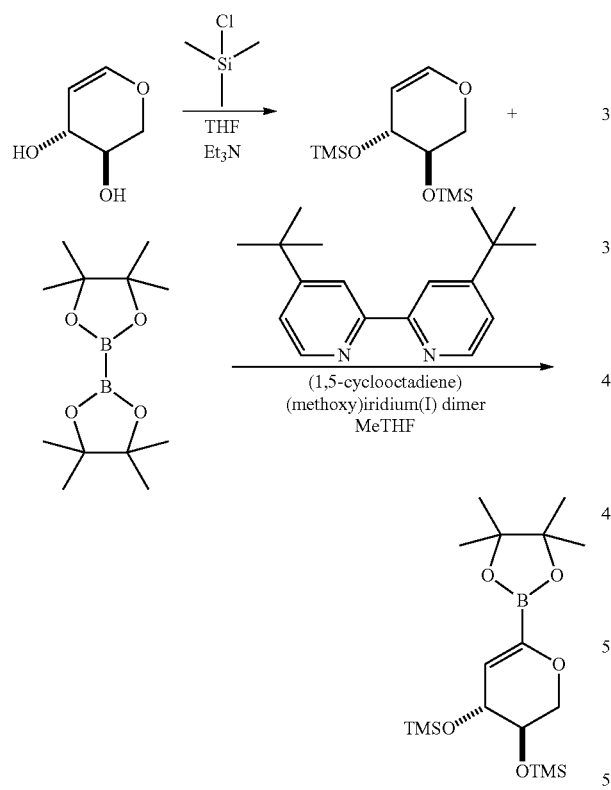

A. (((3R,4R)-3,4-dihydro-2H-pyran-3,4-diyl)bis(oxy))bis(trimethylsilane)

To a solution of (3R,4R)-3,4-dihydro-2H-pyran-3,4-diol (2.30 g, 19.8 mmol) in THF (140 mL) at 0° C. were added TEA (12.4 mL, 89.1 mmol), then dropwise TMSCl (8.80 mL, 69.3 mmol). The reaction mixture was allowed to warm to room temperature and stirred for 16 h. The organic solvent was concentrated in vacuo, and the crude product was diluted with $Et_2O$ and water. The organic layer was washed with brine, dried over $MgSO_4$, filtered and evaporated in vacuo to yield (((3R,4R)-3,4-dihydro-2H-pyran-3,4-diyl)bis(oxy))bis(trimethylsilane) as a yellow oil (4.79 g, 93%).

B. (((3R,4R)-6-(4,4,5,5-tetramethyl-1,3,2-dioxaborolan-2-yl)-3,4-dihydro-2H-pyran-3,4-diyl)bis(oxy))bis(trimethylsilane)

In a Schlenck flask, a stirred mixture of bis(1,5-cyclooctadiene)di-μ-methoxydiiridium (I) (25 mg, 0.038 mmol) and 4,4'-di-tert-butyl-2,2'-bipyridine (21 mg, 0.077 mmol) in 2-Me-THF (6.25 mL) was degassed under reduced pressure and purged with $N_2$. The black mixture was stirred at rt for 15 min. In another flask, a solution of (((3R,4R)-3,4-dihydro-2H-pyran-3,4-diyl)bis(oxy))bis(trimethylsilane) (500 mg, 1.92 mmol) and bis(pinacolato)diboron (0.731 g, 2.88 mmol) in 2-Me-THF (6.25 mL) was degassed and transferred to the first flask. The reaction mixture was degassed in vacuo and purged again with $N_2$, then stirred at 80° C. for 2 h to give (((3R,4R)-6-(4,4,5,5-tetramethyl-1,3,2-dioxaborolan-2-yl)-3,4-dihydro-2H-pyran-3,4-diyl)bis(oxy))bis(trimethylsilane), used as such into the next step.

Intermediate Synthesis-30b (((2S,3S,4S)-2-methyl-6-(4,4,5,5-tetramethyl-1,3,2-dioxaborolan-2-yl)-3,4-dihydro-2H-pyran-3,4-diyl)bis(oxy))bis(trimethylsilane)

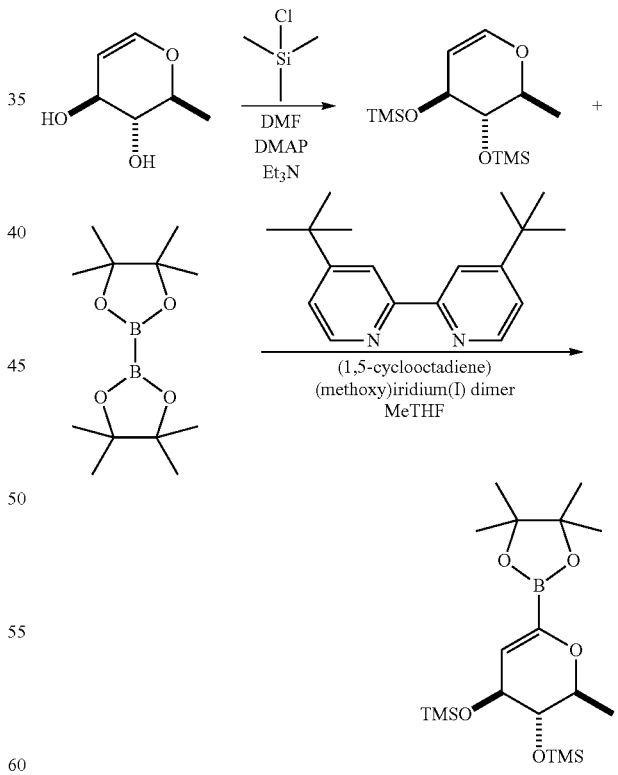

A. (((2S,3S,4S)-2-methyl-3,4-dihydro-2H-pyran-3,4-diyl)bis(oxy)) bis(trimethylsilane)

To a stirred solution of (2S,3R,4S)-2-methyl-3,4-dihydro-2H-pyran-3,4-diol (3.18 g, 24.4 mmol), TEA (17.0 mL, 122 mmol) and DMAP (149 mg, 1.22 mmol) in DMF (100 mL) at 0° C. was added TMSCl (9.30 mL, 73.3 mmol), and the reaction mixture was stirred at room temperature for 17 h. The crude mixture was diluted with Et$_2$O and water. The organic layer was washed with saturated NH$_4$Cl (2x), brine (3x), dried over MgSO$_4$, filtered and evaporated in vacuo to yield (((2S,3R,4S)-2-methyl-3,4-dihydro-2H-pyran-3,4-diyl)bis(oxy))bis(trimethylsilane) as an orange oil (6.76 g, 100%).

B. (((2S,3R,4S)-2-methyl-6-(4,4,5,5-tetramethyl-1,3,2-dioxaborolan-2-yl)-3,4-dihydro-2H-pyran-3,4-diyl)bis(oxy))bis(trimethylsilane)

In a Schlenck flask, a stirred mixture of bis(1,5-cyclooctadiene)di-μ-methoxydiiridium (I) (19 mg, 0.029 mmol) and 4,4'-di-tert-butyl-2,2'-bipyridine (16 mg, 0.058 mmol) in 2-Me-THF (5 mL) was degassed under reduced pressure and purged with N2. The black mixture was stirred at room temperature for 15 min. In another flask, a solution of (((2S,3R,4S)-2-methyl-3,4-dihydro-2H-pyran-3,4-diyl)bis(oxy))bis(trimethylsilane) (400 mg, 1.46 mmol) and bis(pinacolato)diboron (555 mg, 2.19 mmol) in 2-Me-THF (5 mL) was degassed and transferred to the first flask. The reaction mixture was degassed in vacuo and purged again with N$_2$, then stirred at 80° C. for 2 h to give (((2S,3R,4S)-2-methyl-6-(4,4,5,5-tetramethyl-1,3,2-dioxaborolan-2-yl)-3,4-dihydro-2H-pyran-3,4-diyl)bis(oxy)) bis(trimethylsilane), used as such into the next step.

Following the procedure described in Example 30, above, selecting and substituting the appropriate reagents, starting materials, and purification methods, and adjusting reaction temperatures, times and other variables or parameters, as needed or desirable, as would be readily recognized by those skilled in the art, the following compounds of formula (I) of the invention were prepared.

Example 31

3-methyl-5-[5-oxo-8-(4-pyrazol-4-ylphenyl)-7-thioxo-6,8-diazaspiro[3.4]oct-6-yl]pyridine-2-carbonitrile, Cpd 4

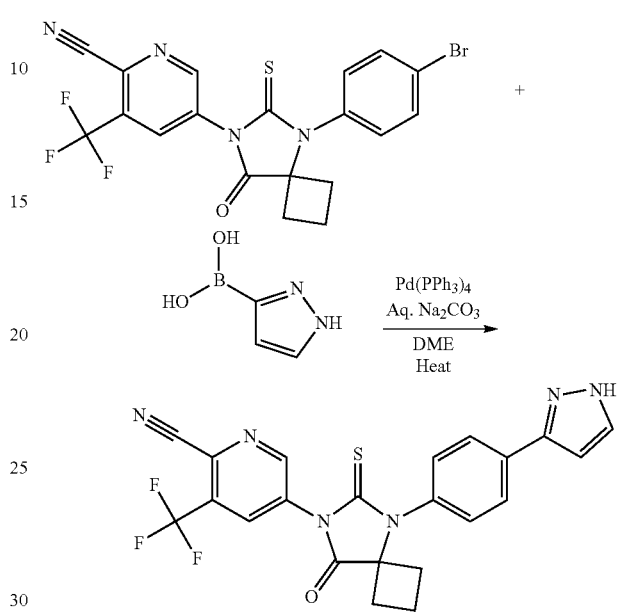

To a solution of 5-(5-(4-bromophenyl)-8-oxo-6-thioxo-5,7-diazaspiro[3.4]octan-7-yl)-3-methylpicolinonitrile (0.306 g, 0.72 mmol) and (1H-pyrazol-3-yl)boronic acid (0.12 g, 1.08 mmol) in DME (3 mL) was added, under an Argon atmosphere, aqueous 2M Na$_2$CO$_3$ (0.75 mL, 1.51 mmol) and

| Cpd No. | Structure | Compound Name & Physical Data |
|---|---|---|
| 112 | 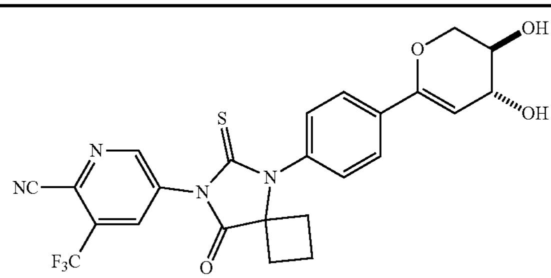 | 5-(5-(4-((3R,4R)-3,4-dihydroxy-3,4-dihydro-2H-pyran-6-yl)phenyl)-8-oxo-6-thioxo-5,7-diazaspiro[3.4]octan-7-yl)-3-(trifluoromethyl)picolinonitrile. $^1$H NMR (400 MHz, DMSO-d6) δ ppm 1.55 (m, 1 H) 1.96 (m, 1 H) 2.38-2.50 (m, 2 H) 2.60-2.69 (m, 2 H) 3.75-3.81 (m, 1 H) 3.91-4.04 (m, 2 H) 4.16-4.21 (m, 1 H) 4.73 (d, J = 6.1 Hz, 1 H) 4.79 (d, J = 5.6 Hz, 1 H) 5.59 (d, J = 4.6 Hz, 1 H) 7.41 (d, J = 8.6 Hz, 2 H) 7.80 (d, J = 8.1 Hz, 2 H) 8.76 (s, 1 H) 9.23 (s, 1 H). C$_{24}$H$_{19}$F$_3$N$_4$O$_4$S MS m/z 575.3 (M + CH$_3$COO)+ |
| 135 | 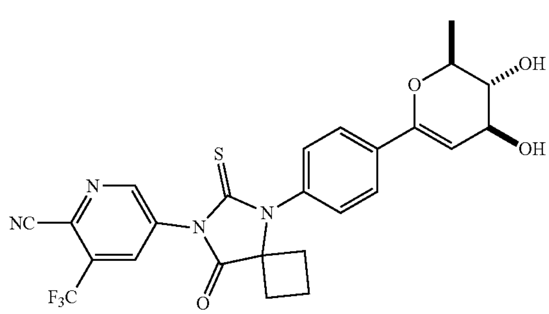 | 5-(5-(4-((2S,3R,4S)-3,4-dihydroxy-2-methyl-3,4-dihydro-2H-pyran-6-yl)phenyl)-8-oxo-6-thioxo-5,7-diazaspiro[3.4]octan-7-yl)-3-(trifluoromethyl)picolinonitrile. $^1$H NMR (500 MHz, DMSO-d$_6$) δ ppm 1.39 (d, J = 6.3 Hz, 3 H) 1.50-1.58 (m, 1 H) 1.91-2.01 (m, 1 H) 2.41-2.47 (m, 2 H) 2.60-2.67 (m, 2 H) 3.21-3.29 (m, 1 H) 3.88-3.94 (m, 1 H) 4.11-4.15 (m, 1 H) 5.08 (d, J = 6.0 Hz, 1 H) 5.31 (d, J = 5.7 Hz, 1 H) 5.45 (d, J = 2.8 Hz, 1 H) 7.40 (d, J = 8.5 Hz, 2 H) 7.78 (d, J = 8.5 Hz, 2 H) 8.76 (d, J = 1.9 Hz, 1 H) 9.22 (d, J = 1.9 Hz, 1 H). C$_{25}$H$_{21}$F$_3$N4O$_4$S MS m/z 531.1 (M + H)+ |

Pd(PPh$_3$)$_4$ (0.032 g, 0.028 mmol). The reaction mixture was refluxed for 16 h, filtered and concentrated under reduced pressure and the resulting residue was purified by preparative reverse-phase chromatography to yield 3-methyl-5-[5-oxo-8-(4-pyrazol-4-ylphenyl)-7-thioxo-6, 8-diazaspiro[3.4]oct-6-yl]pyridine-2-carbonitrile as a solid (0.179 g, 60%). $^1$H NMR (500 MHz, DMSO-d6) a ppm 1.53-1.61 (m, 1H), 1.92-2.02 (m, 1H), 2.37-2.49 (m, 2H), 2.55-2.66 (m, 2H), 2.59 (s, 3H), 7.39-7.42 (m, 2H, J=8.2 Hz), 7.81-7.85 (m, 2H, J=8.2 Hz), 7.97-8.11 (m, 1H), 8.16 (d, 1H, J=1.9 Hz), 8.22-8.37 (m, 1H), 8.73 (d, 1H, J=1.9 Hz), 13.00-13.21 (m, 1H). C$_{22}$H$_{18}$N$_6$OS MS m/z 415.2 (M+H)$^+$.

Following the procedure described in Example 31, above, selecting and substituting the appropriate reagents, starting materials, and purification methods, and adjusting reaction temperatures, times and other variables or parameters, as needed or desirable, as would be readily recognized by those skilled in the art, the following compounds of Formula (I) of the invention were prepared.

Example 32

6-{7-[6-cyano-5-(trifluoromethyl)(3-pyridyl)]-8-oxo-6-thioxo-5,7-diazaspiro[3.4]oct-5-yl}-pyridine-2-sulfonamide, Cpd 22

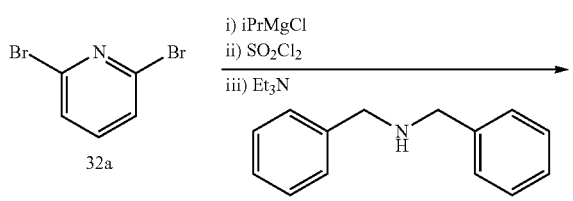

| Cpd No. | Structure | Compound Name & Physical Data |
|---|---|---|
| 5 | 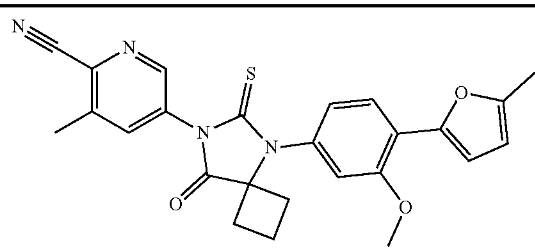 | 5-{8-[3-methoxy-4-(5-methyl(2-furyl))phenyl]-5-oxo-7-thioxo-6,8-diazaspiro[3.4]oct-6-yl}-3-methylpyridine-2-carbonitrile. $^1$H NMR (500 MHz, DMSO-d$_6$) δ ppm 1.62-1.66 (m, 1H), 2.0-2.08 (m, 1H), 2.43 (s, 3H), 2.59-2.62 (m, 2H), 2.65-2.70 (m, 5H), 4.00 (s, 3H), 6.32 (d, J = 2.84 Hz, 1H), 6.99 (d, J = 3.15 Hz, 1H), 7.14 (dd, J = 8.20, 1.89 Hz, 1H), 7.21 (d, J = 1.58 Hz, 1H), 7.94 (d, J = 8.20 Hz, 1H), 8.21 (d, J = 1.89 Hz, 1H), 8.78 (d, J = 2.21 Hz, 1H). C$_{25}$H$_{22}$N$_4$O$_3$S MS m/z 459.1 (M + H)+ |
| 6 | 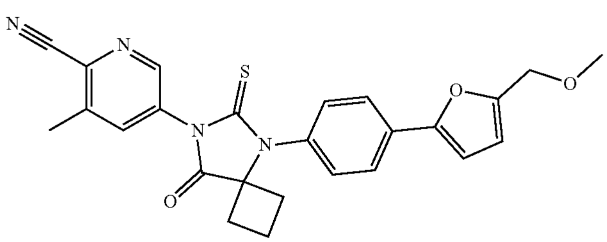 [SMILES: COCc1ccc(-c2ccc(N3C(=S)N(c4cnc(C#N)c(C)c4)C(=O)C34CCC4)cc2)o1] | 5-(8-{4-[5-(methoxymethyl)(2-furyl)]phenyl}-5-oxo-7-thioxo-6,8-diazaspiro[3.4]oct-6-yl)-3-methylpyridine-2-carbonitrile. $^1$H NMR (500 MHz, DMSO-d$_6$) δ ppm 1.58-1.62 (m, 1H), 1.98-2.04 (m, 1H), 2.48-2.52 (m, 2 H), 2.63 (s, 3 H) 2.65-2.69 (m, 2 H), 3.34 (s, 3 H), 4.48 (s, 2 H), 6.66 (d, J = 3.15 Hz, 1 H), 7.10 (d, J = 3.15 Hz, 1 H), 7.53 (m, J = 8.51 Hz, 2 H), 7.95 (m, J = 8.51 Hz, 2 H), 8.19 (s, 1 H), 8.77 (d, J = 1.89 Hz, 1 H) C$_{25}$H$_{22}$N$_4$O$_3$S MS m/z 459.2 (M + H)+ |
| 7 | 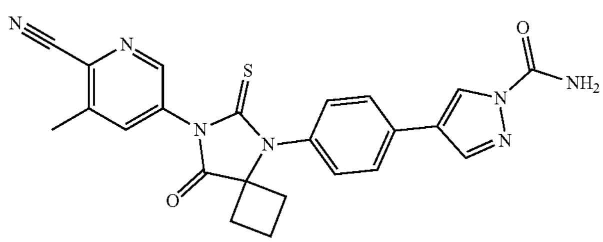 [SMILES: Cc1cc(N2C(=O)C3(CCC3)N(c3ccc(-c4cnn(C(N)=O)c4)cc3)C2=S)cnc1C#N] | 4-{4-[7-(6-cyano-5-methyl(3-pyridyl))-8-oxo-6-thioxo-5,7-diazaspiro[3.4]oct-5-yl]phenyl}pyrazolecarboxamide. $^1$H NMR (500 MHz, DMSO-d$_6$) δ ppm 1.61-1.64 (m, 1 H), 2.0-2.06 (m, 1 H), 2.50-2.54 (m, 1 H), 2.64-2.71 (m, 6 H), 7.51 (d, J = 8.20 Hz, 2 H), 7.96 (br s, 1 H), 8.03 (m, 3 H), 8.21 (d, J = 1.89 Hz, 1 H), 8.40 (s, 1 H), 8.79 (d, J = 1.89 Hz, 1 H), 8.93 (s, 1 H). C$_{23}$H$_{19}$N$_7$O$_2$S MS m/z 458.2 (M + H)+ |
| 10 | 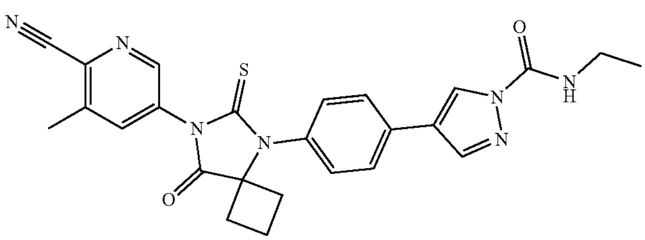 [SMILES: CCNC(=O)n1cc(-c2ccc(N3C(=S)N(c4cnc(C#N)c(C)c4)C(=O)C34CCC4)cc2)cn1] | (4-{4-[7-(6-cyano-5-methyl(3-pyridyl))-8-oxo-6-thioxo-5,7-diazaspiro[3.4]oct-5-yl]phenyl}pyrazolyl)-N-ethylcarboxamide. $^1$H NMR (500 MHz, DMSO-d$_6$) δ ppm 1.17 (t, J = 7.09 Hz, 3H), 1.56-1.59 (m, 1H), 1.97-2.01 (m, 1H), 2.45-2.48 (m, 1H), 2.59-2.66 (m, 6H), 3.30-3.31 (m, 2H), 7.46 (d, J = 8.20 Hz, 2H), 7.99 (d, J = 8.51 Hz, 2H), 8.16 (d, J = 1.89 Hz, 1H), 8.37 (s, 1H), 8.64 (t, J = 5.99 Hz, 1H), 8.74 (d, J = 1.89 Hz, 1H), 8.89 (s, 1H) C$_{25}$H$_{23}$N$_7$O$_2$S MS m/z 486.1 (M + H)$^+$ |

-continued

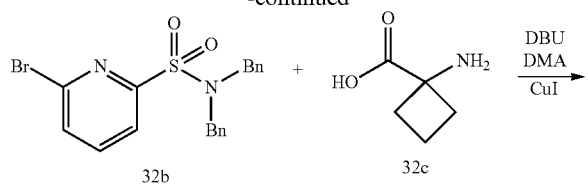

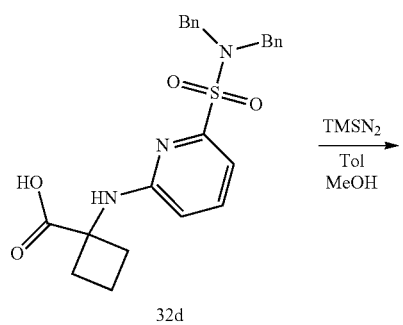

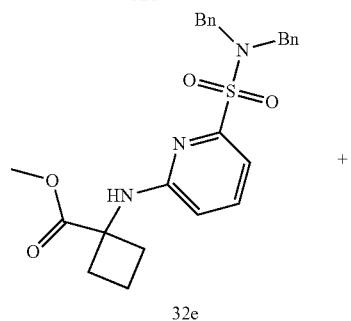

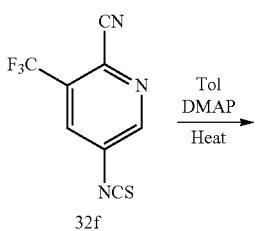

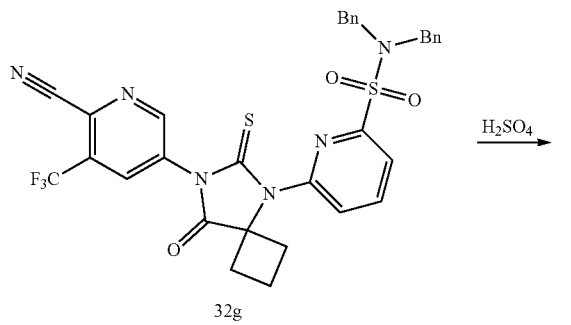

Cpd No. 22

A. N,N-dibenzyl-6-bromopyridine-2-sulfonamide, 32b

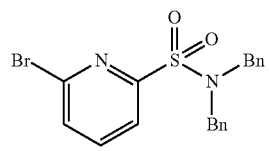 [SMILES: O=S(=O)(c1cccc(Br)n1)N(Cc1ccccc1)Cc1ccccc1]

To a solution of 2,6-dibromopyridine (2.37 g, 10 mmol) in THF (7.5 mL) was added a solution of 2.0M isopropylmagnesium bromide in THF (7.5 mL, 15 mmol) and the mixture was stirred at RT for 90 min to give a dark solution. This solution was added dropwise to a solution of sulfuryl chloride (1.62 mL, 20 mmol) in hexanes (75 mL) and cooled at 0° C. The resulting yellow solution was stirred at 0° C. for 15 min and concentrated under reduced pressure. The residue was diluted with heptane and the solution concentrated under reduced pressure to give a yellow residue. The residue was dissolved in DCM (35 mL) and cooled to 0° C. Et$_3$N (2.5 mL, 18 mmol) was added followed by dibenzylamine (1.93 mL, 10 mmol). The mixture was stirred for 1 h at RT, diluted with water and extracted with DCM. The organic layer was washed with brine, dried over MgSO$_4$, filtered and concentrated under reduced pressure. The crude material was purified by chromatography over silica gel (gradient of EA in heptane from 10 to 50%). The fractions with product were collected and concentrated under reduced pressure to yield N,N-dibenzyl-6-bromopyridine-2-sulfonamide as an orange oil (1.45 g, 34%).

B. 1-((6-(N,N-dibenzylsulfamoyl)pyridin-2-yl)amino)cyclobutanecarboxylic acid, 32d

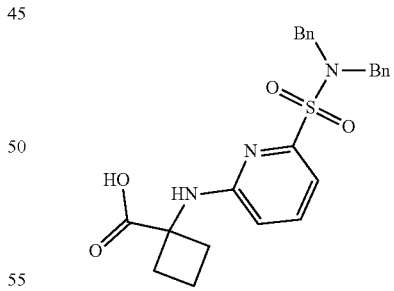

A mixture of N,N-dibenzyl-6-bromopyridine-2-sulfonamide (0.65 g, 1.56 mmol), 1-aminocyclobutanecarboxylic acid (0.197 g, 1.71 mmol), DBU (0.6 mL, 4 mmol), copper (I) iodide (0.029 g, 0.152 mmol) in DMA (3 mL) was stirred at 110° C. for 3 h. More copper (I) iodide (0.089 g, 0.476 mmol) was added and the mixture stirred at 110° C. overnight. The mixture was allowed to cool to RT, then diluted with water and EtOAc. The aqueous layer was then acidified with aqueous 1M HCl to pH 5 and extracted with EtOAc.

The organic layer was dried over MgSO₄, filtered and concentrated under reduced pressure. The crude material was purified by chromatography over silica gel (gradient of MeOH in DCM from 0 to 20%). The fractions with product were collected and concentrated under reduced pressure to yield 1-((6-(N,N-dibenzylsulfamoyl)pyridin-2-yl)amino) cyclobutanecarboxylic acid (0.3 g, 39%).

C. Methyl 1-((6-(N,N-dibenzylsulfamoyl)pyridin-2-yl)amino) cyclobutanecarboxylate, 32e

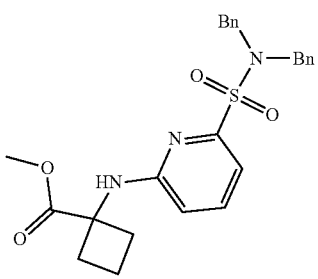 [SMILES: COC(=O)C1(Nc2cccc(S(=O)(=O)N(Cc3ccccc3)Cc3ccccc3)n2)CCC1]

A mixture of 1-((6-(N,N-dibenzylsulfamoyl)pyridin-2-yl) amino) cyclobutanecarboxylic acid (0.3 g, 0.66 mmol), 2.0M solution of (trimethylsilyl) diazomethane (0.66 mL, 1.33 mmol) in toluene (2 mL) and methanol (2 mL) was stirred at RT for 90 min. The mixture was then absorbed on silica gel and purified by chromatography over silica gel (gradient of EtOAc in hexanes from 10 to 100%) to give methyl 1-((6-(N,N-dibenzylsulfamoyl) pyridin-2-yl)amino) cyclobutanecarboxylate as a white solid (0.209 g, 68%).

D. N,N-dibenzyl-6-(7-(6-cyano-5-(trifluoromethyl) pyridin-3-yl)-8-oxo-6-thioxo-5,7-diazaspiro[3.4] octan-5-yl)pyridine-2-sulfonamide, 32g

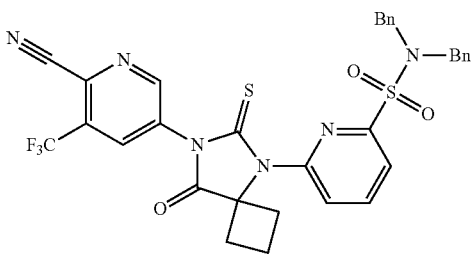 [SMILES: N#Cc1ncc(N2C(=O)C3(CCC3)N(c3cccc(S(=O)(=O)N(Cc4ccccc4)Cc4ccccc4)n3)C2=S)cc1C(F)(F)F]

Methyl 1-((6-(N,N-dibenzylsulfamoyl)pyridin-2-yl) amino)cyclobutanecarboxylate (0.209 g, 0.45 mmol), DMAP (0.137 g, 1.12 mmol) and freshly prepared 5-Isothiocyanato-3-trifluoromethyl-pyridine-2-carbonitrile (0.308 g, 1.35 mmol) were heated at 105° C. in toluene (4 mL) overnight and then allowed to cool to room temperature. The mixture was concentrated and the residue purified by chromatography over silica gel (gradient of EA in heptane from 0 to 50%). The fractions with product were collected and concentrated under reduced pressure and purified by reverse phase preparative HPLC to yield N,N-dibenzyl-6-(7-(6-cyano-5-(trifluoromethyl)pyridin-3-yl)-8-oxo-6-thioxo-5,7-diazaspiro[3.4]octan-5-yl)pyridine-2-sulfonamide as a yellow solid (0.046 g, 15%).

E. 6-{7-[6-cyano-5-(trifluoromethyl)(3-pyridyl)]-8-oxo-6-thioxo-5,7-diazaspiro[3.4]oct-5-yl}pyridine-2-sulfonamide, Cpd 22

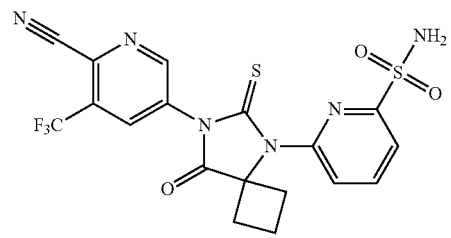 [SMILES: N#Cc1ncc(N2C(=O)C3(CCC3)N(c3cccc(S(N)(=O)=O)n3)C2=S)cc1C(F)(F)F]

A solution of N,N-dibenzyl-6-(7-(6-cyano-5-(trifluoromethyl)pyridin-3-yl)-8-oxo-6-thioxo-5,7-diazaspiro[3.4]octan-5-yl)pyridine-2-sulfonamide (0.046 g, 0.069 mmol) in sulfuric acid (1 mL) was vortexed for 1 h and diluted with ice-water and EtOAc. The organic layer was separated, washed with aqueous saturated NaHCO₃, brine, dried over MgSO₄, filtered and concentrated to dryness. The crude material was purified by chromatography over silica gel (gradient of EA in heptane from 0 to 50%) to yield 6-{7-[6-cyano-5-(trifluoromethyl)(3-pyridyl)]-8-oxo-6-thioxo-5,7-diazaspiro[3.4]oct-5-yl}pyridine-2-sulfonamide as a white solid (0.025 g, 75%). $^1$H NMR (500 MHz, DMSO-d6) d ppm 1.80 (ddt, 1H, J=15.8, 10.6, 5.2 Hz), 1.92-2.04 (m, 1H), 2.55-2.73 (m, 2H), 2.87-2.98 (m, 2H), 7.70 (s, 2H), 8.03-8.08 (m, 2H), 8.33 (t, 1H, J=7.9 Hz), 8.81 (d, 1H, J=1.9 Hz), 9.25 (d, 1H, J=1.9 Hz). $C_{18}H_{13}F_3N_6O_3S2$ MS m/z 483.1 (M+H)⁺.

Example 33

Methyl 4-[6-[6-cyano-5-(trifluoromethyl)-3-pyridyl]-5-oxo-7-thioxo-6,8-diazaspiro[3.4]octan-8-yl]cyclohexanecarboxylate, Cpd 57

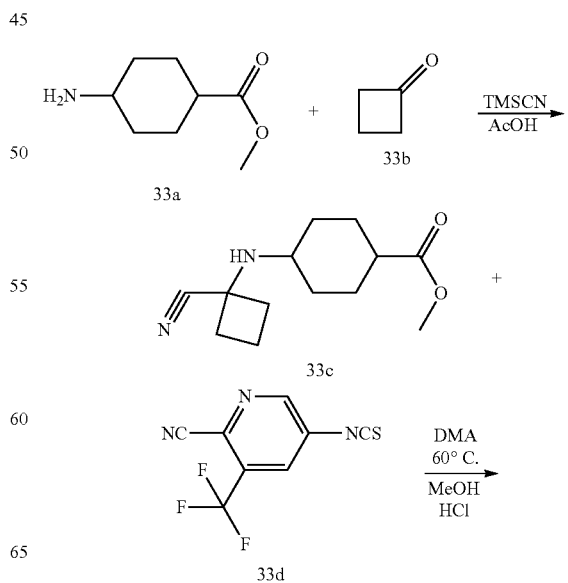

-continued

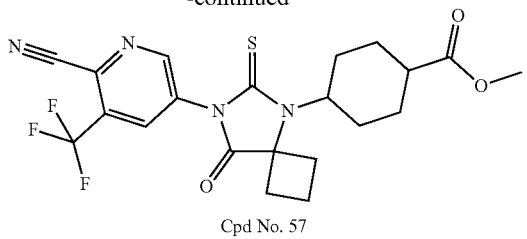

Cpd No. 57

A. Methyl 4-((1-cyanocyclobutyl)amino)cyclohexanecarboxylate, 33c

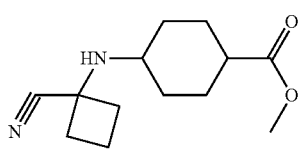 [SMILES: COC(=O)C1CCC(NC2(C#N)CCC2)CC1]

Cyclobutanone (1.074 mL, 14.37 mmol) was added to a solution of methyl 4-aminocyclohexanecarboxylate (0.753 g, 4.79 mmol) in Acetic acid (0.5 mL) and MeOH (4.5 mL). The solution was stirred 15 min at room temperature before trimethylsilyl cyanide (1.798 mL, 14.37 mmol) was added dropwise. After stirring at RT overnight, aqueous 1.0M $Na_2CO_3$ (50 mL) was added carefully and the solution was extracted with EtOAc. The combined organic layers were dried over $MgSO_4$, filtered and concentrated to give methyl 4-((1-cyanocyclobutyl)amino)cyclohexanecarboxylate (1.13 g, 100%), directly used into the next step. $C_{13}H_{20}N_2O_2$ MS m/z 237 $(M+H)^+$.

B. Methyl 4-[6-[6-cyano-5-(trifluoromethyl)-3-pyridyl]-5-oxo-7-thioxo-6,8-diazaspiro[3.4]octan-8-yl]cyclohexanecarboxylate, Cpd 57

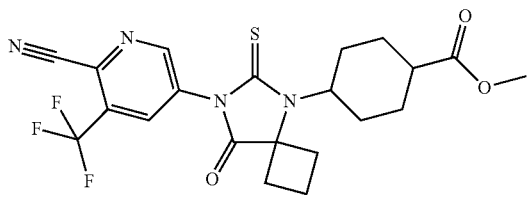 [SMILES: COC(=O)C1CCC(N2C(=S)N(c3cnc(C#N)c(C(F)(F)F)c3)C(=O)C23CCC3)CC1]

A solution of of 5-isothiocyanato-3-(trifluoromethyl)picolinonitrile (1.215 g, 5.3 mmol) in DMA (6 mL) was added to a solution of methyl 4-((1-cyanocyclobutyl)amino) cyclohexanecarboxylate (1.132 g, 4.79 mmol) in DMA (5 mL). The mixture was heated at 60° C. for 3 h and then allowed to cool to room temperature. The mixture was treated with MeOH (9 mL) and 2M HCl (9 mL). The resulting mixture was stirred at 40° C. for 2 h and extracted with EtOAc (100 mL). The organic layer was washed with aqueous saturated $NaHCO_3$, water, brine and dried over $MgSO_4$, filtered and concentrated under reduced pressure. Chromatography was performed on silica gel (gradient of EA in heptane from 0 to 100%), followed by purification by preparative reverse phase HPLC [C18 column using gradient of a mixture 50% (65 mM aqueous $NH_4OAc+ACN$ (90:10))–50% (MeOH) to 25% (65 mM $NH_4OAc+ACN$ (90:10))–75% (MeOH)). The pure fractions were collected and concentrated to dryness to give methyl 4-(7-(6-cyano-5-(trifluoromethyl)pyridin-3-yl)-8-oxo-6-thioxo-5,7-diazaspiro[3.4]octan-5-yl)cyclohexanecarboxylate as a solid (0.354 g, 16%). $^1$H NMR (300 MHz, Chloroform-0 δ 1.65 (tt, J=13.7, 4.4 Hz, 2H), 1.75-1.90 (m, 2H), 1.94-2.13 (m, 1H), 2.35-2.45 (m, 3H), 2.58-2.69 (m, 2H), 2.69-2.95 (m, 5H), 3.75 (s, 3H), 4.15-4.35 (m, 1H), 8.26 (d, J=2.2 Hz, 1H), 8.99 (d, J=2.2 Hz, 1H). $C_{21}H_{21}F_3N_4O_3S$ MS m/z 467 $(M+H)^+$.

Example 34

5-[5-oxo-8-(4-phenoxycyclohexyl)-7-thioxo-6,8-diazaspiro[3.4]octan-6-yl]-3-(trifluoromethyl)pyridine-2-carbonitrile, Cpd 42

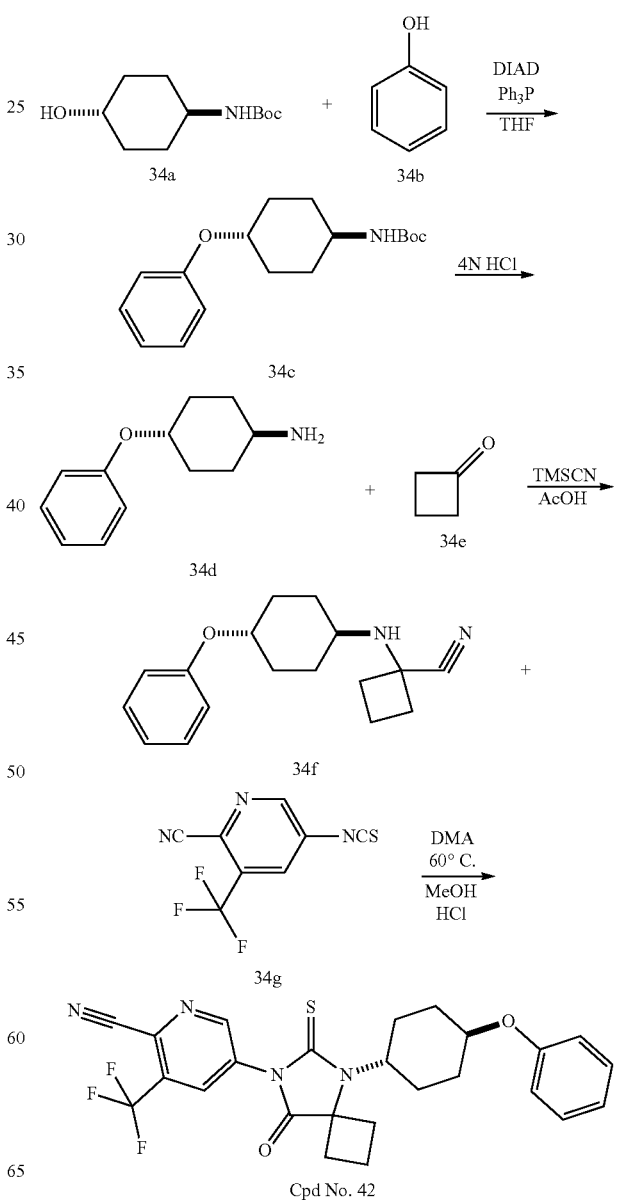

Cpd No. 42

A. (Trans)-tert-butyl 4-phenoxycyclohexyl)carbamate, 34c

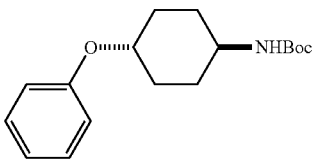

Trans-tert-butyl 4-hydroxycyclohexyl)carbamate (1.705 g, 7.92 mmol), phenol (0.745 g, 7.92 mmol) and triphenylphosphine (3.74 g, 14.25 mmol) were dissolved in dry THF (15 mL) under a nitrogen atmosphere. A solution of Diisopropyl azodicarboxylate (DIAD, 2.81 mL, 14.25 mmol) in THF (30 mL) was added dropwise over 15-20 min. Upon completion of the addition, the reaction was continued for 3 h at RT. The mixture was then concentrated and the crude residue was chromatographed over silica gel (gradient of EtOAc in Heptane from 0 to 50%). The pure fractions were concentrated to give Trans-tert-butyl 4-phenoxycyclohexyl)carbamate (0.853 g, 30%), directly used into the next step. $C_{17}H_{25}NO_3$ MS m/z 192 (M+H-Boc)$^+$.

B. (Trans)-4-phenoxycyclohexanamine, 34d

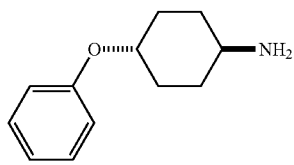

(Trans)-tert-butyl 4-phenoxycyclohexyl)carbamate (0.853 g, 2.92 mmol) was taken in dioxane (15 mL). Dry 4N HCl in dioxane (7.32 mL, 29.27 mmol) was added with stirring. The mixture was stirred overnight at room temperature and concentrated under reduced pressure. The residue was diluted with DCM and washed with aqueous 1M $Na_2CO_3$. The organic layer was dried over $MgSO_4$, filtered and concentrated under reduced pressure. Chromatography over silica gel (gradient of DCM/MeOH/NH$_3$ (9/1/0.1)/DCM, from 0 to 100% and then 100%) yielded (trans)-4-phenoxycyclohexanamine as a pale foam (0.28 g, 50%), which was directly used into the next step. C12H17NO MS m/z 192 (M+H)$^+$.

C. 1-((trans)-4-phenoxycyclohexyl)amino)cyclobutanecarbonitrile, 34f

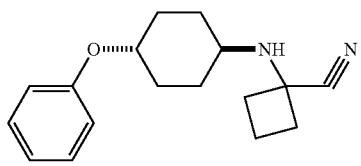

Cyclobutanone (0.328 mL, 4.39 mmol) was added to a solution of (trans)-4-phenoxycyclohexanamine (0.28 g, 1.46 mmol) in Acetic acid (0.5 mL) and MeOH (4.5 mL). The solution was stirred 15 min at room temperature before trimethylsilyl cyanide (0.549 mL, 4.39 mmol) was added dropwise. After stirring at RT overnight, additional cyclobutanone (0.164 mL, 2.19 mmol) and trimethylsilyl cyanide (0.275 mL, 2.19 mmol) were added. After stirring at RT overnight, water was added carefully and the solution was extracted with EtOAc. The organic layers were dried over $MgSO_4$, filtered and concentrated. Chromatography over silica gel (gradient of AcOEt in Heptane, from 0 to 50%) yielded 1-((trans)-4-phenoxycyclohexyl)amino)cyclobutanecarbonitrile (0.109 g, 28%) directly used into the next step. $C_{17}H_{22}N_2O$ MS m/z 271 (M+H)$^+$.

D. 5-[5-oxo-8-(4-phenoxycyclohexyl)-7-thioxo-6,8-diazaspiro[3.4]octan-6-yl]-3-(trifluoromethyl)pyridine-2-carbonitrile, Cpd 42

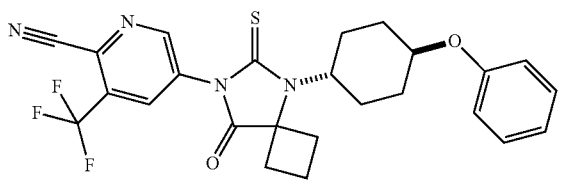

A solution of of 5-isothiocyanato-3-(trifluoromethyl)picolinonitrile (0.092 g, 0.403 mmol) and 1-((trans)-4-phenoxycyclohexyl)amino)cyclobutanecarbonitrile (0.109 g, 0.403 mmol) in DMA (5 mL) was heated at 60° C. for 6 h and then allowed to cool to room temperature. The mixture was treated with MeOH (5 mL) and 2M HCl (5 mL). The resulting mixture was stirred at RT overnight and extracted with EtOAc (50 mL). The organic layer was washed with aqueous saturated $NaHCO_3$, water, brine, and dried over $MgSO_4$, then filtered and concentrated under reduced pressure. Chromatography over silica gel (gradient of EA in heptane from 0 to 50%) yielded a residue which was further recrystallized from diethyl ether to yield 5-[5-oxo-8-(4-phenoxycyclohexyl)-7-thioxo-6,8-diazaspiro[3.4]octan-6-yl]-3-(trifluoromethyl)pyridine-2-carbonitrile as a solid (0.07 g, 34%). $^1$H NMR (300 MHz, Chloroform-d) δ 1.58-1.87 (m, 4H), 1.96-2.17 (m, 1H), 2.10-2.45 (m, 3H), 2.60-2.75 (m, 2H), 2.82-3.02 (m, 4H), 4.30-4.54 (m, 1H), 4.64 (br s, 1H), 6.95-6.99 (m, 3H), 7.28-7.34 (m, 2H), 8.28 (d, J=2.1 Hz, 1H), 9.02 (d, J=2.1 Hz, 1H). $C_{25}H_{23}F_3N_4O_2S$ MS m/z 501 (M+H)$^+$.

Example 35

N-[4-[6-[6-cyano-5-(trifluoromethyl)-3-pyridyl]-5-oxo-7-thioxo-6,8-diazaspiro[3.4]octan-8-yl]cyclohexyl]benzamide, Cpd 134

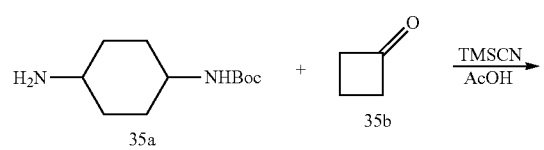

-continued

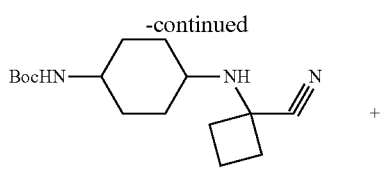

35c

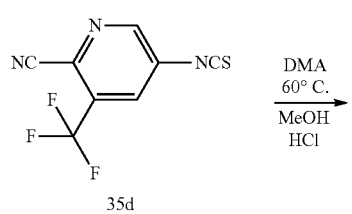

35d

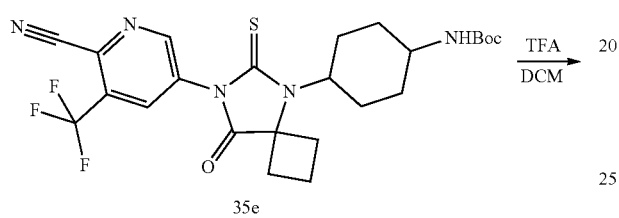

35e

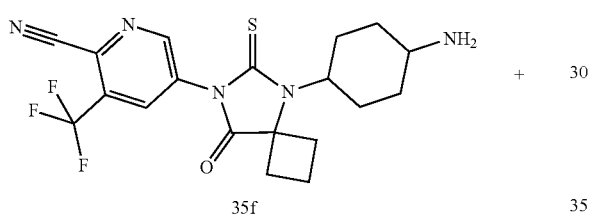

35f

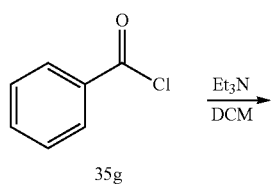

35g

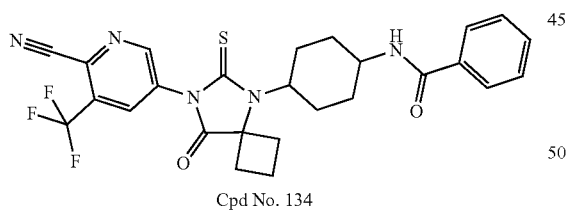

Cpd No. 134

A. tert-Butyl (4-((1-cyanocyclobutyl)amino)cyclohexyl)carbamate, 35c

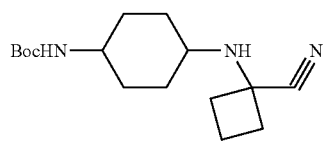 [SMILES: CC(C)(C)OC(=O)NC1CCC(NC2(C#N)CCC2)CC1]

Cyclobutanone (0.314 mL, 4.2 mmol) was added to a solution of tert-butyl (4-aminocyclohexyl)carbamate (0.3 g, 1.4 mmol) in acetic acid (0.5 mL) and MeOH (4.5 mL). The solution was stirred 15 min at room temperature before trimethylsilyl cyanide (0.525 mL, 4.2 mmol) was added dropwise. After stirring at RT overnight, water was added carefully and the solution was extracted with EtOAc. The organic layers were dried over MgSO$_4$, filtered and concentrated to yield tert-butyl (4-((1-cyanocyclobutyl)amino) cyclohexyl)carbamate, used directly into the next step.

B. tert-Butyl (4-(7-(6-cyano-5-(trifluoromethyl)pyridin-3-yl)-8-oxo-6-thioxo-5,7-diazaspiro[3.4]octan-5-yl)cyclohexyl)carbamate, 35e

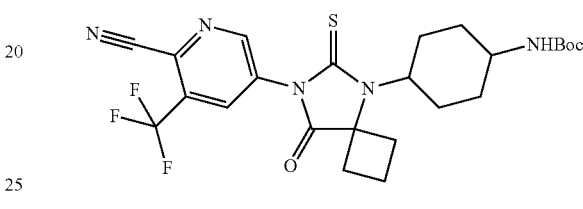

A solution of of 5-isothiocyanato-3-(trifluoromethyl)picolinonitrile (0.367 g, 1.6 mmol) and tert-butyl (4-((1-cyanocyclobutyl)amino) cyclohexyl)carbamate (0.411 g, 1.4 mmol) in DMA (6 mL) was heated at 60° C. for 3 h and then allowed to cool to room temperature. The mixture was treated with MeOH (9 mL) and 1N HCl (9 mL). The resulting mixture was stirred at RT overnight and extracted with EtOAc (100 mL). The organic layer was washed with aqueous saturated NaHCO$_3$, water, brine and dried over MgSO$_4$, filtered and concentrated under reduced pressure to give tert-butyl (4-(7-(6-cyano-5-(trifluoromethyl)pyridin-3-yl)-8-oxo-6-thioxo-5,7-diazaspiro[3.4]octan-5-yl)cyclohexyl)carbamate (0.64 g, 87%), used directly into the next step. C$_{24}$H$_{28}$F$_3$N$_5$O$_3$S MS m/z 424 (M+H-Boc)$^+$.

C. 5-(5-(4-aminocyclohexyl)-8-oxo-6-thioxo-5,7-diazaspiro[3.4]octan-7-yl)-3-(trifluoromethyl)picolinonitrile, 35f

Trifluoroacetic acid (2 mL) was added to a solution of tert-butyl (4-(7-(6-cyano-5-(trifluoromethyl)pyridin-3-yl)-8-oxo-6-thioxo-5, 7-diazaspiro[3.4]octan-5-yl)cyclohexyl) carbamate (0.64 g, 1.222 mmol). After stirring for 2 h at RT, the solvent was concentrated under reduced pressure and the residue co-evaporated twice with toluene to yield 5-(5-(4-aminocyclohexyl)-8-oxo-6-thioxo-5,7-diazaspiro[3.4]octan-7-yl)-3-(trifluoromethyl)picolinonitrile (0.97 g, 100%), used directly into the next step. C$_{19}$H$_{20}$F$_3$N$_5$OS MS m/z 424 (M+H)$^+$.

D. N-[4-[6-[6-cyano-5-(trifluoromethyl)-3-pyridyl]-5-oxo-7-thioxo-6,8-diazaspiro[3.4]octan-8-yl]cyclohexyl]benzamide, Cpd 134

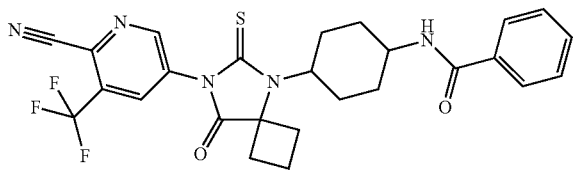 [SMILES: N#Cc1ncc(N2C(=O)C3(CCC3)N(C3CCC(NC(=O)c4ccccc4)CC3)C2=S)cc1C(F)(F)F]

To a solution of 5-(5-(4-aminocyclohexyl)-8-oxo-6-thioxo-5,7-diazaspiro[3.4]octan-7-yl)-3-(trifluoromethyl)picolinonitrile (0.517 g, 1.222 mmol) in DCM (10 mL) was added at 0° C. Et$_3$N (0.186 mL, 1.344 mmol) and benzoyl chloride (0.156 mL, 1.344 mmol). After stirring at RT for 2 h, the mixture was washed with aqueous saturated NH$_4$Cl, brine, dried over MgSO$_4$, filtered and concentrated under reduced pressure. Chromatography over silica gel (gradient of MeOH in DCM from 0 to 5%) gave a residue, which was then purified by preparative reverse phase HPLC (isocratic method, eluting 50% acetonitrile and 50% 25 mM NH$_4$HCO$_3$). The pure fractions were collected and concentrated to dryness to give N-[4-[6-[6-cyano-5-(trifluoromethyl)-3-pyridyl]-5-oxo-7-thioxo-6,8-diazaspiro[3.4]octan-8-yl]cyclohexyl]benzamide (0.045 g, 7%) as a solid. $^1$H NMR (300 MHz, Chloroform-d) δ 1.65-1.85 (m, 4H), 1.96-2.19 (m, 3H), 2.27-2.50 (m, 1H), 2.62-2.78 (m, 4H), 3.26-3.51 (m, 2H), 3.77-3.95 (m, 1H), 4.49-4.64 (m, 1H), 6.74 (d, J=8.5 Hz, 1H), 7.37-7.53 (m, 3H), 7.86 (d, J=6.7 Hz, 2H), 8.25 (d, J=2.2 Hz, 1H), 8.99 (d, J=2.1 Hz, 1H). C$_{26}$H$_{24}$F$_3$N$_5$O$_2$S MS m/z 528 (M+H)$^+$.

Example 36

Formulation of Compound 43 Hydrochloride Salt (HCl)

Preparation of Blend in Capsule of 10 mg, 40 mg and 100 mg of Cpd 43, HCl Salt
1. Weigh compound 43, HCl salt (API) and excipients
2. Screening through 35 mesh except magnesium stearate
3. Blending except magnesium stearate
4. Screen the magnesium stearate through 60 mesh
5. Lubrication upon addition of magnesium stearate
6. Encapsulation Formulations were assigned the following formulation numbers:
Cpd 43 HCl salt-G001 comprises a 10 mg blend of Cpd 43, HCl in capsule form (G001).
Cpd 43 HCl salt-G002 comprises a 40 mg blend Cpd 43, HCl in capsule form (G002).
Cpd 43 HCl salt-G003 comprises a 100 mg blend Cpd 43, HCl in capsule form (G003).

TABLE 36A

Quantitative and qualitative composition of Cpd 43 HCl salt (10 mg blend in capsule)

| Function | Component | mg/capsule* | % |
|---|---|---|---|
| API | Cpd 43, HCl salt | 10.73 | 7.7% |
| Filler | mannitol | 61.00 | 43.6% |
| Filler | Lactose monohydrate | 61.00 | 43.6% |
| Disintegrant | Croscarmellose Sodium (Ac-Di-Sol) | 4.96 | 3.5% |
| Glidant | Colloidal Silicon dioxide (Aerosil 200) | 0.96 | 0.7% |
| Lubricant | Magnesium Stearate | 1.28 | 0.9% |
| Total Fill Weight | | 139.93 | 100.0% |

*Size # and color of hard gelatin Capsule: #3, grey/grey

TABLE 36B

Quantitative and qualitative composition of Cpd 43 HCl salt (40 mg blend in capsule)

| Function | Component | mg/capsule* | % |
|---|---|---|---|
| API | Cpd 43, HCl salt | 42.92 | 30.7% |
| Filler | mannitol | 44.80 | 32.1% |
| Filler | Lactose monohydrate | 44.80 | 32.1% |
| Disintegrant | Croscarmellose Sodium (Ac-Di-Sol) | 4.96 | 3.5% |
| Glidant | Colloidal Silicon dioxide (Aerosil 200) | 0.96 | 0.7% |
| Lubricant | Magnesium Stearate | 1.28 | 0.9% |
| Total Fill Weight | | 139.72 | 100.0% |

*Size # and color of hard gelatin Capsule: #3, white/white

TABLE 36C

Quantitative and qualitative composition of Cpd 43 HCl salt (100 mg blend in capsule)

| Function | Component | mg/capsule* | % |
|---|---|---|---|
| API | Cpd 43, HCl salt | 107.30 | 30.7% |
| Filler | Mannitol | 112.00 | 32.1% |
| Filler | Lactose Monohydrate | 112.00 | 32.1% |
| Disintegrant | Croscarmellose Sodium (Ac-Di-Sol) | 12.40 | 3.5% |
| Glidant | Colloidal Silicon dioxide (Aerosil 200) | 2.40 | 0.7% |
| Lubricant | Magnesium Stearate | 3.20 | 0.9% |
| Total Fill Weight | | 349.30 | 100.0% |

*Size # and color of hard gelatin Capsule: #0, red/red

The stability of 10 mg Screen Batch was performed as follows using an UPLC method. Samples were pulled at the time points predefined and analyzed by UPLC. The detailed chromatographic conditions are listed below. The parent drug and related substance were integrated for calculation.

| Instrument Column | Agilent 1290 UPLC | |
|---|---|---|
| Column: | ACQUITY UPLC BEH C18 | |
| Column length: | 150 mm | |
| Column diameter: | 2.1 mm | |
| Particle size: | 1.7 μm | |
| Part No.: | 186002353 | |
| Serial No.: | 02653527518375 | |

| | Time (min) | A: B: Water + 0.2% TFA | B: Methanol + 0.2% TFA |
|---|---|---|---|
| Gradient | 0 | 68 | 32 |
| | 15 | 46 | 54 |
| | 20 | 5 | 95 |
| | 25 | 0 | 100 |
| | 35 | 0 | 100 |
| | 36 | 68 | 32 |
| | 42 | 68 | 32 |
| Flow | | 0.4 mL/min | |
| Column Temp | | 55° C. | |
| Wavelength | | 270 nm | |
| Inject volume | | 7 μL | |

Stability of 10 mg Screening Batch

| | | RRT | | | | | | | | | | TRS % |
|---|---|---|---|---|---|---|---|---|---|---|---|---|
| | Sample | 0.33 | 0.82 | 0.84 | 1.42 | 1.46 | 1.49 | 1.50 | 1.51 | 1.56 | 1.66 | |
| API control | Initial | — | 0.231 | — | 0.134 | — | 0.071 | — | — | 0.091 | 0.133 | 0.66 |
| API in capsule | Initial | — | 0.230 | — | 0.134 | — | 0.071 | — | — | 0.091 | 0.133 | 0.66 |
| | 60° C./75% RH-7 day open | — | 0.234 | — | 0.134 | 0.103 | 0.071 | — | — | 0.094 | 0.102 | 0.74 |
| | 60° C./75% RH-14 day open | — | 0.238 | 0.058 | 0.130 | 0.151 | 0.071 | — | — | 0.105 | 0.07 | 0.82 |
| 10 mg | Initial | — | 0.220 | — | 0.136 | — | 0.072 | — | — | 0.095 | 0.130 | 0.65 |
| | 60° C./75% RH-7 day open | — | 0.214 | — | 0.136 | 0.263 | 0.074 | — | — | 0.108 | 0.134 | 0.93 |
| | 60° C./75% RH-14 day open | 0.046 | 0.255 | 0.146 | 0.130 | 0.622 | 0.078 | 0.157 | 0.050 | 0.157 | 0.134 | 1.78 |
| | 40° C./75% RH-1 M open | — | 0.214 | — | 0.136 | — | — | — | 0.073 | 0.095 | 0.147 | 0.67 |
| | 40° C./75% RH-1 M close | — | 0.213 | — | 0.137 | — | — | — | 0.073 | 0.095 | 0.147 | 0.67 |
| | 50° C./75% RH-1 M open | — | 0.217 | — | 0.136 | — | — | — | 0.074 | 0.099 | 0.148 | 0.67 |
| | 40° C./75% RH-3 M open | — | 0.282 | — | 0.136 | — | — | — | 0.073 | 0.092 | 0.143 | 0.73 |
| | 50° C./75% RH-3 M open | — | 0.280 | — | 0.133 | 0.101 | — | — | 0.074 | 0.094 | 0.141 | 0.82 |

Conclusion: The prototype formula is chemically stable stressed under 40° C./75% RH open up to 3 months.

Biological Examples

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Antagonism of receptors in a biological sample is useful for a variety of purposes that are known to one of skill in the art. Examples of such purposes include, but are not limited to, biological assays, gene expression studies, and biological target identification.

Certain embodiments of the present invention are directed to a method of treatment by antagonizing AR in a patient or a subject in need of such treatment comprising the step of administering to said patient a compound of Formula (I) of the present invention, or a composition comprising said compound.

The activity of a compound of Formula (I) as an antagonist of AR or for the treatment of an AR-mediated disease, disorder or condition, may be assayed in vitro or in vivo. An in vivo assessment of the efficacy of the compounds of the invention may be made using an animal model of an AR-mediated disease, disorder or condition, e.g., a rodent or primate model. The in vivo assessment may be further defined as an androgen dependent organ development (Hershberger) assay or as a tumor xenograft model. Cell-based assays may be performed using, e.g., a cell line isolated from a tissue that expresses either wild type or mutant AR. Additionally, biochemical or mechanism based assays, e.g., transcription assays using a purified protein, Northern blot, RT-PCR, etc., may be performed.

In vitro assays include assays that determine cell morphology, protein expression, and/or the cytotoxicity, enzyme inhibitory activity, and/or the subsequent functional consequences of treatment of cells with compounds of the invention. Alternate or additional in vitro assays may be used to quantitate the ability of the inhibitor to bind to protein or nucleic acid molecules within the cell.

Inhibitor binding may be measured by radiolabelling the inhibitor prior to binding, isolating the inhibitor/target molecule complex and determining the amount of radiolabel bound. Alternatively or additionally, inhibitor binding may be determined by running a competition experiment where new inhibitors are incubated with purified proteins or nucleic acids bound to known radioligands. Detailed conditions of exemplary systems for assaying a compound of Formula (I) of the present invention as an antagonist of AR are set forth in the Biological Examples below.

Such assays are exemplary and not intended to limit the scope of the invention. The skilled practitioner can appreciate that modifications can be made to conventional assays to develop equivalent or other assays that can be employed to comparably assess activity or otherwise characterize compounds and/or compositions as described herein.

In Vitro Assays

Biological Example 1

Radioligand Binding of Compounds to AR, GR and ER

Radioligand binding assays were performed with the cell extracts and ligands as detailed below. Complete methodology is contained within the cited publications. $K_d$ values were determined by Non-Specific Incubation Detection Method.
Receptors
GR (human) (agonist radioligand) IM-9 cells (cytosol)
[$^3$H]dexamethasone 1.5 nM 1.5 nM triamcinolone (10 µM) 6 h 4° C. Scintillation counting (Clark, A. F et al. (1996) Invest. Ophtalmol. Vis. Sci., 37: 805-813).
ER (nonselective) (human) (agonist radioligand) MCF-7 cells (cytosol)
[$^3$H]estradiol 0.4 nM 0.2 nM 17β-estradiol (6 µM) 20 h 4° C. Scintillation counting
(Parker, G. J et al. (2000) J. Biomol. Screen., 5: 77-88).
AR (human) (agonist radioligand) LNCaP cells (cytosol)
[$^3$H]methyltrienolone 1 nM 0.8 nM mibolerone (1 µM) 24 h 4° C. Scintillation counting.
Zava, D. T et al. (1979) Endocrinology, 104: 1007-1012.

The results are expressed as a percent of control specific binding measured specific binding*100 control specific binding and as a percent inhibition of control specific binding 100-(measured specific binding*100) control specific binding obtained in the presence of compound.

The $IC_{50}$ values (concentration causing a half-maximal inhibition of control specific binding) and Hill coefficients (nH) were determined by non-linear regression analysis of the competition curves generated with mean replicate values using Hill equation curve fitting.

$$Y=D+[A-D]$$

$$1+(C/C50)nH$$

wherein Y=specific binding, A=left asymptote of the curve, D=right asymptote of the curve, C=compound concentration, C50=$IC_{50}$, and nH=slope factor. This analysis was performed using software developed at Cerep (Hill software) and validated by comparison with data generated by the commercial software SigmaPlot® 4.0 for Windows® (© 1997 by SPSS Inc.).

The inhibition constants (Ki) were calculated using the Cheng Prusoff equation:

$$Ki=IC_{50}(1+L/KD)$$

wherein L=concentration of radioligand in the assay, and KD=affinity of the radioligand for the receptor. A scatchard plot is used to determine the KD. Resultant data are shown in Table 2.

TABLE 2

| | AR | | GR | | ER | |
|---|---|---|---|---|---|---|
| | $IC_{50}$ (nM) | Ki (nM) | $IC_{50}$ (nM) | Ki (nM) | $IC_{50}$ (nM) | Ki (nM) |
| Cpd 43 | 6.9 | 3 | >30000 | NC | NC | NC |

Radioligand binding inhibition and affinity calculations were determined using [$^3$H]-methyltrienolone, [$^3$H]-dexamethasone and [$^3$H]-estradiol for AR, GR and ER, respectively. For ER, it was not possible to determine inhibition or affinity and data are not shown.
AR=androgen receptor, ER=estrogen receptor, GR=glucocorticoid receptor Biological Example 2

Antagonism of AR (WT or F876L) Reporter Assay

LNCaP AR (cs) and LNCaP F876L luciferase cell lines were generated by transduction of each cell line (description of cell line generation Joseph J D, Lu N, Qian J, Sensintaffar J, Shao G, Brigham D, Moon M, Maneval E C, Chen I, Darimont B, Hager J H. A clinically relevant androgen receptor mutation confers resistance to second-generation antiandrogens enzalutamide and ARN-509. Cancer Discov 2013; 3:1020-1029) with an Androgen Response Element Firefly Luciferase lentiviral construct at an MOI (multiplicity of infection) of 50 following the manufacturer's instructions (Qiagen). A stable pooled-population cell line was generated using puromycin (Life Technologies) selection at 1:10,000 v/v. The protocol below was used for both cell lines and for testing of the compounds of Formula (I) of the present invention.

LNCaP cells were grown to about 80% confluence, media removed and cells rinsed in Hank's balanced salt solution prior to separation from the plate with 0.05% Trypsin EDTA. Cells were lifted and trypsin negated in complete CSS (charcoal stripped serum) culture media. CSS was maintained on cells for 24 h prior to assay, at which time 5,000 cells/20 µL were seeded in Greiner 384 well White/White Tissue Culture Treated Plates and incubated for a further 1-2 hours at 37° C., 5% $CO_2$, prior to addition of 104, of 4× Test Compounds (compounds described herein) or Assay Controls (all diluted in complete media containing 10% css). A further 104, of 4× R-1881 Agonist Challenge (antagonist assay) or Buffer (agonist assay) was then added (all diluted in complete media containing 10% css). Agonist challenge was at 400 pM for WT assay and 600 pM for F876L assay. Plates containing cells and compounds herein were incubated for a further 20-24 hours at 37° C., 5% $CO_2$ before addition of 40 µL/well of Steady-Glo Luciferase Assay System Reagent (Promega #E2520). After 1 h, plates were read for luminescence on a BMG Pherastar.
Agonist challenge: R-1881 (Metribolone)—Agonist
Antagonist control (low control): 5-(5-(4-(1-Methylpiperidin-4-yl)oxy)phenyl)-8-oxo-6-thioxo-5,7-diazaspiro[3.4]

octan-7-yl)-3-(trifluoromethyl)picolinonitrile (WO 2011/103202, EXAMPLE 19, Compound 129, CAS #1332390-06-3).

Calculations and Formulae:

RLU results were collected from the Pherastar and used directly for data calculation.

Percent Max & Inhibition Calculated for Assays:

% Inhibition:(1−(Sample RLU−Ave Low Control RLU[10 µM Antagonist Control])/(Ave High Control RLU[400 µM R−1881]−Ave Low Control RLU[10 µM Antagonist Control]))*100.

% of 1 µM R−1881 Agonist Max: ((Sample RLU−Ave Low Control RLU[DMSO/Buffer])/(Ave High Control RLU [1 µM R−1881]−Ave Low Control RLU[DMSO/Buffer]))*100.

EC/IC50 calculations were achieved utilizing calculated RLU data and data fitting macros. Data were fit using least-squares methods to the following formula:

$$Y_{[fit]} = Y_{[low\ cmpd]} + \frac{(Y_{[high\ cmpd]} - Y_{[low\ cmpd]}) * Y_{[cmpd]}^{Hill}}{Y_{[cmpd]}^{Hill} + IC50^{Hill}}$$

wherein $Y_{[low\ cmpd]}$=Y value with inactive compound
$Y_{[high\ cmpd]}$=Y value with fully active compound effector
Hill=Hill coefficient
$EC/IC_{50}$=concentration of compound with 50% effect
Resultant data are shown in Table 3.

TABLE 3

| | LNCaP-AR-wt ANT | | LNCaP-AR-wt AG | | LNCaP-AR-F876L ANT | | LNCaP-AR-F876L AG | |
|---|---|---|---|---|---|---|---|---|
| | pIC50 | MAX % Inh | pEC50 | MAX % Stim | pIC50 | MAX % Inh | pEC50 | MAX % Stim |
| 1 | 6.94 | 101.3 | <4.82 | −0.1 | 7.07 | 100.6 | <4.82 | 0.1 |
| 2 | 6.61 | 100.6 | <4.82 | 0.5 | 6.91 | 99.9 | <4.82 | 0.2 |
| 3 | 6.39 | 97.8 | <4.82 | 2.2 | 6.49 | 98.9 | <4.82 | 1.8 |
| 4 | 6.46 | 97.6 | <4.82 | 1.6 | 6.68 | 99.5 | <4.82 | 0.4 |
| 5 | 6.17 | 98.8 | <4.82 | 1.2 | 6.18 | 90.3 | <4.82 | 3.3 |
| 6 | 6.53 | 99.7 | <4.82 | 0.3 | 6.72 | 98.1 | <4.82 | 0.9 |
| 7 | 6.54 | 99.1 | <4.82 | 0.3 | 6.87 | 98.2 | <4.82 | 2.8 |
| 8 | 5.93 | 86.6 | <4.82 | 0.4 | 5.94 | 96.0 | <4.82 | −0.1 |
| 9 | 5.92 | 94.2 | <4.82 | 0.1 | 6.24 | 98.4 | <4.82 | 0.5 |
| 10 | 6.47 | 101.7 | <4.82 | 0.5 | 6.56 | 100.0 | <4.82 | 0.9 |
| 11 | 5.72 | 99.4 | <4.82 | 2.8 | 5.98 | 95.3 | <4.82 | 2.0 |
| 12 | 6.18 | 100.6 | <4.82 | 0.5 | 6.93 | 98.5 | <4.82 | 0.7 |
| 13 | 6.27 | 100.9 | <4.82 | 0.5 | 6.44 | 98.1 | <4.82 | 1.0 |
| 14 | 6.25 | 97.1 | <4.82 | 0.4 | 6.63 | 98.4 | <4.82 | 0.2 |
| 15 | 6.62 | 101.4 | <4.82 | −0.1 | 6.72 | 100.1 | <4.82 | 1.1 |
| 16 | 5.95 | 98.8 | <4.82 | 0.5 | 6.44 | 97.5 | <4.82 | 0.8 |
| 17 | 5.82 | 98.5 | <4.82 | 0.3 | 6.34 | 100.5 | <4.82 | 0.1 |
| 18 | 5.65 | 93.5 | <4.82 | 0.0 | 6.00 | 99.0 | <4.82 | 0.0 |
| 19 | 6.18 | 100.9 | <4.82 | 0.3 | 6.70 | 100.6 | <4.82 | 1.6 |
| 20 | 5.74 | 93.2 | <4.82 | 0.2 | 6.29 | 97.7 | <4.82 | −0.5 |
| 21 | 6.30 | 80.6 | <4.82 | −0.1 | 6.51 | 69.9 | <4.82 | 0.3 |
| 22 | 5.64 | 95.7 | <4.82 | −0.1 | 5.62 | 99.0 | <4.82 | −0.1 |
| 23 | 6.52 | 102.2 | <4.82 | 0.4 | 6.67 | 100.8 | <4.82 | 0.4 |
| 24 | 6.77 | 101.4 | <4.82 | 0.6 | 7.08 | 100.9 | <4.82 | 0.5 |
| 25 | 6.79 | 100.8 | <4.82 | 0.0 | 6.99 | 100.0 | <4.82 | 0.2 |
| 26 | 7.26 | 101.1 | <4.82 | 0.4 | 7.16 | 100.1 | <4.82 | 0.5 |
| 27 | 6.66 | 100.6 | <4.82 | 0.0 | 6.97 | 100.7 | <4.82 | −0.1 |
| 28 | 6.51 | 101.3 | <4.82 | 0.2 | 6.51 | 99.4 | <4.82 | 0.8 |
| 29 | 6.05 | 91.5 | <4.82 | 1.5 | 6.40 | 101.3 | <4.82 | 3.4 |
| 30 | 6.15 | 99.7 | <4.82 | 0.3 | 7.04 | 100.6 | <4.82 | 0.3 |
| 31 | 5.89 | 80.3 | <4.82 | 0.3 | 6.21 | 87.1 | <4.82 | 0.1 |
| 32 | 5.67 | 64.9 | <4.82 | 0.4 | 5.95 | 74.1 | <4.82 | −0.1 |
| 33 | 6.15 | 98.9 | <4.82 | 0.2 | 6.41 | 98.2 | <4.82 | 2.8 |
| 34 | 5.48 | 82.7 | <4.82 | −0.4 | 5.90 | 89.7 | <4.82 | 0.2 |
| 35 | 6.04 | 100.0 | <4.82 | 0.2 | 6.43 | 99.5 | <4.82 | 0.3 |
| 36 | 6.12 | 100.4 | <4.82 | −0.2 | 6.20 | 99.1 | <4.82 | 1.0 |
| 37 | 5.90 | 99.8 | <4.82 | 0.1 | 6.39 | 99.5 | <4.82 | 0.0 |
| 38 | 6.15 | 100.7 | <4.82 | 0.0 | 6.49 | 99.9 | <4.82 | 0.3 |
| 39 | 6.17 | 100.5 | <4.82 | 0.9 | 6.61 | 101.3 | <4.82 | −0.1 |
| 40 | 6.27 | 97.6 | <4.82 | 0.2 | 6.00 | 96.0 | <4.82 | 1.5 |
| 41 | 6.37 | 99.3 | <4.82 | 0.1 | 6.59 | 99.9 | <4.82 | 0.1 |
| 42 | 6.21 | 100.2 | <4.82 | 0.2 | 6.51 | 99.9 | <4.82 | 0.2 |
| 43 | 7.27 | 101.1 | <4.82 | −0.1 | 7.43 | 100.0 | <4.82 | 0.1 |
| 44 | 7.12 | 98.8 | <4.82 | 0.7 | 7.43 | 100.8 | <4.82 | 0.1 |
| 45 | 5.52 | 92.9 | <4.82 | −0.3 | 5.90 | 99.2 | <4.82 | 0.0 |
| 46 | 6.66 | 100.9 | <4.82 | 1.1 | 6.96 | 97.6 | <4.82 | 0.3 |
| 47 | 6.50 | 100.5 | <4.82 | 0.7 | 6.84 | 100.2 | <4.82 | 0.5 |
| 48 | 6.45 | 101.6 | <4.82 | 0.0 | 6.69 | 100.3 | <4.82 | 0.2 |
| 49 | 6.98 | 100.7 | <4.82 | 0.3 | 7.25 | 99.5 | <4.82 | 0.4 |
| 50 | 7.79 | 100.9 | <4.82 | 0.1 | 8.06 | 98.0 | <4.82 | 1.4 |
| 51 | 7.27 | 98.0 | <4.82 | 2.3 | 7.61 | 100.6 | <4.82 | 1.7 |
| 52 | 6.76 | 98.3 | <4.82 | 2.8 | 7.36 | 98.9 | <4.82 | 0.8 |
| 53 | 6.91 | 101.7 | <4.82 | 0.4 | 7.34 | 100.0 | <4.82 | 0.1 |
| 54 | 7.09 | 100.7 | <4.82 | 1.3 | 7.03 | 97.1 | <4.82 | 0.7 |
| 55 | 7.14 | 103.5 | <4.82 | 0.6 | 7.39 | 101.1 | <4.82 | 0.5 |

TABLE 3-continued

| | LNCaP-AR-wt ANT | | LNCaP-AR-wt AG | | LNCaP-AR-F876L ANT | | LNCaP-AR-F876L AG | |
|---|---|---|---|---|---|---|---|---|
| | pIC50 | MAX % Inh | pEC50 | MAX % Stim | pIC50 | MAX % Inh | pEC50 | MAX % Stim |
| 56 | 6.20 | 84.5 | <4.82 | 0.4 | 6.17 | 85.2 | <4.82 | 0.1 |
| 57 | 6.31 | 100.3 | <4.82 | 0.3 | 6.70 | 99.1 | <4.82 | 0.3 |
| 58 | 7.06 | 101.1 | <4.82 | 0.0 | 7.03 | 98.1 | <4.82 | 1.0 |
| 59 | 6.87 | 101.9 | <4.82 | 0.0 | 7.25 | 100.5 | <4.82 | 0.1 |
| 60 | 7.64 | 99.2 | <4.82 | 0.8 | 8.02 | 98.1 | <4.82 | 0.6 |
| 61 | 7.53 | 99.2 | <4.82 | 0.4 | 7.44 | 98.8 | <4.82 | 0.3 |
| 62 | 7.42 | 100.0 | <4.82 | 0.5 | 7.57 | 98.4 | <4.82 | 0.2 |
| 63 | 7.09 | 101.6 | <4.82 | 0.0 | 7.16 | 100.6 | <4.82 | 0.1 |
| 64 | 7.30 | 100.9 | <4.82 | −0.2 | 7.33 | 100.5 | <4.82 | 0.1 |
| 65 | 8.14 | 100.7 | <4.82 | 0.4 | 8.07 | 99.3 | <4.82 | 0.4 |
| 66 | 7.31 | 99.0 | <4.82 | 0.5 | 7.34 | 95.5 | <4.82 | 0.9 |
| 67 | 7.37 | 99.6 | <4.82 | 0.4 | 7.33 | 97.4 | <4.82 | 0.7 |
| 68 | 7.40 | 100.9 | <4.82 | 0.6 | 7.76 | 99.7 | <4.82 | 0.4 |
| 69 | 6.94 | 100.9 | <4.82 | 0.2 | 7.16 | 98.9 | <4.82 | 0.1 |
| 70 | 7.47 | 98.8 | <4.82 | 0.8 | 7.41 | 97.1 | <4.82 | 3.6 |
| 71 | 6.99 | 100.6 | <4.82 | 0.2 | 6.75 | 98.3 | <4.82 | 0.5 |
| 72 | 6.56 | 100.8 | <4.82 | −0.1 | 6.76 | 100.3 | <4.82 | 0.0 |
| 73 | 6.30 | 100.6 | <4.82 | 1.0 | 6.65 | 97.6 | <4.82 | 0.5 |
| 74 | 7.14 | 100.2 | <4.82 | 0.2 | 7.67 | 98.1 | <4.82 | 1.5 |
| 75 | 6.83 | 102.1 | <4.82 | 0.2 | 7.05 | 100.7 | <4.82 | 0.1 |
| 76 | 7.03 | 102.5 | <4.82 | 0.6 | 6.85 | 97.5 | <4.82 | 2.2 |
| 77 | 7.43 | 101.5 | <4.82 | 0.2 | 7.51 | 100.1 | <4.82 | 0.3 |
| 78 | 7.03 | 100.8 | <4.82 | 1.2 | 7.64 | 100.0 | <4.82 | 0.0 |
| 79 | 8.17 | 101.3 | <4.82 | 1.2 | 8.09 | 98.5 | <4.82 | 1.3 |
| 80 | 7.60 | 102.2 | <4.82 | 0.6 | 7.95 | 100.0 | <4.82 | 0.1 |
| 81 | 7.55 | 102.1 | <4.82 | 0.4 | 7.77 | 101.1 | <4.82 | 0.1 |
| 82 | 6.81 | 98.7 | <4.82 | 0.4 | 7.00 | 97.5 | <4.82 | 0.8 |
| 83 | 6.64 | 101.5 | <4.82 | −0.2 | 6.89 | 99.0 | <4.82 | 0.2 |
| 84 | 6.28 | 100.6 | <4.82 | 0.2 | 7.09 | 101.0 | <4.82 | 0.1 |
| 85 | 6.46 | 88.3 | <4.82 | −0.1 | 6.37 | 85.8 | <4.82 | 0.6 |
| 86 | 6.91 | 100.4 | <4.82 | 0.0 | 7.12 | 99.7 | <4.82 | 0.1 |
| 87 | 6.92 | 100.9 | <4.82 | 0.1 | 7.09 | 100.2 | <4.82 | 0.1 |
| 88 | 7.13 | 101.8 | <4.82 | 0.4 | 7.48 | 99.5 | <4.82 | 0.4 |
| 89 | 7.17 | 101.2 | <4.82 | 0.2 | 7.26 | 98.4 | <4.82 | 3.3 |
| 90 | 7.05 | 99.7 | <4.82 | 0.6 | 7.17 | 99.3 | <4.82 | 0.9 |
| 91 | 7.33 | 98.3 | <4.82 | 0.6 | 7.49 | 98.6 | <4.82 | 0.4 |
| 92 | 7.11 | 101.4 | <4.82 | 0.3 | 7.22 | 98.2 | <4.82 | 0.5 |
| 93 | 6.77 | 104.9 | <4.82 | 0.5 | 7.34 | 101.8 | <4.82 | 0.2 |
| 94 | 6.78 | 101.3 | <4.82 | 0.8 | 7.15 | 100.9 | <4.82 | 0.2 |
| 95 | 6.95 | 101.0 | <4.82 | 0.1 | 7.35 | 99.7 | <4.82 | 0.3 |
| 96 | 6.90 | 100.5 | <4.82 | 0.9 | 7.13 | 99.9 | <4.82 | 0.4 |
| 97 | 7.26 | 102.2 | <4.82 | 0.0 | 7.60 | 99.9 | <4.82 | 0.2 |
| 98 | 7.33 | 101.3 | <4.82 | 0.3 | 7.68 | 100.2 | <4.82 | 0.1 |
| 99 | 6.76 | 100.7 | <4.82 | 0.5 | 7.14 | 99.7 | <4.82 | 0.2 |
| 100 | 6.79 | 100.5 | <4.82 | 0.1 | 7.23 | 98.9 | <4.82 | 0.5 |
| 101 | 6.81 | 102.2 | <4.82 | 0.3 | 6.91 | 98.3 | <4.82 | 0.7 |
| 102 | 7.10 | 99.7 | <4.82 | 0.4 | 7.31 | 99.6 | <4.82 | 0.3 |
| 103 | 7.02 | 102.8 | <4.82 | 0.0 | 6.66 | 98.0 | <4.82 | 2.0 |
| 104 | 7.16 | 101.4 | <4.82 | 0.5 | 7.38 | 99.6 | <4.82 | 0.7 |
| 105 | 6.91 | 100.3 | <4.82 | 0.1 | 7.18 | 97.6 | <4.82 | 0.8 |
| 106 | 6.76 | 102.2 | <4.82 | 0.1 | 6.66 | 99.7 | <4.82 | 0.7 |
| 107 | 7.64 | 100.8 | <4.82 | 0.5 | 7.61 | 97.5 | <4.82 | 1.9 |
| 108 | 5.78 | 98.3 | <4.82 | 0.7 | 5.99 | 94.8 | <4.82 | 0.2 |
| 109 | 5.55 | 96.1 | <4.82 | 0.0 | 5.87 | 98.8 | <4.82 | 0.2 |
| 110 | 6.88 | 101.1 | <4.82 | 0.3 | 7.04 | 100.3 | <4.82 | 0.2 |
| 111 | 6.88 | 101.2 | <4.82 | 0.8 | 6.93 | 100.8 | <4.82 | 0.4 |
| 112 | 6.57 | 102.0 | <4.82 | 0.3 | 6.55 | 100.0 | <4.82 | 0.2 |
| 113 | 6.35 | 89.0 | <4.82 | 0.3 | 6.26 | 83.6 | <4.82 | 1.8 |
| 114 | 5.57 | 101.8 | <4.82 | −0.1 | 5.99 | 101.1 | <4.82 | 0.3 |
| 115 | 6.24 | 87.0 | <4.82 | −0.1 | 6.54 | 104.2 | <4.82 | 0.1 |
| 116 | 5.96 | 102.2 | <4.82 | 0.5 | 6.01 | 101.8 | <4.82 | 0.8 |
| 117 | 7.01 | 102.3 | <4.82 | 0.0 | 6.95 | 99.4 | <4.82 | 0.9 |
| 118 | 6.31 | 101.3 | <4.82 | 0.1 | 6.17 | 93.7 | <4.82 | 0.8 |
| 119 | 6.27 | 102.0 | <4.82 | 0.1 | 6.71 | 100.1 | <4.82 | 2.7 |
| 120 | 6.70 | 100.2 | <4.82 | 0.2 | 6.47 | 100.6 | <4.82 | 1.1 |
| 121 | 6.86 | 97.9 | <4.82 | −0.1 | 6.89 | 99.8 | <4.82 | 0.5 |
| 122 | 6.55 | 98.0 | <4.82 | 0.3 | 6.55 | 96.4 | <4.82 | 0.7 |
| 123 | 5.64 | 103.0 | <4.82 | 0.3 | 6.03 | 101.6 | <4.82 | 0.2 |
| 124 | 6.94 | 103.0 | <4.82 | 0.3 | 7.40 | 102.6 | <4.82 | 0.5 |
| 125 | 5.57 | 99.5 | <4.82 | 0.6 | 5.80 | 98.1 | <4.82 | 0.0 |
| 126 | 6.56 | 100.7 | <4.82 | 0.2 | 6.69 | 100.5 | <4.82 | 0.8 |
| 127 | 6.23 | 101.9 | <4.82 | 0.5 | 6.37 | 101.8 | <4.82 | 0.4 |
| 128 | 5.97 | 100.7 | <4.82 | 0.2 | 6.33 | 100.7 | <4.82 | 0.3 |
| 129 | 7.11 | 101.6 | <4.82 | 0.9 | 7.44 | 100.3 | <4.82 | 0.1 |
| 130 | 6.46 | 100.2 | <4.82 | 0.2 | 6.31 | 100.5 | <4.82 | 0.2 |

TABLE 3-continued

| | LNCaP-AR-wt ANT | | LNCaP-AR-wt AG | | LNCaP-AR-F876L ANT | | LNCaP-AR-F876L AG | |
|---|---|---|---|---|---|---|---|---|
| | pIC50 | MAX % Inh | pEC50 | MAX % Stim | pIC50 | MAX % Inh | pEC50 | MAX % Stim |
| 131 | 6.23 | 100.9 | <4.82 | −0.1 | 6.15 | 97.9 | <4.82 | 0.3 |
| 132 | 6.43 | 100.8 | <4.82 | 0.5 | 6.83 | 98.7 | <4.82 | 0.9 |
| 133 | 5.80 | 98.3 | <4.82 | 0.7 | 6.01 | 99.0 | <4.82 | 0.6 |
| 134 | 6.12 | 102.7 | <4.82 | 0.6 | 6.47 | 104.3 | <4.82 | 0.1 |
| 135 | 6.41 | 104.2 | <4.82 | 0.1 | 6.81 | 102.4 | <4.82 | −0.1 |
| 136 | 6.88 | 104.8 | <4.82 | −0.1 | 6.90 | 102.1 | <4.82 | 0.3 |
| 137 | 7.31 | 102.3 | <4.82 | 0.3 | 7.08 | 98.7 | <4.82 | 0.9 |
| 138 | 6.37 | 103.2 | <4.82 | −0.1 | 6.57 | 100.1 | <4.82 | 0.1 |
| 139 | 6.23 | 101.7 | <4.82 | 1.2 | 6.29 | 99.8 | <4.82 | 0.1 |
| 140 | 6.00 | 99.9 | <4.82 | 0.3 | 6.47 | 99.5 | <4.82 | 0.0 |
| 141 | 6.30 | 84.9 | <4.82 | −0.1 | 6.51 | 66.8 | <4.82 | 0.0 |
| 142 | 6.95 | 100.9 | <4.82 | −0.2 | 6.93 | 99.0 | <4.82 | 0.8 |
| 143 | 5.87 | 102.7 | <4.82 | −0.2 | 6.45 | 101.0 | <4.82 | 0.4 |
| 144 | 5.96 | 98.3 | <4.82 | 0.3 | 6.44 | 99.9 | <4.82 | 0.6 |
| 145 | 6.75 | 101.1 | <4.82 | 0.5 | 6.52 | 98.8 | <4.82 | 1.8 |
| 146 | 7.00 | 102.6 | <4.82 | 0.1 | 7.21 | 101.1 | <4.82 | −0.1 |
| 147 | 6.65 | 102.2 | <4.82 | −0.1 | 6.68 | 100.7 | <4.82 | −0.1 |
| 148 | 6.52 | 100.9 | <4.82 | 0.1 | 6.90 | 101.0 | <4.82 | 0.6 |
| 149 | 7.09 | 99.8 | <4.82 | 0.5 | 6.98 | 97.9 | <4.82 | 1.5 |
| 150 | 6.31 | 102.2 | <4.82 | 0.4 | 6.61 | 103.0 | <4.82 | −0.2 |
| 151 | 6.63 | 105.9 | <4.82 | 0.0 | 6.84 | 103.7 | <4.82 | −0.1 |
| 152 | 6.38 | 101.1 | <4.82 | 0.2 | 6.37 | 99.9 | <4.82 | 0.1 |
| 153 | 6.40 | 100.6 | <4.82 | 0.1 | 6.47 | 100.2 | <4.82 | −0.1 |
| 154 | 6.33 | 102.2 | <4.82 | −0.1 | 6.57 | 100.4 | <4.82 | −0.1 |
| 155 | 6.52 | 97.4 | <4.82 | 1.1 | 6.66 | 98.0 | <4.82 | 2.6 |
| 156 | 6.55 | 100.3 | <4.82 | 1.0 | 6.75 | 101.2 | <4.82 | 0.9 |
| 157 | 6.14 | 102.5 | <4.82 | −0.2 | 6.30 | 99.8 | <4.82 | 0.0 |
| 158 | 6.50 | 100.2 | <4.82 | 0.3 | 6.37 | 95.6 | <4.82 | 2.3 |
| 159 | 5.87 | 100.3 | <4.82 | 0.2 | 6.51 | 100.0 | <4.82 | 0.2 |
| 160 | 5.91 | 103.1 | <4.82 | 0.1 | 6.15 | 101.0 | <4.82 | 0.0 |
| 161 | 5.98 | 97.2 | <4.82 | 0.2 | 6.33 | 99.3 | <4.82 | 0.3 |
| 162 | 6.49 | 96.4 | <4.82 | −0.1 | 6.80 | 99.2 | <4.82 | 0.0 |
| 163 | 6.14 | 100.1 | <4.82 | 0.4 | 6.54 | 99.3 | <4.82 | 0.1 |
| 164 | 6.27 | 101.6 | <4.82 | 0.3 | 6.53 | 101.0 | <4.82 | 0.0 |
| 165 | 6.49 | 101.1 | <4.82 | 0.2 | 6.50 | 100.0 | <4.82 | 0.0 |
| 166 | 6.48 | 102.3 | <4.82 | 0.2 | 6.70 | 101.1 | <4.82 | 0.1 |
| 167 | 6.08 | 100.9 | <4.82 | −0.2 | 6.54 | 101.5 | <4.82 | 0.0 |
| 168 | 7.02 | 101.1 | <4.82 | 0.0 | 6.84 | 99.3 | <4.82 | 0.8 |
| 169 | 6.73 | 99.6 | <4.82 | 0.2 | 6.95 | 100.4 | <4.82 | 0.2 |
| 170 | 6.23 | 101.3 | <4.82 | 0.2 | 6.51 | 101.7 | <4.82 | 0.1 |
| 171 | 6.45 | 101.3 | <4.82 | 0.2 | 6.80 | 100.8 | <4.82 | 0.1 |
| 172 | 6.47 | 99.2 | <4.82 | 0.2 | 6.76 | 100.5 | <4.82 | −0.1 |
| 173 | 6.36 | 100.0 | <4.82 | 0.4 | 6.73 | 100.4 | <4.82 | 0.1 |
| 174 | 6.39 | 101.5 | <4.82 | 0.0 | 6.66 | 100.9 | <4.82 | 0.1 |
| 175 | 6.57 | 100.8 | <4.82 | 0.1 | 6.85 | 100.7 | <4.82 | 0.0 |
| 176 | 6.32 | 104.2 | <4.82 | 0.3 | 6.57 | 101.3 | <4.82 | 0.1 |
| 177 | 6.28 | 102.1 | <4.82 | 0.2 | 6.34 | 100.0 | <4.82 | 0.4 |
| 178 | 6.76 | 103.8 | <4.82 | 0.3 | 6.63 | 102.3 | <4.82 | 0.0 |
| 179 | 5.91 | 100.2 | <4.82 | −0.2 | 6.33 | 100.6 | <4.82 | −0.2 |
| 180 | 6.66 | 106.5 | <4.82 | 0.2 | 7.01 | 103.8 | <4.82 | 0.2 |
| 181 | 6.47 | 96.8 | <4.82 | 1.9 | 6.80 | 101.9 | <4.82 | 0.3 |
| 182 | 6.26 | 103.2 | <4.82 | 0.0 | 6.72 | 102.0 | <4.82 | 0.1 |
| 183 | 6.29 | 100.4 | <4.82 | 0.3 | 6.56 | 100.9 | <4.82 | −0.1 |
| 184 | 6.09 | 100.5 | <4.82 | 0.2 | 6.35 | 99.6 | <4.82 | 0.4 |
| 185 | 6.15 | 102.1 | <4.82 | 0.2 | 6.37 | 101.5 | <4.82 | 0.8 |
| 186 | 5.50 | 99.8 | <4.82 | 0.1 | 5.65 | 100.0 | <4.82 | 0.0 |
| 187 | 5.90 | 100.7 | <4.82 | 0.3 | 6.29 | 100.9 | <4.82 | 0.2 |
| 188 | 6.66 | 103.9 | <4.82 | −0.2 | 6.77 | 103.7 | <4.82 | 0.3 |
| 189 | 7.16 | 100.3 | <4.82 | 0.0 | 7.09 | 99.1 | <4.82 | 1.7 |
| 190 | 5.52 | 95.3 | <4.82 | −0.1 | 5.78 | 97.4 | <4.82 | 0.1 |
| 191 | 5.86 | 99.4 | <4.82 | −0.2 | 5.95 | 99.8 | <4.82 | 0.0 |
| 192 | 5.80 | 100.6 | <4.82 | 0.0 | 6.16 | 101.7 | <4.82 | 0.1 |
| 193 | 6.64 | 100.6 | <4.82 | 0.1 | 6.72 | 101.4 | <4.82 | 0.4 |
| 194 | 6.81 | 103.2 | <4.82 | −0.3 | 6.73 | 103.4 | <4.82 | 0.4 |
| 195 | 6.73 | 101.7 | <4.82 | 0.0 | 6.76 | 100.2 | <4.82 | 0.6 |
| 196 | 6.23 | 100.3 | <4.82 | −0.2 | 6.36 | 99.9 | <4.82 | 0.2 |
| 197 | 5.97 | 99.3 | <4.82 | 0.1 | 6.35 | 100.6 | <4.82 | 0.3 |
| 198 | 6.25 | 101.8 | <4.82 | 0.1 | 6.25 | 102.4 | <4.82 | 0.1 |
| 199 | 5.79 | 88.9 | <4.82 | −0.2 | 5.82 | 102.4 | <4.82 | 0.9 |
| 200 | 6.15 | 99.6 | <4.82 | 0.4 | 6.10 | 99.1 | <4.82 | 0.5 |
| 201 | 6.45 | 100.8 | <4.82 | −0.3 | 6.67 | 100.6 | <4.82 | 0.0 |
| 202 | 5.96 | 101.9 | <4.82 | −0.1 | 6.22 | 100.7 | <4.82 | 0.0 |
| 203 | 6.05 | 102.5 | <4.82 | −0.1 | 6.25 | 100.4 | <4.82 | 0.0 |
| 204 | 5.61 | 101.7 | <4.82 | 0.1 | 5.71 | 99.7 | <4.82 | 0.0 |
| 205 | 5.96 | 101.1 | <4.82 | −0.1 | 6.15 | 100.0 | <4.82 | 0.1 |

TABLE 3-continued

| | LNCaP-AR-wt ANT | | LNCaP-AR-wt AG | | LNCaP-AR-F876L ANT | | LNCaP-AR-F876L AG | |
|---|---|---|---|---|---|---|---|---|
| | pIC50 | MAX % Inh | pEC50 | MAX % Stim | pIC50 | MAX % Inh | pEC50 | MAX % Stim |
| 206 | 6.07 | 101.4 | <4.82 | 0.1 | 6.21 | 99.3 | <4.82 | 0.1 |
| 207 | 6.39 | 100.9 | <4.82 | 0.0 | 6.42 | 100.3 | <4.82 | 0.0 |
| 208 | 6.06 | 103.0 | <4.82 | 0.0 | 5.99 | 101.3 | <4.82 | 0.0 |
| 209 | 6.34 | 99.0 | <4.82 | −0.1 | 6.38 | 100.3 | <4.82 | 0.0 |
| 210 | 5.93 | 102.4 | <4.82 | 0.1 | 5.96 | 100.1 | <4.82 | 0.1 |
| 211 | 5.98 | 101.0 | <4.82 | 0.5 | 6.44 | 100.8 | <4.82 | 0.1 |
| 212 | 6.87 | 101.8 | <4.82 | 0.2 | 6.48 | 96.1 | <4.82 | 1.5 |
| 213 | 6.26 | 101.8 | <4.82 | 0.2 | 6.55 | 100.4 | <4.82 | 0.1 |
| 214 | 6.54 | 100.4 | <4.82 | 0.3 | 6.66 | 99.9 | <4.82 | 0.0 |
| 215 | 6.46 | 101.3 | <4.82 | 0.0 | 6.62 | 100.9 | <4.82 | 0.1 |
| 216 | 5.79 | 98.8 | <4.82 | 0.1 | 5.83 | 98.7 | <4.82 | 0.0 |
| 217 | 6.43 | 102.4 | <4.82 | 0.4 | 6.45 | 100.5 | <4.82 | 0.1 |
| 218 | 5.93 | 101.7 | <4.82 | 0.0 | 6.04 | 99.6 | <4.82 | 0.1 |
| 219 | 6.43 | 101.9 | <4.82 | 0.3 | 6.46 | 100.7 | <4.82 | 0.2 |
| 220 | 6.13 | 101.5 | <4.82 | 0.1 | 6.23 | 100.7 | <4.82 | 0.1 |
| 221 | 6.05 | 101.1 | <4.82 | −0.1 | 6.23 | 100.5 | <4.82 | 0.1 |
| 222 | 6.89 | 99.6 | <4.82 | 2.3 | 7.09 | 99.6 | <4.82 | 0.2 |
| 223 | 6.43 | 100.7 | <4.82 | 0.5 | 6.64 | 100.0 | <4.82 | 0.4 |
| 224 | 5.75 | 101.2 | <4.82 | 0.0 | 5.83 | 100.0 | <4.82 | 0.1 |
| 225 | 6.47 | 101.1 | <4.82 | 0.4 | 6.68 | 100.3 | <4.82 | 0.5 |
| 226 | 7.22 | 101.0 | <4.82 | 0.4 | 7.44 | 100.5 | <4.82 | 0.2 |
| 227 | 6.29 | 101.8 | <4.82 | −0.2 | 6.38 | 100.5 | <4.82 | 0.1 |
| 228 | 6.68 | 102.5 | <4.82 | −0.2 | 6.94 | 101.3 | <4.82 | 0.1 |
| 229 | 6.58 | 101.3 | <4.82 | 0.0 | 6.89 | 100.7 | <4.82 | 0.0 |
| 230 | 5.92 | 103.8 | <4.82 | 0.5 | 5.84 | 101.5 | <4.82 | −0.1 |
| 231 | 6.20 | 99.3 | <4.82 | 0.9 | 6.23 | 99.2 | <4.82 | 0.7 |
| 232 | 6.40 | 102.7 | <4.82 | −0.1 | 6.43 | 101.2 | <4.82 | 0.2 |
| 233 | 6.62 | 108.4 | <4.82 | −0.2 | 6.73 | 103.2 | <4.82 | 0.0 |
| 234 | 6.32 | 100.1 | <4.82 | 0.1 | 6.59 | 101.6 | <4.82 | 0.0 |
| 235 | 5.97 | 100.9 | <4.82 | 0.2 | 6.25 | 100.8 | <4.82 | 0.1 |
| 236 | 6.34 | 102.6 | <4.82 | 0.6 | 6.57 | 101.0 | <4.82 | 0.2 |
| 237 | 6.08 | 103.5 | <4.82 | 0.4 | 6.33 | 100.4 | <4.82 | 0.1 |
| 238 | 5.85 | 101.4 | <4.82 | 0.0 | 6.09 | 100.8 | <4.82 | 0.1 |
| 239 | 6.22 | 102.8 | <4.82 | −0.1 | 6.46 | 101.6 | <4.82 | 0.2 |
| 240 | 6.34 | 105.9 | <4.82 | 1.0 | 6.65 | 105.0 | <4.82 | 0.0 |
| 241 | 6.65 | 103.1 | <4.82 | −0.1 | 6.80 | 103.0 | <4.82 | 1.1 |
| 242 | 6.25 | 99.9 | <4.82 | 0.1 | 6.61 | 104.1 | <4.82 | −0.1 |
| 243 | 5.79 | 100.7 | <4.82 | 0.2 | 6.46 | 100.2 | <4.82 | 0.7 |
| 244 | 6.19 | 98.7 | <4.82 | 0.2 | 6.61 | 101.3 | <4.82 | −0.5 |
| 245 | 6.32 | 99.3 | <4.82 | 0.0 | 6.82 | 101.5 | <4.82 | 0.5 |
| 246 | 5.95 | 0.0 | <4.82 | 0.1 | 5.94 | 99.5 | <4.82 | 0.2 |
| 247 | 6.00 | 0.0 | <4.82 | −0.1 | 5.92 | 99.4 | <4.82 | 0.2 |
| 248 | 6.38 | 0.0 | <4.82 | 0.0 | 6.43 | 101.5 | <4.82 | 0.4 |
| 249 | 6.39 | 0.0 | <4.82 | 0.0 | 6.50 | 103.4 | <4.82 | 0.0 |
| 250 | 5.93 | 0.0 | <4.82 | 0.0 | 6.01 | 101.1 | <4.82 | 0.1 |
| 251 | 6.54 | 0.0 | <4.82 | −0.1 | 6.76 | 101.0 | <4.82 | 0.1 |
| 252 | 6.39 | 0.0 | <4.82 | −0.1 | 6.08 | 100.3 | <4.82 | −0.1 |
| 253 | 5.76 | 0.0 | <4.82 | 0.4 | 6.08 | 100.1 | <4.82 | 0.1 |
| 254 | 6.05 | 0.0 | <4.82 | −0.1 | 6.15 | 99.3 | <4.82 | 0.4 |
| 255 | 5.60 | 94.7 | <4.82 | 0.4 | 5.56 | 99.0 | <4.82 | 0.1 |
| 256 | 5.32 | 95.9 | <4.82 | 0.4 | 5.87 | 96.8 | <4.82 | 0.6 |

As used herein:

$pIC_{50}$ is defined as $-Log_{10}(IC_{50}$ expressed in [Molar]).

$pEC_{50}$ is defined as $-Log_{10}(EC_{50}$ expressed in [Molar]).

MAX % Inh is defined as the maximum % inhibition of R1881 control response observed for a compound over the tested concentration range.

MAX % Stim is defined as the maximum % stimulation (agonist response) observed for a compound over the tested concentration range.

LNCaP-AR-wt ANT refers to the reporter assay using LNCaP cells stably transfected with the Androgen Response Element Firefly Luciferase lentiviral construct and wild-type Androgen Receptor (AR-wt) in Antagonist mode.

LNCaP-AR-wt AG refers to the reporter assay using LNCaP cells stably transfected with the Androgen Response Element Firefly Luciferase lentiviral construct and wild-type Androgen Receptor (AR-wt) in Agonist mode.

LNCaP-AR-F876L ANT refers to the reporter assay using LNCaP cells stably transfected with the Androgen Response Element Firefly Luciferase lentiviral construct and F876L mutant Androgen Receptor (AR-F876L) in Antagonist mode.

LNCaP-AR-F876L AG refers to the reporter assay using LNCaP cells stably transfected with the Androgen Response Element Firefly Luciferase lentiviral construct and F876L mutant Androgen Receptor (AR-F876L) in Agonist mode.

Biological Example 3

AR in Cell Western Assay

LNCaP cells (8,000/well) are plated in RPMI media containing 10% Charcoal Dextran Stripped Serum into plates coated with poly-d-lysine. After 24 h cells are treated with compound from 30 µM to 0.0003 µM. At 20 h post compound addition the cells were fixed (30% formaldehyde in PBS) for 20'. Cells are permeabilized in PBS 0.1% Triton (50 µL/well, three times for 5' each) and blocked with LiCor blocking buffer (50 µL/well, 90'). The wells are then incubated overnight at 4° C. with the rabbit IgG androgen receptor antibody (AR-N20, Santa Cruz antibody) diluted 1:1000 in LiCor blocking buffer/0.1% Tween-20. Wells are washed with 0.1% Tween-20/PBS (50 µL/well, 5' each) and then incubated in goat anti-rabbit IRDye<™>800CW (1:1000) and DRAQ5 DNA dye (1:10,0000 for 5 mM stock) diluted in 0.2% Tween-20/0.01% SDS/LiCor blocking buffer in the dark (90'). Cells are washed (50 µL/well, 5' each) in 0.1% Tween-20/PBS. Wash buffer is removed and plates were read using the LiCor Odyssey.

Biological Example 4

LNCaP AR Localization Assay

LNCaP cells were expanded in RPMI 10% FBS in T150 flasks. The cells were dislodged with 0.25% Trypsin, washed in complete media, centrifuged (300 g, 3 min), and the supernatant aspirated. The cells were resuspended in RPMI phenol-red free media with 1% charcoal-stripped serum (CSS) and counted using a ViCELL (Beckman-Coulter). Three million cells in 7 mL of RPMI CSS were seeded into 100 mm dishes and incubated overnight at 37° C. 5% $CO_2$. The following morning, compound dilutions were prepared in RPMI CSS using 50 mM stock solutions and added directly to the cells to obtain the final concentration of 10 µM. The dishes were placed into the incubator for 4 h. After 4 h, cell scrapers were used to dislodge the cells and the media/cell solution was centrifuged, supernatant aspirated, and then washed with Cell Wash Buffer (Protein Simple). The pellets were stored at −80° C. or processed immediately using the Subcellular Protein Fractionation Kit for Cultured Cells (Thermo-Fisher). The fractions obtained from this kit were stored at −80° C. Later, the samples' protein concentration was determined using the BCA Assay Kit (Thermo-Fisher) and the fraction lysates normalized to 0.6 mg/mL. The lysates were run on the Wes Simple Western platform (ProteinSimple). The data was analyzed, normalized to the total AR, and plotted in GraphPad Prism. ANOVA with Tukey's Multiple Comparisons Test was used for statistical analyses.

| Compound | Inhibition of translocation |
| --- | --- |
| 43 | 50% |

Biological Example 5

AR FP Assay

A compound of Formula (I) may be diluted to 2× the final desired concentration in AR Green Assay Buffer (final DMSO: 0.6%). Fluormone AL Green and the rat AR Ligand Binding Domain is diluted to 2× the final desired concentration (Fluormone: 2 nM, AR LBD: 50 nM) in AR Green Assay Buffer containing 2 mM DTT. The AR LBD/Fluormone solution is added to all the wells of a 384 well black plate (10 µL/well). A compound of Formula (I) may be added to the AR LBD/Fluormone solution (10 µL/well). The plate is incubated for 4 h in the dark. The fluorescence polarization of each well is measured using an excitation wavelength of 485 nm and emission wavelength of 530 nm.

Biological Example 6

Prostate Cancer Cell Viability Assay-VCaP

VCaP cells were counted and seeded into black 384-well plates with clear bottoms at a concentration of 125,000 cells per mL in phenol red-free DMEM containing 10% Charcoal Stripped Serum. 16 µL of the suspension was added per well and incubated for 48 h to allow the cells to adhere. After 48 hours, a 12 point serial semilog dilution of each compound was added to the cells in 16 µL at a final concentration of 100 µM to 0.0003 µM. The compounds of Formula (I) were also run in antagonist mode using 30 pM R1881 in which 8 µL of the compound was added to the cells followed by 8 µL of R1881. After 5 days of incubation at 37° C., 16 µL Of CellTiter-Glo (Promega) was added to the cells and the relative luminescence units (RLUs) of each well determined using the Envision. The percent stimulation and % inhibition were determined for each sample and plotted using GraphPad Prism. Resultant data are shown in Table 4.

TABLE 4

| Compound | $IC_{50}$ (nM) |
| --- | --- |
| 43 | 270 |

Biological Example 7

LNCaP Proliferation Assays

LNCaP cells were expanded in RPMI 10% FBS in T150 flasks. The cells were dislodged with 0.25% Trypsin, washed in complete media, centrifuged (300 g, 3 min), and the supernatant aspirated. The cells were resuspended in RPMI phenol-red free media with 1% charcoal-stripped serum (CSS) and counted using a ViCELL (Beckman-Coulter). 7500 cells were added to each well of a white optical bottom 384-well plate and incubated for 2 days at 37° C. 5% $CO_2$. Compound dilutions were prepared in RPMI CSS using 50 mM stock solutions and added to the cells either alone (agonist mode) or in combination with 0.1 nM R1881 (antagonist mode). The plates were incubated for 4 days, followed by addition of CellTiter-Glo Luminescent Cell Viability kit reagent (Promega). The plates were placed on a shaker at 3000 rpm for 10 minutes and then read on an EnVision plate reader (Perkin Elmer) using Luminescence assay default settings. The data was analyzed, normalized to 0.1 nM R1881 stimulation, and plotted in GraphPad Prism. Resultant data are shown in Table 5.

TABLE 5

| Compound | $IC_{50}$ (nM) | |
| --- | --- | --- |
| | LNCaP WT | LNCaP F876L |
| 43 | 435 | 197 |

Biological Example 8

Luciferase Transcriptional Reporter Assays (WT and Mutant AR)

HepG2 cells were maintained in EMEM supplemented with 10% FBS. One day before transfection, the media was changed to EMEM with 10% CSS. T-150 flasks were transiently transfected using 120 μL Lipofectamine 2000 (Life Technologies), 30 μg mutant cDNA (expression vector)—mutant cDNA tested were L701H, T877A, W741C and H874Y—and 40 μg 4×ARE-Luciferase (reporter vector) in OptiMEM and the flasks were incubated overnight. Cells were then trypsinized, counted and resuspended at 500,000 cells/mL. For agonist mode, the compounds of Formula (I) were serially diluted and 50 μL of the compound was added per well. 50 μL of the cells were added to each well and incubated for 48 hours. For antagonist mode, a final concentration of 90 pM R1881 was added to the diluted compounds and incubated for 48 hours. The plates were then assayed using SteadyGlo and read on the Envision. Percent Stimulation and Inhibition were determined and analyzed using GraphPad Prism. Resultant data are shown in Table 6.

TABLE 6

Summary of Antagonist Activity, $IC_{50}$ and Agonist Activity, $EC_{50}$, for compounds of Formula (I) in AR Mutant Reporter Assays.

| | Antagonism; $IC_{50}$ μM [% $E_{max}$] AR construct | | | |
|---|---|---|---|---|
| Compound | L701H | T877A | W741C | H874Y |
| 43 | 10[90%] | 6.81[80%] | 12.3[85%] | 16.8[80%] |

| | Agonism; $EC_{50}$ μM [% $E_{max}$] AR construct | | | |
|---|---|---|---|---|
| Compound | L701H | T877A | W741C | H874Y |
| 43 | NA[0%] | 2.29[10%] | 2.83[0%] | NA[0%] |

F876L agonism was evident at 3 and 10 μM (5%) but zero at 30 μM.

The antagonistic ($IC_{50}$) and agonistic ($EC_{50}$) values for each of the AR cDNA used in the reporter assays are summarized. All values are calculated relative to the activity of R1881 induced androgen receptor activity (n≥3). Also indicated are the maximal inhibition and extent of induction of androgen dependent signaling (%).

Biological Example 9

AR-VP16 DNA Binding Assays

HepG2 cells were maintained in EMEM supplemented with 10% FBS. One day before transfection, the media was changed to EMEM with 10% CSS. T-150 flasks were transiently transfected using 120 μL Lipofectamine 2000 (Life Technologies), 24.5 μg AR-VP16 or F876L-VP16 (expression vector) and 49 μg 4×ARE-Luciferase (reporter vector) in OptiMEM and the flasks were incubated overnight. Cells were then trypsinized, counted and resuspended at 500,000 cells/mL. For agonist mode, the compounds were serially diluted and 50 μL of the compound was added per well. 50 μL of the cells were added to each well and incubated for 48 hours. For antagonist mode, a final concentration of 90 pM (VP16 AR) or 1 nM (VP16 F876L) R1881 was added to the plate and incubated for 48 hours. The plates were then assayed using SteadyGlo and read on the Envision. Percent Stimulation and Inhibition were determined and analyzed using GraphPad Prism. Resultant data are shown in Table 7.

TABLE 7

| | $IC_{50}$ (nM) | |
|---|---|---|
| Compound | VP16 WT | VP16 F876L |
| 43 | 7750 | 15 |

No agonism of DNA binding observed

Biological Example 10

GABA-Gated Cl Channel Antagonist Radioligand Binding Assay

GABA-gated Cl Chanel assays were performed at CEREP according to the following method. Membrane homogenates of cerebral cortex (120 μg protein) were incubated for 120 min at 22° C. with 3 nM [$^{35}$S]-TBPS in the absence or presence of the test compound in a buffer containing 50 mM $Na_2HPO_4/KH_2PO_4$ (pH 7.4) and 500 mM NaCl. Nonspecific binding was determined in the presence of 20 μM picrotoxinin. Following incubation, the samples were filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters were dried then counted for radioactivity in a scintillation counter (Topcount, Packard) using a scintillation cocktail (Microscint 0, Packard). The results are expressed as a percent inhibition of the control radio ligand specific binding. The standard reference compound is picrotoxinin, which was tested in each experiment at several concentrations to obtain a competition curve from which its $IC_{50}$ was calculated. In this assay, the following representative compounds disclosed herein had recorded activities at a 10 μM single point concentration in the GABA-gated Cl— Channel Binding Assay. Resultant data are shown in Table 8.

TABLE 8

| Cpd No. | rGABA-gated Cl⁻ channel % inh @10 μM |
|---|---|
| 1 | 6.3 |
| 2 | 1.6 |
| 23 | 4.8 |
| 24 | 25.4 |
| 25 | 1.4 |
| 26 | 21.6 |
| 29 | 39.9 |
| 30 | 53.6 |
| 31 | 79.0 |
| 33 | 99.2 |
| 34 | 91.2 |
| 35 | 49.9 |
| 36 | 96.2 |
| 37 | 18.8 |
| 38 | 69.2 |
| 39 | 86.2 |
| 40 | 67.5 |
| 41 | 20.4 |
| 43 | 1.9, 28 (n = 2) |
| 44 | −0.5 |
| 48 | 37.2 |
| 49 | 86.4 |
| 50 | 13.2 |
| 52 | 13.1 |
| 53 | 52.4 |
| 54 | 93.0 |
| 55 | 100.0 |
| 58 | 88.1 |
| 59 | 16.0 |

TABLE 8-continued

| Cpd No. | rGABA-gated Cl− channel % inh @10 μM |
|---|---|
| 60 | 91.5 |
| 61 | 26.1 |
| 62 | 61.0 |
| 63 | 13.0 |
| 64 | 5.8 |
| 65 | 67.2 |
| 66 | 83.0 |
| 67 | 53.4 |
| 68 | 34.9 |
| 69 | 77.5 |
| 70 | 9.2 |
| 71 | 82.1 |
| 72 | 20.0 |
| 73 | 80.1 |
| 74 | 13.9 |
| 75 | −32.5 |
| 76 | 85.4 |
| 77 | 53.8 |
| 78 | 3.8 |
| 79 | 11.5 |
| 80 | 33.7 |
| 81 | 28.8 |
| 82 | 36.7 |
| 83 | 20.5 |
| 84 | 21.9 |
| 86 | 15.3 |
| 87 | −14.8 |
| 88 | 49.7 |
| 90 | 20.8 |
| 91 | 36.7 |
| 92 | 73.4 |
| 93 | 74.4 |
| 94 | 91.0 |
| 95 | 26.5 |
| 96 | 26.5 |
| 97 | 4.0 |
| 98 | −7.6 |
| 100 | 2.3 |
| 101 | 83.9 |
| 102 | 52.1 |
| 103 | 82.7 |
| 104 | 98.9 |
| 105 | 23.9 |
| 106 | 87.1 |
| 107 | 87.2 |
| 108 | 17.1 |
| 109 | 20.6 |
| 111 | 2.8 |
| 112 | 99.1 |
| 115 | 40.0 |
| 119 | 43.1 |
| 129 | 64.0 |
| 131 | 97.4 |
| 133 | −8.5 |
| 135 | 99.6 |
| 138 | 35.6 |
| 141 | 56.1 |
| 144 | 42.3 |
| 148 | 77.3 |
| 149 | 35.4 |
| 152 | 15.1 |
| 154 | −22.2 |
| 161 | 77.9 |
| 162 | 48.5 |
| 169 | 80.8 |
| 172 | 94.9 |
| 174 | 94.9 |
| 175 | 25.6 |
| 180 | 36.7 |
| 181 | 26.0 |
| 183 | 37.9 |
| 189 | 90.4 |
| 191 | 47.9 |
| 195 | 94.2 |
| 207 | 27.9 |
| 222 | 61.4 |
| 225 | 18.6 |
| 233 | 80.2 |
| 234 | 57.4 |
| 240 | 44.7 |
| 241 | 87.4 |
| 242 | 60.2 |
| 243 | 57.2 |

Biological Example 11

22RV1 AR-FL and AR-V7 Transcriptional Reporter Assays

22RV1 were obtained from ATCC and cultured in RPMI 1640 supplemented with 10% FBS. Cells were seeded at a density of 15,000 cells/well into Greiner 384-well, white, optical-bottom plates in RPMI 1640 phenol red-free medium with 1% charcoal stripped FBS and incubated for 2 days at 37° C. The cells were treated with a compound or Formula (I) in 12-point dose-response, both in the presence and absence of 0.1 nM R1881 for 18-24 hrs. At the end of assay, Steady-Glo reagent (Promega) was added to each well according to the manufacturer's instructions, placed on a shaker at 300 rpm for 10 min, and luminescence recorded using an EnVision plate reader (Perkin Elmer). The data was exported to GraphPad Prism and analyzed using the Four Parameter equation to obtain $IC_{50}$ values for each compound. Each compound was tested in at least three independent experiments.

Resultant Data

Antagonist mode: In the presence of 0.1 nM R1881, the $IC_{50}$ of Cpd 43 was 347.6 nM.

Agonist mode: In the absence of 0.1 nM R1881, the $IC_{50}$ of Cpd 43 was 120.8 μM.

Biological Example 12

22RV1 Proliferation Assay

22RV1 were obtained from ATCC and cultured in RPMI 1640 supplemented with 10% FBS. Cells were seeded at a density of 4,500 cells/well into Greiner 384-well, white, optical-bottom plates in RPMI 1640 phenol red-free medium with 1% charcoal stripped FBS and incubated for 2 days at 37° C. The cells were treated with a compound of Formula (I) in 12-point dose-response both in the presence and absence of 0.1 nM R1881 for 5 days. To determine cell viability, CellTiter-Glo reagent (Promega) was added to each well according to the manufacturer's instructions, placed on a shaker at 300 rpm for 10 min, and luminescence recorded using an EnVision plate reader (Perkin Elmer). The data was exported to GraphPad Prism and analyzed using the Four Parameter equation to obtain $IC_{50}$ values for each compound. Each compound was tested in at least three independent experiments.

Resultant Data

Antagonist mode: In the presence of 0.1 nM R1881, the $IC_{50}$ of Cpd 43 was 259.8 μM.

Agonist mode: In the absence of 0.1 nM R1881, the $IC_{50}$ of Cpd 43 was 491.5 μM.

In-vivo Assays

Biological Example V1

Hershberger Assay

The effect of AR antagonists on androgen dependent signaling in vivo was assessed using the Hershberger assay. In this assay, peripubertal castrated male Sprague-Dawley rats were administered AR antagonists described herein in the presence of testosterone (0.4 mg/kg testosterone propionate) and the weights of androgen dependent organs measured. Dosing was continued for 10 days and measurements taken 24 h after the last dose. The extent of antagonism of AR and consequent inhibition of organ growth was evaluated by comparison to the castration control. Compounds of Formula (I) were dosed orally QD and an endpoint assessment made by change in weight of 5 androgen sensitive organs (ASO): Paired Cowper's Glands (CG), Seminal Vesicles with Fluids and Coagulating Glands (SVCG), Glans Penis (GP), Ventral Prostate (VP) and Levator Ani-Bulbocavernosus Complex (LABC)). According to assay guidelines, statistically significant suppression of ASO is required in 2 of 5 organs for a compound to be classified as an anti-androgen (analysis was performed by t-test/Mann-Whitney).

Unless otherwise stated, compounds defined herein were administered at 30 mg/kg and flutamide (FT), positive control, at 3 mg/kg. All compounds were co-administered with testosterone propionate (TP, 0.4 mg/kg) which was also administered alone, untreated control, (castrated only rats served as the control for complete androgen blockade). A statistically significant change in ASO achieved in at least 2 of 5 organs was indicative of an active compound. Administration of Compound 43 resulted in significant reduction in ASO versus TP control (p≤0.05) in all 5 organs. Data for the inhibition of growth of the Seminal Vesicle and Coagulating Glands (SVCG) and Ventral Prostate (VP) was reported for all studies (mean organ weight (% of TP control)±SD (n=6)).

|  | ASO Organ Growth (% of TP control) | |
|---|---|---|
| Compound | SVCG | VP |
| Flutamide (+ve control) | 16.6 ± 16.3 | 24.4 ± 35.5 |
| Compound 43 | 26.0 ± 17.8 | 24.1 ± 48.1 |

Biological Example V2

Castrate Resistant Prostate Cancer Xenograft Studies

Castrate six to seven week old male SCID Hairless Outbred mice (SHO, Charles Rivers Laboratories) were used as the host strain for xenograft studies. LNCaP SRαF876L cells were cultured as 3-D spheroids and expanded prior to subcutaneous injection on the flank of the animals (supplied post castration). Briefly, 5 mls of cells in media+5 mls of cultrex were premixed prior to plating of 500 μl=2×10⁵ cells per well of a 24-well plate. Plates were incubated @ 37° C. for 30 min before addition of complete media on top and returned to incubator for growth of 3-D colonies. After 7 days, media was removed, plates chilled and contents of each well, 500 μl cultrex and cells, injected into flank of a recipient mouse. Tumor volume (length× width²/2) was monitored weekly. When tumors reached an average volume of ~200 mm³, animals were randomized into treatment groups. During the treatment period tumor volume was monitored bi-weekly. At study end, tumor growth inhibition (TGI) was calculated: 100−(Treated/Control*100). At the termination of study tumors were collected and stored for further analyses.

|  | TGI | |
|---|---|---|
| Compound | 30 mg/kg | 50 mg/kg |
| Compound 43 | 91% (n = 9) | 87% (n = 10) |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A method of treating prostate cancer in a human, comprising administering a compound of Formula (I),

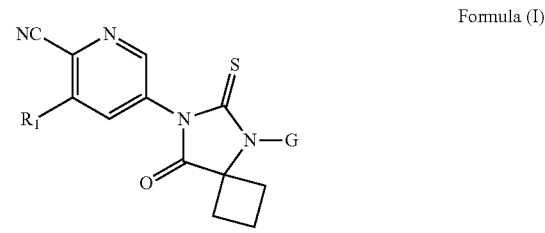

Formula (I)

or an N-oxide, enantiomer, diastereomer, or pharmaceutically acceptable salt form thereof, to a human in need of such treatment, wherein the human expresses an androgen receptor comprising a mutation of phenylalanine 876 (Phe876), and wherein R₁ is chloro, methyl, methoxy, difluoromethyl, or trifluoromethyl;

G is wherein

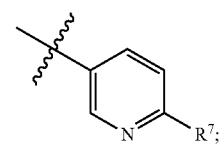

wherein
R⁷ is

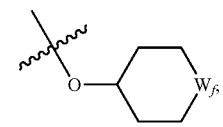

wherein
W_f is NH, N(methyl), N(2-hydroxyethyl), N(2-methoxyethyl), N(2-fluoroethyl), N(2,2,2-trifluoroethyl), N(cyanomethyl), N(allyl), N(isopentyl), N(cyclopropyl), N(prop-2-yn-1-yl), N(3,3-dimethylbutyl), N(3-fluoropropyl), N(3,3,3-trifluoropropyl), N(methoxycarbonylmethyl), N(3-amino-2-hydroxypropyl), N(3,3-dimethyl-butyl), CH(amino), CH(methylamino), or CH(dimethylamino).

2. The method of claim 1, wherein $R_1$ is chloro, methyl, methoxy, or trifluoromethyl.

3. The method of claim 2, wherein $R_1$ is chloro, methyl, or trifluoromethyl.

4. The method of claim 2, wherein $R_1$ is methyl or trifluoromethyl.

5. The method of claim 1, wherein $W_f$ is NH, N(methyl), N(2-hydroxyethyl), N(2-methoxyethyl), N(2-fluoroethyl), N(2,2,2-trifluoroethyl), N(3,3-dimethylbutyl), N(3-fluoropropyl), N(3,3,3-trifluoropropyl), N(isopentyl), N(cyclopropyl), or N(prop-2-yn-1-yl).

6. The method of claim 1, wherein $W_f$ is NH, N(methyl), N(2-hydroxyethyl), N(cyanomethyl), N(allyl), N(methoxycarbonylmethyl), N(3-amino-2-hydroxy-propyl), N(3,3-dimethyl-butyl), CH(amino), CH(methylamino), or CH(dimethylamino).

7. The method of claim 4, wherein $W_f$ is NH or N(methyl).

8. The method of claim 1, wherein $W_f$ is NH or N(2-fluoroethyl).

9. The method of claim 1, wherein the compound is:
5-[8-[6-[(1-methyl-4-piperidyl)oxy]-3-pyridyl]-5-oxo-7-thioxo-6,8-diazaspiro[3.4]octan-6-yl]-3-(trifluoromethyl)pyridine-2-carbonitrile;
5-[8-[4-[(1-cyclopropyl-4-piperidyl)oxy]phenyl]-5-oxo-7-thioxo-6,8-diazaspiro[3 0.4]octan-6-yl]-3-(trifluoromethyl)pyridine-2-carbonitrile;
5-[5-oxo-8-[6-(4-piperidyloxy)-3-pyridyl]-7-thioxo-6,8-diazaspiro[3.4]octan-6-yl]-3-(trifluoromethyl)pyridine-2-carbonitrile;
5-[8-[6-[[1-(cyanomethyl)-4-piperidyl]oxy]-3-pyridyl]-5-oxo-7-thioxo-6,8-diazaspiro[3.4]octan-6-yl]-3-(trifluoromethyl)pyridine-2-carbonitrile;
5-[8-[6-[[1-(2-methoxyethyl)-4-piperidyl]oxy]-3-pyridyl]-5-oxo-7-thioxo-6,8-diazaspiro[3.4]octan-6-yl]-3-(trifluoromethyl)pyridine-2-carbonitrile;
5-[8-[6-[[1-(2-hydroxyethyl)-4-piperidyl]oxy]-3-pyridyl]-5-oxo-7-thioxo-6,8-diazaspiro[3.4]octan-6-yl]-3-(trifluoromethyl)pyridine-2-carbonitrile;
5-[5-oxo-7-thioxo-8-[6-[[1-(2,2,2-trifluoroethyl)-4-piperidyl]oxy]-3-pyridyl]-6,8-diazaspiro[3.4]octan-6-yl]-3-(trifluoromethyl)pyridine-2-carbonitrile;
5-[8-[6-[[1-(2-fluoroethyl)-4-piperidyl]oxy]-3-pyridyl]-5-oxo-7-thioxo-6,8-diazaspiro[3.4]octan-6-yl]-3-(trifluoromethyl)pyridine-2-carbonitrile;
5-[8-[6-[(1-allyl-4-piperidyl)oxy]-3-pyridyl]-5-oxo-7-thioxo-6,8-diazaspiro[3.4]octan-6-yl]-3-(trifluoromethyl)pyridine-2-carbonitrile;
5-[5-oxo-8-[6-[(1-prop-2-ynyl-4-piperidyl)oxy]-3-pyridyl]-7-thioxo-6, 8-diazaspiro[3 0.4]octan-6-yl]-3-(trifluoromethyl)pyridine-2-carbonitrile;
or a pharmaceutically acceptable salt form thereof.

10. The method of claim 1, wherein the compound is
5-[8-[6-[(1-methyl-4-piperidyl)oxy]-3-pyridyl]-5-oxo-7-thioxo-6,8-diazaspiro[3.4]octan-6-yl]-3-(trifluoromethyl)pyridine-2-carbonitrile;
or a pharmaceutically acceptable salt form thereof.

11. The method of claim 1, wherein the compound is
5-[5-oxo-8-[6-(4-piperidyloxy)-3-pyridyl]-7-thioxo-6,8-diazaspiro[3.4]octan-6-yl]-3-(trifluoromethyl)pyridine-2-carbonitrile;
or a pharmaceutically acceptable salt form thereof.

12. The method of claim 1, wherein the mutation is a substitution of Phe876 with leucine, isoleucine, valine, serine, cysteine or tyrosine.

13. The method of claim 12, wherein the mutation is a substitution of Phe876 with leucine.

14. The method of claim 1, wherein the androgen receptor comprises one or more additional amino acid mutations selected from A597T, S648G, P683T, D696E, R727H, N728I, I738F, W741L, W741C, W741L, M743V, G751S, A871V, H874Y, T878A, T878S, and P914S.

15. The method of claim 1, wherein the prostate cancer is resistant to treatment using enzalutamide or ARN-509.

16. The method of claim 1, wherein the prostate cancer is castration-resistant prostate cancer.

17. The method of claim 1, wherein the prostate cancer is metastatic castration-resistant prostate cancer.

18. The method of claim 1, further comprising administering abiraterone acetate to the human in need of treatment.

19. The method of claim 18, further comprising administering prednisone or dexamethasone to the human in need of treatment.

20. The method of claim 1, further comprising administering a gonadotropin-releasing hormone (GnRH) agonist or antagonist to the human in need of treatment.

21. The method of claim 20, wherein the GnRH agonist or antagonist is leuprolide acetate, goserelin acetate, degarelix, ozarelix, ABT-620 (Elagolix), TAK-385 (Relugolix), EP-100 or KLH-2109.

22. The method of claim 9, wherein the mutation is a substitution of Phe876 with leucine, isoleucine, valine, serine, cysteine or tyrosine.

23. The method of claim 22, wherein the mutation is a substitution of Phe876 with leucine.

24. The method of claim 9, wherein the androgen receptor comprises one or more additional amino acid mutations selected from A597T, S648G, P683T, D696E, R727H, N728I, I738F, W741L, W741C, W741L, M743V, G751S, A871V, H874Y, T878A, T878S, and P914S.

25. The method of claim 9, wherein the prostate cancer is resistant to treatment using enzalutamide or ARN-509.

26. The method of claim 9, wherein the prostate cancer is castration-resistant prostate cancer.

27. The method of claim 9, wherein the prostate cancer is metastatic castration-resistant prostate cancer.

28. The method of claim 9, further comprising administering abiraterone acetate to the human in need of treatment.

29. The method of claim 28, further comprising administering prednisone or dexamethasone to the human in need of treatment.

30. The method of claim 9, further comprising administering a gonadotropin-releasing hormone (GnRH) agonist or antagonist to the human in need of treatment.

31. The method of claim 30, wherein the GnRH agonist or antagonist is leuprolide acetate, goserelin acetate, degarelix, ozarelix, ABT-620 (Elagolix), TAK-385 (Relugolix), EP-100 or KLH-2109.

32. The method of claim 10, wherein the mutation is a substitution of Phe876 with leucine, isoleucine, valine, serine, cysteine or tyrosine.

33. The method of claim 32, wherein the mutation is a substitution of Phe876 with leucine.

34. The method of claim 10, wherein the androgen receptor comprises one or more additional amino acid mutations selected from A597T, S648G, P683T, D696E, R727H, N728I, I738F, W741L, W741C, W741L, M743V, G751S, A871V, H874Y, T878A, T878S, and P914S.

35. The method of claim 10, wherein the prostate cancer is resistant to treatment using enzalutamide or ARN-509.

36. The method of claim 10, wherein the prostate cancer is castration-resistant prostate cancer.

37. The method of claim 10, wherein the prostate cancer is metastatic castration-resistant prostate cancer.

38. The method of claim 10, further comprising administering abiraterone acetate to the human in need of treatment.

39. The method of claim 38, further comprising administering prednisone or dexamethasone to the human in need of treatment.

40. The method of claim 10, further comprising administering a gonadotropin releasing hormone (GnRH) agonist or antagonist to the human in need of treatment.

41. The method of claim 40, wherein the GnRH agonist or antagonist is leuprolide acetate, goserelin acetate, degarelix, ozarelix, ABT-620 (Elagolix), TAK-385 (Relugolix), EP-100 or KLH-2109.

42. The method of claim 11, wherein the mutation is a substitution of Phe876 with leucine, isoleucine, valine, serine, cysteine or tyrosine.

43. The method of claim 42, wherein the mutation is a substitution of Phe876 with leucine.

44. The method of claim 11, wherein the androgen receptor comprises one or more additional amino acid mutations selected from A597T, S648G, P683T, D696E, R727H, N728I, I738F, W741L, W741C, W741L, M743V, G751S, A871V, H874Y, T878A, T878S, and P914S.

45. The method of claim 11, wherein the prostate cancer is resistant to treatment using enzalutamide or ARN-509.

46. The method of claim 11, wherein the prostate cancer is castration-resistant prostate cancer.

47. The method of claim 11, wherein the prostate cancer is metastatic castration-resistant prostate cancer.

48. The method of claim 11, further comprising administering abiraterone acetate to the human in need of treatment.

49. The method of claim 48, further comprising administering prednisone or dexamethasone to the human in need of treatment.

50. The method of claim 11, further comprising administering a gonadotropin-releasing hormone (GnRH) agonist or antagonist to the human in need of treatment.

51. The method of claim 50, wherein the GnRH agonist or antagonist is leuprolide acetate, goserelin acetate, degarelix, ozarelix, ABT-620 (Elagolix), TAK-385 (Relugolix), EP-100 or KLH-2109.

* * * * *